(12) United States Patent
Sugimoto et al.

(10) Patent No.: US 9,139,609 B2
(45) Date of Patent: Sep. 22, 2015

(54) C-4" POSITION SUBSTITUTED MACROLIDE DERIVATIVE

(75) Inventors: Tomohiro Sugimoto, Saitama (JP); Naoki Sasamoto, Saitama (JP); Jun Kurosaka, Saitama (JP); Masato Hayashi, Saitama (JP); Kanako Yamamoto, Saitama (JP); Masato Kashimura, Saitama (JP); Yasunobu Ushiki, Saitama (JP); Haruhisa Ogita, Saitama (JP); Tomoaki Miura, Kanagawa (JP); Kenichi Kanemoto, Chiba (JP); Kou Kumura, Tokyo (JP); Satoshi Yoshida, Tokyo (JP); Keiji Tamura, Tokyo (JP); Eiki Shitara, Kanagawa (JP)

(73) Assignees: TAISHO PHARMACEUTICAL CO., LTD., Tokyo (JP); MEIJI SEIKA PHARMA CO., LTD., Tokyo (JP)

( * ) Notice: Subject to any disclaimer, the term of this patent is extended or adjusted under 35 U.S.C. 154(b) by 0 days.

(21) Appl. No.: 14/000,556

(22) PCT Filed: Feb. 20, 2012

(86) PCT No.: PCT/JP2012/054677
§ 371 (c)(1),
(2), (4) Date: Oct. 4, 2013

(87) PCT Pub. No.: WO2012/115256
PCT Pub. Date: Aug. 30, 2012

(65) Prior Publication Data
US 2014/0046043 A1 Feb. 13, 2014

(30) Foreign Application Priority Data
Feb. 21, 2011 (JP) ................................. 2011-034578

(51) Int. Cl.
*A61K 31/70* (2006.01)
*C07H 17/08* (2006.01)

(52) U.S. Cl.
CPC ...................................... *C07H 17/08* (2013.01)

(58) Field of Classification Search
CPC ....................................................... C07H 17/08
See application file for complete search history.

(56) References Cited

U.S. PATENT DOCUMENTS

| | | | |
|---|---|---|---|
| 4,474,768 A | 10/1984 | Bright | |
| 4,517,359 A | 5/1985 | Kobrehel et al. | |
| 5,866,549 A | 2/1999 | Or et al. | |
| 6,028,181 A | 2/2000 | Or et al. | |
| 6,075,133 A | 6/2000 | Or et al. | |
| 6,100,404 A | 8/2000 | Agouridas et al. | |
| 6,147,197 A | 11/2000 | Or et al. | |
| 6,407,074 B1 | 6/2002 | Bronk et al. | |
| 6,576,749 B2 | 6/2003 | Bronk et al. | |
| 6,777,543 B2 * | 8/2004 | Wu et al. | 536/7.4 |
| RE39,591 E | 4/2007 | Or et al. | |

FOREIGN PATENT DOCUMENTS

| | | |
|---|---|---|
| CN | 1237183 A | 12/1999 |
| CN | 1259955 A | 7/2000 |
| EP | 0680967 A1 | 11/1995 |
| JP | 2000-514097 A | 10/2000 |
| JP | 2001-500855 A | 1/2001 |
| WO | 9501794 A1 | 1/1995 |
| WO | 98/09978 A1 | 3/1998 |
| WO | 9813373 A1 | 4/1998 |
| WO | 98/56801 A1 | 12/1998 |
| WO | 00/71557 A1 | 11/2000 |
| WO | 02/32919 A2 | 4/2002 |
| WO | 2008/106244 A1 | 9/2008 |

OTHER PUBLICATIONS

European search report issued with respect to application No. 12749570.3, mail date is Jun. 30, 2014.
Saudi Arabia Office Action issued with respect to Saudi Arabia application No. 112330287, mail date is Aug. 8, 2014.
International Search Report PCT/JP2012/054677, mail date is Mar. 27, 2012.
International Preliminary Report on Patentability PCT/JP2012/054677, mail date is Mar. 27, 2012.
First examination report issued with respect to New Zealand application No. 613956, mail date is May 21, 2014.
Japanese Office Action issued with respect to application No. 2013-554176, mail date is Oct. 28, 2014.

(Continued)

*Primary Examiner* — Elli Peselev
(74) *Attorney, Agent, or Firm* — Greenblum & Bernstein, P.L.C.

(57) ABSTRACT

A macrolide compound represented by the formula (I) effective against erythromycin resistant bacteria (for example, resistant pneumococci, streptococci and mycoplasmas).

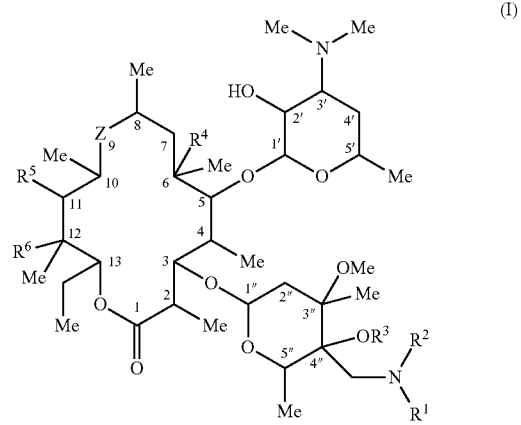

6 Claims, No Drawings

(56) References Cited

OTHER PUBLICATIONS

Colombian Office Action issued with respect to U.S. Appl. No. 13/218,145, mail date is Oct. 6, 2014.
Chines Office Action issued with respect to application No. 201280009809.
Singapore Written Opinion issued with respect to application No. 2013059985, mailing date is Jan. 26, 2015.
Eric Hunt et al., The Journal of Abtibiotics, "9,11-Cyclic Acetal Derivatives of (9S)-9-Dihydroerythromycin A", vol. XLII No. 2, pp. 293-298, Jun. 27, 1988.
Masato Kashimura et al., The journal of Antibiotics, "The synthesis and Antibacterial Activity of Tetracyclic Macrolides", vol. 56, No. 12, pp. 1062-1065, Dec. 2003.
Chines Office Action issued with respect to application No. 201280009809, 2014.
Colombian Office Action issued with respect to application No. 13-218.145, Mail date is Apr. 29, 2015.
Saudi Arabian Office Action issued with respect to application No. 112330287, Mail date is May 24, 2015.
Taiwanese Office Action issued for application No. 101105515, mail date is May 5, 2015.
Sarbani Pal, "A Journey across the sequential development of macrolides and ketolides related to erythromycin", Tetrahedron 62, pp. 3171-3200.
Mexican Office Action issued with respect to application No. 2013/009585, mail date is May 20, 2015.
Singaporean Office Action issued with repect to application No. 201305998-5, mail date is Jul. 21, 2015.
Chinese Office Action issued with respect to application No. 201280009809.X, mail date is Jul. 13, 2015.

\* cited by examiner

C-4" POSITION SUBSTITUTED MACROLIDE DERIVATIVE

TECHNICAL FIELD

The present invention relates to a novel antibiotic having an erythromycin-like structure. More specifically, the present invention relates to a macrolide compound having a methyl group substituted with a substituent having nitrogen atom at the 4"-position of the cladinose, and a synthetic intermediate thereof.

BACKGROUND ART

Erythromycin A is an antibiotic which has been widely used as a therapeutic agent for infectious diseases caused by Gram-positive bacteria, mycoplasmas, and the like. However, due to decomposition by gastric acid, erythromycin has a drawback of inconstant pharmacokinetics. Therefore, derivatives of erythromycin having increased stability to acids were researched. As a result, macrolides having stable pharmacokinetics such as clarithromycin, azithromycin (Patent documents 1 and 2) and roxithromycin have been developed. These macrolide agents have been applied in a therapeutic field of respiratory infectious diseases of ambulatory patients, and therefore, they are required to have a potent antibacterial activity especially against pneumococci, streptococci, and *Haemophilus influenzae* which are frequently isolated clinically. Furthermore, since macrolide-resistant pneumococci have been highly frequently isolated from community acquired pneumonia patients, it has been considered important that they are effective against the resistant pneumococci.

As a result of various researches in recent years, Agouridas et al. found HMR3647 (telithromycin, Patent document 3) in 1995, and successively Or et al. found ABT-773 (cethromycin, Patent document 4) in 1998 as macrolides that are effective against both erythromycin resistant pneumococci and erythromycin resistant streptococci. Then, 2-fluoroketolide (Patent document 5) of which efficacy was further enhanced was reported.

However, most of the macrolide compounds having a methyl group substituted with a substituent having nitrogen atom at the 4"-position of the cladinose are azalide type compounds structurally characterized by having nitrogen atom in the lactone ring (Patent document 6), and almost no compounds having a structure other than azalide have been reported.

PRIOR ART DOCUMENTS

Patent Documents

Patent document 1: U.S. Pat. No. 4,474,768
Patent document 2: U.S. Pat. No. 4,517,359
Patent document 3: EP680967
Patent document 4: WO98/09978
Patent document 5: WO02/32919
Patent document 6: WO98/56801

DISCLOSURE OF THE INVENTION

Object to be Achieved by the Invention

An object of the present invention is to provide a compound having a novel structure which is effective against erythromycin resistant bacteria (for example, resistant pneumococci, streptococci and mycoplasmas) as well as against conventional erythromycin sensitive bacteria.

Means for Achieving the Object

The inventors of the present invention conducted various researches on novel macrolide compounds, and as a result, found that the compounds described below had superior antibacterial activity and accomplished the present invention.

The present invention thus provides:
(1) A compound represented by the following formula (I):
Formula (I):

[Formula 1]

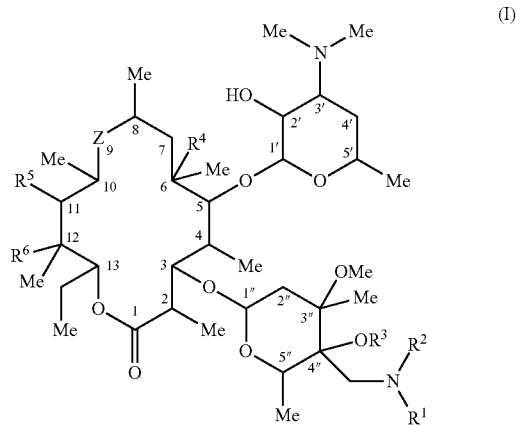

wherein, in the formula,
Me represents methyl group,
$R^1$ represents hydrogen atom, a $C_{1-6}$ alkyl group (the $C_{1-6}$ alkyl group may be substituted with one or two substituents selected from hydroxy group, a $C_{1-6}$ alkoxy group, amino group, a $C_{1-6}$ alkylamino group, and a group represented by the formula $-NR^{78}COR^{79}$, or the formula $-NR^{80}SO_2R^{81}$, wherein $R^{78}$ and $R^{80}$, which may be the same or different, represent hydrogen atom, or a $C_{1-6}$ alkyl group, and wherein $R^{79}$ and $R^{81}$, which may be the same or different, represent a $C_{1-6}$ alkyl group), or a $C_{1-6}$ alkylsulfonyl group,
$R^2$ represents hydrogen atom, a 4- to 8-membered saturated heterocyclic group (the saturated heterocyclic group may be substituted with one or two substituents selected from a $C_{7-12}$ aralkyl group, and a $C_{1-6}$ alkyl group), a $C_{1-6}$ alkanoyl group (the $C_{1-6}$ alkanoyl group may be substituted with amino group, or a $C_{1-6}$ alkylamino group), or a $C_{1-6}$ alkyl group which may be substituted with 1 to 3 substituents selected from the substituent group 1, or
$R^1$ and $R^2$ may combine together to form, together with the nitrogen atom to which they bind, a 4- to 8-membered saturated nitrogen-containing heterocyclic group (the saturated nitrogen-containing heterocyclic group may be substituted with 1 to 3 substituents selected from hydroxy group, amino group, a $C_{1-6}$ alkylamino group, and a $C_{1-6}$ alkyl group (the $C_{1-6}$ alkyl group may be substituted with amino group, or a $C_{1-6}$ alkylamino group)),
the substituent group 1 is a group consisting of a $C_{1-6}$ alkylsulfonyl group, a $C_{1-6}$ alkoxy group, a $C_{3-6}$ cycloalkyl group, hydroxy group, phenyl group (the phenyl group may be substituted with 1 to 3 $C_{1-6}$ alkoxy groups), a 4- to 8-membered saturated heterocyclic group (the saturated heterocyclic group may be substituted with 1 to 3 $C_{1-6}$ alkyl groups), and a group represented by the formula $-CONR^7R^8$, the formula —SO$_2$NR$^9$R$^{10}$, the formula —NR$^{11}$COR$^{12}$, the formula —NR$^{13}$CO$_2$R$^{14}$, the formula —NR$^{15}$SO$_2$R$^{16}$, or the formula —NR$^{17}$R$^{18}$, R$^7$, R$^8$, R$^9$, R$^{10}$, R$^{11}$, R$^{13}$, R$^{14}$, and R$^{15}$, which may be the same or different, represent hydrogen atom, or a C$_{1-6}$ alkyl group, R$^{12}$ represents phenyl group (the phenyl group may be substituted with 1 to 3 C$_{1-6}$ alkoxy groups), R$^{16}$ represents a C$_{1-6}$ alkyl group, or phenyl group (the phenyl group may be substituted with 1 to 3 C$_{1-6}$ alkoxy groups), R$^{17}$ and R$^{18}$, which may be the same or different, represent hydrogen atom, a C$_{1-6}$ alkyl group (the C$_{1-6}$ alkyl group may be substituted with 1 to 3 substituents selected from hydroxy group, a C$_{1-6}$ alkoxy group, and a C$_{3-6}$ cycloalkyl group), a C$_{2-6}$ alkenyl group, a C$_{3-6}$ cycloalkyl group, a C$_{1-6}$ alkanoyl group, a C$_{7-12}$ aralkyl group (the C$_{7-12}$ aralkyl group may be substituted with 1 to 3 C$_{1-6}$ alkoxy groups), or a heteroaralkyl group (the heteroaralkyl group may be substituted with 1 to 3 C$_{1-6}$ alkoxy groups), or R$^{17}$ and R$^{18}$ may combine together to form, together with the nitrogen atom to which they bind, a 4- to 8-membered saturated nitrogen-containing heterocyclic group which may be substituted with 1 to 3 substituents selected from the substituent group 2, or a 6-membered partially saturated nitrogen-containing heterocyclic group which may be substituted with 1 to 3 substituents selected from the substituent group 2, the substituent group 2 is a group consisting of hydroxy group, a C$_{1-6}$ alkoxy group, oxo group, a C$_{1-6}$ alkoxyimino group, amino group, a C$_{1-6}$ alkylamino group, a group represented by the formula —CONR$^{19}$R$^{20}$ (R$^{19}$ and R$^{20}$, which may be the same or different, represent hydrogen atom, or a C$_{1-6}$ alkyl group), a C$_{1-6}$ haloalkyl group, and a C$_{1-6}$ alkyl group (the C$_{1-6}$ alkyl group may be substituted with 1 to 3 substituents selected from hydroxy group, a C$_{1-6}$ alkoxy group, amino group, and a C$_{1-6}$ alkylamino group), R$^3$ represents hydrogen atom, or R$^3$ and R$^1$ may combine together to form carbonyl group, R$^4$ represents hydroxy group, a C$_{1-6}$ alkoxy group, or a group represented by the formula OCONR$^{21}$R$^{22}$ (R$^{21}$ and R$^{22}$, which may be the same or different, represent hydrogen atom, a C$_{1-6}$ alkyl group, or a C$_{2-6}$ alkenyl group substituted with one heteroaryl group), Z represents a group represented by the formula CHR$^{28}$ (R$^{28}$ represents hydroxy group, or amino group), the formula C(=O), or the formula C(=N—OR$^{24}$), R$^{24}$ represents hydrogen atom, a C$_{1-6}$ alkyl group (the C$_{1-6}$ alkyl group may be substituted with a C$_{1-6}$ alkoxy group, amino group, or a C$_{1-6}$ alkylamino group), or a 4- to 8-membered saturated heterocyclic group, or R$^4$ and Z may combine together to represent, together with the carbon atoms to which they bind, a cyclic structure represented by the formula (II):

[Formula 2]

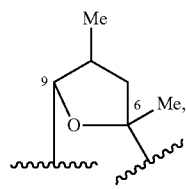

R$^5$ represents hydroxy group, a C$_{1-6}$ alkoxy group, or a group represented by the formula OCONR$^{25}$R$^{26}$ (R$^{25}$ and R$^{26}$, which may be the same or different, represent hydrogen atom, or a C$_{1-6}$ alkyl group), R$^6$ represents hydrogen atom, or hydroxy group, or R$^5$ and R$^6$ may combine together to represent, together with the carbon atoms to which they bind, a cyclic structure represented by the formula (III):

[Formula 3]

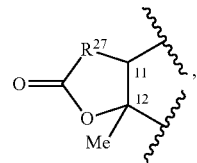

R$^{27}$ represents oxygen atom, or a group represented by the formula CHR$^{28}$, or the formula NR$^{29}$, R$^{28}$ represents hydrogen atom, cyano group, or a C$_{1-6}$ alkylsulfanyl group (the C$_{1-6}$ alkylsulfanyl group may be substituted with a heteroaryl group which may be substituted with one amino group), R$^{29}$ represents hydrogen atom, hydroxy group, a C$_{1-6}$ alkoxy group (the C$_{1-6}$ alkoxy group may be substituted with phenyl group), a 4- to 8-membered saturated heterocyclic group (the saturated heterocyclic group may be substituted with a C$_{1-6}$ alkylsulfonyl group, or diphenylmethyl group), a group represented by the formula —NR$^{30}$R$^{31}$, the formula —NR$^{32}$CSNR$^{33}$R$^{34}$, the formula —NR$^{32}$CO$_2$R$^{35}$, the formula —NR$^{32}$COR$^{36}$, the formula —NR$^{32}$SO$_2$R$^{37}$, the formula —NR$^{32}$CONR$^{38}$R$^{39}$, the formula —NR$^{32}$SO$_2$NR$^{40}$R$^{41}$, or the formula —N=C—NR$^{42}$R$^{43}$, or a C$_{1-6}$ alkyl group which may be substituted with 1 to 3 substituents selected from the substituent group 3, R$^{30}$ and R$^{31}$, which may be the same or different, represent hydrogen atom, or a C$_{1-6}$ alkyl group (the C$_{1-6}$ alkyl group may be substituted with a C$_{1-6}$ alkylsulfonyl group, phenyl group, or a heteroaryl group), R$^{32}$, R$^{33}$, R$^{34}$, R$^{37}$, R$^{40}$, R$^{41}$, R$^{42}$, and R$^{43}$, which may be the same or different, represent hydrogen atom, or a C$_{1-6}$ alkyl group, R$^{35}$ represents hydrogen atom, a C$_{1-6}$ alkyl group, or a C$_{7-12}$ aralkyl group, R$^{36}$ represents hydrogen atom, a C$_{1-6}$ alkyl group (the C$_{1-6}$ alkyl group may be substituted with a C$_{1-6}$ alkylsulfonyl group), or a C$_{7-12}$ aralkyl group, R$^{38}$ and R$^{39}$, which may be the same or different, represent hydrogen atom, a C$_{1-6}$ alkyl group (the C$_{1-6}$ alkyl group may be substituted with a C$_{3-6}$ cycloalkyl group), a C$_{2-6}$ alkenyl group, a C$_{7-12}$ aralkyl group (the C$_{7-12}$ aralkyl group may be substituted with 1 to 3 substituents selected from a halogen atom, a C$_{1-6}$ alkyl group, and a C$_{1-6}$ alkoxy group), or a heteroaralkyl group, the substituent group 3 is a group consisting of hydroxy group, a C$_{1-6}$ alkoxy group, a C$_{3-6}$ cycloalkyl group, a C$_{1-6}$ alkylsulfonyl group, a C$_{1-6}$ alkylsulfonyl group, a C$_{1-6}$ alkylsulfonyl group, phenyl group, phenoxy group, benzyloxy group, phenylsulfanyl group, phenylsulfonyl group, cyano group, a C$_{7-12}$ aralkyl group, a 4- to 8-membered saturated heterocyclic group (the saturated heterocyclic group may be substituted with a C$_{1-6}$ alkylsulfonyl group, or diphenylmethyl group), a heteroaryl group (the heteroaryl group may be substituted with 1 to 3 substituents selected from a C$_{1-6}$ alkyl group, a C$_{7-12}$ aralkyl group, phenyl group, and a heteroaryl group), and a group represented by the formula —NR$^{44}$CO$_2$R$^{45}$, the formula —OSO$_2$NR$^{46}$R$^{47}$, the formula —NR$^{49}$SO$_2$NR$^{50}$R$^{51}$, the formula —CONR$^{52}$SO$_2$NR$^{53}$R$^{54}$, the formula —OCONR$^{55}$R$^{56}$, the formula —NR$^{57}$COR$^{58}$, the formula —CONR$^{59}$R$^{60}$, the formula —NR$^{61}$CONR$^{62}$R$^{63}$, the formula —OCOR$^{64}$, the formula —SO$_2$NR$^{65}$R$^{66}$, the formula —NR$^{67}$SO$_2$R$^{68}$, the formula —NR$^{69}$R$^{70}$, or the formula —CONR$^{71}$SO$_2$R$^{72}$, R$^{44}$ to R$^{57}$, R$^{61}$, R$^{67}$, R$^{71}$, and R$^{72}$, which may be the same or different, represent hydrogen atom, or a C$_{1-6}$ alkyl group, R$^{58}$ represents a C$_{1-6}$ alkyl group, a C$_{1-6}$ haloalkyl group, or phenyl group, R$^{59}$ and R$^{60}$, which may be the same or different, represent hydrogen atom, a C$_{1-6}$ alkyl group, phenyl group, a C$_{7-12}$ aralkyl group, or a heteroaralkyl group, R$^{62}$ and R$^{63}$, which may be the same or different, represent hydrogen atom, or a C$_{1-6}$ alkyl group (the C$_{1-6}$ alkyl group may be substituted with amino group, or a C$_{1-6}$ alkylamino group), R$^{64}$ represents a C$_{1-6}$ alkyl group, or phenyl group, R$^{65}$ and R$^{66}$, which may be the same or different, represent hydrogen atom, a C$_{1-6}$ alkyl group, or phenyl group, R$^{68}$ represents a C$_{1-6}$ alkyl group, a C$_{1-6}$ haloalkyl group, a C$_{3-6}$ cycloalkyl group, phenyl group (the phenyl group may be substituted with 1 to 3 substituents selected from a C$_{1-6}$ alkyl group, a C$_{1-6}$ alkylsulfonyl group, a C$_{1-6}$ alkoxy group, cyano group, and carboxy group), or a heteroaryl group which may be substituted with 1 to 3 C$_{1-6}$ alkyl groups, R$^{69}$ and R$^{70}$, which may be the same or different, represent hydrogen atom, a C$_{1-6}$ alkyl group, phenyl group, a heteroaryl group which may be substituted with one cyano group, a C$_{7-12}$ aralkyl group, or a heteroaralkyl group, or R$^{69}$ and R$^{70}$ may combine together to form, together with the nitrogen atom to which they bind, a 4- to 8-membered saturated nitrogen-containing heterocyclic group (the saturated nitrogen-containing heterocyclic group may be substituted with 1 to 3 substituents selected from a C$_{1-6}$ alkyl group, and oxo group), when R$^{27}$ is oxygen atom, R$^4$ and Z may combine together to represent, together with the carbon atoms to which they bind, a cyclic structure represented by the formula (IV):

[Formula 4]

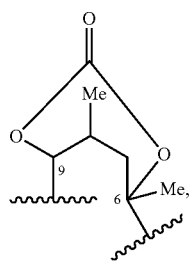

(IV)

or

R$^5$ and Z may combine together to represent a cyclic structure represented by the formula (V):

[Formula 5]

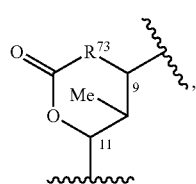

(V)

R$^{73}$ represents oxygen atom, or a group represented by the formula NH, or

R$^5$, R$^6$, and Z may combine together to represent a cyclic structure represented by the formula (VI):

[Formula 6]

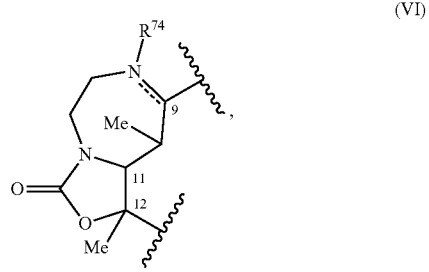

(VI)

the double bond containing a broken line represents a single bond, or a double bond, and R$^{74}$ exists only when the double bond containing a broken line is a single bond to represent hydrogen atom, or R$^5$, R$^6$, Z and R$^4$ may combine together to represent a cyclic structure represented by the formula (VII):

[Formula 7]

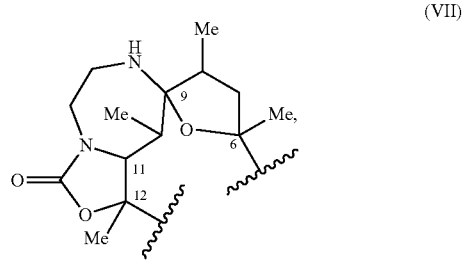

(VII)

provided that when R$^1$ and R$^3$ are both hydrogen atoms, R$^4$ is methoxy group, Z is a group represented by the formula C(=O), and R$^5$ and R$^6$ are both hydroxy groups, R$^2$ is not 2-aminoethyl group, 2-(N-2-methoxybenzylamino)ethyl group, or 2-(N-isobutyl-N-methoxybenzylamino)ethyl group, or a salt thereof, or a hydrate or a solvate thereof.

According to preferred embodiments of the aforementioned invention, there are provided:

(2) The compound according to (1) mentioned above or a salt thereof, or a hydrate or a solvate thereof, wherein R$^1$ is hydrogen atom, a C$_{1-6}$ alkyl group, or a C$_{1-6}$ alkylsulfonyl group, R$^2$ is a 4- to 8-membered saturated heterocyclic group (the saturated heterocyclic group may be substituted with one or two substituents selected from a C$_{7-12}$ aralkyl group, and a C$_{1-6}$ alkyl group), a C$_{1-6}$ alkanoyl group (the C$_{1-6}$ alkanoyl group may be substituted with amino group, or a C$_{1-6}$ alkylamino group), or a C$_{1-6}$ alkyl group which may be substituted with 1 to 3 substituents selected from the substituent group 1, or R$^1$ and R$^2$ may combine together to form, together with the nitrogen atom to which they bind, a 4- to 8-membered saturated nitrogen-containing heterocyclic group (the saturated nitrogen-containing heterocyclic group may be substituted with 1 to 3 substituents selected from hydroxy group, amino group, a C$_{1-6}$ alkylamino group, and a C$_{1-6}$ alkyl group (the C$_{1-6}$ alkyl group may be substituted with amino group, or a C$_{1-6}$ alkylamino group)), and $R^{38}$ and $R^{39}$, which may be the same or different, represent hydrogen atom, a $C_{1-6}$ alkyl group (the $C_{1-6}$ alkyl group may be substituted with a $C_{3-6}$ cycloalkyl group), a $C_{7-12}$ aralkyl group (the $C_{7-12}$ aralkyl group may be substituted with 1 to 3 substituents selected from a halogen atom, a $C_{1-6}$ alkyl group, and a $C_{1-6}$ alkoxy group), or a heteroaralkyl group;

(3) The compound according to (1) or (2) mentioned above or a salt thereof, or a hydrate or a solvate thereof, wherein $R^2$ is a $C_{1-6}$ alkyl group substituted with 1 to 3 substituents selected from the substituent group 1;

(4) The compound according to (1) or (2) mentioned above or a salt thereof, or a hydrate or a solvate thereof, wherein $R^2$ is a $C_{1-6}$ alkyl group substituted with 1 to 3 substituents selected from the substituent group 4, and the substituent group 4 is a group consisting of hydroxy group, and a group represented by the formula $-NR^{17}R^{18}$;

(5) The compound according to (4) mentioned above or a salt thereof, or a hydrate or a solvate thereof, wherein $R^{17}$ and $R^{18}$, which may be the same or different, represent hydrogen atom, or a $C_{1-6}$ alkyl group (the $C_{1-6}$ alkyl group may be substituted with a $C_{3-6}$ cycloalkyl group);

(6) The compound according to any one of (1) to (5) mentioned above or a salt thereof, or a hydrate or a solvate thereof, wherein $R^5$ and $R^6$ represent, together with the carbon atoms to which they bind, a cyclic structure represented by the formula (III);

(7) The compound according to (6) mentioned above or a salt thereof, or a hydrate or a solvate thereof, wherein $R^{27}$ is a group represented by the formula $NR^{29}$;

(8) The compound according to (7) mentioned above or a salt thereof, or a hydrate or a solvate thereof, wherein $R^{29}$ is hydrogen atom, a group represented by the formula $-NR^{30}R^{31}$, the formula $-NR^{32}CO_2R^{35}$, the formula $-NR^{32}SO_2R^{37}$, the formula $-NR^{32}CONR^{38}R^{39}$, or the formula $-NR^{32}SO_2NR^{40}R^{41}$, or a $C_{1-6}$ alkyl group substituted with 1 to 3 substituents selected from the substituent group 3;

(9) The compound according to (7) mentioned above or a salt thereof, or a hydrate or a solvate thereof, wherein $R^{29}$ is a $C_{1-6}$ alkyl group substituted with 1 to 3 substituents selected from the substituent group 5, and the substituent group 5 is a group consisting of hydroxy group, a $C_{1-6}$ alkylsulfonyl group, a 4- to 8-membered saturated heterocyclic group (the saturated heterocyclic group may be substituted with a $C_{1-6}$ alkylsulfonyl group), and a group represented by the formula $-OSO_2NR^{46}R^{47}$, the formula $-NR^{49}SO_2NR^{50}R^{51}$, the formula $-CONR^{59}R^{60}$, the formula $-SO_2NR^{65}R^{66}$, the formula $-NR^{67}SO_2R^{68}$, or the formula $-NR^{69}R^{70}$;

(10) The compound according to (7) mentioned above or a salt thereof, or a hydrate or a solvate thereof, wherein $R^{29}$ is a $C_{1-6}$ alkyl group substituted with 1 to 3 substituents selected from the substituent group 6, and the substituent group 6 is a group consisting of a $C_{1-6}$ alkylsulfonyl group, and a group represented by the formula $-OSO_2NR^{46}R^{47}$, the formula $-SO_2NR^{65}R^{66}$, or the formula $-NR^{67}SO_2R^{68}$.

(11) The compound according to (7) mentioned above or a salt thereof, or a hydrate or a solvate thereof, wherein $R^{29}$ is a $C_{1-6}$ alkyl group substituted with a $C_{1-6}$ alkylsulfonyl group;

(12) The compound according to any one of (1) to (11) mentioned above or a salt thereof, or a hydrate or a solvate thereof, wherein $R^1$ is a $C_{1-6}$ alkyl group;

(13) The compound according to any one of (1) to (12) mentioned above or a salt thereof, or a hydrate or a solvate thereof, wherein $R^4$ is hydroxy group, or a $C_{1-6}$ alkoxy group;

(14) The compound according to any one of (1) to (12) mentioned above or a salt thereof, or a hydrate or a solvate thereof, wherein $R^4$ is methoxy group;

(15) The compound according to any one of (1) to (14) mentioned above or a salt thereof, or a hydrate or a solvate thereof, wherein $R^3$ is hydrogen atom;

(16) The compound according to any one of (1) to (15) mentioned above or a salt thereof, or a hydrate or a solvate thereof, wherein Z is a group represented by the formula $C(=O)$, or a group represented by the formula $C(=N-OR^{24})$; and

(17) The compound according to any one of (1) to (15) mentioned above or a salt thereof, or a hydrate or a solvate thereof, wherein Z is a group represented by the formula $C(=O)$.

As another aspect of the present invention, there are provided:

(18) A medicament containing a substance selected from the group consisting of the compound according to any one of (1) to (17) mentioned above, a salt thereof, a hydrate thereof, and a solvate thereof as an active ingredient; and

(19) The medicament according to (18) mentioned above, which is used for prophylactic and/or therapeutic treatment of an infectious disease.

Furthermore, as an intermediate for the preparation of the compound according to (1) mentioned above or a salt thereof, or a hydrate thereof or a solvate thereof, there is provided a compound represented by the following formula (VIII) or a salt thereof, a hydrate thereof or a solvate thereof.

(20) A compound represented by the following formula (VIII):

Formula (VIII):

[Formula 8]

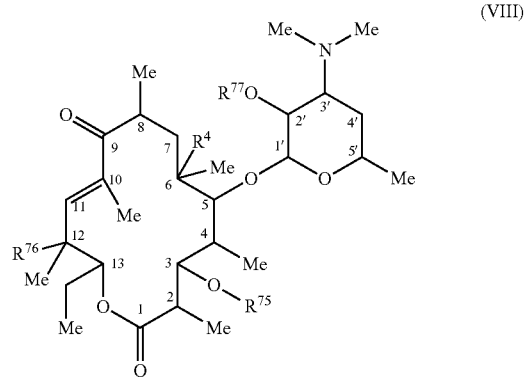

(VIII)

wherein, in the formula, $R^{75}$ represents a group represented by the formula (IX):

[Formula 9]

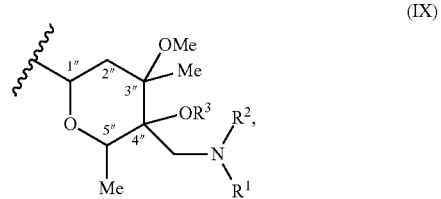

(IX)

or
a group represented by the formula (X):

[Formula 10]

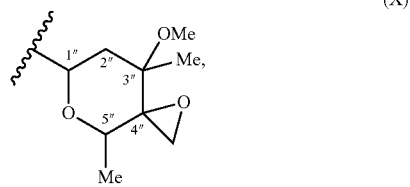

$R^{76}$ represents hydroxy group, or imidazolylcarbonyloxy group,
$R^{77}$ represents hydrogen atom, or a protective group of hydroxy group, and
Me, $R^1$, $R^2$, $R^3$, and $R^4$ have the same meanings as those defined in claim 1, or a salt thereof, or a hydrate or a solvate thereof.

According to preferred embodiments of the invention of (20) mentioned above, there are also provided (21) and (22) mentioned below:
(21) The compound according to (20) mentioned above or a salt thereof, or a hydrate or a solvate thereof, wherein $R^1$ is hydrogen atom, a $C_{1-6}$ alkyl group, or a $C_{1-6}$ alkylsulfonyl group,
$R^2$ is a 4- to 8-membered saturated heterocyclic group (the saturated heterocyclic group may be substituted with one or two substituents selected from a $C_{7-12}$ aralkyl group, and a $C_{1-6}$ alkyl group), a $C_{1-6}$ alkanoyl group (the $C_{1-6}$ alkanoyl group may be substituted with amino group, or a $C_{1-6}$ alkylamino group), or a $C_{1-6}$ alkyl group which may be substituted with 1 to 3 substituents selected from the substituent group 1, or $R^1$ and $R^2$ may combine together to form, together with the nitrogen atom to which they bind, a 4- to 8-membered saturated nitrogen-containing heterocyclic group (the saturated nitrogen-containing heterocyclic group may be substituted with 1 to 3 substituents selected from hydroxy group, amino group, a $C_{1-6}$ alkylamino group, and a $C_{1-6}$ alkyl group (the $C_{1-6}$ alkyl group may be substituted with amino group, or a $C_{1-6}$ alkylamino group)); and
(22) The compound according to (20) or (21) mentioned above or a salt thereof, or a hydrate or a solvate thereof, wherein $R^{77}$ is trimethylsilyl group, triethylsilyl group, t-butyldimethylsilyl group, acetyl group, propionyl group, benzoyl group, benzyloxycarbonyl group, or t-butyloxycarbonyl group.

As another aspect of the present invention, there is provided a macrolide antibiotic comprising a substance selected from the group consisting of a compound represented by the aforementioned formula (I), a physiologically acceptable salt thereof, a hydrate thereof, and a solvate thereof. The present invention also provides a medicament, preferably a medicament for prophylactic and/or therapeutic treatment of an infectious disease, comprising a substance selected from the group consisting of a compound represented by the aforementioned formula (I), a physiologically acceptable salt thereof, a hydrate thereof, and a solvate thereof as an active ingredient.

The present invention further provides an antimicrobial agent comprising a substance selected from the group consisting of a compound represented by the aforementioned formula (I), a physiologically acceptable salt thereof, a hydrate thereof, and a solvate thereof as an active ingredient, and a prophylactic and/or therapeutic agent for an infectious disease, which comprises a substance selected from the group consisting of a compound represented by the aforementioned formula (I), a physiologically acceptable salt thereof, a hydrate thereof, and a solvate thereof as an active ingredient.

In addition to these, the present invention also provides use of a substance selected from the group consisting of a compound represented by the aforementioned formula (I), a physiologically acceptable salt thereof, a hydrate thereof, and a solvate thereof for manufacture of the aforementioned medicament, and a method for prophylactic and/or therapeutic treatment of an infectious disease, which comprises the step of administering an effective amount of a substance selected from the group consisting of a compound represented by the aforementioned formula (I), a physiologically acceptable salt thereof, a hydrate thereof, and a solvate thereof to a mammal including human.

Effect of the Invention

The compounds of the present invention, salts thereof, hydrates thereof, and solvates thereof have an antibacterial activity against a wide variety of microorganisms, preferably aerobic or anaerobic bacteria such as Gram-positive or Gram-negative bacteria, mycoplasmas, chlamydiae, and the like, and they are characterized in, in particular, that they have superior antibacterial activity also against erythromycin resistant bacteria (for example, resistant pneumococci, streptococci and mycoplasmas), and the like, against which sufficient antibacterial activity cannot be obtained with conventional macrolide antibiotics.

BEST MODE FOR CARRYING OUT THE INVENTION

In the present invention, the symbol "$C_{x-y}$" means that the group mentioned after that has x to y of carbon atoms.
The "halogen atom" is fluorine, chlorine, bromine, or iodine.
The "alkyl group" is a linear or branched alkyl group, and examples include, for example, methyl group, ethyl group, n-propyl group, isopropyl group, n-butyl group, 2-butyl group, t-butyl group, n-pentyl group, isopentyl group, 1,1-dimethylpropyl group, n-hexyl group, and the like. In this specification, methyl group may sometimes be indicated as "Me".
The "alkenyl group" is a linear or branched alkenyl group corresponding to the aforementioned "alkyl group" having one or more double bonds at arbitrary positions, and examples include, for example, vinyl group, 1-propenyl group, 2-propenyl group, 1-butenyl group, 1,3-butadienyl group, 2-pentenyl group, 3-pentenyl group, 2-hexenyl group, and the like.
The "alkoxy group" is a linear or branched alkoxy group, and examples include, for example, methoxy group, ethoxy group, 1-propoxy group, isopropoxy group, 1-butoxy group, 1-methyl-1-propoxy group, t-butoxy group, 1-pentyloxy group, and the like.
The "alkoxyimino group" is a linear or branched alkoxyimino group, and examples include, for example, methoxyimino group, ethoxyimino group, 1-propoxyimino group, isopropoxyimino group, 1-butoxyimino group, 1-methyl-1-propoxyimino group, t-butoxyimino group, 1-pentyloxyimino group, and the like.
The "haloalkyl group" is an alkyl group corresponding to the aforementioned "alkyl group" of which one or two or more hydrogen atoms are substituted with one or two or more halogen atoms, and examples of include, for example, fluoromethyl group, difluoromethyl group, trifluoromethyl group, 2,2,2-trifluoroethyl group, 2,2,2-trichloroethyl group, pentafluoroethyl group, 3,3,3-trifluoropropyl group, perfluoropropyl group, 4-fluorobutyl group, 4-chlorobutyl group, 4-bromobutyl group, perfluorohexyl group, and the like.

The "alkylamino group" is a group formed by bonding one or two of the aforementioned "alkyl groups" and amino group, and examples include, for example, methylamino group, dimethylamino group, diethylamino group, N-ethyl-N-methylamino group, and the like.

The "alkylsulfanyl group" is a linear or branched alkylsulfanyl group, and examples include, for example, methylsulfanyl group, ethylsulfanyl group, 1-propylsulfanyl group, isopropylsulfanyl group, 1-butylsulfanyl group, 1-methyl-1-propylsulfanyl group, t-butylsulfanyl group, 1-pentylsulfanyl group, and the like.

The "alkylsulfinyl group" is a linear or branched alkylsulfinyl group, and examples include, for example, methylsulfinyl group, ethylsulfinyl group, 1-propylsulfinyl group, isopropylsulfinyl group, 1-butylsulfinyl group, 1-methyl-1-propylsulfinyl group, t-butylsulfinyl group, 1-pentylsulfinyl group, and the like.

The "alkylsulfonyl group" is a linear or branched alkylsulfonyl group, and examples include, for example, methylsulfonyl group, ethylsulfonyl group, 1-propylsulfonyl group, isopropylsulfonyl group, 1-butylsulfonyl group, 1-methyl-1-propylsulfonyl group, t-butylsulfonyl group, 1-pentylsulfonyl group, and the like.

Examples of the "cycloalkyl group" include, for example, cyclopropyl group, cyclobutyl group, cyclopentyl group, cyclohexyl group, and the like.

The "aralkyl group" is an alkyl group corresponding to the aforementioned "alkyl group" of which one hydrogen atom is substituted with phenyl group or naphthyl group, and examples include, for example, benzyl group, phenethyl group, naphthalen-1-ylmethyl group, naphthalen-2-ylmethyl group, and the like.

The "heteroaryl group" contains 1 to 4 atoms arbitrarily selected from nitrogen atom, oxygen atom, and sulfur atom as ring-constituting atoms, and examples include, for example, pyridyl group, pyridazinyl group, pyrimidinyl group, pyrazinyl group, quinolyl group (e.g., 2-quinolyl, 3-quinolyl group, 4-quinolyl group, 5-quinolyl group), isoquinolyl group, thienyl group (e.g., 2-thienyl group, 3-thienyl group), pyrrolyl group (e.g., 1-pyrrolyl group, 2-pyrrolyl group, 3-pyrrolyl group), thiazolyl group (e.g., 2-thiazolyl group, 4-thiazolyl group, 5-thiazolyl group), isothiazolyl group (e.g., 3-isothiazolyl group, 4-isothiazolyl group, 5-isothiazolyl group), pyrazolyl group (e.g., 1-pyrazolyl group, 3-pyrazolyl group, 4-pyrazolyl group), imidazolyl group (e.g., 1-imidazolyl group, 2-imidazolyl group, 3-imidazolyl group), furyl group (e.g., 2-furyl group, 3-furyl group), oxazolyl group (e.g., 2-oxazolyl group, 4-oxazolyl group, 5-oxazolyl group), isoxazolyl group (e.g., 3-isoxazolyl group, 4-isoxazolyl group, 5-isoxazolyl group), oxadiazolyl group (e.g., 1,2,3-oxadiazolyl group, 1,3,4-oxadiazolyl group), thiadiazolyl group (e.g., 1,2,3-thiadiazolyl group, 1,3,4-thiadiazolyl group), triazolyl group (e.g., 1,2,4-triazolyl group), tetrazolyl group, benzofuranyl group (e.g., 2-benzofuranyl group, 3-benzofuranyl group, 4-benzofuranyl group, 5-benzofuranyl group), benzothienyl group (e.g., 2-benzothienyl group, 3-benzothienyl group, 4-benzothienyl group, 5-benzothienyl group), indolyl group (e.g., 2-indolyl group, 3-indolyl group, 4-indolyl group, 5-indolyl group), benzoxazolyl group (e.g., 2-benzoxazolyl group, 4-benzoxazolyl group, 5-benzoxazolyl group, 6-benzoxazolyl group), benzisoxazolyl group (e.g., 3-benzo[c]isoxazolyl group, 4-benzo[c]isoxazolyl group, 5-benzo[c]isoxazolyl group, 6-benzo[c]isoxazolyl group, 3-benzo[d]isoxazolyl group, 4-benzo[d]isoxazolyl group, 5-benzo[d]isoxazolyl group, 6-benzo[d]isoxazolyl group), indazolyl group (e.g., 3-indazolyl group, 4-indazolyl group, 5-indazolyl group, 6-indazolyl group), benzimidazolyl group (e.g., 2-benzimidazolyl group, 4-benzimidazolyl group, 5-benzimidazolyl group, 6-benzimidazolyl group), benzooxadiazolyl group (e.g. 4-benzo[1,2,5]oxadiazolyl group, 5-benzo[1,2,5]oxadiazolyl group, 4-benzo[1,2,3]oxadiazolyl group, 5-benzo[1,2,3]oxadiazolyl group), benzothiadiazolyl group (e.g., 4-benzo[1,2,5]thiadiazolyl group, 5-benzo[1,2,5]thiadiazolyl group, 4-benzo[1,2,3]thiadiazolyl group, 5-benzo[1,2,3]thiadiazolyl group), indolidinyl group (e.g., 1-indolidinyl group, 2-indolidinyl group, 3-indolidinyl group, 5-indolidinyl group), thienopyridyl group (e.g., 2-thieno[2,3-b]pyridyl group, 3-thieno[2,3-b]pyridyl group, 5-thieno[2,3-b]pyridyl group, 6-thieno[2,3-b]pyridyl group, 2-thieno[3,2-b]pyridyl group, 3-thieno[3,2-b]pyridyl group, 5-thieno[3,2-b]pyridyl group, 6-thieno[3,2-b]pyridyl group), pyrazolopyridyl group (e.g., 2-pyrazolopyridyl group, 3-pyrazolopyridyl group, 5-pyrazolopyridyl group, 6-pyrazolopyridyl group), imidazopyridyl group (e.g., 1-imidazo[1,5-a]pyridyl group, 3-imidazo[1,5-a]pyridyl group, 5-imidazo[1,5-a]pyridyl group, 7-imidazo[1,5-a]pyridyl group, 2-imidazo[1,2-a]pyridyl group, 3-imidazo[1,2-a]pyridyl group, 5-imidazo[1,2-a]pyridyl group, 7-imidazo[1,2-a]pyridyl group), imidazopyrazyl group (e.g., 1-imidazo[1,5-a]pyrazyl group, 3-imidazo[1,5-a]pyrazyl group, 5-imidazo[1,5-a]pyrazyl group, 8-imidazo[1,5-a]pyrazyl group, 2-imidazo[1,2-a]pyrazyl group, 3-imidazo[1,2-a]pyrazyl group, 5-imidazo[1,2-a]pyrazyl group, 8-imidazo[1,2-a]pyrazyl group), pyrazolopyrimidyl group (e.g., 2-pyrazolo[1,5-a]pyrimidyl group, 3-pyrazolo[1,5-a]pyrimidyl group, 5-pyrazolo[1,5-a]pyrimidyl group, 6-pyrazolo[1,5-a]pyrimidyl group, 2-pyrazolo[1,5-c]pyrimidyl group, 3-pyrazolo[1,5-c]pyrimidyl group, 4-pyrazolo[1,5-c]pyrimidyl group, 5-pyrazolo[1,5-c]pyrimidyl group), triazolopyrimidyl group (e.g., 3-[1,2,3]triazolo[1,5-a]pyrimidyl group, 5-[1,2,3]triazolo[1,5-a]pyrimidyl group, 6-[1,2,3]triazolo[1,5-a]pyrimidyl group, 3-[1,2,3]triazolo[1,5-c]pyrimidyl group, 4-[1,2,3]triazolo[1,5-c]pyrimidyl group, 5-[1,2,3]triazolo[1,5-c]pyrimidyl group, 2-[1,2,4]triazolo[1,5-a]pyrimidyl group, 5-[1,2,4]-triazolo[1,5-a]pyrimidyl group, 6-[1,2,4]triazolo[1,5-a]pyrimidyl group, 7-[1,2,4]triazolo[1,5-a]pyrimidyl group, 2-[1,2,4]triazolo[1,5-c]pyrimidyl group, 5-[1,2,4]triazolo[1,5-c]pyrimidyl group, 7-[1,2,4]triazolo[1,5-c]pyrimidyl group, 8-[1,2,4]triazolo[1,5-c]pyrimidyl group), thienothienyl group (e.g., 2-thieno[2,3-b]thienyl group, 3-thieno[2,3-b]thienyl group, 2-thieno[3,2-b]thienyl group, 3-thieno[3,2-b]thienyl group), imidazothiazolyl group (e.g., 2-imidazo[2,1-b]thiazolyl group, 3-imidazo[2,1-b]thiazolyl group, 5-imidazo[2,1-b]thiazolyl group, 2-imidazo[5,1-b]thiazolyl group, 3-imidazo[5,1-b]thiazolyl group, 5-imidazo[5,1-b]thiazolyl group), and the like.

The "4- to 8-membered saturated heterocyclic group" is a 4- to 8-membered saturated heterocyclic group containing 1 to 3 atoms arbitrarily selected from nitrogen atom, oxygen atom, and sulfur atom (which may be oxidized) as ring-constituting atoms, and may have a cross linkage structure, and examples include azetidinyl group, oxetanyl group, pyrrolidinyl group, imidazolidinyl group, pyrazolidinyl group, oxolanyl group, thiolanyl group, tetrahydrothienyl group, dioxotetrahydrothienyl group, isothiazolidinyl group, dioxoisothiazolidinyl group, oxazolidinyl group, thiadiazolidinyl group, dioxothiadiazolidinyl group, tetrahydropyranyl group, tetrahydrothiopyranyl group, dioxotetrahydrothiopyranyl group, piperidinyl group, piperazinyl group, morpholinyl group, thiomorpholinyl group, dioxothiomorpholinyl group, 7-azabicyclo[2.2.1]heptanyl group, 3-oxa-8-azabicyclo[3.2.1]octanyl group, and the like. The "4- to 8-membered saturated heterocyclic group" may be substituted with oxo group, and examples include, for example, 2,5-dioxoimidazolidinyl group, 2-oxooxazolidinyl group, and 2-oxoimidazolidinyl group.

The "4- to 8-membered saturated nitrogen-containing heterocyclic group" is the aforementioned "4- to 8-membered saturated heterocyclic group" containing at least one nitrogen atom as a ring-constituting atom.

The "6-membered partially saturated nitrogen-containing heterocyclic group" is a 6-membered partially saturated nitrogen-containing heterocyclic group containing 1 to 3 nitrogen atoms as ring-constituting atoms, and examples include, for example, tetrahydropyridyl group, and the like.

The "heteroaralkyl group" is an alkyl group corresponding to the aforementioned "alkyl group" of which one hydrogen atom is substituted with the aforementioned "heteroaryl group". Examples of the "heteroaralkyl group" include, for example, pyridylmethyl group, and the like.

The "alkanoyl group" is a group comprising hydrogen atom or an alkyl group bonding via carbonyl group, and examples include, for example, formyl group, acetyl group, propionyl group, butyryl group, isobutyryl group, pivaloyl group, and the like.

The "alkylene group" is a linear or branched alkylene group, and examples include, for example, $-CH_2-$, $-(CH_2)_2-$, $-(CH_2)_3-$, $-CH(CH_3)-$, $-CH(CH_3)CH_2-$, $-(CH(CH_3))_2-$, $-(CH_2)_2-CH(CH_3)-$, $-(CH_2)_3-CH(CH_3)-$, $-CH(CH(CH_3)_2)-CH_2-$, $-(CH_2)_2-CH(C_2H_5)-$, $-(CH_2)_6-$, and the like.

In the aforementioned formula (I), the preferred examples of $R^1$ to $R^6$ and Z are as follows. The compounds one of which $R^1$ to $R^6$ and Z corresponds to any one of the preferred examples of $R^1$ to $R^6$ and Z explained below are preferred compounds, and the compounds having two or more of the preferred examples of $R^1$ to $R^6$ and Z are more preferred compounds. However, the scope of the present invention is not limited to the following preferred examples.

It is preferred that $R^1$ is a $C_{1-6}$ alkyl group, and it is more preferred that $R^1$ is methyl group.

It is preferred that $R^2$ is a $C_{1-6}$ alkyl group substituted with 1 to 3 substituents selected from the substituent group 1, it is more preferred that $R^2$ is a $C_{1-6}$ alkyl group substituted with 1 to 3 substituents selected from the substituent group 4, and it is still more preferred that $R^2$ is a $C_{1-6}$ alkyl group substituted with a group represented by the formula $-NR^{17}R^{18}$. In this case, it is preferred that $R^{17}$ and $R^{18}$, which may be the same or different, represent hydrogen atom, or a $C_{1-6}$ alkyl group (the $C_{1-6}$ alkyl group may be substituted with a $C_{3-6}$ cycloalkyl group).

It is preferred that $R^3$ is hydrogen atom.

It is preferred that $R^4$ is hydroxy group, or a $C_{1-6}$ alkoxy group, and it is more preferred that $R^4$ is methoxy group.

It is preferred that $R^5$ and $R^6$ combine together to represent, together with the carbon atoms to which they bind, a cyclic structure represented by the formula (III). In this case, it is preferred that $R^{27}$ is a group represented by the formula $NR^{29}$, and it is preferred that $R^{29}$ is hydrogen atom, a group represented by the formula $-NR^{30}R^{31}$, the formula $-NR^{32}CO_2R^{35}$, the formula $-NR^{32}SO_2R^{37}$, the formula $-NR^{32}CONR^{38}R^{39}$, or the formula $-NR^{32}SO_2NR^{40}R^{41}$, or a $C_{1-6}$ alkyl group substituted with 1 to 3 substituents selected from the substituent group 3, more preferably a $C_{1-6}$ alkyl group substituted with 1 to 3 substituents selected from the substituent group 5, still more preferably a $C_{1-6}$ alkyl group substituted with a $C_{1-6}$ alkylsulfonyl group.

It is preferred that Z is a group represented by the formula C(=O).

The salt of the compound represented by the aforementioned formula (I) may be an acid addition salt or a base addition salt. Examples of the acid addition salt include, for example, salts with an acid such as acetic acid, propionic acid, butyric acid, formic acid, trifluoroacetic acid, maleic acid, tartaric acid, citric acid, stearic acid, succinic acid, ethylsuccinic acid, lactobionic acid, gluconic acid, glucoheptonic acid, benzoic acid, methanesulfonic acid, ethanesulfonic acid, 2-hydroxyethanesulfonic acid, benzenesulfonic acid, paratoluenesulfonic acid, laurylsulfuric acid, malic acid, aspartic acid, glutamic acid, adipic acid, cysteine, N-acetylcysteine, hydrochloric acid, hydrobromic acid, phosphoric acid, sulfuric acid, hydroiodic acid, nicotinic acid, oxalic acid, picric acid, thiocyanic acid, undecanoic acid, acrylic acid polymer, and carboxyvinyl polymer, and examples of the base addition salt include salts with an inorganic base such as sodium salts, potassium salts and calcium salts, salts with an organic amine such as morpholine and piperidine, and salts with an amino acid, but the salt is not limited to these. Among them, physiologically acceptable salts are preferred.

The compounds of the present invention represented by the aforementioned formula (I) and salts thereof may exist as hydrates or arbitrary solvates, and these hydrates and solvates also fall within the scope of the present invention. Further, the compounds of the present invention represented by the aforementioned formula (I) have two or more asymmetric carbons, and these asymmetric carbons may be in arbitrary configurations. Stereoisomers such as optical isomers and diastereoisomers in pure forms based on these asymmetric carbons, arbitrary mixtures of stereoisomers, racemates, and the like are all encompassed within the scope of the present invention. Moreover, the compounds of the present invention represented by the aforementioned formula (I) may have one or more double bonds, and geometrical isomers thereof originating in a double bond or a ring structure may also exist. It should be understood that any geometrical isomers of pure forms or arbitrary mixtures of geometrical isomers fall within the scope of the present invention. One class of the preferred stereoisomers is shown below. However, the compounds of the present invention are not limited to the following specific type of stereoisomers. The configurations shown in the following structural formulas are absolute configurations, and represented with usual indications.

[Formula 11]

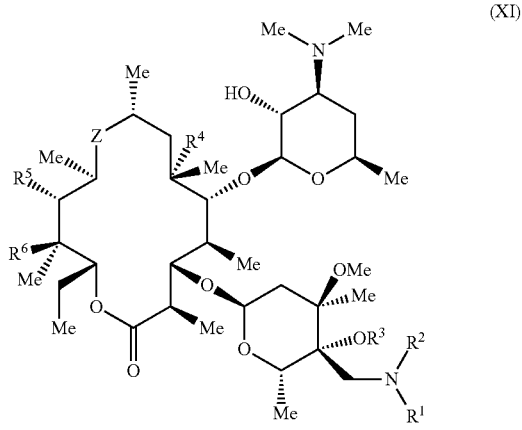

(XI)

The compounds of the present invention represented by the aforementioned formula (I), salts thereof, hydrates or solvates thereof have superior safety. The safety can be evaluated by various tests, for example, cytotoxic test, hERG test, cytochrome P-450 (CYP) activity inhibition test, and the like.

The compounds of the present invention represented by the aforementioned formula (I), salts thereof, hydrates or solvates thereof have superior metabolic stability. The metabolic stability can be evaluated by various tests, for example, human hepatic microsome metabolic stability test, and the like.

The compounds of the present invention can be synthesized by, for example, the following methods. However, the preparation methods of the compounds of the present invention are not limited to these methods.

Although all of the compounds of the present invention are novel compounds not having been described in literatures, they can be prepared by known methods described in literatures, or similar methods. Examples of such literatures include S. R. Sandler et al., Organic Functional Group Preparations, Academic Press Inc., New York and London, 1968; S. R. Wagner et al., Synthetic Organic Chemistry, John Wiley, 1961; R. C. Larock, Comprehensive Organic Transformations, 1989; L. A. Paquette et al., Encyclopedia of Reagents for Organic Synthesis, 1995; Compendium of Organic Synthetic Methods, and the like.

In the following explanations, the term base means, unless specifically indicated, for example, an organic base (e.g., an amine such as triethylamine, diisopropylethylamine, 1,8-diazabicyclo[5,4,0]-7-undecene, pyridine and 4-dimethylaminopyridine, a metal alkoxide such as sodium methoxide, and the like), or an inorganic base (e.g., an alkali metal carbonate such as sodium carbonate and potassium carbonate, an alkaline earth metal carbonate such as calcium carbonate, a metal hydroxide such as sodium hydroxide and potassium hydroxide, and the like), but the base is not limited to these.

The term solvent means, unless specifically indicated, for example, a polar solvent (e.g., water, an alcohol type solvent such as methanol, and the like), an inert solvent (e.g., a halogenated hydrocarbon type solvent such as chloroform and methylene chloride, an ether type solvent such as diethyl ether, tetrahydrofuran and dioxane, an amide type solvent such as dimethylformamide and dimethylacetamide, an aprotic solvent such as dimethyl sulfoxide and acetonitrile, an aromatic hydrocarbon type solvent such as toluene, a hydrocarbon such as cyclohexane, and the like), or a mixed solvent thereof, but the solvent is not limited to these.

The condensing agent means, unless specifically indicated, for example, a chloroformic acid ester (e.g., isobutyl chloroformate, ethyl chloroformate, methyl chloroformate and the like), an acid chloride (e.g., pivaloyl chloride, oxalyl chloride, 2,4,6-trichlorobenzoyl chloride and the like), a dehydration condensing agent (e.g., a carbodiimide reagent such as 1-ethyl-3-(3-dimethylaminopropyl)carbodiimide hydrochloride and dicyclohexylcarbodiimide, 1,1'-carbonyldiimidazole, 2-chloro-1-methylpyridinium iodide salt, and the like), and the like, but the condensing agent is not limited to these.

In the following explanations, P represents hydrogen atom or a protective group. As the protective group, a silyl type protective group such as trimethylsilyl group, triethylsilyl group and t-butyldimethylsilyl group, an acyl type protective group such as acetyl group, propionyl group and benzoyl group, an ether type protective group such as benzyl group, p-methoxybenzyl group and 2-chlorobenzyl group, an acetal type protective group such as tetrahydropyranyl group, tetrahydrofuranyl group and 1-ethoxyethyl group, a carbonate type protective group such as benzyloxycarbonyl group and t-butyloxycarbonyl group, and the like are preferred, and more preferred examples include acetyl group, propionyl group, benzoyl group, trimethylsilyl group, and triethylsilyl group. However, the protective group is not limited to the aforementioned protective groups, and includes the protective groups described in Protective Groups in Organic Synthesis (Third Edition, 1999, Ed. by P. G. M. Wuts, T. Green), and the like.

P mentioned in the formulas of the compounds can be mutually converted between hydrogen atom and a protective group as desired by such methods as described below. However, the methods for the conversion are not limited to these methods.

When P is an acyl type protective group, the group can be converted into hydrogen atom as follows. More specifically, the protective group can be converted into hydrogen atom by reaction in an alcohol type solvent (for example, methanol is preferred) in the presence or absence of a base (examples include, for example, 1,8-diazabicyclo[5,4,0]-7-undecene, and the like). The reaction temperature is chosen from the range of, for example, from 0° C. to the boiling temperature of the solvent, and a temperature in the range of from room temperature to the boiling temperature of the solvent is preferred.

When P is hydrogen atom, the hydrogen can be converted into an acyl type protective group as follows. More specifically, the hydrogen can be converted into an acyl type protective by reaction with a carboxylic anhydride or a carboxylic acid halide in a solvent (examples include, for example, acetone, chloroform, dichloromethane, and the like) in the presence or absence of a base (examples include, for example, triethylamine, diisopropylamine, pyridine, and the like) and in the presence or absence of 4-dimethylaminopyridine. The reaction temperature is chosen from the range of, for example, from −20° C. to the boiling temperature of the solvent, and a temperature in the range of from 0° C. to room temperature is preferred.

When P is a silyl group type protective group, the group can be converted into hydrogen atom as follows. More specifically, the protective group can be converted into hydrogen atom by reaction in a fluorinating agent (examples include, for example, hydrogen fluoride, tetrabutylammonium fluoride, and the like) and a solvent (examples include, for example, tetrahydrofuran, and the like). The reaction temperature is chosen from the range of, for example, from −20° C. to the boiling temperature of the solvent, and a temperature in the range of from 0° C. to room temperature is preferred.

When P is hydrogen atom, the hydrogen can be converted into a silyl type protective group as follows. More specifically, the hydrogen can be converted into a silyl type protective group by reaction with a silyl halide in a solvent (examples include, for example, chloroform, dimethylformamide, and the like) in the presence or absence of a base (examples include, for example, imidazole, triethylamine, and the like). The reaction temperature is chosen from the range of, for example, from −20° C. to the boiling temperature of the solvent, and a temperature in the range of from 0° C. to room temperature is preferred.

<Scheme 1>

[Formula 12]

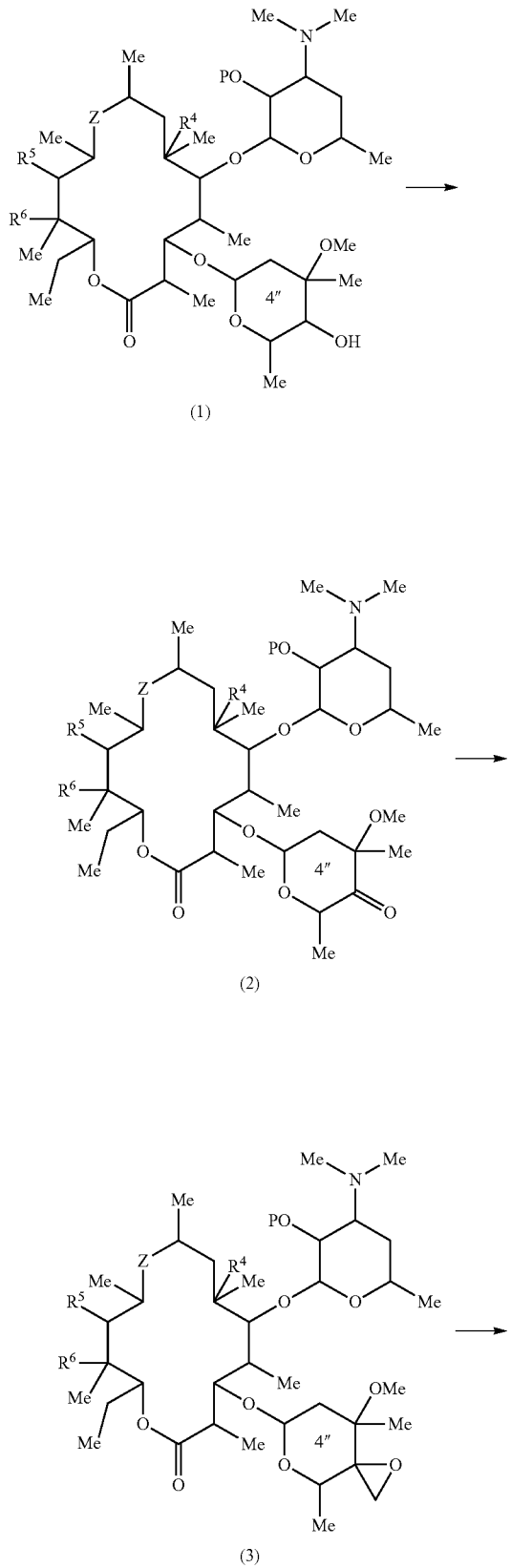

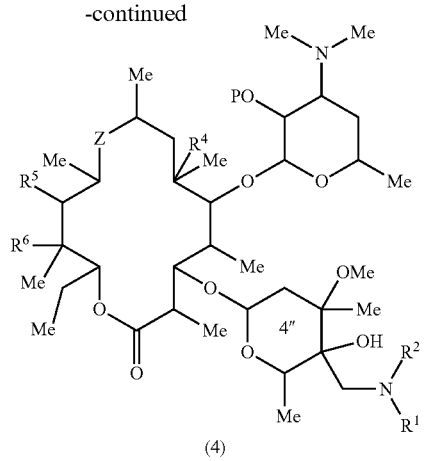

(In the formulas, the symbols of Me, $R^1$, $R^2$, $R^4$, $R^5$, $R^6$, P and Z have the same meanings as those defined above.)

The compounds represented by the formula (1) can be synthesized by, for example, a method similar to the methods described in the literatures (for example, Journal of Medicinal Chemistry, 2003, vol. 46, p. 2706; Tetrahedron, 2003, vol. 59, p. 7033; Journal of Organic Chemistry, 1988, vol. 53, p. 2340; The Journal of Antibiotics, 1984, vol. 37, p. 182; The Journal of Antibiotics, 1990, vol. 43, p. 544; The Journal of Antibiotics, 1993, vol. 46, p. 647; The Journal of Antibiotics, 2001, vol. 54, p. 664; The Journal of Antibiotics, 2003, vol. 56, p. 1062; Polish Journal of Chemistry, 1979, vol. 53, p. 2551; International Patent Publication WO97/31929, Japanese Patent Unexamined Publication No. 6/247996, International Patent Publications WO99/21867, WO02/016380, WO04/106354, European Patent Nos. 284203, 216169, 180415, 248279, and the like).

The compounds represented by the formula (2) can be obtained by using a compound represented by the formula (1) as a starting material according to a method similar to the methods described in the literatures (Tetrahedron, 1978, vol. 34, p. 1651; Journal of American Chemical Society, 1965, vol. 87, p. 5661; Journal of American Chemical Society, 1972, vol. 94, p. 7586), specifically, by oxidizing the compound by the Swan oxidation, Moffat oxidation, or Corey-Kim oxidation. Among them, the Corey-Kim oxidation is especially preferred, and the compounds represented by the formula (2) can be obtained by activating a sulfide reagent (for example, dimethyl sulfide, dodecylmethyl sulfide, and the like are preferred) with an activating agent (for example, N-chlorosuccinimide and the like are preferred) in an inert solvent (for example, chloroform and dichloromethane are preferred), and then successively adding a compound represented by the formula (1) and an organic base (for example, triethylamine and the like are preferred) to perform a reaction. The reaction temperature is chosen from the range of, for example, from −78° C. to room temperature, and a temperature of from −40° C. to 0° C. is especially preferred.

The compounds represented by the formula (3) can be obtained by using a compound represented by the formula (2) as a starting material according to a method similar to the methods described in the literatures (Journal of American Chemical Society, 1965, vol. 87, p. 1353; Journal of American Chemical Society, 1962, vol. 84, p. 867), specifically, the Corey-Tchaikovsky reaction, and the like.

The compounds represented by the formula (3) wherein the steric configuration of the 4″-position is the (R)-configuration can be obtained by a method similar to the methods described in the literatures (for example, International Patent Publication WO98/56801), specifically, by reacting a compound represented by the formula (2) with $(CH_3)_3S(O)W^1$ (examples of $W^1$ include, for example, a halogen, $—BF_4$ and $—PF_6$, and iodine is preferred) in a solvent (examples include, for example, tetrahydrofuran, diethyl ether, dimethylformamide, dimethyl sulfoxide, and the like, and two or more kinds of these solvents may be used as a mixture) in the presence of an organic base or an inorganic base (for example, sodium hydride is preferred). The reaction temperature of the aforementioned reaction is chosen from the range of, for example, from 0° C. to 60° C., and a temperature in the range of from 0° C. to room temperature is preferred.

The compounds represented by the formula (3) wherein the steric configuration of the 4"-position is the (S)-configuration can be obtained by a method similar to the methods described in the literatures (for example, International Patent Publication WO98/56801), specifically, by reacting a compound represented by the formula (2) with $(CH_3)_3SW^2$ (examples of $W^2$ include, for example, a halogen, $—BF_4$ and $—PF_6$, and $—BF_4$ is preferred) in a solvent (examples include, for example, tetrahydrofuran, diethyl ether, dimethylformamide, dimethyl sulfoxide, and the like, and two or more kinds of these solvents may be used as a mixture) in the presence of an organic base or an inorganic base. The reaction temperature of the aforementioned reaction is chosen from the range of, for example, –50 to 60° C., and a temperature in the range of from –30° C. to room temperature is preferred.

The compounds represented by the formula (4) can be obtained by reacting a compound represented by the formula (3) and a corresponding amine in the presence or absence of a salt containing a halogen ion (for example, potassium iodide, ammonium chloride, pyridine hydrochloride, and the like) or a Lewis acid (for example, ytterbium triflate), in the presence or absence of a base (for example, diisopropylethylamine, and the like are preferred), and in the presence or absence of a solvent (for example, ethanol, butanol, dimethylformamide, and the like are preferred). The reaction temperature is preferably in the range of, for example, room temperature to 120° C. Although this reaction can be performed under ordinary pressure, it can also be performed in a sealed tube. This reaction can also be performed by using a microwave device, and the reaction temperature in such a case is preferably in the range of, for example, from the boiling temperature of the solvent to 200° C. The amine used in the aforementioned reaction may be an acid addition salt, and as the acid addition salt, for example, a salt with hydrochloric acid or the like is preferred.

The compounds represented by the formula (1), (2), (3), or (4) shown in Scheme 1 wherein $R^4$ is a group represented by the formula $—OCONR^{21}R^{22}$ ($R^{21}$ and $R^{22}$, which may be the same or different, represent hydrogen atom, a $C_{1-6}$ alkyl group, or an alkenyl group substituted with one heteroaryl group) can be obtained by reacting a compound represented by the formula (1), (2), (3), or (4) wherein $R^4$ is hydroxy group and a corresponding isocyanate in a solvent in the presence of a base. The aforementioned compounds wherein $R^4$ is a group represented by the formula $—OCONH_2$ can be obtained by reacting a compound represented by the formula (1), (2), (3), or (4) wherein $R^4$ is hydroxy group and trichloroacetyl isocyanate in a solvent (for example, chloroform and dichloromethane are preferred), and then reacting the resultant with an alcohol (for example, methanol is preferred) in a solvent (for example, a mixed solvent of methanol and water is preferred) in the presence of a base (for example, triethylamine is preferred). The reaction temperature is chosen from the range of, for example, from 0° C. to the boiling temperature of the solvent, and a temperature in the range of from room temperature to the boiling temperature of the solvent is preferred.

The compounds represented by the formula (1), (2), (3), or (4) shown in Scheme 1 wherein $R^5$ and $R^6$ combine together to represent, together with the carbon atoms to which they bind, a cyclic structure represented by the formula (III), and $R^{27}$ is oxygen atom can be obtained by, for example, reacting a compound represented by the formula (1), (2), (3), or (4) wherein $R^5$ and $R^6$ are hydroxy groups according to a method similar to the method described in the literatures (for example, Journal of Medicinal Chemistry, 2003, vol. 46, p. 2706). Specifically, they can be obtained by reacting the compound in a solvent (for example, chloroform and dichloromethane are preferred) in the presence of a carbonating agent (for example, triphosgene is preferred) and a base (for example, pyridine is preferred). The reaction temperature is chosen from the range of, for example, from –20° C. to the boiling temperature of the solvent, and a temperature in the range of from 0° C. to room temperature is preferred.

Further, among the compounds represented by the formula (1) shown in Scheme 1, those compounds shown in Scheme 2 can also be obtained by the steps shown in Scheme 2, as well as the steps shown in Scheme 1.

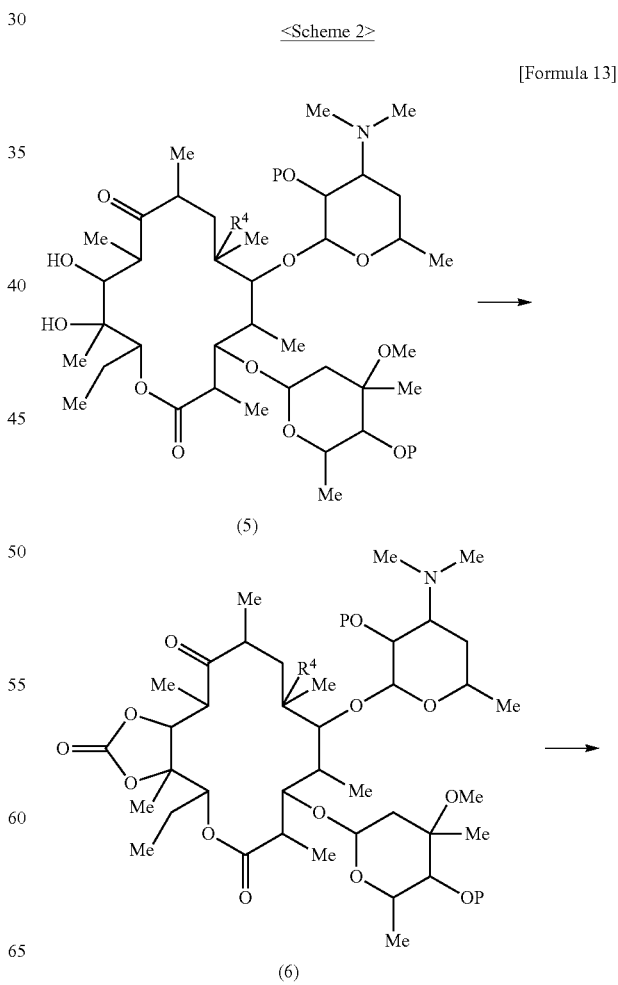

<Scheme 2>

[Formula 13]

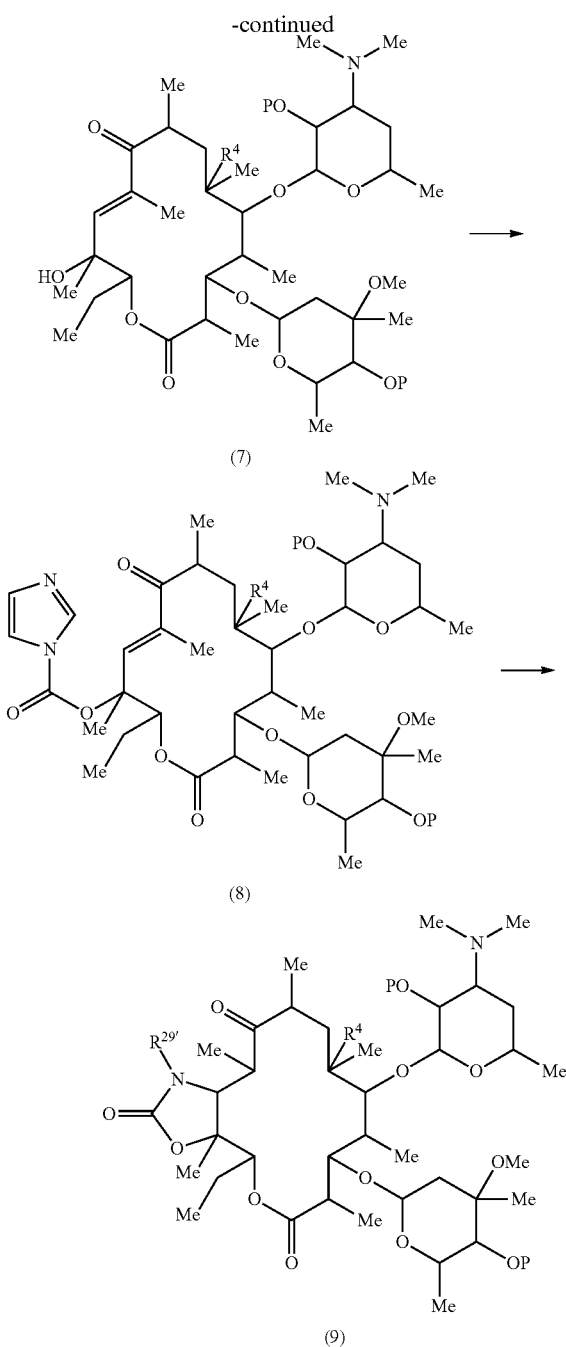

(In the formulas, $R^{29'}$ is hydroxy group, a $C_{1-6}$ alkoxy group (the $C_{1-6}$ alkoxy group may be substituted with phenyl group), a group represented by the formula —$NR^{30}R^{31}$, or a $C_{1-6}$ alkyl group which may be substituted with 1 to 3 substituents selected from the substituent group 3, and Me, $R^{30}$, $R^{31}$, $R^4$ and P have the same meanings as those defined above.)

The compounds represented by the formula (6) can be obtained by reacting a compound represented by the formula (5) with a carbonating agent (examples include, for example, triphosgene and diethyl carbonate, and among them, triphosgene is preferred) in an inert solvent (chloroform and dichloromethane are preferred) in the presence or absence of an organic base (for example, an amine such as pyridine is preferred). The reaction temperature is chosen from the range of, for example, from −20° C. to the boiling temperature of the solvent, and within that range, a temperature of from 0° C. to room temperature is preferred.

The compounds represented by the formula (7) can be obtained by reacting a compound represented by the formula (6) in a solvent (for example, dimethylformamide is preferred) in the presence or absence of a base (for example, 1,1,3,3-tetramethylguanidine is preferred). The reaction temperature is chosen from the range of, for example, from 0° C. to the boiling temperature of the solvent, and a temperature of from room temperature to 100° C. is especially preferred.

The compounds represented by the formula (8) can be obtained by using a compound represented by the formula (7) as a starting material according to a method similar to the methods described in the literatures (for example, Journal of Organic Chemistry, 1988, vol. 53, p. 2340; European Patent No. 248279, and the like), for example, by reacting the compound with 1,1'-carbonyldiimidazole in a solvent (examples include, for example, tetrahydrofuran, diethyl ether, dimethylformamide, dimethyl sulfoxide, and the like, and two or more kinds of these solvents may be used as a mixture) in the presence of a base (for example, sodium hydride is preferred). The reaction temperature is chosen from the range of for example, from −20° C. to the boiling temperature of the solvent, and a temperature of from 0° C. to room temperature is preferred.

Alternatively, the compounds represented by the formula (8) can be obtained by using a compound represented by the formula (5), and reacting the compound with, for example, 1,1'-carbonyldiimidazole in a solvent (examples include, for example, tetrahydrofuran, diethyl ether, dimethylformamide, dimethyl sulfoxide, and the like, and two or more kinds of these solvents may be used as a mixture) in the presence or absence of a base (examples include, for example, sodium hydride, 1,8-diazabicyclo[5,4,0]-7-undecene and the like). The reaction temperature is preferably in the range of, for example, from room temperature to the boiling temperature of the solvent.

The compounds represented by the formula (9) can be obtained by using a compound represented by the formula (8) as a starting material according to a method similar to the methods described in the literatures (for example, Journal of Organic Chemistry, 1988, vol. 53, p. 2340; European patent No. 248279, International Patent Publication WO97/31929, and the like), specifically, by reacting the compound with a corresponding amine, a corresponding compound represented by the formula $H_2NOR^{24}$ or the formula $H_2NNR^{30}R^{31}$, in a solvent (examples include, for example, acetonitrile, tetrahydrofuran, dimethylformamide, ethyl acetate, and the like) in the presence or absence of a base (for example, 1,8-diazabicyclo[5,4,0]-7-undecene, 1,1,3,3-tetramethylguanidine, and the like). The aforementioned amine, the corresponding compound represented by the formula $H_2NOR^{24}$ or the formula $H_2NNR^{30}R^{31}$, may be an acid addition salt, and as the acid addition salt, for example, a salt with hydrochloric acid or the like is preferred. The reaction temperature of the aforementioned reaction is chosen from the range of, for example, from −20° C. to the boiling temperature of the solvent, and a temperature in the range of from 0° C. to room temperature is preferred.

Further, among the compounds represented by the formula (3) shown in Scheme 1, those compounds shown in Scheme 3 can also be obtained by the steps shown in Scheme 3, as well as the steps shown in Scheme 1.

<Scheme 3>

[Formula 14]

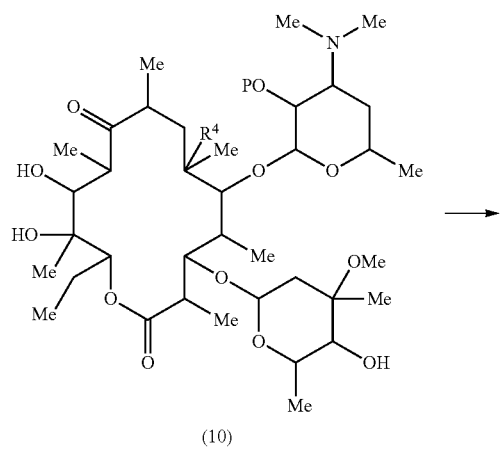

(10)

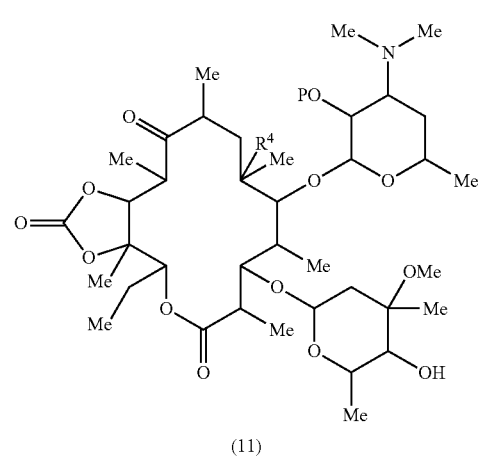

(11)

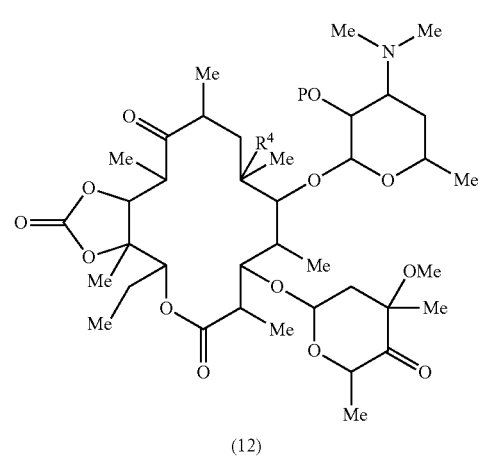

(12)

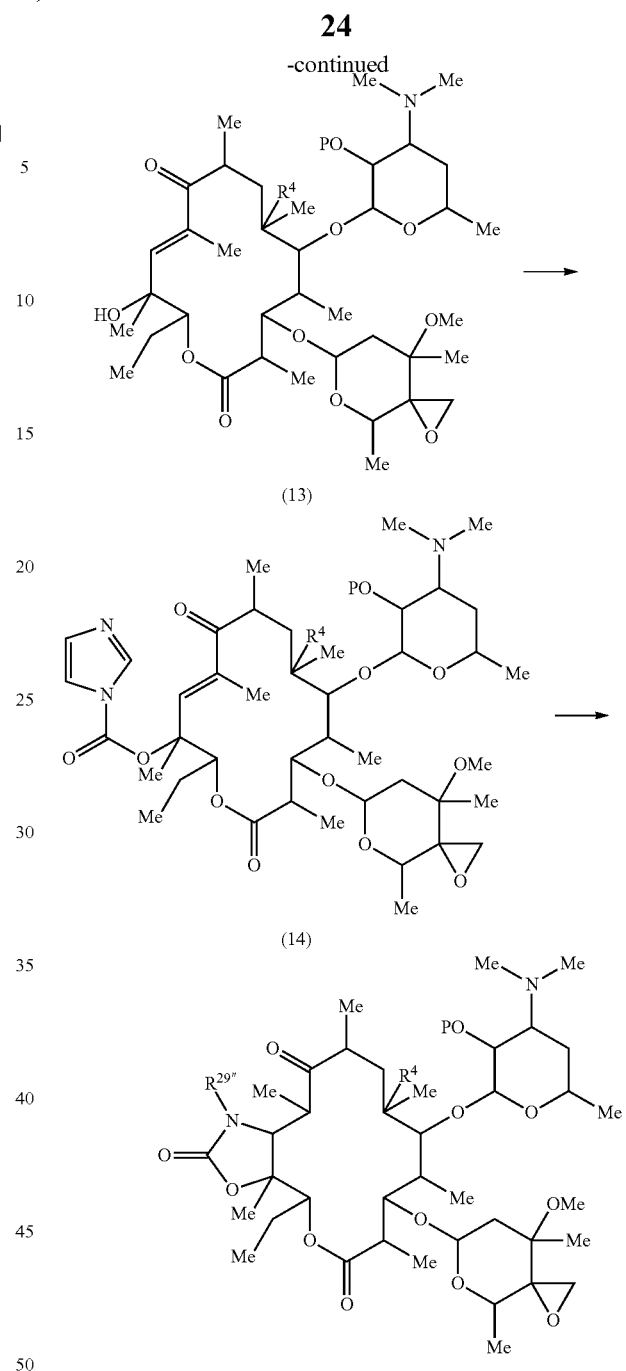

(13)

(14)

(15)

(In the formulas, $R^{29''}$ is hydroxy group, a $C_{1-6}$ alkoxy group (the $C_{1-6}$ alkoxy group may be substituted with phenyl group), a group represented by the formula —$NR^{30}R^{31}$, or a $C_{1-6}$ alkyl group which may be substituted with 1 to 3 substituents selected from the substituent group 3, and Me, $R^4$, $R^{30}$, $R^{31}$ and P have the same meanings as those defined above.)

The compounds represented by the formula (11) can be obtained by reacting a compound represented by the formula (10) with a carbonating agent (examples include, for example, triphosgene and diethyl carbonate, and among them, triphosgene is preferred) in an inert solvent (chloroform and dichloromethane are preferred) in the presence or absence of an organic base (for example, an amine such as pyridine is preferred). The reaction temperature is chosen from the range of, for example, from −20° C. to the boiling temperature of the solvent, and within that range, a temperature of from 0° C. to room temperature is preferred.

The compounds represented by the formula (12) can be obtained by using a compound represented by the formula (11) as a starting material according to a method similar to the methods described in the literatures (Tetrahedron, 1978, vol. 34, p. 1651; Journal of American Chemical Society, 1965, vol. 87, p. 5661; Journal of American Chemical Society, 1972, vol. 94, p. 7586), specifically, by oxidizing the compound by the Swan oxidation, Moffat oxidation, Corey-Kim oxidation, or the like. Among them, the Corey-Kim oxidation is especially preferred, and the compounds represented by the formula (12) can be obtained by activating a sulfide reagent (for example, dimethyl sulfide, dodecylmethyl sulfide, and the like are preferred) with an activating agent (for example, N-chlorosuccinimide and the like are preferred) in an inert solvent (for example, chloroform and dichloromethane are preferred) and then successively adding a compound represented by the formula (11) and an organic base (for example, triethylamine and the like are preferred) to perform a reaction. The reaction temperature is chosen from the range of, for example, from −78° C. to room temperature, and a temperature of from −40° C. to 0° C. is especially preferred.

The compounds represented by the formula (13) can be obtained by reacting a compound represented by the formula (12) with $(CH_3)_3S(O)W^3$ (examples of $W^3$ include, for example, a halogen, $-BF_4$ and $-PF_6$, and iodine is preferred) in a solvent (examples include, for example, tetrahydrofuran, diethyl ether, dimethylformamide, dimethyl sulfoxide, and the like, and two or more kinds of these solvents may be used as a mixture) in the presence of an organic base or an inorganic base (for example, sodium hydride is preferred). The reaction temperature of the aforementioned reaction is chosen from the range of, for example, −50 to 60° C., and a temperature in the range of from −30° C. to room temperature is preferred.

The compounds represented by the formula (14) can be obtained by using a compound represented by the formula (13) as a starting material according to a method similar to the methods described in the literatures (for example, Journal of Organic Chemistry, 1988, vol. 53, p. 2340; European Patent No. 248279, and the like), for example, by reacting the compound with 1,1'-carbonyldiimidazole in a solvent (examples include, for example, tetrahydrofuran, diethyl ether, dimethylformamide, dimethyl sulfoxide, and the like, and two or more kinds of these solvents may be used as a mixture) in the presence of a base (for example, sodium hydride is preferred). The reaction temperature is chosen from the range of, for example, from −20° C. to the boiling temperature of the solvent, and a temperature of from 0° C. to room temperature is preferred.

The compounds represented by the formula (15) can be obtained by using a compound represented by the formula (14) as a starting material according to a method similar to the methods described in the literatures (for example, Journal of Organic Chemistry, 1988, vol. 53, p. 2340; European patent No. 248279; International Patent Publication WO97/31929, and the like), specifically, by reacting the compound with a corresponding amine, a compound represented by the formula $H_2NOY'$ or the formula $H_2NNR^{30}R^{31}$, in a solvent (examples include, for example, acetonitrile, tetrahydrofuran, dimethylformamide, ethyl acetate, and the like) in the presence or absence of a base (examples include, for example, 1,8-diazabicyclo[5,4,0]-7-undecene, 1,1,3,3-tetrameth- ylguanidine, and the like). The aforementioned amine, the compound represented by the formula $H_2NOY'$ or the formula $H_2NNR^{30}R^{31}$, may be an acid addition salt, and as the acid addition salt, for example, a salt with hydrochloric acid or the like is preferred. The reaction temperature of the aforementioned reaction is chosen from the range of, for example, from −20° C. to the boiling temperature of the solvent, and a temperature in the range of from 0° C. to 50° C. is preferred. Y' is hydrogen atom or a $C_{1-6}$ alkyl group (the $C_{1-6}$ alkyl group may be substituted with phenyl group).

Further, among the compounds represented by the formulas (1) to (4) shown in Scheme 1, those compounds shown in Scheme 4 can also be obtained by the steps shown in Scheme 4, as well as the steps shown in Scheme 1.

<Scheme 4>

[Formula 15]

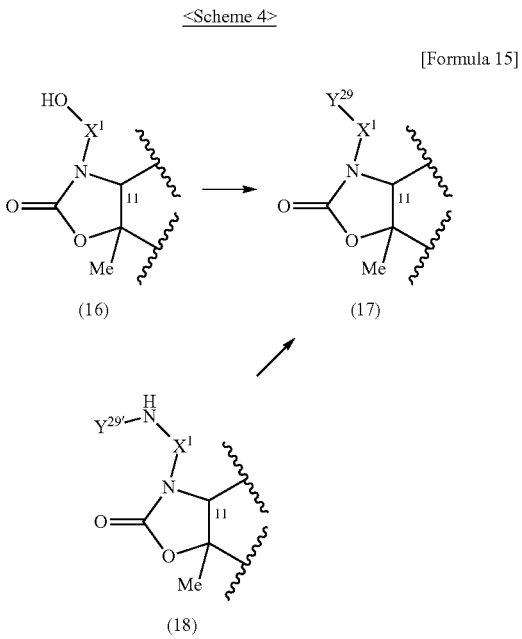

(The formulas (16) to (18) show conversion of the cyclic carbamate structure moiety of the 11- and 12-positions of the compounds of the formulas (1), (2), (3) and (4) shown in Scheme 1 wherein $R^5$ and $R^6$ constitute, together with the carbon atoms to which they bind, a group represented by the formula (III), wherein, in the formulas, $X^1$ represents a $C_{1-6}$ alkylene group, or a single bond,
when $X^1$ is $C_{1-6}$ alkylene group,
$Y^{29}$ is a $C_{1-6}$ alkoxy group, phenoxy group, benzyloxy group, a group represented by the formula $-OSO_2NR^{46}R^{47}$, the formula $-OCONR^{55}R^{56}$, the formula $-OCOR^{64}$, the formula $-NR^{44}CO_2R^{45}$, the formula $-NR^{49}SO_2NR^{50}R^{51}$, the formula $-NR^{57}COR^{58}$, the formula $-NR^{61}CONR^{62}R^{63}$, the formula $-NR^{67}SO_2R^{68}$, or the formula $-NR^{60}R^{70}$,
$Y^{29'}$ is a group represented by $R^{44}$, $R^{49}$, $R^{57}$, $R^{61}$, $R^{67}$ or $R^{69}$, and when $X^1$ is a single bond,
$Y^{29}$ is a group represented by the formula $-NR^{30}R^{31}$, the formula $-NR^{32}CSNR^{33}R^{34}$, the formula $-NR^{32}CO_2R^{35}$, the formula $-NR^{32}COR^{36}$, the formula $-NR^{32}SO_2R^{37}$, the formula $-NR^{32}CONR^{38}R^{39}$, the formula $-NR^{32}SO_2NR^{40}R^{41}$, or the formula $-N=C-NR^{42}R^{43}$,
$Y^{29'}$ is a group represented by $R^{30}$ or $R^{32}$, and
$R^{30}, R^{31}, R^{32}, R^{33}, R^{34}, R^{35}, R^{36}, R^{37}, R^{38}, R^{39}, R^{40}, R^{41}, R^{42}, R^{43}, R^{44}, R^{45}, R^{46}, R^{47}, R^{48}, R^{49}, R^{50}, R^{51}, R^{55}, R^{56}, R^{57}, R^{58},$ $R^{61}$, $R^{62}$, $R^{63}$, $R^{64}$, $R^{67}$, $R^{68}$, $R^{69}$, and $R^{70}$ have the same meanings as those defined above.)

The compounds represented by the formula (17) wherein $Y^{29}$ is a group represented by the formula —OCOR$^{64}$ can be obtained by using a compound represented by the formula (16) as a starting material, and reacting the compound with a corresponding carboxylic acid halide or carboxylic anhydride in a solvent (chloroform and dichloromethane are preferred) in the presence or absence of 4-dimethylaminopyridine, and in the presence or absence of a base (for example, triethylamine is preferred), or by reacting the compound with a corresponding carboxylic acid in the presence of a dehydration condensing agent. The reaction temperature is chosen from the range of, for example, from −20° C. to 60° C., and a temperature in the range of from 0° C. to room temperature is preferred.

The compounds represented by the formula (17) wherein $Y^{29}$ is a group represented by the formula —OCONR$^{55}$R$^{56}$ can be obtained by using a compound represented by the formula (16) as a starting material, and reacting the compound with a corresponding isocyanate in a solvent (for example, toluene is preferred) in the presence of a base (1,4-diazabicyclo[2,2,2]octane is preferred). Further, the compounds wherein $Y^{29}$ is a group represented by the formula —OCONH$_2$ can be obtained by using a compound represented by the formula (16) as a starting material, reacting the compound in a solvent (for example, chloroform and dichloromethane are preferred) in the presence of trichloroacetyl isocyanate, and reacting the resulting trichloroacetylamide compound in a solvent (examples include, methanol, water, and the like, and two or more kinds of these solvents may be used as a mixture) in the presence of a base (for example, potassium carbonate or triethylamine is preferred). The reaction temperature is preferably in the range of from 0° C. to the boiling point of the solvent.

The compounds represented by the formula (17) wherein $Y^{29}$ is a group represented by the formula —OSO$_2$NR$^{46}$R$^{47}$ can be obtained by using a compound represented by the formula (16) as a starting material, and reacting the compound with a corresponding sulfamoyl chloride in a solvent in the presence of a base. Further, the compounds wherein $Y^{29}$ is a group represented to be by formula —OSO$_2$NH$_2$ can be obtained by using a compound represented by the formula (16) as a starting material, and reacting the compound with chlorosulfonyl isocyanate in a solvent (for example, acetonitrile or N,N-dimethylacetamide is preferred) in the presence of formic acid. The reaction temperature is preferably in the range of from 0° C. to the boiling temperature of the solvent.

The compounds represented by the formula (17) wherein $Y^{29}$ is a group represented by the formula —NR$^{57}$COR$^{58}$ or the formula —NR$^{32}$COR$^{26}$ can be obtained by using a compound represented by the formula (18) as a starting material, and subjecting the compound to an amidation reaction in the presence of a corresponding carboxylic acid and a dehydration condensing agent, or using a corresponding carboxylic anhydride or a corresponding carboxylic acid halide. Examples of the dehydration condensing agent include 1-ethyl-3-(3-dimethylaminopropyl)carbodiimide hydrochloride, dicyclohexylcarbodiimide, diphenylphosphoryl azide, 1,1'-carbonyldiimidazole, and the like, and an activating agent such as 1-hydroxybenzotriazole and hydroxysuccinimide can be used, if needed. Examples of the reaction solvent for such a case include dichloromethane, chloroform, 1,2-dichloroethane, dimethylformamide, tetrahydrofuran, dioxane, toluene, ethyl acetate, a mixed solvent thereof, and the like. This reaction can be performed by using a base, and examples of the base include an organic amine such as triethylamine and diisopropylethylamine, an organic acid salt such as sodium 2-ethylhexanoate and potassium 2-ethylhexanoate, an inorganic base such as potassium carbonate, and the like. Further, the reaction can be performed in the presence or absence of 4-dimethylaminopyridine. The reaction temperature is preferably in the range of, for example, from −50° C. to the boiling temperature of the reaction solvent. Further, the carboxylic anhydride can also be obtained by reacting a corresponding carboxylic acid and an activating agent (for example, isobutyl chloroformate is preferred), and the compounds can be obtained by reacting a compound represented by the formula (18) and a carboxylic anhydride in a base (for example, triethylamine is preferred) and a solvent (for example, tetrahydrofuran is preferred). The reaction temperature is chosen from the range of from −78° C. to the boiling temperature of the solvent, and a temperature in the range of from −78° C. to room temperature is preferred. Further, when a carboxylic acid halide is used, the reaction can be performed in a base (for example, triethylamine is preferred) using a solvent (for example, chloroform is preferred) in the presence of a carboxylic acid halide. The reaction temperature is chosen from the range of from −30° C. to the boiling temperature of the solvent, and a temperature in the range of from 0° C. to room temperature is preferred.

The compounds represented by the formula (17) wherein $Y^{29}$ is a group represented by the formula —NR$^{69}$R$^{70}$ or the formula —NR$^{30}$R$^{31}$ can be obtained by reacting a compound represented by the formula (18) and a corresponding aldehyde in a solvent (for example, chloroform, methanol or the like is preferred) in the presence of a hydride reducing agent (for example, sodium triacetoxyborohydride, sodium cyanoborohydride and the like). The reaction temperature of the aforementioned reaction is preferably in the range of, for example, from 0° C. to 50° C.

The compounds represented by the formula (17) wherein $Y^{29}$ is a group represented by the formula —NR$^{61}$CONR$^{62}$R$^{63}$ or the formula —NR$^{32}$CONR$^{38}$R$^{39}$ can be obtained by using a compound represented by the formula (18) as a starting material, and reacting the compound with a corresponding isocyanate, or with a corresponding amine in the presence of triphosgene. When an isocyanate is used, the compounds can be obtained by reacting the compounds in a solvent (toluene is preferred) in the presence of a base (1,4-diazabicyclo[2,2,2]octane is preferred). The reaction temperature is preferably in the range of, for example, from 0° C. to room temperature is preferred. When triphosgene is used, the compounds can be obtained by reacting a compound represented by the formula (18) and triphosgene in a solvent (chloroform is preferred) in the presence of a base (pyridine is preferred), and then adding a corresponding amine. The reaction temperature is preferably in the range of, for example, from 0° C. to room temperature.

Further, the compounds can also be obtained by using a compound represented by the formula (18) as a starting material, activating the compound in a solvent (pyridine is preferred) in the presence of bis(4-nitrophenyl)carbonate, and then adding a corresponding amine to perform a reaction. The reaction temperature is chosen from the range of from 0° C. to the boiling temperature of the solvent, and a temperature of from room temperature to 80° C. is preferred. The amine used in the aforementioned reaction may be an acid addition salt, and as the acid addition salt, for example, a salt with hydrochloric acid is preferred.

The compounds represented by the formula (17) wherein $Y^{29}$ is a group represented by the formula. —$NR^{67}SO_2R^{68}$ or the formula —$NR^{32}SO_2R^{37}$ can be obtained by using a compound represented by the formula (18) as a starting material, and reacting the compound in a solvent (chloroform and dichloromethane are preferred) in the presence of a corresponding sulfonyl halide and in the presence or absence of a base (for example, triethylamine is preferred). The reaction temperature is chosen from the range of, for example, from 0° C. to 60° C., and a temperature in the range of from 0° C. to room temperature is preferred.

The compounds represented by the formula (17) wherein $Y^{29}$ is a group represented by the formula —$NR^{32}CSNR^{33}R^{34}$ can be obtained by using a compound represented by the formula (18) as a starting material, and reacting the compound in a solvent (toluene is preferred) in the presence of a corresponding thioisocyanate, and in the presence or absence of a base (for example, pyridine, 1,4-diazabicyclo[2.2.2]octane, and the like are preferred, and these may be used together). The reaction temperature is chosen from the range of, for example, from 0° C. to the boiling temperature of the solvent, and a temperature in the range of from room temperature to 80° C. is preferred.

The compounds represented by the formula (17) wherein $Y^{29}$ is a group represented by the formula —$N\!=\!C\!-\!NR^{42}R^{43}$ can be obtained by using a compound represented by the formula (18) as a starting material, reacting the compound in a solvent (toluene is preferred) in the presence of a corresponding formamide and dimethylsulfamoyl chloride and in the presence or absence of a base (for example, 4-dimethylaminopyridine is preferred), and then reacting the resultant in a base (1,4-diazabicyclo[2.2.2]octane is preferred) and a solvent (methanol is preferred). The reaction temperature is chosen from the range of, for example, from 0° C. to the boiling temperature of the solvent, and a temperature in the range of from room temperature to 80° C. is preferred.

The compounds represented by the formula (17) wherein $Y^{29}$ is a group represented by the formula —$NR^{32}SO_2NR^{40}R^{41}$ or the formula —$NR^{49}SO_2NR^{50}R^{51}$ can be obtained by using a compound represented by the formula (18) as a starting material, and reacting the compound in a solvent (chloroform is preferred) in the presence of a corresponding sulfamoyl halide, in the presence or absence of a base (triethylamine is preferred), and in the presence or absence of 4-dimethylaminopyridine. The reaction temperature is chosen from the range of, for example, from 0° C. to the boiling temperature of the solvent, and a temperature in the range of 0° C. to room temperature is preferred.

The compounds represented by the formula (17) wherein $Y^{29}$ is a group represented by the formula —$NR^{32}CO_2R^{35}$ or the formula —$NR^{44}CO_2R^{45}$ can be obtained by using a compound represented by the formula (18) as a starting material, and reacting the compound in a solvent (tetrahydrofuran is preferred) in the presence of a corresponding haloformic acid ester and in the presence or absence of a base (for example, pyridine is preferred). The reaction temperature is chosen from the range of, for example, from 0° C. to 60° C., and a temperature in the range of from 0° C. to room temperature is preferred.

Further, among the compounds represented by the formulas (1) to (4) shown in Scheme 1, those compounds shown in Scheme 5 can also be obtained by the steps shown in Scheme 5, as well as the steps shown in Scheme 1.

<Scheme 5>

[Formula 16]

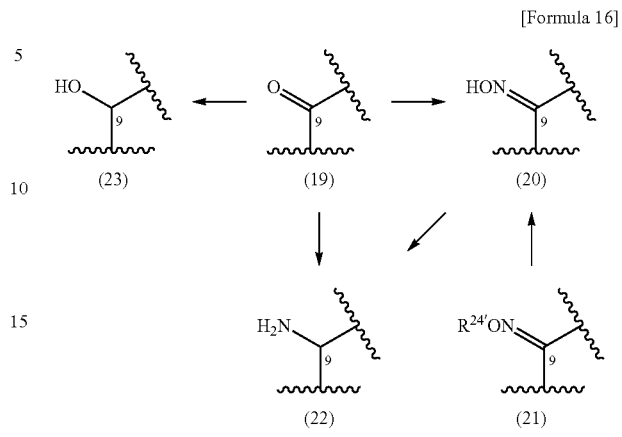

(The formulas (19) to (23) show conversion of the Z moiety of the compounds of the formulas (1), (2), (3) and (4) shown in Scheme 1, wherein, in the formula, $R^{24'}$ represents $R^{24}$ except for hydrogen atom, and $R^{24}$ has the same meaning as that defined above.)

The compounds represented by the formula (20) can be obtained by reacting a compound represented by the formula (19) and hydroxylamine in a solvent (for example, methanol is preferred) in the presence or absence of a base (for example, imidazole is preferred). The reaction temperature of the aforementioned reaction is preferably in the range of, for example, from room temperature to the boiling temperature of the solvent. Hydroxylamine used in the aforementioned reaction may be an acid addition salt, and as the acid addition salt, for example, a salt with hydrochloric acid or the like is preferred.

The compounds represented by the formula (21) can be obtained by reacting a compound represented by the formula (19) and a compound represented by the formula $H_2NOR^{24'}$ in a solvent (for example, methanol is preferred) in the presence or absence of a base (for example, imidazole is preferred). The reaction temperature of the aforementioned reaction is preferably in the range of, for example, from room temperature to the boiling temperature of the solvent. The compound represented by the formula $H_2NOR^{24'}$ used in the aforementioned reaction may be an acid addition salt, and as the acid addition salt, for example, a salt with hydrochloric acid or the like is preferred. Further, the compounds represented by the formula (21) can also be obtained by reacting a compound represented by the formula (20) and a corresponding alkyl halide or the like in a solvent (examples include, for example, tetrahydrofuran, and the like) in the presence or absence of a base (examples include, for example, potassium hydroxide, and the like). The reaction temperature of the aforementioned reaction is chosen from the range of, for example, from −20° C. to the boiling temperature of the solvent, and a temperature in the range of from 0° C. to room temperature is preferred.

The compounds represented by the formula (22) can be obtained by reacting a compound represented by the formula (19) with a reducing agent (examples include, for example, sodium triacetoxyborohydride, sodium cyanoborohydride, and sodium borohydride, and sodium cyanoborohydride is preferred) in a solvent (for example, methanol, chloroform or the like is preferred) in the presence of an ammonium salt (examples include, for example, ammonium acetate, ammonium carbonate, ammonium chloride, and the like, and ammonium acetate is preferred). The reaction temperature of the aforementioned reaction is preferably in the range of, for example, from room temperature to the boiling temperature of the solvent. Alternatively, the compounds can also be obtained by using a compound represented by the formula (19) as a starting material according to a method similar to the methods described in the literatures (Tetrahedron Letters, 1971, vol. 2, p. 195; Tetrahedron Letters, 1972, vol. 1, p. 29), specifically, by reacting the carbonyl group with hydrazine in a polar solvent to convert it into hydrazono group, and reacting the hydrazono group with sodium nitrite or the like, or by using a compound represented by the formula (20) as a starting material, reacting the compound with titanium chloride or the like, and reducing the resulting imino compound with a hydride reducing agent or the like.

The compounds represented by the formula (23) can be obtained by reacting a compound represented by the formula (19) and a reducing agent (sodium borohydride is preferred) in a solvent (examples include, for example, tetrahydrofuran, methyl t-butyl ether, methanol, and the like, and two or more kinds of these solvents may be used as a mixture). The reaction temperature is chosen from the range of, for example, from −20° C. to the boiling temperature of the solvent, and a temperature in the range of from 0° C. to room temperature is preferred.

Further, among the compounds represented by the formula (4) shown in Scheme 1, those compounds shown in Scheme 6 can also be obtained by the step shown in Scheme 6, as well as the steps shown in Scheme 1.

<Scheme 6>

[Formula 17]

(24) → (25)

(The formulas (24) and (25) show conversion of the moiety at the 4"-position of the compounds of the formula (4) shown in Scheme 1, wherein, in the formulas, $R^{1'}$ represents a $C_{1-6}$ alkylsulfonyl group, $R^{2'}$ represents $R^2$ except for a $C_{1-6}$ alkanoyl group (the $C_{1-6}$ alkanoyl group may be substituted with amino group, or a $C_{1-6}$alkylamino group), and $R^2$ has the same meaning as that defined above.)

The compounds represented by the formula (25) can be obtained by using a compound represented by the formula (24) as a starting material, and reacting the compound in a solvent (chloroform and dichloromethane are preferred) in the presence of a corresponding sulfonyl halide and in the presence or absence of a base (for example, triethylamine is preferred). The reaction temperature is chosen from the range of, for example, from 0° C. to 60° C., and a temperature in the range of from 0° C. to room temperature is preferred.

Further, among the compounds represented by the formula (4) shown in Scheme 1, those compounds shown in Scheme 7 can also be obtained by the step shown in Scheme 7, as well as the steps shown in Scheme 1.

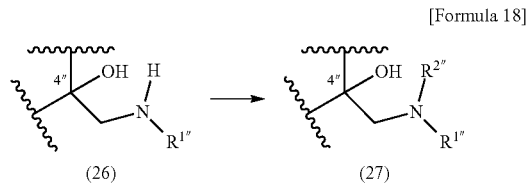

<Scheme 7>

[Formula 18]

(26) → (27)

(The formulas (26) and (27) show conversion of the moiety at the 4"-position of the compounds of the formula (4) shown in Scheme 1, wherein, in the formulas, $R^{1'''}$ represents $R^1$ except for a $C_{1-6}$ alkylsulfonyl group, $R^{2''}$ represents a $C_{1-6}$ alkanoyl group (the $C_{1-6}$ alkanoyl group may be substituted with amino group, or a $C_{1-6}$ alkylamino group), and $R^1$ has the same meaning as that defined above.)

The compounds represented by the formula (27) can be obtained by using a compound represented by the formula (26) as a starting material, and subjecting the compound to an amidation reaction in the presence of a corresponding carboxylic acid and a dehydration condensing agent, or using a corresponding carboxylic anhydride or a corresponding carboxylic acid halide. Examples of the dehydration condensing agent include 1-ethyl-3-(3-dimethylaminopropyl)carbodiimide hydrochloride, dicyclohexylcarbodiimide, diphenylphosphoryl azide, 1,1'-carbonyldiimidazole, and the like, and an activating agent such as 1-hydroxybenzotriazole and hydroxysuccinimide can be used, if needed. Examples of the reaction solvent for such a case include dichloromethane, chloroform, 1,2-dichloroethane, dimethylformamide, tetrahydrofuran, dioxane, toluene, ethyl acetate, a mixed solvent thereof, and the like. This reaction can be performed by using a base, and examples of the base include an organic amine such as triethylamine and diisopropylethylamine, an organic acid salt such as sodium 2-ethylhexanoate and potassium 2-ethylhexanoate, an inorganic base such as potassium carbonate, and the like. Further, the reaction can be performed in the presence or absence of 4-dimethylaminopyridine. The reaction temperature is preferably in the range of, for example, from −50° C. to the boiling temperature of the reaction solvent. Further, the carboxylic anhydride can also be obtained by reacting a corresponding carboxylic acid and an activating agent (for example, isobutyl chloroformate is preferred), and the compounds can be obtained by reacting a compound represented by the formula (26) and a carboxylic anhydride in a base (for example, triethylamine is preferred) and a solvent (for example, tetrahydrofuran is preferred). The reaction temperature is chosen from the range of from −78° C. to the boiling temperature of the solvent, and a temperature in the range of from −78° C. to room temperature is preferred. Further, when a carboxylic acid halide is used, the reaction can be performed in a base (for example, triethylamine is preferred) using a solvent (for example, chloroform is preferred) in the presence of a carboxylic acid halide. The reaction temperature is chosen from the range of from −30° C. to the boiling temperature of the solvent, and a temperature in the range of from 0° C. to room temperature is preferred.

Further, among the compounds represented by the formula (4) shown in Scheme 1, those compounds shown in Scheme 8 can also be obtained by the step shown in Scheme 8, as well as the steps shown in Scheme 1.

<Scheme 8>

[Formula 19]

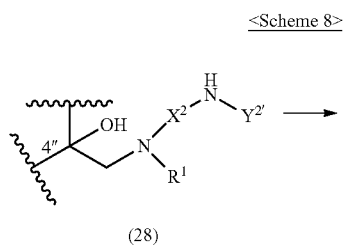

(28)

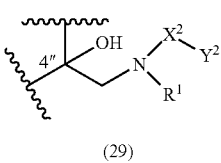

(29)

(The formulas (28) and (29) show conversion of the moiety at the 4″-position of the compounds of the formula (4) shown in Scheme 1, wherein, in the formulas, $X^2$ represents a $C_{1-6}$ alkylene group, $Y^2$ represents, a group represented by the formula —$NR^{11}COR^{12}$,
a group represented by the formula —$NR^{13}CO_2R^{14}$,
a group represented by the formula —$NR^{15}SO_2R^{16}$, or
a group represented by the formula —$NR^{17}R^{18}$, $Y^{2'}$ represents $R^{11}$, $R^{13}$, $R^{15}$, or $R^{17}$, and $R^{11}$, $R^{12}$, $R^{13}$, $R^{14}$, $R^{15}$, $R^{16}$, $R^{17}$, and $R^{18}$ have the same meanings as those defined above.)

The compounds represented by the formula (29) wherein $Y^2$ is a group represented by the formula —$NR^{11}COR^{12}$ can be obtained by using a compound represented by the formula (28) wherein $Y^{2'}$ is $R^{11}$ as a starting material, and subjecting the compound to an amidation reaction in the presence of a corresponding carboxylic acid and a dehydration condensing agent, or using a corresponding carboxylic anhydride or a corresponding carboxylic acid halide. Examples of the dehydration condensing agent include 1-ethyl-3-(3-dimethylaminopropyl)carbodiimide hydrochloride, dicyclohexylcarbodiimide, diphenylphosphoryl azide, 1,1'-carbonyldiimidazole, and the like, and an activating agent such as 1-hydroxybenzotriazole and hydroxysuccinimide can be used, if needed. Examples of the reaction solvent for such a case include dichloromethane, chloroform, 1,2-dichloroethane, dimethylformamide, tetrahydrofuran, dioxane, toluene, ethyl acetate, a mixed solvent thereof, and the like. This reaction can be performed by using a base, and examples of the base include an organic amine such as triethylamine and diisopropylethylamine, an organic acid salt such as sodium 2-ethylhexanoate and potassium 2-ethylhexanoate, an inorganic base such as potassium carbonate, and the like. Further, the reaction can be performed in the presence or absence of 4-dimethylaminopyridine. The reaction temperature is preferably in the range of, for example, from −50° C. to the boiling temperature of the reaction solvent. Further, the carboxylic anhydride can also be obtained by reacting a corresponding carboxylic acid and an activating agent (for example, isobutyl chloroformate is preferred), and the compounds can be obtained by reacting a compound represented by the formula (28) and a carboxylic anhydride in a base (for example, triethylamine is preferred) and a solvent (for example, tetrahydrofuran is preferred). The reaction temperature is chosen from the range of from −78° C. to the boiling temperature of the solvent, and a temperature in the range of from −78° C. to room temperature is preferred. Further, when a carboxylic acid halide is used, the reaction can be performed in a base (for example, triethylamine is preferred) by using a solvent (for example, chloroform is preferred) in the presence of a carboxylic acid halide. The reaction temperature is chosen from the range of from −30° C. to the boiling temperature of the solvent, and a temperature in the range of from 0° C. to room temperature is preferred.

The compounds represented by the formula (29) wherein $Y^2$ is a group represented by the formula —$NR^{13}CO_2R^{14}$ can be obtained by using a compound represented by the formula (28) wherein $Y^{2'}$ is $R^{13}$ as a starting material, and reacting the compound in a solvent (chloroform and dichloromethane are preferred) in the presence of a corresponding haloformic acid ester and in the presence or absence of a base (for example, triethylamine is preferred). The reaction temperature is chosen from the range of, for example, from 0° C. to 60° C., and a temperature in the range of from 0° C. to room temperature is preferred.

The compounds represented by the formula (29) wherein $Y^2$ is a group represented by the formula —$NR^{15}SO_2R^{16}$ can be obtained by using a compound represented by the formula (28) wherein $Y^{2'}$ is $R^{15}$ as a starting material, and reacting the compound in a solvent (chloroform and dichloromethane are preferred) in the presence of a corresponding sulfonyl halide and in the presence or absence of a base (for example, triethylamine is preferred). The reaction temperature is chosen from the range of, for example, from 0° C. to 60° C., and a temperature in the range of from 0° C. to room temperature is preferred.

The compounds represented by the formula (29) wherein $Y^2$ is a group represented by the formula —$NR^{17}R^{18}$ can be obtained by using a compound represented by the formula (28) wherein $Y^{2'}$ is $R^{17}$ as a starting material, and reacting the compound with a corresponding aldehyde in a solvent (examples include, for example, chloroform, methanol, and the like) in the presence of a hydride reducing agent (for example, sodium triacetoxyborohydride, sodium cyanoborohydride and the like). The reaction temperature of the aforementioned reaction is preferably in the range of, for example, from 0° C. to 50° C.

Further, among the compounds represented by the formulas (1) to (4) shown in Scheme 1, those compounds shown in Scheme 9 can also be obtained by the steps shown in Scheme 9, as well as the steps shown in Scheme 1.

<Scheme 9>

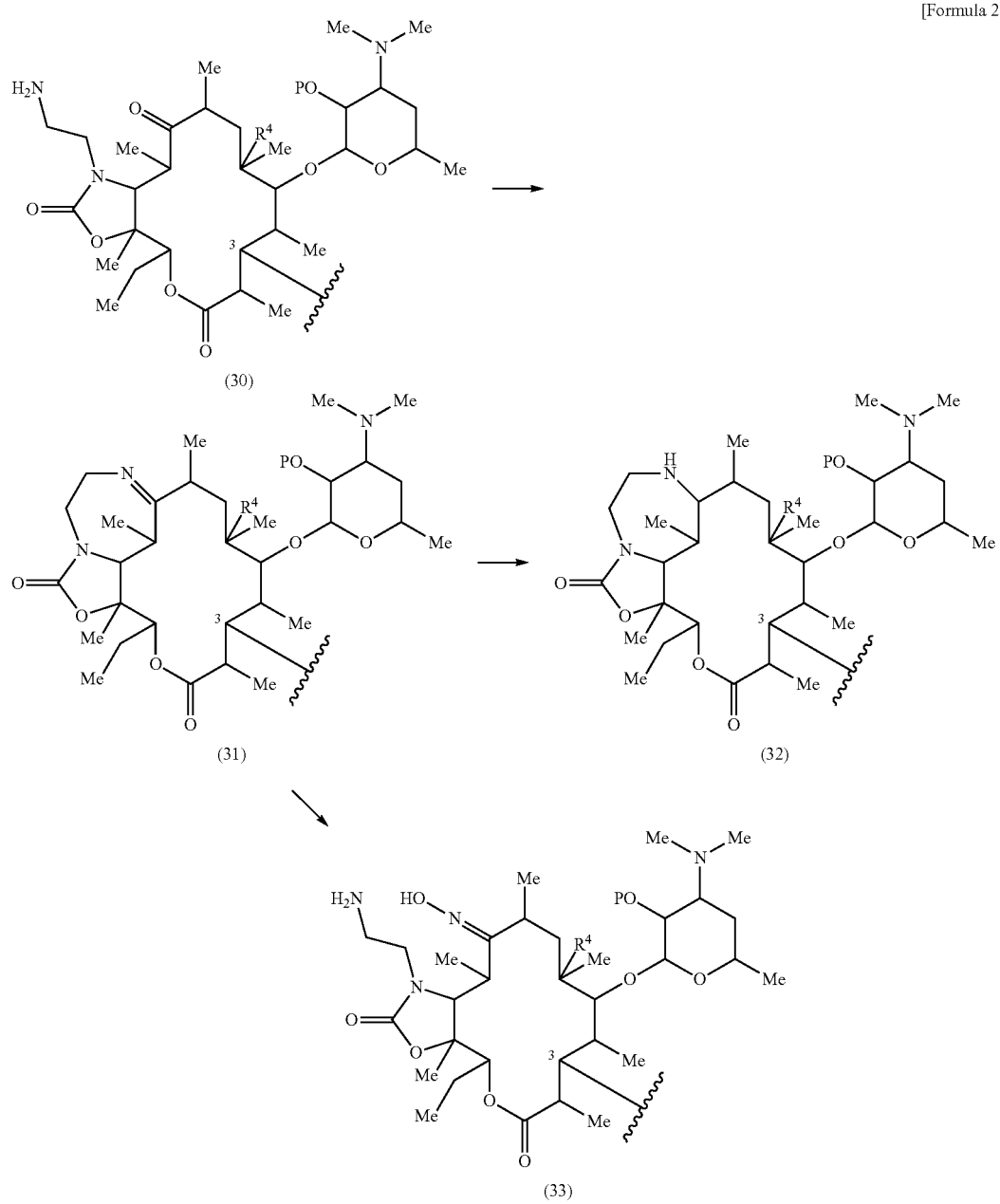

[Formula 20]

(The formulas (30) to (33) show conversion of a partial structure consisting of each of the compounds of the formulas (1), (2), (3) and (4) shown in Scheme 1 except for the substituent at the 3-position, wherein, in the formulas, $R^4$ and P have the same meanings as those defined above.)

The compounds represented by the formula (31) can be obtained by using a compound represented by the formula (30) as a starting material, and reacting the compound in a solvent (for example, toluene is preferred) in the presence or absence of an acid (for example, acetic acid, and the like are preferred). The reaction temperature is chosen from the range of, for example, from 0° C. to the boiling temperature of the solvent, and a temperature in the range of from room temperature to the boiling temperature of the solvent is preferred.

The compounds represented by the formula (32) can be obtained by using a compound represented by the formula (31) as a starting material, and reacting the compound in a solvent (for example, ethanol, and the like are preferred) in the presence or absence of a reducing agent (for example, sodium cyanoborohydride is preferred) and an acid (for example, acetic acid, and the like are preferred). The reaction temperature is chosen from the range of, for example, from 0° C. to the boiling temperature of the solvent, and a temperature in the range of from room temperature to the boiling temperature of the solvent is preferred.

The compounds represented by the formula (33) can be obtained by using a compound represented by the formula (31) as a starting material, and reacting the compound with hydroxylamine in a solvent (for example, methanol is preferred) in the presence or absence of a base (for example, imidazole is preferred). Hydroxylamine used in the aforementioned reaction may be an acid addition salt, and as the acid addition salt, for example, a salt with hydrochloric acid is preferred. The reaction temperature of the aforementioned reaction is preferably in the range of, for example, from room temperature to the boiling temperature of the solvent.

Further, among the compounds represented by the formulas (1) to (4) shown in Scheme 1, those compounds shown in Scheme 10 can also be obtained by the step shown in Scheme 10, as well as the steps shown in Scheme 1.

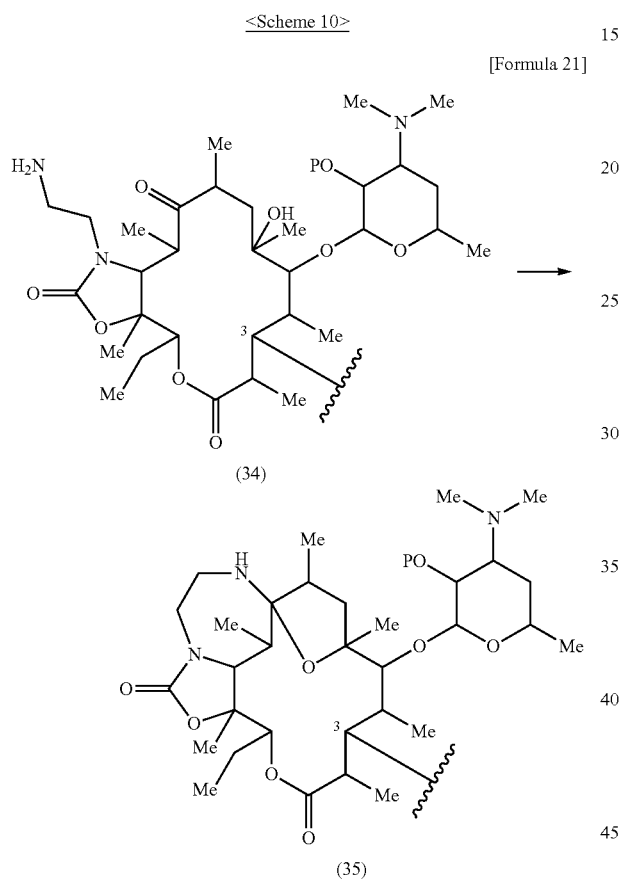

(The formulas (34) and (35) show conversion of a partial structure consisting of each of the compounds of the formulas (1), (2), (3) and (4) shown in Scheme 1 except for the substituent at the 3-position, wherein, in the formulas, P has the same meaning as that defined above.)

The compounds represented by the formula (35) can be obtained, for example, according to a method similar to the methods described in the literatures (for example, Journal of Antibiotics, 2003, vol. 56, p. 1062). Specifically, they can be obtained by using a compound represented by the formula (34) as a starting material and reacting the compound in a solvent (ethanol is preferred) in the presence or absence of an acid (for example, acetic acid, and the like are preferred). The reaction temperature is chosen from the range of, for example, from 0° C. to the boiling temperature of the solvent, and a temperature in the range of from room temperature to 60° C. is preferred.

Further, among the compounds represented by the formulas (1) to (4) shown in Scheme 1, those compounds shown in Scheme 11 can also be obtained by the step shown in Scheme 11, as well as the steps shown in Scheme 1.

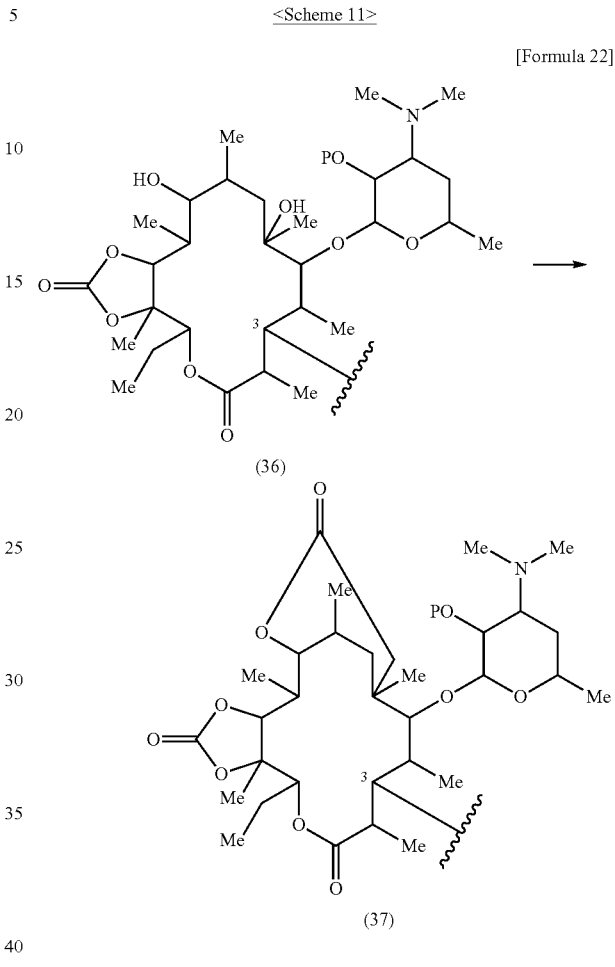

(The formulas (36) and (37) show conversion of a partial structure consisting of each of the compounds of the formulas (1), (2), (3) and (4) shown in Scheme 1 except for the substituent at the 3-position, wherein, in the formulas, P has the same meaning as that defined above.)

The compounds represented by the formula (37) can be obtained, for example according to a method similar to the methods described in the literatures (for example, Journal of Medicinal Chemistry, 2003, vol. 46, p. 2706). Specifically, they can be obtained by using a compound represented by the formula (36) as a starting material, and reacting the compound in a solvent (for example, chloroform and dichloromethane are preferred) in the presence of a carbonating agent (for example, triphosgene is preferred) and a base (for example, pyridine is preferred). The reaction temperature is chosen from the range of, for example, from −20° C. to the boiling temperature of the solvent, and a temperature in the range of from 0° C. to room temperature is preferred.

Further, among the compounds represented by the formulas (1) to (4) shown in Scheme 1, those compounds shown in Scheme 12 can also be obtained by the steps shown in Scheme 12, as well as the steps shown in Scheme 1.

<Scheme 12>

[Formula 23]

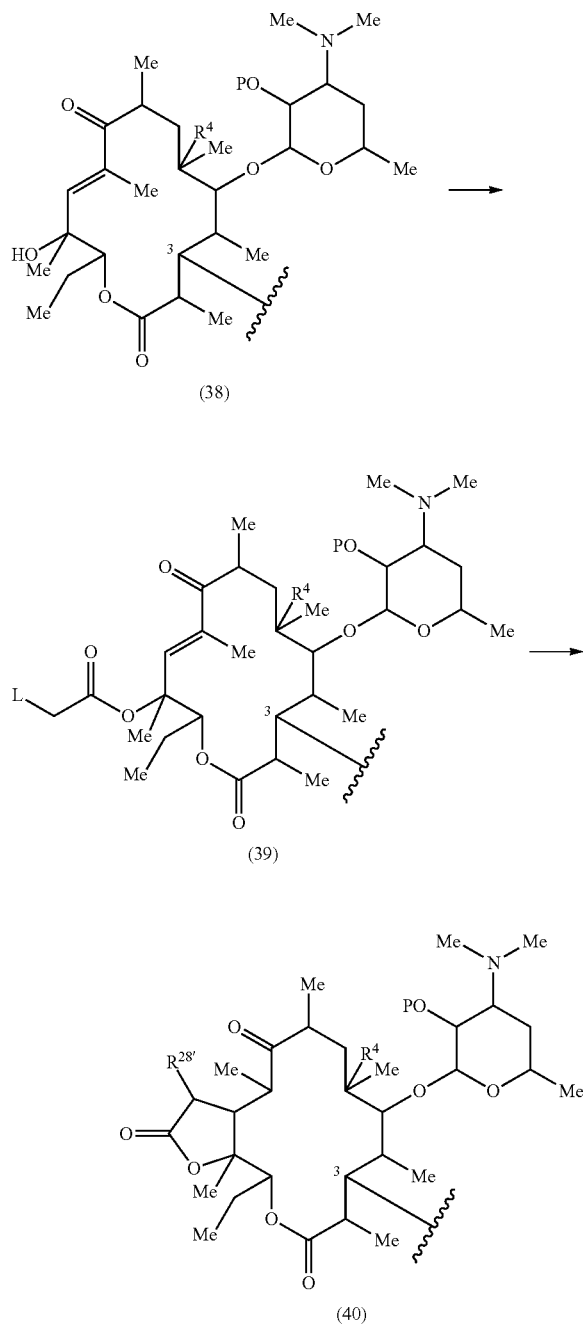

(The formula (40) shows a partial structure consisting of each of the compounds of the formulas (1), (2), (3) and (4) shown in Scheme 1 except for the substituent at the 3-position, wherein, in the formula, $R^{28'}$ represents $R^{28}$ except for hydrogen atom, L represents a halogen atom, and $R^4$, $R^{28}$ and P have the same meanings as those defined above.)

The compounds represented by the formula (39) can be obtained by using a compound represented by the formula (38) as a starting material, and reacting the compound in a solvent (for example, dichloromethane is preferred) in the presence of a haloacetic anhydride (for example, chloroacetic anhydride is preferred), in the presence or absence of a base (for example, pyridine is preferred), and in the presence or absence of 4-dimethylaminopyridine. The reaction temperature is chosen from the range of, for example, from −20° C. to the boiling temperature of the solvent, and a temperature in the range of from 0° C. to room temperature is preferred.

The compounds represented by the formula (40) wherein $R^{28'}$ is cyano group can be obtained by using a compound represented by the formula (39) as a starting material, and reacting an α-cyanoketone compound, which can be obtained by reacting the starting material and a cyanating agent (for example, sodium cyanide is preferred) in a solvent (for example, dimethylformamide is preferred), with a base (for example, potassium t-butoxide is preferred) in a solvent (examples include, for example, tetrahydrofuran, dimethylformamide, and the like, and a mixed solvent of them and the like are preferred). The reaction temperature is chosen from the range of, for example, from −20° C. to the boiling temperature of the solvent, and a temperature in the range of from 0° C. to room temperature is preferred.

The compounds represented by the formula (40) wherein $R^{28'}$ is a $C_{1-6}$ alkylsulfanyl group can be obtained by using a compound represented by the formula (39) as a starting material, and reacting an α-thioketone compound, which can be obtained by reacting the starting material with a corresponding thiol and a base (for example, sodium hydride is preferred) in a solvent (for example, dimethylformamide is preferred), with a base (for example, sodium hydride is preferred) in a solvent (examples include, for example, tetrahydrofuran, dimethylformamide, and the like, and a mixed solvent of them and the like are preferred). The reaction temperature is chosen from the range of, for example, from −20° C. to the boiling temperature of the solvent, and a temperature in the range of from 0° C. to room temperature is preferred.

Further, among the compounds represented by the formulas (1) to (4) shown in Scheme 1, those compounds shown in Scheme 13 can also be obtained by the step shown in Scheme 13, as well as the steps shown in Scheme 1.

<Scheme 13>

[Formula 24]

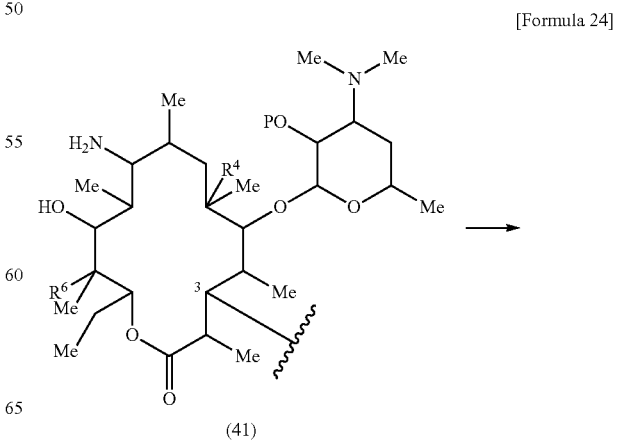

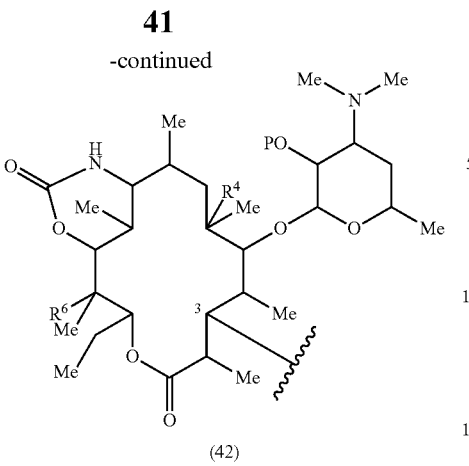

(42)

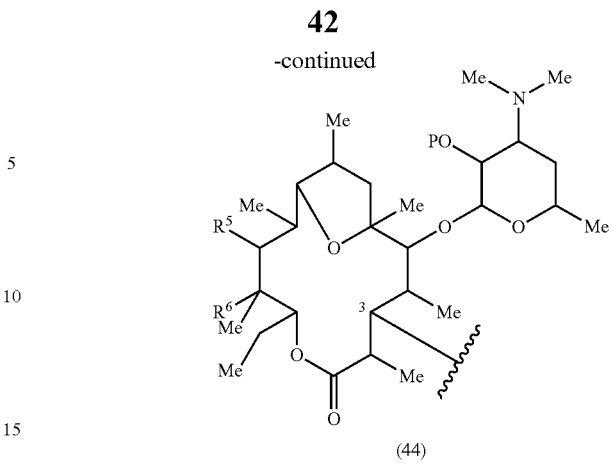

(44)

(The formulas (41) and (42) show a partial structure consisting of each of the compounds of the formulas (1), (2), (3) and (4) shown in Scheme 1 except for the substituent at the 3-position, wherein, in the formulas, $R^4$, $R^6$ and P have the same meanings as those defined above.)

The compounds represented by the formula (42) can be obtained by using a compound represented by the formula (41) as a starting material, and reacting a compound, which can be obtained by reacting the starting material with di-t-butyl dicarbonate, benzyl chloroformate, or the like in a solvent (for example, a mixed solvent of chloroform and water is preferred) in the presence or absence of a base (for example, sodium hydrogencarbonate and the like are preferred), in a solvent (for example, isopropanol is preferred) in the presence or absence of a base (for example, potassium carbonate is preferred). The reaction temperature is chosen from the range of, for example, from 0° C. to the boiling temperature of the solvent, and a temperature in the range of from room temperature to the boiling temperature of the solvent is preferred.

Further, among the compounds represented by the formulas (1) to (4) shown in Scheme 1, those compounds shown in Scheme 14 can also be obtained by the step shown in Scheme 14, as well as the steps shown in Scheme 1.

(The formulas (43) and (44) show a partial structure consisting of each of the compounds of the formulas (1), (2), (3) and (4) shown in Scheme 1 except for the substituent at the 3-position, wherein, in the formulas, $R^5$, $R^6$ and P have the same meanings as those defined above.)

The compounds represented by the formula (44) can be obtained by using a compound represented by the formula (43) as a starting material, and reacting the compound in a solvent (for example, chloroform is preferred) in the presence of triphosgene and a base (for example, pyridine is preferred). The reaction temperature is chosen from the range of, for example, from −78° C. to room temperature, and within that range, a temperature of from −50° C. to 0° C. is preferred.

Further, among the compounds represented by the formulas (1) to (4) shown in Scheme 1, those compounds shown in Scheme 15 can also be obtained by the step shown in Scheme 15, as well as the steps shown in Scheme 1.

<Scheme 15>

[Formula 26]

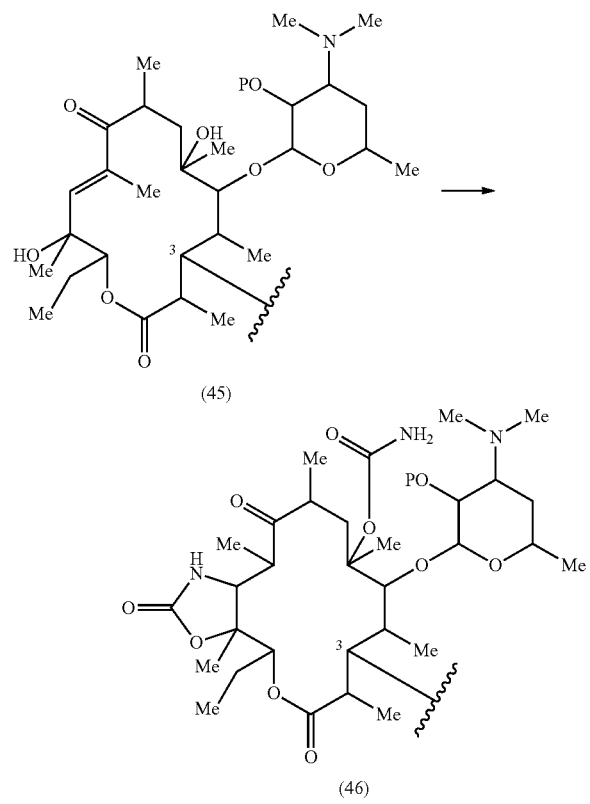

<Scheme 14>

[Formula 25]

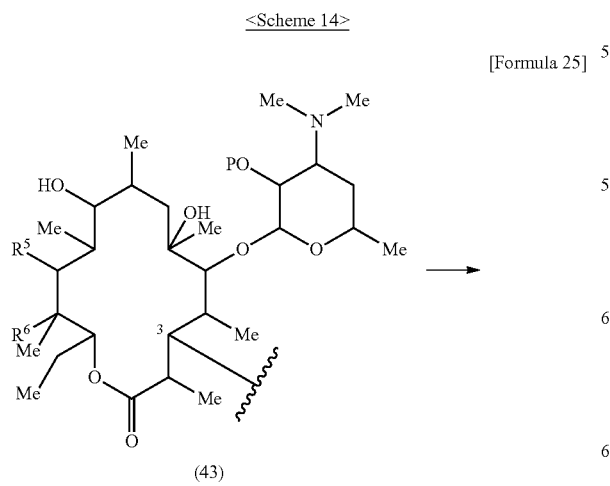

(43)

(The formula (46) shows a partial structure consisting of each of the compounds of the formulas (1), (2), (3) and (4) shown in Scheme 1 except for the substituent at the 3-position, wherein, in the formula, P has the same meaning as that defined above.)

The compounds represented by the formula (46) can be obtained, for example, by using a compound represented by the formula (45) obtainable according to a method similar to the methods described in the literatures (for example, International Patent Publication WO02/046204) as a starting material, reacting the compound in a solvent (for example, chloroform and dichloromethane are preferred) in the presence of trichloroacetyl isocyanate, and reacting the resultant with an alcohol (for example, methanol is preferred) in a solvent (for example, a mixed solvent of methanol and water is preferred) in the presence of a base (for example, triethylamine is preferred). The reaction temperature is chosen from the range of, for example, from 0° C. to the boiling temperature of the solvent, and a temperature in the range of from 0° C. to room temperature is preferred.

Further, among the compounds represented by the formulas (1) to (4) shown in Scheme 1, those compounds shown in Scheme 16 can also be obtained by the steps shown in Scheme 16, as well as the steps shown in Scheme 1.

<Scheme 16>

[Formula 27]

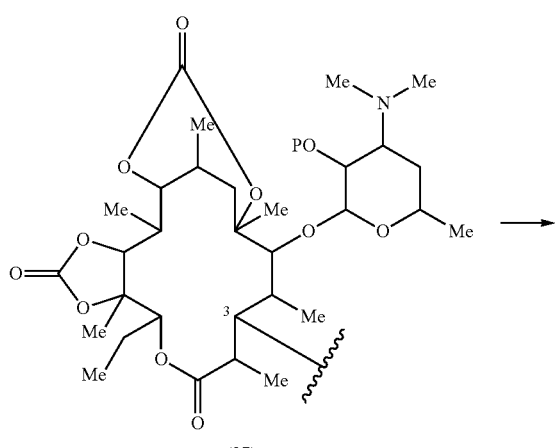

(37)

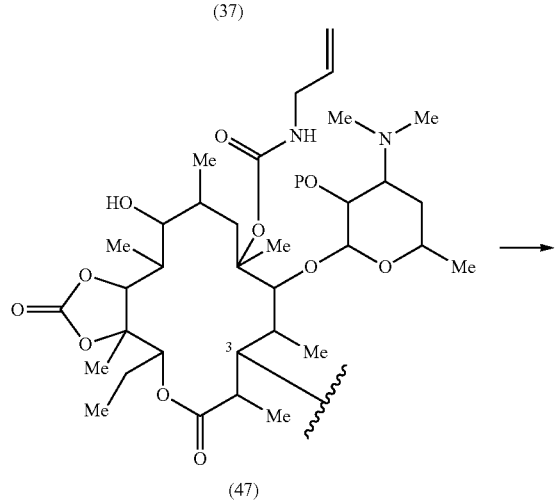

(47)

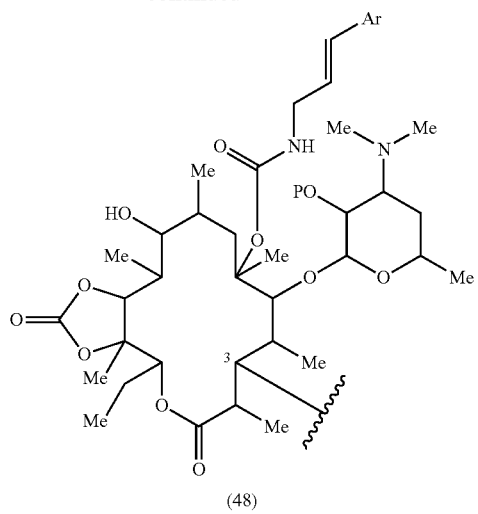

(48)

(The formulas (47) and (48) show a partial structure consisting of each of the compounds of the formulas (1), (2), (3) and (4) shown in Scheme 1 except for the substituent at the 3-position, wherein, in the formulas, Ar represents a heteroaryl group, and P has the same meaning as that defined above.)

The compounds represented by the formula (47) can be obtained by using a compound represented by the formula (37) as a starting material, and reacting the compound in a solvent (for example, tetrahydrofuran is preferred) in the presence of allylamine. The reaction temperature is chosen from the range of, for example, from 0° C. to the boiling temperature of the solvent, and a temperature in the range of from 0° C. to room temperature is preferred.

The compounds represented by the formula (48) can be obtained by the Mizoroki-Heck reaction using a compound represented by the formula (47) as a starting material. Specifically, they can be obtained by reacting the starting material with a base (for example, triethylamine is preferred) in a solvent (for example, acetonitrile is preferred) in the presence of an aryl halide, zero-valent palladium or divalent palladium, and a phosphine ligand. The reaction temperature is chosen from the range of, for example, from 0° C. to the boiling temperature of the solvent, and a temperature in the range of from room temperature to the boiling temperature of the solvent is preferred. Further, this reaction can also be performed by using a microwaves device. A comprehensive review of the Mizoroki-Heck reaction is shown in Angewandte Chemie International Edition, 1994, vol. 33, p. 2379 and Chemical Reviews, 2000, vol. 100, p. 3009.

Further, among the compounds represented by the formulas (1) to (4) shown in Scheme 1, those compounds shown in Scheme 17 can also be obtained by the step shown in Scheme 17, as well as the steps shown in Scheme 1.

<Scheme 17>

[Formula 28]

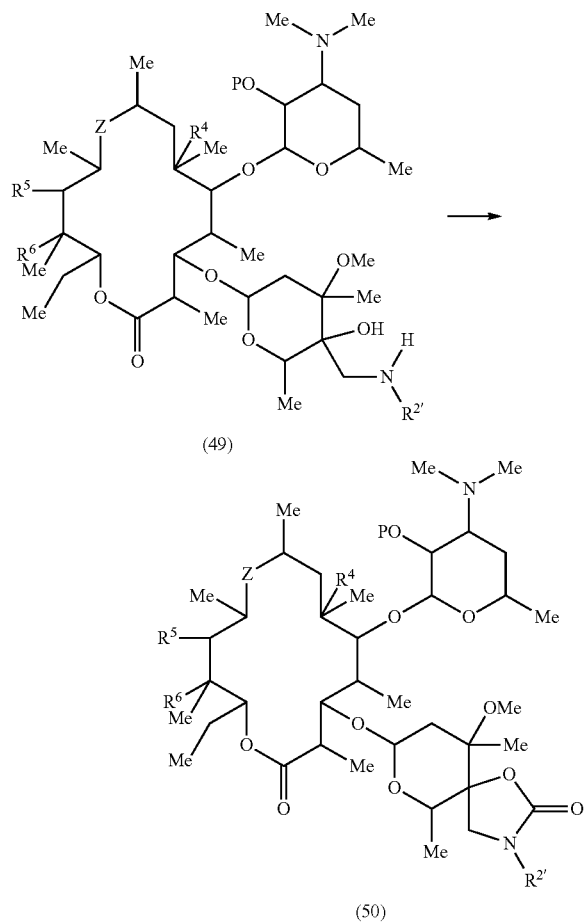

(In the formulas, the symbols of R$^{2'}$, R$^4$, R$^5$, R$^6$, P and Z have the same meanings as those defined above, and P has the same meaning as that defined above.)

The compounds represented by the formula (50) can be obtained by using a compound represented by the formula (49) as a starting material, and reacting the compound in a solvent (for example, chloroform or dichloromethane is preferred) in the presence of a carbonating agent (for example, triphosgene and the like are preferred) and in the presence or absence of a base (for example, pyridine is preferred). The reaction temperature is chosen from the range of, for example, from −20° C. to the boiling temperature of the solvent, and a temperature in the range of from 0° C. to room temperature is preferred.

Hydroxy groups, amino groups, carboxy groups and oxime groups contained in the compounds represented by the formulas (1) to (50) mentioned in these synthesis methods may be protected with selectively removable protective groups known in this field, and by removing them at a desired stage, intermediates for the synthesis of the compounds represented by the formula (I) can be provided. Examples of the protective group include a silyl type protective group such as trimethylsilyl group, triethylsilyl group and t-butyldimethylsilyl group, an acyl type protective group such as acetyl group, propionyl group and benzoyl group, an ether type protective group such as benzyl group, 4-methoxybenzyl group and 2-chlorobenzyl group, an acetal type protective group such as tetrahydropyranyl group, tetrahydrofuranyl group and 1-ethoxyethyl group, a carbonate type protective group such as benzyloxycarbonyl group and t-butyloxycarbonyl group, and the like. However, besides those mentioned above, protective groups described in Protective Groups in Organic Syntheses (Third Edition, 1999, Ed. by P. G. M. Wuts, T. Green), and the like can also be used. Further, the substituents of the compounds represented by the formulas (1) to (50) mentioned in these synthesis methods can be interchangeably converted by known methods.

The intermediates and the objective compounds mentioned in the aforementioned preparation methods can be isolated and purified by purification methods commonly used in organic synthetic chemistry, for example, neutralization, filtration, extraction, washing, drying, concentration, recrystallization using a solvent such as ethyl acetate, ethyl acetate-hexane, isopropyl alcohol, ethanol, hydrated ethanol, acetone, hydrated acetone and the like, various chromatography techniques, and the like. The intermediates can also be used in subsequent reactions without particular purification.

A substance selected from the group consisting of the compounds represented by the aforementioned formula (I), physiologically acceptable salts thereof, and hydrates and solvates thereof can be used as a medicament for prophylactic and/or therapeutic treatment of a microbial infectious disease as a novel macrolide antibiotic. Preferably, a pharmaceutical composition containing the aforementioned substance together with one or more kinds of usually used pharmaceutical additives can be prepared and administered for prophylactic and/or therapeutic treatment of a microbial infectious disease of a mammal including human. The administration route is not particularly limited, and administration route of oral administration, or parenteral administration may be chosen. Examples of the pharmaceutical composition suitable for oral administration include, for example, tablets, capsules, powders, granules, syrups, and the like, and examples of the pharmaceutical composition suitable for parenteral administration include, for example, injections for subcutaneous injection, intramuscular injection, or intravenous injection, drip infusions, suppositories, and the like, but the pharmaceutical composition is not limited to these examples. Injections or drip infusions can also be prepared as a pharmaceutical composition in the form of a lyophilized preparation. For manufacture of solid preparations such as tablets and capsules, usually used excipients, stabilizers. binders, coating agents, and the like can be suitably used, for manufacture of injections, drip infusions, and the like, usually used pharmaceutical additives, for example, excipients, pH modifiers, soothing agents, stabilizers, dissolving aids, and the like, can be suitably used, and these can be suitably chosen by those skilled in the art.

Although type of microbial infectious disease as the application object of the medicament of the present invention is not particularly limited, preferred examples include bacterial infectious diseases, mycoplasmal infectious diseases, chlamydial infectious diseases, and the like. Examples of the bacterial infectious diseases include Gram-positive or Gram-negative bacterial infectious diseases, and the medicament of the present invention can be used for the above diseases in a similar manner as that used for conventionally used macrolides. However, the medicament of the present invention is characterized by showing superior antibacterial activities even against, in particular, erythromycin resistant bacteria (for example, resistant pneumococci, streptococci and mycoplasmas), against which the conventional macrolides cannot show sufficient antibacterial activity, and has an extremely wide antibacterial spectrum. Therefore, the medicament is usable even for an infectious disease of which causal bacterium is not specified.

The medicament of the present invention can be used for prophylactic and/or therapeutic treatment of infectious diseases caused by, for example, microorganisms of the genera *Staphylococcus*, and *Streptococcus*, pneumococci, *Moraxella (Branhamella) catarrhalis, Haemophilus influenzae*, microorganisms of the genera *Legionella, Campylobacter, Peptostreptococcus, Prevotella, Chlamydia, Chlamydophila*, and *Mycoplasma*, and the like, and can be used for, but not limited to, superficial skin infection, profound skin infection, lymphangitis and lymphadenitis, chronic pyoderma, secondary infection after traumatic injury, thermal burn, operative wound, and the like, perianal abscess, pharyngitis and laryngitis (laryngopharyngitis), tonsillitis, acute bronchitis, pneumonia, lung abscess, secondary infection in chronic respiratory diseases (including chronic bronchitis and diffuse panbronchiolitis), bronchiectasis, urethritis, cervicitis, enteritis infectious, otitis media, sinusitis, scarlet fever, pertussis, periodontitis, pericoronitis, jaw inflammation, disseminated *Mycobacterium avium* complex (MAC) disease accompanying acquired immunodeficiency syndrome (AIDS), *Helicobacter Pylori* infectious disease in gastric ulcer and duodenal ulcer, and the like.

Dose of the medicament of the present invention is not particularly limited, and the dose can be suitably chosen depending on type of infectious disease, purpose of administration (prophylactic or therapeutic treatment), age, weight and the like of patient, severity of infectious disease, and the like. For example, in the case of oral administration, 100 to 1,000 mg as a daily dose can be administered at one time or several times as divided portions. Further, the medicament of the present invention can be administered together with one or more kinds of other antibacterial agents or antibiotics.

EXAMPLES

The present invention will be more specifically explained with reference to reference examples, examples and test example. However, the scope of the present invention is not limited to these examples.

Reference Example 1

Synthesis of N-methyl-2-[(2R)-2-methylpyrrolidin-1-yl]ethanamine (1) Methyl-(2-oxoethyl)-carbamic acid t-butyl ester (11.2 g) was dissolved in chloroform (200 ml), (R)-2-methylpyrrolidine (5.0 g) and sodium triacetoxyborohydride (18.7 g) were added to the solution, and the mixture was stirred at room temperature for 2 hours. Saturated aqueous sodium hydrogencarbonate was added to the reaction mixture, and the layers were separated. The organic layer was filtered with a phase separator to further separate the layers, and the resulting organic layer was concentrated under reduced pressure to obtain a residue. The resulting residue was purified by silica gel column chromatography (chloroform:methanol:28% aqueous ammonia=20:1:0.1 to 10:1:0.1) to obtain an alkyl compound (11.8 g).

(2) A 4 mol/L solution of hydrochloric acid in ethyl acetate (10.0 ml) was added to the compound obtained in (1) mentioned above (3.0 g) under ice cooling, and the resulting mixture was stirred for 2 hours. The reaction mixture was concentrated under reduced pressure, 15% aqueous sodium hydroxide was added to the resulting residue for neutralization, and the mixture was extracted with dioxane. The resulting organic layer was dried over potassium carbonate, and filtered, and the filtrate was concentrated under reduced pressure to obtain a residue. The resulting residue was purified by silica gel column chromatography (chloroform:methanol: 28% aqueous ammonia=20:1:0.1 to 5:1:0.1) to obtain the title compound (790 mg).

MS (ESI) m/z=143.2 [M+H]$^+$ $^1$H-NMR (600 MHz, CDCl$_3$) δ (ppm): 1.08 (d, J=5.96 Hz, 3H), 1.35-1.43 (m, 1H), 1.62-1.79 (m, 2H), 1.86-1.94 (m, 1H), 2.08 (q, J=8.71 Hz, 1H), 2.12-2.19 (m, 1H), 2.25-2.33 (m, 1H), 2.45 (s, 3H), 2.63-2.75 (m, 2H), 2.91-2.99 (m, 1H), 3.12 (td, J=8.71, 2.75 Hz, 1H)

Reference Example 2

Synthesis of 2-(1,1-dioxido-1,2-thiazolidin-2-yl)-N-methylethanamine (1) N-(2-Aminoethyl)-N-methylcarbamic acid t-butyl ester (1.0 g) was dissolved in tetrahydrofuran (60 ml), diisopropylethylamine (1.2 ml) was added to the solution, then 3-chloropropanesulfonyl chloride (768 µl) was added to the mixture, and the resulting mixture was stirred at room temperature for 2 hours. Saturated aqueous sodium hydrogencarbonate and ethyl acetate were added to the reaction mixture, the layers were separated, and the resulting organic layer was dried over anhydrous magnesium sulfate, and filtered. The filtrate was concentrated under reduced pressure, and the resulting residue was purified by silica gel column chromatography to obtain a sulfonamide compound (1.35 g).

(2) The compound obtained in (1) mentioned above (1.33 g) was dissolved in dimethylformamide (42 ml), 70% sodium hydride (173.8 mg) was added to the solution, and the resulting mixture was stirred at room temperature for 3 hours. Saturated aqueous sodium hydrogencarbonate and ethyl acetate were added to the reaction mixture, the layers were separated, and the organic layer was washed three times with distilled water, then dried over anhydrous magnesium sulfate, and filtered. The filtrate was concentrated under reduced pressure, and the resulting residue was purified by silica gel column chromatography (chloroform to chloroform:methanol:28% aqueous ammonia=10:1:0.1) to obtain a cyclized compound (460 mg).

(3) By using the compound obtained in (2) mentioned above (460 mg) as a starting material, the title compound (89 mg) was obtained in the same manner as that of Reference Example 1, (2).

MS (ESI) m/z=179.1 [M+H]$^+$ $^1$H-NMR (200 MHz, CDCl$_3$) δ (ppm): 2.25-2.49 (m, 5H), 2.76-2.84 (m, 2H), 3.11-3.22 (m, 4H), 3.30 (t, J=6.59 Hz, 2H)

Reference Example 3

Synthesis of N-butyl-N-ethyl-N'-methylethane-1,2-diamine

By using N-ethyl-N-butylamine (2.34 g) as a starting material, the title compound (2.38 g) was obtained in the same manner as that of Reference Example 1.

MS (ESI) m/z=159.2 [M+H]$^+$ $^1$H-NMR (200 MHz, CDCl$_3$) δ (ppm): 0.83-1.06 (m, 6H), 1.19-1.50 (m, 4H), 2.35-2.67 (m, 11H)

Reference Example 4

Synthesis of N-ethyl-N'-methyl-N-(propan-2-yl)ethane-1,2-diamine

By using N-ethyl-N-isopropylamine (2.0 g) as a starting material, the title compound (2.1 g) was obtained in the same manner as that of Reference Example 1.

MS (ESI) m/z=145.2 [M+H]$^+$
$^1$H-NMR (200 MHz, CDCl$_3$) δ (ppm): 0.94-1.06 (m, 9H), 2.39-2.63 (m, 9H), 2.86-3.01 (m, 1H)

Reference Example 5

Synthesis of N-(cyclopropylmethyl)-N-ethyl-N'-methylethane-1,2-diamine (1) By using cyclopropylmethylamine (4.85 g) as a starting material, an alkyl compound (5.4 g) was obtained in the same manner as that of Reference Example 1, (1).
(2) By using the compound obtained in (1) mentioned above (5.4 g) and acetaldehyde (6.35 ml) as starting materials, the title compound (2.74 g) was obtained in the same manner as that of Reference Example 1.

MS (ESI) m/z=157.2 [M+H]$^+$
$^1$H-NMR (200 MHz, CDCl$_3$) δ (ppm): 0.04-0.14 (m, 2H), 0.43-0.55 (m, 2H), 0.77-0.93 (m, 1H), 1.02 (t, J=7.25 Hz, 3H), 2.34 (d, J=6.59 Hz, 2H), 2.45 (s, 3H), 2.55-2.68 (m, 6H)

Reference Example 6

Synthesis of N-methyl-2-[2-(trifluoromethyl)pyrrolidin-1-yl]ethanamine

By using 2-(trifluoromethyl)pyrrolidine (500 mg) as a starting material, the title compound (0.51 g) was obtained in the same manner as that of Reference Example 1.

MS (ESI) m/z=197.2 [M+H]$^+$
$^1$H-NMR (200 MHz, CDCl$_3$) δ (ppm): 1.74-2.01 (m, 4H), 2.36-2.53 (m, 1H), 2.59-2.77 (m, 1H), 2.88 (s, 3H), 2.98-3.44 (m, 5H)

Reference Example 7

Synthesis of N,N-diethyl-N'-methylglycinamide (1) N-Methylbenzylamine (2.02 g) was dissolved in tetrahydrofuran (70 ml), 2-chloro-N,N-diethylacetamide (1.0 g) was added to the solution, and the resulting mixture was stirred at 60° C. for 2 hours. The reaction mixture was concentrated under reduced pressure, ethyl acetate and saturated aqueous ammonium chloride were added to the resulting residue, and the layers were separated. The organic layer was dried over anhydrous magnesium sulfate, and filtered, and the filtrate was concentrated under reduced pressure. The resulting residue was purified by silica gel column chromatography (chloroform:methanol:28% aqueous ammonia=50:1:0.1 to 10:1:0.1) to obtain an alkyl compound (1.83 g).
(2) The compound obtained in (1) mentioned above (1.0 g) was dissolved in methanol (1 ml), 20% palladium hydroxide/carbon (100 mg) was added to the solution, and the resulting mixture was stirred overnight at room temperature under a hydrogen atmosphere of 1 atm. The reaction mixture was filtered, then the filtrate was concentrated under reduced pressure, and the resulting residue was purified by silica gel column chromatography (chloroform:methanol:28% aqueous ammonia=50:1:0.1) to obtain the title compound (808 mg).

MS (ESI) m/z=145.2 [M+H]$^+$
$^1$H-NMR (600 MHz, CDCl$_3$) δ (ppm): 1.13 (t, J=7.11 Hz, 3H), 1.18 (t, J=7.11 Hz, 3H), 2.44 (s, 3H), 3.26 (q, J=7.34 Hz, 2H), 3.36 (s, 2H), 3.40 (q, J=7.34 Hz, 2H)

Reference Example 8

Synthesis of N-methyl-2-(propan-2-yloxy)ethanamine (1) Di-t-butyl dicarbonate (2.09 g) was added to a solution of 2-aminoethyl isopropyl ether (0.9 g) in chloroform (9 ml) at room temperature, and the mixture was stirred for 30 minutes. The reaction mixture was concentrated under reduced pressure, and the resulting residue was purified by silica gel column chromatography (chloroform alone to chloroform:methanol:28% aqueous ammonia=20:1:0.1) to obtain a protected compound (2.3 g).
(2) The compound obtained in (1) mentioned above (2.3 g) was dissolved in dimethylformamide (45 ml), 70% sodium hydride (370 mg) was added to the solution, and the resulting mixture was stirred at room temperature for 15 minutes. Methyl iodide (672 µl) was added to the reaction mixture, and the resulting mixture was stirred at room temperature for 4 hours. 70% Sodium hydride (370 mg) and methyl iodide (672 µl) were further added to the mixture, and the resulting mixture was stirred at room temperature for 2 hours and at 50° C. for 2 hours. The reaction mixture was cooled to room temperature, then distilled water, ethyl acetate and toluene were added to the reaction mixture, and the layers were separated. The organic layer was dried over anhydrous magnesium sulfate, and filtered. The filtrate was concentrated under reduced pressure to obtain a methyl compound.
(3) By using the compound obtained in (2) mentioned above as a starting material, the title compound (650 mg) was obtained in the same manner as that of Reference Example 1, (2).

MS (ESI) m/z=118.2 [M+H]$^+$
$^1$H-NMR (600 MHz, CDCl$_3$) δ (ppm): 1.12-1.19 (m, 6H), 2.46 (s, 3H), 2.71-2.77 (m, 2H), 3.54 (t, J=5.27 Hz, 2H), 3.58 (dt, J=12.26, 6.02 Hz, 1H)

Reference Example 9

Synthesis of N,N-diethyl-2-(methylamino)ethanesulfonamide (1) Diethylamine (1.0 g) was dissolved in chloroform (60 ml), triethylamine (3.8 ml) was added to the solution, 2-phthalimidoethanesulfonyl chloride (3.74 g) was added dropwise to the mixture under ice cooling, and the resulting mixture was stirred for 1 hour. Distilled water was added to the reaction mixture, and the layers were separated. The organic layer was washed with saturated aqueous sodium hydrogencarbonate, and then filtered with a phase separator to separate the layers, the resulting organic layer was concentrated under reduced pressure, and the resulting residue was purified by silica gel column chromatography (hexane:ethyl acetate=3:1 to 1:1) to obtain a sulfonamide compound (3.34 g).
(2) The compound obtained in (1) mentioned above (3.3 g) was dissolved in ethanol (110 ml), hydrazine monohydrate (1.65 ml) was added to the solution, and the resulting mixture was stirred at room temperature for 1 hour, and under reflux by heating for 2 hours. The reaction mixture was left to cool to room temperature, and then filtered, and the filtrate was concentrated under reduced pressure. The resulting residue was purified by silica gel column chromatography (chloroform:methanol:28% aqueous ammonia=500:1:0.1 to 50:1:0.1) to obtain an amine compound (1.35 g).
(3) By using the compound obtained in (2) mentioned above (1.35 g) as a starting material, the title compound (650 mg) was obtained in the same manners as those of Reference Example 8, (1), (2) and Reference Example 1, (2).
MS (ESI) m/z=195.2 [M+H]$^+$
$^1$H-NMR (600 MHz, CDCl$_3$) δ (ppm): 1.21 (t, J=7.11 Hz, 6H), 2.45 (s, 3H), 3.01-3.05 (m, 2H), 3.08-3.13 (m, 2H), 3.30 (q, J=6.88 Hz, 4H)

Reference Example 10

Synthesis of 1-[2-(methylamino)ethyl]pyrrolidin-2-one (1) By using N-benzyl-N-methylethanolamine (5.0 g) and methanesulfonyl chloride (258 µl) as starting materials, a sulfonanamide compound (3.8 g) was obtained in the same manner as that of Reference Example 9, (1).
(2) 2-Pyrrolidone (349.8 mg) was dissolved in dimethylformamide (20 ml), 70% sodium hydride (141 mg) was added to the solution, and the resulting mixture was stirred at room temperature for 5 minutes. The compound obtained in (1) mentioned above (500 mg) was added to the reaction mixture, and the resulting mixture was stirred at room temperature for 2 hours. Ethyl acetate, toluene and distilled water were added to the reaction mixture, and the layers were separated. The organic layer was washed twice with distilled water, then dried over anhydrous magnesium sulfate, and filtered. The filtrate was concentrated under reduced pressure, and the resulting residue was purified by silica gel column chromatography (chloroform:methanol=50:1 to 10:1) to obtain a substituted compound (287 mg).
(3) By using the compound obtained above (280 mg) as a starting material, the title compound (210 mg) was obtained in the same manner as that of Reference Example 7, (2).
MS (ESI) m/z=143.2 [M+H]$^+$
$^1$H-NMR (600 MHz, CDCl$_3$) δ (ppm): 1.98-2.07 (m, 2H), 2.39 (t, J=8.25 Hz, 2H), 2.44 (s, 3H), 2.74-2.77 (m, 2H), 3.37-3.46 (m, 4H)

Reference Example 11

Synthesis of 1-methyl-3-[2-(methylamino)ethyl]imidazolidine-2,4-dione

By using 1-methylhydantoin (468.9 mg) as a starting material, the title compound (205 mg) was obtained in the same manners as those of Reference Example 10, (2) and Reference Example 7, (2).
MS (ESI) m/z=172.2 [M+H]$^+$
$^1$H-NMR (200 MHz, CDCl$_3$) δ (ppm): 2.44 (s, 3H), 2.83 (t, J=6.15 Hz, 2H), 3.00 (s, 3H), 3.65 (t, J=6.15 Hz, 2H), 3.88 (s, 2H)

Reference Example 12

Synthesis of 3-[2-(methylamino)ethyl]-1,3-oxazolidin-2-one

By using 2-oxazolidone (357.9 mg) as a starting material, the title compound (41 mg) was obtained in the same manners as those of Reference Example 10, (2) and Reference Example 7, (2).

MS (ESI) m/z=145.1 [M+H]$^+$
$^1$H-NMR (600 MHz, CDCl$_3$) δ (ppm): 2.45 (s, 3H), 2.80 (t, J=6.19 Hz, 2H), 3.39 (t, J=6.19 Hz, 2H), 3.59-3.67 (m, 2H), 4.29-4.37 (m, 2H)

Reference Example 13

Synthesis of 3-[2-(methylamino)ethyl]imidazolidine-2,4-dione

By using hydantoin (411.3 mg) as a starting material, the title compound (200 mg) was obtained in the same manners as those of Reference Example 10, (2) and Reference Example 7, (2).
MS (ESI) m/z=158.2 [M+H]$^+$
$^1$H-NMR (600 MHz, CDCl$_3$) δ (ppm): 2.44 (s, 3H), 2.84 (t, J=6.19 Hz, 2H), 3.66 (t, J=6.19 Hz, 2H), 3.98 (s, 2H), 5.44 (br. s, 1H)

Reference Example 14

Synthesis of 2-(1,1-dioxidothiomorpholin-4-yl)-N-methylethanamine

By using thiomorpholine-1,1-dioxide (780 mg) as a starting material, the title compound (884 mg) was obtained in the same manner as that of Reference Example 1.
MS (ESI) m/z=193.1 [M+H]$^+$
$^1$H-NMR (200 MHz, CDCl$_3$) δ (ppm): 2.45 (s, 3H), 2.67 (s, 4H), 2.96-3.11 (m, 8H)

Reference Example 15

Synthesis of N-methyl-2-(morpholin-4-yl)ethanamine

By using morpholine (503 mg) as a starting material, the title compound (905 mg) was obtained in the same manner as that of Reference Example 1.
MS (ESI) m/z=145.1 [M+H]$^+$
$^1$H-NMR (200 MHz, CDCl$_3$) δ (ppm): 2.39-2.53 (m, 6H), 2.45 (s, 3H), 2.62-2.72 (m, 2H), 3.65-3.76 (m, 4H)

Reference Example 16

Synthesis of N-methyl-2-(thiomorpholin-4-yl)ethanamine

By using thiomorpholine (328 mg) as a starting material, the title compound (451 mg) was obtained in the same manner as that of Reference Example 1.
MS (ESI) m/z=161.1 [M+H]$^+$
$^1$H-NMR (200 MHz, CDCl$_3$) δ (ppm): 2.44 (s, 3H), 2.48-2.54 (m, 2H), 2.57-2.76 (m, 10H)

Reference Example 17

Synthesis of N-methyl-2-(3-oxa-8-azabicyclo[3.2.1]oct-8-yl)ethanamine

By using 3-oxa-8-azabicyclo[3.2.1]octane (40 mg) obtained by the method described in the publication (International Patent Publication WO10/120854) as a starting material, the title compound (24 mg) was obtained in the same manner as that of Reference Example 1.
MS (ESI) m/z=171.1 [M+H]$^+$ ¹H-NMR (200 MHz, CDCl₃) δ (ppm): 1.80-1.90 (m, 4H), 2.34-2.46 (m, 2H), 2.46 (s, 3H), 2.58-2.67 (m, 2H), 3.01 (br. s., 2H), 3.44-3.55 (m, 2H), 3.63-3.72 (m, 2H)

Reference Example 18

Synthesis of 1-[(2S)-1-ethylpyrrolidin-2-yl]-N-methylmethanamine (1) By using (S)-(−)-2-aminomethyl-1-ethylpyrrolidine (500 mg) as a starting material, a protected compound was obtained in the same manner as that of Reference Example 8, (1).
(2) A solution of the compound obtained in (1) mentioned above in tetrahydrofuran (10 ml) was added dropwise to a suspension of lithium aluminum hydride (590.5 mg) in tetrahydrofuran (20 ml), and the resulting mixture was stirred at room temperature for 0.5 hour, and under reflux by heating for 6 hours. The reaction mixture was cooled to room temperature, then distilled water, 25% aqueous sodium hydroxide and distilled water were added to the reaction mixture in this order under ice cooling, and the resulting mixture was stirred at room temperature for 1 hour. The reaction mixture was filtered thorough Celite, and the filtrate was concentrated under reduced pressure to obtain the title compound (510 mg).
MS (ESI) m/z=143.0 [M+H]⁺
¹H-NMR (200 MHz, CDCl₃) δ (ppm): 1.10 (t, J=7.25 Hz, 3H), 1.55-1.97 (m, 4H), 2.05-2.32 (m, 2H), 2.39-2.58 (m, 5H), 2.60-2.94 (m, 2H), 3.08-3.21 (m, 1H)

Reference Example 19

Synthesis of N,N'-dimethyl-N-propylethane-1,2-diamine (1) By using propylamine (3.41 g) as a starting material, an alkyl compound was obtained in the same manner as that of Reference Example 1, (1).
(2) The compound obtained in (1) mentioned above was dissolved in chloroform (30 ml), 37% aqueous formaldehyde (9.4 ml) and sodium triacetoxyborohydride (3.67 g) were added to the solution, and the resulting mixture was stirred at room temperature for 2 hours. Saturated aqueous sodium hydrogencarbonate was added to the reaction mixture, and the layers were separated. The organic layer was filtered with a phase separator to further separate the layers, and the resulting organic layer was concentrated under reduced pressure to obtain an alkyl compound.
(3) The compound obtained in (2) mentioned above was dissolved in chloroform (1.5 ml), trifluoroacetic acid (1.5 ml) was added to the solution, and the resulting mixture was stirred at room temperature for 4 hours. Trifluoroacetic acid (5 ml) was added to the reaction mixture, and the resulting mixture was stirred at room temperature for 2 hours. The reaction mixture was concentrated under reduced pressure, saturated aqueous potassium carbonate and chloroform were added to the resulting residue, and the layers were separated. The organic layer was filtered with a phase separator to further separate the layers, the resulting organic layer was concentrated under reduced pressure, and the resulting residue was purified by silica gel column chromatography (chloroform to chloroform:methanol:28% aqueous ammonia=10:1:0.1) to obtain the title compound (880 mg).
MS (ESI) m/z=131.0 [M+H]⁺
¹H-NMR (200 MHz, CDCl₃) δ (ppm): 0.89 (t, J=8.35 Hz, 4H), 1.37-1.63 (m, 2H), 2.20 (s, 3H), 2.24-2.35 (m, 2H), 2.40-2.52 (m, 5H), 2.59-2.70 (m, 2H)

Reference Example 20

Synthesis of N,N'-dimethyl-N-(propan-2-yl)ethane-1,2-diamine

By using N-isopropylmethylamine (844.7 mg) as a starting material, the title compound (58 mg) was obtained in the same manners as those of Reference Example 1, (1) and Reference Example 19, (3).
MS (ESI) m/z=131.0 [M+H]⁺
¹H-NMR (200 MHz, CDCl₃) δ (ppm): 0.99 (d, J=6.59 Hz, 6H), 2.19 (s, 3H), 2.44 (s, 3H), 2.46-2.94 (m, 5H)

Reference Example 21

Synthesis of N,N'-dimethyl-N-(prop-2-en-1-yl)ethane-1,2-diamine

By using N-allylmethylamine (821.5 mg) as a starting material, the title compound (246 mg) was obtained in the same manners as those of Reference Example 1, (1) and Reference Example 19, (3).
MS (ESI) m/z=129.0 [M+H]⁺
¹H-NMR (200 MHz, CDCl₃) δ (ppm): 2.21 (s, 3H), 2.44 (s, 3H), 2.45-2.52 (m, 2H), 2.61-2.70 (m, 2H), 3.00 (dt, J=6.59, 1.32 Hz, 2H), 5.07-5.23 (m, 2H), 5.74-5.97 (m, 1H)

Reference Example 22

Synthesis of N-butyl-N,N'-dimethylethane-1,2-diamine

By using N-butylmethylamine (1.0 g) as a starting material, the title compound (612 mg) was obtained in the same manners as those of Reference Example 1, (1) and Reference Example 19, (3).
MS (ESI) m/z=145.0 [M+H]⁺
¹H-NMR (200 MHz, CDCl₃) δ (ppm): 0.84-0.96 (m, 3H), 1.20-1.54 (m, 4H), 2.20 (s, 3H), 2.28-2.38 (m. 2H), 2.41-2.49 (m, 5H), 2.59-2.69 (m, 2H)

Reference Example 23

Synthesis of N-t-butyl-N,N'-dimethylethane-1,2-diamine

By using N-methyl-t-butylamine (580.0 mg) as a starting material, the title compound (75 mg) was obtained in the same manners as those of Reference Example 1, (1) and Reference Example 19, (3).
MS (ESI) m/z=145.0 [M+H]⁺
¹H-NMR (600 MHz, CDCl₃) δ (ppm): 1.05 (s, 9H), 2.18 (s, 3H), 2.44 (s, 3H), 2.48-2.52 (m, 2H), 2.59-2.63 (m, 2H)

Reference Example 24

Synthesis of N-(butan-2-yl)-N,N'-dimethylethane-1,2-diamine

By using s-butylamine (844.7 mg) as a starting material, the title compound (810 mg) was obtained in the same manners as those of Reference Example 1, (1), Reference Example 19, (2) and (3).

MS (ESI) m/z=145.0 [M+H]$^+$
$^1$H-NMR (200 MHz, CDCl$_3$) δ (ppm): 0.81-0.96 (m, 6H), 1.08-1.60 (m, 2H), 2.16 (s, 3H), 2.44 (s, 3H), 2.45-2.65 (m, 5H)

Reference Example 25

Synthesis of N,N'-dimethyl-N-(2-methylpropyl) ethane-1,2-diamine

By using N-methylisobutylamine (1.01 g) as a starting material, the title compound (170 mg) was obtained in the same manners as those of Reference Example 1, (1) and Reference Example 19, (3).
MS (ESI) m/z=145.0 [M+H]$^+$
$^1$H-NMR (200 MHz, CDCl$_3$) δ (ppm): 0.85-0.90 (m, 6H), 1.61-1.85 (m, 1H), 2.06 (d, J=7.47 Hz, 2H), 2.17 (s, 3H), 2.39-2.48 (m, 5H), 2.58-2.66 (m, 2H)

Reference Example 26

Synthesis of N-cyclopropyl-N,N'-dimethylethane-1,2-diamine

By using cyclopropylamine (3.30 g) as a starting material, the title compound (575 mg) was obtained in the same manners as those of Reference Example 1, (1), Reference Example 19, (2) and (3).
MS (ESI) m/z=129.0 [M+H]$^+$ Reference Example 27

Synthesis of N-(cyclopropylmethyl)-N,N'-dimethyl-ethane-1,2-diamine

By using cyclopropylmethylamine (4.11 g) as a starting material, the title compound (868 mg) was obtained in the same manners as those of Reference Example 1, (1), Reference Example 19, (2) and (3).
MS (ESI) m/z=143.0 [M+H]$^+$
$^1$H-NMR (200 MHz, CDCl$_3$) δ (ppm): 0.05-0.16 (m, 1H), 0.44-0.57 (m, 2H), 0.79-1.01 (m, 1H), 2.25 (d, J=6.59 Hz, 2H), 2.29 (s, 3H), 2.45 (s, 3H), 2.49-2.57 (m, 2H), 2.62-2.71 (m, 2H)

Reference Example 28

Synthesis of N-cyclobutyl-N,N'-dimethylethane-1,2-diamine

By using cyclobutylamine (821.5 mg) as a starting material, the title compound (1.16 g) was obtained in the same manners as those of Reference Example 1, (1), Reference Example 19, (2) and (3).
MS (ESI) m/z=142.9 [M+H]$^+$
$^1$H-NMR (600 MHz, CDCl$_3$) δ (ppm): 1.57-2.05 (m, 6H), 2.05-2.07 (m, 3H), 2.32-2.35 (m, 2H), 2.42-2.45 (m, 3H), 2.61-2.65 (m, 2H), 2.72-2.79 (m, 1H)

Reference Example 29

Synthesis of N-cyclopentyl-N,N'-dimethylethane-1,2-diamine

By using cyclopentylamine (983.5 mg) as a starting material, the title compound (126 mg) was obtained in the same manners as those of Reference Example 1, (1), Reference Example 19, (2) and (3).

MS (ESI) m/z=157.0 [M+H]$^+$
$^1$H-NMR (600 MHz, CDCl$_3$) δ (ppm): 1.34-1.42 (m, 2H), 1.47-1.55 (m, 2H), 1.60-1.69 (m, 2H), 1.76-1.83 (m, 2H), 2.19-2.21 (m, 3H), 2.43-2.45 (m, 3H), 2.51 (t, J=6.30 Hz, 2H), 2.64-2.71 (m, 3H)

Reference Example 30

Synthesis of N-methyl-2-(piperidin-1-yl)ethanamine

By using piperidine (983.5 mg) as a starting material, the title compound (120 mg) was obtained in the same manners as those of Reference Example 1, (1) and Reference Example 19, (3).
MS (ESI) m/z=143.0 [M+H]$^+$
$^1$H-NMR (200 MHz, CDCl$_3$) δ (ppm): 1.36-1.71 (m, 10H), 2.32-2.49 (m, 11H), 2.61-2.71 (m, 2H)

Reference Example 31

Synthesis of 2-(3,6-dihydropyridin-1(2H)-yl)-N-methylethanamine

By using 1,2,3,6-tetrahydropyridine (960.2 mg) as a starting material, the title compound (855 mg) was obtained in the same manners as those of Reference Example 1, (1) and Reference Example 19, (3).
MS (ESI) m/z=141.0 [M+H]$^+$
$^1$H-NMR (200 MHz, CDCl$_3$) δ (ppm): 2.08-2.24 (m, 2H), 2.44 (s, 3H), 2.50-2.62 (m, 4H), 2.65-2.78 (m, 2H), 2.92-3.02 (m, 2H), 5.60-5.82 (m, 2H)

Reference Example 32

Synthesis of 2-{methyl[2-(methylamino)ethyl]amino}ethanol

By using 2-(methylamino)ethanol (867.5 mg) as a starting material, the title compound (740 mg) was obtained in the same manners as those of Reference Example 1, (1) and Reference Example 19, (3).
MS (ESI) m/z=133.0 [M+H]$^+$
$^1$H-NMR (600 MHz, CDCl$_3$) δ (ppm): 2.30 (s, 3H), 2.44 (s, 3H), 2.53-2.58 (m, 4H), 2.66-2.70 (m, 2H), 3.58-3.62 (m, 2H)

Reference Example 33

Synthesis of N-(2-methoxyethyl)-N,N'-dimethyl-ethane-1,2-diamine

By using N-(2-methoxyethyl)methylamine (1029.5 mg) as a starting material, the title compound (681 mg) was obtained in the same manners as those of Reference Example 1, (1) and Reference Example 19, (3).
MS (ESI) m/z=147.0 [M+H]$^+$
$^1$H-NMR (200 MHz, CDCl$_3$) δ (ppm): 2.28 (s, 3H), 2.44 (s, 3H), 2.48-2.70 (m, 6H), 3.33-3.37 (m, 3H), 3.47 (t, J=5.93 Hz, 2H)

Reference Example 34

Synthesis of (2R)-2-amino-3-(dimethylamino)propan-1-ol (1) N-(t-Butoxycarbonyl)-O-benzyl-L-serine (2.5 g) was dissolved in chloroform (100 ml), 50% aqueous dimethylamine (3 ml), 4-dimethylaminopyridine (2.07 g), N-ethyl-N'-(3- dimethylaminopropyl)carbodiimide hydrochloride (3.25 g), and 1-hydroxybenzotriazole (2.29 g) were added to the solution, and the resulting mixture was stirred at room temperature for 16 hours. Saturated aqueous sodium hydrogencarbonate was added to the reaction mixture, and the resulting mixture was extracted with chloroform. The resulting organic layer was dried over anhydrous magnesium sulfate, and filtered. The filtrate was concentrated under reduced pressure, and the resulting residue was purified by silica gel column chromatography (chloroform alone to chloroform:methanol=100:1) to obtain an amide compound (2.02 g).

(2) A 2 mol/L solution of hydrochloric acid in isopropanol (20 ml) was added to the compound obtained in (1) mentioned above, and the resulting mixture was stirred at room temperature for 4 hours. The reaction mixture was concentrated under reduced pressure, and 10% aqueous sodium hydroxide and chloroform were added to the resulting residue for extraction. The organic layer was dried over anhydrous magnesium sulfate, and filtered. The filtrate was concentrated under reduced pressure to obtain a deprotected compound (1.36 g).

(3) By using the compound obtained in (2) mentioned above (1.36 g) as a starting material, an amine compound (1.3 g) was obtained in the same manner as that of Reference Example 18, (2).

(4) By using the compound obtained above (1.3 g) as a starting material, the title compound (0.23 g) was obtained in the same manner as that of Reference Example 7, (2).

MS (ESI) m/z=119.0 [M+H]$^+$ $^1$H-NMR (200 MHz, CDCl$_3$) δ (ppm): 2.27 (s, 6H), 2.30-2.49 (m, 3H), 3.56 (d, J=5.71 Hz, 2H)

Reference Example 35

Synthesis of N-ethyl-N-[2-(methylamino)ethyl]acetamide (1) By using ethylamine (43.3 ml) as a starting material, an alkyl compound (1.35 g) was obtained in the same manner as that of Reference Example 1, (1).

(2) The compound obtained in (1) mentioned above (300 mg) was dissolved in pyridine (1 ml), acetyl chloride (159 μl) was added to the solution under ice cooling, and the resulting mixture was stirred at the same temperature for 1 hour. Acetyl chloride (159 μl) was added to the reaction mixture, and the resulting mixture was stirred at room temperature for 1 hour. The reaction mixture was concentrated under reduced pressure, then distilled water and chloroform were added to the resulting residue, and the layers were separated. The organic layer was washed with saturated aqueous sodium hydrogencarbonate, dried over anhydrous magnesium sulfate, and filtered. The filtrate was concentrated under reduced pressure, and the resulting residue was purified by silica gel column chromatography (chloroform to chloroform:methanol:28% aqueous ammonia=10:1:0.1) to obtain an amide compound (338 mg).

(3) By using the compound obtained in (2) mentioned above (338 mg) as a starting material, the title compound (134 mg) was obtained in the same manner as that of Reference Example 19, (3).

MS (ESI) m/z=145.1 [M+H]$^+$ $^1$H-NMR (200 MHz, CDCl$_3$) δ (ppm): 1.06-1.24 (m, 3H), 2.07-2.15 (m, 3H), 2.41-2.49 (m, 3H), 2.70-2.81 (m, 2H), 3.27-3.51 (m, 4H)

Reference Example 36

Synthesis of Methyl ethyl[2-(methylamino)ethyl]carbamate

By using the compound obtained in Reference Example 35, (1) (300 mg) and methyl chloroformate (342 μl) as starting materials, the title compound (171 mg) was obtained in the same manners as those of Reference Example 35, (2) and Reference Example 19, (3).

MS (ESI) m/z=161.1 [M+H]$^+$ $^1$H-NMR (200 MHz, CDCl$_3$) δ (ppm): 1.12 (t, J=7.25 Hz, 3H), 2.45 (s, 3H), 2.73 (t, J=6.59 Hz, 2H), 3.26-3.43 (m, 4H), 3.70 (s, 3H)

Reference Example 37

Synthesis of 1-[2-(methylamino)ethyl]piperidin-4-ol

By using 4-hydroxypiperidine (1.0 g) as a starting material, a mixture (8.0 g) mainly containing the title compound was obtained in the same manners as those of Reference Example 1, (1) and Reference Example 19, (3).

MS (ESI) m/z=159.1 [M+H]$^+$ $^1$H-NMR (200 MHz, CDCl$_3$) δ (ppm): 1.47-1.69 (m, 2H), 2.07-2.26 (m, 2H), 2.46 (s, 3H), 2.46-2.84 (m, 8H), 3.64-3.81 (m, 1H)

Reference Example 38

Synthesis of N-(cyclopropylmethyl)-N-ethyl-N'-methylethane-1,2-diamine (1) By using cyclopropylmethylamine (1.23 g) as a starting material, an alkyl compound was obtained in the same manner as that of Reference Example 1, (1).

(2) By using the compound obtained in (1) mentioned above and acetaldehyde (1.4 ml) as starting materials, the title compound (156 mg) was obtained in the same manners as those of Reference Example 1, (1) and Reference Example 19, (3).

MS (ESI) m/z=157.2 [M+H]$^+$ $^1$H-NMR (200 MHz, CDCl$_3$) δ (ppm): 0.04-0.14 (m, 2H), 0.43-0.54 (m, 2H), 0.78-0.94 (m, 1H), 1.02 (t, J=7.25 Hz, 3H), 2.34 (d, J=6.59 Hz, 2H), 2.45 (s, 3H), 2.54-2.68 (m, 6H)

Reference Example 39

Synthesis of N-ethyl-N-(pyrrolidin-3-ylmethyl)ethanamine (1) By using 1-t-butoxycarbonyl-3-formylpyrrolidine (500 mg) and diethylamine (285 μl) as starting materials, an alkyl compound was obtained in the same manner as that of Reference Example 1, (1).

(2) A 2 mol/L solution of hydrochloric acid in ethanol (20 ml) was added to the compound obtained in (1) mentioned above, and the resulting mixture was stirred at room temperature for 4 hours. The reaction mixture was concentrated under reduced pressure, 10% aqueous sodium hydroxide and chloroform were added to the resulting residue for extraction. The resulting organic layer was dried over anhydrous magnesium sulfate, and filtered. The filtrate was concentrated under reduced pressure, and the resulting residue was purified by NH silica gel column chromatography (hexane:chloroform=1:1 to chloroform to chloroform:methanol:28% aqueous ammonia=10:1:0.1) to obtain the title compound (95 mg).

MS (ESI) m/z=157.1 [M+H]$^+$

¹H-NMR (200 MHz, CDCl₃) δ (ppm): 1.00 (t, J=7.25 Hz, 6H), 1.22-2.00 (m, 3H), 2.15-2.38 (m, 3H), 2.46-2.59 (m, 4H), 2.85-3.11 (m, 3H)

Reference Example 40

Synthesis of 1-(1-ethylpyrrolidin-3-yl)-N-methylmethanamine (1) By using 1-t-butoxycarbonyl-3-formylpyrrolidine (250 mg) and N-methylbenzylamine (180 μl) as starting materials, an alkyl compound (0.25 g) was obtained in the same manners as those of Reference Example 1, (1) and Reference Example 39, (2).
(2) By using the compound obtained in (1) mentioned above (0.25 g) and acetaldehyde (0.4 ml) as starting materials, the title compound (66 mg) was obtained in the same manners as those of Reference Example 1, (1) and Reference Example 7, (2).
¹H-NMR (200 MHz, CDCl₃) δ (ppm): 1.11 (t, J=7.25 Hz, 3H), 1.31-1.54 (m, 2H), 1.89-2.24 (m, 2H), 2.26-2.86 (m, 10H)

Reference Example 41

Synthesis of N-methyl-2-(2-methylpyrrolidin-1-yl)ethanamine

By using 2-methylpyrrolidine (680 μl) as a starting material, the title compound (0.55 g) was obtained in the same manners as those of Reference Example 1,
(1) and Reference Example 39, (2).
MS (ESI) m/z=143.0 [M+H]⁺
¹H-NMR (200 MHz, CDCl₃) δ (ppm): 1.08 (d, J=5.71 Hz, 3H), 1.30-1.52 (m, 1H), 1.61-1.97 (m, 3H), 1.99-2.38 (m, 3H), 2.45 (s, 3H), 2.64-2.74 (m, 2H), 2.88-3.18 (m, 2H)

Reference Example 42

Synthesis of N,N-dimethyl-1-[2-(methylamino)ethyl]prolinamide (1) By using 1-[(benzyloxy)carbonyl]pyrrolidine-2-carboxylic acid (500 mg) and 50% aqueous dimethylamine (2.5 ml) as starting materials, an amide compound (136 mg) was obtained in the same manners as those of Reference Example 34, (1) and Reference Example 7, (2).
(2) By using the compound obtained in (1) mentioned above (136 mg) as a starting material, the title compound (0.15 g) was obtained in the same manners as those of Reference Example 1, (1) and Reference Example 39, (2).
MS (ESI) m/z=200.1 [M+H]⁺
¹H-NMR (200 MHz, CDCl₃) δ (ppm): 1.75-2.17 (m, 4H), 2.26-2.41 (m, 1H), 2.42 (s, 3H), 2.49-2.80 (m, 4H), 2.95 (s, 3H), 3.09 (s, 3H), 3.17-3.42 (m, 2H)

Reference Example 43

Synthesis of {(2R)-1-[2-(methylamino)ethyl]pyrrolidin-2-yl}methanol

By using D-prolinol (500 mg) as a starting material, the title compound (0.17 g) was obtained in the same manners as those of Reference Example 1, (1) and Reference Example 39, (2).
MS (ESI) m/z=159.0 [M+H]⁺
¹H-NMR (200 MHz, CDCl₃) δ (ppm): 1.59-1.93 (m, 4H), 2.27-2.42 (m, 1H), 2.44 (s, 3H), 2.46-2.58 (m, 1H), 2.61-2.97 (m, 4H), 3.10-3.23 (m, 1H), 3.32-3.43 (m, 1H), 3.53-3.64 (m, 1H)

Reference Example 44

Synthesis of {(2S)-1-[2-(methylamino)ethyl]pyrrolidin-2-yl}methanol

By using L-prolinol (500 mg) as a starting material, the title compound (0.22 g) was obtained in the same manners as those of Reference Example 1, (1) and Reference Example 39, (2).
MS (ESI) m/z=159.0 [M+H]⁺
¹H-NMR (200 MHz, CDCl₃) δ (ppm): 1.57-2.04 (m, 4H), 2.27-2.42 (m, 1H), 2.42-2.46 (m, 3H), 2.45-2.58 (m, 1H), 2.60-2.75 (m, 3H), 2.76-2.97 (m, 1H), 3.10-3.23 (m, 1H), 3.31-3.43 (m, 1H), 3.54-3.64 (m, 1H)

Reference Example 45

Synthesis of 2-[(2R)-2-(methoxymethyl)pyrrolidin-1-yl]-N-methylethanamine

By using O-methyl-D-prolinol (500 mg) as a starting material, the title compound (0.45 g) was obtained in the same manners as those of Reference Example 1, (1) and Reference Example 39, (2).
MS (ESI) m/z=173.1 [M+H]⁺
¹H-NMR (200 MHz, CDCl₃) δ (ppm): 1.58-1.96 (m, 4H), 2.12-2.26 (m, 1H), 2.33-2.47 (m, 4H), 2.54-2.72 (m, 3H), 2.94-3.17 (m, 2H), 3.20-3.43 (m, 2H), 3.35 (s, 3H)

Reference Example 46

Synthesis of (3R)-1-[2-(methylamino)ethyl]pyrrolidin-3-ol

By using (R)-3-hydroxypyrrolidine (2.0 g) as a starting material, the title compound (210 mg) was obtained in the same manners as those of Reference Example 1, (1) and Reference Example 19, (3).
MS (ESI) m/z=145.0 [M+H]⁺

Reference Example 47

Synthesis of (3S)-1-[2-(methylamino)ethyl]pyrrolidin-3-ol

By using (S)-3-hydroxypyrrolidine (1.0 g) as a starting material, the title compound (195 mg) was obtained in the same manners as those of Reference Example 1, (1) and Reference Example 19, (3).
MS (ESI) m/z=145.0 [M+H]⁺

Reference Example 48

Synthesis of (3R)—N,N-dimethyl-1-[2-(methylamino)ethyl]pyrrolidin-3-amine

By using (3R)-(+)-3-(dimethylamino)pyrrolidine (200 mg) as a starting material, the title compound (123 mg) was obtained in the same manners as those of Reference Example 1, (1) and Reference Example 19, (3).
MS (ESI) m/z=172.1 [M+H]⁺

$^1$H-NMR (200 MHz, CDCl$_3$) δ (ppm): 1.59-1.80 (m, 1H), 1.86-2.07 (m, 1H), 2.21 (s, 6H), 2.26-2.89 (m, 9H), 2.44 (s, 3H)

Reference Example 49

Synthesis of (3S)—N,N-dimethyl-1-[2-(methylamino)ethyl]pyrrolidin-3-amine

By using (3S)-(−)-3-(dimethylamino)pyrrolidine (200 mg) as a starting material, the title compound (80 mg) was obtained in the same manners as those of Reference Example 1, (1) and Reference Example 19, (3).
MS (ESI) m/z=172.1 [M+H]$^+$
$^1$H-NMR (200 MHz, CDCl$_3$) δ (ppm): 1.59-2.12 (m, 2H), 2.21 (s, 6H), 2.27-2.88 (m, 9H), 2.44 (s, 3H)

Reference Example 50

Synthesis of 2-{(2R)-2-[(dimethylamino)methyl]pyrrolidin-1-yl}-N-methylethanamine (1) By using N-carbobenzyloxy-D-proline (3.0 g) and 50% aqueous dimethylamine (2.5 ml) as starting materials, an amide compound (1.23 g) was obtained in the same manners as those of Reference Example 34, (1) and Reference Example 7, (2).
(2) By using the compound obtained in (1) mentioned above (500 mg) as a starting material, an amine compound was obtained in the same manner as that of Reference Example 18, (2).
(3) By using the compound obtained in (2) mentioned above as a starting material, the title compound (0.17 g) was obtained in the same manners as those of Reference Example 1, (1) and Reference Example 39, (2).
MS (ESI) m/z=186.1 [M+H]$^+$
$^1$H-NMR (600 MHz, CDCl$_3$) δ (ppm): 1.54-1.62 (m, 1H), 1.70-1.77 (m, 2H), 1.93-2.01 (m, 1H), 2.11-2.22 (m, 2H), 2.23 (s, 6H), 2.31-2.37 (m, 2H), 2.43-2.51 (m, 4H), 2.62-2.73 (m, 2H), 2.99-3.05 (m, 1H), 3.09-3.13 (m, 1H)

Reference Example 51

Synthesis of 2-[(3R)-3-methoxypyrrolidin-1-yl]-N-methylethanamine (1) (R)-3-Hydroxypyrrolidine (0.65 g) was dissolved in chloroform (16 ml), saturated aqueous sodium hydrogencarbonate (16 ml) and di-t-butyl dicarbonate (2.45 g) were added to the solution, and the resulting mixture was stirred at room temperature for 16 hours. The layers of the reaction mixture were separated, and the organic layer was dried over anhydrous sodium sulfate, and filtered. The filtrate was concentrated under reduced pressure, and the resulting residue was purified by silica gel column chromatography (chloroform to chloroform:methanol:28% aqueous ammonia=10:1:0.1) to obtain a protected compound (1.51 g).
(2) By using the compound obtained in (1) mentioned above as a starting material, a deprotected compound (0.13 g) was obtained in the same manners as those of Reference Example 8, (2) and Reference Example 39, (2).
(3) By using the compound obtained in (2) mentioned above (0.13 g) as a starting material, the title compound (0.10 g) was obtained in the same manners as those of Reference Example 1, (1) and Reference Example 39, (2).
MS (ESI) m/z=159.2 [M+H]$^+$ Reference Example 52

Synthesis of 2-[(2S)-2-(methoxymethyl)pyrrolidin-1-yl]-N-methylethanamine (1) By using L-prolinol (0.5 g) as a starting material, a deprotected compound (0.31 g) was obtained in the same manners as those of Reference Example 51, (1), Reference Example 8, (2) and Reference Example 39, (2).
(2) By using the compound obtained in (1) mentioned above (0.31 g) as a starting material, the title compound (0.32 g) was obtained in the same manners as those of Reference Example 1, (1) and Reference Example 39, (2).
MS (ESI) m/z=173.2 [M+H]$^+$ Reference Example 53

Synthesis of N-methyl-2-[(2S)-2-methylpyrrolidin-1-yl]ethanamine

By using (S)-2-methyl-pyrrolidine (250 mg) as a starting material, the title compound (0.34 g) was obtained in the same manners as those of Reference Example 1, (1) and Reference Example 39, (2).
MS (ESI) m/z=143.2 [M+H]$^+$
$^1$H-NMR (200 MHz, CDCl$_3$) δ (ppm): 1.08 (d, J=6.15 Hz, 3H), 1.32-1.46 (m, 1H), 1.62-2.36 (m, 6H), 2.45 (s, 3H), 2.65-2.75 (m, 2H), 2.86-3.20 (m, 2H)

Reference Example 54

Synthesis of 2-[3-(methoxyimino)pyrrolidin-1-yl]-N-methylethanamine (1) By using (S)-3-hydroxypyrrolidine (1.0 g) as a starting material, an alkyl compound (1.15 g) was obtained in the same manner as that of Reference Example 1, (1).
(2) The compound obtained in (1) mentioned above (1.0 g) was dissolved in chloroform (100 ml), N-ethyl-N'-(3-dimethylaminopropyl)carbodiimide hydrochloride (2.35 g), pyridine trifluoroacetate (2.37 g), and dimethyl sulfoxide (3.16 ml) were added to the solution, and the resulting mixture was stirred at room temperature for 2 hours. Saturated aqueous sodium hydrogencarbonate was added to the reaction mixture, and the layers were separated. The organic layer was dried over anhydrous magnesium sulfate, and filtered. The filtrate was concentrated under reduced pressure, and the resulting residue was purified by silica gel column chromatography (chloroform:methanol:28% aqueous ammonia=20:1:0.1 to 12.5:1:0.1) to obtain a ketone compound (0.50 g).
(3) The compound obtained in (2) mentioned above (0.50 g) was dissolved in pyridine (8.34 ml), O-methylhydroxylamine hydrochloride (861.7 mg) was added to the solution, and the resulting mixture was stirred overnight at room temperature. Distilled water and ethyl acetate were added to the reaction mixture, and the layers were separated. The organic layer was dried over anhydrous magnesium sulfate, and filtered. The filtrate was concentrated under reduced pressure, and the resulting residue was purified by silica gel column chromatography (chloroform:methanol:28% aqueous ammonia=100:1:0.1 to 20:1:0.1) to obtain a methoxime compound.
(4) By using the compound obtained in (3) mentioned above as a starting material, the title compound (254 mg) was obtained in the same manner as that of Reference Example 19, (3).

MS (ESI) m/z=272.3 [M+H]⁺
¹H-NMR (200 MHz, CDCl₃) δ (ppm): 2.48 (s, 3H), 2.51-2.79 (m, 8H), 3.20 (s, 1H), 3.31 (s, 1H), 3.85 (d, J=1.32 Hz, 3H)

Reference Example 55

Synthesis of 2-(2-ethylpyrrolidin-1-yl)-N-methylethanamine (1) Methyl-(2-oxoethyl)-carbamic acid t-butyl ester (280 mg) was dissolved in chloroform (15 ml), 2-ethylpyrrolidine hydrochloride (200 mg), triethylamine (230 μl), and sodium triacetoxyborohydride (773 mg) were added to the solution, and the resulting mixture was stirred at room temperature for 2 hours. Saturated aqueous sodium hydrogencarbonate was added to the reaction mixture, and the layers were separated. The organic layer was dried over anhydrous magnesium sulfate, and filtered. The filtrate was concentrated under reduced pressure, and the resulting residue was purified by silica gel column chromatography (chloroform to chloroform:methanol:28% aqueous ammonia=10:1:0.1) to obtain an alkyl compound (0.46 g).
(2) By using the compound obtained in (1) mentioned above (0.46 g) as a starting material, the title compound (0.15 g) was obtained in the same manner as that of Reference Example 39, (2).

MS (ESI) m/z=157.2 [M+H]⁺
¹H-NMR (200 MHz, CDCl₃) δ (ppm): 0.81-0.94 (m, 3H), 1.09-2.25 (m, 9H), 2.45 (s, 3H), 2.64-2.74 (m, 2H), 2.88-3.20 (m, 2H)

Reference Example 56

Synthesis of 2-(2,5-dimethylpyrrolidin-1-yl)-N-methylethanamine

By using 2,5-dimethylpyrrolidine (200 mg) as a starting material, the title compound (0.17 g) was obtained in the same manners as those of Reference Example 1, (1) and Reference Example 39, (2).

MS (ESI) m/z=157.2 [M+H]⁺
¹H-NMR (200 MHz, CDCl₃) δ (ppm): 1.08 (s, 3H), 1.09-1.12 (m, 3H), 1.32-1.44 (m, 2H), 1.74-1.89 (m, 2H), 2.44 (s, 3H), 2.52-2.67 (m, 6H)

Reference Example 57

Synthesis of 2-(2,2-dimethylpyrrolidin-1-yl)-N-methylethanamine

By using 2,2-dimethylpyrrolidine (1.0 g) as a starting material, the title compound (1.25 g) was obtained in the same manners as those of Reference Example 1, (1) and Reference Example 19, (3).

MS (ESI) m/z=157.2 [M+H]⁺
¹H-NMR (200 MHz, CDCl₃) δ (ppm): 0.97 (s, 6H), 1.53-1.84 (m, 4H), 2.44 (s, 3H), 2.47-2.78 (m, 6H)

Reference Example 58

Synthesis of 2-methoxy-N-[2-(methylamino)ethyl]benzenesulfonamide (1) N-t-Butoxycarbonyl-N-methylethylenediamine (500 mg) and triethylamine (1.2 ml) were dissolved in chloroform (30 ml), 2-methoxybenzenesulfonyl chloride (770.8 mg) was added to the solution, and the resulting mixture was stirred at room temperature for 2 hours. Saturated aqueous sodium hydrogencarbonate was added to the reaction mixture, and the layers were separated. The organic layer was dried over anhydrous magnesium sulfate, and filtered. The filtrate was concentrated under reduced pressure, and the resulting residue was purified by silica gel column chromatography (chloroform:methanol:28% aqueous ammonia=20:1:0.1) to obtain a sulfonamide compound.
(2) The compound obtained in (1) mentioned above was dissolved in methanol (10 ml), a 4 mol/L solution of hydrochloric acid in dioxane (10 ml) was added to the solution, and the resulting mixture was stirred at room temperature for 4 hours. The reaction mixture was concentrated under reduced pressure, and the resulting residue was purified by NH silica gel column chromatography (chloroform to chloroform:methanol:28% aqueous ammonia=10:1:0.1) to obtain the title compound (212 mg).

MS (ESI) m/z=245.1 [M+H]⁺
¹H-NMR (200 MHz, CDCl₃) δ (ppm): 2.31 (s, 3H), 2.62-2.71 (m, 2H), 2.88-2.98 (m, 2H), 3.98 (s, 3H), 6.98-7.14 (m, 2H), 7.54 (ddd, J=8.35, 7.47, 1.76 Hz, 1H), 7.92 (dd, J=7.47, 1.76 Hz, 1H)

Reference Example 59

Synthesis of N-[2-(methylamino)ethyl]methanesulfonamide

By using N-t-butoxycarbonyl-N-methylethylenediamine (500 mg) and methanesulfonyl chloride (289 μl) as starting materials, the title compound (260 mg) was obtained in the same manner as that of Reference Example 58.

¹H-NMR (200 MHz, CDCl₃) δ (ppm): 2.42 (s, 3H), 2.75-2.83 (m, 2H), 2.97 (s, 21H), 3.16-3.24 (m, 2H)

Reference Example 60

Synthesis of N-methyl-3-(morpholin-4-yl)propan-1-amine

By using N-(3-aminopropyl)morpholine (1.0 g) as a starting material, the title compound (57 mg) was obtained in the same manners as those of Reference Example 51, (1), Reference Example 8, (2) and Reference Example 19, (3).

MS (ESI) m/z=159.1 [M+H]⁺
¹H-NMR (200 MHz, CDCl₃) δ (ppm): 1.58-1.77 (m, 2H), 2.32-2.50 (m, 9H), 2.62 (t, J=7.03 Hz, 2H), 3.65-3.76 (m, 4H)

Reference Example 61

Synthesis of N,N,N'-trimethylpropane-1,2-diamine

By using N,N-dimethylpropane-1,2-diamine (2.0 g) as a starting material, the title compound (493 mg) was obtained in the same manners as those of Reference Example 51, (1) and Reference Example 18, (2).

MS (ESI) m/z=117.0 [M+H]⁺
¹H-NMR (200 MHz, CDCl₃) δ (ppm): 0.98 (d, J=6.15 Hz, 3H), 1.97-2.08 (m, 2H), 2.21 (s, 6H), 2.41 (d, J=0.88 Hz, 3H), 2.50-2.68 (m, 1H)

Reference Example 62

Synthesis of
N-ethyl-N,N'-dimethylethane-1,2-diamine

By using N-ethylmethylamine (682.7 mg) as a starting material, the title compound (62 mg) was obtained in the same manners as those of Reference Example 1, (1) and Reference Example 19, (3).
MS (ESI) m/z=117.0 [M+H]$^+$
$^1$H-NMR (200 MHz, CDCl$_3$) δ (ppm): 1.05 (t, J=7.25 Hz, 3H), 2.21 (s, 3H), 2.36-2.52 (m, 6H), 2.61-2.70 (m, 2H)

Reference Example 63

Synthesis of 4-[4-(pyridin-3-yl)-1H-imidazol-1-yl] butan-1-amine (1) 70% Sodium hydride (827 mg) was suspended in dimethylformamide (20 ml), a solution of 4-(3-pyridinyl)-1H-imidazole (3.0 g) obtained by the method described in the publication (International Patent Publication WO00/02875) in dimethylformamide (10 ml) was added to the suspension under ice cooling, and the resulting mixture was stirred at the same temperature for 5 minutes. A solution of N-(4-bromobutyl)phthalimide (5.84 g) in dimethylformamide (10 ml) was added to the reaction mixture, and the resulting mixture was stirred at 60° C. for 4 hours. Distilled water was added to the reaction mixture, and the resulting mixture was extracted with ethyl acetate. The organic layer was washed with aqueous sodium hydrogencarbonate, dried over anhydrous magnesium sulfate, and filtered. The filtrate was concentrated under reduced pressure, the resulting residue was dissolved in ethyl acetate, and hexane was added to the solution to deposit a solid. The deposited solid was collected by filtration to obtain a phthalimide compound (3.16 g).
(2) By using the compound obtained in (1) mentioned above (3.16 g) as a starting material, the title compound (1.94 g) was obtained in the same manner as that of Reference Example 9, (2).
MS (ESI) m/z=217.0 [M+H]$^+$
$^1$H-NMR (200 MHz, CDCl$_3$) δ (ppm): 1.39-1.57 (m, 2H), 1.81-1.99 (m, 2H), 2.75 (t, J=6.81 Hz, 2H), 4.01 (t, J=7.03 Hz, 2H), 7.28-7.35 (m, 2H), 7.54 (d, J=1.32 Hz, 1H), 8.09 (dt, J=7.90, 2.00 Hz, 1H), 8.47 (dd, J=4.83, 1.76 Hz, 1H), 8.92-8.99 (m, 1H)

Reference Example 64

Synthesis of
4-(4-methyl-1H-imidazol-1-yl)butan-1-amine (1) 4-Methylimidazole (5.0 g) and N-(4-bromobutyl)phthalimide (17.2 g) were dissolved in dimethylformamide (250 ml), triethylamine (25.5 ml) was added to the solution, and the resulting mixture was stirred at 120° C. for 3 hours. The reaction mixture was left to cool to room temperature, then ethyl acetate and distilled water were added to the reaction mixture, and the layers were separated. The organic layer was washed with distilled water, dried over anhydrous magnesium sulfate, and filtered. The filtrate was concentrated under reduced pressure, and the resulting residue was dissolved in ethyl acetate. The reaction mixture was stirred, the deposited solid was removed by filtration, and the resulting filtrate was concentrated under reduced pressure. The resulting residue was purified by silica gel column chromatography (ethyl acetate:methanol=20:1). A mixed solution of ethyl acetate and hexane was added to the resulting roughly purified product, and the resulting mixture was stirred with heating to dissolve the roughly purified product, and then gradually cooled to room temperature to deposit a solid. The deposited solid was collected by filtration to obtain a phthalimide compound (324 mg).
(2) By using the compound obtained in (1) mentioned above (324 mg) as a starting material, the title compound (183 mg) was obtained in the same manner as that of Reference Example 9, (2).
MS (ESI) m/z=154.2 [M+H]$^+$
$^1$H-NMR (200 MHz, CDCl$_3$) δ (ppm): 1.33-1.55 (m, 2H), 1.70-1.90 (m, 2H), 2.22 (s, 3H), 2.71 (t, J=7.00 Hz, 2H), 3.87 (t, J=7.03 Hz, 2H), 6.61 (s, 1H), 7.34 (s, 1H)

Reference Example 65

Synthesis of 4-(1H-imidazol-1-yl)butan-1-amine

By using imidazole (2.00 g) as a starting material, the title compound (0.37 g) was obtained in the same manners as those of Reference Example 63, (1) and Reference Example 9, (2).
MS (ESI) m/z=140.2 [M+H]$^+$
$^1$H-NMR (200 MHz, CDCl$_3$) δ (ppm): 1.36-1.54 (m, 2H), 1.75-1.93 (m, 2H), 2.73 (t, J=7.03 Hz, 2H), 3.96 (t, J=7.03 Hz, 2H), 6.91 (s, 1H), 7.06 (s, 1H), 7.47 (s, 1H)

Reference Example 66

Synthesis of N-phenyl-β-alaninamide Hydrochloride (1) β-alanine (3.0 g) was dissolved in chloroform (50 ml), 5% aqueous sodium hydroxide (50 ml) and a solution of di-t-butyl dicarbonate (7.3 g) in chloroform were added to the solution, and the resulting mixture was stirred at room temperature for 3 hours. The reaction mixture was concentrated under reduced pressure, 1 N hydrochloric acid was added to the resulting residue to make the residue acidic, and the aqueous layer was extracted with ethyl acetate. The organic layer was dried over anhydrous magnesium sulfate, and filtered, and the filtrate was concentrated under reduced pressure. Hexane was added to the resulting residue to deposit a solid, and the deposited solid was collected by filtration to obtain a protected compound (365 mg).
(2) The compound obtained in (1) mentioned above (150 mg) was dissolved in chloroform (2 ml), 4-dimethylaminopyridine (145 mg), aniline (110 mg), and N-ethyl-N'-(3-dimethylaminopropyl)carbodiimide hydrochloride (228 mg) were added to the solution, and the resulting mixture was stirred overnight at room temperature. The reaction mixture was concentrated under reduced pressure, and the resulting residue was purified by silica gel column chromatography (hexane:ethyl acetate=1:1) to obtain an amide compound.
(3) The compound obtained in (2) mentioned above was dissolved in a 4 mol/L solution of hydrochloric acid in dioxane (6 ml), and the solution was stirred overnight at room temperature. The reaction mixture was concentrated under reduced pressure, methanol was added to the resulting residue, and the resulting mixture was concentrated under reduced pressure to obtain the title compound (130 mg).
MS (ESI) m/z=165.2 [M+H]$^+$ ¹H-NMR (200 MHz, CDCl₃) δ (ppm): 2.68-2.94 (m, 2H), 3.12-3.26 (m, 2H), 7.03-7.72 (m, 5H)

Reference Example 67

Synthesis of N-phenylpropane-1,3-diamine Hydrochloride (1) 3-(t-Butoxycarbonylamino)-1-propanol (500 mg) was dissolved in chloroform (20 ml), the Dess-Martin reagent (1.21 g) was added to the solution, and the resulting mixture was stirred at room temperature for 30 minutes. Saturated aqueous sodium hydrogencarbonate and aqueous sodium thiosulfate were added to the reaction mixture, and the layers were separated. The organic layer was dried over anhydrous magnesium sulfate, and filtered. The filtrate was concentrated under reduced pressure, and the resulting residue was purified by silica gel column chromatography (hexane:ethyl acetate=1:1) to obtain an aldehyde compound.
(2) By using the compound obtained in (1) mentioned above and aniline (398 mg) as starting materials, the title compound (424 mg) was obtained in the same manners as those of Reference Example 1, (1) and Reference Example 66, (3).
MS (ESI) m/z=151.2 [M+H]⁺
¹H-NMR (200 MHz, DMSO$_{d-6}$) δ (ppm): 1.85-2.19 (m, 2H), 2.78-3.03 (m, 2H), 3.30 (t, J=7.47 Hz, 2H), 7.09-7.64 (m, 5H)

Reference Example 68

Synthesis of 6-[(4-aminobutyl)amino]pyridine-3-carbonitrile

6-Chloro-3-pyridinecarbonitrile (5.0 g) was dissolved in 1,4-diaminobutane (50 ml), and the solution was stirred at 170° C. for 2 hours with heating. Diethyl ether and distilled water were added to the reaction mixture, the layers were separated, and the aqueous layer was extracted with diethyl ether. The aqueous layer was saturated with sodium chloride, and the resulting mixture was extracted with chloroform. The resulting organic layer was dried over anhydrous magnesium sulfate, and filtered, and the filtrate was concentrated under reduced pressure to obtain the title compound (4.77 g).
MS (ESI) m/z=191.2 [M+H]⁺
¹H-NMR (600 MHz, CDCl₃) δ (ppm): 1.50-1.60 (m, 2H), 1.64-1.73 (m, 2H), 2.64-2.76 (m, 4H), 3.30-3.38 (m, 2H), 5.59 (br. s., 1H), 6.32-6.36 (m, 1H), 7.53 (d, J=8.71 Hz, 1H), 8.33 (d, J=1.83 Hz, 1H)

Reference Example 69

Synthesis of 3-(4-aminobutyl)-1-methylimidazolidine-2,4-dione

By using 1-methylhydantoin (2.8 g) as a starting material, the title compound (1.38 g) was obtained in the same manners as those of Reference Example 63, (1) and Reference Example 9, (2).
MS (ESI) m/z=186.2 [M+H]⁺
¹H-NMR (600 MHz, CDCl₃) δ (ppm): 1.43-1.49 (m, 2H), 1.63-1.69 (m, 2H), 2.72 (t, J=7.11 Hz, 2H), 3.00 (s, 3H), 3.52 (t, J=7.34 Hz, 2H), 3.84-3.86 (m, 2H)

Reference Example 70

Synthesis of 2-(1,1-dioxido-1,2-thiazolidin-2-yl)ethanamine (1) N-t-Butoxycarbonylethylenediamine (1.0 g) and N,N-diisopropylethylamine (1.30 ml) were dissolved in tetrahydrofuran (62 ml), a solution of 3-chloropropanesulfonyl chloride (0.84 ml) in tetrahydrofuran (5 ml) was added dropwise to the solution under ice cooling, and the resulting mixture was stirred at room temperature for 16 hours. Ethyl acetate and distilled water were added to the reaction mixture, and the layers were separated. The organic layer was dried over anhydrous magnesium sulfate, and filtered, and the filtrate was concentrated under reduced pressure to obtain a sulfonamide compound (2.17 g).
(2) The compound obtained in (1) mentioned above (2.17 g) was dissolved in dimethylformamide (75 ml), 70% sodium hydride (0.5 g) was slowly added to the solution under ice cooling, and the resulting mixture was stirred for 3 hours with warming to room temperature. Ethyl acetate was added to the reaction mixture, and the layers were separated. The organic layer was washed with distilled water and saturated aqueous sodium chloride, dried over anhydrous magnesium sulfate, and filtered. The filtrate was concentrated under reduced pressure to obtain a cyclized compound.
(3) By using the compound obtained in (2) mentioned above as a starting material, the title compound (0.89 g) was obtained in the same manner as that of Reference Example 1, (2).
MS (ESI) m/z=165.1 [M+H]⁺
¹H-NMR (600 MHz, CDCl₃) δ (ppm): 2.35-2.41 (m, 2H), 2.86-2.98 (m, 2H), 3.09-3.13 (m, 2H), 3.16-3.20 (m, 2H), 3.28-3.32 (m, 2H)

Reference Example 71

Synthesis of 2-(1H-tetrazol-5-yl)ethanamine (1) 3-Aminopropionitrile (2.00 g) was dissolved in tetrahydrofuran (40 ml), an aqueous solution (40 ml) of sodium hydroxide (0.68 g) and benzyl chloroformate (5.0 ml) were added to the solution, and the resulting mixture was stirred at room temperature for 1.75 hours. An aqueous solution (20 ml) of sodium hydroxide (0.8 g) was added to the reaction mixture, and the resulting mixture was stirred at room temperature for 4 hours. Ethyl acetate was added to the reaction mixture, and the layers were separated. The organic layer was dried over anhydrous magnesium sulfate, and filtered, and the filtrate was concentrated under reduced pressure to obtain a protected compound (6.20 g).
(2) The compound obtained in (1) mentioned above (2.00 g) was dissolved in toluene (90 ml), sodium azide (1.27 g) and triethylamine hydrochloride (2.70 g) were added to the solution, and the resulting mixture was stirred with heating at 100° C. for 22 hours. Distilled water was added to the reaction mixture, the layers were separated, and 1 N hydrochloric acid was added to the aqueous layer to make the aqueous layer acidic and thereby deposit a solid. The deposited solid was collected by filtration to obtain a cyclized compound (1.28 g).
(3) By using the compound obtained in (2) mentioned above (1.28 g) as a starting material, the title compound (877 mg) was obtained in the same manner as that of Reference Example 7, (2).
MS (ESI) m/z=114.1 [M+H]⁺
¹H-NMR (200 MHz, CD₃OD) δ (ppm): 3.38-3.67 (m, 2H), 4.82-5.15 (m, 2H)

Reference Example 72

Synthesis of N-[(2S)-1-amino-3-(benzyloxy)propan-2-yl]methanesulfonamide (1) By using O-benzyl-N-(t-butoxycarbonyl)-D-serine (2.74 g) and 28% aqueous ammonia (6.3 ml) as starting materials, an amide compound (1.96 g) was obtained in the same manner as that of Reference Example 34, (1).

(2) The compound obtained in (1) mentioned above (1.96 g) was dissolved in ethanol (15 ml), concentrated hydrochloric acid (5 ml) was added to the solution, and the resulting mixture was stirred at room temperature for 18 hours. Concentrated hydrochloric acid (2 ml) was added to the reaction mixture, and the resulting mixture was stirred at 55° C. for 4 hours. 15% aqueous sodium hydroxide and chloroform were added to the reaction mixture, and the layers were separated. The organic layer was dried over anhydrous magnesium sulfate, and filtered. The filtrate was concentrated under reduced pressure, and the resulting residue was purified by silica gel column chromatography (chloroform to chloroform:methanol:28% aqueous ammonia=10:1:0.1) to obtain a deprotected compound (0.93 g).

(3) The compound obtained in (2) mentioned above (0.93 g) was dissolved in tetrahydrofuran (50 ml), triethylamine (1.2 ml) and methanesulfonyl chloride (0.69 ml) were added to the solution, and the resulting mixture was stirred at room temperature for 3 hours. Saturated aqueous sodium hydrogencarbonate and chloroform were added to the reaction mixture, and the deposit was collected by filtration. The filtrate was extracted with chloroform, and the resulting organic layer was washed with saturated aqueous ammonium chloride and saturated aqueous sodium chloride, dried over anhydrous magnesium sulfate, and filtered. The filtrate was concentrated under reduced pressure, and the resulting residue and the aforementioned deposit were combined, and washed with chloroform to obtain a sulfonamide compound (1.11 g).

(4) By using the compound obtained in (3) mentioned above (1.11 g) as a starting material, the title compound (0.29 g) was obtained in the same manner as that of Reference Example 18, (2).

MS (ESI) m/z=259.2 [M+H]$^+$ $^1$H-NMR (200 MHz, CDCl$_3$) δ (ppm): 2.88 (d, J=4.83 Hz, 2H), 2.97 (s, 3H), 3.48-3.60 (m, 3H), 3.83-3.91 (m, 1H), 4.53 (s, 2H), 7.28-7.39 (m, 5H)

Reference Example 73

Synthesis of (3R)-1-(methylsulfonyl)pyrrolidin-3-amine

By using (R)-(+)-3-(t-butoxycarbonylamino)pyrrolidine (2.0 g) and methanesulfonyl chloride (1 ml) as starting materials, the title compound (0.98 g) was obtained in the same manners as those of Reference Example 58, (1) and Reference Example 39, (2).

MS (ESI) m/z=165.1 [M+H]$^+$

Reference Example 74

Synthesis of (3S)-1-(methylsulfonyl)pyrrolidin-3-amine

By using (S)-(−)-3-(t-butoxycarbonylamino)pyrrolidine (2.0 g) and methanesulfonyl chloride (1 ml) as starting materials, the title compound (1.03 g) was obtained in the same manners as those of Reference Example 58, (1) and Reference Example 39, (2).

MS (ESI) m/z=165.1 [M+H]$^+$

Reference Example 75

Synthesis of 1-[1-(methylsulfonyl)pyrrolidin-3-yl]methanamine

By using 3-(t-butoxycarbonylaminomethyl)pyrrolidine (1.0 g) and methanesulfonyl chloride (0.48 ml) as starting materials, the title compound (0.78 g) was obtained in the same manners as those of Reference Example 58, (1) and Reference Example 39, (2).

MS (ESI) m/z=179.1 [M+H]$^+$ $^1$H-NMR (200 MHz, CDCl$_3$) δ (ppm): 1.59-1.80 (m, 1H), 2.02-2.20 (m, 1H), 2.24-2.42 (m, 1H), 2.72-2.79 (m, 2H), 2.83 (s, 3H), 3.02-3.13 (m, 1H), 3.23-3.57 (m, 3H)

Reference Example 76

Synthesis of 3-(6-amino-9H-purin-9-yl)propane-1-thiol (1) By using adenine (2.7 g) and 1-bromo-3-chloropropane (3.5 g) as starting materials, an alkyl compound (2.61 g) was obtained in the same manner as that of Reference Example 63, (1).

(2) The compound obtained in (1) mentioned above (1.50 g) and potassium thioacetate (0.82 g) were dissolved in acetone (40 ml), and the resulting mixture was stirred under reflux by heating for 10 hours. The reaction mixture was concentrated under reduced pressure, and the resulting residue was purified by silica gel column chromatography (chloroform:methanol=30:1) to obtain a substituted compound (1.76 g).

(3) A 2 mol/L solution of ammonia in methanol (40 ml) was added to the compound obtained in (2) mentioned above (1.0 g), and the resulting mixture was stirred at room temperature for 2 days. The deposit was collected by filtration, and the filtration residue was washed with a mixed solution of chloroform and methanol (10:1) to obtain the title compound (0.46 g).

$^1$H-NMR (600 MHz, DMSO$_{d-6}$) δ (ppm): 2.13-2.21 (m, 1H), 2.47-2.53 (m, 4H), 2.66-2.72 (m, 1H), 4.18-4.25 (m, 1H), 7.17 (s, 1H), 8.13 (d, J=1.83 Hz, 1H)

Reference Example 77

Synthesis of 2-amino-N,N-dimethylethanesulfonamide (1) 2-Phthalimidoethanesulfonyl chloride (3.04 g) was dissolved in tetrahydrofuran (40 ml), 50% aqueous dimethylamine (2.5 ml) was added dropwise to the solution at room temperature, and the resulting mixture was stirred at room temperature for 30 minutes. The reaction mixture was concentrated under reduced pressure, ethyl acetate and saturated aqueous sodium hydrogencarbonate were added to the resulting residue, and the layers were separated. The organic layer was dried over anhydrous sodium sulfate, and filtered. The filtrate was concentrated under reduced pressure, and the resulting residue was purified by silica gel column chromatography (chloroform:methanol=97:1) to obtain a phthalimide compound (1.60 g).

(2) By using the compound obtained in (1) mentioned above (1.58 g) as a starting material, the title compound (840 mg) was obtained in the same manner as that of Reference Example 9, (2).

MS (ESI) m/z=153 [M+H]$^+$ $^1$H-NMR (400 MHz, CDCl$_3$) δ (ppm): 2.89 (s, 6H), 3.05 (t, J=6.0 Hz, 3H), 3.22 (t, J=6.0 Hz, 3H)

Reference Example 78

Synthesis of N-(2-aminoethyl)-N-methylmethanesulfonamide (1) N-Methylethylenediamine (2.12 g) was dissolved in chloroform (21.2 ml), trifluoroacetic acid (2.12 ml) was added to the solution under ice cooling, and dimethylformamide (4 ml) was further added to the mixture. A solution of di-t-butyl dicarbonate (3.26 g) in chloroform (21.2 ml) was added to the reaction mixture, and the resulting mixture was stirred at room temperature for 1.5 hours. Saturated aqueous sodium hydrogencarbonate (20 ml) and potassium carbonate (18 g) were added to the reaction mixture, and the layers were separated. The organic layer was dried over anhydrous sodium sulfate, and filtered. The filtrate was concentrated under reduced pressure, and the resulting residue was purified by silica gel column chromatography (chloroform to chloroform:methanol:28% aqueous ammonia=5:1:0.1) to obtain a protected compound (560 mg).

(2) By using the compound obtained in (1) mentioned above (560 mg) and methane sulfonyl chloride (249 µl) as starting materials, a sulfonamide compound (731 mg) was obtained in the same manner as that of Reference Example 58, (1).

(3) The compound obtained in (2) mentioned above (731 mg) was dissolved in methanol (7.3 ml), 5 N hydrochloric acid (7.3 ml) was added to the solution under ice cooling, and the resulting mixture was stirred at room temperature for 4 hours. The reaction mixture was concentrated under reduced pressure, 8 N aqueous potassium hydroxide (10 ml) and chloroform (10 ml) were added to the resulting residue, and the layers were separated. The organic layer was dried over anhydrous sodium sulfate, and filtered, and then the filtrate was concentrated under reduced pressure to obtain the title compound (409 mg).

MS (ESI) m/z=153 [M+H]$^+$ $^1$H-NMR (400 MHz, CDCl$_3$) δ (ppm): 2.84 (s, 3H), 2.89 (s, 3H), 2.89 (t, J=5.86 2H), 3.18 (t, J=5.86 2H)

Reference Example 79

Synthesis of 3-amino-N,N-dimethylpropanamide (1) N-Carbobenzyloxy-β-alanine (1.50 g) was dissolved in dimethylformamide (40 ml), 50% aqueous dimethylamine (2.4 ml), hydroxybenzotriazole (3.63 g) and N-ethyl-N'-(3-dimethylaminopropyl)-carbodiimide hydrochloride (5.15 g) were added to the solution, and the resulting mixture was stirred at room temperature for 23 hours. Ethyl acetate and 1 N hydrochloric acid were added to the reaction mixture, the layers were separated, and the aqueous layer was extracted with ethyl acetate. The combined organic layer was washed twice with saturated aqueous sodium hydrogencarbonate and twice with saturated aqueous sodium chloride, dried over anhydrous sodium sulfate, and filtered, and then the filtrate was concentrated under reduced pressure to obtain an amide compound (1.57 g).

(2) The compound obtained in (1) mentioned above (1.57 g) was dissolved in ethanol (12 ml) and ethyl acetate (12 ml), 5% palladium/carbon (160 mg) was added to the solution under an argon atmosphere, and the mixture was stirred at room temperature for 4 hours under a hydrogen atmosphere of 1 atm. The reaction mixture was filtered, and then the filtrate was concentrated under reduced pressure to obtain the title compound (825 mg).

MS (ESI) m/z=117 [M+H]$^+$ $^1$H-NMR (400 MHz, CDCl$_3$) δ (ppm): 3.19-3.24 (m, 2H), 3.28-3.33 (m, 2H), 5.21 (brs, 2H)

Reference Example 80

Synthesis of Methyl 2-aminoethyl(methyl)carbamate (1) t-Butyl(2-hydroxyethyl)methylcarbamate (2 g) obtained by the method described in the literature (Synthetic Communications, 1993, p. 2443), phthalimide (2.02 g) and triphenylphosphine (3.59 g) were dissolved in tetrahydrofuran (40 ml), toluene (2 ml) was further added to the solution, and the resulting mixture was cooled on ice. A 2.2 mol/L solution of diethyl azodicarboxylate in toluene (6.23 ml) was added to the reaction mixture, and the resulting mixture was stirred at the same temperature for 1.5 hours. The reaction mixture was warmed to room temperature, and concentrated under reduced pressure, and the resulting residue was purified by silica gel column chromatography (hexane:ethyl acetate=10:1 to 1:1) to obtain a protected compound (2.67 g).

(2) A 5 mol/L solution of hydrochloric acid in methanol (27 ml) and tetrahydrofuran (4 ml) were added to the compound obtained in (1) mentioned above (2.67 g), and the reaction mixture was stirred at 55° C. for 2 hours. The reaction mixture was left to cool, and then concentrated under reduced pressure to obtain a deprotected compound (2.3 g).

(3) The compound obtained in (2) mentioned above (700 mg) was dissolved in chloroform (7 ml), triethylamine (2.03 ml) and methyl chloroformate (270 µl) were added to the solution under ice cooling, and the resulting mixture was stirred at the same temperature for 1 hour. Saturated aqueous ammonium chloride was added to the reaction mixture, and the layers were separated. The organic layer was dried over anhydrous sodium sulfate, and filtered. The filtrate was concentrated under reduced pressure, and the resulting residue was purified by silica gel column chromatography (hexane:ethyl acetate=10:1 to 1:1) to obtain a methoxycarbonyl compound (562 mg).

(4) By using the compound obtained in (3) mentioned above (562 mg) as a starting material, the title compound (99.5 mg) was obtained in the same manner as that of Reference Example 9, (2).

MS (ESI) m/z=133 [M+H]$^+$ $^1$H-NMR (400 MHz, CDCl$_3$) δ (ppm): 2.81-2.89 (m, 2H), 2.89-2.99 (m, 3H), 3.26-3.39 (m, 2H), 3.70 (s, 3H)

Reference Example 81

Synthesis of 2-aminoethanesulfonamide (1) 2-Phthalimidoethanesulfonyl chloride (2.42 g) was dissolved in tetrahydrofuran (40 ml), concentrated aqueous ammonia (1.08 ml) was added dropwise to the solution at room temperature, and the resulting mixture was stirred at room temperature for 30 minutes. Ethyl acetate and saturated aqueous sodium hydrogencarbonate were added to the reaction mixture, and the layers were separated. The organic layer was dried over anhydrous sodium sulfate, and filtered. The filtrate was concentrated under reduced pressure, ethanol (27 ml) and hydrazine monohydrate (593 µl) were added to the resulting residue, and the mixture was stirred under reflux by heating for 3 hours. The reaction mixture was left to cool to room temperature, and filtered thorough Celite, and then the filtrate was concentrated under reduced pressure. Dioxane (20 ml), distilled water (10 ml), triethylamine (2.02 ml) and N-(benzyloxycarbonyl)succinimide (2.69 g) were added to the resulting residue, and the mixture was stirred at room temperature for 1.5 hours. Ethyl acetate and saturated aqueous sodium hydrogencarbonate were added to the reaction mixture, and the layers were separated. The organic layer was dried over anhydrous sodium sulfate, and filtered. The filtrate was concentrated under reduced pressure, and the resulting crystals were collected by filtration to obtain a benzyloxycarbonyl compound (618 mg).

(2) The compound obtained in (1) mentioned above (618 mg) was dissolved in methanol (18 ml), 10% palladium/carbon (120 mg) was added to the solution under an argon atmosphere, and the resulting mixture was stirred at room temperature for 1 hour under a hydrogen atmosphere of 1 atm. The reaction mixture was filtered, and then the filtrate was concentrated under reduced pressure to obtain the title compound (287 mg).
MS (ESI) m/z=125 [M+H]$^+$
$^1$H-NMR (400 MHz, CDCl$_3$) δ (ppm): 3.19-3.24 (m, 2H), 3.28-3.33 (m, 2H), 5.21 (brs, 2H)

Reference Example 82

Synthesis of 2-amino-N-methylethanesulfonamide

By using 2-phthalimidoethanesulfonyl chloride (2.42 g) and a 40% solution of methylamine in methanol (1.48 ml) as starting materials, the title compound (298 mg) was obtained in the same manner as that of Reference Example 81.
MS (ESI) m/z=139 [M+H]$^+$
$^1$H-NMR (400 MHz, DMSO$_{d-6}$) δ (ppm): 2.55 (s, 3H), 2.86 (t, J=6.8 Hz, 2H), 3.05 (t, J=6.8 Hz, 2H)

Reference Example 83

Synthesis of 4-(methylsulfonyl)butan-1-amine (1) Sodium thiomethoxide (300 mg) was dissolved in methanol (20 ml), N-(4-bromobutyl)phthalimide (1.0 g) was added to the solution, and the resulting mixture was stirred at 65° C. for 18 hours. The reaction mixture was concentrated under reduced pressure, ethyl acetate and distilled water were added to the resulting residue, and the layers were separated. The organic layer was washed with saturated aqueous sodium chloride, dried over anhydrous sodium sulfate, and filtered, and then the filtrate was concentrated under reduced pressure to obtain a phthalimide compound (778 mg).
(2) The compound obtained in (1) mentioned above (775 mg) was dissolved in methylene chloride (23 ml), m-chloroperbenzoic acid (2.06 g) was added to the solution under ice cooling, and the resulting mixture was stirred at room temperature for 17 hours. 10% Aqueous sodium thiosulfate was added to the reaction mixture, the layers were separated, and the organic layer was washed with 10% aqueous sodium thiosulfate, saturated aqueous sodium hydrogencarbonate, distilled water, and saturated aqueous sodium chloride. The organic layer was dried over anhydrous sodium sulfate, and filtered, and then the filtrate was concentrated under reduced pressure to obtain an oxidized compound (854 mg).
(3) By using the compound obtained in (2) mentioned above (850 mg) as a starting material, the title compound (256 mg) was obtained in the same manner as that of Reference Example 9, (2).
MS (ESI) m/z=152 [M+H]$^+$
$^1$H-NMR (400 MHz, CD$_3$OD) δ (ppm): 1.64-1.98 (m, 4H), 2.84 (t, J=7.56 Hz, 2H), 2.93 (s, 3H), 3.15 (t, J=7.56 Hz, 2H)

Reference Example 84

Synthesis of 2-(ethylsulfonyl)ethanamine (1) N-(2-Bromoethyl)phthalimide (500 mg) was dissolved in methanol (7 ml), ethyl mercaptan sodium (199 mg) was added to the solution, and the resulting mixture was stirred overnight under reflux by heating. Ethyl acetate and saturated aqueous sodium hydrogencarbonate were added to the reaction mixture, and the layers were separated. The organic layer was washed twice with saturated aqueous sodium hydrogencarbonate, dried over anhydrous sodium sulfate, and filtered, and then the filtrate was concentrated under reduced pressure to obtain a sulfide compound (348 mg).
(2) By using the compound obtained in (1) mentioned above (346 mg) as a starting material, the title compound (200 mg) was obtained in the same manners as those of Reference Example 83, (2) and Reference Example 9, (2).
MS (ESI) m/z=138 [M+H]$^+$
$^1$H-NMR (400 MHz, CDCl$_3$) δ (ppm): 1.42 (t, J=7.6 Hz, 3H), 3.06-3.12 (m, 4H), 3.25-3.29 (m, 2H)

Reference Example 85

Synthesis of 2-amino-N-phenylethanesulfonamide (1) 2-Phthalimidoethanesulfonyl chloride (500 mg) was dissolved in chloroform (5 ml), aniline (448 μl) was added to the solution at room temperature, and the resulting mixture was stirred under reflux by heating for 3 hours. Ethyl acetate, distilled water, and 1 N hydrochloric acid were added to the reaction mixture, and the layers were separated. The organic layer was washed with distilled water, dried over anhydrous sodium sulfate, and filtered, and then the filtrate was concentrated under reduced pressure to obtain a succinimide compound (464 mg).
(2) By using the compound obtained in (1) mentioned above (460 mg) as a starting material, the title compound (239 mg) was obtained in the same manner as that of Reference Example 9, (2).
MS (ESI) m/z=201 [M+H]$^+$
$^1$H-NMR (400 MHz, CDCl$_3$) δ (ppm): 2.86 (t, J=6.8 Hz, 2H), 3.11 (t, J=6.8 Hz, 2H), 7.06 (dt, J=7.2, 1.2 Hz, 1H), 7.16 (dd, J=7.2, 1.2 Hz, 2H), 7.31 (dd, J=7.2, 1.2 Hz, 1H)

Reference Example 86

Synthesis of Sulfamoyl Chloride

Chlorosulfonyl isocyanate (1.22 ml) was dissolved in methylene chloride (3 ml), a solution (3 ml) of formic acid (533 μl) in methylene chloride was added to the solution under ice cooling, and the resulting mixture was slowly warmed to room temperature, and then stirred at 40° C. for 3 hours. The reaction mixture was left to cool to room temperature, and then concentrated under reduced pressure to obtain the title compound (1.68 g).

Reference Example 87

Synthesis of Methylsulfamoyl Chloride

Methylsulfamic acid (2 g) was dissolved in toluene (20 ml), phosphorus pentoxide (3.75 g) was added to the solution under ice cooling, and the resulting mixture was stirred at 80° C. for 30 minutes. The reaction mixture was filtered, then the filtrate was concentrated under reduced pressure, and the resulting residue was distilled under reduced pressure (1.9 mmHg, boiling point: 67° C.) to obtain the title compound (1.2 g).

Reference Example 88

Synthesis of 2-amino-N-benzylacetamide (1) N-(t-Butoxycarbonyl)glycine (1.0 g) and benzylamine (624 μl) were dissolved in chloroform (10 ml), and the solution was cooled on ice. Hydroxybenzotriazole (874 mg) and N-ethyl-N'-(3-dimethylaminopropyl)-carbodiimide hydrochloride (1.09 g) were added to the solution, and the resulting mixture was stirred at room temperature for 19 hours. 1 N Aqueous potassium hydrogensulfate was added to the reaction mixture, the resulting mixture was filtered, and the organic layer was separated. Saturated aqueous sodium hydrogencarbonate was added to the organic layer, and the layers were separated. The organic layer was dried over anhydrous sodium sulfate, and filtered. The filtrate was concentrated under reduced pressure, and the resulting residue was purified by silica gel column chromatography (hexane:ethyl acetate=1:1 to 1:4) to obtain an amide compound (1.6 g).

(2) By using the compound obtained in (1) mentioned above (1.6 g) as a starting material, the title compound (802 mg) was obtained in the same manner as that of Reference Example 78, (3).

MS (ESI) m/z=165 $[M+H]^+$ $^1$H-NMR (400 MHz, $CDCl_3$) δ (ppm): 3.41 (s, 2H), 4.48 (d, J=6.10 Hz, 2H), 7.27-7.37 (m, 5H), 7.59 (s, 1H)

Reference Example 89

Synthesis of 2-aminoacetanilide (1) N-(t-Butoxycarbonyl)glycine (384 mg) and aniline (204 mg) were dissolved in tetrahydrofuran (5 ml), N,N'-dicyclohexylcarbodiimide (471 mg) was added to the solution, and the resulting mixture was stirred overnight at room temperature. Ethyl acetate was added to the reaction mixture, and the resulting mixture was filtered. Then, 0.1 N hydrochloric acid was added to the filtrate, and the layers were separated. The organic layer was washed with saturated aqueous sodium hydrogencarbonate, dried over anhydrous sodium sulfate, and filtered, and then the filtrate was concentrated under reduced pressure to obtain an amide compound (520 mg).

(2) The compound obtained in (1) mentioned above (395 mg) was dissolved in methylene chloride (10 ml), trifluoroacetic acid (5 ml) was added to the solution under ice cooling, and the resulting mixture was stirred at the same temperature for 30 minutes, and then stirred at room temperature for 40 minutes. The reaction mixture was concentrated under reduced pressure, a mixed solution of chloroform and isopropanol (5:1) and saturated aqueous sodium hydrogencarbonate were added to the resulting residue, and the layers were separated. Further, the aqueous layer was extracted twice with a mixed solution of chloroform and isopropanol (5:1). The organic layer was dried over anhydrous sodium sulfate, and filtered, and then the filtrate was concentrated under reduced pressure to obtain the title compound (171 mg).

MS (ESI) m/z=151 $[M+H]^+$ $^1$H-NMR (400 MHz, $CDCl_3$) δ (ppm): 3.48 (s, 2H), 7.08-7.13 (m, 1H), 7.31-7.36 (m, 2H), 7.58-7.62 (m, 2H), 9.40 (brs, 1H)

Reference Example 90

Synthesis of 2-amino-N-(pyridin-3-ylmethyl)acetamide

By using N-(t-butoxycarbonyl)glycine (1.0 g) and 3-picolylamine (577 μl) as starting materials, the title compound (892 mg) was obtained in the same manners as those of Reference Example 88, (1) and Reference Example 78, (3).

MS (ESI) m/z=166 $[M+H]^+$ $^1$H-NMR (400 MHz, $CDCl_3$) δ (ppm): 3.42 (s, 2H), 4.50 (d, J=6.35 Hz, 2H), 7.25-7.29 (m, 1H), 7.63-7.67 (m, 1H), 7.70-7.81 (m, 1H), 8.53 (dd, J=4.88, 1.71 Hz, 1H), 8.56 (d, J=1.71 Hz, 1H)

Reference Example 91

Synthesis of 2-amino-N-(methylsulfonyl)acetamide (1) N-(Benzyloxycarbonyl)glycine (1.0 g) was dissolved in tetrahydrofuran (20 ml), carbonyldiimidazole (780 mg) was added to the solution at room temperature, and the resulting mixture was stirred at room temperature for 30 minutes, and then stirred under reflux by heating for 1 hour. The reaction mixture was left to cool to room temperature, methanesulfonamide (460 mg) was added to the reaction mixture, and the resulting mixture was stirred for 10 minutes. Then, a solution of 1,8-diazabicyclo[5.4.0]-7-undecene (715 μl) in tetrahydrofuran (5 ml) was added to the reaction mixture, and the resulting mixture was further stirred for 21 hours. The reaction mixture was poured into 0.8 N hydrochloric acid under ice cooling, and the resulting precipitates were collected by filtration, and washed with distilled water to obtain a methanesulfonylamide compound (753 mg).

(2) The compound obtained in (1) mentioned above (753 mg) was dissolved in methanol (10 ml), 5% palladium/carbon (100 mg) was added to the solution under an argon atmosphere, and the resulting mixture was stirred at room temperature for 4 hours under a hydrogen atmosphere of 1 atm. The reaction mixture was filtered, and then the filtrate was concentrated under reduced pressure to obtain the title compound (420 mg).

MS (ESI) m/z=153 $[M+H]^+$ $^1$H-NMR (400 MHz, $D_2O$) δ (ppm): 2.92 (s, 3H), 3.49 (S, 2H)

Reference Example 92

Synthesis of 2-amino-N—(N,N-dimethylsulfamoyl)acetamide (1) N-(Benzyloxycarbonyl)glycine (500 mg) was dissolved in tetrahydrofuran (10 ml), carbonyldiimidazole (390 mg) was added to the solution at room temperature, and the resulting mixture was stirred at room temperature for 30 minutes, and then stirred under reflux by heating for 1 hour. The reaction mixture was left to cool to room temperature, N,N-dimethylsulfamide (297 mg) was added to the reaction mixture, and the resulting mixture was stirred for 10 minutes. Then, 1,8-diazabicyclo[5.4.0]-7-undecene (360 μl) was added to the reaction mixture, and the resulting mixture was further stirred for 16 hours. 0.8 N Hydrochloric acid was added to the reaction mixture under ice cooling, and the resulting mixture was extracted with chloroform. The organic layer was washed with distilled water and saturated aqueous sodium chloride, dried over anhydrous sodium sulfate, and filtered. The filtrate was concentrated under reduced pressure, and the resulting residue was purified by silica gel column chromatography (chloroform:methanol=25:1 to 20:1) to obtain a sulfamide compound (640 mg).

(2) By using the compound obtained in (1) mentioned above (635 mg) as a starting material, the title compound (109 mg) was obtained in the same manner as that of Reference Example 91, (2).

MS (ESI) m/z=182 $[M+H]^+$

¹H-NMR (400 MHz, D₂O) δ (ppm): 2.51 (s, 6H), 3.50 (s, 2H)

Reference Example 93

Synthesis of 2-amino-N-benzyl-N-methylacetamide

By using N-(t-butoxycarbonyl)glycine (1.0 g) and N-methylbenzylamine (736 μl) as a starting material, the title compound (740 mg) was obtained in the same manners as those of Reference Example 88, (1) and Reference Example 78, (3).
MS (ESI) m/z=179 [M+H]⁺
¹H-NMR (400 MHz, CDCl₃) δ (ppm): 2.86-3.00 (m, 3H), 3.50-3.52 (m, 2H), 4.46-4.62 (m, 2H), 7.13-7.39 (m, 5H)

Reference Example 94

Synthesis of 2-amino-N-ethylacetamide

By using N-(t-butoxycarbonyl)glycine (384 mg) and 70% aqueous ethylamine (147 μl) as starting materials, the title compound (116 mg) was obtained in the same manner as that of Reference Example 89.
MS (ESI) m/z=103 [M+H]⁺
¹H-NMR (400 MHz, CDCl₃) δ (ppm): 1.17 (t, J=7.2 Hz, 3H), 1.38 (brs, 2H), 3.29-3.37 (m, 4H), 7.20 (brs, 1H)

Reference Example 95

Synthesis of 2-amino-N—(N-methylsulfamoyl)acetamide (1) N-Methylbenzylamine (335 μl) was dissolved in chloroform (6 ml), triethylamine (1.09 ml) was added to the solution, and the resulting mixture was cooled on ice. The compound obtained in Reference Example 86 (600 mg) was added to the reaction mixture, and the resulting mixture was stirred at the same temperature for 1.5 hours. The reaction mixture was warmed to room temperature, 4-dimethylaminopyridine (31.7 mg) was added to the mixture, and the resulting mixture was stirred at room temperature for 19 hours. Then, 1 N hydrochloric acid was added to the reaction mixture, and the layers were separated. The organic layer was dried over anhydrous sodium sulfate, and filtered. The filtrate was concentrated under reduced pressure, and the resulting residue was purified by silica gel column chromatography (hexane:ethyl acetate=10:1 to 1:1) to obtain a sulfamide compound (262 mg).
(2) By using the compound obtained in (1) mentioned above (262 mg) and N-(benzyloxycarbonyl)glycine (273 mg) as starting materials, the title compound (125 mg) was obtained in the same manner as that of Reference Example 91.
MS (ESI) m/z=168 [M+H]⁺
¹H-NMR (400 MHz, D₂O) δ (ppm): 2.44 (s, 3H), 3.55 (s, 2H)

Reference Example 96

Synthesis of (2-methanesulfonylethyl)hydrazine Hydrochloride (1) Methylvinylsulfone (200 mg) was dissolved in tetrahydrofuran (4 ml), t-butyl carbazate (747 mg) and 1,8-diazabicyclo[5.4.0]-7-undecene (844 μl) were added to the solution, and the resulting mixture was stirred at room temperature for 26 hours. Saturated aqueous sodium hydrogencarbonate and chloroform were added to the reaction mixture, the layers were separated, and the organic layer was dried over anhydrous sodium sulfate, and filtered. The filtrate was concentrated under reduced pressure, and the resulting residue was purified by silica gel column chromatography (chloroform to chloroform:methanol:28% aqueous ammonia=10:1:0.1), and then purified again by silica gel column chromatography (ethyl acetate to ethyl acetate:tetrahydrofuran=10:1) to obtain an N-alkyl compound (234 mg).
(2) A 4 mold, solution of hydrochloric acid in dioxane (4.68 ml) was added to the compound obtained in (1) mentioned above (234 mg), methanol (1 ml) and distilled water (800 μl) were further added to the resulting mixture, and the resulting mixture was stirred at room temperature for 3 hours. The reaction mixture was concentrated under reduced pressure to obtain the title compound (180 mg).
MS (ESI) m/z=139 [M+H]⁺
¹H-NMR (400 MHz, CD₃OD) δ (ppm): 3.06 (s, 3H), 3.41 (s, 4H)

Reference Example 97

4-Nitrobenzyl(R)-3-(aminooxy)piperidine-1-carboxylate Hydrochloride (1) (S)-3-Hydroxypiperidine hydrochloride was dissolved in distilled water (2.5 ml), sodium hydrogencarbonate (889 mg) was added to the solution, a solution (2.5 ml) of 4-nitrobenzyl chloroformate (836 mg) in acetone was slowly was added to the mixture at room temperature, and the resulting mixture was stirred for 2 hours. Ethyl acetate and distilled water were added to the reaction mixture, and the layers were separated. The organic layer was dried over anhydrous sodium sulfate, and filtered. The filtrate was concentrated under reduced pressure, and the resulting residue was purified by silica gel column chromatography (hexane to hexane:ethyl acetate=1:2) to obtain a protected compound (971 mg).
(2) The compound obtained in (1) mentioned above (971 mg) was dissolved in tetrahydrofuran, N-hydroxyphthalimide (848 mg) and triphenylphosphine (1.36 g) were added to the solution. Diisopropyl azodicarboxylate (1.02 ml) was added to the reaction mixture under ice cooling, and then the resulting mixture was stirred at room temperature for 1.5 hours. The reaction mixture was concentrated under reduced pressure, and the resulting residue was purified by silica gel column chromatography (hexane to hexane:ethyl acetate=1:2) to obtain a phthalimide compound (1.52 g).
(3) The compound obtained in (2) mentioned above (1.52 g) was dissolved in ethanol (10 ml) and chloroform (10 ml), hydrazine monohydrate (638 μl) was added to the solution under reflux by heating, and the resulting mixture was stirred for 1.5 hours. The reaction mixture was filtered, and the filtrate was concentrated under reduced pressure. The resulting residue was purified by silica gel column chromatography (hexane to hexane:ethyl acetate=1:2), then a 4 mol/L solution of hydrochloric acid in dioxane (866 μl) was added to the purified residue, and the resulting mixture was concentrated under reduced pressure to obtain the title compound (825 mg).
MS (ESI) m/z=296 [M+H]⁺
¹H-NMR (400 MHz, CDCl₃) δ (ppm): 1.40-1.53 (m, 1H), 1.67-1.85 (m, 3H), 314-3.72 (m, 4H), 3.72-4.05 (m, 1H), 5.25 (s, 2H), 5.28-5.49 (m, 2H), 7.48-7.57 (m, 2H), 8.20-8.24 (m, 2H)

Reference Example 98

Synthesis of N,N-diisopropyl-N-methylethane-1,2-diamine (1) N,N-Diisopropylethane-1,2-diamine (3.0 g) was dissolved in chloroform (30 ml), di-t-butyl dicarbonate (4.3 ml)

was added to the solution under ice cooling, and the resulting mixture was stirred overnight at room temperature. The reaction mixture was concentrated under reduced pressure, then ethyl acetate and distilled water were added to the resulting residue, and the layers were separated. The organic layer was washed three times with distilled water, dried over anhydrous sodium sulfate, and filtered, and then the filtrate was concentrated under reduced pressure to obtain a protected compound (4.6 g).

(2) By using the compound obtained in (1) mentioned above (4.6 g) as a starting material, the title compound (2.3 g) was obtained in the same manner as that of Reference Example 18, (2).

MS (ESI) m/z=159 [M+H]$^+$
$^1$H-NMR (400 MHz, CDCl$_3$) δ (ppm): 0.99 (d, J=1.71 Hz, 6H), 1.00 (d, J=1.71 Hz, 6H), 2.43 (s, 3H), 2.54-2.57 (m, 4H), 2.96-3.03 (m, 2H)

Reference Example 99

Synthesis of N-methyl-2-(pyrrolidin-1-yl)ethanamine (1) By using pyrrolidine (0.24 ml) as a starting material, an alkyl compound (475 mg) was obtained in the same manner as that of Reference Example 1, (1).
(2) By using the compound obtained in (1) mentioned above (462 mg) as a starting material, the title compound (183 mg) was obtained in the same manner as that of Reference Example 78, (3).

MS (ESI) m/z=129 [M+H]$^+$
$^1$H-NMR (400 MHz, CDCl$_3$) δ (ppm): 1.75-1.79 (m, 4H), 2.45 (s, 3H), 2.48-2.52 (m, 4H), 2.59 (t, J=6.35 Hz, 2H), 2.70 (t, J=6.35 Hz, 2H)

Reference Example 100

Synthesis of 2-(2-methoxyphenyl)propan-2-amine

2-Methoxybenzonitrile (6 g) was dissolved in diethyl ether (140 ml), a 3 mol/L solution of methyl magnesium bromide in diethyl ether (45 ml) was added to the solution, and the resulting mixture was stirred at room temperature for 1 hour. Titanium tetraisopropoxide (13.1 ml) was added to the reaction mixture, and the resulting mixture was stirred under reflux by heating for 4 hours. 10% Aqueous sodium hydroxide (160 ml) and ethyl acetate (160 ml) were added to the reaction mixture, and the resulting mixture was stirred at room temperature for 1 hour. The reaction mixture was filtered thorough Celite, and then the layers of the filtrate were separated. The aqueous layer was extracted with chloroform, and the organic layer was dried over anhydrous magnesium sulfate, and filtered. The filtrate was concentrated under reduced pressure, and the resulting residue was purified by silica gel column chromatography (chloroform:methanol: 28% aqueous ammonia=40:1:0.1 to 10:1:0.1) to obtain the title compound (2.76 g).

MS (ESI) m/z=166 [M+H]$^+$
$^1$H-NMR (400 MHz, CDCl$_3$) δ (ppm): 1.53 (s, 6H), 3.89 (s, 3H), 6.89-6.94 (m, 2H), 7.19-7.25 (m, 1H), 7.32-7.36 (m, 1H)

Reference Example 101

Synthesis of 2-methoxy-N-methyl-N-[2-(methylamino)ethyl]benzamide (1) By using benzylamine (375 mg) as a starting material, an alkyl compound (440 mg) was obtained in the same manner as that of Reference Example 1, (1).

(2) By using the compound obtained in (1) mentioned above (435 mg) as a starting material, a methyl compound (445 mg) was obtained in the same manner as that of Reference Example 19, (2).
(3) By using the compound obtained in (2) mentioned above (324 mg) as a starting material, a debenzylated compound (207 mg) was obtained in the same manner as that of Reference Example 91, (2).
(4) The compound obtained in (3) mentioned above (201 mg) was dissolved in chloroform (2.5 ml), triethylamine (225 μl) and a solution of 2-methoxybenzoyl chloride (237 mg) in chloroform (1.5 ml) were added to the solution under ice cooling, and the resulting mixture was stirred for 1 hour. Saturated aqueous sodium hydrogencarbonate and ethyl acetate were added to the reaction mixture, and the layers were separated. The organic layer was washed with distilled water and saturated aqueous sodium chloride, dried over anhydrous sodium sulfate, and filtered, then the filtrate was concentrated under reduced pressure, and the resulting residue was purified by silica gel column chromatography (hexane:ethyl acetate=1:1 to 1:4) to obtain an amide compound (335 mg).
(5) The compound obtained in (4) mentioned above (420 mg) was dissolved in methylene chloride (8 anisole (690 μl) and trifluoroacetic acid (1.2 ml) were added to the solution, and the resulting mixture was stirred at room temperature for 3 hours. 5 N Hydrochloric acid and ethyl acetate were added to the reaction mixture, and the layers were separated. The aqueous layer was neutralized with potassium carbonate, and then extracted with chloroform. The organic layer was dried over anhydrous sodium sulfate, and filtered, and then the filtrate was concentrated under reduced pressure to obtain the title compound (270 mg).

MS (ESI) m/z=223 [M+H]$^+$
$^1$H-NMR (200 MHz, CDCl$_3$) δ (ppm): 2.27 and 2.50 (each s, 3H), 2.60-2.73 (m, 1H), 2.85 and 3.12 (each s, 3H), 2.89 and 3.27 (each t, J=6.59 Hz, 3H), 3.83 and 3.84 (each s, 3H), 6.91 (d, J=8.30 Hz, 1H), 6.95-7.03 (m, 1H), 7.18-7.40 (m, 2H)

Reference Example 102

Synthesis of N-ethyl-N-[(1S)-1-(2-methoxyphenyl) ethyl]ethane-1,2-diamine (1) (1S)-1-(2-Methoxyphenyl)ethylamine (8.86 g) obtained by the method described in the publication (Japanese Patent Unexamined Publication No. 54/154724) was dissolved in chloroform (100 ml), acetic anhydride (12.0 g) and 4-dimethylaminopyridine (14.3 g) were added to the solution, and the resulting mixture was stirred at 70° C. for 30 minutes. The reaction mixture was left to cool, and then successively washed with 1 N hydrochloric acid and 10% aqueous sodium hydroxide. The organic layer was dried over anhydrous magnesium sulfate, and filtered, and then the filtrate was concentrated under reduced pressure to obtain an acetyl compound (11.23 g).
(2) By using the compound obtained in (1) mentioned above (11.2 g) as a starting material, an N-ethyl compound (10.86 g) was obtained in the same manner as that of Reference Example 18, (2).
(3) Phthalimidoacetaldehyde (125 mg) obtained by the method described in the literature (Tetrahedron Letters, 2001, vol. 42, p. 315) was dissolved in chloroform (20 ml), the compound obtained in (2) mentioned above (0.6 g) and sodium triacetoxyborohydride (1.06 g) were added to the solution, and the resulting mixture was stirred at room temperature for 2 hours. Saturated aqueous sodium hydrogencarbonate and chloroform were added to the reaction mixture, and the layers were separated. The organic layer was dried over anhydrous magnesium sulfate, and filtered. The filtrate was concentrated under reduced pressure, and the resulting residue was purified by silica gel column chromatography (hexane:ethyl acetate=2:1) to obtain a phthalimide compound (0.93 g).
(4) By using the compound obtained in (3) mentioned above (0.93 g) as a starting material, the title compound (484 mg) was obtained in the same manner as that of Reference Example 9, (2).
MS (ESI) m/z=223.2 [M+H]$^+$
$^1$H-NMR (200 MHz, CDCl$_3$) δ (ppm): 0.98 (t, J=7.03 Hz, 3H), 1.29 (d, J=7.03 Hz, 3H), 2.38-2.72 (m, 6H), 3.82 (s, 3H), 4.37 (q, J=7.03 Hz, 1H), 6.83-6.97 (m, 2H), 7.15-7.25 (m, 1H), 7.36 (dd, J=7.47, 1.76 Hz, 1H)

Reference Example 103

Synthesis of (2R)-2-amino-3-{ethyl[(1S)-1-(2-methoxyphenyl)ethyl]amino}propan-1-ol (1) N-t-Butoxycarbonyl-O-benzyl-(L)-serine (2.14 g) and hydroxybenzotriazole (980 mg) were dissolved in dimethylformamide (20 ml), dicyclohexylcarbodiimide (1.50 g) was added to the solution, and the resulting mixture was stirred at room temperature for 5 minutes. Then, the compound obtained in Reference Example 102, (2) (1.0 g) was added to the reaction mixture, and the resulting mixture was stirred at room temperature for 5 hours. Ethyl acetate was added to the reaction mixture, the resulting mixture was filtered, and the filtrate was concentrated under reduced pressure. Ethyl acetate and saturated aqueous sodium hydrogencarbonate were added to the resulting residue, and the layers were separated. The organic layer was washed with saturated aqueous sodium hydrogencarbonate and saturated aqueous sodium chloride, then dried over anhydrous sodium sulfate, and filtered. The filtrate was concentrated under reduced pressure, and the resulting residue was purified by silica gel column chromatography (hexane alone to hexane:ethyl acetate=4:1) to obtain an amide compound (1.76 g).
(2) By using the compound obtained in (1) mentioned above (197 mg) as a starting material, a debenzylated compound (155 mg) was obtained in the same manner as that of Reference Example 81, (2).
(3) By using the compound obtained in (2) mentioned above (155 mg) as a starting material, the title compound (68.6 mg) was obtained in the same manners as those of Reference Example 101, (5) and Reference Example 18, (2).
MS (FAB) m/z=253 [M+H]$^+$
$^1$H-NMR (400 MHz, CDCl$_3$) δ (ppm): 1.06 (t, J=7.1 Hz, 3H), 1.36 (d, J=6.8 Hz, 1H), 2.37-2.57 (m, 3H), 2.63-2.75 (m, 1H), 3.02-3.11 (m, 1H), 3.47-3.58 (m, 2H), 3.83 (s, 3H), 4.45 (q, J=6.8 Hz, 1H), 6.88 (d, J=8.3 Hz, 1H), 6.96 (dt, J=7.6, 1.0 Hz, 1H), 7.21-7.31 (m, 2H)

Reference Example 104

Synthesis of N-[2-(2-methoxyphenyl)propan-2-yl]-N,N'-dimethylethane-1,2-diamine (1) By using the compound obtained in Reference Example 100 (1.50 g) as a starting material, an alkyl compound (1.24 g) was obtained in the same manner as that of Reference Example 1, (1).
(2) By using the compound obtained in (1) mentioned above (300 mg) as a starting material, an alkyl compound (299 mg) was obtained in the same manner as that of Reference Example 19, (2).
(3) The compound obtained in (2) mentioned above (295 mg) was dissolved in methanol (2 ml), a 5 to 10% solution of hydrochloric acid in methanol (5 ml) was added to the solution, and the resulting mixture was stirred at room temperature for 1 day. 10 N Aqueous sodium hydroxide was added to the reaction mixture, and the resulting mixture was extracted with chloroform. The organic layer was concentrated under reduced pressure, and the resulting residue was purified by silica gel column chromatography (chloroform:methanol:28% aqueous ammonia=10:1:0.1) to obtain the title compound (130.5 mg).
MS (ESI) m/z=237.2 [M+H]$^+$
$^1$H-NMR (200 MHz, CDCl$_3$) δ (ppm): 1.45 (s, 6H), 2.13 (s, 3H), 2.36 (s, 3H), 2.48-2.63 (m, 4H), 3.82 (s, 3H), 6.83-6.95 (m, 2H), 7.14-7.25 (m, 1H), 7.41 (dd, J=7.91, 1.76 Hz, 1H)

Reference Example 105

Synthesis of N-[2-(2-methoxypyridin-3-yl)propan-2-yl]-N,N'-dimethylethane-1,2-diamine (1) 2-Chloro-3-cyanopyridine (10.0 g) was dissolved in methanol (200 ml), a 28% solution of sodium methoxide in methanol (27.8 g) was added to the solution, and the resulting mixture was stirred at room temperature for 18 hours. The reaction mixture was filtered, and then concentrated under reduced pressure, and the deposited crystals were collected by filtration to obtain a methoxy compound (4.15 g).
(2) By using the compound obtained in (1) mentioned above (4.15 g) as a starting material, a dimethyl compound (350 mg) was obtained in the same manner as that of Reference Example 100.
(3) By using the compound obtained in (2) mentioned above (50 mg) as a starting material, an alkyl compound (53.8 mg) was obtained in the same manner as that of Reference Example 1, (1).
(4) By using the compound obtained in (3) mentioned above (290 mg) as a starting material, the title compound (46.3 mg) was obtained in the same manners as those of Reference Example 19, (2) and Reference Example 104, (3).
MS (ESI) m/z=238.2 [M+H]$^+$
$^1$H-NMR (200 MHz, CDCl$_3$) δ (ppm): 1.43 (s, 6H), 2.14 (s, 3H), 2.39 (s, 3H), 2.47-2.69 (m, 4H), 3.96 (s, 3H), 6.84 (dd, J=7.47, 4.83 Hz, 1H), 7.69 (dd, J=7.47, 2.20 Hz, 1H), 8.04 (dd, J=4.83, 2.20 Hz, 1H)

Reference Example 106

Synthesis of N-[2-(2-methoxyphenyl)propan-2-yl]ethane-1,2-diamine

By using the compound obtained in Reference Example 100 (480 mg) as a starting material, the title compound (34.7 mg) was obtained in the same manners as those of Reference Example 102, (3) and Reference Example 9, (2).
MS (ESI) m/z=209.0 [M+H]$^+$
$^1$H-NMR (600 MHz, CDCl$_3$) δ (ppm): 1.50 (s, 6H), 2.24 (t, J=6.19 Hz, 2H), 2.70 (t, J=6.19 Hz, 2H), 3.85 (s, 3H), 6.86-6.94 (m, 2H), 7.19-7.25 (m, 2H)

Reference Example 107

Synthesis of (2S)—N-[2-(2-methoxyphenyl)propan-2-yl]-N-methylpropane-1,2-diamine (1) By using the compound obtained in Reference Example 100 (1.18 g) and N-t-butoxycarbonyl-(L)-alanine (2.70 g) as starting materials, an amide compound (1.00 g) was obtained in the same manner as that of Reference Example 88, (1).

(2) The compound obtained in (1) mentioned above (1.00 g) was dissolved in tetrahydrofuran (15 ml), a 1 mol/L solution of borane/tetrahydrofuran complex in tetrahydrofuran (15 ml) was added to the solution under ice cooling, and the resulting mixture was stirred overnight at room temperature. Methanol was added to the reaction mixture under ice cooling, the resulting mixture was concentrated under reduced pressure, and the resulting residue was purified by silica gel column chromatography (chloroform:methanol:28% aqueous ammonia=40:1:0.1 to 20:1:0.1) to obtain a reduced compound (241 mg).

(3) By using the compound obtained in (2) mentioned above (82.8 mg) as a starting material, the title compound (21.8 mg) was obtained in the same manners as those of Reference Example 19, (2) and Reference Example 104, (3).

MS (ESI) m/z=237.2 [M+H]$^+$ $^1$H-NMR (600 MHz, CDCl$_3$) δ (ppm): 0.94 (d, J=6.42 Hz, 3H), 1.44 (s, 6H), 1.70 (br s., 2H), 2.10 (s, 3H), 2.13 (dd, J=12.38, 3.67 Hz, 1H), 2.19-2.26 (m, 1H), 2.87-2.96 (m, 1H), 3.80 (s, 3H), 6.85-6.90 (m, 2H), 7.16-7.22 (m, 1H), 7.34-7.38 (m, 1H)

Reference Example 108

Synthesis of (2S)—N-[2-(2-methoxypyridin-3-yl)propan-2-yl]-N-methylpropane-1,2-diamine By using the compound obtained in Reference Example 105, (2) (604 mg) and N-t-butoxycarbonyl-(L)-alanine (1.37 g) as starting materials, the title compound (23.2 mg) was obtained in the same manners as those of Reference Example 103, (1), Reference Example 107, (2), Reference Example 19, (2), and Reference Example 89, (2).

MS (ESI) m/z=238.2 [M+H]$^+$ $^1$H-NMR (600 MHz, CDCl$_3$) δ (ppm): 0.95 (d, J=5.96 Hz, 3H), 1.41 (s, 6H), 2.10 (s, 3H), 2.11-2.26 (m, 2H), 2.84-3.03 (m, 1H), 3.92 (s, 3H), 6.82 (dd, J=7.57, 4.81 Hz, 1H), 7.64 (dd, J=7.57, 1.83 Hz, 1H), 8.03 (dd, J=4.81, 1.83 Hz, 1H)

Reference Example 109

Synthesis of N,N'-dimethyl-N'-(2-phenylpropan-2-yl)ethane-1,2-diamine (1) By using 2-phenylpropan-2-amine (270 mg) as a starting material, an amine compound (505 mg) was obtained in the same manner as that of Reference Example 1, (1).

(2) By using the compound obtained in (1) mentioned above (200 mg) as a starting material, the title compound (110 mg) was obtained in the same manners as those of Reference Example 19, (2) and Reference Example 101, (5).

MS (ESI) m/z=207 [M+H]$^+$ $^1$H-NMR (400 MHz, CDCl$_3$) δ (ppm): 1.35 (s, 6H), 2.15 (s, 3H), 2.33 (s, 3H), 2.43 (t, J=5.98 Hz, 2H), 2.58 (t, J=5.98 Hz, 2H), 7.17-7.22 (m, 1H), 7.27-7.33 (m, 2H), 7.47-7.52 (m, 2H)

Reference Example 110

Synthesis of (2R)-3-(dimethylamino)-2-(methylamino)propan-1-ol

By using N-(t-butoxycarbonyl)-O-benzyl-(L)-serine (2.50 g) and 50% aqueous dimethylamine (3 ml) as starting materials, the title compound (0.58 g) was obtained in the same manners as those of Reference Example 34, (1), Reference Example 107, (2) and Reference Example 7, (2).

MS (ESI) m/z=132.9 [M+H]$^+$ $^1$H-NMR (600 MHz, CDCl$_3$) δ (ppm): 2.33 (s, 6H), 2.35-2.39 (m, 1H), 2.70-2.76 (m, 4H), 2.97-3.04 (m, 1H), 3.73 (dd, J=13.30, 5.96 Hz, 1H), 3.90 (dd, J=13.30, 3.21 Hz, 1H)

Reference Example 111

Synthesis of 3-(methylsulfinyl)propan-1-amine Hydrochloride (1) By using 3-(methylthio)propylamine (25 g) as a starting material, a protected compound (54.0 g) was obtained in the same manner as that of Reference Example 8, (1).

(2) The compound obtained in (1) mentioned above (3.0 g) was dissolved in chloroform (300 ml), m-chloroperbenzoic acid (3.88 g) was added portionwise to the solution under ice cooling, and the resulting mixture was stirred at the same temperature for 2 hours. 25% Aqueous sodium hydroxide was added to the reaction mixture, and the layers were separated. The organic layer was dried over anhydrous sodium sulfate, and filtered. The filtrate was concentrated under reduced pressure, and the resulting residue was purified by silica gel column chromatography (chloroform:methanol:28% aqueous ammonia=200:1:0.1 to 50:1:0.1) to obtain an oxidized compound (2.59 g).

(3) By using the compound obtained in (2) mentioned above (2.5 g) as a starting material, the title compound (1.57 g) was obtained in the same manner as that of Reference Example 66, (3).

$^1$H-NMR (200 MHz, DMSO$_{d-6}$) δ (ppm): 1.86-2.07 (m, 2H), 2.47-3.27 (m, 7H), 8.15 (br. s., 3H)

Reference Example 112

Synthesis of N-cyclobutyl-N-ethyl-N'-methylethane-1,2-diamine (1) By using cyclobutylamine (10.3 g) as a starting material, an alkyl compound (6.80 g) was obtained in the same manner as that of Reference Example 1, (1).

(2) By using the compound obtained in (1) mentioned above (3.4 g) and acetaldehyde 3.64 ml) as starting materials, the title compound (358 mg) was obtained in the same manner as that of Reference Example 1.

MS (ESI) m/z=157.2 [M+H]$^+$ $^1$H-NMR (600 MHz, CDCl$_3$) δ (ppm): 0.96 (t, J=7.02 Hz, 3H), 1.56-1.71 (m, 2H), 1.81-1.88 (m, 2H), 1.97-2.04 (m, 2H), 2.43 (s, 3H), 2.47-2.54 (m, 4H), 2.57-2.63 (m, 2H), 3.04-3.11 (m, 1H)

Reference Example 113

Synthesis of
N-methyl-2-(3-methylthiomorpholino)ethanamine (1) By using 3-methylthiomorpholine (163 mg) as a starting material, an alkyl compound (337 mg) was obtained in the same manner as that of Reference Example 1, (1).

(2) By using the compound obtained in (1) mentioned above (200 mg) as a starting material, the title compound (100.6 mg) was obtained in the same manner as that of Reference Example 1, (2).

MS (ESI) m/z=175.1 [M+H]$^+$ $^1$H-NMR (200 MHz, CDCl$_3$) δ (ppm): 1.17 (d, J=6.15 Hz, 3H), 2.36-3.06 (m, 11H), 2.44 (s, 3H)

Reference Example 114

Synthesis of 2-(2-aminoethyl)-1,2,5-thiadiazolidine 1,1-dioxide Hydrochloride (1) t-Butyl {2-[(2-aminoethyl)amino]ethyl}carbamate (3.00 g) was dissolved in pyridine (30 mL), sulfamide (1.42 g) was added to the solution, and the resulting mixture was stirred at 110° C. for 6 hours. Saturated aqueous sodium hydrogencarbonate and ethyl acetate were added to the reaction mixture, and the layers were separated. The organic layer was washed with saturated aqueous sodium hydrogencarbonate and saturated aqueous sodium chloride, then dried over anhydrous sodium sulfate, and filtered. The filtrate was concentrated under reduced pressure, and the resulting residue was purified by silica gel column chromatography (chloroform:methanol: 28% aqueous ammonia=100:1:0.1 to 20:1:0.1) to obtain a cyclized compound (1.84 g).

(2) By using the compound obtained in (1) mentioned above (1.84 g) as a starting material, the title compound (1.35 g) was obtained in the same manner as that of Reference Example 66, (3).

MS (ESI) m/z=166.1 [M+H]$^+$ $^1$H-NMR (600 MHz, DMSO$_{d-6}$) δ (ppm): 2.96-3.58 (m, 8H)

Reference Example 115

Synthesis of 2-(7-azabicyclo[2.2.1]heptan-7-yl)-N-methylethanamine (1) By using 7-azabicyclo[2.2.1]heptane (122 mg) as a starting material, an alkyl compound (150 mg) was obtained in the same manner as that of Reference Example 1, (1).

(2) A 4 mol/L solution of hydrochloric acid in dioxane (5 ml) was added to the compound obtained in (1) mentioned above (145 mg) under ice cooling, and the resulting mixture was stirred for 16 hours. Saturated aqueous sodium hydrogencarbonate and chloroform were added to the reaction mixture, the resulting mixture was filtered with a phase separator to separate the layers, and the organic layer was concentrated under reduced pressure. The resulting residue was purified by NH silica gel column chromatography (hexane:chloroform=4:1 to 0:1) to obtain the title compound (20.4 mg).

MS (ESI) m/z=155.2 [M+H]$^+$ $^1$H-NMR (600 MHz, CDCl$_3$) δ (ppm): 1.23-1.29 (m, 4H), 1.61-1.66 (m, 2H), 1.69-1.74 (m, 4H), 2.45 (s, 3H), 2.48 (t, J=6.40 Hz, 2H), 2.66 (t, J=6.61 Hz, 2H)

Reference Example 116

Synthesis of 3-(ethylsulfonyl)propan-1-amine Hydrochloride (1) Sodium methoxide (33 mg) was added to ethanethiol (2 g), acrylonitrile (8 ml) was added to the mixture under ice cooling, and then the reaction mixture was left to return to room temperature, and stirred for 3 hours. The reaction mixture was filtered thorough Celite, and the filtrate was concentrated under reduced pressure to obtain a nitrile compound (3.7 g).

(2) The compound obtained in (1) mentioned above (1.4 g) was dissolved in chloroform (19 ml), m-chloroperbenzoic acid (11 g) was added to the solution under ice cooling, and the resulting mixture was stirred at room temperature for 1 hour. Saturated aqueous sodium thiosulfate was added to the reaction mixture, and the layers were separated. Then, the organic layer was washed with saturated aqueous sodium hydrogencarbonate and saturated aqueous sodium chloride, dried over anhydrous sodium sulfate, and filtered, and then the filtrate was concentrated under reduced pressure to obtain a sulfone compound (0.74 g).

(3) A 1 mol/L solution of borane/tetrahydrofuran complex in tetrahydrofuran (15 ml) was heated to 40° C., the compound obtained in (2) mentioned above (0.74 g) was slowly added to the solution. The reaction mixture was left to cool to room temperature, and stirred overnight, then methanol (10 ml) was added to the reaction mixture under ice cooling, and the resulting mixture was stirred under reflux by heating for 30 minutes. The reaction mixture was cooled to room temperature, and concentrated under reduced pressure, and then addition of methanol (10 ml) and concentration under reduced pressure were further repeated twice. A 5 mol/L solution of hydrochloric acid in methanol (8 ml) was added to the resulting concentration residue under ice cooling, and the resulting mixture was stirred under reflux by heating 1 hour. The reaction mixture was left to cool to room temperature, and concentrated under reduced pressure, the deposited solid was suspended in a 5 mol/L solution of hydrochloric acid in methanol (7.0 ml), and the suspension was stirred under reflux by heating for 20 minutes. The reaction mixture was left to cool to room temperature, dichloromethane (10 ml) was added dropwise to the mixture, and then the resulting mixture was stirred overnight as it was at room temperature. The precipitates were collected by suction filtration, and washed with dichloromethane to obtain the title compound (0.43 g).

MS (ESI) m/z=152 [M+H]$^+$ $^1$H-NMR (400 MHz, D$_2$O) δ (ppm): 3.20 (t, J=7.57 Hz, 2H), 3.12 (q, J=7.45 Hz, 2H), 3.03 (t, J=7.81 Hz, 2H), 2.09-2.02 (m, 2H), 1.21 (t, J=7.45 Hz, 3H)

Reference Example 117

Synthesis of 3-methyl-2-buten-1-amine Hydrochloride 2-(3-Methylbut-2-enyl)isoindoline-1,3-dione (5.3 g) obtained by the method described in the publication (International Patent Publication WO09/087,395) was dissolved in ethanol (53 ml), 79% hydrazine monohydrate (1.2 ml) was added to the solution at room temperature, and the resulting mixture was stirred under reflux by heating for 1 hour. The reaction mixture was left to cool to room temperature, 5 N hydrochloric acid (5.9 ml) was added to the reaction mixture, and the resulting mixture was stirred under reflux by heating for 1 hour. The reaction mixture was filtered, the resulting filtration residue was further washed with distilled water, and then the filtrate was concentrated under reduced pressure to obtain the title compound (3.0 g).

MS (ESI) m/z=122 [M+H]$^+$
$^1$H-NMR (400 MHz, CD$_3$COCD$_3$) δ (ppm): 5.27-5.23 (m, 1H), 4.22 (d, J=6.80 Hz, 2H), 1.80 (s. 3H), 1.68 (s. 3H)

Examples 1 to 147

Preparation methods of the compound represented by the formula (A) and the compounds represented by the formula (B) having R$^{29a}$ and R$^2$ defined in Table 1 are shown below.

TABLE 1

Formula (A)

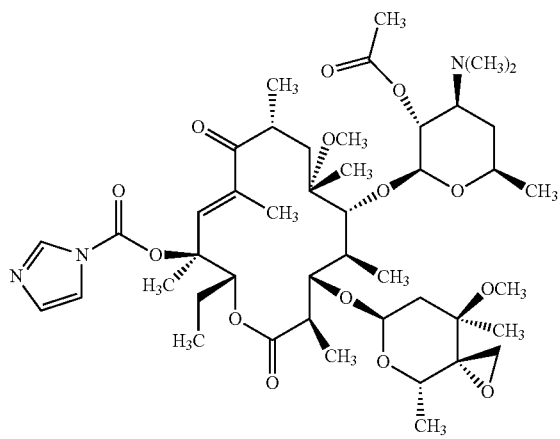

[Formula 29]

Formula (B)

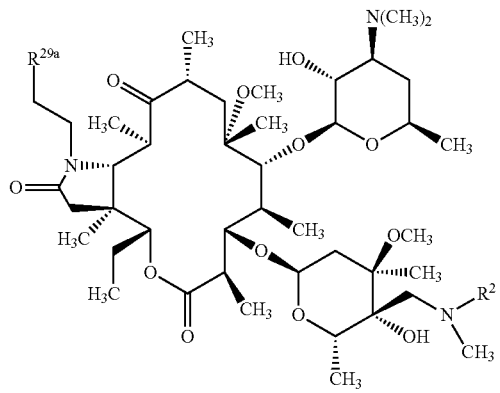

[Formula 30]

| Example | R$^{29a}$ | R$^2$ | ESI MS (M + H) | $^1$H-NMR, CDCl$_3$, δ (ppm) |
|---|---|---|---|---|
| 1 | HO― | ―N(CH$_2$CH$_3$)$_2$ (N,N-diethylaminopropyl) | 959.7 | (500 MHz): 0.85 (t, J = 7.27 Hz, 3 H) 0.98-1.07 (m, 9 H) 1.08-1.27 (m, 19 H) 1.40 (s, 6 H) 1.50-2.12 (m, 9 H) 2.29 (s, 6 H) 2.34 (s, 3 H) 2.39-2.63 (m, 10 H) 2.83 (d, J = 14.53 Hz, 1 H) 2.89-2.97 (m, 1 H) 3.04-3.14 (m, 4 H) 3.19 (dd, J = 10.28, 7.27 Hz, 1 H) 3.28 (s, 3 H) 3.44-3.51 (m, 1 H) 3.65-3.87 (m, 7 H) 4.09 (q, J = 6.31 Hz, 1 H) 4.42 (d, J = 7.13 Hz, 1 H) 4.97-5.06 (m, 2 H) |

| | | | |
|---|---|---|---|
| 2 | (pyridine-imidazole structure) | (t-butyl group) | 1029.7 (600 MHz): 0.79 (t, J = 7.34 Hz, 3 H) 1.00 (d, J = 6.88 Hz, 3 H) 1.08-1.11 (m, 3 H) 1.11-1.14 (m, 6 H) 1.15-1.18 (m, 3 H) 1.19-1.25 (m, 7 H) 1.35-1.41 (m, 6 H) 1.47-1.61 (m, 2 H) 1.68-1.75 (m, 3 H) 1.83-2.00 (m, 7 H) 2.04-2.09 (m, 1 H) 2.29 (br. s., 6 H) 2.36 (s, 6 H) 2.39-2.47 (m, 1 H) 2.58-2.61 (m, 1 H) 2.73 (d, J = 15.13 Hz, 1 H) 2.87-2.94 (m, 1 H) 3.03 (s, 3 H) 3.07-3.12 (m, 1 H) 3.15-3.21 (m, 1 H) 3.28 (s, 3 H) 3.39-3.46 (m, 1 H) 3.62 (s, 1 H) 3.63-3.68 (m, 2 H) 3.73 (d, J = 9.17 Hz, 1 H) 3.75-3.81 (m, 1 H) 3.99-4.05 (m, 2 H) 4.08-4.13 (m, 1 H) 4.38-4.41 (m, 1 H) 4.90-4.95 (m, 1 H) 4.98 (d, J = 5.04 Hz, 1 H) 7.26-7.30 (m, 1 H) 7.33-7.35 (m, 1 H) 7.54-7.58 (m, 1 H) 8.05-8.09 (m, 1 H) 8.43 (dd, J = 4.58, 1.83 Hz, 1 H) 8.92-8.97 (m, 1 H) |
| 3 | (pyridine-imidazole structure) | (dimethylaminopropyl group) | 1086.7 (600 MHz): 0.79 (t, J = 7.34 Hz, 3 H) 1.00 (d, J = 7.34 Hz, 3 H) 1.09 (d, J = 7.34 Hz, 3 H) 1.12 (d, J = 7.34 Hz, 3 H) 1.16-1.23 (m, 12 H) 1.22-1.25 (m, 1 H) 1.38 (s, 6 H) 1.48-1.55 (m, 1 H) 1.63-1.75 (m, 4 H) 1.85-1.96 (m, 5 H) 1.95-2.04 (m, 2 H) 2.13 (d, J = 14.67 Hz, 1 H) 2.24 (s, 6 H) 2.29 (s, 6 H) 2.34 (s, 3 H) 2.36-2.66 (m, 4 H) 2.41-2.46 (m, 1 H) 2.56-2.61 (m, 1 H) 2.81 (d, J = 14.67 Hz, 1 H) 2.86-2.93 (m,1 H) 3.02 (s, 3 H) 3.07-3.12 (m, 1 H) 3.15-3.20 (m, 1 H) 3.28 (s, 3 H) 3.44-3.50 (m, 1 H) 3.63 (s, 1 H) 3.64-3.74 (m, 3 H) 3.74-3.80 (m, 1 H) 3.98-4.05 (m, 2 H) 4.09-4.14 (m,1 H) 4.41 (d, J = 7.34 Hz, 1 H) 4.91-4.95 (m, 1 H) 4.96-4.99 (m, 1 H) 7.26-7.29 (m, 1 H) 7.34 (s, 1 H) 7.55 (d, J = 1.38 Hz, 1 H) 8.04-8.09 (m, 1 H) 8.40-8.45 (m, 1 H) 8.93-8.96 (m, 1 H) |
| 4 | (pyrrolidinone structure) | (dimethylaminopropyl group) | 1027.0 (600 MHz): 0.82 (t, J = 7.34 Hz, 3 H) 0.99 (d, J = 6.88 Hz, 3 H) 1.08 (d, J = 7.34 Hz, 3 H) 1.11 (d, J = 6.88 Hz, 3 H) 1.17 (s, 3 H) 1.17-1.20 (m, 6 H) 1.20-1.24 (m, 1 H) 1.22 (d, J = 6.42 Hz, 3 H) 1.37-1.38 (m, 3 H) 1.37-1.40 (m, 1 H) 1.38 (s, 3 H) 1.48-1.54 (m, 1 H) 1.52-1.68 (m, 4 H) 1.63-1.68 (m, 1 H) 1.72 (d, J = 6.88 Hz, 1 H) 1.87-2.03 (m, 7 H) 2.14 (d, J = 14.67 Hz, 1 H) 2.24 (br. s., 6 H) 2.29 (br. s., 6 H) 2.34 (s, 3 H) 2.35-2.37 (m, 1 H) 2.36-2.65 (m, 4 H) 2.40-2.47 (m, 1 H) 2.56-2.61 (m, 1 H) 2.81 (d, J = 14.67 Hz, 1 H) 2.87 (dd, J = 9.40, 7.11 Hz, 1 H) 3.00 (s, 3 H) 3.03-3.09 (m, 1 H) 3.16-3.21 (m, 1 H) 3.23-3.41 (m, 4 H) 3.27 (s, 3 H) 3.45-3.51 (m, 1 H) 3.55-3.67 (m, 2 H) 3.64 (s, 1 H) 3.67-3.72 (m, 2 H) 4.07-4.12 (m, 1 H) 4.41 (d, J = 7.34 Hz, 1 H) 4.90-5.00 (m, 2 H) |
| 5 | (pyrrolidinone structure) | (t-butyl group) | 969.9 (500 MHz): 0.83 (t, J = 7.40 Hz, 3 H) 1.00 (d, J = 6.86 Hz, 3 H) 1.08-1.12 (m, 6 H) 1.13 (s, 3 H) 1.17 (d, J = 6.31 Hz, 3 H) 1.20 (d, J = 7.13 Hz, 3 H) 1.23 (d, J = 6.03 Hz, 3 H) 1.23-1.27 (m, 1 H) 1.38 (s, 3 H) 1.39-1.40 (m, 1 H) 1.39 (s, 3 H) 1.48-1.69 (m, 4 H) 1.49-1.56 (m, 1 H) 1.64-1.69 (m, 1 H) 1.73 (d, J = 6.86 Hz, 1 H) 1.87-2.09 (m, 7 H) 2.30 (s, 6 H) 2.34-2.40 (m, 2 H) 2.37 (s, 6 H) 2.40-2.48 (m, 1 H) 2.55-2.63 (m, 1 H) 2.74 (d, J = 14.53 Hz, 1 H) 2.85-2.94 (m, 1 H) 3.03 (s, 3 H) 3.05-3.10 (m, 1 H) 3.18 (dd, J = 10.28, 7.27 Hz, 1 H) 3.24-3.35 (m, 2 H) 3.28 (s, 3H) 3.36-3.47 (m, 3 H) 3.56-3.70 (m, 2 H) 3.63 (s, 1 H) 3.67 (d, J = 7.40 Hz, 1 H) 3.73 (d, J = 9.32 Hz, 1 H) 4.07-4.14 (m, 1 H) 4.41 (d, J = 7.13 Hz, 1 H) 4.93-5.00 (m, 2 H) |
| 6 | (pyrimidine-amine structure) | (t-butyl group) | 979.8 (600 MHz): 0.83 (t, J = 7.34 Hz, 3 H) 1.01 (d, J = 6.88 Hz, 3 H) 1.08-1.18 (m, 12 H) 1.18-1.28 (m, 7 H) 1.38-1.40 (m, 6 H) 1.48-2.09 (m, 13 H) 2.30 (s, 6 H) 2.37 (s, 6 H) 2.41-2.47 (m, 1 H) 2.58-2.64 (m, 1 H) 2.74 (d, J = 14.67 Hz, 1 H) 2.86-2.94 (m, 1 H) 3.01 (s, 3 H) 3.06-3.12 (m, 1 H) 3.16-3.21 (m, 1 H) 3.28 (s, 3 H) 3.40-3.49 (m, 3 H) 3.60-3.75 (m, 5 H) 4.07-4.13 (m, 1 H) 4.40 (d, J = 6.88 Hz, 1 H) 4.96-5.03 (m, 2 H) 5.43-5.48 (m, 1 H) 6.46 (t, J = 4.81 Hz, 1 H) 8.25 (d, J = 4.59 Hz, 2 H) |

TABLE 1-continued

| | Structure 1 | Structure 2 | Value | NMR |
|---|---|---|---|---|
| 7 | pyrimidin-2-ylamino-propyl group | N,N-dimethylaminopropyl group | 1036.8 | (600 MHz): 0.83 (t, J = 7.34 Hz, 3 H) 1.01 (d, J = 6.88 Hz, 3 H) 1.10 (d, J = 7.79 Hz, 3 H) 1.13 (d, J = 6.88 Hz, 3 H) 1.16-1.26 (m, 13 H) 1.39 (s, 6 H) 1.48-1.78 (m, 8 H) 1.88-2.05 (m, 4 H) 2.14 (d, J = 15.13 Hz, 1 H) 2.24 (s, 6 H) 2.29 (s, 6 H) 2.31-2.48 (m, 6 H) 2.51-2.65 (m, 3 H) 2.82 (d, J = 14.67 Hz, 1 H) 2.86-2.92 (m, 1 H) 3.00-3.02 (m, 3 H) 3.06-3.12 (m, 1 H) 3.19 (dd, J = 10.09, 7.34 Hz, 1 H) 3.28 (s, 3 H) 3.44-3.49 (m, 3 H) 3.61-3.74 (m, 5 H) 4.07-4.14 (m, 1 H) 4.42 (d, J = 7.34 Hz, 1 H) 4.95-5.02 (m, 2 H) 5.43-5.48 (m, 1 H) 6.46 (t, J = 4.81 Hz, 1 H) 8.25 (d, J = 4.59 Hz, 2 H) |
| 8 | pyrimidin-2-ylamino-propyl group | N-methyl-N-[2-(2-methoxyphenyl)propan-2-yl]aminopropyl group | 1171.0 | (600 MHz): 0.83 (t, J = 7.34 Hz, 3 H) 1.01 (d, J = 6.88 Hz, 3 H) 1.07-1.26 (m, 19 H) 1.39 (s, 3 H) 1.39 (s, 3 H) 1.43 (br. s., 3 H) 1.44 (br. s., 3 H) 1.48-1.85 (m, 7 H) 1.87-2.07 (m, 6 H) 2.19 (s, 3 H) 2.26 (s, 3 H) 2.28-2.30 (m, 6 H) 2.38-2.65 (m, 6 H) 2.82 (d, J = 15.13 Hz, 1 H) 2.86-2.93 (m, 1 H) 3.01 (s, 3 H) 3.07-3.12 (m, 1 H) 3.18 (dd, J = 10.09, 7.34 Hz, 1 H) 3.28 (s, 3 H) 3.40-3.50 (m, 3 H) 3.60-3.75 (m, 5 H) 3.80 (s, 3 H) 4.06-4.12 (m, 1 H) 4.41 (d, J = 7.34 Hz, 1 H) 4.95-5.04 (m, 2 H) 5.43-5.48 (m, 1 H) 6.45 (t, J = 4.81 Hz, 1 H) 6.85-6.90 (m, 2 H) 7.15-7.20 (m, 1 H) 7.58-7.63 (m, 1 H) 8.24 (d, J = 5.04 Hz, 2 H) |
| 9 | 4-methylimidazol-1-yl-propyl group | N,N-dimethylaminopropyl group | 1023.9 | (600 MHz): 0.82 (t, J = 7.34 Hz, 3 H) 1.00 (d, J = 6.88 Hz, 3 H) 1.10 (d, J = 7.34 Hz, 3 H) 1.13 (d, J = 6.88 Hz, 3 H) 1.16-1.26 (m, 13 H) 1.39 (s, 3 H) 1.40 (s, 3 H) 1.49-1.93 (m, 10 H) 1.96-2.05 (m, 2 H) 2.14 (d, J = 14.67 Hz, 1 H) 2.20-2.21 (m, 3 H) 2.24 (s, 6 H) 2.29 (s, 6 H) 2.35 (s, 3 H) 2.21-2.66 (m, 6 H) 2.82 (d, J = 14.67 Hz, 1 H) 2.87-2.93 (m, 1 H) 3.01-3.04 (m, 3 H) 3.09 (s, 1 H) 3.16-3.21 (m, 1 H) 3.28 (s, 3 H) 3.42-3.51 (m, 2 H) 3.59-3.66 (m, 2 H) 3.68-3.77 (m, 3 H) 3.89 (t, J = 7.57 Hz, 2 H) 4.10-4.15 (m, 1 H) 4.42 (d, J = 7.34 Hz, 1 H) 4.92-4.96 (m, 1 H) 5.00 (d, J = 5.04 Hz, 1 H) 6.64 (s, 1 H) 7.35 (d, J = 1.38 Hz, 1 H) |
| 10 | 4-methylimidazol-1-yl-propyl group | tert-butyl group | 966.8 | (600 MHz): 0.82 (t, J = 7.34 Hz, 3 H) 1.00 (d, J = 6.88 Hz, 3 H) 1.10 (d, J = 7.79 Hz, 3 H) 1.12-1.14 (m, 6 H) 1.16-1.26 (m, 10 H) 1.39 (s, 3 H) 1.40 (s, 3 H) 1.49-2.00 (m, 12 H) 2.05-2.09 (m, 1 H) 2.19-2.22 (m, 3 H) 2.29 (s, 6 H) 2.37 (s, 6 H) 2.40-2.46 (m, 1 H) 2.56-2.62 (m, 1 H) 2.74 (d, J = 14.67 Hz, 1 H) 2.88-2.94 (m, 1 H) 3.03 (s, 3 H) 3.07-3.12 (m, 1 H) 3.16-3.21 (m, 1 H) 3.29 (s, 3 H) 3.40-3.46 (m, 2 H) 3.59-3.69 (m, 3 H) 3.71-3.77 (m, 2 H) 3.90 (t, J = 7.57 Hz, 2 H) 4.09-4.15 (m, 1 H) 4.40 (d, J = 7.34 Hz, 1 H) 4.93 (dd, J = 11.00, 2.29 Hz, 1 H) 5.01 (d, J = 5.04 Hz, 1 H) 6.64 (s, 1 H) 7.36 (s, 1 H) |
| 11 | 4-methylimidazol-1-yl-propyl group | N,N-diethylaminopropyl group | 1051.7 | (600 MHz): 0.82 (t, J = 7.43 Hz, 3 H) 0.98-1.05 (m, 9 H) 1.10 (d, J = 7.43 Hz, 3 H) 1.13 (d, J = 7.02 Hz, 3 H) 1.16 (s, 3 H) 1.17-1.26 (m, 10 H) 1.39 (s, 3 H) 1.40 (s, 3 H) 1.48-1.94 (m, 10 H) 1.97-2.06 (m, 2 H) 2.09 (d, J = 14.86 Hz, 1 H) 2.20-2.21 (m, 3 H) 2.29 (s, 6 H) 2.34 (s, 3 H) 2.38-2.63 (m, 10 H) 2.84 (d, J = 14.86 Hz, 1 H) 2.87-2.93 (m, 1 H) 3.02 (s, 3 H) 3.07-3.12 (m, 1 H) 3.18 (dd, J = 10.11, 7.22 Hz, 1 H) 3.28 (s, 3 H) 3.44-3.50 (m, 1 H) 3.59-3.77 (m, 5 H) 3.89 (t, J = 7.43 Hz, 2 H) 4.08-4.13 (m, 1 H) 4.42 (d, J = 7.02 Hz, 1 H) 4.93 (dd, J = 10.73, 2.06 Hz, 1 H) 5.01 (d, J = 4.54 Hz, 1 H) 6.64 (s, 1 H) 7.36 (d, J = 1.24 Hz, 1 H) |

TABLE 1-continued

| | | | | |
|---|---|---|---|---|
| 12 | 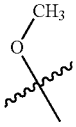 | 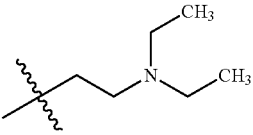 [SMILES: *CCN(CC)CC] | 973.7 | (500 MHz): 0.84 (t, J = 7.40 Hz, 3 H) 0.99-1.27 (m, 28 H) 1.39 (s, 6 H) 1.44-1.54 (m, 1 H) 1.63-1.80 (m, 3 H) 1.88-2.12 (m, 5 H) 2.29 (s, 6 H) 2.34 (s, 3 H) 2.39-2.64 (m, 10 H) 2.81-2.91 (m, 2 H) 3.04 (s, 3 H) 3.06-3.11 (m, 1 H) 3.19 (dd, J = 10.28, 7.27 Hz, 1 H) 3.28 (s, 3 H) 3.38 (s, 3 H) 3.45-3.51 (m, 1 H) 3.61-3.71 (m, 4 H) 3.74 (d, J = 9.05 Hz, 1 H) 3.83-3.95 (m, 2 H) 4.10 (q, J = 6.31 Hz, 1 H) 4.42 (d, J = 7.40 Hz, 1 H) 5.00 (d, J = 4.39 Hz, 1 H) 5.10 (dd, J = 10.42, 2.74 Hz, 1 H) |
| 13 |  | 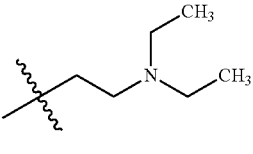 [SMILES: *CCN(CC)CC] | 968.8 | (600 MHz): 0.85 (t, J = 7.34 Hz, 3 H) 0.98-1.05 (m, 9 H) 1.10 (d, J = 7.34 Hz, 3 H) 1.13 (d, J = 7.34 Hz, 3 H) 1.16 (s, 3 H) 1.18-1.22 (m, 6 H) 1.23 (d, J = 9.17 Hz, 3 H) 1.22-1.26 (m, 1 H) 1.39 (s, 3 H) 1.41 (s, 3 H) 1.51-1.57 (m, 1 H) 1.63-1.67 (m, 1 H) 1.70-1.77 (m, 2 H) 1.82-1.93 (m, 2 H) 1.96-2.04 (m, 2 H) 2.10 (d, J = 14.67 Hz, 1 H) 2.29 (s, 6 H) 2.34 (s, 3 H) 2.39-2.61 (m, 8 H) 2.41-2.46 (m, 1 H) 2.57-2.61 (m, 1 H) 2.75-2.86 (m, 3 H) 2.87-2.92 (m, 1 H) 3.05 (s, 3 H) 3.06-3.09 (m, 1 H) 3.18 (dd, J = 10.09, 7.34 Hz, 1 H) 3.28 (s, 3 H) 3.44 (br. s., 1 H) 3.46-3.50 (m, 1 H) 3.62 (s, 1 H) 3.70-3.72 (m, 2 H) 3.87-3.94 (m, 1 H) 3.95-4.01 (m, 1 H) 4.07-4.11 (m, 1 H) 4.42 (d, J = 6.88 Hz, 1 H) 4.93 (dd, J = 11.00, 2.29 Hz, 1 H) 4.99 (d, J = 4.13 Hz, 1 H) |
| 14 | 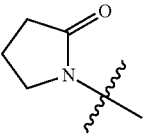 [SMILES: *N1CCCC1=O] | 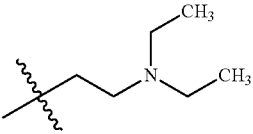 [SMILES: *CCN(CC)CC] | 1026.7 | (500 MHz): 0.85 (t, J = 7.45 Hz, 3 H) 0.98-1.27 (m, 28 H) 1.38 (s, 3H) 1.40 (s, 3 H) 1.47-2.13 (m, 11 H) 2.29 (s, 6 H) 2.32-2.38 (m, 4 H) 2.41-2.64 (m, 10 H) 2.80-2.92 (m, 2 H) 3.03-3.13 (m, 4 H) 3.19 (dd, J = 10.32, 7.26 Hz, 1 H) 3.28 (s, 3 H) 3.40-3.57 (m, 5 H) 3.61-3.75 (m, 5 H) 3.79-3.87 (m, 1 H) 4.09 (q, J = 6.12 Hz, 1 H) 4.42 (d, J = 7.26 Hz, 1 H) 4.98 (d, J = 3.82 Hz, 1 H) 5.07 (dd, J = 10.89, 2.10 Hz, 1 H) |
| 15 | 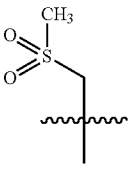 [SMILES: *CS(C)(=O)=O] | 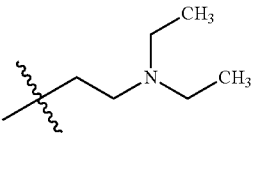 [SMILES: *CCN(CC)CC] | 1035.7 | (500 MHz): 0.84 (t, J = 7.27 Hz, 3 H) 0.98-1.05 (m, 9 H) 1.10 (d, J = 7.68 Hz, 3 H) 1.13 (d, J = 7.13 Hz, 3 H) 1.15-1.27 (m, 13 H) 1.39 (s, 3 H) 1.40 (s, 3 H) 1.49-1.78 (m, 4 H) 1.84-2.20 (m, 6 H) 2.21-2.31 (m, 7 H) 2.35 (s, 3 H) 2.38-2.64 (m, 10 H) 2.83 (d, J = 14.81 Hz, 1 H) 2.88-2.96 (m, 4 H) 3.03 (s, 3 H) 3.06-3.21 (m, 4 H) 3.28 (s, 3 H) 3.43-3.51 (m, 1 H) 3.63 (s, 1 H) 3.66-3.77 (m, 3 H) 3.87-3.94 (m, 1 H) 4.10 (q, J = 6.31 Hz, 1 H) 4.41 (d, J = 7.13 Hz, 1 H) 4.88 (dd, J = 11.11, 2.06 Hz, 1 H) 4.98 (d, J = 4.39 Hz, 1 H) |
| 16 | 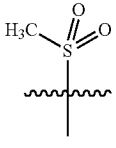 | 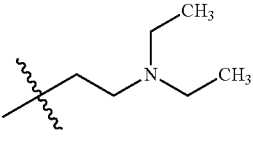 [SMILES: *CCN(CC)CC] | 1021.7 | (600 MHz): 0.84 (t, J = 7.34 Hz, 3 H) 0.98-1.28 (m, 28 H) 1.38 (s, 3 H) 1.40 (s, 3 H) 1.49-1.53 (m, 1 H) 1.65 (d, J = 12.38 Hz, 1 H) 1.73-1.76 (m, 2 H) 1.82-1.92 (m, 2 H) 1.98-2.02 (m, 2 H) 2.09 (d, J = 15.13 Hz, 1 H) 2.29 (s, 6 H) 2.34 (s, 3 H) 2.39-2.64 (m, 10 H) 2.83 (d, J = 14.67 Hz, 1 H) 2.86-2.93 (m, 1 H) 3.02 (s, 3 H) 3.05-3.11 (m, 1 H) 3.07 (s, 3 H) 3.18 (dd, J = 10.32, 7.11 Hz, 1 H) 3.28 (s, 3 H) 3.40-3.58 (m, 3 H) 3.63 (s, 1 H) 3.69-3.73 (m, 2 H) 4.01-4.17 (m, 3 H) 4.42 (d, J = 7.34 Hz, 1 H) 4.96 (dd, J = 11.00, 1.83 Hz, 1 H) 4.99 (d, J = 3.67 Hz, 1 H) |
| 17 | 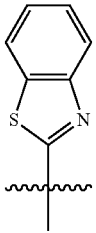 [SMILES: *c1nc2ccccc2s1] | 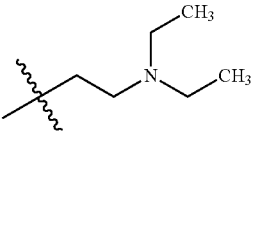 [SMILES: *CCN(CC)CC] | 1076.7 | (600 MHz): 0.75-0.85 (m, 3 H) 0.92-1.27 (m, 28 H) 1.39 (br. s., 6 H) 1.43-2.04 (m, 8 H) 2.06-2.13 (m, 1 H) 2.29 (s, 6 H) 2.37 (br. s., 3 H) 2.38-2.64 (m, 10 H) 2.79-3.23 (m, 7 H) 3.27 (s, 3 H) 3.36-4.03 (m, 8 H) 4.05-4.12 (m, 1 H) 4.37-4.45 (m, 1 H) 4.95-5.00 (m, 1 H) 5.07-5.14 (m, 1 H) 7.32-7.50 (m, 4 H) |

| | | | | |
|---|---|---|---|---|
| 18 | (imidazo[1,2-a]pyridin-2-yl structure) | (N,N-diethylaminopropyl structure) | 1059.7 | (600 MHz): 0.79 (t, J = 7.22 Hz, 3 H) 0.99-1.07 (m, 9 H) 1.10 (d, J = 7.43 Hz, 3 H) 1.14 (d, J = 7.02 Hz, 3 H) 1.16 (s, 3 H) 1.17-1.25 (m, 10 H) 1.40 (s, 3 H) 1.41 (s, 3 H) 1.47-1.79 (m, 4 H) 1.85-2.04 (m, 4 H) 2.07-2.13 (m, 1 H) 2.29 (s, 6 H) 2.34 (s, 3 H) 2.38-2.66 (m, 10 H) 2.81-2.91 (m, 2 H) 3.12 (s, 3 H) 3.09-3.14 (m, 1 H) 3.16-3.24 (m, 1 H) 3.28 (s, 3 H) 3.39-3.51 (m, 4 H) 3.69-3.77 (m, 3 H) 4.03-4.17 (m, 3 H) 4.40-4.44 (m, 1 H) 4.96-5.01 (m, 2 H) 7.33 (s, 1 H) 7.38 (d, J = 8.26 Hz, 2 H) 7.86-7.92 (m, 2 H) |
| 19 | (sec-butyl structure) | (N,N-diethylaminopropyl structure) | 971.7 | (500 MHz): 0.83 (t, J = 7.45 Hz, 3 H) 0.95 (t, J = 7.45 Hz, 3 H) 0.99-1.05 (m, 9 H) 1.07-1.27 (m, 19 H) 1.30-1.42 (m, 8 H) 1.45-1.69 (m, 5 H) 1.70-1.76 (m, 2 H) 1.88-2.12 (m, 5 H) 2.29 (s, 6 H) 2.34 (s, 3 H) 2.38-2.65 (m, 10 H) 2.80-2.92 (m, 2 H) 3.03-3.10 (m, 4 H) 3.18 (dd, J = 10.32, 7.26 Hz, 1 H) 3.28 (s, 3 H) 3.44-3.51 (m, 1 H) 3.56-3.61 (m, 2 H) 3.65 (s, 1 H) 3.69 (d, J = 7.26 Hz, 1 H) 3.74 (d, J = 9.17 Hz, 1 H) 4.10 (q, J = 6.12 Hz, 1 H) 4.42 (d, J = 7.26 Hz, 1 H) 4.95-5.02 (m, 2 H) |
| 20 | (methylthio structure) | (N,N-diethylaminopropyl structure) | 1003.7 | (600 MHz): 0.83 (t, J = 7.34 Hz, 3 H) 0.99-1.04 (m, 9 H) 1.10 (d, J = 7.34 Hz, 3 H) 1.13 (d, J = 7.34 Hz, 3 H) 1.14-1.26 (m, 13 H) 1.38 (s, 3 H), 1.39-1.41 (m, 3 H) 1.48-1.56 (m, 1 H) 1.62-1.67 (m, 1 H) 1.72-1.76 (m, 2 H) 1.87-2.05 (m, 6 H) 2.07-2.13 (m, 4 H) 2.29 (s, 6 H) 2.34 (s, 3 H) 2.40-2.63 (m, 12 H) 2.81-2.85 (m, 1 H) 2.85-2.91 (m, 1 H) 3.05 (s, 3 H) 3.06-3.11 (m, 1 H) 3.16-3.21 (m, 1 H) 3.28 (s, 3 H) 3.44-3.50 (m, 1 H) 3.65 (s, 1 H) 3.67-3.75 (m, 4 H) 4.10 (q, J = 6.42 Hz, 1 H) 4.42 (d, J = 7.34 Hz, 1 H) 4.94-5.01 (m, 2 H) |
| 21 | (methoxy structure) | (N,N-diethylaminopropyl structure) | 987.7 | (500 MHz): 0.84 (t, J = 7.45 Hz, 3 H) 0.99-1.05 (m, 9 H) 1.07-1.14 (m, 6 H) 1.14-1.27 (m, 13 H) 1.38 (s, 3 H) 1.39 (s, 3 H) 1.46-1.68 (m, 2 H) 1.72-1.76 (m, 2 H) 1.87-2.12 (m, 7 H) 2.29 (s, 6 H) 2.34 (s, 3 H) 2.39-2.64 (m, 10 H) 2.80-2.92 (m, 2 H) 3.02-3.10 (m, 4 H) 3.18 (dd, J = 9.94, 7.26 Hz, 1 H) 3.28 (s, 3 H) 3.32 (s, 3 H) 3.39-3.51 (m, 3 H) 3.61-3.76 (m, 5 H) 4.10 (q, J = 6.24 Hz, 1 H) 4.42 (d, J = 7.26 Hz, 1 H) 4.95-5.02 (m, 2 H) |
| 22 | (imidazolyl structure) | (N,N-diethylaminopropyl structure) | 1037.7 | (600 MHz): 0.82 (t, J = 7.34 Hz, 3 H) 1.00 (d, J = 6.88 Hz, 3 H) 1.01-1.04 (m, 6 H) 1.10 (d, J = 7.79 Hz, 3 H) 1.13 (d, J = 6.88 Hz, 3 H) 1.17 (s, 3 H) 1.20 (d, J = 6.42 Hz, 3 H) 1.22 (d, J = 6.88 Hz, 3 H) 1.23-1.26 (m, 1 H) 1.24 (d, J = 6.42 Hz, 3 H) 1.39 (s, 3 H) 1.40 (s, 3 H) 1.49-1.56 (m, 1 H) 1.58-1.71 (m, 2 H) 1.64-1.69 (m, 1 H) 1.72-1.76 (m, 2 H) 1.79-1.93 (m, 4 H) 1.96-2.06 (m, 2 H) 2.09 (d, J = 14.67 Hz, 1 H) 2.29 (s, 6 H) 2.34 (s, 3 H) 2.39-2.60 (m, 8 H) 2.41-2.46 (m, 1 H) 2.57-2.61 (m, 1 H) 2.82-2.85 (m, 1 H) 2.87-2.93 (m, 1 H) 3.03 (s, 3 H) 3.07-3.12 (m, 1 H) 3.16-3.21 (m, 1 H) 3.28 (s, 3 H) 3.41-3.45 (m, 1 H) 3.45-3.50 (m, 1 H) 3.60-3.67 (m, 1 H) 3.63 (s, 1 H) 3.69 (d, J = 7.34 Hz, 1 H) 3.73 (d, J = 8.71 Hz, 1 H) 3.73-3.78 (m, 1 H) 3.96-4.00 (m, 2 H) 4.09-4.13 (m, 1 H) 4.42 (d, J = 6.88 Hz, 1 H) 4.92-4.94 (m, 1 H) 5.01 (d, J = 4.13 Hz, 1 H) 6.93-6.94 (m, 1 H) 7.03 (s, 1 H) 7.48 (s, 1 H) |

| 23 | [phenyl-S-CH2-C(CH3)2- structure] | [-CH2CH2CH2-N(Et)2 with CH3 structure] | 1065.7 | (500 MHz): 0.81 (t, J = 7.40 Hz, 3 H) 0.88-1.05 (m, 9 H) 1.07-1.27 (m, 21 H) 1.38 (s, 6 H) 1.47-1.68 (m, 2 H) 1.73 (d, J = 6.86 Hz, 2 H) 1.85-2.12 (m, 7 H) 2.29 (s, 6 H) 2.34 (s, 3 H) 2.40-2.64 (m, 9 H) 2.80-2.90 (m, 2 H) 2.94-3.01 (m, 4 H) 3.08 (q, J = 6.76 Hz, 1 H) 3.15-3.21 (m, 1 H) 3.28 (s, 3 H) 3.44-3.50 (m, 1 H) 3.64 (s, 1 H) 3.67-3.80 (m, 4 H) 4.09 (q, J = 6.31 Hz, 1 H) 4.42 (d, J = 7.13 Hz, 1 H) 4.93 (dd, J = 10.97, 2.19 Hz, 1 H) 4.99 (d, J = 4.11 Hz, 1 H) 7.12-7.17 (m, 1 H) 7.23-7.28 (m, 2 H) 7.35-7.39 (m, 2 H) |
|---|---|---|---|---|
| 24 | [phenyl-SO2-CH2-C(CH3)2- structure] | [-CH2CH2CH2-N(Et)2 with CH3 structure] | 1097.7 | (500 MHz): 0.80 (t, J = 7.40 Hz, 3 H) 0.94 (d, J = 6.88 Hz, 3 H) 1.00-1.12 (m, 12 H) 1.15-1.29 (m, 13 H) 1.35 (s, 6 H) 1.46-2.14 (m, 11 H) 2.28 (s, 6 H) 2.33-2.37 (m, 3 H) 2.40-2.64 (m, 10 H) 2.77 (s, 3 H) 2.81-2.91 (m, 2 H) 3.03-3.08 (m, 1 H) 3.14-3.34 (m, 6 H) 3.43-3.51 (m, 1 H) 3.54 (s, 1 H) 3.60-3.69 (m, 3 H) 3.73-3.81 (m, 1 H) 4.09 (q, J = 6.40 Hz, 1 H) 4.41 (d, J = 7.40 Hz, 1 H) 4.77-4.82 (m, 1 H) 5.00 (d, J = 3.56 Hz, 1 H) 7.49-7.55 (m, 2 H) 7.61-7.66 (m, 1 H) 7.93-7.98 (m, 2 H) |
| 25 | [phenyl-O-CH2-C(CH3)2- structure] | [-CH2CH2CH2-N(Et)2 with CH3 structure] | 1049.7 | (600 MHz): 0.65 (t, J = 7.57 Hz, 3 H) 1.00-1.05 (m, 9 H) 1.09 (d, J = 7.34 Hz, 3 H) 1.13 (d, J = 7.34 Hz, 3 H) 1.16 (s, 3 H) 1.18-1.26 (m, 10 H) 1.38 (s, 3 H) 1.39 (s, 3 H) 1.41-1.51 (m, 1 H) 1.62-1.68 (m, 1 H) 1.70-1.79 (m, 2 H) 1.81-1.88 (m, 1 H) 1.89-1.95 (m, 1 H) 1.95-2.05 (m, 2 H) 2.10 (d, J = 14.67 Hz, 1 H) 2.29 (s, 6 H) 2.35 (s, 3 H) 2.40-2.63 (m, 10 H) 2.81-2.90 (m, 2 H) 3.04 (s, 3 H) 3.10 (q, J = 6.88 Hz, 1 H) 3.17-3.21 (m, 1 H) 3.28 (s, 3 H) 3.45-3.51 (m, 1 H) 3.58-3.63 (m, 1 H) 3.67-3.77 (m, 4 H) 3.88-3.93 (m, 1 H) 3.96-4.02 (m, 1 H) 4.10 (m, 1 H) 4.42 (d, J = 7.34 Hz, 1 H) 4.58-4.63 (m, 2 H) 5.01 (d, J = 5.04 Hz, 1 H) 5.10 (dd, J = 10.55, 2.29 Hz, 1 H) 7.20-7.24 (m, 1 H) 7.28-7.31 (m, 2 H) 7.33-7.36 (m, 2 H) |
| 26 | [CH3-SO2-CH2-C(CH3)2- structure] | [2-methylpyrrolidine with -CH2CH2CH2- linker] | 1047.6 | (600 MHz): 0.84 (t, J = 7.34 Hz, 3 H) 1.00 (d, J = 6.88 Hz, 3 H) 1.06-1.11 (m, 6 H) 1.13 (d, J = 7.34 Hz, 3 H) 1.15 (s, 3 H) 1.18-1.20 (m, 6 H) 1.21-1.26 (m, 1 H) 1.23 (d, J = 5.96 Hz, 3 H) 1.37-1.42 (m, 7 H) 1.51-1.58 (m, 2 H) 1.63-1.71 (m, 2 H) 1.72-1.81 (m, 3 H) 1.86-1.93 (m, 3 H) 1.95-2.05 (m, 2 H) 2.08-2.19 (m, 4 H) 2.22-2.29 (m, 1 H) 2.28-2.30 (m, 6 H) 2.30-2.35 (m, 1 H) 2.36 (s, 3 H) 2.39-2.46 (m, 1 H) 2.55-2.66 (m, 3 H) 2.84-2.93 (m, 3 H) 2.93 (s, 3 H) 3.03 (s, 3 H) 3.08-3.20 (m, 4 H) 3.28 (s, 3 H) 3.42-3.49 (m, 2 H) 3.63 (s, 1 H) 3.66-3.75 (m, 3 H) 3.86-3.93 (m, 1 H) 4.10 (q, J = 6.42 Hz, 1 H) 4.41 (d, J = 7.34 Hz, 1 H) 4.85-4.92 (m, 1 H) 4.98 (d, J = 4.58 Hz, 1 H) |
| 27 | [H3C-SO2-CH2-C(CH3)2- structure] | [2-methylpyrrolidine with -CH2CH2CH2- linker] | 1033.7 | (500 MHz): 0.84 (t, J = 7.26 Hz, 3 H) 1.02 (d, J = 6.88 Hz, 3 H) 1.07-1.29 (m, 22 H) 1.39 (s, 3 H) 1.40 (s, 3 H) 1.48-2.19 (m, 14 H) 2.29 (s, 6 H) 2.31-2.38 (m, 4 H) 2.40-2.47 (m, 1 H) 2.56-2.68 (m, 3 H) 2.83-2.95 (m, 3 H) 3.02 (s, 3 H) 3.04-3.22 (m, 6 H) 3.28 (s, 3 H) 3.40-3.59 (m, 4 H) 3.63 (s, 1 H) 3.68-3.74 (m, 2 H) 3.99-4.19 (m, 3 H) 4.42 (d, J = 7.26 Hz, 1 H) 4.93-5.02 (m, 2 H) |

TABLE 1-continued

| 28 | [phenyl-NH-C(=O)-C(CH3)- structure] | [-CH2-CH2-C(CH3)-N(CH2CH3)2 structure] | 1062.8 | (600 MHz): 0.54 (t, J = 7.34 Hz, 3 H) 0.99-1.05 (m, 9 H) 1.11 (d, J = 7.34 Hz, 3 H) 1.14-1.16 (m, 3 H) 1.17 (s, 3 H) 1.18-1.26 (m, 10 H) 1.38 (s, 3 H) 1.42 (s, 3 H) 1.43-1.51 (m, 2 H) 1.63-1.69 (m, 1 H) 1.71-1.83 (m, 3 H) 1.87-1.93 (m, 1 H) 1.97-2.06 (m, 2 H) 2.07-2.12 (m, 1 H) 2.29 (s, 6 H) 2.35 (s, 3 H) 2.38-2.70 (m, 12 H) 2.81-2.87 (m, 1 H) 2.90-2.97 (m, 1 H) 3.11 (s, 3 H) 3.14-3.22 (m, 2 H) 3.28 (s, 3 H) 3.42-3.51 (m, 2 H) 3.69-3.73 (m, 2 H) 3.74-3.79 (m, 1 H) 4.00-4.07 (m, 1 H) 4.08-4.14 (m, 1 H) 4.20-4.28 (m, 1 H) 4.42 (d, J = 7.34 Hz, 1 H) 4.84-4.90 (m, 1 H) 5.01-5.04 (m, 1 H) 7.02-7.06 (m, 1 H) 7.23-7.28 (m, 1 H) 7.54 (d, J = 7.34 Hz, 2 H) 8.41-8.45 (m, 1 H) |
| --- | --- | --- | --- | --- |
| 29 | [phenyl-NH-CH(CH3)- structure] | [-CH2-CH2-C(CH3)-N(CH2CH3)2 structure] | 1048.7 | (600 MHz): 0.79 (t, J = 7.34 Hz, 3 H) 0.99-1.03 (m, 9 H) 1.09 (d, J = 7.34 Hz, 3 H) 1.13 (d, J = 7.34 Hz, 3 H) 1.15 (s, 3 H) 1.17 (d, J = 6.42 Hz, 3 H) 1.18-1.24 (m, 7 H) 1.38 (s, 3 H) 1.39 (s, 3 H) 1.47-1.54 (m, 1 H) 1.61-1.66 (m, 1 H) 1.70-1.76 (m, 2 H) 1.85-2.06 (m, 6 H) 2.07-2.11 (m, 1 H) 2.28 (s, 6 H) 2.33 (s, 3 H) 2.38-2.64 (m, 10 H) 2.81-2.85 (m, 1 H) 2.86-2.92 (m, 1 H) 3.01 (s, 3 H) 3.06-3.25 (m, 4 H) 3.27 (s, 3 H) 3.41 (s, 1 H) 3.43-3.49 (m, 1 H) 3.65-3.79 (m, 5 H) 4.06-4.11 (m, 1 H) 4.19-4.23 (m, 1 H) 4.41 (d, J = 7.34 Hz, 1 H) 4.94-4.97 (m, 1 H) 4.98-5.00 (m, 1 H) 6.60-6.66 (m, 3 H) 7.11-7.17 (m, 2 H) |
| 30 | [CH3-S-CH2-C(CH3)- structure] | [-CH2-CH2-C(CH3)-N(isothiazolidine 1,1-dioxide) structure] | 1051.6 | (600 MHz): 0.83 (t, J = 7.57 Hz, 3 H) 1.01 (d, J = 6.88 Hz, 3 H) 1.10 (d, J = 7.34 Hz, 3 H) 1.13 (d, J = 6.88 Hz, 3 H) 1.14 (s, 3 H) 1.18-1.21 (m, 6 H) 1.22-1.25 (m, 1 H) 1.24 (d, J = 5.96 Hz, 3 H) 1.38 (s, 3 H) 1.40 (s, 3 H) 1.49-1.56 (m, 1 H) 1.66-1.70 (m, 1 H) 1.72-1.76 (m, 2 H) 1.87-2.00 (m, 5 H) 2.03-2.11 (m, 2 H) 2.12 (s, 3 H) 2.29 (s, 6 H) 2.34-2.39 (m, 2 H) 2.39-2.42 (m, 1 H) 2.41 (s, 3 H) 2.42-2.45 (m, 1 H) 2.50-2.62 (m, 3 H) 2.67-2.73 (m, 1 H) 2.86-2.93 (m, 2 H) 3.05 (s, 3 H) 3.06-3.10 (m, 1 H) 3.11-3.21 (m, 5 H) 3.24-3.32 (m, 2 H) 3.28 (s, 3 H) 3.40-3.46 (m, 1 H) 3.64 (s, 1 H) 3.65-3.75 (m, 4 H) 4.12 (q, J = 6.11 Hz, 1 H) 4.40 (d, J = 7.34 Hz, 1 H) 4.95 (dd, J = 10.55, 2.29 Hz, 1 H) 4.99 (d, J = 5.04 Hz, 1 H) |
| 31 | [H3C-S(=O)2-C(CH3)- structure] | [-CH2-CH2-C(CH3)-N(CH2CH2CH3)2 structure] | 1049.7 | (600 MHz): 0.84 (t, J = 7.34 Hz, 3 H) 0.90 (t, J = 7.34 Hz, 3 H) 0.99-1.32 (m, 28 H) 1.36-1.46 (m, 1 H) 1.38 (s, 3 H) 1.40 (s, 3 H) 1.50-1.53 (m, 1 H) 1.63-1.67 (m, 1 H) 1.74 (d, J = 5.96 Hz, 2 H) 1.84-1.90 (m, 2 H) 1.96-2.03 (m, 2 H) 2.08 (d, J = 14.67 Hz, 1 H) 2.29 (s, 6 H) 2.34 (s, 3 H) 2.36-2.64 (m, 10 H) 2.83 (d, J = 14.67 Hz, 1 H) 2.90 (dd, J = 9.86, 7.11 Hz, 1 H) 3.02 (s, 3 H) 3.05-3.11 (m, 1 H) 3.07 (s, 3 H) 3.18 (dd, J = 10.55, 7.34 Hz, 1 H) 3.28 (s, 3 H) 3.40-3.50 (m, 3 H) 3.52-3.58 (m, 1 H) 3.63 (s, 1 H) 3.69-3.73 (m, 2 H) 4.01-4.16 (m, 3 H) 4.41 (d, J = 7.34 Hz, 1 H) 4.94-4.98 (m, 1 H) 4.98-5.01 (m, 1 H) |
| 32 | [H3C-S(=O)2-C(CH3)- structure] | [-CH2-CH2-C(CH3)-N(CH2CH3)(CH(CH3)2) structure] | 1035.7 | (600 MHz): 0.84 (t, J = 7.43 Hz, 3 H) 0.95-1.07 (m, 12 H) 1.09 (d, J = 7.43 Hz, 3 H) 1.13 (d, J = 7.02 Hz, 3 H) 1.15 (s, 3 H) 1.17-1.27 (m, 10 H) 1.38 (s, 3 H) 1.40 (s, 3 H) 1.48-1.57 (m, 1 H) 1.63-1.70 (m, 1 H) 1.72-1.77 (m, 2 H) 1.82-1.91 (m, 2 H) 1.95-2.09 (m, 3 H) 2.30 (s, 6 H) 2.34 (s, 3 H) 2.40-2.64 (m, 9 H) 2.82-2.94 (m, 2 H) 3.01 (s, 3 H) 3.07 (s, 3 H) 3.04-3.11 (m, 1 H) 3.16-3.21 (m, 1 H) 3.28 (s, 3 H) 3.41-3.59 (m, 3 H) 3.63 (s, 1 H) 3.68-3.74 (m, 2 H) 4.01-4.17 (m, 3 H) 4.41 (d, J = 7.43 Hz, 1 H) 4.96 (dd, J = 10.94, 1.86 Hz, 1 H) 4.99 (d, J = 4.54 Hz, 1 H) |

TABLE 1-continued

| | | | |
|---|---|---|---|
| 33 | H₃C-S(=O)(=O)- [structure] | [structure with N, CH₃, cyclopropyl, ethyl] | 1047.7 (600 MHz): 0.46-0.51 (m, 4 H) 0.84 (t, J = 7.34 Hz, 3 H) 0.86-0.90 (m, 1 H) 1.01-1.05 (m, 6 H) 1.09 (d, J = 7.34 Hz, 3 H) 1.13 (d, J = 6.88 Hz, 3 H) 1.20 (d, J = 6.88 Hz, 3 H) 1.20 (d, J = 10.55 Hz, 3 H) 1.20 (d, J = 10.09 Hz, 3 H) 1.20 (d, J = 8.71 Hz, 3 H) 1.14-1.26 (m, 1 H) 1.38 (s, 3 H) 1.40 (s, 3 H) 1.49-1.68 (m, 2 H) 1.72-1.76 (m, 2 H) 1.83-1.91 (m, 2 H) 1.95-2.04 (m, 2 H) 2.09 (d, J = 14.67 Hz, 1 H) 2.29 (s, 6 H) 2.49 (s, 3 H) 2.30-2.68 (m, 10 H) 2.82-2.93 (m, 2 H) 3.01 (s, 3 H) 3.07 (s, 3 H) 3.07-3.10 (m, 1 H) 3.16-3.20 (m, 1 H) 3.28 (s, 3 H) 3.41-3.50 (m, 2 H) 3.52-3.59 (m, 1 H) 3.63 (s, 1 H) 3.69-3.73 (m, 2 H) 4.01-4.17 (m, 3 H) 4.42 (d, J = 6.88 Hz, 1 H) 4.96 (dd, J = 10.77, 2.06 Hz, 1 H) 4.99 (d, J = 4.13 Hz, 1 H) |
| 34 | H₃C-S(=O)- [structure] | [structure with N(Et)(CH₃)] | 1019.6 (500 MHz): 0.79-0.86 (m, 3 H) 0.98-1.27 (m, 28 H) 1.37-1.42 (m, 6 H) 1.48-2.19 (m, 10 H) 2.29 (s, 6 H) 2.34 (s, 3 H) 2.39-2.63 (m, 13 H) 2.77-2.94 (m, 4 H) 3.00-3.06 (m, 3 H) 3.10 (t, J = 6.99 Hz, 1 H) 3.18 (dd, J = 10.15, 7.13 Hz, 1 H) 3.28 (s, 3 H) 3.40-3.52 (m, 2 H) 3.63 (d, J = 10.15 Hz, 1 H) 3.66-3.77 (m, 3 H) 3.79-3.91 (m, 1 H) 4.06-4.14 (m, 1 H) 4.42 (d, J = 7.40 Hz, 1 H) 4.85-4.93 (m, 1 H) 4.96-5.02 (m, 1 H) |
| 35 | -S(=O)(=O)CH₃ [structure] | [isothiazolidine 1,1-dioxide structure] | 1083.7 (600 MHz): 0.84 (t, J = 7.34 Hz, 3 H) 1.00 (d, J = 6.88 Hz, 3 H) 1.10 (d, J = 7.34 Hz, 3 H) 1.12-1.15 (m, 6 H) 1.17-1.21 (m, 6 H) 1.22-1.26 (m, 1 H) 1.24 (d, J = 6.42 Hz, 3 H) 1.39 (s, 3 H) 1.40 (s, 3 H) 1.53-1.58 (m, 1 H) 1.66-1.70 (m, 1 H) 1.71-1.77 (m, 2 H) 1.86-1.99 (m, 3 H) 2.03-2.11 (m, 2 H) 2.12-2.20 (m, 1 H) 2.23-2.28 (m, 1 H) 2.29 (s, 6 H) 2.33-2.45 (m, 5 H) 2.41 (s, 3 H) 2.56-2.63 (m, 1 H) 2.67-2.75 (m, 1 H) 2.88-2.93 (m, 2 H) 2.93 (s, 3 H) 3.03 (s, 3 H) 3.08-3.21 (m, 7 H) 3.28 (s, 3 H) 3.29-3.35 (m, 2 H) 3.40-3.44 (m, 1 H) 3.63 (s, 1 H) 3.66 (d, J = 7.34 Hz, 1 H) 3.70 (m, 2 H) 3.87-3.93 (m, 1 H) 4.10-4.14 (m, 1 H) 4.39 (d, J = 7.34 Hz, 1 H) 4.86-4.91 (m, 1 H) 4.98 (d, J = 5.04 Hz, 1 H) |
| 36 | H₃C-S- [structure] | [structure with N(Et)(CH₃)] | 989.7 (600 MHz): 0.84 (t, J = 7.34 Hz, 3 H) 0.99-1.05 (m, 9 H) 1.09 (d, J = 7.34 Hz, 3 H) 1.13 (d, J = 7.34 Hz, 3 H) 1.16 (s, 3 H) 1.17-1.21 (m, 6 H) 1.22-1.25 (m, 1 H) 1.23 (d, J = 6.42 Hz, 3 H) 1.38 (s, 3 H) 1.39 (s, 3 H) 1.48-1.54 (m, 1 H) 1.63-1.67 (m, 1 H) 1.72-1.75 (m, 2 H) 1.85-2.04 (m, 4 H) 2.09 (d, J = 14.67 Hz, 1 H) 2.16 (s, 3 H) 2.29 (s, 6 H) 2.34 (s, 3 H) 2.41-2.46 (m, 1 H) 2.43-2.59 (m, 8 H) 2.57-2.61 (m, 1 H) 2.75-2.80 (m, 2 H) 2.83 (d, J = 14.67 Hz, 1 H) 2.86-2.90 (m, 1 H) 3.04 (s, 3 H) 3.06-3.11 (m, 1 H) 3.18 (dd, J = 10.09, 7.34 Hz, 1 H) 3.28 (s, 3 H) 3.42 (br. s., 1 H) 3.44-3.50 (m, 1 H) 3.63 (s, 1 H) 3.69 (d, J = 7.34 Hz, 1 H) 3.72 (d, J = 9.63 Hz, 1 H) 3.77-3.83 (m, 1 H) 3.88-3.94 (m, 1 H) 4.06-4.11 (m, 1 H) 4.42 (d, J = 7.34 Hz, 1 H) 4.99 (d, J = 4.13 Hz, 1 H) 5.13 (dd, J = 10.55, 2.29 Hz, 1 H) |
| 37 | H₃C-S- [structure] | [isothiazolidine 1,1-dioxide structure] | 1037.6 (600 MHz): 0.84 (t, J = 7.57 Hz, 3 H) 1.02 (d, J = 6.88 Hz, 3 H) 1.09 (d, J = 7.79 Hz, 3 H) 1.12-1.15 (m, 6 H) 1.18 (d, J = 6.42 Hz, 3 H) 1.20 (d, J = 7.34 Hz, 3 H) 1.21-1.25 (m, 1 H) 1.24 (d, J = 6.42 Hz, 3 H) 1.38 (s, 3 H) 1.39 (s, 3 H) 1.49-1.53 (m, 1 H) 1.65-1.70 (m, 1 H) 1.73-1.76 (m, 2 H) 1.87-1.99 (m, 3 H) 2.03-2.11 (m, 2 H) 2.16 (s, 3 H) 2.29 (s, 6 H) 2.34-2.39 (m, 2 H) 2.40 (s, 3 H) 2.42-2.45 (m, 1 H) 2.57-2.62 (m, 1 H) 2.67-2.81 (m, 4 H) 2.86-2.91 (m, 2 H) 3.03 (s, 3 H) 3.06-3.21 (m, 6 H) 3.28 (s, 3 H) 3.29-3.33 (m, 2 H) 3.40-3.46 (m, 1 H) 3.62 (s, 1 H) 3.66 (d, J = 7.34 Hz, 1 H) 3.71-3.74 (m, 1 H) 3.77-3.84 (m, 1 H) 3.89-3.95 (m, 1 H) 4.10-4.14 (m, 1 H) 4.40 (d, J = 7.34 Hz, 1 H) 4.98 (d, J = 5.04 Hz, 1 H) 5.11-5.16 (m, 1 H) |

TABLE 1-continued

| 38 | 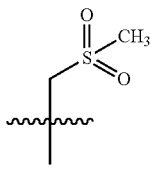 | 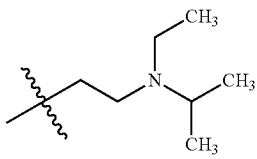 [SMILES: *CCN(CC)C(C)C] | 1049.7 (600 MHz): 0.84 (t, J = 7.34 Hz, 3 H) 0.96 (d, J = 6.42 Hz, 3 H) 0.99 (s, 3 H) 1.01 (s, 3 H) 1.04 (t, J = 7.11 Hz, 3 H) 1.10 (d, J = 7.34 Hz, 3 H) 1.13 (d, J = 6.88 Hz, 3 H) 1.15 (s, 3 H) 1.18-1.20 (m, 6 H) 1.20-1.27 (m, 1 H) 1.24 (d, J = 6.42 Hz, 3 H) 1.39 (s, 3 H) 1.40 (s, 3 H) 1.51-1.58 (m, 1 H) 1.63-1.67 (m, 1 H) 1.72-1.75 (m, 2 H) 1.85-1.94 (m, 2 H) 1.96-2.05 (m, 2 H) 2.06 (d, J = 15.13 Hz, 1 H) 2.11-2.19 (m, 1 H) 2.22-2.29 (m, 1 H) 2.29 (s, 6 H) 2.34 (s, 3 H) 2.36-2.62 (m, 8 H) 2.83 (d, J = 14.67 Hz, 1 H) 2.88-2.97 (m, 2 H) 2.93 (s, 3 H) 3.04 (s, 3 H) 3.08-3.20 (m, 4 H) 3.28 (s, 3 H) 3.43-3.49 (m, 2 H) 3.63 (s, 1 H) 3.66-3.76 (m, 3 H) 3.87-3.93 (m, 1 H) 4.06-4.11 (m, 1 H) 4.41 (d, J = 7.34 Hz, 1 H) 4.89 (dd, J = 10.77, 2.06 Hz, 1 H) 4.98 (d, J = 4.58 Hz, 1 H) |
| --- | --- | --- | --- |
| 39 | 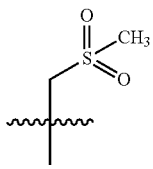 | 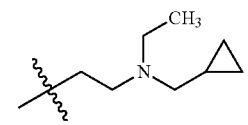 [SMILES: *CCN(CC)CC1CC1] | 1061.8 (500 MHz): 0.07-0.11 (m, 2 H) 0.47-0.51 (m, 2 H) 0.84 (t, J = 7.27 Hz, 3 H) 0.87-0.91 (m, 1 H) 0.99-1.06 (m, 6 H) 1.10 (d, J = 7.68 Hz, 3 H) 1.13 (d, J = 6.86 Hz, 3 H) 1.16 (s, 3 H) 1.18-1.21 (m, 6 H) 1.22-1.27 (m, 1 H) 1.24 (d, J = 6.03 Hz, 3 H) 1.39 (s, 3 H) 1.40 (s, 3 H) 1.49-1.56 (m, 1 H) 1.62-1.68 (m, 1 H) 1.72-1.76 (m, 2 H) 1.85-1.94 (m, 2 H) 1.95-2.05 (m, 2 H) 2.06-2.12 (m, 1 H) 2.13-2.26 (m, 2 H) 2.29 (s, 6 H) 2.31-2.69 (m, 10 H) 2.35 (s, 3 H) 2.81-2.87 (m, 1 H) 2.88-2.92 (m, 1 H) 2.92-2.96 (m, 3 H) 3.03 (s, 3 H) 3.06-3.21 (m, 4 H) 3.28 (s, 3 H) 3.44-3.49 (m, 1 H) 3.63 (s, 1 H) 3.66-3.77 (m, 3 H) 3.86-3.94 (m, 1 H) 4.10 (q, J = 6.03 Hz, 1 H) 4.41 (d, J = 7.13 Hz, 1 H) 4.85-4.91 (m, 1 H) 4.94-5.00 (m, 1 H) |
| 40 | 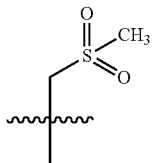 [SMILES: *CS(C)(=O)=O] | 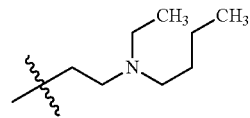 [SMILES: *CCN(CC)CCCC] | 1063.8 (500 MHz): 0.84 (t, J = 7.27 Hz, 3 H) 0.90 (t, J = 7.27 Hz, 3 H) 0.98-1.04 (m, 6 H) 1.10 (d, J = 7.40 Hz, 3 H) 1.13 (d, J = 7.13 Hz, 3 H) 1.16 (s, 3 H) 1.17-1.20 (m, 6 H) 1.19-1.25 (m, 1 H) 1.24 (d, J = 6.03 Hz, 3 H) 1.25-1.34 (m, 2 H) 1.39 (s, 3 H) 1.40 (s, 3 H) 1.41-1.46 (m, 2 H) 1.47-1.55 (m, 1 H) 1.63-1.68 (m, 1 H) 1.71-1.78 (m, 2 H) 1.85-2.06 (m, 4 H) 2.08 (d, J = 14.81 Hz, 1 H) 2.12-2.20 (m, 1 H) 2.21-2.27 (m, 1 H) 2.29 (s, 6 H) 2.34 (s, 3 H) 2.36-2.64 (m, 10 H) 2.83 (d, J = 14.81 Hz, 1 H) 2.88-2.93 (m, 1 H) 2.92-2.95 (m, 3 H) 3.03 (s, 3 H) 3.07-3.21 (m, 4 H) 3.28 (s, 3 H) 3.42-3.50 (m, 1 H) 3.63 (s, 1 H) 3.66-3.76 (m, 3 H) 3.86-3.94 (m, 1 H) 4.09 (q, J = 6.22 Hz, 1 H) 4.39-4.42 (m, 1 H) 4.86-4.91 (m, 1 H) 4.98 (d, J = 4.39 Hz, 1 H) |
| 41 | 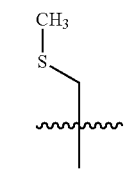 | 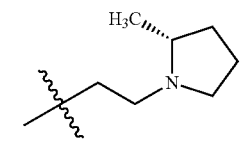 [SMILES: *CCN1CCC[C@H]1C] | 1015.6 (600 MHz): 0.83 (t, J = 7.34 Hz, 3 H) 1.01 (d, J = 6.88 Hz, 3 H) 1.07-1.10 (m, 6 H) 1.12 (d, J = 7.34 Hz, 3 H) 1.15 (s, 3 H) 1.17-1.22 (m, 6 H) 1.22-1.24 (m, 3 H) 1.23-1.26 (m, 1 H) 1.38 (s, 3 H) 1.39 (s, 3 H) 1.40-1.44 (m, 1 H) 1.48-1.57 (m, 1 H) 1.62-1.70 (m, 2 H) 1.72-1.80 (m, 3 H) 1.87-2.00 (m, 6 H) 2.01-2.05 (m, 1 H) 2.07-2.18 (m, 3 H) 2.12 (s, 3 H) 2.29 (s, 6 H) 2.31-2.35 (m, 1 H) 2.36 (s, 3 H) 2.41-2.46 (m, 1 H) 2.50-2.65 (m, 5 H) 2.84-2.93 (m, 3 H) 3.05 (s, 3 H) 3.06-3.11 (m, 1 H) 3.12-3.17 (m, 1 H) 3.19 (d, J = 7.34 Hz, 1 H) 3.28 (s, 3 H) 3.39-3.43 (m, 1 H) 3.44-3.49 (m, 1 H) 3.64-3.73 (m, 5 H) 4.10 (q, J = 6.42 Hz, 1 H) 4.42 (d, J = 7.34 Hz, 1 H) 4.96 (dd, J = 11.00, 2.29 Hz, 1 H) 4.99 (d, J = 4.58 Hz, 1 H) |

| | | | | |
|---|---|---|---|---|
| 42 | [structure: OH on quaternary carbon] | [structure: N(ethyl)(CH2-cyclopropyl) with propyl linker] | 985.7 | (600 MHz): 0.07-0.11 (m, 2 H) 0.45-0.52 (m, 2 H) 0.82-0.91 (m, 4 H) 1.00-1.27 (m, 28 H) 1.40 (s, 6 H) 1.52-1.58 (m, 1 H) 1.63-1.67 (m, 1 H) 1.70-1.79 (m, 2 H) 1.87-2.04 (m, 4 H) 2.10 (d, J = 14.67 Hz, 1 H) 2.29 (s, 6 H) 2.31-2.68 (m, 12 H) 2.84 (d, J = 14.67 Hz, 1 H) 2.89-2.97 (m, 1 H) 3.08 (s, 3 H) 3.08-3.13 (m, 1 H) 3.16-3.22 (m, 1 H) 3.28 (s, 3 H) 3.44-3.50 (m, 1 H) 3.67-3.86 (m, 5 H) 4.09 (q, J = 6.11 Hz, 1 H) 4.42 (d, J = 7.34 Hz, 1 H) 4.98 (d, J = 4.13 Hz, 1 H) 5.04 (dd, J = 11.00, 2.29 Hz, 1 H) |
| 43 | [structure: H3C-N(SO2CH3)-] | [structure: N(Et)(Et) with propyl linker] | 1050 | (400 MHz): 0.86 (t, J = 7.32 Hz, 3 H) 1.01 (d, J = 7.32 Hz, 3 H) 1.02 (t, J = 7.32 Hz, 6 H) 1.09 (d, J = 7.57 Hz, 3 H) 1.13 (d, J = 7.08 Hz, 3 H) 1.16 (s, 3 H) 1.17-1.26 (m, 1 H) 1.19 (d, J = 6.10 Hz, 3 H) 1.21 (d, J = 5.62 Hz, 3 H) 1.24 (d, J = 5.86 Hz, 3 H) 1.38 (s, 3 H) 1.41 (s, 3 H) 1.48-1.94 (m, 7 H) 1.95-2.14 (m, 3 H) 2.29 (s, 6 H) 2.34 (s, 3 H) 2.38-2.64 (m, 10 H) 2.80-2.92 (m, 2 H) 2.87 (s, 3 H) 2.98 (s, 3 H) 3.06 (s, 3 H) 3.06-3.11 (m, 1 H) 3.19 (dd, J = 10.25, 7.32 Hz, 1 H) 3.28 (s, 3 H) 3.34-3.56 (m, 4 H) 3.63 (s, 1 H) 3.66-3.78 (m, 3 H) 3.86-3.96 (m, 1 H) 4.10 (q, J = 6.35 Hz, 1 H) 4.41 (d, J = 7.08 Hz, 1 H) 4.93 (d, J = 9.52 Hz, 1 H) 4.99 (d, J = 3.91 Hz, 1 H) |
| 44 | [structure: H3C-N(CH3)-C(=O)-] | [structure: N(Et)(Et) with propyl linker] | 1014 | (400 MHz): 0.88 (t, J = 7.1 Hz, 3 H) 1.00 (d, J = 6.6 Hz, 3 H) 1.02 (d, J = 6.8 Hz, 3 H) 1.08-1.14 (m, 7 H) 1.15-1.22 (m, 6 H) 1.22-1.27 (m, 3 H) 1.29-1.37 (m, 4 H) 1.39 (s, 3 H) 1.50-1.65 (m, 2 H) 1.97-2.20 (m, 2 H) 2.29 (s, 6 H) 2.35 (d, J = 14.1 Hz, 1 H) 2.40-2.70 (m, 5 H) 2.83-2.95 (m, 3 H) 2.99-3.05 (m, 1 H) 3.13-3.24 (m, 3 H) 3.27-3.43 (m, 8 H) 3.47-3.62 (m, 1 H) 3.67-3.73 (m, 1 H) 3.83 (s, 3 H) 3.89-3.93 (m, 1H) 4.15 (q, J = 6.9 Hz, 1 H) 4.19-4.31 (m, 1 H) 4.45-4.11 (m, 1 H) 4.60-4.65 (m, 1 H) 4.90-4.991 (m, 1 H) 4.99-5.05 (m, 1 H) 6.83-6.89 (m, 1 H) 6.90-6.96 (m, 1 H) 7.18-7.26 (m, 2 H) |
| 45 | [structure: O=C-NH2] | [structure: N(Et)(Et) with propyl linker] | 986 | (400 MHz): 0.87 (t, J = 7.0 Hz, 3 H) 0.93-1.00 (m, 9 H) 1.01 (d, J = 6.8 Hz, 3 H) 1.06 (d, J = 6.4 Hz, 3 H) 1.10 (d, J = 7.5 Hz, 3 H) 1.15 (d, J = 5.9 Hz, 3 H) 1.24 (d, J = 7.1 Hz, 3 H) 1.30 (d, J = 6.9 Hz, 3 H) 1.37 (s, 3 H) 1.51-1.70 (m, 2 H) 1.92-2.05 (m, 2 H) 2.08-2.23 (m, 2 H) 2.29 (s, 6 H) 2.40-2.62 (m, 1 H) 2.77-2.93 (m, 2 H) 2.99-3.23 (m, 3 H) 3.27 (s, 3 H) 3.34 (s, 3 H) 3.37-3.474 (m, 1 H) 3.56-3.62 (m, 1 H) 3.65-3.70 (m, 1 H) 3.81 (s, 3 H) 3.90 (d, J = 6.1 Hz, 1 H) 4.14 (q, J = 6.2 Hz, 1 H) 4.39-4.51 (m, 2 H) 4.63 (t, J = 4.4 Hz, 1 H) 4.92-5.03 (m, 2 H) 6.79-6.86 (m, 1 H) 6.87-6.94 (m, 1 H) 7.16-7.22 (m, 1 H) 7.33-7.36 (m, 1 H) |
| 46 | [structure: H3C-N(CH3)-C(=O)-O-CH3 carbamate] | [structure: N(Et)(Et) with propyl linker] | 1030 | (400 MHz): 0.84 (t, J = 7.32 Hz, 3 H) 1.01 (d, J = 7.32 Hz, 3 H) 1.02 (t, J = 7.08 Hz, 6 H) 1.10 (d, J = 7.57 Hz, 3 H) 1.13 (d, J = 7.08 Hz, 3 H) 1.16 (s, 3 H) 1.17-1.26 (m, 1 H) 1.19 (d, J = 6.10 Hz, 3 H) 1.21 (d, J = 6.59 Hz, 3 H) 1.24 (d, J = 5.89 Hz, 3 H) 1.38 (s, 3 H) 1.41 (s, 3 H) 1.46-1.78 (m, 5 H) 1.82-1.96 (m, 2 H) 1.96-2.13 (m, 3 H) 2.29 (s, 6 H) 2.34 (s, 3 H) 2.39-2.63 (m, 10 H) 2.84 (d, J = 14.89 Hz, 1 H) 2.84-3.11 (m, 6 H) 3.06 (s, 3 H) 3.19 (dd, J = 10.01, 7.32 Hz, 1 H) 3.28 (s, 3 H) 3.40-3.82 (m, 9 H) 3.68 (s, 3 H) 4.10 (q, J = 5.86 Hz, 1 H) 4.42 (d, J = 7.08 Hz, 1 H) 4.92 (d, J = 10.50 Hz, 1 H) 5.00 (d, J = 3.91 Hz, 1 H) |

TABLE 1-continued

| | | | | |
|---|---|---|---|---|
| 47 | imidazolidinone-methyl | CH2CH2N(Et)(CH2CH3) branched | 1027 | (400 MHz): 0.84 (t, J = 7.32 Hz, 3 H) 1.01 (d, J = 7.08 Hz, 3 H) 1.02 (t, J = 7.32 Hz, 6 H) 1.08 (d, J = 7.32 Hz, 3 H) 1.13 (d, J = 7.08 Hz, 3 H) 1.16 (s, 3 H) 1.18 (d, J = 6.59 Hz, 3 H) 1.20 (d, J = 7.57 Hz, 3 H) 1.23 (d, J = 6.10 Hz, 3 H) 1.38 (s, 3 H) 1.39 (s, 3 H) 1.44-1.68 (m, 2 H) 1.74 (d, J = 6.84 Hz, 2 H) 1.84-1.96 (m, 2 H) 1.96-2.06 (m, 2 H) 2.09 (d, J = 14.9 Hz, 1 H) 2.29 (s, 6 H) 2.34 (s, 3 H) 2.39-2.65 (m, 10 H) 2.83 (d, J = 14.9 Hz, 1 H) 2.84-2.92 (m, 1 H) 3.06 (s, 3 H) 3.10 (q, J = 6.84 Hz, 1 H) 3.18 (dd, J = 10.3, 7.32 Hz, 1 H) 3.28 (s, 3 H) 3.37-3.65 (m, 8 H) 3.68 (s, 3 H) 3.69-3.77 (m, 3 H) 3.78-3.87 (m, 1 H) 4.08 (q, J = 6.35 Hz, 1 H) 4.15 (br s, 1 H) 4.42 (d, J = 7.32 Hz, 1 H) 4.98 (d, J = 4.15 Hz, 1 H) 5.07 (dd, J = 10.6, 1.57 Hz, 1 H) |
| 48 | CH3-NH-SO2- | CH2CH2N(Et)(CH2CH3) branched | 1036.7 | (400 MHz): 0.85 (t, J = 7.3 Hz, 3 H) 0.99-1.05 (m, 9 H) 1.07-1.27 (m, 19 H) 1.38 (s, 3 H) 1.40 (s, 3 H) 1.46-1.79 (m, 4 H) 1.81-1.93 (m, 2 H) 1.94-2.05 (m, 2 H) 2.06-2.13 (m, 1 H) 2.29 (s, 6 H) 2.34 (s, 3 H) 2.39-2.64 (m, 9 H) 2.80-2.86 (m, 4 H) 2.86-2.94 (m, 1 H) 3.04 (s, 3 H) 3.09 (q, J = 6.8 Hz, 1 H) 3.18 (dd, J = 10.3, 7.3 Hz, 1 H) 3.28 (s, 3 H) 3.37-3.55 (m, 4 H) 3.65-3.75 (m, 3 H) 3.96-4.05 (m, 1 H) 4.09 (q, J = 6.3 Hz, 1 H) 4.20 (dt, J = 14.9, 5.8 Hz, 1 H) 4.42 (d, J = 7.3 Hz, 1 H) 4.96-5.02 (m, 2 H) 5.21 (dd, J = 11.0, 2.0, 1 H) |
| 49 | phenylpropyl | CH2CH2N(Et)(CH2CH3) branched | 1047.7 | (400 MHz): 0.82 (t, J = 7.3 Hz, 3 H) 0.99-1.05 (m, 9 H) 1.07-1.26 (m, 19 H) 1.39 (s, 3 H) 1.39 (s, 3 H) 1.46-1.57 (m, 1 H) 1.59-1.78 (m, 7 H) 1.86-2.14 (m, 5 H) 2.29 (s, 6 H) 2.34 (s, 3 H) 2.41-2.68 (m, 12 H) 2.82-2.91 (m, 2 H) 3.01 (s, 3 H) 3.08 (q, J = 6.9 Hz, 1 H) 3.19 (dd, J = 10.3, 7.3 Hz, 1 H) 3.29 (s, 3 H) 3.40-3.53 (m, 2 H) 3.60-3.71 (m, 4 H) 3.74 (d, J = 9.5 Hz, 1 H) 4.10 (q, J = 6.2 Hz, 1 H) 4.42 (d, J = 7.1 Hz, 1 H) 4.96-5.04 (m, 2 H) 7.13-7.28 (m, 5 H) |
| 50 | phenoxymethyl | CH2CH2N(Et)(CH2CH3) branched | 1049.7 | (400 MHz): 0.92 (t, J = 7.4 Hz, 3 H) 1.03 (d, J = 6.6 Hz, 3 H) 1.06 (d, J = 6.8 Hz, 3 H) 1.08 (d, J = 7.1 Hz, 3 H) 1.13 (s, 3 H) 1.15-1.28 (m, 11 H) 1.39 (s, 3 H) 1.42 (s, 3 H) 1.50-1.88 (m, 10 H) 1.95 (dd, J = 15.0, 5.0 Hz, 1 H) 2.03 (d, J = 13.2 Hz, 1 H) 2.06 (d, J = 14.6 Hz, 1 H) 2.18 (s, 3 H) 2.20-2.34 (m, 10 H) 2.38-2.55 (m, 4 H) 2.58-2.73 (m, 3 H) 2.80 (d, J = 14.4 Hz, 1 H) 3.19 (dd, J = 10.0, 7.4 Hz, 1 H) 3.30 (s, 3 H) 3.40-3.52 (m, 1 H) 3.61 (d, J = 10.3 Hz, 1 H) 3.81 (s, 3 H) 3.91 (d, J = 9.8 Hz, 1 H) 4.08 (s, 1 H) 4.11 (q, J = 6.3 Hz, 1 H) 4.33 (d, J = 7.3 Hz, 1 H) 4.91 (dd, J = 9.9, 3.1 Hz, 1 H) 5.21 (s, 1 H) 5.35 (d, J = 4.9 Hz, 1 H) 6.84-6.93 (m, 2 H) 7.14-7.23 (m, 1 H) 7.60 (d, J = 7.3 Hz, 1 H) |
| 51 | ethylsulfonyl-methyl | CH2CH2N(Et)(CH2CH3) branched | 1035 | (400 MHz): 0.83 (t, J = 7.3 Hz, 3 H) 1.01 (t, J = 7.1 Hz, 6 H) 1.02 (d, J = 7.3 Hz, 3 H) 1.03 (d, J = 7.3 Hz, 3 H) 1.09 (d, J = 7.6 Hz, 3 H) 1.12 (d, J = 7.1 Hz, 3 H) 1.13 (d, J = 7.1 Hz, 3 H) 1.16 (s, 3 H) 1.17 (d, J = 6.6 Hz, 3 H) 1.20 (d, J = 7.3 Hz, 3 H) 1.23 (d, J = 6.1 Hz, 3 H) 1.48-1.56 (m, 1 H) 1.61-1.68 (m, 2 H) 1.71-1.76 (m, 3 H) 1.81-1.90 (m, 3 H) 1.97-2.04 (m, 3 H) 2.08 (d, J = 14.9 Hz, 1 H) 2.28 (s, 6 H) 2.34 (s, 3 H) 2.38-2.63 (m, 9 H) 2.82 (d, J = 14.9 Hz, 1 H) 2.86-2.94 (m, 1 H) 3.06 (s, 3 H) 3.07-3.13 (m, 2 H) 3.18 (dd, J = 10.3, 7.3 Hz, 1 H) 3.27 (s, 3 H) 3.36-3.54 (m, 4 H) 3.62 (s, 1 H) 3.67-3.74 (m, 2 H) 3.98-4.15 (m, 3 H) 4.41 (d, J = 7.3 Hz, 1 H) 4.94 (dd, J = 10.7, 2.0 Hz, 1 H) 4.97-5.00 (m, 1 H) |

TABLE 1-continued

| 52 | [structure: PhNH-SO2-C(CH3)-] | [structure: -CH2-C(CH3)2-CH2-CH2-N(Et)2] | 1098.7 | (400 MHz): 0.82 (t, J = 7.3 Hz, 3 H) 0.98-1.07 (m, 9 H) 1.09-1.27 (m, 19 H) 1.40 (s, 3 H) 1.40 (s, 3 H) 1.45-1.80 (m, 2 H) 1.85-2.23 (m, 7 H) 2.29 (s, 6 H) 2.34 (s, 3 H) 2.38-2.66 (m, 10 H) 2.83 (d, J = 14.6 Hz, 1 H) 2.85-2.95 (m, 1 H) 3.03-3.13 (m, 4 H) 3.19 (dd, J = 10.1, 7.2 Hz, 1 H) 3.28 (s, 3 H) 3.41-3.53 (m, 2 H) 3.68-3.88 (m, 5 H) 4.03 (t, J = 6.1 Hz, 2 H) 4.09 (q, J = 6.3 Hz, 1 H) 4.42 (d, J = 7.3 Hz, 1 H) 4.95-5.01 (m, 2 H) 6.87-6.94 (m, 3 H) 7.21-7.30 (m, 2 H) |
| --- | --- | --- | --- | --- |
| 53 | [structure: thiomorpholine-1,1-dioxide linked via N, with -C(CH3)-] | [structure: -CH2-C(CH3)2-CH2-CH2-N(Et)2] | 1076 | (400 MHz): 0.85 (t, J = 7.32 Hz, 3 H) 1.01 (d, J = 7.32 Hz, 3 H) 1.02 (t, J = 7.08 Hz, 6 H) 1.08 (d, J = 7.57 Hz, 3 H) 1.14 (d, J = 7.08 Hz, 3 H) 1.16 (s, 3 H) 1.19 (d, J = 6.35 Hz, 3 H) 1.21 (d, J = 6.35 Hz, 3 H) 1.24 (d, J = 6.10 Hz, 3 H) 1.39 (s, 3 H) 1.40 (s, 3 H) 1.45-1.70 (m, 3 H) 1.72-1.77 (m, 1 H) 1.84-1.98 (m, 2 H) 1.98-2.03 (m, 1 H) 2.08 (d, J = 14.6 Hz, 1 H) 2.29 (s, 6 H) 2.34 (s, 3 H) 2.37-2.63 (m, 10 H) 2.80-2.90 (m, 4 H) 2.90-3.14 (m, 10 H) 3.18 (dd, J = 10.3, 7.08 Hz, 1 H) 3.20-3.28 (m, 2 H) 3.28 (s, 3 H) 3.40-3.51 (m, 2 H) 3.56 (s, 3 H) 3.66 (d, J = 7.57 Hz, 1 H) 3.72 (d, J = 9.28 Hz, 3 H) 3.84-3.91 (m, 2 H) 4.10 (q, J = 6.35 Hz, 1 H) 4.98 (d, J = 3.91 Hz, 1 H) 5.16 (dd, J = 10.6, 1.57 Hz, 1 H) |
| 54 | [structure: H3C-S(O2)-CH2-CH2-C(CH3)-] | [structure: -CH2-C(CH3)2-CH2-CH2-N(Et)2] | 1049 | (400 MHz): 0.83 (t, J = 7.32 Hz, 3 H) 1.01 (t, J = 6.84 Hz, 6 H) 1.03 (d, J = 6.84 Hz, 3 H) 1.09 (d, J = 7.57 Hz, 3 H) 1.13 (d, J = 7.08 Hz, 3 H) 1.17 (s, 3 H) 1.20 (d, J = 6.35 Hz, 6 H) 1.24 (d, J = 6.10 Hz, 3 H) 1.39 (s, 3 H) 1.40 (s, 3 H) 1.46-1.60 (m, 2 H) 1.62-1.70 (m, 1 H) 1.71-1.82 (m, 4 H) 1.83-1.97 (m, 4 H) 1.97-2.03 (m, 1 H) 2.10 (d, J = 14.9 Hz, 1 H) 2.29 (s, 6 H) 2.34 (s, 3 H) 2.48-2.64 (m, 9 H) 2.83 (d, J = 14.9 Hz, 1 H) 2.90 (s, 3 H) 3.03 (s, 3 H) 3.06-3.13 (m, 3 H) 3.18 (dd, J = 10.5, 7.32 Hz, 1 H) 3.28 (s, 3 H) 3.40-3.51 (m, 2 H) 3.58-3.80 (m, 5 H) 4.10 (q, J = 6.35 Hz, 1 H) 4.41 (d, J = 7.08 Hz, 1 H) 4.92 (dd, J = 5.68, 2.26 Hz, 1 H) 4.99 (d, J = 3.42 Hz, 1 H) |
| 55 | [structure: 2-pyridyl-CH2-N(CH3)-C(CH3)-] | [structure: -CH2-C(CH3)2-CH2-CH2-N(CH3)-C(CH3)2-(2-methoxyphenyl)] | 1169.8 | (600 MHz): 0.75 (t, J = 7.43 Hz, 3 H) 1.04 (d, J = 6.61 Hz, 3 H) 1.09 (d, J = 7.43 Hz, 3 H) 1.11-1.27 (m, 16 H) 1.37-1.40 (m, 6 H) 1.44 (br. s., 6 H) 1.48-1.79 (m, 4 H) 1.86-2.07 (m, 5 H) 2.18 (s, 6 H) 2.22-2.63 (m, 16 H) 2.77-2.93 (m, 3 H) 3.03 (s, 3 H) 3.08-3.14 (m, 1 H) 3.15-3.23 (m, 1 H) 3.28 (s, 3 H) 3.40-3.49 (m, 2 H) 3.62-3.69 (m, 2 H) 3.71-3.84 (m, 5 H) 3.84-3.98 (m, 2 H) 4.05-4.13 (m, 1 H) 4.41 (d, J = 7.43 Hz, 1 H) 4.99 (d, J = 4.95 Hz, 1 H) 5.06-5.13 (m, 1 H) 6.84-6.94 (m, 2 H) 7.14-7.24 (m, 2 H) 7.58-7.63 (m, 1 H) 7.72 (d, J = 7.84 Hz, 1 H) 8.44-8.52 (m, 2 H) |
| 56 | [structure: 2-pyridyl-CH2-N(CH3)-C(CH3)-] | [structure: -CH2-C(CH3)2-CH2-CH2-N(CH3)2] | 1035.7 | (600 MHz): 0.75 (t, J = 7.34 Hz, 3 H) 1.03 (d, J = 6.88 Hz, 3 H) 1.09 (d, J = 7.34 Hz, 3 H) 1.14 (d, J = 6.88 Hz, 3 H) 1.17 (s, 3 H) 1.18-1.26 (m, 10 H) 1.39 (s, 6 H) 1.48-1.56 (m, 1 H) 1.62-1.79 (m, 3 H) 1.87-1.98 (m, 3 H) 2.00-2.04 (m, 1 H) 2.14 (d, J = 14.67 Hz, 1 H) 2.18 (s, 3 H) 2.24 (s, 6 H) 2.29 (s, 6 H) 2.34 (s, 3 H) 2.35-2.66 (m, 7 H) 2.79-2.92 (m, 3 H) 3.03 (s, 3 H) 3.08-3.13 (m, 1 H) 3.16-3.21 (m, 1 H) 3.28 (s, 3 H) 3.43-3.50 (m, 2 H) 3.64 (s, 1 H) 3.68 (d, J = 7.34 Hz, 1 H) 3.72-3.74 (m, 1 H) 3.75-3.79 (m, 1 H) 3.84-3.98 (m, 2 H) 4.09-4.14 (m, 1 H) 4.41 (d, J = 6.88 Hz, 1 H) 4.96-5.00 (m, 1 H) 5.08-5.12 (m, 1 H) 7.20-7.23 (m, 1 H) 7.69-7.74 (m, 1 H) 8.44-8.47 (m, 1 H) 8.49 (s, 1 H) |

TABLE 1-continued

| | | | | |
|---|---|---|---|---|
| 57 | | | 978.6 | (600 MHz): 0.75 (t, J = 7.43 Hz, 3 H) 1.03 (d, J = 6.61 Hz, 3 H) 1.09 (d, J = 7.43 Hz, 3 H) 1.12 (s, 3 H) 1.14 (d, J = 7.02 Hz, 3 H) 1.16-1.26 (m, 10 H) 1.40 (s, 6 H) 1.46-1.80 (m, 4 H) 1.87-2.00 (m, 4 H) 2.03-2.08 (m, 1 H) 2.18 (s, 3 H) 2.29 (s, 6 H) 2.37 (s, 6 H) 2.40-2.48 (m, 1 H) 2.49-2.64 (m, 2 H) 2.73 (d, J = 14.45 Hz, 1 H) 2.83-2.92 (m, 2 H) 3.03 (s, 3 H) 3.08-3.14 (m, 1 H) 3.19 (dd, J = 10.11, 7.22 Hz, 1 H) 3.28 (s, 3 H) 3.39-3.49 (m, 3 H) 3.63-3.68 (m, 2 H) 3.72-3.80 (m, 2 H) 3.85-3.97 (m, 2 H) 4.09-4.14 (m, 1 H) 4.40 (d, J = 7.43 Hz, 1 H) 4.99 (d, J = 5.37 Hz, 1 H) 5.10 (dd, J = 10.94, 2.27 Hz, 1 H) 7.21 (dd, J = 7.84, 4.54 Hz, 1 H) 7.70-7.73 (m, 1 H) 8.46 (dd, J = 4.54, 1.65 Hz, 1 H) 8.49 (d, J = 1.65 Hz, 1 H) |
| 58 | | | 1012.9 | (600 MHz): 0.84 (t, J = 7.34 Hz, 3 H) 0.99 (d, J = 6.88 Hz, 3 H) 1.09 (d, J = 7.34 Hz, 3 H) 1.12 (d, J = 7.34 Hz, 3 H) 1.18 (s, 3 H) 1.19-1.26 (m, 10 H) 1.38 (s, 3 H) 1.40 (s, 3 H) 1.47-1.75 (m, 4 H) 1.82-2.07 (m, 8 H) 2.15 (d, J = 14.67 Hz, 1 H) 2.25 (s, 6 H) 2.29 (s, 6 H) 2.35 (s, 3 H) 2.31-2.66 (m, 8 H) 2.82 (d, J = 14.67 Hz, 1 H) 2.85-2.92 (m, 1 H) 3.03 (s, 3 H) 3.08 (d, J = 7.34 Hz, 1 H) 3.19 (dd, J = 10.09, 7.34 Hz, 1 H) 3.28 (s, 3 H) 3.30-3.51 (m, 5 H) 3.57-3.64 (m, 2 H) 3.66-3.73 (m, 3 H) 4.09-4.15 (m, 1 H) 4.42 (d, J = 7.34 Hz, 1 H) 4.94-5.00 (m, 2 H) |
| 59 | | | 1064.8 | (500 MHz): 0.83 (t, J = 7.40 Hz, 3 H) 0.98-1.06 (m, 9 H) 1.10 (d, J = 7.40 Hz, 3 H) 1.13 (d, J = 7.13 Hz, 3 H) 1.15-1.27 (m, 13 H) 1.39 (s, 3 H) 1.39 (s, 3 H) 1.47-1.80 (m, 8 H) 1.86-2.12 (m, 5 H) 2.29 (s, 6 H) 2.34 (s, 3 H) 2.40-2.65 (m, 10 H) 2.81-2.93 (m, 2 H) 3.01 (s, 3 H) 3.06-3.12 (m, 1 H) 3.15-3.22 (m, 1 H) 3.28 (s, 3 H) 3.40-3.52 (m, 3 H) 3.60-3.74 (m, 5 H) 4.09 (q, J = 6.12 Hz, 1 H) 4.41 (d, J = 7.40 Hz, 1 H) 4.94-5.04 (m, 2 H) 5.39-5.46 (m, 1 H) 6.46 (t, J = 4.80 Hz, 1 H) 8.25 (d, J = 4.66 Hz, 2 H) |
| 60 | | | 1007.7 | (500 MHz): 0.83 (t, J = 7.27 Hz, 3 H) 0.98-1.17 (m, 21 H) 1.20-1.29 (m, 7 H) 1.39 (s, 6 H) 1.48-1.79 (m, 9 H) 1.88-2.00 (m, 3 H) 2.04-2.10 (m, 1 H) 2.21 (s, 3 H) 2.32 (s, 6 H) 2.44-2.52 (m, 1 H) 2.56-2.65 (m, 1 H) 2.85-2.95 (m, 2 H) 3.02 (s, 3 H) 3.06-3.13 (m, 1 H) 3.20 (dd, J = 9.94, 7.26 Hz, 1 H) 3.29 (s, 3 H) 3.42-3.51 (m, 3 H) 3.60-3.75 (m, 6 H) 4.08-4.14 (m, 1 H) 4.43 (d, J = 7.26 Hz, 1 H) 4.96-5.03 (m, 2 H) 5.44-5.50 (m, 1 H) 6.46 (t, J = 4.78 Hz, 1 H) 8.25 (d, J = 4.59 Hz, 2 H) |
| 61 | | | 993.7 | (500 MHz): 0.83 (t, J = 7.72 Hz, 3 H) 1.01 (d, J = 6.86 Hz, 3 H) 1.03-1.17 (m, 15 H) 1.18-1.30 (m, 7 H) 1.39 (s, 6 H) 1.47-1.79 (m, 8 H) 1.88-2.09 (m, 5 H) 2.31 (br. s., 6 H) 2.33 (s, 3 H) 2.41-2.66 (m, 4 H) 2.76-2.94 (m, 2 H) 3.02 (s, 3 H) 3.09 (q, J = 7.04 Hz, 1 H) 3.17-3.23 (m, 1 H) 3.29 (s, 3 H) 3.41-3.51 (m, 3 H) 3.60-3.75 (m, 5 H) 4.10 (q, J = 6.31 Hz, 1 H) 4.41 (d, J = 7.13 Hz, 1 H) 4.94-5.05 (m, 2 H) 5.42-5.49 (m, 1 H) 6.46 (t, J = 4.80 Hz, 1 H) 8.25 (d, J = 4.66 Hz, 2 H) |

TABLE 1-continued

| | | | | |
|---|---|---|---|---|
| 62 | 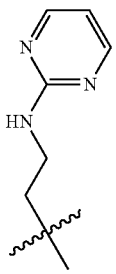 [SMILES: *CCNc1ncccn1] | 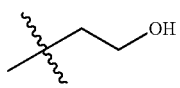 [SMILES: *CCO] | 1009.7 | (600 MHz): 0.83 (t, J = 7.34 Hz, 3 H) 1.01 (d, J = 6.88 Hz, 3 H) 1.10 (d, J = 7.34 Hz, 3 H) 1.13 (d, J = 7.34 Hz, 3 H) 1.18-1.20 (m, 6 H) 1.21-1.25 (m, 7 H) 1.39 (s, 3 H) 1.39 (s, 3 H) 1.48-1.78 (m, 8 H) 1.87-1.97 (m, 3 H) 2.04-2.09 (m, 1 H) 2.14-2.19 (m, 1 H) 2.30 (br. s., 6 H) 2.38 (s, 3 H) 2.41-2.49 (m, 1 H) 2.57-2.79 (m, 3 H) 2.86-2.93 (m, 2 H) 3.01 (s, 3 H) 3.06-3.12 (m, 1 H) 3.16-3.23 (m, 1 H) 3.29 (s, 3 H) 3.39-3.50 (m, 4 H) 3.65 (s, 7 H) 4.12-4.18 (m, 1 H) 4.38-4.43 (m, 1 H) 4.96-5.01 (m, 2 H) 5.41-5.45 (m, 1 H) 6.46 (s, 1 H) 8.24 (d, J = 4.59 Hz, 2 H) |
| 63 | 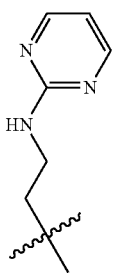 [SMILES: *CCNc1ncccn1] | 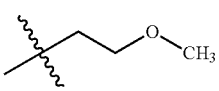 [SMILES: *CCOC] | 1023.7 | (600 MHz): 0.83 (t, J = 7.34 Hz, 3 H) 1.01 (d, J = 6.88 Hz, 3 H) 1.10 (d, J = 7.79 Hz, 3 H) 1.13 (d, J = 6.88 Hz, 3 H) 1.15 (s, 3 H) 1.16-1.26 (m, 10 H) 1.39 (s, 3 H) 1.39 (s, 3 H) 1.47-1.78 (m, 8 H) 1.87-1.94 (m, 2 H) 1.95-2.00 (m, 1 H) 2.04 (s, 1 H) 2.09-2.14 (m, 1 H) 2.29 (s, 5 H) 2.38 (s, 3 H) 2.40-2.47 (m, 1 H) 2.57-2.70 (m, 2 H) 2.76-2.82 (m, 1 H) 2.85-2.92 (m, 2 H) 3.01 (s, 3 H) 3.07-3.12 (m, 1 H) 3.16-3.22 (m, 1 H) 3.28 (s, 3 H) 3.35 (s, 3 H) 3.40-3.51 (m, 6 H) 3.61-3.71 (m, 4 H) 3.71-3.74 (m, 1 H) 4.08-4.14 (m, 1 H) 4.41 (d, J = 7.34 Hz, 1 H) 4.96-4.99 (m, 1 H) 5.00-5.02 (m, 1 H) 5.40-5.45 (m, 1 H) 6.46 (t, J = 4.81 Hz, 1 H) 8.25 (d, J = 4.59 Hz, 2 H) |
| 64 | 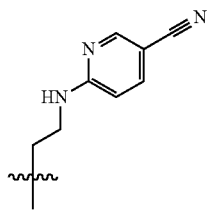 [SMILES: *CCNc1ccc(C#N)cn1] | 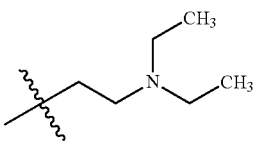 [SMILES: *CCN(CC)CC] | 1088.8 | (600 MHz): 0.81 (t, J = 7.34 Hz, 3 H) 0.97-1.05 (m, 9 H) 1.11 (d, J = 7.34 Hz, 3 H) 1.14 (d, J = 6.88 Hz, 3 H) 1.16-1.19 (m, 6 H) 1.20-1.26 (m, 7 H) 1.38 (s, 3 H) 1.40 (s, 3 H) 1.51-1.59 (m, 1 H) 1.61-1.80 (m, 7 H) 1.88-1.95 (m, 2 H) 1.88-2.06 (m, 2 H) 2.10 (s, 1 H) 2.29 (s, 6 H) 2.35 (s, 3 H) 2.40-2.46 (m, 1 H) 2.42-2.63 (m, 8 H) 2.57-2.61 (m, 1 H) 2.84 (d, J = 14.67 Hz, 1 H) 2.90-2.95 (m, 1 H) 2.97 (s, 3 H) 3.07-3.13 (m, 1 H) 3.16-3.20 (m, 1 H) 3.29 (s, 3 H) 3.42-3.50 (m, 3 H) 3.63 (s, 1 H) 3.65-3.70 (m, 1 H) 3.69 (d, J = 6.88 Hz, 1 H) 3.73 (d, J = 9.63 Hz, 1 H) 3.76-3.82 (m, 1 H) 4.06-4.12 (m, 1 H) 4.42 (d, J = 7.34 Hz, 1 H) 4.94-4.97 (m, 1 H) 5.00 (d, J = 4.58 Hz, 1 H) 5.66-5.72 (m, 1 H) 6.44 (d, J = 8.71 Hz, 1 H) 7.52-7.57 (m, 1 H) 8.34 (d, J = 2.29 Hz, 1 H) |
| 65 | 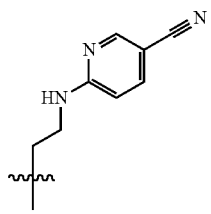 [SMILES: *CCNc1ccc(C#N)cn1] | 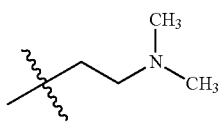 [SMILES: *CCN(C)C] | 1060.8 | (600 MHz): 0.82 (t, J = 7.57 Hz, 3 H) 1.01 (d, J = 6.88 Hz, 3 H) 1.11 (d, J = 7.34 Hz, 3 H) 1.14 (d, J = 6.88 Hz, 3 H) 1.17-1.20 (m, 6 H) 1.21-1.26 (m, 7 H) 1.37 (s, 3 H) 1.40 (s, 3 H) 1.51-1.58 (m, 1 H) 1.63-1.79 (m, 7 H) 1.87-1.96 (m, 2 H) 1.97-2.07 (m, 2 H) 2.14 (d, J = 14.67 Hz, 1 H) 2.25 (s, 6 H) 2.29 (s, 6 H) 2.35 (s, 3 H) 2.36-2.65 (m, 4 H) 2.42-2.47 (m, 1 H) 2.57-2.62 (m, 1 H) 2.82 (d, J = 14.67 Hz, 1 H) 2.90-2.96 (m, 1 H) 2.96 (s, 3 H) 3.08-3.13 (m, 1 H) 3.18 (dd, J = 10.09, 7.34 Hz, 1 H) 3.29 (s, 3 H) 3.38-3.51 (m, 3 H) 3.63 (s, 1 H) 3.65-3.69 (m, 1 H) 3.69 (d, J = 7.34 Hz, 1 H) 3.73 (d, J = 9.63 Hz, 1 H) 3.76-3.82 (m, 1 H) 4.09-4.14 (m, 1 H) 4.42 (d, J = 6.88 Hz, 1 H) 4.96 (dd, J = 11.00, 2.29 Hz, 1 H) 5.00 (d, J = 4.58 Hz, 1 H) 5.67-5.72 (m, 1 H) 6.44 (d, J = 9.17 Hz, 1 H) 7.56 (dd, J = 8.71, 1.83 Hz, 1 H) 8.34 (d, J = 2.29 Hz, 1 H) |

TABLE 1-continued

| # | Structure 1 | Structure 2 | Data |
|---|---|---|---|
| 66 | 6-(alkylamino)nicotinonitrile group | tert-butyl / methyl branch | 1003.6 (600 MHz): 0.82 (t, J = 7.34 Hz, 3 H) 1.01 (d, J = 6.88 Hz, 3 H) 1.09-1.17 (m, 12 H) 1.19-1.27 (m, 7 H) 1.37 (s, 3 H) 1.39-1.42 (m, 1 H) 1.40 (s, 3 H) 1.50-1.80 (m, 7 H) 1.88-2.02 (m, 4 H) 2.07-2.11 (m, 1 H) 2.29 (s, 8 H) 2.37 (s, 6 H) 2.40-2.45 (m, 1 H) 2.56-2.62 (m, 1 H) 2.74 (d, J = 14.67 Hz, 1 H) 2.91-2.95 (m, 1 H) 2.96 (s, 3 H) 3.08-3.13 (m, 1 H) 3.15-3.20 (m, 1 H) 3.29 (s, 3 H) 3.40-3.48 (m, 3 H) 3.63 (s, 1 H) 3.64-3.70 (m, 1 H) 3.67 (d, J = 7.34 Hz, 1 H) 3.74 (s, 1 H) 3.76-3.82 (m, 1 H) 4.07-4.13 (m, 1 H) 4.41 (d, J = 7.34 Hz, 1 H) 4.96 (dd, J = 11.00, 2.29 Hz, 1 H) 5.01 (d, J = 5.04 Hz, 1 H) 5.68-5.73 (m, 1 H) 6.44 (d, J = 8.71 Hz, 1 H) 7.56 (dd, J = 8.71, 2.29 Hz, 1 H) 8.34 (d, J = 1.83 Hz, 1 H) |
| 67 | 1-methyl-3-(alkyl)hydantoin | N,N-diethylaminoethyl branch | 1083.8 (600 MHz): 0.85 (t, J = 7.34 Hz, 3 H) 0.99 (d, J = 6.88 Hz, 3 H) 1.02 (t, J = 6.88 Hz, 6 H) 1.08 (d, J = 7.34 Hz, 3 H) 1.11 (d, J = 6.88 Hz, 3 H) 1.16 (s, 3 H) 1.18 (d, J = 6.42 Hz, 3 H) 1.20 (d, J = 7.34 Hz, 3 H) 1.22-1.25 (m, 1 H) 1.23 (d, J = 5.96 Hz, 3 H) 1.38 (s, 3 H) 1.38 (s, 3 H) 1.47-1.54 (m, 1 H) 1.55-1.74 (m, 5 H) 1.70-1.74 (m, 2 H) 1.87-1.93 (m, 2 H) 1.93-1.99 (m, 1 H) 2.01-2.05 (m, 1 H) 2.09 (d, J = 14.67 Hz, 1 H) 2.29 (s, 6 H) 2.34 (s, 3 H) 2.39-2.62 (m, 8 H) 2.41-2.46 (m, 1 H) 2.57-2.60 (m, 1 H) 2.83 (d, J = 14.67 Hz, 1 H) 2.88 (dd, J = 9.63, 7.34 Hz, 1 H) 2.96 (s, 3 H) 3.00 (s, 3 H) 3.06 (q, J = 6.72 Hz, 1 H) 3.18 (dd, J = 10.32, 7.11 Hz, 1 H) 3.28 (s, 3 H) 3.43-3.50 (m, 1 H) 3.52-3.72 (m, 4 H) 3.61 (s, 1 H) 3.67 (d, J = 7.34 Hz, 1 H) 3.71 (d, J = 9.17 Hz, 1 H) 3.79-3.92 (m, 2 H) 4.07-4.11 (m, 1 H) 4.42 (d, J = 7.34 Hz, 1 H) 4.91-4.95 (m, 1 H) 4.96 (d, J = 4.58 Hz, 1 H) |
| 68 | N,N-dimethylsulfamoyl group | N,N-diethylaminoethyl branch | 1050.7 (400 MHz): 0.84 (t, J = 7.3 Hz, 3 H) 1.01-1.04 (m, 9 H) 1.07-1.25 (m, 19 H) 1.38 (s, 3 H) 1.40 (s, 3 H) 1.49-1.77 (m, 5 H) 1.84-1.94 (m, 2 H) 2.09 (d, J = 14.9 Hz, 1 H) 2.29 (s, 6 H) 2.34 (s, 3 H) 2.40-2.61 (m, 9 H) 2.83 (d, J = 14.9 Hz, 1 H) 2.87-2.92 (m, 1 H) 2.93 (s, 6 H) 3.04-3.09 (m, 4 H) 3.18 (dd, J = 10.1, 7.2 Hz, 1 H) 3.28 (s, 3 H) 3.34-3.49 (m, 4 H) 3.62 (s, 1 H) 3.69 (d, J = 7.2 Hz, 1 H) 3.72 (d, J = 10.0 Hz, 1 H) 4.13-3.98 (m, 3 H) 4.42 (d, J = 7.3 Hz, 1 H) 4.91-4.95 (m, 1 H) 4.99 (d, J = 3.7 Hz, 1 H) |
| 69 | benzyl group | N,N-diethylaminoethyl branch | 1033 (400 MHz): 0.82 (t, J = 7.32 Hz, 3 H) 1.02 (t, J = 6.84 Hz, 6 H) 1.04 (d, J = 7.08 Hz, 3 H) 1.09 (d, J = 7.57 Hz, 3 H) 1.12 (d, J = 7.08 Hz, 3 H) 1.17 (s, 3 H) 1.19 (d, J = 6.10 Hz, 3 H) 1.20 (d, J = 8.79 Hz, 3 H) 1.24 (d, J = 5.86 Hz, 3 H) 1.38 (s, 3 H) 1.45-1.60 (m, 1 H) 1.62-1.69 (m, 1 H) 1.73 (d, J = 6.84 Hz, 2 H) 1.85-2.07 (m, 5 H) 2.10 (d, J = 14.9 Hz, 1 H) 2.29 (s, 6 H) 2.35 (s, 3 H) 2.39-2.74 (m, 11 H) 2.84 (d, J = 14.9 Hz, 1 H) 2.85-2.91 (m, 1 H) 2.92 (s, 3 H) 3.07 (q, J = 6.84 Hz, 1 H) 3.19 (dd, J = 10.0, 7.32 Hz, 1 H) 3.28 (s, 3 H) 3.37-3.51 (m, 2 H) 3.60-3.75 (m, 4 H) 4.10 (q, J = 6.35 Hz, 1 H) 4.42 (d, J = 7.08 Hz, 1 H) 4.96-5.03 (m, 2 H) 7.14-7.34 (m, 5 H) |
| 70 | sulfamoyl (H₂N-SO₂-) group | N,N-diethylaminoethyl branch | 1022.7 (400 MHz): 0.85 (t, J = 7.3 Hz, 3 H) 0.99-1.27 (m, 28 H) 1.39 (s, 3 H) 1.40 (s, 3 H) 1.46-1.79 (m, 4 H) 1.81-2.06 (m, 4 H) 2.29 (s, 6 H) 2.34 (s, 3 H) 2.39-2.65 (m, 9 H) 2.83 (d, J = 14.9 Hz, 1 H) 2.87-2.94 (m, 1 H) 3.04 (s, 3 H) 3.07-3.14 (m, 1 H) 3.18 (dd, J = 10.1, 7.4 Hz, 1 H) 3.28 (s, 3 H) 3.38-3.52 (m, 3 H) 3.53-3.63 (m, 1 H) 3.66-3.75 (m, 3 H) 4.05-4.34 (m, 2 H) 4.42 (d, J = 7.3 Hz, 1 H) 4.99 (d, J = 3.7 Hz, 1 H) 5.08-5.15 (m, 2 H) 5.29 (d, J = 10.7 Hz, 1 H) |

| | | | |
|---|---|---|---|
| 71 | ![structure](methanesulfonamide group) | ![structure](diethylaminopropyl group) | 1050.7 (500 MHz): 0.84 (t, J = 7.26 Hz, 3 H) 0.99-1.06 (m, 9 H) 1.10 (d, J = 7.64 Hz, 3 H) 1.13 (d, J = 7.26 Hz, 3 H) 1.16 (s, 3 H) 1.17-1.27 (m, 10 H) 1.39 (s, 3 H) 1.40 (s, 3 H) 1.50-1.77 (m, 4 H) 1.85-2.05 (m, 6 H) 2.09 (d, J = 14.91 Hz, 1 H) 2.29 (s, 6 H) 2.34 (s, 3 H) 2.40-2.67 (m, 10 H) 2.80-3.05 (m, 8 H) 3.07-3.21 (m, 3 H) 3.24-3.33 (m, 5 H) 3.42-3.51 (m, 1 H) 3.61-3.73 (m, 3 H) 3.83-3.91 (m, 1 H) 4.07-4.12 (m, 1 H) 4.41 (d, J = 7.26 Hz, 1 H) 4.90 (dd, J = 10.89, 2.10 Hz, 1 H) 4.98 (d, J = 4.20 Hz, 1 H) 5.15-5.21 (m, 1 H) |
| 72 | ![structure](acetamide group) | ![structure](diethylaminopropyl group) | 1014.7 (600 MHz): 0.81-0.86 (m, 3 H) 0.99-1.05 (m, 9 H) 1.08-1.11 (m, 3 H) 1.12-1.15 (m, 3 H) 1.16 (s, 3 H) 1.19 (d, J = 6.42 Hz, 10 H) 1.39 (s, 6 H) 1.49-1.58 (m, 5 H) 1.63-2.04 (m, 10 H) 2.07-2.12 (m, 1 H) 2.29 (s, 6 H) 2.34 (s, 3 H) 2.38-2.64 (m, 10 H) 2.81-2.93 (m, 2 H) 3.02 (s, 3 H) 3.08-3.21 (m, 2 H) 3.28 (s, 3 H) 3.44-3.51 (m, 1 H) 3.59-3.66 (m, 2 H) 3.68-3.72 (m, 2 H) 3.74-3.79 (m, 1 H) 4.06-4.12 (m, 1 H) 4.42 (d, J = 7.34 Hz, 1 H) 4.91-4.95 (m, 1 H) 4.97-5.00 (m, 1 H) 6.44-6.49 (m, 1 H) |
| 73 | ![structure](dimethylamino group) | ![structure](diethylaminopropyl group) | 1000.7 (600 MHz): 0.83 (t, J = 7.34 Hz, 3 H) 0.98-1.06 (m, 9 H) 1.09 (d, J = 7.79 Hz, 3 H) 1.12 (d, J = 6.88 Hz, 3 H) 1.16 (s, 3 H) 1.18-1.26 (m, 10 H) 1.38 (s, 3 H) 1.40 (s, 3 H) 1.49-2.05 (m, 12 H) 2.08-2.12 (m, 1 H) 2.23 (br. s., 6 H) 2.29 (s, 6 H) 2.34 (s, 3 H) 2.39-2.63 (m, 10 H) 2.80-2.91 (m, 2 H) 3.04 (s, 3 H) 3.05-3.11 (m, 1 H) 3.15-3.21 (m, 1 H) 3.28 (s, 3 H) 3.43-3.50 (m, 1 H) 3.60-3.66 (m, 3 H) 3.68 (d, J = 7.34 Hz, 1 H) 3.72 (d, J = 9.17 Hz, 1 H) 4.07-4.13 (m, 1 H) 4.42 (d, J = 7.34 Hz, 1 H) 4.95-5.02 (m, 2 H) |
| 74 | ![structure](methanesulfonamide group) | ![structure](diethylaminopropyl group) | 1064.7 (600 MHz): 0.84 (t, J = 7.43 Hz, 3 H) 0.99-1.05 (m, 9 H) 1.10 (d, J = 7.43 Hz, 3 H) 1.13 (d, J = 7.02 Hz, 3 H) 1.16 (s, 3 H) 1.17-1.26 (m, 10 H) 1.39 (s, 3 H) 1.40 (s, 3 H) 1.50-1.58 (m, 1 H) 1.62-1.76 (m, 7 H) 1.86-2.05 (m, 4 H) 2.09 (d, J = 14.86 Hz, 1 H) 2.29 (s, 6 H) 2.34 (s, 3 H) 2.40-2.66 (m, 11 H) 2.83 (d, J = 14.86 Hz, 1 H) 2.87-2.94 (m, 1 H) 2.95 (s, 3 H) 3.07 (s, 3 H) 3.08-3.25 (m, 4 H) 3.28 (s, 3 H) 3.43-3.50 (m, 1 H) 3.55-3.63 (m, 1 H) 3.63 (s, 1 H) 3.67-3.74 (m, 3 H) 4.09 (q, J = 6.47 Hz, 1 H) 4.42 (d, J = 7.43 Hz, 1 H) 4.70 (s, 1 H) 4.94 (dd, J = 10.94, 1.86 Hz, 1 H) 4.98 (d, J = 4.54 Hz, 1 H) |
| 75 | ![structure](acetamide group) | ![structure](diethylaminopropyl group) | 1028.6 (600 MHz): 0.81-0.87 (m, 3 H) 0.99-1.06 (m, 6 H) 1.09-1.26 (m, 22 H) 1.39 (s, 3 H) 1.40 (s, 3 H) 1.48-2.04 (m, 15 H) 2.07-2.12 (m, 1 H) 2.29 (s, 6 H) 2.34 (s, 3 H) 2.40-2.63 (m, 9 H) 2.83 (d, J = 15.59 Hz, 1 H) 2.90-2.96 (m, 1 H) 3.03 (s, 3 H) 3.08-3.12 (m, 1 H) 3.15-3.21 (m, 1 H) 3.24-3.37 (m, 5 H) 3.41-3.51 (m, 2 H) 3.58-3.65 (m, 2 H) 3.67-3.77 (m, 3 H) 4.06-4.11 (m, 1 H) 4.41-4.44 (m, 1 H) 4.93-4.99 (m, 2 H) 6.27-6.31 (m, 1 H) |

TABLE 1-continued

| # | R1 | R2 | MS | NMR |
|---|---|---|---|---|
| 76 | (methyl carbamate-propyl group) | -CH2CH2N(CH2CH3)2 branched | 1044.7 | (600 MHz): 0.80-0.87 (m, 3 H) 0.98-1.28 (m, 28 H) 1.39 (s, 3 H) 1.40 (s, 3 H) 1.48-2.12 (m, 9 H) 2.25-2.64 (m, 20 H) 2.81-2.95 (m, 2 H) 3.03 (s, 3 H) 3.07-3.12 (m, 1 H) 3.16-3.35 (m, 7 H) 3.44-3.76 (m, 11 H) 4.07-4.12 (m, 1 H) 4.40-4.44 (m, 1 H) 4.93-5.00 (m, 2 H) 5.35-5.41 (m, 1 H) |
| 77 | (isothiazolidine 1,1-dioxide) | -CH2CH2N(CH2CH3)2 branched | 1062.8 | (500 MHz): 0.85 (t, J = 7.45 Hz, 3 H) 0.99-1.07 (m, 9 H) 1.09 (d, J = 7.26 Hz, 3 H) 1.13 (d, J = 7.26 Hz, 3 H) 1.16 (s, 3 H) 1.17-1.27 (m, 10 H) 1.38 (s, 3 H) 1.40 (s, 3 H) 1.47-1.56 (m, 1 H) 1.63-1.68 (m, 1 H) 1.74 (d, J = 6.50 Hz, 2 H) 1.85-2.05 (m, 4 H) 2.09 (d, J = 14.91 Hz, 1 H) 2.29 (s, 6 H) 2.31-2.38 (m, 5 H) 2.40-2.64 (m, 10 H) 2.81-2.92 (m, 2 H) 3.05 (s, 3 H) 3.07-3.55 (m, 9 H) 3.28 (s, 3 H) 3.65 (s, 1 H) 3.66-3.77 (m, 3 H) 3.82-3.91 (m, 1 H) 4.09 (q, J = 6.50 Hz, 1 H) 4.41 (d, J = 7.26 Hz, 1 H) 4.99 (d, J = 4.20 Hz, 1 H) 5.12 (dd, J = 11.08, 2.29 Hz, 1 H) |
| 78 | (N-methyl-N-benzyl) | -CH2CH2N(CH2CH3)2 branched | 1062.7 | (600 MHz): 0.76 (t, J = 7.43 Hz, 3 H) 0.99-1.05 (m, 9 H) 1.09 (d, J = 7.43 Hz, 3 H) 1.14 (d, J = 7.02 Hz, 3 H) 1.16 (s, 3 H) 1.16-1.26 (m, 10 H) 1.39 (s, 6 H) 1.48-1.56 (m, 1 H) 1.63-1.68 (m, 1 H) 1.70-1.79 (m, 2 H) 1.86-2.04 (m, 4 H) 2.09 (d, J = 14.86 Hz, 1 H) 2.19 (s, 3 H) 2.29 (s, 6 H) 2.34 (s, 3 H) 2.38-2.64 (m, 11 H) 2.80-2.89 (m, 3 H) 3.02 (s, 3 H) 3.07-3.13 (m, 1 H) 3.16-3.22 (m, 1 H) 3.28 (s, 3 H) 3.37-3.53 (m, 3 H) 3.64-3.76 (m, 4 H) 3.82-3.95 (m, 2 H) 4.07-4.13 (m, 1 H) 4.41 (d, J = 7.43 Hz, 1 H) 4.98 (d, J = 4.95 Hz, 1 H) 5.08-5.14 (m, 1 H) 7.17-7.23 (m, 1 H) 7.24-7.29 (m, 2 H) 7.30-7.34 (m, 2 H) |
| 79 | (N-methyl benzamide) | -CH2CH2N(CH2CH3)2 branched | 1076.7 | (600 MHz): 0.74-0.83 (m, 3 H) 0.89-1.26 (m, 28 H) 1.28-1.40 (m, 6 H) 1.42-2.03 (m, 8 H) 2.08 (d, J = 14.86 Hz, 1 H) 2.27 (s, 6 H) 2.33 (br. s., 3 H) 2.36-2.65 (m, 10 H) 2.77-2.92 (m, 5 H) 2.99-3.21 (m, 5 H) 3.26 (s, 3 H) 3.37-4.00 (m, 8 H) 4.05-4.11 (m, 1 H) 4.36-4.44 (m, 1 H) 4.69-4.75 (m, 1 H) 4.94-.499 (m, 1 H) 5.06-5.13 (m, 1 H) 7.31-7.49 (m, 5 H) |
| 80 | (N-methyl benzenesulfonamide) | -CH2CH2N(CH2CH3)2 branched | 1112.7 | (600 MHz): 0.80 (t, J = 7.22 Hz, 3 H) 0.95 (d, J = 7.02 Hz, 3 H) 0.96-1.01 (m, 6 H) 1.05 (d, J = 7.84 Hz, 3 H) 1.08 (d, J = 7.02 Hz, 3 H) 1.13 (s, 3 H) 1.14-1.21 (m, 10 H) 1.33 (s, 3 H) 1.34 (s, 3 H) 1.44-1.51 (m, 1 H) 1.59-1.63 (m, 1 H) 1.66-1.71 (m, 2 H) 1.79-1.87 (m, 2 H) 1.92-2.02 (m, 2 H) 2.06 (d, J = 14.86 Hz, 1 H) 2.25 (s, 6 H) 2.31 (s, 3 H) 2.36-2.60 (m, 10 H) 2.80 (d, J = 14.86 Hz, 1 H) 2.83 (s, 3 H) 2.83-2.87 (m, 1 H) 2.90 (s, 3 H) 3.00-3.05 (m, 1 H) 3.12-3.20 (m, 2 H) 3.24 (s, 3 H) 3.33-3.46 (m, 3 H) 3.56 (s, 1 H) 3.62-3.70 (m, 3 H) 3.78-3.86 (m, 1 H) 4.03-4.08 (m, 1 H) 4.38 (d, J = 7.43 Hz, 1 H) 4.87-4.93 (m, 1 H) 4.95-5.00 (m, 1 H) 7.42-7.49 (m, 2 H) 7.51-7.57 (m, 1 H) 7.81-7.87 (m, 2 H) |

TABLE 1-continued

| | | | | |
|---|---|---|---|---|
| 81 | 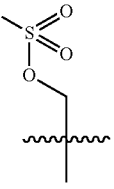 | 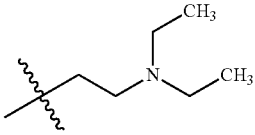 [SMILES: *CCN(CC)CC] | 1052.7 | (600 MHz): 0.86 (t, J = 7.34 Hz, 3 H) 0.96-1.29 (m, 29 H) 1.40 (s, 3 H) 1.40 (s, 3 H) 1.45-1.51 (m, 1 H) 1.63-1.76 (m, 3 H) 1.85-2.15 (m, 7 H) 2.29 (s, 6 H) 2.34 (s, 3 H) 2.38-2.64 (m, 10 H) 2.83 (d, J = 14.67 Hz, 1 H) 2.87-2.95 (m, 1 H) 3.03 (s, 3 H) 3.11 (q, J = 7.18 Hz, 1 H) 3.18 (dd, J = 10.32, 7.11 Hz, 1 H) 3.28 (s, 3 H) 3.43 (br. s, 1 H) 3.44-3.50 (m, 1 H) 3.66 (s, 1 H) 3.67-3.72 (m, 2 H) 3.76 (ddd, J = 14.67, 8.71, 5.96 Hz, 1 H) 3.91 (dt, J = 14.67, 5.50 Hz, 1 H) 4.09 (q, J = 6.57 Hz, 1 H) 4.27-4.34 (m, 1 H) 4.34-4.44 (m, 2 H) 4.93-5.02 (m, 2 H) 5.26 (br. s., 2 H) |
| 82 | 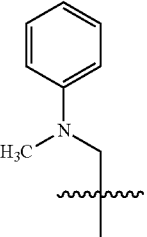 [SMILES: *CN(C)c1ccccc1] | 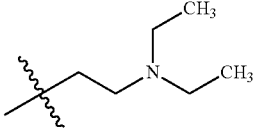 [SMILES: *CCN(CC)CC] | 1062.8 | (600 MHz): 0.82 (t, J = 7.57 Hz, 3 H) 0.98-1.05 (m, 9 H) 1.08 (d, J = 7.34 Hz, 3 H) 1.12 (d, J = 6.88 Hz, 3 H) 1.15 (s, 3 H) 1.16-1.25 (m, 10 H) 1.35 (s, 3 H) 1.38 (s, 3 H) 1.45-1.75 (m, 4 H) 1.86-2.04 (m, 6 H) 2.07-2.12 (m, 1 H) 2.29 (br. s., 6 H) 2.34 (s, 3 H) 2.37-2.63 (m, 10 H) 2.80-2.89 (m, 2 H) 2.91 (s, 3 H) 2.93 (s, 3 H) 3.05-3.11 (m, 1 H) 3.16-3.21 (m, 1 H) 3.27 (s, 3 H) 3.36-3.48 (m, 3 H) 3.63-3.73 (m, 5 H) 4.06-4.12 (m, 1 H) 4.38-4.42 (m, 1 H) 4.95-4.99 (m, 2 H) 6.62-6.67 (m, 1 H) 6.71-6.75 (m, 2 H) 7.18-7.22 (m, 2 H) |
| 83 | 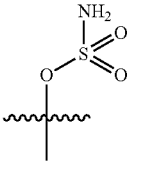 [SMILES: *OS(N)(=O)=O] | 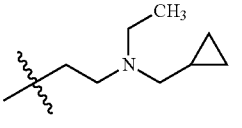 [SMILES: *CCN(CC)CC1CC1] | 1064.8 | (600 MHz): 0.06-0.12 (m, 2 H) 0.44-0.53 (m, 2 H) 0.82-0.91 (m, 4 H) 1.00-1.04 (m, 6 H) 1.09 (d, J = 7.34 Hz, 3 H) 1.14 (d, J = 6.88 Hz, 3 H) 1.16 (s, 3 H) 1.17-1.25 (m, 10 H) 1.39 (s, 3 H) 1.42 (s, 3 H) 1.48-1.68 (m, 2 H) 1.73-1.78 (m, 2 H) 1.87-2.11 (m, 5 H) 2.29 (s, 6 H) 2.35 (s, 6 H) 2.47-2.69 (m, 7 H) 2.82-2.93 (m, 2 H) 3.03 (s, 3 H) 3.09-3.13 (m, 1 H) 3.16-3.20 (m, 1 H) 3.28 (s, 3 H) 3.44-3.50 (m, 1 H) 3.64-3.72 (m, 3 H) 3.90-3.95 (m, 1 H) 4.04-4.14 (m, 2 H) 4.21-4.25 (m, 1 H) 4.41 (d, J = 7.34 Hz, 1 H) 4.59-4.66 (m, 1 H) 4.94 (d, J = 4.58 Hz, 1 H) 5.20 (dd, J = 10.55, 2.75 Hz, 1 H) 5.46 (br. s, 2 H) |
| 84 | 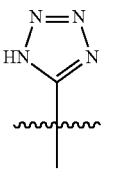 | 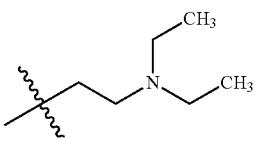 [SMILES: *CCN(CC)CC] | 1011.8 | (600 MHz, DMSO$_{d-6}$): 0.80-0.85 (m, 3 H) 0.89-0.93 (m, 3 H) 0.95-1.01 (m, 6 H) 1.03 (d, J = 7.34 Hz, 3 H) 1.07-1.13 (m, 9 H) 1.13-1.18 (m, 7 H) 1.28 (s, 3 H) 1.41 (s, 3 H) 1.52-1.88 (m, 7 H) 1.95-2.00 (m, 1 H) 2.05-2.10 (m, 1 H) 2.25 (s, 6 H) 2.27 (s, 3 H) 2.38-2.42 (m, 1 H) 2.44-2.57 (m, 9 H) 2.74 (d, J = 14.67 Hz, 1 H) 2.81-2.91 (m, 2 H) 2.96 (s, 3 H) 3.02-3.12 (m, 2 H) 3.13-3.18 (m, 2 H) 3.20-3.24 (m, 3 H) 3.38-3.45 (m, 1 H) 3.55-3.71 (m, 4 H) 4.03-4.12 (m, 2 H) 4.29 (d, J = 7.34 Hz, 1 H) 4.81 (d, J = 5.04 Hz, 1 H) 4.93-4.98 (m, 1 H) |
| 85 | 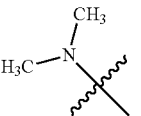 | 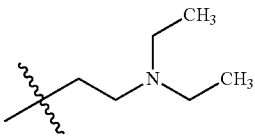 [SMILES: *CCN(CC)CC] | 986.7 | (600 MHz): 0.83 (t, J = 7.57 Hz, 3 H) 0.99-1.05 (m, 9 H) 1.09 (d, J = 7.79 Hz, 3 H) 1.13 (d, J = 7.34 Hz, 3 H) 1.16 (s, 3 H) 1.17-1.26 (m, 10 H) 1.38 (s, 3 H) 1.39 (s, 3 H) 1.45-1.52 (m, 1 H) 1.62-1.67 (m, 1 H) 1.72-1.76 (m, 2 H) 1.87-2.05 (m, 4 H) 2.07-2.11 (m, 1 H) 2.29 (s, 12 H) 2.34 (s, 3 H) 2.32-2.70 (m, 12 H) 2.80-2.91 (m, 2 H) 3.05 (s, 3 H) 3.06-3.11 (m, 1 H) 3.16-3.21 (m, 1 H) 3.28 (s, 3 H) 3.39-3.50 (m, 2 H) 3.61 (s, 1 H) 3.68 (d, J = 7.34 Hz, 1 H) 3.73-3.80 (m, 3 H) 4.08-4.13 (m, 1 H) 4.41 (d, J = 7.34 Hz, 1 H) 4.98-5.01 (m, 1 H) 5.07-5.12 (m, 1 H) |

| | | | |
|---|---|---|---|
| 86 | [structure: CH₃-S(=O)(=O)-NH-] | [structure: branched chain with -CH₂CH₂CH₂-N(CH₃)CH₃] | 1008.8 (600 MHz): 0.86 (t, J = 7.34 Hz, 3 H) 1.02 (d, J = 6.88 Hz, 3 H) 1.11 (d, J = 7.34 Hz, 3 H) 1.13 (d, J = 7.34 Hz, 3 H) 1.18 (s, 3 H) 1.19-1.26 (m, 10 H) 1.40 (s, 6 H) 1.51-1.76 (m, 4 H) 1.82-2.04 (m, 4 H) 2.15 (d, J = 14.67 Hz, 1 H) 2.24 (s, 6 H) 2.29 (s, 6 H) 2.35 (s, 3 H) 2.31-2.47 (m, 3 H) 2.49-2.66 (m, 3 H) 2.82 (d, J = 14.67 Hz, 1 H) 2.90-2.96 (m, 1 H) 2.98 (s, 3 H) 3.05 (s, 3 H) 3.12 (d, J = 6.88 Hz, 1 H) 3.18 (dd, J = 10.55, 7.34 Hz, 1 H) 3.28 (s, 3 H) 3.29-3.35 (m, 1 H) 3.42-3.57 (m, 3 H) 3.59 (s, 1 H) 3.68 (d, J = 9.63 Hz, 1 H) 3.72 (d, J = 7.34 Hz, 1 H) 3.77-3.83 (m, 1 H) 3.87 (dd, J = 10.09, 4.13 Hz, 1 H) 4.11 (d, J = 6.42 Hz, 1 H) 4.42 (d, J = 6.88 Hz, 1 H) 4.93-4.99 (m, 2 H) 5.54 (t, J = 5.73 Hz, 1 H) |
| 87 | [structure: CH₃-S(=O)(=O)-NH-] | [structure: branched chain with -CH₂CH₂CH₂-N(CH₂CH₃)CH₂CH₃] | 1037.7 (500 MHz): 0.85 (t, J = 7.34 Hz, 3 H) 1.00-1.04 (m, 9 H) 1.09-1.14 (m, 6 H) 1.14-1.17 (m, 3 H) 1.17-1.26 (m, 10 H) 1.38-1.41 (m, 6 H) 1.52-1.68 (m, 2 H) 1.74 (d, J = 6.42 Hz, 2 H) 1.83-2.04 (m, 4 H) 2.09 (d, J = 14.67 Hz, 1 H) 2.29 (s, 6 H) 2.34 (s, 3 H) 2.40-2.62 (m, 10 H) 2.83 (d, J = 14.67 Hz, 1 H) 2.91-2.96 (m, 1 H) 2.98 (s, 3 H) 3.05 (s, 3 H) 3.12 (m, 1 H) 3.12-3.13 (m, 1 H) 3.18 (dd, J = 10.09, 7.34 Hz, 1 H) 3.27 (s, 3 H) 3.29-3.35 (m, 1 H) 3.46-3.50 (m, 1 H) 3.51-3.57 (m, 1 H) 3.59 (s, 1 H) 3.67-3.73 (m, 2 H) 3.78-3.83 (m, 1 H) 3.85-3.92 (m, 1 H) 4.09 (q, J = 6.11 Hz, 1 H) 4.42 (d, J = 7.34 Hz, 1 H) 4.93-5.00 (m, 2 H) 5.54 (t, J = 5.73 Hz, 1 H) |
| 88 | [structure: CH₃-S(=O)(=O)-NH-] | [structure: 2-methylpyrrolidine attached via propyl linker] | 1048.6 (600 MHz): 0.86 (t, J = 7.34 Hz, 3 H) 1.02 (d, J = 6.88 Hz, 3 H) 1.05-1.16 (m, 12 H) 1.17-1.27 (m, 10 H) 1.40 (s, 6 H) 1.53-2.19 (m, 1 6 H) 2.29 (s, 6 H) 2.31-2.38 (m, 4 H) 2.40-2.46 (m, 3 H) 2.56-2.67 (m, 1 H) 2.84-2.96 (m, 3 H) 2.99 (s, 3 H) 3.05 (s, 3 H) 3.09-3.20 (m, 3 H) 3.27 (s, 3 H) 3.30-3.35 (m, 1 H) 3.43-3.50 (m, 1 H) 3.51-3.57 (m, 1 H) 3.59 (s, 1 H) 3.68 (d, J = 9.63 Hz, 1 H) 3.72 (d, J = 7.34 Hz, 1 H) 3.77-3.82 (m, 1 H) 3.84-3.91 (m, 1 H) 4.09 (q, J = 6.40 Hz, 1 H) 4.42 (d, J = 7.34 Hz, 1 H) 4.93-5.01 (m, 2 H) 5.52-5.56 (m, 1 H) |
| 89 | [structure: CH₃-S(=O)(=O)-NH-] | [structure: isothiazolidine 1,1-dioxide attached via propyl linker] | 1084.7 (600 MHz): 0.86 (t, J = 7.43 Hz, 3 H) 0.99-1.26 (m, 22 H) 1.40 (s, 6 H) 1.52-1.62 (m, 1 H) 1.66-1.71 (m, 1 H) 1.74 (d, J = 6.61 Hz, 2 H) 1.82-2.12 (m, 5 H) 2.29 (s, 6 H) 2.34-2.46 (m, 6 H) 2.55-2.63 (m, 1 H) 2.70 (br. s., 2 H) 2.87-2.96 (m, 2 H) 2.98 (s, 3 H) 3.05 (s, 3 H) 3.09-3.21 (m, 6 H) 3.26-3.35 (m, 6 H) 3.40-3.46 (m, 1 H) 3.49-3.54 (m, 1 H) 3.58 (s, 1 H) 3.66-3.72 (m, 2 H) 3.78-3.91 (m, 2 H) 4.11 (q, J = 6.19 Hz, 1 H) 4.40 (d, J = 7.02 Hz, 1 H) 4.71 (br s., 1 H) 4.94-5.00 (m, 2 H) |
| 90 | [structure: CH₃-S(=O)(=O)-NH-] | [structure: 2-(trifluoromethyl)pyrrolidine attached via propyl linker] | 1102.7 (500 MHz): 0.86 (t, J = 7.27 Hz, 3 H) 1.02 (d, J = 7.13 Hz, 3 H) 1.08-1.15 (m, 9 H) 1.16-1.28 (m, 10 H) 1.36-1.43 (m, 6 H) 1.52-2.10 (m, 13 H) 2.25-2.39 (m, 10 H) 2.41-2.77 (m, 5 H) 2.81-2.96 (m, 2 H) 2.98 (s, 3 H) 3.00-3.15 (m, 6 H) 3.16-3.22 (m, 1 H) 3.24-3.37 (m, 5 H) 3.41-3.49 (m, 1 H) 3.50-3.57 (m, 1 H) 3.58 (s, 1 H) 3.67-3.73 (m, 2 H) 3.77-3.83 (m, 1 H) 3.84-3.92 (m, 1 H) 4.07-4.13 (m, 1 H) 4.39-4.43 (m, 1 H) 4.93-5.01 (m, 2 H) 5.52-5.57 (m, 1 H) |

TABLE 1-continued

| # | R1 | R2 | MS | NMR |
|---|---|---|---|---|
| 91 | CH3-S(=O)(=O)-NH- | -CH2CH2-N(Et)(iPr) with gem-dimethyl | 1050.7 | (600 MHz): 0.85 (t, J = 7.34 Hz, 3 H) 0.96 (d, J = 6.42 Hz, 3 H) 0.98-1.06 (m, 9 H) 1.09-1.14 (m, 6 H) 1.16 (s, 3 H) 1.17-1.26 (m, 10 H) 1.39-1.41 (m, 6 H) 1.52-1.67 (m, 2 H) 1.74 (d, J = 6.42 Hz, 2 H) 1.82-2.08 (m, 5 H) 2.29 (s, 6 H) 2.34 (s, 3 H) 2.35-2.62 (m, 8 H) 2.84 (d, J = 14.67 Hz, 1 H) 2.90-2.97 (m, 1 H) 2.98 (s, 3 H) 3.06 (s, 3 H) 3.09-3.14 (m, 1 H) 3.18 (dd, J = 10.09, 7.34 Hz, 1 H) 3.27 (s, 3 H) 3.29-3.35 (m, 1 H) 3.45-3.49 (m, 1 H) 3.51-3.56 (m, 1 H) 3.59 (s, 1 H) 3.68-3.72 (m, 2 H) 3.77-3.82 (m, 1 H) 3.84-3.91 (m, 1 H) 4.08 (q, J = 6.42 Hz, 1 H) 4.41 (d, J = 7.34 Hz, 1 H) 4.93-5.02 (m, 2 H) 5.53 (t, J = 5.73 Hz, 1 H) |
| 92 | CH3-S(=O)(=O)-NH- | -CH2CH2-N(Et)(CH2-cyclopropyl) with gem-dimethyl | 1062.8 | (500 MHz): 0.10 (d, J = 4.20 Hz, 2 H) 0.45-0.53 (m, 2 H) 0.86 (t, J = 7.26 Hz, 4 H) 0.98-1.27 (m, 25 H) 1.40 (s, 6 H) 1.51-2.12 (m, 9 H) 2.29 (s, 6 H) 2.35 (s, 3 H) 2.38-2.70 (m, 9 H) 2.84 (d, J = 14.91 Hz, 1 H) 2.93 (br. s., 1 H) 2.98 (s, 3 H) 3.05 (s, 3 H) 3.09-3.22 (m, 2 H) 3.28 (s, 3 H) 3.29-3.36 (m, 1 H) 3.47 (d, J = 3.06 Hz, 3 H) 3.59 (s, 1 H) 3.66-3.74 (m, 2 H) 3.77-3.92 (m, 2 H) 4.10 (d, J = 6.50 Hz, 1 H) 4.42 (d, J = 7.26 Hz, 1 H) 4.92-5.01 (m, 2 H) 5.54 (br. s., 1 H) |
| 93 | CH3-S(=O)(=O)-NH- | -CH2CH2-N(Et)(n-Pr) with gem-dimethyl | 1064.8 | (600 MHz): 0.85 (t, J = 7.34 Hz, 3 H) 0.90 (t, J = 7.34 Hz, 3 H) 0.98-1.04 (m, 6 H) 1.08-1.33 (m, 21 H) 1.37-1.46 (m, 8 H) 1.62-1.76 (m, 4 H) 1.83-2.10 (m, 5 H) 2.29 (s, 6 H) 2.32-2.36 (m, 3 H) 2.37-2.63 (m, 10 H) 2.83 (d, J = 14.67 Hz, 1 H) 2.80-2.97 (m, 1 H) 2.98 (s, 3 H) 3.06 (s, 3 H) 3.09-3.21 (m, 2 H) 3.25-3.36 (m, 4 H) 3.43-3.57 (m, 3 H) 3.59 (s, 1 H) 3.67-3.73 (m, 2 H) 3.77-3.91 (m, 2 H) 4.06-4.11 (m, 1 H) 4.41 (d, J = 7.34 Hz, 1 H) 4.94-5.01 (m, 2 H) 5.52-5.55 (m, 1 H) |
| 94 | CH3-S(=O)(=O)-NH- | -CH2-C(=O)-N(Et)2 with gem-dimethyl | 1050.6 | (500 MHz): 0.86 (t, J = 7.27 Hz, 3 H) 1.02 (d, J = 6.86 Hz, 3 H) 1.09-1.24 (m, 25 H) 1.39 (s, 3 H) 1.40 (s, 3 H) 1.51-2.09 (m, 9 H) 2.26-2.31 (m, 6 H) 2.35 (d, J = 15.63 Hz, 1 H) 2.40-2.48 (m, 1 H) 2.51-2.62 (m, 4 H) 2.91-2.96 (m, 1 H) 2.98 (s, 3 H) 3.06 (s, 3 H) 3.09-3.40 (m, 11 H) 3.42-3.48 (m, 2 H) 3.49-3.57 (m, 1 H) 3.59 (s, 1 H) 3.67-3.73 (m, 2 H) 3.77-3.92 (m, 2 H) 4.12 (q, J = 6.31 Hz, 1 H) 4.40 (d, J = 7.13 Hz, 1 H) 4.93-5.02 (m, 2 H) 5.54 (t, J = 5.90 Hz, 1 H) |
| 95 | CH3-S(=O)(=O)-NH- | -CH2CH2-O-iPr with gem-dimethyl | 1023.6 | (600 MHz): 0.86 (t, J = 7.34 Hz, 3 H) 1.02 (d, J = 6.88 Hz, 3 H) 1.08-1.27 (m, 25 H) 1.39-1.42 (m, 6 H) 1.49-2.06 (m, 8 H) 2.08-2.12 (m, 1 H) 2.29 (s, 6 H) 2.38 (s, 3 H) 2.40-2.45 (m, 1 H) 2.50-2.78 (m, 3 H) 2.87-2.96 (m, 2 H) 2.98 (s, 3 H) 3.06 (s, 3 H) 3.10-3.14 (m, 1 H) 3.15-3.20 (m, 1 H) 3.28 (s, 3 H) 3.30-3.36 (m, 1 H) 3.42-3.60 (m, 6 H) 3.68-3.72 (m, 2 H) 3.78-3.91 (m, 2 H) 4.07-4.13 (m, 1 H) 4.38-4.43 (m, 1 H) 4.93-5.01 (m, 2 H) 5.50-5.55 (m, 1 H) |
| 96 | CH3-S(=O)(=O)-NH- | -CH2CH2-S(=O)(=O)-N(Et)2 with gem-dimethyl | 1100.6 | (600 MHz): 0.86 (t, J = 7.22 Hz, 3 H) 1.02 (d, J = 7.02 Hz, 3 H) 1.09-1.27 (m, 25 H) 1.40 (s, 6 H) 1.52-1.62 (m, 2 H) 1.66-1.77 (m, 3 H) 1.83-1.99 (m, 3 H) 2.03-2.13 (m, 2 H) 2.29 (s, 6 H) 2.36 (s, 3 H) 2.40-2.46 (m, 1 H) 2.56-2.63 (m, 1 H) 2.87-3.20 (m, 14 H) 3.24-3.35 (m, 8 H) 3.39-3.46 (m, 1 H) 3.50-3.56 (m, 1 H) 3.59 (s, 1 H) 3.66-3.72 (m, 2 H) 3.78-3.91 (m, 2 H) 4.12 (q, J = 6.20 Hz, 1 H) 4.39 (d, J = 7.02 Hz, 1 H) 4.93-4.89 (m, 2 H) |

TABLE 1-continued

| # | Structure 1 | Structure 2 | MS / NMR |
|---|---|---|---|
| 97 | CH₃–S(=O)(=O)–NH– | pyrrolidin-2-one-N-CH₂CH₂C(CH₃)₂– | 1048.6 (600 MHz): 0.86 (t, J = 7.34 Hz, 3 H) 1.02 (d, J = 6.88 Hz, 3 H) 1.09-1.17 (m, 12 H) 1.18-1.27 (m, 7 H) 1.40 (s, 3 H) 1.40 (s, 3 H) 1.49-1.62 (m, 2 H) 1.71-1.75 (m, 2 H) 1.85-1.98 (m, 3 H) 2.01-2.09 (m, 4 H) 2.29-2.46 (m, 11 H) 2.56-2.77 (m, 3 H) 2.85-2.89 (m, 1 H) 2.92-2.95 (m, 1 H) 2.98 (s, 3 H) 3.05 (s, 3 H) 3.11 (q, J = 6.42 Hz, 1 H) 3.18-3.22 (m, 1 H) 3.28 (s, 3 H) 3.31-3.56 (m, 8 H) 3.58 (s, 1 H) 3.66-3.72 (m, 2 H) 3.76-3.91 (m, 2 H) 4.08-4.13 (m, 1 H) 4.38-4.42 (m, 1 H) 4.93-5.00 (m, 2 H) 5.49-5.54 (m, 1 H) |
| 98 | CH₃–S(=O)(=O)–NH– | 1-methylhydantoin-N3-CH₂CH₂C(CH₃)₂– | 1077.6 (600 MHz): 0.86 (t, J = 7.02 Hz, 3 H) 1.00-1.26 (m, 22 H) 1.40 (s, 6 H) 1.51-1.77 (m, 4 H) 1.82-1.96 (m, 3 H) 2.01-2.09 (m, 2 H) 2.29 (s, 6 H) 2.38-2.45 (m, 4 H) 2.55-2.63 (m, 1 H) 2.72-3.01 (m, 10 H) 3.04 (s, 3 H) 3.09-3.20 (m, 2 H) 3.28 (s, 3 H) 3.28-3.34 (m, 1 H) 3.37-3.44 (m, 1 H) 3.50-3.56 (m, 1 H) 3.56-3.73 (m, 6 H) 3.78-3.93 (m, 4 H) 4.04-4.10 (m, 1 H) 4.37 (d, J = 7.43 Hz, 1 H) 4.93-4.99 (m, 2 H) |
| 99 | CH₃–S(=O)(=O)–NH– | oxazolidin-2-one-N-CH₂CH₂C(CH₃)₂– | 1050.6 (600 MHz): 0.86 (t, J = 7.34 Hz, 1 H) 1.01-1.04 (m, 3 H) 1.09-1.15 (m, 9 H) 1.16-1.18 (m, 3 H) 1.19-1.26 (m, 7 H) 1.40 (s, 6 H) 1.47-1.60 (m, 1 H) 1.66-2.13 (m, 8 H) 2.29 (s, 6 H) 2.38-2.45 (m, 4 H) 2.56-2.62 (m, 1 H) 2.70-2.76 (m, 1 H) 2.88-2.96 (m, 2 H) 2.98 (s, 3 H) 3.05 (s, 3 H) 3.09-3.14 (m, 1 H) 3.16-3.20 (m, 1 H) 3.28 (s, 3 H) 3.29-3.48 (m, 5 H) 3.51-3.72 (m, 6 H) 3.77-3.91 (m, 2 H) 4.10-4.16 (m, 1 H) 4.31-4.41 (m, 3 H) 4.93-5.00 (m, 2 H) 5.49-5.54 (m, 1 H) |
| 100 | CH₃–S(=O)(=O)–NH– | hydantoin-N3-CH₂CH₂C(CH₃)₂– | 1063.5 (600 MHz): 0.85 (t, J = 7.34 Hz, 1 H) 1.02 (d, J = 6.88 Hz, 1 H) 1.07-1.15 (m, 12 H) 1.17-1.26 (m, 7 H) 1.40 (s, 6 H) 1.49-1.60 (m, 1 H) 1.64-1.78 (m, 3 H) 1.81-1.96 (m, 3 H) 2.01-2.09 (m, 2 H) 2.29 (s, 6 H) 2.44 (s, 4 H) 2.56-2.63 (m, 1 H) 2.78-2.96 (m, 4 H) 2.98 (s, 3 H) 3.04 (s, 3 H) 3.08-3.14 (m, 1 H) 3.16-3.21 (m, 1 H) 3.26 (s, 3 H) 3.28-3.45 (m, 2 H) 3.51-3.73 (m, 6 H) 3.77-3.91 (m, 2 H) 3.93-4.02 (m, 2 H) 4.04-4.11 (m, 1 H) 4.34-4.38 (m, 1 H) 4.41-4.46 (m, 1 H) 4.93-4.97 (m, 2 H) 5.49-5.54 (m, 1 H) |
| 101 | CH₃–S(=O)(=O)–NH– | thiomorpholine-1,1-dioxide-N-CH₂CH₂C(CH₃)₂– | 1098.6 (600 MHz): 0.86 (t, J = 7.34 Hz, 3 H) 1.02 (d, J = 6.88 Hz, 3 H) 1.10 (d, J = 7.34 Hz, 3 H) 1.12-1.15 (m, 6 H) 1.17 (d, J = 5.96 Hz, 3 H) 1.19-1.26 (m, 7 H) 1.38-1.42 (m, 6 H) 1.57 (d, J = 3.67 Hz, 1 H) 1.64-1.67 (m, 1 H) 1.72-1.76 (m, 2 H) 1.84-2.06 (m, 4 H) 2.10 (d, J = 14.67 Hz, 1 H) 2.29 (s, 6 H) 2.36 (s, 3 H) 2.40-2.63 (m, 5 H) 2.86 (d, J = 14.67 Hz, 1 H) 2.90-2.96 (m, 1 H) 2.99 (s, 3 H) 3.00-3.14 (m, 9 H) 3.06 (s, 3 H) 3.16-3.21 (m, 1 H) 3.28 (s, 3 H) 3.30-3.36 (m, 1 H) 3.41-3.48 (m, 1 H) 3.51-3.56 (m, 1 H) 3.59 (s, 1 H) 3.67-3.71 (m, 2 H) 3.78-3.83 (m, 1 H) 3.85-3.90 (m, 1 H) 4.07-4.12 (m, 1 H) 4.40 (d, J = 7.34 Hz, 1 H) 4.94-4.98 (m, 2 H) 5.53 (t, J = 5.73 Hz, 1 H) |

| | | | |
|---|---|---|---|
| 102 | CH₃–S(=O)(=O)–NH– (methanesulfonamide) | morpholinylpropyl group | 1050.6 (600 MHz): 0.86 (t, J = 7.34 Hz, 3 H) 1.02 (d, J = 6.88 Hz, 3 H) 1.11 (d, J = 7.79 Hz, 3 H) 1.13 (d, J = 6.88 Hz, 3 H) 1.17 (s, 3 H) 1.19 (d, J = 6.42 Hz, 3 H) 1.20-1.25 (m, 7 H) 1.39-1.41 (m, 6 H) 1.53-1.59 (m, 1 H) 1.63-1.67 (m, 1 H) 1.72-1.75 (m, 2 H) 1.84-1.95 (m, 2 H) 1.97-2.05 (m, 2 H) 2.13 (d, J = 14.67 Hz, 1 H) 2.29 (s, 6 H) 2.35 (s, 3 H) 2.37-2.49 (m, 7 H) 2.52-2.64 (m, 3 H) 2.82 (d, J = 14.67 Hz, 1 H) 2.90-2.96 (m, 1 H) 2.98 (s, 3 H) 3.05 (s, 3 H) 3.09-3.14 (m, 1 H) 3.18 (dd, J = 10.09, 7.34 Hz, 1 H) 3.28 (s, 3 H) 3.29-3.36 (m, 1 H) 3.44-3.50 (m, 1 H) 3.51-3.56 (m, 1 H) 3.59 (s, 1 H) 3.66-3.74 (m, 6 H) 3.77-3.83 (m, 1 H) 3.85-3.90 (m, 1 H) 4.10 (q, J = 6.27 Hz, 1 H) 4.42 (d, J = 6.88 Hz, 1 H) 4.93-4.99 (m, 2 H) 5.54 (t, J = 5.73 Hz, 1 H) |
| 103 | CH₃–S(=O)(=O)–NH– | thiomorpholinylpropyl group | 1066.6 (600 MHz): 0.86 (t, J = 7.22 Hz, 3 H) 1.02 (d, J = 6.61 Hz, 3 H) 1.11 (d, J = 7.84 Hz, 3 H) 1.13 (d, J = 7.02 Hz, 3 H) 1.17 (s, 3 H) 1.18 (d, J = 6.19 Hz, 3 H) 1.20-1.26 (m, 7 H) 1.39-1.42 (m, 6 H) 1.53-1.60 (m, 1 H) 1.66 (d, J = 11.56 Hz, 1 H) 1.72-1.76 (m, 2 H) 1.83-1.95 (m, 2 H) 1.97-2.04 (m, 2 H) 2.10 (d, J = 14.86 Hz, 1 H) 2.29 (s, 6 H) 2.34 (s, 3 H) 2.38-2.47 (m, 3 H) 2.48-2.53 (m, 1 H) 2.56-2.62 (m, 2 H) 2.65-2.76 (m, 8 H) 2.82 (d, J = 14.86 Hz, 1 H) 2.91-2.96 (m, 1 H) 2.98 (s, 3 H) 3.06 (s, 3 H) 3.09-3.14 (m, 1 H) 3.16-3.21 (m, 1 H) 3.28 (s, 3 H) 3.29-3.35 (m, 1 H) 3.44-3.49 (m, 1 H) 3.51-3.56 (m, 1 H) 3.59 (s, 1 H) 3.69 (d, J = 9.50 Hz, 1 H) 3.72 (d, J = 7.43 Hz, 1 H) 3.77-3.83 (m, 1 H) 3.84-3.92 (m, 1 H) 4.09 (q, J = 6.19 Hz, 1 H) 4.42 (d, J = 7.43 Hz, 1 H) 4.93-5.01 (m, 2 H) 5.54 (t, J = 5.57 Hz, 1 H) |
| 104 | CH₃–S(=O)(=O)–NH– | 2-oxa-5-azabicyclo group with propyl linker | 1076.6 (600 MHz): 0.86 (t, J = 7.22 Hz, 3 H) 1.02 (d, J = 7.02 Hz, 3 H) 1.11 (d, J = 7.43 Hz, 3 H) 1.13 (d, J = 7.43 Hz, 3 H) 1.18 (s, 3 H) 1.19-1.27 (m, 7 H) 1.24 (d, J = 6.19 Hz, 3 H) 1.38-1.43 (m, 6 H) 1.54-1.60 (m, 1 H) 1.63-1.68 (m, 1 H) 1.72-1.75 (m, 2 H) 1.85-1.94 (m, 6 H) 1.99-2.02 (m, 2 H) 2.11 (d, J = 14.45 Hz, 1 H) 2.29 (s, 6 H) 2.32-2.36 (m, 2 H) 2.34-2.35 (m, 3 H) 2.41-2.62 (m, 4 H) 2.86 (d, J = 14.45 Hz, 1 H) 2.92-2.95 (m, 1 H) 2.97-3.01 (m, 2 H) 2.98 (s, 3 H) 3.06 (s, 3 H) 3.09-3.14 (m, 1 H) 3.16-3.20 (m, 1 H) 3.28 (s, 3 H) 3.31-3.35 (m, 1 H) 3.44-3.50 (m, 3 H) 3.51-3.56 (m, 1 H) 3.59 (s, 1 H) 3.68-3.77 (m, 4 H) 3.78-3.83 (m, 1 H) 3.85-3.91 (m, 1 H) 4.07-4.12 (m, 1 H) 4.42 (d, J = 7.43 Hz, 1 H) 4.94-5.00 (m, 2 H) 5.50-5.56 (m, 1 H) |
| 105 | CH₃–S(=O)(=O)–NH– | –CH₂CH₂–S(=O)(=O)–CH₃ group | 1043.5 (600 MHz): 0.86 (t, J = 7.34 Hz, 3 H) 1.00-1.27 (m, 22 H) 1.40 (s, 6 H) 1.52-1.76 (m, 4 H) 1.85-1.99 (m, 3 H) 2.03-2.12 (m, 2 H) 2.29 (s, 6 H) 2.36 (s, 3 H) 2.40-2.45 (m, 1 H) 2.50-2.62 (m, 2 H) 2.87-2.96 (m, 2 H) 2.98 (s, 3 H) 3.04-3.14 (m, 5 H) 3.15-3.20 (m, 1 H) 3.26-3.35 (m, 7 H) 3.39-3.48 (m, 2 H) 3.51-3.57 (m, 1 H) 3.59 (s, 1 H) 3.66-3.72 (m, 2 H) 3.77-3.91 (m, 2 H) 4.10-4.15 (m, 2 H) 4.39 (d, J = 6.88 Hz, 1 H) 4.93-4.99 (m, 2 H) 5.50-5.53 (m, 1 H) |

TABLE 1-continued

| | | | |
|---|---|---|---|
| 106 | cyclopropyl-S(=O)₂-NH-C(CH₃)< | -CH₂CH₂CH₂-N(CH₂CH₃)₂ | 1062.8 (600 MHz): 0.86 (t, J = 7.34 Hz, 3 H) 0.90-0.96 (m, 1 H) 0.97-1.05 (m, 10 H) 1.09-1.26 (m, 21 H) 1.40 (s, 6 H) 1.52-2.04 (m, 9 H) 2.09 (d, J = 14.67 Hz, 1 H) 2.29 (s, 6 H) 2.34 (s, 3 H) 2.39-2.63 (m, 10 H) 2.80-2.85 (m, 1 H) 2.90-2.97 (m, 1 H) 3.06 (s, 3 H) 3.10-3.21 (m, 2 H) 3.25-3.35 (m, 4 H) 3.44-3.50 (m, 1 H) 3.52-3.61 (m, 2 H) 3.68 (d, J = 10.09 Hz, 1 H) 3.72 (d, J = 7.34 Hz, 1 H) 3.75-3.80 (m, 1 H) 3.90-3.97 (m, 1 H) 4.09 (q, J = 6.11 Hz, 1 H) 4.42 (d, J = 7.34 Hz, 1 H) 4.96-5.01 (m, 2 H) 5.60 (t, J = 6.19 Hz, 1 H) |
| 107 | H₃C-CH₂-S(=O)₂-NH- | -CH₂CH₂CH₂-N(CH₂CH₃)₂ | 1050.7 (600 MHz): 0.85 (t, J = 7.34 Hz, 2 H) 1.00-1.05 (m, 9 H) 1.11 (d, J = 7.79 Hz, 3 H) 1.13 (d, J = 6.88 Hz, 3 H) 1.16 (s, 3 H) 1.18-1.27 (m, 10 H) 1.35 (t, J = 7.34 Hz, 3 H) 1.40 (s, 3 H) 1.40 (s, 3 H) 1.50-1.68 (m, 2 H) 1.72-1.76 (m, 2 H) 1.83-2.04 (m, 4 H) 2.07-2.12 (m, 1 H) 2.29 (s, 6 H) 2.34 (s, 3 H) 2.39-2.63 (m, 10 H) 2.81-2.86 (m, 1 H) 2.91-2.96 (m, 1 H) 3.03-3.20 (m, 7 H) 3.27 (s, 3 H) 3.43-3.56 (m, 3 H) 3.59 (s, 1 H) 3.67-3.89 (m, 4 H) 4.06-4.12 (m, 1 H) 4.42 (d, J = 7.34 Hz, 1 H) 4.96-5.01 (m, 2 H) 5.49 (t, J = 5.73 Hz, 1 H) |
| 108 | 2-(methylsulfonyl)phenyl-S(=O)₂-NH- | -CH₂CH₂CH₂-N(CH₂CH₃)₂ | 1176.7 (600 MHz): 0.84 (t, J = 7.34 Hz, 3 H) 0.92 (d, J = 6.88 Hz, 3 H) 1.00-1.10 (m, 12 H) 1.17 (s, 3 H) 1.18-1.26 (m, 10 H) 1.33 (s, 3 H) 1.37 (s, 3 H) 1.46-1.72 (m, 4 H) 1.80-1.90 (m, 2 H) 1.95-2.05 (m, 2 H) 2.08-2.12 (m, 1 H) 2.28 (s, 6 H) 2.35 (s, 3 H) 2.39-2.65 (m, 10 H) 2.84 (d, J = 15.13 Hz, 2 H) 2.89 (s, 3 H) 3.01-3.05 (m, 1 H) 3.15-3.25 (m, 2 H) 3.27 (s, 3 H) 3.32-3.38 (m, 1 H) 3.38-3.41 (m, 4 H) 3.43-3.50 (m, 1 H) 3.57 (s, 1 H) 3.58-3.67 (m, 3 H) 3.74-3.81 (m, 1 H) 4.06-4.11 (m, 1 H) 4.40 (d, J = 7.34 Hz, 1 H) 4.91-4.97 (m, 2 H) 7.76-7.80 (m, 2 H) 8.25-8.33 (m, 2 H) |
| 109 | 3-cyanophenyl-S(=O)₂-NH- | -CH₂CH₂CH₂-N(CH₂CH₃)₂ | 1123.7 (500 MHz): 0.84 (t, J = 7.34 Hz, 3 H) 0.93 (d, J = 6.88 Hz, 3 H) 1.00-1.28 (m, 25 H) 1.37 (s, 6 H) 1.50-2.12 (m, 9 H) 2.28 (s, 6 H) 2.35 (s, 3 H) 2.39-2.64 (m, 10 H) 2.80-2.97 (m, 5 H) 3.03-3.08 (m, 1 H) 3.15-3.29 (m, 5 H) 3.37-3.52 (m, 3 H) 3.62-3.77 (m, 4 H) 4.06-4.11 (m, 1 H) 4.40 (d, J = 7.34 Hz, 1 H) 4.82-4.85 (m, 1 H) 4.97-5.00 (m, 1 H) 6.24 (t, J = 5.04 Hz, 1 H) 7.62-7.66 (m, 1 H) 7.80-7.83 (m, 1 H) 8.01-8.13 (m, 1 H) 8.17-8.19 (m, 1 H) |
| 110 | 2-cyanophenyl-S(=O)₂-NH- | -CH₂CH₂CH₂-N(CH₂CH₃)₂ | 1123.7 (500 MHz): 0.75-1.31 (m, 31 H) 1.34-1.45 (m, 6 H) 1.46-2.14 (m, 9 H) 2.26-2.36 (m, 9 H) 2.39-2.71 (m, 10 H) 2.81-3.30 (m, 11 H) 3.40-4.43 (m, 10 H) 4.79-5.26 (m, 2 H) 7.61-8.85 (m, 4 H) |

TABLE 1-continued

| | | | |
|---|---|---|---|
| 111 | 4-cyanophenyl-SO2-NH- (benzene with CN para to SO2NH) | -C(CH3)2-CH2-CH2-N(CH2CH3)2 | 1123.7 (500 MHz): 0.82 (t, J = 7.40 Hz, 3 H) 0.93 (d, J = 6.86 Hz, 3 H) 1.00-1.27 (m, 25 H) 1.36 (s, 3 H) 1.37 (s, 3 H) 1.50-2.14 (m, 9 H) 2.28 (s, 6 H) 2.35 (s, 3 H) 2.39-2.64 (m, 10 H) 2.78-2.97 (m, 5 H) 3.02-3.09 (m, 1 H) 3.13-3.24 (m, 2 H) 3.28 (s, 3 H) 3.34-3.52 (m, 3 H) 3.64-3.80 (m, 4 H) 4.09 (q, J = 6.22 Hz, 1 H) 4.41 (d, J = 7.13 Hz, 1 H) 4.85 (dd, J = 10.97, 1.92 Hz, 1 H) 5.01 (d, J = 3.29 Hz, 1 H) 6.31-6.45 (m, 1 H) 7.78-7.81 (m, 2 H) 7.99-8.03 (m, 2 H) |
| 112 | phenyl-SO2-NH- | -C(CH3)2-CH2-CH2-N(CH2CH3)2 | 1098.7 (500 MHz): 0.83 (t, J = 7.40 Hz, 3 H) 0.93 (d, J = 7.13 Hz, 3 H) 1.00-1.11 (m, 12 H) 1.14-1.26 (m, 13 H) 1.34 (s, 3 H) 1.36 (s, 3 H) 1.47-2.12 (m, 9 H) 2.28 (s, 6 H) 2.35 (s, 3 H) 2.38-2.64 (m, 10 H) 2.77-2.81 (m, 3 H) 2.84 (d, J = 14.81 Hz, 1 H) 2.88-2.96 (m, 1 H) 3.02-3.09 (m, 1 H) 3.12-3.20 (m, 2 H) 3.28 (s, 3 H) 3.30-3.37 (m, 1 H) 3.42-3.52 (m, 2 H) 3.59-3.71 (m, 3 H) 3.72-3.81 (m, 1 H) 4.08 (d, J = 6.31 Hz, 1 H) 4.41 (d, J = 7.13 Hz, 1 H) 4.89 (dd, J = 10.83, 2.06 Hz, 1 H) 5.00 (d, J = 3.57 Hz, 1 H) 6.03 (t, J = 6.03 Hz, 1 H) 7.43-7.55 (m, 3 H) 7.85-7.95 (m, 2 H) |
| 113 | thiophen-2-yl-SO2-NH- | -C(CH3)2-CH2-CH2-N(CH2CH3)2 | 1104.6 (500 MHz): 0.85 (t, J = 7.27 Hz, 3 H) 0.96 (d, J = 6.86 Hz, 3 H) 1.01-1.05 (m, 6 H) 1.10 (t, J = 7.13 Hz, 6 H) 1.14-1.27 (m, 13 H) 1.36 (s, 3 H) 1.37-1.38 (m, 3 H) 1.48-2.12 (m, 9 H) 2.29 (s, 6 H) 2.35 (s, 3 H) 2.39-2.64 (m, 10 H) 2.80-2.95 (m, 5 H) 3.04-3.11 (m, 1 H) 3.15-3.30 (m, 5 H) 3.38-3.50 (m, 2 H) 3.53 (s, 1 H) 3.62-3.73 (m, 3 H) 3.76-3.84 (m, 1 H) 4.08 (q, J = 6.22 Hz, 1 H) 4.41 (d, J = 7.40 Hz, 1 H) 4.90 (dd, J = 10.97, 1.92 Hz, 1 H) 4.99 (d, J = 3.84 Hz, 1 H) 6.22 (br. s., 1 H) 7.05 (dd, J = 4.94, 3.84 Hz, 1 H) 7.53 (dd, J = 4.94, 1.37 Hz, 1 H) 7.62 (dd, J = 3.84, 1.37 Hz, 1 H) |
| 114 | 4-methoxyphenyl-SO2-NH- | -C(CH3)2-CH2-CH2-N(CH2CH3)2 | 1128.7 (600 MHz): 0.83 (t, J = 7.34 Hz, 3 H) 0.91-1.26 (m, 28 H) 1.35 (s, 3 H) 1.36 (s, 3 H) 1.48-1.57 (m, 1 H) 1.62-1.75 (m, 3 H) 1.79-1.92 (m, 2 H) 1.97-2.05 (m, 2 H) 2.09 (d, J = 14.67 Hz, 1 H) 2.28 (s, 6 H) 2.35 (s, 3 H) 2.38-2.64 (m, 10 H) 2.83 (d, J = 10.09 Hz, 1 H) 2.85 (s, 3 H) 2.88-2.95 (m, 1 H) 3.06 (q, J = 6.88 Hz, 1 H) 3.10-3.20 (m, 2 H) 3.25-3.34 (m, 1 H) 3.27 (s, 3 H) 3.40-3.46 (m, 1 H) 3.58-3.73 (m, 4 H) 3.76 (s, 1 H) 3.86 (s, 3 H) 4.08 (q, J = 6.42 Hz, 1 H) 4.40 (d, J = 7.34 Hz, 1 H) 4.89 (dd, J = 11.00, 2.29 Hz, 1 H) 4.99 (d, J = 3.67 Hz, 1 H) 5.92 (t, J = 5.96 Hz, 1 H) 6.94 (d, J = 8.71 Hz, 2 H) 7.82 (d, J = 8.71 Hz, 2 H) |
| 115 | -C(CH3)2-CH2-CH2-N(CH2CH3)2 | 3-methoxyphenyl-SO2-NH- | 1128.7 (600 MHz): 0.82 (t, J = 7.34 Hz, 3 H) 0.91 (d, J = 6.88 Hz, 3 H) 0.96-1.25 (m, 25 H) 1.34 (s, 3 H) 1.35 (s, 3 H) 1.48-1.58 (m, 1 H) 1.60-1.72 (m, 3 H) 1.77-1.90 (m, 2 H) 1.95-2.04 (m, 2 H) 2.08 (d, J = 14.67 Hz, 1 H) 2.27 (s, 6 H) 2.33 (s, 3 H) 2.37-2.64 (m, 10 H) 2.81 (s, 3 H) 2.83-2.93 (m, 2 H) 3.04 (q, J = 6.88 Hz, 1 H) 3.12-3.19 (m, 2 H) 3.26 (s, 3 H) 3.30-3.36 (m, 1 H) 3.40-3.51 (m, 3 H) 3.59-3.70 (m, 3 H) 3.71-3.78 (m, 1 H) 3.84 (s, 3 H) 4.06 (q, J = 6.27 Hz, 1 H) 4.39 (d, J = 7.34 Hz, 1 H) 4.87 (dd, J = 11.00, 2.29 Hz, 1 H) 4.97 (d, J = 4.13 Hz, 1 H) 6.01 (t, J = 5.96 Hz, 1 H) 7.00-7.04 (m, 1 H) 7.34-7.38 (m, 1 H) 7.39-7.41 (m, 1 H) 7.45 (d, J = 7.79 Hz, 1 H) |

TABLE 1-continued

| 116 | 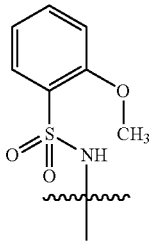 [SMILES: *NS(=O)(=O)c1ccccc1OC] | 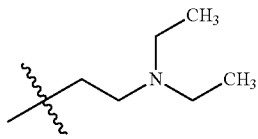 [SMILES: *CCN(CC)CC] | 1128.7 | (600 MHz): 0.86 (t, J = 7.34 Hz, 3 H) 0.91-1.28 (m, 28 H) 1.36 (s, 3 H) 1.37 (s, 3 H) 1.50-1.57 (m, 1 H) 1.65 (d, J = 11.92 Hz, 1 H) 1.71 (d, J = 6.88 Hz, 2 H) 1.82-2.05 (m, 4 H) 2.10 (d, J = 14.67 Hz, 1 H) 2.29 (s, 6 H) 2.35 (s, 3 H) 2.39-2.66 (m, 10 H) 2.84 (d, J = 14.67 Hz, 1 H) 2.87-2.97 (m, 1 H) 2.94 (s, 3 H) 3.06 (q, J = 6.88 Hz, 1 H) 3.13-3.21 (m, 3 H) 3.28 (s, 3 H) 3.38-3.50 (m, 2 H) 3.55 (s, 1 H) 3.62-3.77 (m, 4 H) 3.96 (s, 3 H) 4.09 (q, J = 6.27 Hz, 1 H) 4.41 (d, J = 7.34 Hz, 1 H) 4.97 (d, J = 5.04 Hz, 1 H) 5.01 (dd, J = 11.00, 1.83 Hz, 1 H) 6.04 (t, J = 5.96 Hz, 1 H) 6.98 (d, J = 8.25 Hz, 1 H) 7.04 (t, J = 7.57 Hz, 1 H) 7.46-7.53 (m, 1 H) 7.94 (dd, J = 7.57, 1.60 Hz, 1 H) |
| 117 | 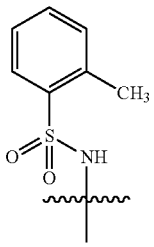 [SMILES: *NS(=O)(=O)c1ccccc1C] | 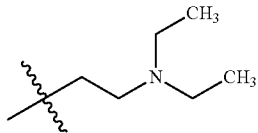 [SMILES: *CCN(CC)CC] | 1112.7 | (500 MHz): 0.85 (t, J = 7.45 Hz, 3 H) 0.94 (d, J = 6.88 Hz, 3 H) 1.03 (t, J = 7.07 Hz, 6 H) 1.09 (d, J = 7.26 Hz, 6 H) 1.15-1.28 (m, 13 H) 1.36 (s, 3 H) 1.36-1.38 (m, 3 H) 1.50-1.73 (m, 4 H) 1.80-2.12 (m, 5 H) 2.28 (s, 6 H) 2.35 (s, 3 H) 2.39-2.63 (m, 10 H) 2.65 (s, 3 H) 2.84 (d, J = 14.14 Hz, 1 H) 2.92 (s, 4 H) 3.03-3.20 (m, 3 H) 3.24-3.32 (m, 4 H) 3.42-3.51 (m, 2 H) 3.54 (s, 1 H) 3.59-3.74 (m, 4 H) 4.05-4.11 (m, 1 H) 4.41 (d, J = 7.26 Hz, 1 H) 4.93-5.02 (m, 2 H) 6.15-6.20 (m, 1 H) 7.27-7.31 (m, 2 H) 7.39-7.43 (m, 1 H) 7.97-8.01 (m, 1 H) |
| 118 | 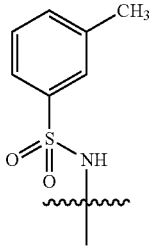 [SMILES: *NS(=O)(=O)c1cccc(C)c1] | 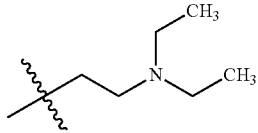 [SMILES: *CCN(CC)CC] | 1112.7 | (500 MHz): 0.83 (t, J = 7.26 Hz, 3 H) 0.93 (d, J = 6.88 Hz, 3 H) 1.00-1.11 (m, 12 H) 1.15-1.27 (m, 13 H) 1.35 (s, 3 H) 1.36 (s, 3 H) 1.47-1.74 (m, 4 H) 1.79-1.92 (m, 2 H) 1.95-2.05 (m, 2 H) 2.09 (d, J = 14.91 Hz, 1 H) 2.29 (s, 6 H) 2.35 (s, 3 H) 2.39-2.64 (m, 13 H) 2.81-2.87 (m, 4 H) 2.92 (dd, J = 9.56, 7.26 Hz, 1 H) 3.03-3.09 (m, 1 H) 3.11-3.20 (m, 2 H) 3.27 (s, 3 H) 3.30-3.37 (m, 1 H) 3.42-3.49 (m, 1 H) 3.51 (s, 1 H) 3.60-3.79 (m, 4 H) 4.08 (q, J = 6.12 Hz, 1 H) 4.41 (d, J = 6.88 Hz, 1 H) 4.89 (dd, J = 11.08, 1.91 Hz, 1 H) 4.99 (d, J = 4.20 Hz, 1 H) 5.97 (t, J = 6.12 Hz, 1 H) 7.30-7.39 (m, 2 H) 7.67-7.72 (m, 2 H) |
| 119 | 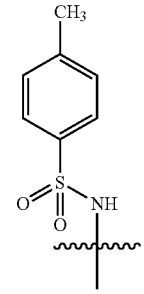 [SMILES: *NS(=O)(=O)c1ccc(C)cc1] | 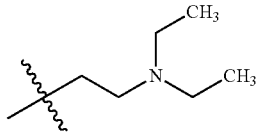 [SMILES: *CCN(CC)CC] | 1112.7 | (500 MHz): 0.83 (t, J = 7.45 Hz, 3 H) 0.93 (d, J = 6.88 Hz, 3 H) 1.00-1.12 (m, 12 H) 1.15-1.27 (m, 13 H) 1.35 (s, 3 H) 1.36 (s, 3 H) 1.47-1.74 (m, 4 H) 1.78-1.93 (m, 2 H) 1.97-2.12 (m, 3 H) 2.29 (s, 6 H) 2.35 (s, 3 H) 2.37-2.64 (m, 13 H) 2.79-2.86 (m, 4 H) 2.88-2.96 (m, 1 H) 3.02-3.20 (m, 3 H) 3.25-3.35 (m, 4 H) 3.42-3.49 (m, 1 H) 3.50 (s, 1 H) 3.60-3.70 (m, 3 H) 3.73-3.81 (m, 1 H) 4.08 (q, J = 6.12 Hz, 1 H) 4.40 (d, J = 7.26 Hz, 1 H) 4.89 (dd, J = 10.89, 1.72 Hz, 1 H) 4.99 (d, J = 3.06 Hz, 1 H) 5.94-6.00 (m, 1 H) 7.27 (d, J = 8.03 Hz, 2 H) 7.77 (d, J = 8.03 Hz, 2 H) |

TABLE 1-continued

| | | | | |
|---|---|---|---|---|
| 120 | (1-methylpyrazol-3-yl sulfonamide structure) | (diethylaminoalkyl structure with CH₃) | 1102.6 | (600 MHz): 0.89 (t, J = 7.34 Hz, 3 H) 0.94-1.27 (m, 28 H) 1.37 (s, 3 H) 1.38 (s, 3 H) 1.56 (ddd, J = 14.44, 11.00, 7.11 Hz, 1 H) 1.62-1.67 (m, 1 H) 1.69-1.76 (m, 2 H) 1.81-1.94 (m, 2 H) 1.95-2.04 (m, 2 H) 2.09 (d, J = 14.67 Hz, 1 H) 2.28 (s, 6 H) 2.34 (s, 3 H) 2.39-2.64 (m, 10 H) 2.84 (d, J = 14.67 Hz, 1 H) 2.93 (dd, J = 9.86, 7.11 Hz, 1 H) 2.99 (s, 3 H) 3.10 (q, J = 6.88 Hz, 1 H) 3.17 (dd, J = 10.09, 7.34 Hz, 1 H) 3.22-3.29 (m, 1 H) 3.27 (s, 3 H) 3.44 (br. s, 1 H) 3.45-3.50 (m, 1 H) 3.51-3.62 (m, 2 H) 3.55 (s, 1 H) 3.67 (d, J = 9.63 Hz, 1 H) 3.71 (d, J = 6.88 Hz, 1 H) 3.77 (ddd, J = 13.87, 9.97, 4.13 Hz, 1 H) 3.94 (s, 3 H) 4.08 (q, J = 5.96 Hz, 1 H) 4.42 (d, J = 7.34 Hz, 1 H) 4.98 (d, J = 4.58 Hz, 1 H) 5.02 (dd, J = 10.77, 2.06 Hz, 1 H) 6.20 (t, J = 5.96 Hz, 1 H) 6.67 (d, J = 2.29 Hz, 1 H) 7.37 (d, J = 2.29 Hz, 1 H) |
| 121 | (pyridin-3-yl sulfonamide structure) | (tert-butyl CH₃ structure) | 1014.6 | (500 MHz): 0.83 (t, J = 7.40 Hz, 3H) 0.95 (d, J = 7.13 Hz, 3 H) 1.02 (d, J = 7.13 Hz, 3 H) 1.07-1.15 (m, 9 H) 1.16-1.27 (m, 7 H) 1.35 (s, 3 H) 1.37 (s, 3 H) 1.45-2.17 (m, 9 H) 2.30 (s, 6 H) 2.37 (s, 6 H) 2.43-2.51 (m, 1 H) 2.75 (d, J = 14.81 Hz, 1 H) 2.82 (s, 3 H) 2.84-2.90 (m, 2 H) 2.96-3.02 (m, 1 H) 3.16 (dd, J = 10.15, 7.40 Hz, 1 H) 3.23 (s, 3 H) 3.29-3.46 (m, 4 H) 3.51 (s, 1 H) 3.57-3.68 (m, 3 H) 3.74 (d, J = 10.15 Hz, 1 H) 4.10 (q, J = 6.49 Hz, 1 H) 4.24 (d, J = 7.13 Hz, 1 H) 4.78-4.87 (m, 2 H) 7.41-7.45 (m, 1 H) 8.16-8.20 (m, 1 H) 8.76-8.79 (m, 1 H) 9.08-9.12 (m, 1 H) |
| 122 | (pyridin-3-yl sulfonamide structure) | (dimethylaminoalkyl structure with CH₃) | 1071.7 | (500 MHz): 0.84 (t, J = 7.45 Hz, 3 H) 0.93 (d, J = 6.88 Hz, 3 H) 1.06-1.12 (m, 6 H) 1.16-1.27 (m, 13 H) 1.35 (s, 3 H) 1.36 (s, 3 H) 1.47-2.06 (m, 8 H) 2.14 (d, J = 14.91 Hz, 1 H) 2.25 (s, 6 H) 2.29 (s, 6 H) 2.32-2.67 (m, 9 H) 2.79-2.85 (m, 4 H) 2.88-2.96 (m, 1 H) 3.06 (q, J = 6.88 Hz, 1 H) 3.15-3.30 (m, 5 H) 3.37-3.51 (m, 3 H) 3.61 (d, J = 9.94 Hz, 1 H) 3.65-3.81 (m, 3 H) 4.10 (q, J = 6.12 Hz, 1 H) 4.40 (d, J = 7.26 Hz, 1 H) 4.85 (dd, J = 10.70, 1.91 Hz, 1 H) 4.99 (d, J = 3.82 Hz, 1 H) 6.24-6.32 (m, 1 H) 7.41-7.47 (m, 1 H) 8.13-8.21 (m, 1 H) 8.74-8.79 (m, 1 H) 9.08-9.12 (m, 1 H) |
| 123 | (pyridin-3-yl sulfonamide structure) | (diethylaminoalkyl structure with CH₃) | 1099.7 | (500 MHz): 0.84 (t, J = 7.26 Hz, 3 H) 0.93 (d, J = 6.88 Hz, 3 H) 0.99-1.27 (m, 25 H) 1.35 (s, 3 H) 1.36 (s, 3 H) 1.49-1.73 (m, 4 H) 1.76-1.92 (m, 2 H) 1.97-2.12 (m, 3 H) 2.28 (s, 6 H) 2.35 (s, 3 H) 2.39-2.64 (m, 10 H) 2.80-2.87 (m, 4 H) 2.89-2.96 (m, 1 H) 3.06 (q, J = 6.63 Hz, 1 H) 3.14-3.30 (m, 5 H) 3.36-3.53 (m, 3 H) 3.58-3.81 (m, 4 H) 4.04-4.11 (m, 1 H) 4.40 (d, J = 7.26 Hz, 1 H) 4.85 (dd, J = 11.08, 1.91 Hz, 1 H) 5.00 (d, J = 2.68 Hz, 2 H) 6.22-6.36 (m, 1 H) 7.41-7.47 (m, 1 H) 8.14-8.20 (m, 1 H) 8.74-8.80 (m, 1 H) 9.08-9.12 (m, 1 H) |

TABLE 1-continued

| 124 | 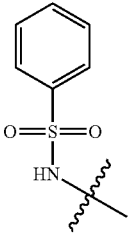 | 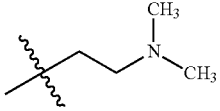 [SMILES: *CCN(C)C] | 1070.6 | (500 MHz): 0.83 (t, J = 7.26 Hz, 3 H) 0.93 (d, J = 6.88 Hz, 3 H) 1.06-1.11 (m, 6 H) 1.16-1.26 (m, 13 H) 1.34 (s, 3 H) 1.36 (s, 3 H) 1.48-2.07 (m, 8 H) 2.15 (d, J = 14.91 Hz, 1 H) 2.23-2.27 (m, 6 H) 2.27-2.31 (m, 6 H) 2.33-2.66 (m, 9 H) 2.77-2.96 (m, 5 H) 3.02-3.08 (m, 1 H) 3.11-3.20 (m, 2 H) 3.28 (s, 3 H) 3.29-3.36 (m,1 H) 3.43-3.52 (m, 2 H) 3.58-3.80 (m, 4 H) 4.10 (q, J = 6.37 Hz, 1 H) 4.41 (d, J = 7.26 Hz, 1 H) 4.89 (dd, J = 11.09, 1.91 Hz, 1 H) 5.00 (d, J = 3.82 Hz, 1 H) 6.00-6.06 (m, 1 H) 7.44-7.55 (m, 3 H) 7.87-7.92 (m, 2 H) |
| --- | --- | --- | --- | --- |
| 125 | 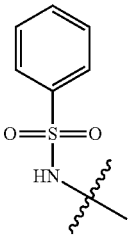 [SMILES: *NS(=O)(=O)c1ccccc1] | 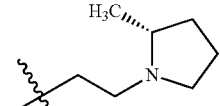 | 1110.7 | (500 MHz): 0.83 (t, J = 7.45 Hz, 3 H) 0.93 (d, J = 6.88 Hz, 3 H) 1.06-1.27 (m, 22 H) 1.34 (s, 3 H) 1.35-1.38 (m, 3 H) 1.46-1.72 (m, 3 H) 1.75-2.20 (m, 9 H) 2.28 (s, 6 H) 2.31-2.55 (m, 7 H) 2.62-2.68 (m, 2 H) 2.80 (s, 3 H) 2.84-2.96 (m, 3 H) 3.03-3.20 (m, 4 H) 3.27 (s, 3 H) 3.30-3.52 (m, 5 H) 3.60-3.70 (m, 3 H) 3.73-3.80 (m, 1 H) 4.06-4.11 (m, 1 H) 4.39-4.43 (m, 1 H) 4.86-4.81 (m, 1 H) 5.00 (d, J = 3.82 Hz, 1 H) 6.02 (t, J = 5.35 Hz, 1 H) 7.44-7.55 (m, 3 H) 7.90 (d, J = 7.26 Hz, 2 H) |
| 126 | 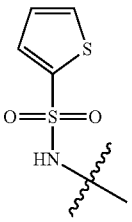 [SMILES: *NS(=O)(=O)c1cccs1] | 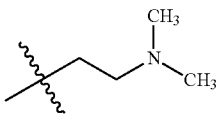 [SMILES: *CCN(C)C] | 1076.6 | (600 MHz): 0.85 (t, J = 7.34 Hz, 3 H) 0.96 (d, J = 6.88 Hz, 3 H) 1.10 (t, J = 7.34 Hz, 6 H) 1.16-1.28 (m, 13 H) 1.36 (s, 3 H) 1.37 (s, 3 H) 1.62-1.68 (m, 1 H) 1.68-1.73 (m, 2 H) 1.80-1.93 (m, 2 H) 1.95-2.05 (m, 2 H) 2.15 (d, J = 14.67 Hz, 1 H) 2.21-2.47 (m, 18 H) 2.50-2.66 (m, 3 H) 2.82 (d, J = 15.13 Hz, 1 H) 2.86 (s, 3 H) 2.89-2.96 (m, 1 H) 3.04-3.09 (m, 1 H) 3.15-3.26 (m, 2 H) 3.27 (s, 3 H) 3.39-3.50 (m, 3 H) 3.53 (s, 1 H) 3.62-3.72 (m, 3 H) 3.76-3.83 (m, 1 H) 4.10 (q, J = 6.27 Hz, 1 H) 4.41 (d, J = 7.34 Hz, 1 H) 4.88-4.93 (m, 1 H) 4.99 (d, J = 5.04 Hz, 1 H) 6.18-6.23 (m, 1 H) 7.03-7.07 (m, 1 H) 7.52-7.55 (m, 1 H) 7.59-7.63 (m, 1 H) |
| 127 | 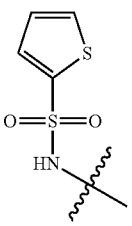 [SMILES: *NS(=O)(=O)c1cccs1] | 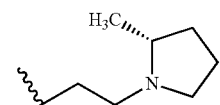 | 1116.6 | (600 MHz): 0.85 (t, J = 7.34 Hz, 3 H) 0.96 (d, J = 6.88 Hz, 3 H) 1.05-1.27 (m, 22 H) 1.36 (s, 3 H) 1.37 (s, 3 H) 1.50-1.59 (m, 1 H) 1.62-1.93 (m, 7 H) 1.95-2.06 (m, 2 H) 2.07-2.19 (m, 3 H) 2.28 (s, 6 H) 2.31-2.38 (m, 4 H) 2.39-2.46 (m, 1 H) 2.51-2.58 (m, 1 H) 2.60-2.69 (m, 2 H) 2.83-2.95 (m, 6 H) 3.04-3.10 (m, 1 H) 3.12-3.27 (m, 3 H) 3.26-3.29 (m, 3 H) 3.39-3.48 (m, 3 H) 3.53 (s, 1 H) 3.62-3.72 (m, 3 H) 3.76-3.83 (m, 1 H) 4.06-4.12 (m, 1 H) 4.39-4.43 (m, 1 H) 4.88-4.92 (m, 1 H) 4.98-5.01 (m, 1 H) 6.18-6.22 (m, 1 H) 7.03-7.06 (m, 1 H) 7.51-7.54 (m, 1 H) 7.60-7.63 (m, 1 H) |
| 128 | 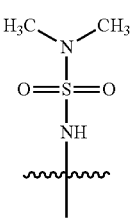 | 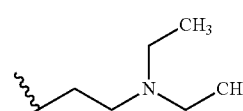 | 1065 | (400 MHz): 0.85 (t, J = 7.32 Hz, 3 H) 1.02 (d, J = 6.59 Hz, 3 H) 1.03 (t, J = 7.08 Hz, 6 H) 1.10 (d, J = 7.57 Hz, 3 H) 1.13 (d, J = 7.32 Hz, 3 H) 1.16 (s, 3 H) 1.17-1.26 (m, 1 H) 1.19 (d, J = 6.35 Hz, 3 H) 1.21 (d, J = 6.59 Hz, 3 H) 1.24 (d, J = 6.10 Hz, 3 H) 1.39 (s, 3 H) 1.40 (s, 3 H) 1.50-2.04 (m, 9 H) 2.10 (d, J = 14.65 Hz, 1 H) 2.29 (s, 6 H) 2.34 (s, 3 H) 2.39-2.63 (m, 10 H) 2.80 (s, 6 H) 2.83 (d, J = 14.89 Hz, 1 H) 2.88-2.98 (m, 1 H) 3.06 (s, 3 H) 3.12 (q, J = 6.84 Hz, 1 H) 3.18 (dd, J = 10.25, 7.08 Hz, 1 H) 3.24-3.31 (m, 1 H) 3.28 (s, 3 H) 3.40-3.52 (m, 3 H) 3.58 (s, 1 H) 3.67-3.75 (m, 3 H) 3.80-3.90 (m, 1 H) 4.09 (q, J = 6.35 Hz, 1 H) 4.42 (d, J = 7.08 Hz, 1 H) 4.96-5.02 (m, 2 H) 5.54 (t, J = 5.86 Hz, 1 H) |

TABLE 1-continued

| | | | | |
|---|---|---|---|---|
| 129 | 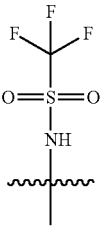 | 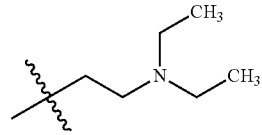 [SMILES: *CCN(CC)CC] | 1091 | (400 MHz): 0.85 (t, J = 7.32 Hz, 3 H) 1.02 (t, J = 7.08 Hz, 6 H) 1.03 (d, J = 6.84 Hz, 3 H) 1.11 (d, J = 7.57 Hz, 3 H) 1.13 (d, J = 7.32 Hz, 3 H) 1.17 (s, 3 H) 1.20 (d, J = 6.35 Hz, 3 H) 1.22 (d, J = 8.06 Hz, 3 H) 1.24 (d, J = 6.10 Hz, 3 H) 1.40 (s, 6 H) 1.46-1.71 (m, 3 H) 1.72-1.78 (m, 1 H) 1.79-1.98 (m, 2 H) 1.98-2.03 (m, 1 H) 2.09 (d, J = 14.6 Hz, 1 H) 2.29 (s, 6 H) 2.34 (s, 3 H) 2.38-2.64 (m, 10 H) 2.83 (d, J = 14.6 Hz, 1 H) 2.88-3.00 (m, 1 H) 3.06 (s, 3 H) 3.08-3.15 (m, 1 H) 3.18 (dd, J = 10.3, 7.32 Hz, 1 H) 3.28 (s, 3 H) 3.41-3.53 (m, 3 H) 3.56 (s, 1 H) 3.64-3.78 (m, 4 H) 3.82-3.90 (m, 1 H) 4.09 (q, J = 6.34 Hz, 1 H) 4.89 (dd, J = 10.6, 1.57 Hz, 1 H) 4.97-5.02 (m, 1 H) |
| 130 | 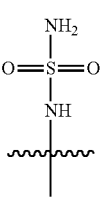 | 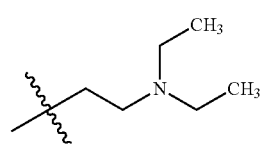 [SMILES: *CCN(CC)CC] | 1037 | (400 MHz): 0.86 (t, J = 7.57 Hz, 3 H) 1.02 (d, J = 7.08 Hz, 3 H) 1.03 (t, J = 7.08 Hz, 6 H) 1.11 (d, J = 7.57 Hz, 3 H) 1.14 (d, J = 7.08 Hz, 3 H) 1.16 (s, 3 H) 1.17-1.26 (m, 1 H) 1.19 (d, J = 6.10 Hz, 3 H) 1.20 (d, J = 5.89 Hz, 3 H) 1.24 (d, J = 6.10 Hz, 3 H) 1.40 (s, 3 H) 1.41 (s, 3 H) 1.50-1.77 (m, 4 H) 1.82-2.05 (m, 4 H) 2.09 (d, J = 14.65 Hz, 1 H) 2.29 (s, 6 H) 2.34 (s, 3 H) 2.39-2.66 (m, 10 H) 2.84 (d, J = 6.84 Hz, 1 H) 2.89-2.98 (m, 1 H) 3.04 (s, 3 H) 3.09-3.23 (m, 2 H) 3.28 (s, 3 H) 3.28-3.33 (m, 1 H) 3.40-3.54 (m, 3 H) 3.59 (s, 1 H) 3.67 (d, J = 9.77 Hz, 1 H) 3.70 (d, J = 7.32 Hz, 1 H) 3.87-3.94 (m, 1 H) 3.98-4.08 (m, 1 H) 4.09 (q, J = 6.59 Hz, 1 H) 4.41 (d, J = 7.08 Hz, 1 H) 4.91 (s, 2 H) 4.97 (d, J = 3.42 Hz, 1 H) 5.03 (dd, J = 10.09, 1.95 Hz, 1 H) 5.18-5.25 (m, 1 H) |
| 131 | 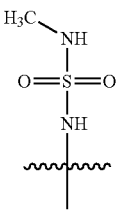 | 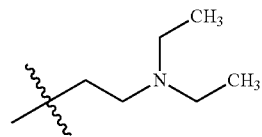 [SMILES: *CCN(CC)CC] | 1051 | (400 MHz): 0.85 (t, J = 7.32 Hz, 3 H) 1.02 (d, J = 6.84 Hz, 3 H) 1.03 (t, J = 6.59 Hz, 3 H) 1.11 (d, J = 7.32 Hz, 3 H) 1.13 (d, J = 7.08 Hz, 3 H) 1.16 (s, 3 H) 1.17-1.26 (m, 1 H) 1.19 (d, J = 6.35 Hz, 3 H) 1.21 (d, J = 7.57 Hz, 3 H) 1.24 (d, J = 6.10 Hz, 3 H) 1.40 (s, 6 H) 1.49-1.77 (m, 4 H) 1.82-2.05 (m, 4 H) 2.09 (d, J = 14.65 Hz, 1 H) 2.29 (s, 6 H) 2.34 (s, 3 H) 2.39-2.63 (m, 10 H) 2.72 (d, J = 5.37 Hz, 3 H) 2.84 (d, J = 14.65 Hz, 1 H) 2.88-2.97 (m, 1 H) 3.05 (s, 3 H) 3.12 (q, J = 7.08 Hz, 1 H) 3.18 (dd, J = 10.25, 7.32 Hz, 1 H) 3.22-3.28 (m, 1 H) 3.28 (s, 3 H) 3.40-3.52 (m, 3 H) 3.59 (s, 1 H) 3.68 (d, J = 9.77 Hz, 1 H) 3.71 (d, J = 7.32 Hz, 1 H) 3.76-3.83 (m, 1 H) 3.86-3.94 (m, 1 H) 3.99 (q, J = 6.35 Hz, 1 H) 4.42 (d, J = 7.32 Hz, 1 H) 4.42-4.47 (m, 1 H) 4.97-5.23 (m, 1 H) 5.34 (t, J = 5.62 Hz, 1 H) |
| 132 | 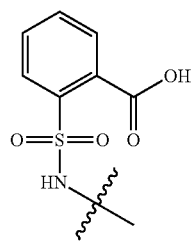 [SMILES: *NS(=O)(=O)c1ccccc1C(=O)O] | 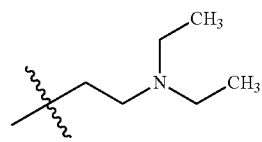 [SMILES: *CCN(CC)CC] | 1142.7 | (600 MHz, CD$_3$OD): 0.73 (t, J = 7.34 Hz, 3 H) 1.01 (d, J = 6.88 Hz, 3 H) 1.09 (d, J = 7.34 Hz, 3 H) 1.14-1.35 (m, 22 H) 1.41 (s, 3 H) 1.45 (s, 3 H) 1.50-1.59 (m, 1 H) 1.70-1.96 (m, 6 H) 2.11-2.18 (m, 1 H) 2.22-2.30 (m, 2 H) 2.38 (s, 3 H) 2.42 (br. s., 6 H) 2.45-3.12 (m, 15 H) 3.17-3.36 (m, 5 H) 3.49-3.55 (m, 1 H) 3.57-3.64 (m, 1 H) 3.66-3.70 (m, 1 H) 3.70-3.76 (m, 2 H) 3.77-3.81 (m, 1 H) 3.84-3.90 (m, 1 H) 3.93-4.00 (m, 1 H) 4.24 (q, J = 6.27 Hz, 1 H) 4.37-4.42 (m, 1 H) 4.91-4.96 (m, 1 H) 4.97-5.01 (m, 1 H) 7.39-7.50 (m, 2 H) 7.56-7.61 (m, 1 H) 7.93-7.97 (m, 1 H) |

TABLE 1-continued

| | | | |
|---|---|---|---|
| 133 | 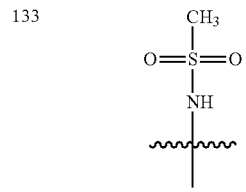 | 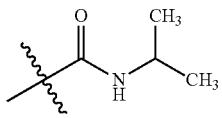 [SMILES: *C(=O)NC(C)C] | 1022.7 (600 MHz): 0.86 (t, J = 7.22 Hz, 3 H) 1.02 (d, J = 7.02 Hz, 3 H) 1.10-1.18 (m, 12 H) 1.19-1.26 (m, 13 H) 1.40-1.42 (m, 6 H) 1.53-1.60 (m, 1 H) 1.64-1.78 (m, 3 H) 1.85-1.95 (m, 3 H) 1.98-2.02 (m, 1 H) 2.28 (s, 6 H) 2.40-2.45 (m, 1 H) 2.57-2.62 (m, 1 H) 2.89 (s, 3 H) 2.89-2.93 (m, 1 H) 2.99 (s, 3 H) 3.03 (s, 3 H) 3.09-3.14 (m, 1 H) 3.16-3.22 (m, 2 H) 3.31 (s, 3 H) 3.32-3.37 (m, 1 H) 3.41 (br. s., 1 H) 3.47-3.57 (m, 3 H) 3.59 (s, 1 H) 3.66 (d, J = 9.50 Hz, 1 H) 3.72 (d, J = 7.43 Hz, 1 H) 3.76-3.82 (m, 1 H) 3.84-3.90 (m, 1 H) 3.91-3.98 (m, 1 H) 4.21-4.26 (m, 1 H) 4.40 (d, J = 7.02 Hz, 1 H) 4.61-4.66 (m, 1 H) 4.90-4.92 (m, 1 H) 4.94-4.97 (m, 1 H) 5.51 (t, J = 5.78 Hz, 1 H) |
| 134 | 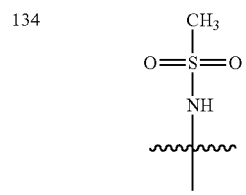 | 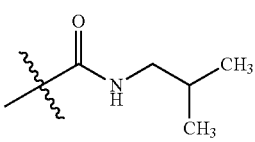 [SMILES: *C(=O)NCC(C)C] | 1036.6 (600 MHz): 0.86 (t, J = 7.43 Hz, 3 H) 0.91 (d, J = 6.61 Hz, 6 H) 1.02 (d, J = 7.02 Hz, 3 H) 1.12 (d, J = 7.43 Hz, 3 H) 1.14 (d, J = 7.02 Hz, 3 H) 1.16-1.28 (m, 13 H) 1.39-1.44 (m, 6 H) 1.53-1.59 (m, 1 H) 1.62-1.69 (m, 1 H) 1.69-1.80 (m, 3 H) 1.83-2.03 (m, 4 H) 2.28 (s, 6 H) 2.38-2.46 (m, 1 H) 2.55-2.63 (m, 1 H) 2.88-2.94 (m, 4 H) 2.98 (s, 3 H) 3.03 (s, 3 H) 3.04-3.14 (m, 3 H) 3.15-3.23 (m, 2 H) 3.31 (s, 3 H) 3.28-3.36 (m, 1 H) 3.37-3.61 (m, 5 H) 3.67 (d, J = 9.91 Hz, 1 H) 3.72 (d, J = 7.43 Hz, 1 H) 3.75-3.82 (m, 1 H) 3.83-3.90 (m, 1 H) 4.21-4.27 (m, 1 H) 4.39 (d, J = 7.02 Hz, 1 H) 4.89-4.99 (m, 3 H) 5.27-5.41 (m, 1 H) 5.51 (t, J = 5.57 Hz, 1 H) |
| 135 | 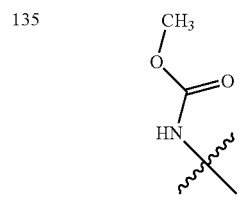 | 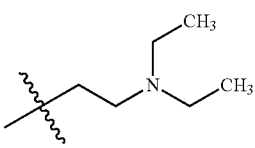 [SMILES: *CCN(CC)CC] | 1016.7 (600 MHz): 0.84 (t, J = 7.22 Hz, 3 H) 0.98-1.06 (m, 9 H) 1.10 (d, J = 7.43 Hz, 3 H) 1.12 (d, J = 7.02 Hz, 3 H) 1.16 (s, 3 H) 1.17-1.26 (m, 10 H) 1.39 (s, 3 H) 1.40 (s, 3 H) 1.48-1.79 (m, 4 H) 1.84-1.95 (m, 2 H) 1.95-2.04 (m, 2 H) 2.09 (d, J = 14.45 Hz, 1 H) 2.29 (s, 6 H) 2.34 (s, 3 H) 2.39-2.64 (m, 10 H) 2.84 (d, J = 14.45 Hz, 1 H) 2.90-2.97 (m, 1 H) 3.05 (s, 3 H) 3.09-3.14 (m, 1 H) 3.16-3.24 (m, 2 H) 3.28 (s, 3 H) 3.37-3.51 (m, 2 H) 3.54-3.58 (m, 1 H) 3.59 (s, 1 H) 3.62-3.74 (m, 3 H) 3.64 (s, 3 H) 3.89-3.96 (m, 1 H) 4.07-4.11 (m, 1 H) 4.42 (d, J = 7.02 Hz, 1 H) 4.95 (dd, J = 11.5, 2.06 Hz, 1 h) 4.99 (d, J = 4.54 Hz, 1 H) 5.87-5.91 (m, 1 H) |
| 136 | 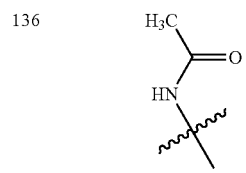 | 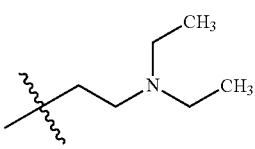 [SMILES: *CCN(CC)CC] | 1000.7 (600 MHz): 0.84 (t, J = 7.34 Hz, 3 H) 0.99-1.04 (m, 9 H) 1.10-1.15 (m, 6 H) 1.17 (s, 3 H) 1.19 (d, J = 6.42 Hz, 3 H) 1.20-1.26 (m, 7 H) 1.40 (s, 3 H) 1.41 (s, 3 H) 1.49-1.69 (m, 2 H) 1.71-1.77 (m, 2 H) 1.95 (s, 3 H) 1.84-2.06 (m, 4 H) 2.07-2.12 (m, 1 H) 2.29 (s, 3 H) 2.34 (s, 6 H) 2.38-2.64 (m, 10 H) 2.80-2.88 (m, 1 H) 2.93-3.00 (m, 1 H) 3.04 (s, 3 H) 3.09-3.14 (m, 1 H) 3.16-3.20 (m, 1 H) 3.21-3.30 (m, 1 H) 3.28 (s, 3 H) 3.42-3.52 (m, 2 H) 3.58-3.66 (m, 2 H) 3.69-3.77 (m, 3 H) 3.84-3.91 (m, 1 H) 4.06-4.13 (m, 1 H) 4.43 (d, J = 7.34 Hz, 1 H) 4.92-4.97 (m, 1 H) 4.98-5.01 (m, 1 H) 6.90-6.95 (m, 1 H) |
| 137 | 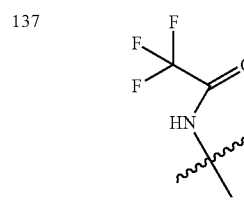 | 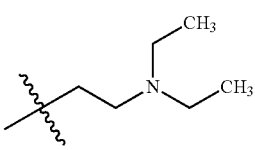 [SMILES: *CCN(CC)CC] | 1054.7 (600 MHz): 0.83 (t, J = 7.34 Hz, 3 H) 0.98-1.05 (m, 9 H) 1.09-1.27 (m, 19 H) 1.40 (s, 3 H) 1.41 (s, 3 H) 1.51-2.11 (m, 9 H) 2.29 (s, 6 H) 2.34 (s, 3 H) 2.39-2.63 (m, 10 H) 2.81-2.86 (m, 1 H) 2.94-2.98 (m, 1 H) 3.06 (s, 3 H) 3.11-3.21 (m, 2 H) 3.28 (s, 3 H) 3.34-3.40 (m, 1 H) 3.41-3.50 (m, 1 H) 3.62 (s, 1 H) 3.67-3.78 (m, 3 H) 3.79-3.86 (m, 1 H) 3.91-3.97 (m, 1 H) 4.07-4.12 (m, 1 H) 4.42 (d, J = 7.34 Hz, 1 H) 4.82-4.86 (m, 1 H) 4.97-5.01 (m, 1 H) |

| | | | | |
|---|---|---|---|---|
| 138 | ![structure: benzamide] | ![structure: diethylaminoethyl chain] | 1062.8 | (600 MHz): 0.63 (t, J = 7.34 Hz, 3 H) 0.98-1.06 (m, 9 H) 1.09-1.26 (m, 19 H) 1.39 (s, 3 H) 1.42 (s, 3 H) 1.46-2.12 (m, 9 H) 2.29 (s, 6 H) 2.34 (s, 3 H) 2.39-2.65 (m, 10 H) 2.81-2.86 (m, 1 H) 2.91-2.98 (m, 1 H) 3.09 (s, 3 H) 3.11-3.21 (m, 2 H) 3.28 (s, 3 H) 3.39-3.51 (m, 3 H) 3.69 (s, 1 H) 3.71-3.81 (m, 3 H) 3.95-4.12 (m, 3 H) 4.43 (d, J = 7.34 Hz, 1 H) 4.87-4.92 (m, 1 H) 4.98-5.02 (m, 1 H) 7.32-7.37 (m, 2 H) 7.41 (d, J = 7.34 Hz, 1 H) 7.76-7.81 (m, 1 H) 7.82-7.86 (m, 2 H) |
| 139 | ![structure: urea] | ![structure: diethylaminoethyl chain] | 1001.7 | (600 MHz): 0.79-0.93 (m, 3 H) 0.98-1.27 (m, 28 H) 1.38-1.42 (m, 6 H) 1.62 (s, 9 H) 2.29 (s, 6 H) 2.32-2.35 (m, 3 H) 2.39-2.74 (m, 10 H) 2.81-3.07 (m, 5 H) 3.07-3.13 (m, 1 H) 3.15-3.36 (m, 6 H) 3.40-3.86 (m, 8 H) 4.06-4.13 (m, 1 H) 4.32-4.45 (m, 1 H) 4.53-4.75 (m, 1 H) 4.84-5.00 (m, 2 H) |
| 140 | ![structure: N-methyl-N'-(2-diethylaminoethyl)urea] | ![structure: diethylaminoethyl chain] | 1114.8 | (500 MHz): 0.79-0.88 (m, 3 H) 0.98-1.27 (m, 33 H) 1.39 (s, 6 H) 1.51-1.78 (m, 5 H) 1.85-2.06 (m, 4 H) 2.09 (d, J = 14.53 Hz, 1 H) 2.25-2.31 (m, 6 H) 2.34 (s, 3 H), 2.39-2.64 (m, 16 H) 2.81-2.87 (m, 3 H) 2.89-2.95 (m, 1 H) 3.05 (s, 3 H) 3.07-3.13 (m, 1 H) 3.14-3.50 (m, 10 H) 3.64-3.74 (m, 4 H) 3.80-3.88 (m, 1 H) 4.05-4.16 (m, 1 H) 4.42 (m, 1 H) 4.88-5.03 (m, 2 H) 6.04-6.15 (m, 1 H) |
| 141 | ![structure: N,N-dimethylurea] | ![structure: diethylaminoethyl chain] | 1029.7 | (600 MHz): 0.82 (t, J = 7.34 Hz, 2 H) 0.98-1.04 (m, 9 H) 1.09-1.27 (m, 19 H) 1.39 (s, 6 H) 1.48-1.78 (m, 4 H) 1.86-2.04 (m, 4 H) 2.09 (d, J = 14.67 Hz, 1 H) 2.29 (s, 6 H) 2.34 (s, 3 H) 2.39-2.63 (m, 10 H) 2.80-2.87 (m, 7 H) 2.89-2.95 (m, 1 H) 3.05 (s, 3 H) 3.09-3.21 (m, 3 H) 3.28 (s, 3 H) 3.44-3.51 (m, 2 H) 3.64-3.76 (m, 5 H) 3.84-3.90 (m, 1 H) 4.07-4.12 (m, 1 H) 4.40-4.44 (m, 1 H) 4.96-5.02 (m, 2 H) 5.76 (t, J = 5.27 Hz, 1 H) |
| 142 | ![structure: sulfamate] | ![structure: diethylaminoethyl chain] | 1038.7 | (600 MHz): 0.86 (t, J = 7.34 Hz, 3 H) 0.96-1.27 (m, 28 H) 1.39 (s, 3 H) 1.42 (s, 3 H) 1.48-1.52 (m, 1 H) 1.62-1.69 (m, 1 H) 1.70-1.79 (m, 2 H) 1.85-2.05 (m, 4 H) 2.09 (d, J = 14.67 Hz, 1 H) 2.29 (s, 6 H) 2.34 (s, 3 H) 2.37-2.64 (m, 10 H) 2.83 (d, J = 14.67 Hz, 1 H) 2.86-2.93 (m, 1 H) 3.02 (s, 3 H) 3.11 (q, J = 6.88 Hz, 1 H) 3.18 (dd, J = 10.09, 7.34 Hz, 1 H) 3.28 (s, 3 H) 3.43 (br. s., 1 H) 3.44-3.50 (m, 1 H) 3.63-3.68 (m, 1 H) 3.66 (s, 1 H) 3.70 (d, J = 8.71 Hz, 1 H) 3.93 (ddd, J = 15.36, 5.73, 2.75 Hz, 1 H) 4.03-4.13 (m, 2 H) 4.23 (ddd, J = 10.55, 5.73, 2.98 Hz, 1 H) 4.41 (d, J = 7.34 Hz, 1 H) 4.63 (ddd, J = 10.55, 7.79, 2.75 Hz, 1 H) 4.94 (d, J = 5.04 Hz, 1 H) 5.21 (dd, J = 10.55, 2.29 Hz, 1 H) 5.45 (br. s., 2 H) |
| 143 | ![structure: acetate] | ![structure: diethylaminoethyl chain] | 1001.7 | (600 MHz): 0.84 (t, J = 7.34 Hz, 3 H) 0.97-1.29 (m, 28 H) 1.39 (s, 3 H) 1.40 (s, 3 H) 1.50-1.52 (m, 1 H) 1.63-1.67 (m, 1 H) 1.72-1.78 (m, 2 H) 1.87-2.04 (m, 4 H) 2.05 (s, 3 H) 2.09 (d, J = 14.67 Hz, 1 H) 2.29 (s, 6 H) 2.34 (s, 3 H) 2.38-2.64 (m, 10 H) 2.83 (d, J = 14.67 Hz, 1 H) 2.87 (dd, J = 9.17, 7.34 Hz, 1 H) 3.03 (s, 3 H) 3.11 (q, J = 6.88 Hz, 1 H) 3.18 (dd, J = 10.09, 7.34 Hz, 1 H) 3.28 (s, 3 H) 3.41 (br. s., 1 H) 3.44-3.50 (m, 1 H) 3.64-3.73 (m, 3 H) 3.88-3.93 (m, 1 H) 3.94-4.00 (m, 1 H) 4.06-4.15 (m, 2 H) 4.40-4.47 (m, 2 H) 4.97 (d, J = 4.58 Hz, 1 H) 5.09 (dd, J = 10.77, 2.52 Hz, 1 H) |

TABLE 1-continued

| | | | | |
|---|---|---|---|---|
| 144 | [benzoate structure] | [N,N-diethylaminopropyl structure with CH₃, CH₃] | 1063.7 | (600 MHz): 0.50 (t, J = 7.34 Hz, 3 H) 0.96-1.30 (m, 28 H) 1.38 (s, 3 H) 1.40 (s, 3 H) 1.43-1.49 (m, 1 H) 1.64 (d, J = 11.92 Hz, 1 H) 1.72-1.91 (m, 4 H) 1.93-2.01 (m, 2 H) 2.09 (d, J = 14.67 Hz, 1 H) 2.29 (s, 6 H) 2.34 (s, 3 H) 2.39-2.64 (m, 10 H) 2.79-2.85 (m, 2 H) 3.08 (s, 3 H) 3.13 (q, J = 7.18 Hz, 1 H) 3.18 (dd, J = 10.32, 7.11 Hz, 1 H) 3.26 (s, 3 H) 3.41 (br. s., 1 H) 3.44-3.51 (m, 1 H) 3.67-3.74 (m, 3 H) 4.05-4.14 (m, 2 H) 4.16-4.23 (m, 1 H) 4.39-4.45 (m, 2 H) 4.58 (ddd, J = 11.58, 4.47, 2.75 Hz, 1 H) 4.94-5.01 (m, 2 H) 7.35-7.40 (m, 2 H) 7.46-7.51 (m, 1 H) 8.02-8.07 (m, 2 H) |
| 145 | [H₂N-carbamate structure] | [N,N-diethylaminopropyl structure with CH₃, CH₃] | 1002.6 | (600 MHz): 0.84 (t, J = 7.34 Hz, 3 H) 0.99-1.26 (m, 28 H) 1.38 (s, 3 H) 1.42 (s, 3 H) 1.47-1.51 (m, 1 H) 1.65 (d, J = 10.55 Hz, 1 H) 1.69-1.79 (m, 2 H) 1.90-2.05 (m, 4 H) 2.09 (d, J = 14.67 Hz, 1 H) 2.29 (s, 6 H) 2.34 (s, 3 H) 2.39-2.63 (m, 10 H) 2.81-2.90 (m, 2 H) 3.01 (s, 3 H) 3.07 (q, J = 6.88 Hz, 1 H) 3.18 (dd, J = 10.32, 7.11 Hz, 1 H) 3.28 (s, 3 H) 3.41 (br. s., 1 H) 3.47 (dd, J = 9.86, 7.11 Hz, 1 H) 3.66 (d, J = 6.88 Hz, 1 H) 3.70-3.76 (m, 3 H) 3.85 (ddd, J = 15.02, 11.12, 3.67 Hz, 1 H) 4.10 (q, J = 6.42 Hz, 1 H) 4.21 (dt, J = 11.46, 3.44 Hz, 1 H) 4.39-4.45 (m, 2 H) 4.96 (d, J = 4.58 Hz, 1 H) 5.23 (dd, J = 10.55, 2.75 Hz, 1 H) |
| 146 | [H₂N-sulfamate structure] | [N-ethyl-N-isopropylaminopropyl structure with CH₃, CH₃, CH₃] | 1052.7 | (600 MHz): 0.86 (t, J = 7.34 Hz, 3 H) 0.94-1.26 (m, 31 H) 1.39 (s, 3 H) 1.42 (s, 3 H) 1.48-1.52 (m, 1 H) 1.63-1.67 (m, 1 H) 1.71-1.79 (m, 2 H) 1.86-2.07 (m, 5 H) 2.29 (s, 6 H) 2.32-2.62 (m, 8 H) 2.34 (s, 3 H) 2.83 (d, J = 14.67 Hz, 1 H) 2.86-2.97 (m, 2 H) 3.03 (s, 3 H) 3.11 (q, J = 7.03 Hz, 1 H) 3.18 (dd, J = 10.55, 7.34 Hz, 1 H) 3.28 (s, 3 H) 3.41-3.50 (m, 2 H) 3.64-3.72 (m, 3 H) 3.90-3.95 (m, 1 H) 4.04-4.11 (m, 2 H) 4.20-4.25 (m, 1 H) 4.41 (d, J = 7.34 Hz, 1 H) 4.63 (ddd, J = 10.66, 7.68, 3.21 Hz, 1 H) 4.95 (d, J = 4.58 Hz, 1 H) 5.21 (dd, J = 10.55, 2.29 Hz, 1 H) 5.45 (br. s, 2 H) |
| 147 | [H₂N-sulfamate structure] | [(S)-2-methylpyrrolidinylpropyl structure with $H_3C$] | 1050.7 | (600 MHz): 0.86 (t, J = 7.34 Hz, 3 H) 0.99-1.45 (m, 33 H) 1.47-1.52 (m, 1 H) 1.63-1.81 (m, 3 H) 1.86-2.19 (m, 5 H) 2.23-2.31 (m, 1 H) 2.29 (s, 6 H) 2.31-2.38 (m, 1 H) 2.37 (s, 3 H) 2.39-2.46 (m, 1 H) 2.55-2.68 (m, 2 H) 2.83-2.96 (m, 5 H) 3.03 (s, 3 H) 3.08-3.21 (m, 4 H) 3.28 (s, 3 H) 3.38-3.50 (m, 3 H) 3.64-3.73 (m, 3 H) 3.93 (ddd, J = 15.47, 5.62, 2.75 Hz, 1 H) 4.03-4.14 (m, 2 H) 4.23 (ddd, J = 10.55, 5.73, 2.98 Hz, 1 H) 4.41 (d, J = 7.34 Hz, 1 H) 4.62 (ddd, J = 10.66, 7.68, 2.75 Hz, 1 H) 4.95 (d, J = 4.58 Hz, 1 H) 5.20 (dd, J = 10.55, 2.29 Hz, 1 H) 5.45 (br. s., 2 H) |

Example 1

(1) Clarithromycin (200 g) was dissolved in acetone (1.5 L), acetic anhydride (30.3 ml) was added dropwise to the solution, and the resulting mixture was stirred overnight at room temperature. The reaction mixture was concentrated under reduced pressure, ethyl acetate, hexane and aqueous sodium hydroxide were added to the resulting residue, and then saturated aqueous sodium hydrogencarbonate was added to the mixture to adjust the mixture to pH 9. The deposited solid was collected by filtration with a glass filter, washed with distilled water, and then dried under reduced pressure to obtain an acetyl compound (202 g).

MS (ESI) m/z=790.6 [M+H]$^+$ (2) The compound obtained in (1) mentioned above (202 g) was dissolved in chloroform (1.8 L), pyridine (210 ml) was added to the solution, then the resulting mixture was cooled on ice, and a solution of triphosgene (77.4 g) in chloroform (0.8 L) was added dropwise to the mixture over 40 minutes. The reaction mixture was warmed to room temperature, and then stirred for 3 hours. Pyridine (158 ml) was added to the reaction mixture, a solution of triphosgene (57.9 g) in chloroform was added dropwise to the resulting mixture under ice cooling, and the resulting mixture was stirred at room temperature for 15 minutes. Distilled water and saturated aqueous sodium hydrogencarbonate were added to the reaction mixture, the resulting mixture was extracted with chloroform, and the organic layer was dried over anhydrous magnesium sulfate, and filtered. The filtrate was concentrated under reduced pressure, and a mixed solvent of ethyl acetate and hexane (1:1) was added to the resulting residue. The resulting mixture was stirred, hexane was further added to the mixture, and the resulting mixture was stirred overnight at room temperature. The deposited solid was collected by filtration, and washed with a mixed solvent of ethyl acetate and hexane (1:2) to obtain a carbonate compound (220 g).

MS (ESI) m/z=816.5 [M+H]$^+$ (3) N-Chlorosuccinimide (99.7 g) was dissolved in chloroform (1 L), and the solution was cooled to −25° C. A solution of dimethyl sulfide (210 ml) in chloroform (0.2 L) was added dropwise to the reaction mixture over 20 minutes, and the resulting mixture was stirred for 15 minutes. Then, a solution of the compound obtained in (2) mentioned above in chloroform (1 L) was added dropwise to the reaction mixture over 30 minutes, and the resulting mixture was stirred for 15 minutes. A solution of triethylamine (136 ml) in chloroform (0.2 L) was added to the reaction mixture, and the resulting mixture was stirred for 30 minutes. Saturated aqueous sodium hydrogencarbonate was added to the reaction mixture, the resulting mixture was warmed to room temperature, chloroform was added to the mixture, and the layers were separated. The organic layer was dried over anhydrous magnesium sulfate, and filtered, and then the filtrate was concentrated under reduced pressure. Ethyl acetate, a mixed solvent of ethyl acetate and hexane (1:1), and hexane were added to the resulting residue, and the resulting mixture was stirred overnight at room temperature. The deposited solid was collected by filtration, and washed with a mixed solvent of ethyl acetate and hexane (1:2) to obtain a ketone compound (109 g). The filtrate was concentrated under reduced pressure, and the resulting residue was purified by silica gel column chromatography (ethyl acetate:hexane=1:1 to acetone:hexane:triethylamine=10:10:0.2), and then crystallized in the same manner as that described above to obtain a ketone compound (59.5 g).

MS (ESI) m/z=814.5 [M+H]$^+$ (4) Trimethylsulfoxonium iodide (210 g) was dissolved in a mixed solvent of dimethyl sulfoxide and tetrahydrofuran (5:1, 1.2 L), 70% sodium hydride (32.6 g) was added portionwise to the solution, and the resulting mixture was stirred at room temperature for 1.5 hours. A solution of the compound obtained in (3) mentioned above (155 g) in tetrahydrofuran (0.8 L) was added dropwise to the reaction mixture under ice cooling, and the resulting mixture was stirred at room temperature for 30 minutes. The reaction mixture was cooled on ice, distilled water and ethyl acetate were added to the reaction mixture, and the layers were separated. The resulting organic layer was washed with distilled water. The aqueous layer was extracted with ethyl acetate, and the organic layer was washed with distilled water. The organic layers were combined, dried over anhydrous magnesium sulfate, and filtered. The filtrate was concentrated under reduced pressure to obtain an epoxy compound (146 g).

MS (ESI) m/z=784.5 [M+H]$^+$ $^1$H-NMR (600 MHz, CDCl$_3$) δ (ppm): 0.90 (t, J=7.57 Hz, 3H), 0.97 (d, J=7.34 Hz, 3H), 1.04 (d, J=6.88 Hz, 3H), 1.07 (s, 3H), 1.14 (d, J=6.88 Hz, 3H), 1.18 (d, J=5.96 Hz, 3H), 1.21-1.36 (m, 7H), 1.42 (s, 3H), 1.47-1.55 (m, 1H), 1.67-1.73 (m, 1H), 1.83-1.98 (m, 5H), 2.02 (d, J=1.83 Hz, 6H), 2.18-2.29 (m, 1H), 2.25 (s, 6H), 2.58-2.69 (m, 1H), 2.63 (d, J=4.13 Hz, 1H), 2.80-2.89 (m, 1H), 2.94 (d, J=4.13 Hz, 1H), 3.12-3.26 (m, 1H), 3.17 (s, 3H), 3.34 (s, 3H), 3.43-3.51 (m, 1H), 3.66 (d, J=6.42 Hz, 1H), 3.94 (br. s., 1H), 4.57 (d, J=7.34 Hz, 1H), 4.73 (dd, J=10.55, 7.34 Hz, 1H), 4.80 (q, J=6.42 Hz, 1H), 4.98-5.06 (m, 2H), 6.50 (s, 1H)

(5) The compound obtained in (4) mentioned above (138 g) was dissolved in a mixed solvent of tetrahydrofuran and dimethylformamide (1:1, 1.4 and 1,1'-carbonyldiimidazole (85.6 g) was added to the solution. 70% Sodium hydride (18.1 g) was added to the mixture over 40 minutes under ice cooling, and the resulting mixture was stirred at room temperature for 0.5 hour. The reaction mixture was cooled on ice, and distilled water was added to the reaction mixture. The resulting mixture was extracted with ethyl acetate, and the organic layer was washed twice with distilled water. The aqueous layer was extracted with ethyl acetate, and the organic layer was washed twice with distilled water. The organic layers were combined, dried over anhydrous magnesium sulfate, and filtered. The filtrate was concentrated under reduced pressure, and the resulting residue was purified by silica gel column chromatography (hexane to hexane:ethyl acetate=1:1 to acetone:hexane:triethylamine=10:10:0.2). Ethyl acetate and hexane were added to the resulting purified product, and the resulting mixture was stirred overnight at room temperature. The deposited solid was collected by filtration, and washed with a mixed solvent of ethyl acetate and hexane (1:4) to obtain the compound represented by the formula (A) (87.1 g).

MS (ESI) m/z=878.6 [M+H]$^+$ $^1$H-NMR (600 MHz, CDCl$_3$) δ (ppm): 0.85-1.41 (m, 25H), 1.64-1.78 (m, 3H), 1.79 (s, 3H), 1.90 (dd, J=14.67, 5.04 Hz, 4H), 1.86 (s, 3H), 2.04 (s, 3H), 2.19-2.28 (m, 1H), 2.25 (s, 6H), 2.60-2.68 (m, 1H), 2.65 (d, J=4.13 Hz, 1H), 2.86-2.97 (m, 1H), 2.95 (d, J=4.13 Hz, 1H), 3.15 (s, 3H), 3.22-3.29 (m, 1H), 3.35 (s, 3H), 3.38-3.47 (m, 1H), 3.66 (d, J=6.42 Hz, 1H), 3.79-3.88 (m, 1H), 4.56 (d, J=6.88 Hz, 1H), 4.72 (dd, J=10.32, 7.57 Hz, 1H), 4.79 (q, J=6.27 Hz, 1H), 5.01-5.09 (m, 1H), 5.83 (dd, J=10.55, 2.75 Hz, 1H), 6.66 (s, 1H), 7.07 (s, 1H), 7.34-7.38 (m, 1H), 8.08 (s, 1H)

(6) The compound obtained in (5) mentioned above (500 mg) was dissolved in acetonitrile (10 ml), 2-aminoethanol (173.9 mg) was added to the solution, and the resulting mixture was stirred overnight at room temperature. 1,1,3,3-Tetramethylguanidine (72 μl) was added to the reaction mixture, and the resulting mixture was stirred at room temperature for 1 hour. Ethyl acetate and saturated aqueous ammonium chloride were added to the reaction mixture, the layers were separated, and the resulting organic layer was dried over anhydrous magnesium sulfate, and filtered. The resulting filtrate was concentrated under reduced pressure to obtain a carbamate compound.

As another method different from the aforementioned method, the aforementioned compound was also obtained by the following method. More specifically, the compound obtained in (5) mentioned above (300 mg) was dissolved in acetonitrile (30 ml), 2-aminoethanol (104.4 mg) and 1,8-diazabicyclo[5,4,0]-7-undecene (52.1 mg) were added to the solution, and the resulting mixture was stirred overnight at room temperature. Ethyl acetate and saturated aqueous ammonium chloride were added to the reaction mixture, the layers were separated, and the resulting organic layer was dried over anhydrous magnesium sulfate, and filtered. The resulting filtrate was concentrated under reduced pressure, and the resulting residue was purified by silica gel column chromatography (chloroform:methanol:28% aqueous ammonia=30:1:0.1 to 10:1:0.1) to obtain a carbamate compound (329 mg).

(7) The compound obtained in (6) mentioned above was dissolved in methanol (20 ml), and the solution was stirred under reflux by heating 4 hours. The reaction mixture was concentrated under reduced pressure, and the resulting residue was purified by silica gel column chromatography (chloroform:methanol:28% aqueous ammonia=100:1:0.1 to 10:1:0.1) to obtain a deprotected compound (406 mg).

As another method different from the aforementioned method, the aforementioned compound was also obtained by the following method. More specifically, the compound obtained in (6) mentioned above (329 mg) was dissolved in methanol (30 ml), 1,8-diazabicyclo[5,4,0]-7-undecene (0.5 ml) was added to the solution, and the resulting mixture was stirred under reflux by heating for 3 hours. The reaction mixture was concentrated under reduced pressure, and the resulting residue was purified by silica gel column chromatography (chloroform:methanol:28% aqueous ammonia=50:1:0.1 to 10:1:0.1) to obtain a deprotected compound (144 mg).

(8) The compound obtained in (7) mentioned above (100 mg) was dissolved in ethanol (1 ml), N,N-dimethyl-N'-methylethane-1,2-diamine (77.2 mg) was added to the solution, and the resulting mixture was stirred at 140° C. for 1 hour under microwave irradiation. The reaction mixture was concentrated under reduced pressure, and the resulting residue was purified by preparative thin layer chromatography (chloroform:methanol:28% aqueous ammonia=10:1:0.1) to obtain the compound shown in Table 1 (87 mg).

As another method different from the aforementioned method, the aforementioned compound was also obtained by the following method. More specifically, the compound obtained in (7) mentioned above (50 mg) was dissolved in ethanol (1 ml), N,N-diethyl-N'-methylethane-1,2-diamine (45.0 mg) was added to the solution, and the resulting mixture was stirred at 110° C. for 4 hours in a sealed tube. The reaction mixture was concentrated under reduced pressure, and the resulting residue was purified by silica gel column chromatography (chloroform:methanol:28% aqueous ammonia=20:1:0.1 to 5:1:0.1) to obtain the compound shown in Table 1 (44 mg).

Formula (SM1)

[Formula 31]

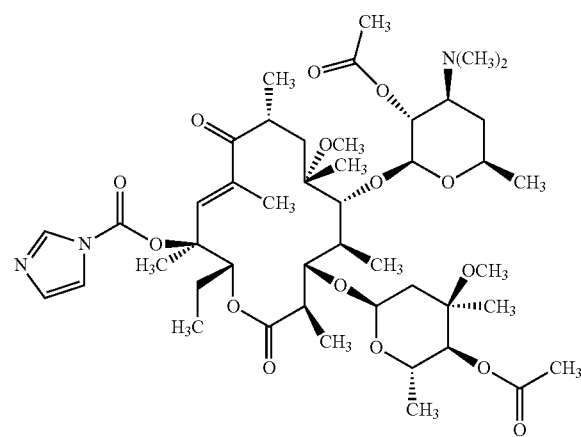

Example 2

(1) The compound represented by the formula (SM1) (1.63 g) obtained by the method described in the publication (International Patent Publication WO93/21199) was dissolved in acetonitrile (30 ml), 1,1,3,3-tetramethylguanidine (225 µl) and the compound obtained in Reference Example 63 (1.94 g) were added to the solution, and the resulting mixture was stirred at room temperature for 20 hours. Distilled water (3 ml) was added to the reaction mixture, and the resulting mixture was stirred at room temperature for 1 hour. The reaction mixture was concentrated under reduced pressure, and the resulting residue was diluted with ethyl acetate, and washed with saturated aqueous sodium hydrogencarbonate. The organic layer was dried over anhydrous magnesium sulfate, and filtered, the filtrate was concentrated under reduced pressure, and the resulting residue was purified by silica gel column chromatography (chloroform:methanol:28% aqueous ammonia=100:1:0.1 to 20:1:0.1) to obtain a carbamate compound (1.57 g).

(2) The compound obtained in (1) mentioned above (1.57 g) was dissolved in methanol (20 ml), 1,8-diazabicyclo[5,4,0]-7-undecene (666 µl) was added to the solution, and the resulting mixture was stirred under reflux by heating for 2 hours. The reaction mixture was concentrated under reduced pressure, chloroform and saturated aqueous sodium hydrogencarbonate were added to the resulting residue, and the layers were separated. The organic layer was dried over anhydrous magnesium sulfate, and filtered, then the filtrate was concentrated under reduced pressure, and the resulting residue was purified by silica gel column chromatography (chloroform:methanol:28% aqueous ammonia=100:1:0.1 to 20:1:0.1) to obtain a deprotected compound (0.94 g).

(3) By using the compound obtained in (2) mentioned above (0.94 g) as a starting material, a ketone compound (0.88 g) was obtained in the same manners as those of Example 1, (1) and (3).

(4) The compound obtained in (3) mentioned above (0.58 g) was dissolved in methanol (10 ml), and the solution was stirred at room temperature for 2 days. The reaction mixture was concentrated under reduced pressure, and by using the resulting residue as a starting material, an epoxy compound (367 mg) was obtained in the same manner as that of Example 1, (4).

(5) The compound obtained in (4) mentioned above (90 mg) was dissolved in ethanol (1 ml), 50% aqueous dimethylamine (41 µl) was added to the solution, and the resulting mixture was stirred at 100° C. for 20 hours in a sealed tube. The reaction mixture was concentrated under reduced pressure, and the resulting residue was purified by preparative thin layer chromatography (chloroform:methanol:28% aqueous ammonia=10:1:0.1) to obtain the compound shown in Table 1 (79.5 mg).

Example 3

By using the compound obtained in Example 2, (4) (90 mg) and N,N,N'-trimethylethylene-1,2-diamine (47 µl) as starting materials, the compound shown in Table 1 (57.2 mg) was obtained in the same manner as that of Example 2, (5).

Example 4

(1) The compound represented by the formula (SM1) (10 g) obtained by the method described in the publication (International Patent Publication WO93/21199) was dissolved in acetonitrile (100 ml), 1,4-diaminobutane (5.5 ml) was added to the solution, and the resulting mixture was stirred overnight at room temperature. The reaction mixture was concentrated under reduced pressure, ethyl acetate and distilled water were added to the resulting residue, the layers were separated, and the aqueous layer was extracted with ethyl acetate. The organic layer was dried over anhydrous magnesium sulfate, and filtered, and then the filtrate was concentrated under reduced pressure. The resulting residue was dissolved in methanol (20 ml), and distilled water was added dropwise to the solution to deposit a solid. The deposited solid was collected by filtration, washed with distilled water, and then dissolved in chloroform. The solution was filtered with a phase separator to separate the layers, and the resulting organic layer was concentrated under reduced pressure to obtain a carbamate compound (8.17 g).
(2) By using the compound obtained in (1) mentioned above (4.18 g) as a starting material, a deprotected compound (9.36 g) was obtained in the same manner as that of Example 2, (2).
(3) The compound obtained in (2) mentioned above (4.68 g) was dissolved in chloroform (23 triethylamine (0.47 ml) was added to the solution, 4-chlorobutyryl chloride (0.26 ml) was added to the mixture under ice cooling, and the resulting mixture was stirred for 2 hours. Saturated aqueous ammonium chloride and chloroform were added to the reaction mixture, and the resulting mixture was filtered with a phase separator to separate the layers. The resulting organic layer was concentrated under reduced pressure, and the resulting residue was purified by silica gel column chromatography (chloroform:methanol:28% aqueous ammonia=50:1:0.1 to 20:1:0.1) to obtain an acyl compound (1.15 g).
(4) The compound obtained in (3) mentioned above (892 mg) was dissolved in tetrahydrofuran (19 ml), 60% sodium hydride (376 mg) was added to the solution, and the resulting mixture was stirred under reflux by heating for 0.5 hour. Saturated aqueous ammonium chloride and chloroform were added to the reaction mixture, and the resulting mixture was filtered with a phase separator to separate the layers. The resulting organic layer was concentrated under reduced pressure, and the resulting residue was purified by silica gel column chromatography (chloroform:methanol:28% aqueous ammonia=50:1:0.1 to 20:1:0.1) to obtain a cyclized compound (425 mg).
(5) By using the compound obtained in (4) mentioned above (422 mg) as a starting material, a ketone compound (232 mg) was obtained in the same manners as those of Example 1, (1) and (3).
(6) The compound obtained in (5) mentioned above (232 mg) was dissolved in methanol (4 ml), and the resulting mixture was stirred under reflux by heating for 4 hours and at room temperature for 12 hours. The reaction mixture was concentrated under reduced pressure to obtain a deprotected compound (230 mg).
(7) By using the compound obtained in (6) mentioned above (227 mg) as a starting material, an epoxy compound (103 mg) was obtained in the same manner as that of Example 1, (4).
(8) The compound obtained in (7) mentioned above (50 mg) was dissolved in ethanol (1 ml), N,N,N'-trimethylethylene-1,2-diamine (35 µl) was added to the solution, and the resulting mixture was stirred at 140° C. for 45 minutes under microwave irradiation. The reaction mixture was concentrated under reduced pressure, chloroform and saturated aqueous ammonium chloride were added to the resulting residue, the layers were separated, and the aqueous layer was extracted with chloroform. The organic layers were combined, and filtered with a phase separator to further separate the layers. The resulting organic layer was concentrated under reduced pressure, and the resulting residue was purified by preparative thin layer chromatography (chloroform:methanol:28% aqueous ammonia=10:1:0.1) to obtain the compound shown in Table 1 (25.6 mg).

Example 5

By using the compound obtained in Example 4, (7) (50.0 mg) and 50% aqueous dimethylamine (24.4 µl) as starting materials, the compound shown in Table 1 (21.5 mg) was obtained in the same manner as that of Example 4, (8).

Example 6

(1) The compound obtained in Example 4, (2) (1.0 g) was dissolved in dimethylformamide (10 ml), 2-chloropyrimidine (204 mg) was added to the solution, and the resulting mixture was stirred at 120° C. Ethyl acetate and distilled water were added to the reaction mixture, and the layers were separated. The organic layer was washed three times with distilled water, then dried over anhydrous magnesium sulfate, and filtered, and the filtrate was concentrated under reduced pressure. The resulting residue was purified by silica gel column chromatography (chloroform:methanol:28% aqueous ammonia) to obtain an adduct compound (239 mg).
(2) By using the compound obtained in (1) mentioned above (300 mg) as a starting material, an acetyl compound (319 mg) was obtained in the same manner as that of Example 1, (1).
(3) The compound obtained in (2) mentioned above (300 mg) was dissolved in chloroform (10 ml), N-ethyl-N'-(3-dimethylaminopropyl)carbodiimide hydrochloride (1.19 g), pyridine trifluoroacetate (1.20 g), and dimethyl sulfoxide (722 µl) were added to the solution, and the resulting mixture was stirred overnight at room temperature. Distilled water was added to the reaction mixture, and the layers were separated. The organic layer was washed with saturated aqueous sodium hydrogencarbonate, then dried over anhydrous magnesium sulfate, and filtered. The filtrate was concentrated under reduced pressure to obtain a ketone compound.
(4) By using the compound obtained in (3) mentioned above as a starting material, an epoxy compound (93 mg) was obtained in the same manners as those of Example 4, (6) and Example 1, (4).
(5) By using the compound obtained in (4) mentioned above (65 mg) and 50% aqueous dimethylamine (63 µl) as starting materials, the compound shown in Table 1 (6 mg) was obtained in the same manner as that of Example 4, (8).

Example 7

By using the compound obtained in Example 6, (4) (65 mg) as a starting material, the compound shown in Table 1 (7 mg) was obtained in the same manner as that of Example 4, (8).

Example 8

By using the compound obtained in Example 6, (4) (45 mg) and the compound obtained in Reference Example 104 (34.2 mg) as starting materials, the compound shown in Table 1 (18 mg) was obtained in the same manner as that of Example 4, (8).

Example 9

(1) By using the compound represented by the formula (A) obtained in Example 1, (5) (393 mg) and the compound obtained in Reference Example 64 (180 mg) as starting materials, a deacetylated compound (220 mg) was obtained in the same manners as those of Example 2, (1) and (2).
(2) By using the compound obtained in (1) mentioned above (70 mg) as a starting material, the compound shown in Table 1 (59 mg) was obtained in the same manner as that of Example 4, (8).

Example 10

By using the compound obtained in Example 9, (1) (70 mg) and 50% aqueous dimethylamine (0.6 ml) as starting materials, the compound shown in Table 1 (59 mg) was obtained in the same manner as that of Example 4, (8).

Example 11

The compound obtained in Example 9, (1) (70 mg) was dissolved in ethanol (0.6 ml), N,N-diethyl-N'-methylethane- 1,2-diamine (50 mg) was added to the solution, and the resulting mixture was stirred at 140° C. for 60 minutes under microwave irradiation. The reaction mixture was concentrated under reduced pressure, and the resulting residue was purified by preparative thin layer chromatography (chloroform:methanol:28% aqueous ammonia=10:1:0.1) to obtain the compound shown in Table 1 (57 mg).

Example 12

(1) By using the compound represented by the formula (A) obtained in Example 1, (5) (500 mg) and 2-methoxyethanamine (214 mg) as starting materials, a deacetylated compound (283 mg) was obtained in the same manners as those of Example 2, (1) and (2).
(2) By using the compound obtained in (1) mentioned above (100 mg) as a starting material, the compound shown in Table 1 (77 mg) was obtained in the same manner as that of Example 11.

Example 13

(1) By using the compound represented by the formula (A) obtained in Example 1, (5) (700 mg) and 3-aminopropionitrile (588 µl) as starting materials, a deacetylated compound (400 mg) was obtained in the same manners as those of Example 2, (1) and (2).
(2) By using the compound obtained in (1) mentioned above (200 mg) as a starting material, the compound shown in Table 1 (144 mg) was obtained in the same manner as that of Example 11.

Example 14

(1) By using the compound represented by the formula (A) obtained in Example 1, (5) (685 mg) and 1-(2-aminoethyl)pyrrolidin-2-one (500 mg) as starting materials, a deacetylated compound (480 mg) was obtained in the same manners as those of Example 2, (1) and (2).
(2) By using the compound obtained in (1) mentioned above (100 mg) as a starting material, the compound shown in Table 1 (86 mg) was obtained in the same manner as that of Example 11.

Example 15

(1) The compound represented by the formula (A) obtained in Example 1, (5) (360 mg) was dissolved in acetonitrile (1.5 ml), 1,8-diazabicyclo[5,4,0]-7-undecene (280 µl) and 3-methanesulfonylpropylamine hydrochloride (273 mg) were added to the solution, and the resulting mixture was stirred at room temperature for 1 day. Ethyl acetate and saturated aqueous ammonium chloride were added to the reaction mixture, and the layers were separated. The organic layer was dried over anhydrous magnesium sulfate, and filtered, the filtrate was concentrated under reduced pressure, and the resulting residue was purified by silica gel column chromatography (chloroform to chloroform:methanol:28% aqueous ammonia=25:1:0.1 to 15:1:0.1) to obtain a carbamate compound (117 mg).
(2) The compound obtained in (1) mentioned above (115 mg) was dissolved in ethanol (1 ml), N,N-diethyl-N'-methylethane-1,2-diamine (195 µl) was added to the solution, and the resulting mixture was stirred at 100° C. for 1 day in a sealed tube. Ethyl acetate and saturated aqueous ammonium chloride were added to the reaction mixture, and the layers were separated. The organic layer was dried over anhydrous magnesium sulfate, and filtered, the filtrate was concentrated under reduced pressure, and the resulting residue was purified by silica gel column chromatography (chloroform to chloroform:methanol:28% aqueous ammonia=12:1:0.1) and preparative thin layer chromatography (chloroform:methanol:28% aqueous ammonia=20:1:0.1) to obtain the compound shown in Table 1 (62.7 mg).

1-Propanol (100 µL) was added to the compound obtained in Example 15, (2) (100 mg), and the compound was dissolved with heating the mixture on a water bath at 80° C. This solution was stirred under ice cooling to deposit crystals. The resulting crystals were dried under reduced pressure to obtain a 1-propanol solvate.
Elemental Analysis
Found: C, 59.04%; H, 9.31%; N, 5.15%; S, 2.92
Melting point: 105 to 120° C.
TG/DTA (peak): 96.0° C., 118.8° C.
XRD peak 2θ(°): 4.6, 6.5, 11.0, 18.0, 21.2

1,4-Dioxane (100 µL) was added to the compound obtained in Example 15, (2) (100 mg), and the compound was dissolved with heating the mixture on a water bath at 80° C. This solution was stirred under ice cooling to deposit crystals. The resulting crystals were dried under reduced pressure to obtain a 1,4-dioxane solvate.
Elemental Analysis
Found: C, 57.83%; H, 9.08%; N, 4.84%; S, 2.73
Melting point: 100 to 125° C.
TG/DTA (peak): 71.0° C., 122.5° C.
XRD peak 2θ(°): 5.3, 7.3, 9.9, 10.3, 12.3

The compound obtained in Example 15, (2) (2.53 g) was recrystallized from diethyl ether/hexane, and the resulting crystals was collected by filtration to obtain a compound identified with the following physicochemical data (1.92 g).
Melting point: 105 to 127° C.
TG/DTA (peak): 127.9° C.
XRD peak 2θ(°): 6.1, 10.3, 15.3, 18.5

The compound obtained in Example 15, (2) (1.00 g) was recrystallized from methanol (20 ml)/water (15 ml), and then dissolved under reflux by heating for 15 minutes. The solution was stirred overnight at room temperature, and the resulting crystals was collected by filtration, and washed with methanol/water=1/2 to obtain a compound identified with the following physicochemical data (682 mg).
Melting point: 155 to 164° C.
TG/DTA (peak): 158.1° C.
XRD peak 2θ(°): 10.0, 12.5, 12.9, 15.8, 17.4, 18.7, 19.9

Ethanol (100 µL) was added to the compound obtained in Example 15, (2) (100 mg), and the compound was completely dissolved with heating the mixture on a water bath at 80° C. This solution was stirred under ice cooling to deposit crystals. The resulting crystals were dried under reduced pressure to obtain a compound identified with the following physicochemical data.

This compound can also be obtained in the following manner. Namely, purified water (2 mL) was added to the compound obtained in Example 15, (2) (100 mg) with heating on a water bath at 80° C., and ethanol (2 mL) was further added to the mixture to completely dissolve the compound. This solution was stirred under ice cooling to deposit crystals. The resulting crystals were dried under reduced pressure to obtain a compound identified with the following physicochemical data.
Melting point: 106 to 115° C.
TG/DTA (peak): 102.3° C., 124.2° C.
XRD peak 2θ(°): 4.4, 5.1, 6.8, 10.9, 12.5

1-Propanol solvate of the compound obtained in Example 15, (2) (50 mg) was heated at 100° C. for 15 minutes to obtain a compound identified with the following physicochemical data.

Melting point: 110 to 126° C.
TG/DTA (peak): 119.7° C.
XRD peak 2θ(°): 5.1, 10.3, 11.2, 13.4, 16.0, 16.9, 18.6

Example 16

(1) By using the compound represented by the formula (A) obtained in Example 1, (5) (300 mg) and 2-aminoethylmethylsulfone hydrochloride (273 mg) as starting materials, a carbamate compound (117 mg) was obtained in the same manner as that of Example 15, (1).
(2) By using the compound obtained in (1) mentioned above (115 mg) as a starting material, the compound shown in Table 1 (57.7 mg) was obtained in the same manner as that of Example 15, (2).

The compound obtained by the method of Example 16, (2) (88.65 g) was dissolved in methanol at 55° C., water was added to the solution to saturate the solution, and then the resulting mixture was stirred overnight at room temperature to deposit crystals. The resulting crystals were collected by filtration, and dried under reduced pressure to obtain a compound identified with the following physicochemical data (68.26 g).

Melting point: 128 to 136° C.
DSC (peak): 135.8° C.
XRD peak 2θ(°): 10.3, 11.5, 13.5, 15.3, 16.1, 18.7

Example 17

By using the compound represented by the formula (A) obtained in Example 1, (5) (200 mg) and 2-(1,3-benzothiazol-2-yl)ethanamine hydrochloride (200 mg) as starting materials, the compound shown in Table 1 (21 mg) was obtained in the same manners as those of Example 15, (1), Example 2, (2) and Example 11.

Example 18

By using the compound represented by the formula (A) obtained in Example 1, (5) (200 mg) and 2-imidazo[1,2-A]pyridin-2-ylethanamine hydrochloride (184 mg) as starting materials, the compound shown in Table 1 (37 mg) was obtained in the same manners as those of Example 15, (1) and Example 11.

Example 19

By using the compound represented by the formula (A) obtained in Example 1, (5) (300 mg) and butylamine (170 µl) as starting materials, the compound shown in Table 1 (38.0 mg) was obtained in the same manners as those of Example 2, (1), (2) and Example 15, (2).

Example 20

(1) By using the compound represented by the formula (A) obtained in Example 1, (5) (300 mg) and 3-(methylthio)propylamine (187 µl) as starting materials, a deacetylated compound (110 mg) was obtained in the same manners as those of Example 2, (1) and (2).
(2) By using the compound obtained in (1) mentioned above (110 mg) as a starting material, the compound shown in Table 1 (65.8 mg) was obtained in the same manner as that of Example 15, (2).

Example 21

By using the compound represented by the formula (A) obtained in Example 1, (5) (450 mg) and 3-methoxypropylamine (175 µl) as starting materials, the compound shown in Table 1 (50.1 mg) was obtained in the same manners as those of Example 2, (1), (2) and Example 15, (2).

Example 22

(1) By using the compound represented by the formula (A) obtained in Example 1, (5) (450 mg) and the compound obtained in Reference Example 65 (356 mg) as starting materials, a deacetylated compound (346 mg) was obtained in the same manners as those of Example 2, (1) and Example 4, (6).
(2) By using the compound obtained in (1) mentioned above (100 mg) as a starting material, the compound shown in Table 1 (69.7 mg) was obtained in the same manner as that of Example 11.

Example 23

By using the compound represented by the formula (A) obtained in Example 1, (5) (178 mg) and 3-(phenylthio)-1-propanamine (170 mg) as starting materials, the compound shown in Table 1 (69.6 mg) was obtained in the same manners as those of Example 2, (1), (2) and Example 15, (2).

Example 24

By using the compound represented by the formula (A) obtained in Example 1, (5) (203 mg) and 3-(benzenesulfonyl)propan-1-amine (230 mg) as starting materials, the compound shown in Table 1 (51.3 mg) was obtained in the same manners as those of Example 2, (1), (2) and Example 15, (2).

Example 25

(1) By using the compound represented by the formula (A) obtained in Example 1, (5) (350 mg) and 2-(benzyloxy)-1-ethanamine (301 mg) as starting materials, a deacetylated compound (281 mg) was obtained in the same manners as those of Example 2, (1) and Example 4, (6).
(2) By using the compound obtained in (1) mentioned above (100 mg) as a starting material, the compound shown in Table 1 (78 mg) was obtained in the same manner as that of Example 11.

Example 26

By using the compound obtained in Example 15, (1) (150 mg) and the compound obtained in Reference Example 1 (255 mg) as starting materials, the compound shown in Table 1 (15.6 mg) was obtained in the same manner as that of Example 2, (5).

Example 27

By using the compound obtained in Example 16, (1) (150 mg) and the compound obtained in Reference Example 1

(229 mg) as starting materials, the compound shown in Table 1 (34.5 mg) was obtained in the same manner as that of Example 2, (5).

Example 28

By using the compound represented by the formula (A) obtained in Example 1, (5) (190 mg) and the compound obtained in Reference Example 66 (130 mg) as starting materials, the compound shown in Table 1 (94 mg) was obtained in the same manners as those of Example 15, (1) and Example 11.

Example 29

By using the compound represented by the formula (A) obtained in Example 1, (5) (190 mg) and the compound obtained in Reference Example 67 (121 mg) as starting materials, the compound shown in Table 1 (85 mg) was obtained in the same manners as those of Example 15, (1) and Example 11.

Example 30

By using the compound obtained in Example 20, (1) (100 mg) and the compound obtained in Reference Example 2 (102 mg) as starting materials, the compound shown in Table 1 (64.8 mg) was obtained in the same manner as that of Example 4, (8).

Example 31

(1) By using the compound represented by the formula (A) obtained in Example 1, (5) (5.0 g) and 2-aminoethylmethylsulfone hydrochloride (2.73 g) as starting materials, a deacetylated compound (2.46 g) was obtained in the same manners as those of Example 15, (1) and Example 2, (2).
(2) By using the compound obtained in (1) mentioned above (200 mg) and the compound obtained in Reference Example 3 (178 mg) as starting materials, the compound shown in Table 1 (87.2 mg) was obtained in the same manner as that of Example 2, (5).

Example 32

By using the compound obtained in Example 31, (1) (200 mg) and the compound obtained in Reference Example 4 (162 mg) as starting materials, the compound shown in Table 1 was obtained in the same manner as that of Example 2, (5).

Example 33

By using the compound obtained in Example 31, (1) (200 mg) and the compound obtained in Reference Example 5 (175 mg) as starting materials, the compound shown in Table 1 was obtained in the same manner as that of Example 2, (5).

Example 34

(1) By using the compound represented by the formula (A) obtained in Example 1, (5) (1.68 g) and the compound obtained in Reference Example 111 (1.5 g) as starting materials, a deacetylated compound (641 mg) was obtained in the same manners as those of Example 15, (1) and Example 4, (6).
(2) By using the compound obtained in (1) mentioned above (200 mg) as a starting material, the compound shown in Table 1 (43 mg) was obtained in the same manner as that of Example 11.

Example 35

(1) By using the compound represented by the formula (A) obtained in Example 1, (5) (1.00 g) and 3-methanesulfonylpropylamine hydrochloride (0.99 g) as starting materials, a deacetylated compound (574 mg) was obtained in the same manners as those of Example 15, (1) and Example 2, (2).
(2) By using the compound obtained in (1) mentioned above (120 mg) and the compound obtained in Reference Example 2 (118 mg) as starting materials, the compound shown in Table 1 (36.3 mg) was obtained in the same manner as that of Example 4, (8).

Example 36

(1) By using the compound represented by the formula (A) obtained in Example 1, (5) (600 mg) and 2-(methylthio) ethylamine (639 mg) as starting materials, a deacetylated compound (522 mg) was obtained in the same manners as those of Example 2, (1) and (2).
(2) By using the compound obtained in (1) mentioned above (100 mg) as a starting material, the compound shown in Table 1 (43 mg) was obtained in the same manner as that of Example 11.

Example 37

By using the compound obtained in Example 36, (1) (100 mg) and the compound obtained in Reference Example 2 (103 mg) as starting materials, the compound shown in Table 1 (35.7 mg) was obtained in the same manner as that of Example 4, (8).

Example 38

By using the compound obtained in Example 35, (1) (105 mg) and the compound obtained in Reference Example 4 (83.6 mg) as starting materials, the compound shown in Table 1 (34.2 mg) was obtained in the same manner as that of Example 4, (8).
The compound obtained by the method of Example 38 (88.46 g) was dissolved in methanol at 55° C., water was added to the solution to saturate the solution, and then the resulting mixture was stirred overnight at room temperature to deposit crystals. The resulting crystals were collected by filtration, and dried under reduced pressure to obtain a compound identified with the following physicochemical data (68.07 g).
Melting point: 121 to 124° C.
DSC (peak): 125.5° C.
XRD peak 2θ(°): 10.3, 11.6, 13.3, 15.1, 16.0, 18.6

Example 39

By using the compound obtained in Example 35, (1) (105 mg) and the compound obtained in Reference Example 5 (90.6 mg) as starting materials, the compound shown in Table 1 (34.9 mg) was obtained in the same manner as that of Example 4, (8).

Example 40

By using the compound obtained in Example 35, (1) (105 mg) and the compound obtained in Reference Example 3

(91.8 mg) as starting materials, the compound shown in Table 1 (28.7 mg) was obtained in the same manner as that of Example 4, (8).

Example 41

By using the compound obtained in Example 20, (1) (100 mg) and the compound obtained in Reference Example 1 (48.9 mg) as starting materials, the compound shown in Table 1 (65.5 mg) was obtained in the same manner as that of Example 4, (8).

Example 42

By using the compound obtained in Example 1, (7) (1000 mg) and the compound obtained in Reference Example 5 (337 mg) as starting materials, the compound shown in Table 1 (920 mg) was obtained in the same manner as that of Example 4, (8).

Example 43

By using the compound represented by the formula (A) obtained in Example 1, (5) (300 mg) and the compound obtained in Reference Example 78 (260 mg) as starting materials, the compound shown in Table 1 (72 mg) was obtained in the same manners as those of Example 2, (1), Example 4, (6) and Example 11.

Example 44

(1) By using the compound represented by the formula (A) obtained in Example 1, (5) (250 mg) and the compound obtained in Reference Example 79 (165 mg) as starting materials, a carbamate compound (224 mg) was obtained in the same manner as that of Example 2, (1).
(2) By using the compound obtained in (1) mentioned above (206 mg) as a starting material, a deacetylated compound (184 mg) was obtained in the same manner as that of Example 4, (6).
(3) By using the compound obtained in (2) mentioned above (50 mg) as a starting material, the compound shown in Table 1 (39 mg) was obtained in the same manner as that of Example 11.

Example 45

(1) By using the compound represented by the formula (A) obtained in Example 1, (5) (250 mg) and β-alaninamide (177 mg) as starting materials, a deacetylated compound (202 mg) was obtained in the same manners as those of Example 2, (1) and Example 4, (6).
(2) By using the compound obtained in (1) mentioned above (60 mg) as a starting material, the compound shown in Table 1 (38 mg) was obtained in the same manner as that of Example 11.

Example 46

(1) By using the compound represented by the formula (A) obtained in Example 1, (5) (125 mg) and the compound obtained in Reference Example 80 (94 mg) as starting materials, a carbamate compound (103 mg) was obtained in the same manner as that of Example 2, (1).
(2) The compound obtained in (1) mentioned above (103 mg) was dissolved in methanol, and the solution was stirred at 75° C. for 20 minutes and at 80° C. for 75 minutes under microwave irradiation. The reaction mixture was concentrated as it was to obtain a deacetylated compound (99 mg).
(3) By using the compound obtained in (2) mentioned above (50 mg) as a starting material, the compound shown in Table 1 (48 mg) was obtained in the same manner as that of Example 11.

Example 47

By using the compound represented by the formula (A) obtained in Example 1, (5) (100 mg) and 1-(2-aminoethyl) imidazolin-2-one (74 mg) as starting materials, the compound shown in Table 1 (41 mg) was obtained in the same manners as those of Example 2, (1), (2) and Example 11.

Example 48

(1) By using the compound represented by the formula (A) obtained in Example 1, (5) (200 mg) and the compound obtained in Reference Example 82 (157 mg) as starting materials, a deacetylated compound (98.5 mg) was obtained in the same manners as those of Example 2, (1) and (2).
(2) By using the compound obtained in (1) mentioned above (50 mg) as a starting material, the compound shown in Table 1 (43.2 mg) was obtained in the same manner as that of Example 11.

Example 49

(1) By using the compound represented by the formula (A) obtained in Example 1, (5) (200 mg) and 4-phenylbutan-1-amine (170 mg) as starting materials, a deacetylated compound (148 mg) was obtained in the same manners as those of Example 2, (1) and Example 4, (6).
(2) By using the compound obtained in (1) mentioned above (50 mg) as a starting material, the compound shown in Table 1 (43.7 mg) was obtained in the same manner as that of Example 11.

Example 50

(1) By using the compound represented by the formula (A) obtained in Example 1, (5) (200 mg) and 3-phenoxypropan-1-amine (172 mg) as starting materials, a deacetylated compound (122 mg) was obtained in the same manners as those of Example 2, (1) and Example 4, (6).
(2) By using the compound obtained in (1) mentioned above (50 mg) as a starting material, the compound shown in Table 1 (39.8 mg) was obtained in the same manner as that of Example 11.

Example 51

By using the compound represented by the formula (A) obtained in Example 1, (5) (100 mg) and the compound obtained in Reference Example 84 (78 mg) as starting materials, the compound shown in Table 1 (39 mg) was obtained in the same manners as those of Example 2, (1), Example 4, (6) and Example 11.

Example 52

(1) By using the compound represented by the formula (A) obtained in Example 1, (5) (200 mg) and the compound obtained in Reference Example 85 (228 mg) as starting materials, a deacetylated compound (125 mg) was obtained in the same manners as those of Example 2, (1) and (2).

(2) By using the compound obtained in (1) mentioned above (50 mg) as a starting material, the compound shown in Table 1 (37.9 mg) was obtained in the same manner as that of Example 11.

Example 53

(1) By using the compound represented by the formula (A) obtained in Example 1, (5) (100 mg) and 4-(2-aminoethyl) thiomorpholine 1,1-dioxide (102 mg) as starting materials, a deacetylated compound (72 mg) was obtained in the same manners as those of Example 4, (1) and Example 2, (2).
(2) The compound obtained in (1) mentioned above (69 mg) was dissolved in a mixed solvent of ethanol and dimethylformamide (1:2, 450 µl), N,N-diethyl-N'-methylethane-1,2-diamine (25 µl) was added to the solution, and the resulting mixture was stirred at 75° C. for 19 hours. Ethyl acetate and distilled water were added to the reaction mixture, and the layers were separated. The organic layer was successively washed twice with distilled water and with saturated aqueous sodium chloride, then dried over anhydrous sodium sulfate, and filtered. The filtrate was concentrated under reduced pressure, and the resulting residue was purified by preparative thin layer chromatography (chloroform:methanol:28% aqueous ammonia=10:1:0.1) to obtain the compound shown in Table 1 (58 mg).

Example 54

By using the compound represented by the formula (A) obtained in Example 1, (5) (100 mg) and the compound obtained in Reference Example 83 (86 mg) as starting materials, the compound shown in Table 1 (43 mg) was obtained in the same manners as those of Example 4, (1), Example 2, (2) and Example 53, (2).

Example 55

(1) By using the compound represented by the formula (SM1) (30 g) obtained by the method described in the publication (International Patent Publication WO93/21199) and ethylenediamine (22.1 ml) as starting materials, a carbamate compound (14.4 g) was obtained in the same manner as that of Example 4, (1).
(2) The compound obtained in (1) mentioned above (11.0 g) was dissolved in methylene chloride (150 ml), 3-formylpyridine (1.26 ml) and sodium triacetoxyborohydride (5.18 g) were added to the solution, and the resulting mixture was stirred at room temperature for 4 hours. 37% Aqueous formaldehyde (2.97 ml) and sodium triacetoxyborohydride (3.89 g) were added to the reaction mixture, and the resulting mixture was stirred at room temperature for 5 hours. Chloroform and saturated aqueous sodium hydrogencarbonate were added to the reaction mixture, and the layers were separated. The organic layer was dried over anhydrous magnesium sulfate, and filtered, and the filtrate was concentrated under reduced pressure. The resulting residue was purified by silica gel column chromatography (chloroform:methanol:28% aqueous ammonia=10:1:0.1), the resulting purified product was dissolved in acetonitrile, and the deposited solid was collected by filtration to obtain an N-alkyl compound (6.36 g).
(3) By using the compound obtained in (2) mentioned above (8.0 g) as a starting material, a ketone compound (3.51 g) was obtained in the same manners as those of Example 2, (2), Example 1, (1), Example 6, (3) and Example 4, (6).
(4) By using the compound obtained in (3) mentioned above (500 mg) as a starting material, an epoxy compound (463 mg) was obtained in the same manner as that of Example 1, (4).
(5) By using the compound obtained in (4) mentioned above (50 mg) and the compound obtained in Reference Example 104 (38 mg) as starting materials, the compound shown in Table 1 (16.7 mg) was obtained in the same manner as that of Example 2, (5).

Example 56

By using the compound obtained in Example 55, (4) (50 mg) and N,N,N'-trimethylethylene-1,2-diamine (22 mg) as starting materials, the compound shown in Table 1 (12 mg) was obtained in the same manner as that of Example 2, (5).

Example 57

By using the compound obtained in Example 55, (4) (52 mg) and 50% aqueous dimethylamine (2 ml) as starting materials, the compound shown in Table 1 (31.4 mg) was obtained in the same manner as that of Example 2, (5).

Example 58

(1) By using the compound represented by the formula (A) obtained in Example 1, (5) (500 mg) and 1-(3-aminopropyl) pyrrolidin-2-one (405 mg) as starting materials, a deacetylated compound (220 mg) was obtained in the same manners as those of Example 4, (1) and Example 4, (6).
(2) By using the compound obtained in (1) mentioned above (100 mg) and N,N,N'-trimethylethylene-1,2-diamine (56 mg) as starting materials, the compound shown in Table 1 (56.8 mg) was obtained in the same manner as that of Example 2, (5).

Example 59

(1) By using the compound represented by the formula (A) obtained in Example 1, (5) (1.83 g) and N-(4-aminobutyl) pyrimidin-2-amine (1.74 g) as starting materials, a deacetylated compound (0.75 g) was obtained in the same manners as those of Example 4, (1) and (6).
(2) By using the compound obtained in (1) mentioned above (107 mg) as a starting material, the compound shown in Table 1 (119 mg) was obtained in the same manner as that of Example 15, (2).

Example 60

By using the compound obtained in Example 59, (1) (50 mg) and N-isopropylmethylamine (56 mg) as starting materials, the compound shown in Table 1 (61 mg) was obtained in the same manner as that of Example 2, (5).

Example 61

By using the compound obtained in Example 59, (1) (50 mg) and N-ethylmethylamine (46 µl) as starting materials, the compound shown in Table 1 (58 mg) was obtained in the same manner as that of Example 2, (5).

Example 62

By using the compound obtained in Example 59, (1) (50 mg) and 2-(methylamino)ethanol (40 mg) as starting materials, the compound shown in Table 1 (50 mg) was obtained in the same manner as that of Example 4, (8).

Example 63

By using the compound obtained in Example 59, (1) (50 mg) and N-(2-methoxyethyl)methylamine (48 mg) as starting materials, the compound shown in Table 1 (55 mg) was obtained in the same manner as that of Example 4, (8).

Example 64

(1) By using the compound represented by the formula (A) obtained in Example 1, (5) (500 mg) and the compound obtained in Reference Example 68 (595 mg) as starting materials, a deacetylated compound (112 mg) was obtained in the same manners as those of Example 4, (1) and Example 4, (6).
(2) By using the compound obtained in (1) mentioned above (36 mg) as a starting material, the compound shown in Table 1 (29.3 mg) was obtained in the same manner as that of Example 11.

Example 65

By using the compound obtained in Example 64, (1) (36 mg) as a starting material, the compound shown in Table 1 (27.2 mg) was obtained in the same manner as that of Example 4, (8).

Example 66

By using the compound obtained in Example 64, (1) (36 mg) and 50% aqueous dimethylamine (16.9 µl) as starting materials, the compound shown in Table 1 (32.8 mg) was obtained in the same manner as that of Example 4, (8).

Example 67

By using the compound represented by the formula (A) obtained in Example 1, (5) (500 mg) and the compound obtained in Reference Example 69 (632 mg) as starting materials, the compound shown in Table 1 (55.6 mg) was obtained in the same manners as those of Example 4, (1), Example 4, (6) and Example 11.

Example 68

(1) By using the compound represented by the formula (A) obtained in Example 1, (5) (250 mg) and the compound obtained in Reference Example 77 (217 mg) as starting materials, a deacetylated compound (178 mg) was obtained in the same manners as those of Example 4, (1) and Example 4, (6).
(2) By using the compound obtained in (1) mentioned above (50 mg) as a starting material, the compound shown in Table 1 (44.8 mg) was obtained in the same manner as that of Example 11.

Example 69

By using the compound represented by the formula (A) obtained in Example 1, (5) (100 mg) and 3-phenylpropylamine (80 µl) as starting materials, the compound shown in Table 1 (24 mg) was obtained in the same manners as those of Example 4, (1), (6) and Example 11.

Example 70

(1) By using the compound represented by the formula (A) obtained in Example 1, (5) (250 mg) and the compound obtained in Reference Example 81 (150.7 mg) as starting materials, a deacetylated compound (162 mg) was obtained in the same manners as those of Example 4, (1) and Example 4, (6).
(2) By using the compound obtained in (1) mentioned above (50 mg) as a starting material, the compound shown in Table 1 (34.6 mg) was obtained in the same manner as that of Example 11.

Example 71

(1) By using the compound represented by the formula (A) obtained in Example 1, (5) (2 g) and 1,3-propanediamine (844 mg) as starting materials, a carbamate compound (1.71 g) was obtained in the same manner as that of Example 2, (1).
(2) The compound obtained in (1) mentioned above (500 mg) and triethylamine (233 µl) were dissolved in chloroform (5 ml), methanesulfonyl chloride (65 µl) was added to the solution under ice cooling, and the resulting mixture was stirred for 30 minutes. Saturated aqueous sodium hydrogencarbonate was added to the reaction mixture, and the layers were separated. The organic layer was dried over anhydrous magnesium sulfate, and filtered. The filtrate was concentrated under reduced pressure, and the resulting residue was purified by silica gel column chromatography (chloroform:methanol:28% aqueous ammonia=50:1:0.1 to 9:1:0.1) to obtain a methanesulfonyl compound (412 mg).
(3) By using the compound obtained in (2) mentioned above (412 mg) as a starting material, a deprotected compound was obtained in the same manner as that of Example 4, (6).
(4) By using the compound obtained in (3) mentioned above (100 mg) as a starting material, the compound shown in Table 1 (33 mg) was obtained in the same manner as that of Example 11.

Example 72

(1) The compound obtained in Example 71, (1) (200 mg) was dissolved in chloroform (5 ml), pyridine (37 µl) and acetic anhydride (32 µl) were added to the solution under ice cooling, and the resulting mixture was stirred for 2 hours with warming to room temperature. Acetic anhydride (32 µl) was added to the reaction mixture, and the resulting mixture was stirred for 1 hour. Then, saturated aqueous sodium hydrogencarbonate was added to the reaction mixture, the layers were separated, and the resulting organic layer was dried over anhydrous magnesium sulfate, and filtered. The filtrate was concentrated under reduced pressure, and the resulting residue was purified by silica gel column chromatography (chloroform:methanol:28% aqueous ammonia=10:1:0.1) to obtain an acetyl compound (169 mg).
(2) By using the compound obtained in (1) mentioned above (169 mg) as a starting material, the compound shown in Table 1 (3 mg) was obtained in the same manners as those of Example 2, (2) and Example 11.

Example 73

(1) The compound obtained in Example 71, (1) (200 mg) was dissolved in chloroform (5 ml), 37% aqueous formaldehyde (184 µl) and sodium triacetoxyborohydride (120 mg) were added to the solution, and the resulting mixture was stirred at room temperature for 2 hours. Saturated aqueous sodium hydrogencarbonate was added to the reaction mixture, and the layers were separated. The organic layer was concentrated under reduced pressure to obtain a residue. The resulting residue was purified by silica gel column chromatography (chloroform to chloroform:methanol:28% aqueous ammonia=12:1:0.1) to obtain a dimethyl compound (172 mg).
(2) By using the compound obtained in (1) mentioned above (172 mg) as a starting material, the compound shown in Table 1 (14 mg) was obtained in the same manners as those of Example 2, (2) and Example 11.

Example 74

(1) By using the compound represented by the formula (A) obtained in Example 1, (5) (2 g) and 1,4-butanediamine (1 g) as starting materials, a carbamate compound (1.63 g) was obtained in the same manner as that of Example 2, (1).
(2) By using the compound obtained in (1) mentioned above (500 mg) as a starting material, the compound shown in Table 1 (81 mg) was obtained in the same manners as those of Example 71, (2), Example 4, (6) and Example 11.

Example 75

By using the compound obtained in Example 74, (1) (200 mg) and acetic anhydride (32 µl) as starting materials, the compound shown in Table 1 (16 mg) was obtained in the same manners as those of Example 71, (2), Example 4, (6) and Example 11.

Example 76

By using the compound obtained in Example 74, (1) (200 mg) and methyl chloroformate (260 as starting materials, the compound shown in Table 1 (25 mg) was obtained in the same manners as those of Example 71, (2), Example 4, (6) and Example 11.

Example 77

By using the compound represented by the formula (A) obtained in Example 1, (5) (500 mg) and the compound obtained in Reference Example 70 (0.89 g) as starting materials, the compound shown in Table 1 (60 mg) was obtained in the same manners as those of Example 4, (1) and Example 11.

Example 78

(1) By using the compound represented by the formula (A) obtained in Example 1, (5) (1.0 g) and N-benzyl-N-methyl-ethane-1,2-diamine (935 mg) as starting materials, a carbamate compound (833 mg) was obtained in the same manner as that of Example 2, (1).
(2) By using the compound obtained in (1) mentioned above (150 mg) as a starting material, the compound shown in Table 1 (65 mg) was obtained in the same manner as that of Example 11.

Example 79

(1) The compound obtained in Example 78, (1) (480 mg) was dissolved in tetrahydrofuran (10 ml), 20% palladium hydroxide/carbon (200 mg) was added to the solution, and the resulting mixture was stirred overnight at room temperature under a hydrogen atmosphere of 1 atm. The reaction mixture was filtered, and then the filtrate was concentrated under reduced pressure. The resulting residue was dissolved in ethanol (10 ml), 20% palladium hydroxide/carbon (200 mg) was added to the solution, and the resulting mixture was stirred at room temperature for 3 hours under a hydrogen atmosphere of 1 atm. The reaction mixture was filtered, and then the filtrate was concentrated under reduced pressure to obtain a debenzylated compound (396 mg).
(2) By using the compound obtained in (1) mentioned above (100 mg) and benzoyl chloride (20 µl) as starting materials, the compound shown in Table 1 (53 mg) was obtained in the same manners as those of Example 71, (2) and (4).

Example 80

By using the compound obtained in Example 79, (1) (290 mg) and benzenesulfonyl chloride (87 mg) as starting materials, the compound shown in Table 1 (87 mg) was obtained in the same manners as those of Example 71, (2) and (4).

Example 81

(1) By using the compound represented by the formula (A) obtained in Example 1, (5) (1.0 g) and 3-aminopropanol (0.87 ml) as starting materials, a carbamate compound (914 mg) was obtained in the same manner as that of Example 2, (1).
(2) By using the compound obtained in (1) mentioned above (192 mg) as a starting material, an acetyl compound (176 mg) was obtained in the same manners as those of Example 11 and Example 1, (1).
(3) Chlorosulfonyl isocyanate (48 µl) and formic acid (21 µl) were dissolved in acetonitrile (1.0 ml) under ice cooling, and the resulting mixture was stirred for 5 hours with warming to room temperature. A solution of the compound obtained in (2) mentioned above (176 mg) in dimethylacetamide (2 ml) was added dropwise to the reaction mixture under ice cooling, and the resulting mixture was stirred at room temperature for 1 hour. Distilled water and chloroform were added to the reaction mixture, and the layers were separated. The organic layer was concentrated under reduced pressure, and the resulting residue was purified by silica gel column chromatography (chloroform to chloroform:methanol:28% aqueous ammonia=10:1:0.1) to obtain a sulfamate compound (217 mg).
(4) By using the compound obtained in (3) mentioned above (120.4 mg) as a starting material, the compound shown in Table 1 (27.5 mg) was obtained in the same manner as that of Example 4, (6).

Example 82

By using the compound obtained in Example 29 (30 mg) as a starting material, the compound shown in Table 1 (13 mg) was obtained in the same manner as that of Example 73, (1).

Example 83

By using the compound obtained in Example 42 (910 mg) as a starting material, the compound shown in Table 1 (182 mg) was obtained in the same manners as those of Example 1, (1), Example 81, (3) and Example 4, (6).

Example 84

(1) The compound represented by the formula (A) obtained in Example 1, (5) (455 mg) was dissolved in dimethylformamide (10 ml), 1,1,3,3-tetramethylguanidine (324 µl) and the compound obtained in Reference Example 71 (586 mg) were added to the solution, and the resulting mixture was stirred at room temperature for 6 days. The reaction mixture was diluted with ethyl acetate, and the diluted reaction mixture was washed with saturated aqueous ammonium chloride and saturated aqueous sodium chloride. The organic layer was dried over anhydrous magnesium sulfate, and filtered, then the filtrate was concentrated under reduced pressure, and a part of the resulting residue was purified by silica gel column chromatography (chloroform:methanol:28% aqueous ammonia=100:1:0.1 to 3:1:0.1) to obtain a carbamate compound (77.1 mg).

(2) By using the compound obtained in (1) mentioned above (75.0 mg) as a starting material, the compound shown in Table 1 (34.4 mg) was obtained in the same manners as those of Example 2, (2) and Example 11.

Example 85

(1) By using the compound represented by the formula (A) obtained in Example 1, (5) (1.5 g) and 1,2-ethylenediamine (513 mg) as starting materials, a carbamate compound (756 mg) was obtained in the same manner as that of Example 4, (1).

(2) By using the compound obtained in (1) mentioned above (100 mg) as a starting material, the compound shown in Table 1 (58 mg) was obtained in the same manners as those of Example 73, (1), Example 2, (2) and Example 11.

Example 86

(1) By using the compound obtained in Example 85, (1) (369 mg) as a starting material, a methanesulfonyl compound (264 mg) was obtained in the same manners as those of Example 71, (2) and Example 2, (2).

(2) By using the compound obtained in (1) mentioned above (54 mg) and N,N,N'-trimethylethylene-1,2-diamine (60 mg) as starting materials, the compound shown in Table 1 (54 mg) was obtained in the same manner as that of Example 2, (5).

Example 87

By using the compound obtained in Example 86, (1) (100 mg) as a starting material, the compound shown in Table 1 (54 mg) was obtained in the same manner as that of Example 15, (2).

Example 88

By using the compound obtained in Example 86, (1) (100 mg) and the compound obtained in Reference Example 1 (79.4 mg) as starting materials, the compound shown in Table 1 (80 mg) was obtained in the same manner as that of Example 4, (8).

Example 89

By using the compound obtained in Example 86, (1) (100 mg) and the compound obtained in Reference Example 2 (78.7 mg) as starting materials, the compound shown in Table 1 (105 mg) was obtained in the same manner as that of Example 4, (8).

Example 90

By using the compound obtained in Example 86, (1) (107 mg) and the compound obtained in Reference Example 6 (0.51 g) as starting materials, the compound shown in Table 1 (116 mg) was obtained in the same manner as that of Example 2, (5).

Example 91

By using the compound obtained in Example 86, (1) (200 mg) and the compound obtained in Reference Example 4 (95.5 mg) as starting materials, the compound shown in Table 1 (140 mg) was obtained in the same manner as that of Example 4, (8).

Example 92

By using the compound obtained in Example 86, (1) (200 mg) and the compound obtained in Reference Example 5 (103.5 mg) as starting materials, the compound shown in Table 1 (143 mg) was obtained in the same manner as that of Example 4, (8).

Example 93

By using the compound obtained in Example 86, (1) (200 mg) and the compound obtained in Reference Example 3 (104.8 mg) as starting materials, the compound shown in Table 1 (121 mg) was obtained in the same manner as that of Example 4, (8).

Example 94

By using the compound obtained in Example 86, (1) (50 mg) and the compound obtained in Reference Example 7 (15.9 mg) as starting materials, the compound shown in Table 1 (49 mg) was obtained in the same manner as that of Example 4, (8).

Example 95

By using the compound obtained in Example 86, (1) (50 mg) and the compound obtained in Reference Example 8 (12.9 mg) as starting materials, the compound shown in Table 1 (34 mg) was obtained in the same manner as that of Example 4, (8).

Example 96

By using the compound obtained in Example 86, (1) (50 mg) and the compound obtained in Reference Example 9 (21.6 mg) as starting materials, the compound shown in Table 1 (41 mg) was obtained in the same manner as that of Example 4, (8).

Example 97

By using the compound obtained in Example 86, (1) (50 mg) and the compound obtained in Reference Example 10 (19 mg) as starting materials, the compound shown in Table 1 (45 mg) was obtained in the same manner as that of Example 2, (5).

Example 98

By using the compound obtained in Example 86, (1) (50 mg) and the compound obtained in Reference Example 11 (23 mg) as starting materials, the compound shown in Table 1 (60 mg) was obtained in the same manner as that of Example 2, (5).

Example 99

By using the compound obtained in Example 86, (1) (50 mg) and the compound obtained in Reference Example 12 (20 mg) as starting materials, the compound shown in Table 1 (42 mg) was obtained in the same manner as that of Example 2, (5).

Example 100

By using the compound obtained in Example 86, (1) (50 mg) and the compound obtained in Reference Example 13 (21 mg) as starting materials, the compound shown in Table 1 (24 mg) was obtained in the same manner as that of Example 2, (5).

Example 101

By using the compound obtained in Example 86, (1) (100 mg) and the compound obtained in Reference Example 14 (64 mg) as starting materials, the compound shown in Table 1 (63.7 mg) was obtained in the same manner as that of Example 4, (8).

Example 102

By using the compound obtained in Example 86, (1) (100 mg) and the compound obtained in Reference Example 15 (64 mg) as starting materials, the compound shown in Table 1 (67.9 mg) was obtained in the same manner as that of Example 4, (8).

Example 103

By using the compound obtained in Example 86, (1) (100 mg) and the compound obtained in Reference Example 16 (53 mg) as starting materials, the compound shown in Table 1 (61.7 mg) was obtained in the same manner as that of Example 4, (8).

Example 104

By using the compound obtained in Example 86, (1) (43 mg) and the compound obtained in Reference Example 17 (24 mg) as starting materials, the compound shown in Table 1 (27.2 mg) was obtained in the same manner as that of Example 4, (8).

Example 105

By using the compound obtained in Example 86, (1) (50 mg) and N-methyl-2-(methylsulfonyl)ethanamine (18.9 mg) obtained by the method described in the literature (Bioorganic & Medicinal Chemistry Letters, 2004, vol. 14, p. 111) as starting materials, the compound shown in Table 1 (26 mg) was obtained in the same manner as that of Example 4, (8).

Example 106

(1) By using the compound obtained in Example 85, (1) (400 mg) and cyclopropanesulfonyl chloride (70 µl) as starting materials, a deacetylated compound (199 mg) was obtained in the same manners as those of Example 71, (2) and Example 2, (2).
(2) By using the compound obtained in (1) mentioned above (100 mg) as a starting material, the compound shown in Table 1 (70 mg) was obtained in the same manner as that of Example 11.

Example 107

(1) By using the compound obtained in Example 85, (1) (400 mg) and ethanesulfonyl chloride (65 µl) as starting materials, a deacetylated compound (153 mg) was obtained in the same manners as those of Example 71, (2) and Example 2, (2).
(2) By using the compound obtained in (1) mentioned above (100 mg) as a starting material, the compound shown in Table 1 (64 mg) was obtained in the same manner as that of Example 11.

Example 108

(1) By using the compound obtained in Example 85, (1) (200 mg) and 2-(methylsulfonyl)benzenesulfonyl chloride (60.1 mg) as starting materials, a deacetylated compound (157 mg) was obtained in the same manners as those of Example 71, (2) and Example 2, (2).
(2) By using the compound obtained in (1) mentioned above (100 mg) as a starting material, the compound shown in Table 1 (43 mg) was obtained in the same manner as that of Example 11.

Example 109

(1) By using the compound obtained in Example 85, (1) (200 mg) and 3-cyanobenzenesulfonyl chloride (47.9 mg) as starting materials, a deacetylated compound (113 mg) was obtained in the same manners as those of Example 71, (2) and Example 2, (2).
(2) By using the compound obtained in (1) mentioned above (100 mg) as a starting material, the compound shown in Table 1 (44 mg) was obtained in the same manner as that of Example 11.

Example 110

(1) By using the compound obtained in Example 85, (1) (200 mg) and 2-cyanobenzenesulfonyl chloride (47.9 mg) as starting materials, a deacetylated compound (128 mg) was obtained in the same manners as those of Example 71, (2) and Example 2, (2).
(2) By using the compound obtained in (1) mentioned above (100 mg) as a starting material, the compound shown in Table 1 (25 mg) was obtained in the same manner as that of Example 11.

Example 111

(1) By using the compound obtained in Example 85, (1) (200 mg) and 4-cyanobenzenesulfonyl chloride (47.9 mg) as starting materials, a deacetylated compound (190 mg) was obtained in the same manners as those of Example 71, (2) and Example 2, (2).
(2) By using the compound obtained in (1) mentioned above (100 mg) as a starting material, the compound shown in Table 1 (40 mg) was obtained in the same manner as that of Example 11.

Example 112

(1) By using the compound obtained in Example 85, (1) (200 mg) and benzenesulfonyl chloride (42.1 mg) as starting materials, a deacetylated compound (170 mg) was obtained in the same manners as those of Example 71, (2) and Example 2, (2).
(2) By using the compound obtained in (1) mentioned above (100 mg) as a starting material, the compound shown in Table 1 (55 mg) was obtained in the same manner as that of Example 11.

Example 113

(1) By using the compound obtained in Example 85, (1) (200 mg) and 2-thiophenesulfonyl chloride (43.5 mg) as starting materials, a deacetylated compound (122 mg) was obtained in the same manners as those of Example 71, (2) and Example 2, (2).
(2) By using the compound obtained in (1) mentioned above (100 mg) as a starting material, the compound shown in Table 1 (61 mg) was obtained in the same manner as that of Example 11.

Example 114

(1) By using the compound obtained in Example 85, (1) (200 mg) and 4-methoxybenzenesulfonyl chloride (71 mg) as starting materials, a deacetylated compound (140 mg) was obtained in the same manners as those of Example 71, (2) and Example 2, (2).
(2) By using the compound obtained in (1) mentioned above (103 mg) as a starting material, the compound shown in Table 1 (78.2 mg) was obtained in the same manner as that of Example 11.

Example 115

(1) By using the compound obtained in Example 85, (1) (200 mg) and 3-methoxybenzenesulfonyl chloride (49 μl) as starting materials, a deacetylated compound (176 mg) was obtained in the same manners as those of Example 71, (2) and Example 2, (2).
(2) By using the compound obtained in (1) mentioned above (99.3 mg) as a starting material, the compound shown in Table 1 (78.3 mg) was obtained in the same manner as that of Example 11.

Example 116

(1) By using the compound obtained in Example 85, (1) (250 mg) and 2-methoxybenzenesulfonyl chloride (89 mg) as starting materials, a deacetylated compound (185 mg) was obtained in the same manners as those of Example 71, (2) and Example 2, (2).
(2) By using the compound obtained in (1) mentioned above (106 mg) as a starting material, the compound shown in Table 1 (108 mg) was obtained in the same manner as that of Example 11.

Example 117

By using the compound obtained in Example 85, (1) (200 mg) and 2-methylbenzenesulfonyl chloride (49 μl) as starting materials, the compound shown in Table 1 (38.2 mg) was obtained in the same manners as those of Example 71, (2), Example 2, (2) and Example 15, (2).

Example 118

By using the compound obtained in Example 85, (1) (200 mg) and 3-methylbenzenesulfonyl chloride (50 μl) as starting materials, the compound shown in Table 1 (52.1 mg) was obtained in the same manners as those of Example 71, (2), Example 2, (2) and Example 15, (2).

Example 119

By using the compound obtained in Example 85, (1) (200 mg) and 4-methylbenzenesulfonyl chloride (66 mg) as starting materials, the compound shown in Table 1 (78.9 mg) was obtained in the same manners as those of Example 71, (2), Example 2, (2) and Example 15, (2).

Example 120

(1) By using the compound obtained in Example 85, (1) (200 mg) and 1-methyl-1H-pyrazole-3-sulfonyl chloride (62 mg) as starting materials, a deacetylated compound (192 mg) was obtained in the same manners as those of Example 71, (2) and Example 2, (2).
(2) By using the compound obtained in (1) mentioned above (101 mg) as a starting material, the compound shown in Table 1 (46.1 mg) was obtained in the same manner as that of Example 11.

Example 121

(1) By using the compound obtained in Example 85, (1) (720 mg) and pyridine-3-sulfonyl chloride hydrochloride (265 mg) as starting materials, a deacetylated compound (462 mg) was obtained in the same manners as those of Example 71, (2) and Example 4, (6).
(2) By using the compound obtained in (1) mentioned above (160 mg) and 50% aqueous dimethylamine (1.0 ml) as starting materials, the compound shown in Table 1 (78 mg) was obtained in the same manner as that of Example 4, (8).

Example 122

By using the compound obtained in Example 121, (1) (160 mg) as a starting material, the compound shown in Table 1 (73 mg) was obtained in the same manner as that of Example 4, (8).

Example 123

By using the compound obtained in Example 121, (1) (160 mg) as a starting material, the compound shown in Table 1 (69 mg) was obtained in the same manner as that of Example 11.

Example 124

By using the compound obtained in Example 112, (1) (500 mg) as a starting material, the compound shown in Table 1 (214 mg) was obtained in the same manner as that of Example 4, (8).

Example 125

By using the compound obtained in Example 112, (1) (500 mg) and the compound obtained in Reference Example 1 (367 mg) as starting materials, the compound shown in Table 1 (254 mg) was obtained in the same manner as that of Example 4, (8).

Example 126

(1) By using the compound obtained in Example 85, (1) (650 mg) and 2-thiophenesulfonyl (272 mg) as starting materials, a deacetylated compound (230 mg) was obtained in the same manners as those of Example 71, (2) and Example 2, (2).
(2) By using the compound obtained in (1) mentioned above (50 mg) as a starting material, the compound shown in Table 1 (29 mg) was obtained in the same manner as that of Example 4, (8).

Example 127

By using the compound obtained in Example 126, (1) (50 mg) and the compound obtained in Reference Example 1 (36.5 mg) as starting materials, the compound shown in Table 1 (36 mg) was obtained in the same manner as that of Example 4, (8).

Example 128

(1) The compound obtained in Example 85, (1) (80 mg) was dissolved in chloroform (800 μl), triethylamine (38.4 μl) was added to the solution, and the resulting mixture was cooled on ice. Dimethylsulfamoyl chloride (24.2 μl) was added to the reaction mixture, the resulting mixture was warmed to room temperature, then 4-dimethylaminopyridine (2.2 mg) was added to the mixture, and the resulting mixture was stirred for 24 hours. Saturated aqueous sodium hydrogencarbonate was added to the reaction mixture, and the layers were separated. The organic layer was dried over anhydrous sodium sulfate, and filtered. The filtrate was concentrated under reduced pressure, and the resulting residue was purified by preparative thin layer chromatography (chloroform:methanol:28% aqueous ammonia=15:1:0.1) to obtain a dimethylsulfamoyl compound (70 mg).
(2) By using the compound obtained in (1) mentioned above (70 mg) as a starting material, the compound shown in Table 1 (37 mg) was obtained in the same manners as those of Example 2, (2) and Example 11.

Example 129

(1) The compound obtained in Example 85, (1) (80 mg) was dissolved in methylene chloride (2 triethylamine (20 μl) and trifluoromethanesulfonic anhydride (20 μl) were added to the solution under ice cooling, and the resulting mixture was stirred at the same temperature for 30 minutes. Saturated aqueous sodium hydrogencarbonate and ethyl acetate were added to the reaction mixture, and the layers were separated. The organic layer was washed with distilled water and saturated aqueous sodium chloride, then dried over anhydrous sodium sulfate, and filtered. The filtrate was concentrated under reduced pressure, and the resulting residue was purified by preparative thin layer chromatography (chloroform:methanol:28% aqueous ammonia=15:1:0.1) to obtain a trifluoroacetyl compound (67 mg).
(2) The compound obtained in (1) mentioned above (64 mg) was dissolved in methanol (2.5 ml), 1,8-diazabicyclo[5,4,0]-7-undecene (2.7 μl) was added to the solution, and the resulting mixture was stirred at 60° C. for 18 hours. The reaction mixture was concentrated under reduced pressure, and the resulting residue was purified by preparative thin layer chromatography (chloroform:methanol:28% aqueous ammonia=15:1:0.1) to obtain a deprotected compound (47 mg).
(3) The compound obtained in (2) mentioned above (45 mg) was dissolved in ethanol (200 μl), N,N-diethyl-N'-methylethane-1,2-diamine (25 μl) was added to the solution, and the resulting mixture was stirred at 75° C. for 17 hours. The reaction mixture was concentrated under reduced pressure, and the resulting residue was purified by preparative thin layer chromatography (chloroform:methanol:28% aqueous ammonia=10:1:0.1) to obtain the compound shown in Table 1 (38 mg).

Example 130

By using the compound obtained in Example 85, (1) (80 mg) and the compound obtained in Reference Example 86 (31.8 mg) as starting materials, the compound shown in Table 1 (6.1 mg) was obtained in the same manners as those of Example 128, (1), Example 2, (2) and Example 11.

Example 131

By using the compound obtained in Example 85, (1) (80 mg) and the compound obtained in Reference Example 87 (17.9 mg) as starting materials, the compound shown in Table 1 (50 mg) was obtained in the same manners as those of Example 128, (1), Example 2, (2) and Example 11.

Example 132

By using the compound obtained in Example 85, (1) (3 g) and methyl 2-(chlorosulfonyl)benzoate (108 mg) as starting materials, the compound shown in Table 1 (38 mg) was obtained in the same manners as those of Example 71, (2), Example 2, (2) and Example 11.

Example 133

(1) The compound obtained in Example 86, (1) (1.0 g) was dissolved in ethanol (4 ml), 40% aqueous methylamine (1.0 ml) was added to the solution, and the resulting mixture was stirred overnight under reflux by heating. The reaction mixture was concentrated under reduced pressure, and the resulting residue was purified by silica gel column chromatography (chloroform:methanol:28% aqueous ammonia=100:1:0.1 to 10:1:0.1) to obtain an adduct compound (837 mg).
(2) The compound obtained in (1) mentioned above (50 mg) was dissolved in chloroform (1.0 ml), isopropyl isocyanate (5.2 μl) was added to the solution, and the resulting mixture was stirred at room temperature for 1 hour. The reaction mixture was concentrated under reduced pressure, and the resulting residue was purified by preparative thin layer chromatography (chloroform:methanol:28% aqueous ammonia=10:1:0.1) to obtain the compound shown in Table 1 (43.3 mg).

Example 134

By using the compound obtained in Example 133, (1) (50 mg) and 1-isocyanato-2-methylpropane (5.3 mg) as starting materials, the compound shown in Table 1 (59.8 mg) was obtained in the same manner as that of Example 133, (2).

Example 135

(1) By using the compound obtained in Example 85, (1) (100 mg) and methyl chloroformate (16 mg) as starting materials, a carbamate compound (89 mg) was obtained in the same manner as that of Example 71, (2).
(2) By using the compound obtained in (1) mentioned above (89 mg) as a starting material, the compound shown in Table 1 (56 mg) was obtained in the same manners as those of Example 2, (2) and Example 11.

Example 136

By using the compound obtained in Example 85, (1) (100 mg) as a starting material, the compound shown in Table 1 (62 mg) was obtained in the same manners as those of Example 1, (1), Example 2, (2) and Example 11.

Example 137

(1) The compound obtained in Example 85, (1) (200 mg) was dissolved in chloroform (5 ml), triethylamine (96 μl) and trifluoroacetic anhydride (49 μl) were added to the solution under ice cooling, and the resulting mixture was stirred for 1 hour. Saturated aqueous sodium hydrogencarbonate was added to the reaction mixture, and the layers were separated. The organic layer was concentrated under reduced pressure, and the resulting residue was purified by silica gel column chromatography (chloroform:methanol:28% aqueous ammonia=100:1:0.1 to 10:1:0.1) to obtain a trifluoroacetyl compound (230 mg).
(2) By using the compound obtained in (1) mentioned above (100 mg) as a starting material, the compound shown in Table 1 (19 mg) was obtained in the same manner as that of Example 11.

Example 138

By using the compound obtained in Example 85, (1) (150 mg) and benzoyl chloride (29.7 μl) as starting materials, the compound shown in Table 1 (81 mg) was obtained in the same manners as those of Example 71, (2), Example 2, (2) and Example 11.

Example 139

(1) The compound obtained in Example 85, (1) (100 mg) was dissolved in chloroform (1 ml), pyridine (93 μl) was added to the solution, and the resulting mixture was cooled on ice. Triphosgene (68.3 mg) was added portionwise to the reaction mixture, and the resulting mixture was stirred for 10 minutes. Then, 37% aqueous ammonia (1 ml) was added to the mixture, and the resulting mixture was stirred for 1 hour. Saturated aqueous sodium hydrogencarbonate and chloroform were added to the reaction mixture, and the layers were separated. The organic layer was concentrated under reduced pressure to obtain a urea compound.
(2) By using the compound obtained in (1) mentioned above as a starting material, the compound shown in Table 1 (41 mg) was obtained in the same manners as those of Example 2, (2) and Example 11.

Example 140

(1) By using the compound obtained in Example 85, (1) (150 mg) and dimethylamine (1 ml) as starting materials, a deprotected compound (50 mg) was obtained in the same manners as those of Example 139, (1) and Example 2, (2).
(2) By using the compound obtained in (1) mentioned above (50 mg) as a starting material, the compound shown in Table 1 (33 mg) was obtained in the same manner as that of Example 11.

Example 141

By using the compound obtained in Example 140, (1) (50 mg) and N,N-diethyl-N'-methylethane-1,2-diamine (89.7 mg) as starting materials, the compound shown in Table 1 (19 mg) was obtained in the same manner as that of Example 2, (5).

Example 142

By using the compound obtained in Example 1 (1.61 g) as a starting material, the compound shown in Table 1 (491 mg) was obtained in the same manners as those of Example 1, (1), Example 81, (3) and Example 4, (6).

Example 143

(1) The compound obtained in Example 1 (103 mg) was dissolved in chloroform (1.1 ml), acetic anhydride (22 tri- ethylamine (77 μl) and a catalytic amount of 4-dimethylaminopyridine were added to the solution, and the resulting mixture was stirred overnight at room temperature. Distilled water was added to the reaction mixture, and the resulting mixture was extracted with ethyl acetate. The organic layer was washed with saturated aqueous sodium hydrogencarbonate, dried over anhydrous magnesium sulfate, and filtered. The filtrate was concentrated under reduced pressure, and the resulting residue was purified by preparative thin layer chromatography (chloroform:methanol:28% aqueous ammonia=10:1:0.1) to obtain an acetyl compound (47.9 mg).
(2) By using the compound obtained in (1) mentioned above (47.9 mg) as a starting material, the compound shown in Table 1 (32.7 mg) was obtained in the same manner as that of Example 4, (6).

Example 144

(1) By using the compound obtained in Example 1 (121 mg) as a starting material, an acetyl compound (127.2 mg) was obtained in the same manner as that of Example 1, (1).
(2) The compound obtained in (1) mentioned above (22.4 mg) was dissolved in chloroform (1.0 ml), benzoyl chloride (4 μl), triethylamine (9 μl) and a catalytic amount of 4-dimethylaminopyridine were added to the solution, and the resulting mixture was stirred overnight at room temperature. Distilled water was added to the reaction mixture, and the resulting mixture was extracted with ethyl acetate. The organic layer was washed with saturated aqueous sodium hydrogencarbonate, dried over anhydrous magnesium sulfate, and filtered. The filtrate was concentrated under reduced pressure, and the resulting residue was purified by preparative thin layer chromatography (chloroform:methanol:28% aqueous ammonia=10:1:0.1) to obtain a benzoyl compound (11.4 mg).
(3) By using the compound obtained in (2) mentioned above (10.7 mg) as a starting material, the compound shown in Table 1 (8.7 mg) was obtained in the same manner as that of Example 4, (6).

Example 145

(1) The compound obtained in Example 1 (100 mg) was dissolved in chloroform (1.0 ml), trichloroacetyl isocyanate (14 μl) was added dropwise to the solution, and the resulting mixture was stirred at room temperature for 1 hour. Methanol (1.0 ml) and potassium carbonate (7 mg) were added to the reaction mixture, and the resulting mixture was stirred overnight at room temperature. Distilled water was added to the reaction mixture, and the resulting mixture was extracted with ethyl acetate. The organic layer was dried over anhydrous sodium sulfate, and filtered. The filtrate was concentrated under reduced pressure, and the resulting residue was purified by preparative thin layer chromatography (chloroform:methanol:28% aqueous ammonia=10:1:0.1) to obtain a carbamoyl compound (60.1 mg).
(2) By using the compound obtained in (1) mentioned above (60 mg) as a starting material, the compound shown in Table 1 (51.2 mg) was obtained in the same manner as that of Example 4, (6).

Example 146

(1) By using the compound obtained in Example 1, (6) (300 mg) and the compound obtained in Reference Example 4 (147 mg) as starting materials, the compound shown in Table 1 (57.2 mg) was obtained in the same manners as those of Example 4, (8), Example 1, (1), Example 81, (3) and Example 4, (6).

Example 147

(1) By using the compound obtained in Example 1, (6) (300 mg) and the compound obtained in Reference Example 1 (145 mg) as starting materials, the compound shown in Table 1 (49.6 mg) was obtained in the same manners as those of Example 4, (8), Example 1, (1), Example 81, (3) and Example 4, (6).

Examples 148 to 171

Preparation methods of the compounds represented by the formula (C) having $R^{29}$ defined in Table 2 are shown below.

TABLE 2

Formula (C)

[Formula 32]

| Example | $R^{29}$ | ESI MS (M + H) | $^1$H-NMR, CDCl$_3$, δ (ppm) |
|---|---|---|---|
| 148 | (oxetanyl group) | 971.7 | (500 MHz): 0.86 (t, J = 7.45 Hz, 3 H) 1.00-1.07 (m, 8 H) 1.10 (d, J = 7.26 Hz, 6 H) 1.16 (s, 3 H) 1.18-1.27 (m, 10 H) 1.37 (s, 3 H) 1.39 (s, 3 H) 1.49-1.78 (m, 4 H) 1.81-2.05 (m, 4 H) 2.10 (d, J = 14.52 Hz, 1 H) 2.29 (s, 6 H) 2.35 (s, 3 H) 2.40-2.87 (m, 10 H) 2.81-2.95 (m, 2 H) 3.03 (q, J = 6.88 Hz, 1 H) 3.06-3.10 (m, 3 H) 3.18 (dd, J = 10.32, 7.26 Hz, 1 H) 3.28 (s, 3 H) 3.43-3.51 (m, 1 H) 3.59 (s, 1 H) 3.68-3.75 (m, 2 H) 4.09 (q, J = 6.24 Hz, 1 H) 4.42 (d, J = 7.26 Hz, 1 H) 4.62-4.74 (m, 2 H) 4.95-5.05 (m, 4 H) 5.18 (t, J = 6.68 Hz, 1 H) |
| 149 | (methanesulfonamide-benzyloxy group) | 1156.7 | (600 MHz): 0.82 (t, J = 7.34 Hz, 2 H) 1.00-1.26 (m, 28 H) 1.35 (s, 3 H) 1.39 (s, 3 H) 1.49-1.89 (m, 6 H) 1.95-2.04 (m, 2 H) 2.07-2.12 (m, 1 H) 2.28 (s, 6 H) 2.34 (s, 3 H) 2.39-2.63 (m, 10 H) 2.81-2.90 (m, 2 H) 2.93 (s, 3 H) 3.03 (s, 3 H) 3.05-3.10 (m, 1 H) 3.15-3.23 (m, 2 H) 3.27 (s, 3 H) 3.44-3.50 (m, 1 H) 3.58-3.80 (m, 6 H) 4.05-4.10 (m, 1 H) 4.19-4.26 (m, 1 H) 4.39-4.43 (m, 1 H) 4.50-4.59 (m, 2 H) 4.96-5.00 (m, 1 H) 5.03-5.07 (m, 1 H) 5.51-5.56 (m, 1 H) 7.22-7.37 (m, 5 H) |
| 150 | (phenyl-oxadiazolyl-methyl group) | 1073.7 | (600 MHz): 0.90 (t, J = 7.34 Hz, 3 H) 0.95-1.27 (m, 28 H) 1.33 (s, 3 H) 1.46 (s, 3 H) 1.49-1.53 (m, 1 H) 1.60-1.66 (m, 1 H) 1.69-1.79 (m, 2 H) 1.81-2.03 (m, 4 H) 2.06 (d, J = 15.13 Hz, 1 H) 2.28 (s, 6 H) 2.32 (s, 3 H) 2.37-2.63 (m, 10 H) 2.75 (s, 3 H) 2.76-2.83 (m, 2 H) 3.10-3.20 (m, 2 H) 3.25 (s, 3 H) 3.38 (br. s, 1 H) 3.44 (br. s, 1 H) 3.58-3.64 (m, 2 H) 3.79 (s, 1 H) 4.03 (q, J = 6.57 Hz, 1 H) 4.39 (d, J = 7.34 Hz, 1 H) 4.87 (d, J = 5.04 Hz, 1 H) 5.06 (d, J = 17.88 Hz, 1 H) 5.45 (d, J = 17.42 Hz, 1 H) 5.52 (dd, J = 10.32, 2.52 Hz, 1 H) 7.40-7.48 (m, 3 H) 8.11-8.15 (m, 2 H) |

TABLE 2-continued

Formula (C)

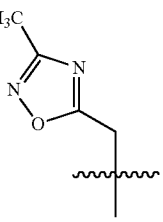

[Formula 32]

| Example | R²⁹ | ESI MS (M + H) | ¹H-NMR, CDCl₃, δ (ppm) |
|---|---|---|---|
| 151 | 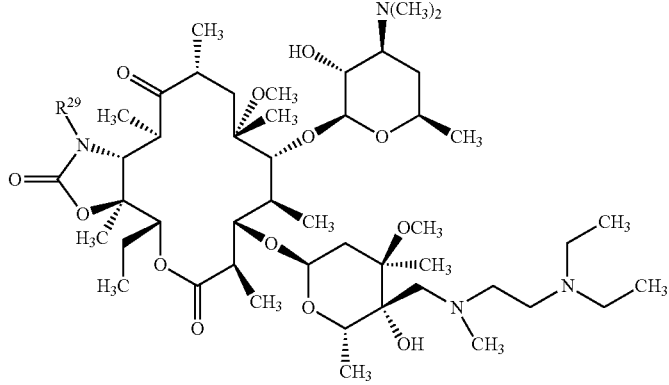 | 1011.6 | (600 MHz): 0.89 (t, J = 7.34 Hz, 3 H) 0.96-1.28 (m, 28 H) 1.33 (s, 3 H) 1.44 (s, 3 H) 1.46-1.53 (m, 1 H) 1.61-1.79 (m, 3 H) 1.84 (t, J = 7.34 Hz, 1 H) 1.92-2.03 (m, 3 H) 2.08 (d, J = 14.67 Hz, 1 H) 2.28 (s, 6 H) 2.33 (s, 3 H) 2.39 (s, 3 H) 2.41-2.62 (m, 10 H) 2.65 (s, 3 H) 2.75-2.80 (m, 1 H) 2.82 (d, J = 14.67 Hz, 1 H) 3.09 (q, J = 6.88 Hz, 1 H) 3.17 (dd, J = 10.09, 7.34 Hz, 1 H) 3.27 (s, 3 H) 3.38 (br. s, 1 H) 3.41-3.47 (m, 1 H) 3.58-3.64 (m, 3 H) 4.03-4.09 (m, 1 H) 4.39 (d, J = 6.88 Hz, 1 H) 4.93 (d, J = 4.58 Hz, 1 H) 4.99 (d, J = 17.88 Hz, 1 H) 5.39 (d, J = 17.42 Hz, 1 H) 5.53 (dd, J = 10.09, 2.75 Hz, 1 H) |
| 152 | 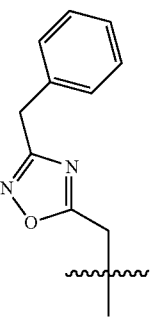 [SMILES: *Cc1nc(Cc2ccccc2)no1] | 1087.7 | (600 MHz): 0.86 (t, J = 7.34 Hz, 3 H) 0.98-1.27 (m, 28 H) 1.32 (s, 3 H) 1.43 (s, 3 H) 1.46-1.49 (m, 1 H) 1.62-1.78 (m, 3 H) 1.82-2.05 (m, 4 H) 2.08 (d, J = 15.59 Hz, 1 H) 2.28 (s, 6 H) 2.34 (s, 3 H) 2.39-2.64 (m, 10 H) 2.62 (s, 3 H) 2.77-2.86 (m, 2 H) 3.06-3.11 (m, 1 H) 3.17 (dd, J = 9.86, 7.11 Hz, 1 H) 3.27 (s, 3 H) 3.39 (br. s., 1 H) 3.46 (br. s., 1 H) 3.58-3.66 (m, 3 H) 4.04-4.13 (m, 3 H) 4.40 (d, J = 7.34 Hz, 1 H) 4.94-5.01 (m, 2 H) 5.40 (d, J = 17.42 Hz, 1 H) 5.49 (dd, J = 10.09, 2.75 Hz, 1 H) 7.19-7.35 (m, 5 H) |
| 153 | 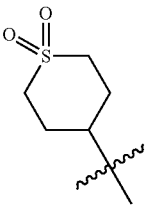 [SMILES: *C1CCS(=O)(=O)CC1] | 1047.7 | (600 MHz): 0.84 (t, J = 7.34 Hz, 3 H) 1.00-1.28 (m, 32 H) 1.36 (s, 3 H) 1.41 (s, 3 H) 1.49-1.54 (m, 1 H) 1.64-1.78 (m, 3 H) 1.81-1.93 (m, 2 H) 1.98-2.02 (m, 2 H) 2.10 (d, J = 14.67 Hz, 1 H) 2.29 (s, 6 H) 2.35 (s, 3 H) 2.38-2.64 (m, 11 H) 2.80-2.91 (m, 3 H) 2.99 (q, J = 6.72 Hz, 1 H) 3.05 (s, 3 H) 3.11-3.31 (m, 3 H) 3.28 (s, 3 H) 3.38-3.51 (m, 3 H) 3.57 (s, 1 H) 3.68-3.75 (m, 2 H) 4.07-4.11 (m, 1 H) 4.42 (d, J = 7.34 Hz, 1 H) 4.85 (dd, J = 11.00, 1.83 Hz, 1 H) 4.99 (d, J = 4.58 Hz, 1 H) |
| 154 | 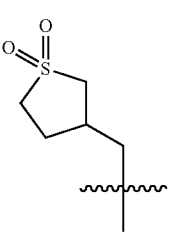 [SMILES: *CC1CCS(=O)(=O)C1] | 1047.7 | (600 MHz): 0.81-0.87 (m, 3 H) 0.95-1.27 (m, 28 H) 1.40 (s, 6 H) 1.50-1.53 (m, 1 H) 1.74 (d, J = 3.21 Hz, 3 H) 1.83-2.05 (m, 5 H) 2.09 (d, J = 15.13 Hz, 1 H) 2.28 (s, 6 H) 2.34 (s, 3 H) 2.36-2.64 (m, 12 H) 2.77-2.95 (m, 4 H) 2.97-3.21 (m, 5 H) 3.28 (s, 3 H) 3.29-3.36 (m, 1 H) 3.42-3.51 (m, 3 H) 3.62-3.74 (m, 4 H) 3.88-3.98 (m, 1 H) 4.06-4.11 (m, 1 H) 4.41 (d, J = 7.34 Hz, 1 H) 4.81-4.91 (m, 1 H) 4.96-5.01 (m, 1 H) |

TABLE 2-continued

Formula (C)

[Chemical structure of Formula (C) - macrolide compound with R29N group]

[Formula 32]

| Example | R[29] | ESI MS (M + H) | $^1$H-NMR, CDCl$_3$, δ (ppm) |
|---|---|---|---|
| 155 | [Structure: N-methyl-N-benzyl amide group, H$_3$C-N(CH$_2$Ph)-C(=O)-CH$_2$-] | 1076 | (400 MHz): 0.93 (t, J = 7.32 Hz, 3 H) 1.00-1.29 (m, 28 H) 1.32-1.39 (m, 3 H) 1.42-1.46 (m, 3 H) 1.47-1.81 (m, 4 H) 1.89-2.06 (m, 4 H) 2.10 (d, J = 14.89 Hz, 1 H) 2.29 (s, 6 H) 2.34 (s, 3 H) 2.40-2.64 (m, 10 H) 2.76-2.89 (m, 6 H) 2.92 (s, 3 H) 3.04-3.14 (m, 1 H) 3.18 (dd, J = 10.01, 7.57 Hz, 1 H) 3.28 (s, 3 H) 3.39 (s, 1 H) 3.42-3.52 (m, 1 H) 3.66 (d, J = 7.32 Hz, 1 H) 3.69-3.76 (m, 2 H) 4.08 (q, J = 8.10 Hz, 1 H) 4.39-4.51 (m, 3 H) 4.62-4.92 (m, 2 H) 4.96-5.02 (m, 1 H) 5.76-5.85 (m, 1 H) 7.21-7.40 (m, 5 H) |
| 156 | [Structure: H$_2$N-C(=O)-C(CH$_3$)$_2$-CH$_2$-] | | (500 MHz): 0.87 (t, J = 7.26 Hz, 3 H) 0.98-1.06 (m, 9 H) 1.09 (d, J = 7.64 Hz, 3 H) 1.11-1.27 (m, 16 H) 1.38 (s, 3 H) 1.43 (s, 3 H) 1.53-1.79 (m, 4 H) 1.84-2.04 (m, 4 H) 2.09 (d, J = 14.52 Hz, 1 H) 2.29 (s, 6 H) 2.34 (s, 3 H) 2.40-2.64 (m, 2 H) 2.80-2.92 (m, 2 H) 2.99 (s, 3 H) 3.06-3.12 (m, 1 H) 3.15-3.21 (m, 1 H) 3.27 (s, 3 H) 3.41-3.51 (m, 1 H) 3.65-3.74 (m, 2 H) 3.78 (s, 3 H) 4.03-4.11 (m, 1 H) 4.22 (d, J = 17.00 Hz, 1 H) 4.41 (d, J = 7.26 Hz, 1 H) 4.58 (d, J = 17.00 Hz, 1 H) 4.97 (d, J = 4.20 Hz, 1 H) 5.17 (dd, J = 10.70, 1.91 Hz, 1 H) 5.29-5.40 (m, 1 H) 6.36-6.48 (m, 1 H) |
| 157 | [Structure: (CH$_3$)$_2$N-C(=O)-CH$_2$-] | 1000.7 | (600 MHz): 0.91 (t, J = 7.34 Hz, 3 H) 1.02 (t, J = 7.11 Hz, 6 H) 1.06 (t, J = 7.11 Hz, 6 H) 1.14 (d, J = 6.88 Hz, 3 H) 1.15 (s, 3 H) 1.17 (d, J = 6.42 Hz, 3 H) 1.19 (d, J = 7.34 Hz, 3 H) 1.20-1.24 (m, 3 H) 1.22 (d, J = 6.42 Hz, 3 H) 1.36 (s, 3 H) 1.43 (s, 3 H) 1.47-1.54 (m, 1 H) 1.62-1.67 (m, 1 H) 1.70-1.79 (m, 2 H) 1.90-1.99 (m, 3 H) 2.00-2.05 (m, 1 H) 2.09 (d, J = 15.13 Hz, 1 H) 2,25-2.31 (m, 6 H) 2.34 (s, 3 H) 2.39-2.60 (m, 8 H) 2.43 (d, J = 8.25 Hz, 1 H) 2.54-2.58 (m, 1 H) 2.77-2.80 (m, 1 H) 2.83 (d, J = 14.67 Hz, 1 H) 2.89 (s, 3 H) 2.93 (s, 3 H) 3.04 (s, 3 H) 3.05-3.10 (m, 1 H) 3.18 (dd, J = 10.09, 7.34 Hz, 1 H) 3.27 (s, 3 H) 3.38 (br. s., 1 H) 3.44-3.49 (m, 1 H) 3.66 (d, J = 7.34 Hz, 1 H) 3.88-3.72 (m, 1 H) 3.70 (s, 1 H) 4.05-4.10 (m, 1 H) 4.34 (d, J = 16.96 Hz, 1 H) 4.41 (d, J = 7.34 Hz, 1 H) 4.76 (d, J = 16.96 Hz, 1 H) 4.97 (d, J = 4.13 Hz, 1 H) 6.73 (dd, J = 9.86, 3.44 Hz, 1 H) |
| 158 | [Structure: phenyl-CH$_2$-CH$_2$-] | 1005.8 | (600 MHz): 0.83 (t, J = 7.34 Hz, 3 H) 0.99-1.05 (m, 9 H) 1.07 (d, J = 6.88 Hz, 3 H) 1.11-1.16 (m, 12 H) 1.17-1.21 (m, 1 H) 1.21 (d, J = 6.42 Hz, 3 H) 1.31 (s, 3 H) 1.42 (s, 3 H) 1.45-1.52 (m, 1 H) 1.58-1.74 (m, 3 H) 1.82-1.87 (m, 1 H) 1.91-2.02 (m, 3 H) 2.07 (d, J = 14.67 Hz, 1 H) 2.28 (s, 6 H) 2.33 (s, 3 H) 2.37-2.62 (m, 9 H) 2.39-2.42 (m, 1 H) 2.44 (s, 3 H) 2.78 (d, J = 7.34 Hz, 1 H) 2.81 (d, J = 14.67 Hz, 1 H) 3.10-3.19 (m, 2 H) 3.26 (s, 3 H) 3.37-3.41 (m, 1 H) 3.41-3.47 (m, 1 H) 3.54 (d, J = 8.71 Hz, 1 H) 3.56 (d, J = 7.79 Hz, 1 H) 3.58 (s, 1 H) 4.02-4.07 (m, 1 H) 4.37 (d, J = 7.34 Hz, 1 H) 4.82-4.96 (m, 2 H) 4.90 (d, J = 4.58 Hz, 1 H) 4.97-5.02 (m, 1 H) 7.21-7.25 (m, 1 H) 7.30 (t, J = 7.34 Hz, 2 H) 7.42 (d, J = 7.34 Hz, 2 H) |
| 159 | [Structure: cyclopropyl-CH$_2$-CH$_2$-] | 969.8 | (600 MHz): 0.29-0.33 (m, 1 H) 0.34-0.39 (m, 1 H) 0.51-0.54 (m, 2 H) 0.85 (t, J = 7.34 Hz, 3 H) 0.99-1.04 (m, 9 H) 1.10 (d, J = 7.34 Hz, 3 H) 1.13 (d, J = 7.34 Hz, 3 H) 1.16 (s, 3 H) 1.18 (d, J = 5.96 Hz, 3 H) 1.20 (d, J = 7.34 Hz, 3 H) 1.21-1.25 (m, 2 H) 1.23 (d, J = 5.96 Hz, 3 H) 1.39 (s, 3 H) 1.40 (s, 3 H) 1.49-1.55 (m, 1 H) 1.65 (d, J = 13.30 Hz, 1 H) 1.70-1.81 (m, 2 H) 1.90-1.99 (m, 3 H) 2.00-2.05 (m, 1 H) 2.09 (d, J = 14.67 Hz, 1 H) 2.29 (s, 6 H) 2.34 (s, 3 H) 2.40-2.83 (m, 10 H) 2.83 (d, J = 14.67 Hz, 1 H) 2.85-2.91 (m, 1 H) 3.03 (s, 3 H) 3.07-3.12 (m, 1 H) 3.13-3.22 (m, 2 H) 3.28 (s, 3 H) 3.42 (br. s., 1 H) 3.44-3.51 (m, 1 H) 3.69-3.74 (m, 3 H) 3.77-3.83 (m, 1 H) 4.07-4.12 (m, 1 H) 4.42 (d, J = 7.34 Hz, 1 H) 4.98 (d, J = 4.58 Hz, 1 H) 5.15 (dd, J = 10.77, 2.52 Hz, 1 H) |

TABLE 2-continued

Formula (C)

[Formula 32]

| Example | R²⁹ | ESI MS (M + H) | ¹H-NMR, CDCl₃, δ (ppm) |
|---|---|---|---|
| 160 | (1-diphenylmethyl-azetidin-3-yl) | 1136.9 | (500 MHz): 0.83 (t, J = 7.40 Hz, 3 H) 0.97 (d, J = 6.86 Hz, 3 H) 1.00-1.10 (m, 12 H) 1.14-1.17 (m, 3 H) 1.17-1.27 (m, 10 H) 1.34 (s, 3 H) 1.35 (s, 3 H) 1.46-1.66 (m, 1 H) 1.62-1.74 (m, 3 H) 1.82-1.91 (m, 2 H) 1.94-2.05 (m, 2 H) 2.10 (d, J = 14.81 Hz, 1 H) 2.28 (s, 6 H) 2.35 (s, 3 H) 2.53 (m, 10 H) 2.81-2.90 (m, 2 H) 2.91 (s, 3 H) 2.95-3.01 (m, 1 H) 3.17 (dd, J = 10.28, 7.27 Hz, 1 H) 3.27 (s, 3 H) 3.38-3.49 (m, 2 H) 3.55 (s, 1 H) 3.62 (t, J = 7.68 Hz, 1 H) 3.60-3.63 (m, 1 H) 3.65-3.75 (m, 3 H) 3.85 (t, J = 6.99 Hz, 1 H) 4.06-4.17 (m, 2 H) 4.42 (d, J = 7.13 Hz, 1 H) 4.63 (s, 1 H) 4.92-4.96 (m, 1 H) 4.99 (d, J = 4.11 Hz, 1 H) 7.11-7.17 (m, 2 H) 7.22-7.26 (m, 4 H) 7.41-7.49 (m, 4 H) |
| 161 | (azetidin-3-yl) | 970.7 | (500 MHz): 0.85 (t, J = 7.27 Hz, 3 H) 1.00-1.05 (m, 9 H) 1.07-1.12 (m, 6 H) 1.16 (s, 3 H) 1.18-1.26 (m, 10 H) 1.36 (s, 3 H) 1.39 (s, 3 H) 1.50-1.58 (m, 1 H) 1.62-1.68 (m, 1 H) 1.70-1.75 (m, 2 H) 1.82-2.05 (m, 4 H) 2.10 (d, J = 14.81 Hz, 1 H) 2.29 (s, 6 H) 2.34 (s, 3 H) 2.39-2.63 (m, 10 H) 2.83 (d, J = 14.81 Hz, 1 H) 2.86-2.92 (m, 1 H) 2.96-3.03 (m, 1 H) 3.08 (s, 3 H) 3.16-3.21 (m, 1 H) 3.28 (s, 3 H) 3.45-3.51 (m, 1 H) 3.58 (s, 1 H) 3.61-3.66 (m, 1 H) 3.69-3.74 (m, 2 H) 3.92-3.98 (m, 1 H) 4.09 (q, J = 6.31 Hz, 1 H) 4.17 (t, J = 7.68 Hz, 1 H) 4.28-4.39 (m, 2 H) 4.43 (d, J = 7.40 Hz, 1 H) 4.94-5.01 (m, 2 H) |
| 162 | (1-methanesulfonyl-azetidin-3-yl) | 1048.7 | (500 MHz): 0.85 (t, J = 7.27 Hz, 3 H) 0.99-1.06 (m, 9 H) 1.07-1.12 (m, 6 H) 1.16 (s, 3 H) 1.20 (d, J = 6.31 Hz, 6 H) 1.22-1.27 (m, 4 H) 1.37 (s, 3 H) 1.40 (s, 3 H) 1.51-1.60 (m, 1 H) 1.63-1.69 (m, 1 H) 1.70-1.76 (m, 2 H) 1.77-1.90 (m, 2 H) 1.94-2.04 (m, 2 H) 2.10 (d, J = 14.81 Hz, 1 H) 2.29 (s, 6 H) 2.35 (s, 3 H) 2.39-2.64 (m, 10 H) 2.81-2.92 (m, 2 H) 2.95-3.00 (m, 1 H) 3.04 (s, 3 H) 3.09 (s, 3 H) 3.15-3.20 (m, 1 H) 3.27 (s, 3 H) 3.44-3.52 (m, 1 H) 3.61 (s, 1 H) 3.72 (t, J = 7.54 Hz, 2 H) 4.04-4.12 (m, 2 H) 4.15-4.22 (m, 1 H) 4.39-4.47 (m, 3 H) 4.64 (t, J = 7.54 Hz, 1 H) 4.84 (dd, J = 10.97, 1.92 Hz, 1 H) 4.99 (d, J = 3.29 Hz, 1 H) |
| 163 | (1-methanesulfonyl-pyrrolidin-3-yl) | 1062.7 | (500 MHz): 0.85 (t, J = 7.45 Hz, 3 H) 1.00-1.13 (m, 15 H) 1.16 (s, 3 H) 1.18-1.27 (m, 10 H) 1.36 (s, 3 H) 1.40 (s, 3 H) 1.49-1.59 (m, 1 H) 1.63-1.78 (m, 3 H) 1.82-1.92 (m, 2 H) 1.94-2.05 (m, 2 H) 2.10 (d, J = 14.91 Hz, 1 H) 2.25-2.33 (m, 7 H) 2.34 (s, 3 H) 2.36-2.85 (m, 11 H) 2.81-2.92 (m, 2 H) 2.94 (s, 3 H) 2.95-3.00 (m, 1 H) 3.02 (s, 3 H) 3.18 (dd, J = 10.32, 7.26 Hz, 1 H) 3.28 (s, 3 H) 3.31-3.37 (m, 1 H) 3.44-3.51 (m, 1 H) 3.55-3.62 (m, 1 H) 3.64 (s, 1 H) 3.68-3.76 (m, 2 H) 3.91-4.05 (m, 2 H) 4.09 (q, J = 6.50 Hz, 1 H) 4.12-4.18 (m, 1 H) 4.42 (d, J = 7.26 Hz, 1 H) 4.88 (dd, J = 10.89, 2.10 Hz, 1 H) 4.99 (d, J = 4.59 Hz, 1 H) |

TABLE 2-continued

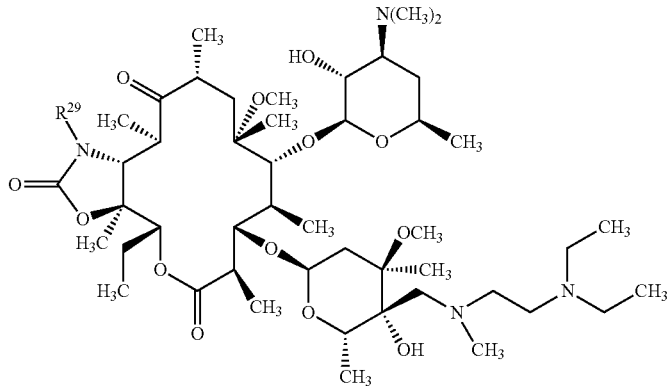

Formula (C)

[Formula 32]

| Example | R[29] | ESI MS (M + H) | $^1$H-NMR, CDCl$_3$, δ (ppm) |
|---|---|---|---|
| 164 | (methanesulfonyl-pyrrolidin-3-yl) | 1062.7 | (500 MHz): 0.86 (t, J = 7.26 Hz, 3 H) 1.01-1.06 (m, 6 H) 1.09 (d, J = 6.88 Hz, 6 H) 1.12 (d, J = 7.26 Hz, 3 H) 1.16 (s, 3 H) 1.17-1.27 (m, 10 H) 1.36 (s, 3 H) 1.40 (s, 3 H) 1.49-1.59 (m, 1 H) 1.62-1.68 (m, 1 H) 1.71-1.78 (m, 2 H) 1.80-1.89 (m, 2 H) 1.94-2.05 (m, 2 H) 2.10 (d, J = 14.52 Hz, 1 H) 2.29 (s, 6 H) 2.34 (s, 3 H) 2.40-2.77 (m, 12 H) 2.81-2.91 (m, 5 H) 2.97-3.03 (m, 1 H) 3.03-3.06 (m, 3 H) 3.18 (dd, J = 10.32, 7.26 Hz, 1 H) 3.27 (s, 3 H) 3.39-3.52 (m, 3 H) 3.56-3.62 (m, 1 H) 3.63-3.66 (m, 1 H) 3.69-3.74 (m, 2 H) 3.78 (t, J = 8.98 Hz, 1 H) 3.98-4.12 (m, 2 H) 4.43 (d, J = 7.26 Hz, 1 H) 4.81 (dd, J = 10.89, 2.10 Hz, 1 H) 4.99 (d, J = 3.44 Hz, 1 H) |
| 165 | (methanesulfonyl-pyrrolidin-3-ylmethyl) | 1076.8 | (500 MHz): 0.81-0.88 (m, 3 H) 0.96-1.06 (m, 9 H) 1.06-1.27 (m, 19 H) 1.37-1.42 (m, 6 H) 1.50-1.60 (m, 1 H) 1.64 (br. s., 1 H) 1.69-2.25 (m, 9 H) 2.29 (s, 6 H) 2.34 (s, 3 H) 2.39-2.72 (m, 11 H) 2.81-2.86 (m, 2 H) 2.86-2.94 (m, 2 H) 3.02 (s, 3 H) 3.04-3.21 (m, 3 H) 3.28 (s, 3 H) 3.29-3.39 (m, 1 H) 3.43-3.72 (m, 8 H) 3.83-3.94 (m, 1 H) 4.07-4.13 (m, 1 H) 4.41 (dd, J = 7.26, 1.15 Hz, 1 H) 4.84-4.94 (m, 1 H) 4.95-5.00 (m, 1 H) |
| 166 | (methanesulfonyl-azetidin-3-yl methyl) | 1062.7 | (500 MHz): 0.82 (t, J = 7.40 Hz, 3 H) 0.97-1.28 (m, 28 H) 1.38 (s, 3 H) 1.40 (s, 3 H) 1.47-2.13 (m, 9 H) 2.29 (s, 6 H) 2.34 (s, 3 H) 2.40-2.64 (m, 10 H) 2.84 (d, J = 14.81 Hz, 1 H) 2.86-3.14 (m, 10 H) 3.18 (dd, J = 10.15, 7.40 Hz, 1 H) 3.28 (s, 3 H) 3.43-3.51 (m, 1 H) 3.58 (s, 1 H) 3.68-3.73 (m, 3 H) 3.77 (dd, J = 7.95, 5.76 Hz, 1 H) 3.92 (d, J = 7.68 Hz, 2 H) 4.02 (t, J = 8.23 Hz, 1 H) 4.06-4.18 (m, 2 H) 4.42 (d, J = 7.40 Hz, 1 H) 4.74 (dd, J = 10.97, 1.92 Hz, 1 H) 5.00 (d, J = 3.84 Hz, 1 H) |
| 167 | (methanesulfonamido-2-hydroxy-2-methylpropyl) | 1066.7 | (600 MHz): 0.85 (t, J = 7.34 Hz, 3 H) 0.99-1.08 (m, 9 H) 1.08-1.27 (m, 19 H) 1.40 (s, 6 H) 1.54-1.78 (m, 4 H) 1.82-2.04 (m, 4 H) 2.09 (d, J = 14.67 Hz, 1 H) 2.29 (s, 6 H) 2.34 (s, 3 H) 2.40-2.65 (m, 10 H) 2.83 (d, J = 14.67 Hz, 1 H) 2.95 (dd, J = 10.09, 7.34 Hz, 1 H) 3.00 (s, 3 H) 3.08 (s, 3 H) 3.12-3.21 (m, 3 H) 3.28 (s., 3 H) 3.31-3.37 (m, 1 H) 3.43-3.51 (m, 2 H) 3.63 (s, 1 H) 3.65-3.79 (m, 4 H) 3.96-4.02 (m, 1 H) 4.06-4.11 (m, 1 H) 4.42 (d, J = 7.34 Hz, 1 H) 4.90 (br. s., 1 H) 4.96-5.01 (m, 2 H) |

TABLE 2-continued

Formula (C)

[Formula 32]

| Example | R²⁹ | ESI MS (M + H) | ¹H-NMR, CDCl₃, δ (ppm) |
|---|---|---|---|
| 168 | (methanesulfonamido-hydroxybutyl group) | 1066.7 | (600 MHz): 0.86 (t, J = 7.34 Hz, 3 H) 1.00-1.26 (m, 28 H) 1.40 (s, 3 H) 1.40 (s, 3 H) 1.51-2.12 (m, 9 H) 2.29 (s, 6 H) 2.34 (s, 3 H) 2.40-2.64 (m, 10 H) 2.80-2.95 (m, 2 H) 2.98-3.02 (m, 3 H) 3.06 (s, 4 H) 3.15-3.22 (m, 2 H) 3.27 (s, 3 H) 3.34-3.83 (m, 4 H) 3.68-3.73 (m, 3 H) 4.06-4.11 (m, 1 H) 4.19-4.26 (m, 1 H) 4.41 (d, J = 7.34 Hz, 1 H) 4.89-4.93 (m, 1 H) 4.96-4.99 (m, 1 H) 5.01-5.06 (m, 1 H) |
| 169 | (benzyloxy-methyl group) | 1021.6 | (600 MHz) : 0.83 (t, J = 7.34 Hz, 3 H) 0.99 (d, J = 6.88 Hz, 3 H) 1.01-1.05 (m, 6 H) 1.12 (d, J = 6.42 Hz, 6 H) 1.17 (s, 3 H) 1.18-1.22 (m, 3 H) 1.21-1.27 (m, 7 H) 1.42 (s, 3 H) 1.45 (s, 3 H) 1.45-1.54 (m, 2 H) 1.62-1.67 (m, 1 H) 1.72-1.78 (m, 1 H) 1.79-1.88 (m, 1 H) 1.89-1.94 (m, 1 H) 1.98-2.08 (m, 2 H) 2.10 (d, J = 15.13 Hz, 1 H) 2.28 (s, 6 H) 2.35 (s, 3 H) 2.39-2.63 (m, 8 H) 2.40-2.45 (m, 1 H) 2.84 (d, J = 14.87 Hz, 1 H) 2.88-2.96 (m, 3 H) 3.15 (dd, J = 10.32, 7.11 Hz, 1 H) 3.25 (s, 3 H) 3.28 (s, 3 H) 3.40-3.48 (m, 1 H) 3.71 (d, J = 7.79 Hz, 1 H) 3.81 (d, J = 9.63 Hz, 1 H) 4.11-4.15 (m, 1 H) 4.29 (s, 1 H) 4.38 (d, J = 7.34 Hz, 1 H) 4.91-4.97 (m, 2 H) 5.03 (d, J = 4.58 Hz, 1 H) 5.15 (dd, J = 10.77, 2.52 Hz, 1 H) 7.28-7.38 (m, 3 H) 7.47-7.53 (m, 2 H) |
| 170 | (hydroxy-methyl group) | 931.7 | (600 MHz): 0.86 (t, J = 7.34 Hz, 3 H) 1.02 (t, J = 6.88 Hz, 6 H) 1.08 (d, J = 7.34 Hz, 3 H) 1.15 (d, J = 6.88 Hz, 3 H) 1.16-1.16 (m, 3 H) 1.17-1.19 (m, 6 H) 1.21 (d, J = 7.34 Hz, 3 H) 1.23 (d, J = 5.96 Hz, 3 H) 1.23-1.25 (m, 1 H) 1.39 (s, 3 H) 1.40 (s, 3 H) 1.47-1.54 (m, 1 H) 1.63-1.69 (m, 1 H) 1.75-1.85 (m, 3 H) 1.85-1.92 (m, 1 H) 1.93-2.04 (m, 2 H) 2.09 (d, J = 14.67 Hz, 1 H) 2.29 (s, 6 H) 2.34 (s, 3 H) 2.39-2.61 (m, 8 H) 2.41-2.46 (m, 1 H) 2.66-2.73 (m, 1 H) 2.78-2.86 (m, 2 H) 3.00 (s, 3 H) 3.09-3.14 (m, 1 H) 3.17 (dd, J = 10.09, 7.34 Hz, 1 H) 3.28 (s, 3 H) 3.44-3.50 (m, 1 H) 3.69 (d, J = 7.34 Hz, 1 H) 3.76 (d, J = 8.71 Hz, 1 H) 3.79 (s, 1 H) 4.04-4.11 (m, 1 H) 4.42 (d, J = 7.34 Hz, 1 H) 4.99 (d, J = 3.67 Hz, 1 H) 5.18 (dd, J = 10.77, 2.52 Hz, 1 H) 8.86 (br. s., 1 H) |
| 171 | (methoxy-methyl group) | 945.7 | (600 MHz): 0.86 (t, J = 7.34 Hz, 3 H) 1.02 (t, J = 7.11 Hz, 6 H) 1.09-1.15 (m, 9 H) 1.17 (s, 3 H) 1.18-1.22 (m, 4 H) 1.22-1.28 (m, 6 H) 1.43 (s, 3 H) 1.46 (s, 3 H) 1.48 (d, J = 7.79 Hz, 1 H) 1.51-1.69 (m, 1 H) 1.65 (d, J = 12.40 Hz, 1 H) 1.75 (dd, J = 14.67, 5.96 Hz, 1 H) 1.84-1.93 (m, 2 H) 1.97-2.06 (m, 2 H) 2.10 (d, J = 14.67 Hz, 1 H) 2.28 (s, 6 H) 2.34 (br. s., 3 H) 2.39-2.46 (m, 1 H) 2.41-2.63 (m, 8 H) 2.84 (d, J = 14.67 Hz, 1 H) 2.84-2.89 (m, 1 H) 2.90-2.99 (m, 2 H) 3.15 (dd, J = 10.09, 7.34 Hz, 1 H) 3.24 (s, 3 H) 3.28 (s, 3 H) 3.43-3.47 (m, 1 H) 3.71 (d, J = 7.79 Hz, 1 H) 3.78 (s, 3 H) 3.81 (d, J = 10.09 Hz, 1 H) 4.10-4.15 (m, 1 H) 4.29 (s, 1 H) 4.37 (d, J = 7.34 Hz, 1 H) 5.02 (d, J = 4.58 Hz, 1 H) 5.18 (dd, J = 11.00, 2.29 Hz, 1 H) |

Example 148

(1) By using the compound represented by the formula (A) obtained in Example 1, (5) (500 mg) and 3-oxetanamine hydrochloride (0.32 g) as starting materials, a deacetylated compound (0.33 g) was obtained in the same manners as those of Example 15, (1) and Example 4, (6).
(2) By using the compound obtained in (1) mentioned above (130 mg) as a starting material, the compound shown in Table 2 (114 mg) was obtained in the same manner as that of Example 15, (2).

Example 149

(1) By using the compound represented by the formula (A) obtained in Example 1, (5) (329 mg) and the compound obtained in Reference Example 72 (290 mg) as starting materials, a deacetylated compound (114 mg) was obtained in the same manners as those of Example 2, (1) and (2).
(2) By using the compound obtained in (1) mentioned above (64 mg) as a starting material, the compound shown in Table 2 (38 mg) was obtained in the same manner as that of Example 11.

Example 150

By using the compound represented by the formula (A) obtained in Example 1, (5) (200 mg) and (3-phenyl-1,2,4-oxadiazol-5-yl)methylamine (200 mg) as starting materials, the compound shown in Table 2 (46.0 mg) was obtained in the same manners as those of Example 2, (1), (2) and Example 11.

Example 151

By using the compound represented by the formula (A) obtained in Example 1, (5) (200 mg) and [(3-methyl-1,2,4-oxadiazol-5-yl)methyl]amine hydrochloride (172 mg) as starting materials, the compound shown in Table 2 (41.4 mg) was obtained in the same manners as those of Example 15, (1), (2) and Example 11.

Example 152

By using the compound represented by the formula (A) obtained in Example 1, (5) (153 mg) and (3-benzyl-[1,2,4]oxadiazol-5-yl)-methylamine hydrochloride (118 mg) as starting materials, the compound shown in Table 2 (53.3 mg) was obtained in the same manners as those of Example 15, (1), Example 4, (6) and Example 11.

Example 153

(1) By using the compound represented by the formula (A) obtained in Example 1, (5) (329 mg) and 4-aminotetrahydro-2H-thiopyrane 1,1-dioxide hydrochloride (159 mg) as starting materials, a deacetylated compound (226 mg) was obtained in the same manners as those of Example 15, (1) and Example 2, (2).
(2) By using the compound obtained in (1) mentioned above (108 mg) as a starting material, the compound shown in Table 2 (27.3 mg) was obtained in the same manner as that of Example 11.

Example 154

By using the compound represented by the formula (A) obtained in Example 1, (5) (150 mg) and [(1,1-dioxidotetrahydro-3-thienyl)methyl]amine hydrochloride (95 mg) as starting materials, the compound shown in Table 2 (56.5 mg) was obtained in the same manners as those of Example 15, (1), Example 4, (6) and Example 11.

Example 155

By using the compound represented by the formula (A) obtained in Example 1, (5) (100 mg) and the compound obtained in Reference Example 93 (94 mg) as starting materials, the compound shown in Table 2 (55 mg) was obtained in the same manners as those of Example 2, (1), (2) and Example 11.

Example 156

(1) By using the compound represented by the formula (A) obtained in Example 1, (5) (500 mg) and glycinamide hydrochloride (0.32 g) as starting materials, a deacetylated compound (0.32 g) was obtained in the same manners as those of Example 15, (1) and Example 4, (6).
(2) By using the compound obtained in (1) mentioned above (100 mg) as a starting material, the compound shown in Table 2 (75 mg) was obtained in the same manner as that of Example 15, (2).
The compound represented by the formula (A) obtained in Example 1, (5)

Example 157

By using the compound represented by the formula (A) obtained in Example 1, (5) (325 mg) and 2-amino-N,N-dimethylacetamide (189 mg) as starting materials, the compound shown in Table 2 (62.3 mg) was obtained in the same manners as those of Example 4, (1), Example 2, (2) and Example 11.

Example 158

By using the compound represented by the formula (A) obtained in Example 1, (5) (500 mg) and benzylamine (622 µl) as starting materials, the compound shown in Table 2 (50.1 mg) was obtained in the same manners as those of Example 4, (1), (6) and Example 11.

Example 159

By using the compound represented by the formula (A) obtained in Example 1, (5) (500 mg) and cyclopropylmethylamine (487 µl) as starting materials, the compound shown in Table 2 (34.9 mg) was obtained in the same manners as those of Example 4, (1), (6) and Example 11.

Example 160

(1) The compound represented by the formula (A) obtained in Example 1, (5) (500 mg) and 1-(diphenylmethyl)-3-aminoazetidine hydrochloride (783 mg) were dissolved in a mixed solvent of acetonitrile and chloroform (1:1, 6 ml), 1,8-diazabicyclo[5,4,0]-7-undecene (400 µl) was added to the solution, and the resulting mixture was stirred at room temperature for 16 hours. The reaction mixture was concentrated under reduced pressure, and the resulting residue was purified by silica gel column chromatography (hexane:acetone:triethylamine=10:10:0.2) to obtain a carbamate compound (0.83 g).
(2) By using the compound obtained in (1) mentioned above (0.83 g) and N,N-diethyl-N'-methylethane-1,2-diamine (0.40 g) as starting materials, the compound shown in Table 2 (200 mg) was obtained in the same manner as that of Example 2, (5).

Example 161

The compound obtained in Example 160 (190 mg) was dissolved in tetrahydrofuran (5 ml), 20% palladium hydrox-

193 ide/carbon (800 mg) was added to the solution, and the resulting mixture was stirred at room temperature for 2 days under a hydrogen atmosphere of 1 atm. The reaction mixture was filtered thorough Celite, the filtrate was concentrated under reduced pressure, and the resulting residue was purified by silica gel column chromatography (chloroform:methanol: 28% aqueous ammonia=10:1:0.1) to obtain the compound shown in Table 2 (110 mg).

Example 162

The compound obtained in Example 161 (54 mg) was dissolved in tetrahydrofuran (5 ml), methanesulfonyl chloride (5 µl) was added to the solution, and the resulting mixture was stirred at room temperature for 30 minutes. Saturated aqueous sodium hydrogencarbonate was added to the reaction mixture, and the resulting mixture was extracted with chloroform. The organic layer was washed with saturated aqueous sodium chloride, dried over anhydrous magnesium sulfate, and filtered. The filtrate was concentrated under reduced pressure, and the resulting residue was purified by preparative thin layer chromatography (chloroform:methanol:28% aqueous ammonia=10:1:0.1) to obtain the compound shown in Table 2 (52 mg).

Example 163

(1) The compound represented by the formula (A) obtained in Example 1, (5) (500 mg) and the compound obtained in Reference Example 73 (1.10 g) were dissolved in chloroform (2 ml), and the resulting mixture was stirred at room temperature for 3 hours. 1,1,3,3-Tetramethylguanidine (72 µl) was added to the reaction mixture, and the resulting mixture was stirred at room temperature for 16 hours. 1,1,3,3-Tetramethylguanidine (72 µl) was added to the reaction mixture, and the resulting mixture was stirred at room temperature for 24 hours. Saturated aqueous ammonium chloride was added to the reaction mixture, and the resulting mixture was extracted with chloroform. The organic layer was dried over anhydrous magnesium sulfate, and filtered. The filtrate was concentrated under reduced pressure, and the resulting residue was purified by silica gel column chromatography (chloroform:methanol: 28% aqueous ammonia=200:1:0.1) to obtain a carbamate compound (0.29 g).
(2) By using the compound obtained in (1) mentioned above (140 mg) and N,N-diethyl-N'-methylethane-1,2-diamine (190 mg) as starting materials, the compound shown in Table 2 (77 mg) was obtained in the same manner as that of Example 2, (5).

Example 164

(1) By using the compound represented by the formula (A) obtained in Example 1, (5) (500 mg) and the compound obtained in Reference Example 74 (0.96 g) as starting materials, a carbamate compound (0.36 g) was obtained in the same manner as that of Example 163, (1).
(2) By using the compound obtained in (1) mentioned above (180 mg) and N,N-diethyl-N'-methylethane-1,2-diamine (240 mg) as starting materials, the compound shown in Table 2 (118 mg) was obtained in the same manner as that of Example 2, (5).

Example 165

(1) By using the compound represented by the formula (A) obtained in Example 1, (5) (500 mg) and the compound obtained in Reference Example 75 (0.78 g) as starting materials, a carbamate compound (150 mg) was obtained in the same manner as that of Example 163, (1).

194

(2) By using the compound obtained in (1) mentioned above (140 mg) and N,N-diethyl-N'-methylethane-1,2-diamine (0.18 ml) as starting materials, the compound shown in Table 2 (100 mg) was obtained in the same manner as that of Example 2, (5).

Example 166

(1) By using the compound represented by the formula (A) obtained in Example 1, (5) (1.91 g), and 3-amino-1-diphenylmethylazetidine (2.75 g) as starting materials, a carbamate compound (1.71 g) was obtained in the same manner as that of Example 2, (1).
(2) The compound obtained in (1) mentioned above (1.7 g) was dissolved in tetrahydrofuran (5 ml), 20% palladium hydroxide/carbon (3.4 g) was added to the solution, and the resulting mixture was stirred overnight at room temperature under a hydrogen atmosphere of 1 atm. A mixed solvent of chloroform:methanol:28% aqueous ammonia=10:1:0.1 was added to the reaction mixture, and the resulting mixture was stirred for 0.5 hour. The reaction mixture was filtered, the filtrate was concentrated under reduced pressure, and the resulting residue was purified by silica gel column chromatography (chloroform:methanol:28% aqueous ammonia=100:1:0.1 to 10:1:0.1) to obtain a deprotected compound (877 mg).
(3) By using the compound obtained in (2) mentioned above (200 mg) as a starting material, a deprotected compound (149 mg) was obtained in the same manners as those of Example 71, (2) and Example 2, (2).
(4) By using the compound obtained in (3) mentioned above (50 mg) as a starting material, the compound shown in Table 2 (31 mg) was obtained in the same manner as that of Example 11.

Example 167

(1) By using the compound represented by the formula (A) obtained in Example 1, (5) (500 mg) and 1,3-diamino-2-propanol (0.51 g) as starting materials, a carbamate compound (0.34 g) was obtained in the same manner as that of Example 2, (1).
(2) By using the compound obtained in (1) mentioned above (155 mg) as a starting material, a methanesulfonyl compound was obtained in the same manner as that of Example 162.
(3) By using the compound obtained in (2) mentioned above and N,N-diethyl-N'-methylethane-1,2-diamine (0.23 ml) as starting materials, the compound shown in Table 2 (52 mg) was obtained in the same manner as that of Example 2, (5).

Example 168

(1) By using the compound represented by the formula (A) obtained in Example 1, (5) (500 mg) and 1,3-diamino-2-propanol (0.51 g) as starting materials, a carbamate compound (0.34 g) was obtained in the same manner as that of Example 2, (1).
(2) By using the compound obtained in (1) mentioned above (155 mg) as a starting material, a methanesulfonyl compound was obtained in the same manner as that of Example 162.
(3) By using the compound obtained in (2) mentioned above and N,N-diethyl-N'-methylethane-1,2-diamine (230 µl) as starting materials, the compound shown in Table 2 (28 mg) was obtained in the same manner as that of Example 2, (5).

Example 169

(1) The compound represented by the formula (SM1) (2.0 g) obtained by the method described in the publication (International Patent Publication WO93/21199) was dissolved in acetonitrile (20 ml), imidazole (900 mg) and O-benzylhydroxylamine hydrochloride (1.76 g) was added to the solution, and the resulting mixture was stirred under reflux by heating for 4 hours. The reaction mixture was concentrated under reduced pressure, ethyl acetate and saturated aqueous sodium hydrogencarbonate were added to the resulting residue, and the layers were separated. The organic layer was washed with saturated aqueous sodium hydrogencarbonate, dried over anhydrous magnesium sulfate, and filtered. The filtrate was concentrated under reduced pressure, and the resulting residue was purified by silica gel column chromatography (chloroform:methanol:28% aqueous ammonia=100:1:0.1 to 10:1:0.1) to obtain a carbamate compound (722 mg).
(2) By using the compound obtained in (1) mentioned above (722 mg) as a starting material, an epoxy compound (163 mg) was obtained in the same manners as those of Example 2, (2), Example 1, (1), (3), Example 4, (6) and Example 1, (4).
(3) By using the compound obtained in (2) mentioned above (50.0 mg) as a starting material, the compound shown in Table 2 (33.2 mg) was obtained in the same manner as that of Example 11.

Example 170

(1) The compound obtained in Example 169, (2) (113 mg) was dissolved in methanol (3 ml), 10% palladium/carbon (113 mg) was added to the solution, and the resulting mixture was stirred at room temperature for 6 hours under a hydrogen atmosphere of 1 atm. The reaction mixture was filtered, and then the filtrate was concentrated under reduced pressure. The resulting residue was dissolved in methanol (3 ml), 10% palladium/carbon (220 mg) was added to the solution, and the resulting mixture was stirred at room temperature for 11 hours under a hydrogen atmosphere of 1 atm. The reaction mixture was filtered, then the filtrate was concentrated under reduced pressure, and the resulting residue was purified by silica gel column chromatography (chloroform:methanol: 28% aqueous ammonia=100:1:0.1 to 10:1:0.1) to obtain a debenzylated compound (77.7 mg).
(2) By using the compound obtained in (1) mentioned above (77.7 mg) as a starting material, the compound shown in Table 2 (37.3 mg) was obtained in the same manner as that of Example 11.

Example 171

(1) By using the compound represented by the formula (SM1) (4.0 g) obtained by the method described in the publication (International Patent Publication WO93/21199) and O-methylhydroxylamine hydrochloride (1.8 g) as starting materials, an epoxy compound (355 mg) was obtained in the same manners as those of Example 169, (1), Example 2, (2), Example 1, (1), (3), Example 4, (6) and Example 1, (4).
(2) By using the compound obtained in (1) mentioned above (100 mg) as a starting material, the compound shown in Table 2 (55.6 mg) was obtained in the same manner as that of Example 11.

Examples 172 to 182

Preparation methods of the compounds represented by the formula (D) having $R^{29b}$ and $R^{2a}$ defined in Table 3 are shown below.

TABLE 3

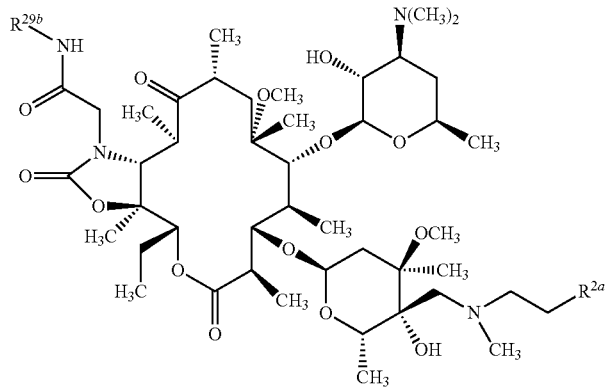

Formula (D)

[Formula 33]

| Example | $R^{29b}$ | $R^{2a}$ | ESI MS (M + H) | $^1$H-NMR, CDCl$_3$, δ (ppm) |
|---|---|---|---|---|
| 172 | ![benzyl] | ![N(CH3)(CH2CH3)] | 1062 | (400 MHz): 0.68 (t, J = 7.32 Hz, 3 H) 0.99 (d, J = 6.84 Hz, 3 H) 1.03 (t, J = 7.08 Hz, 6 H) 1.08 (d, J = 7.57 Hz, 3 H) 1.12 (d, J = 7.08 Hz, 3 H) 1.16 (s, 3 H) 1.17-1.26 (m, 1 H) 1.18 (d, J = 7.08 Hz, 3 H) 1.19 (d, J = 6.35 Hz, 3 H) 1.24 (d, J = 6.10 Hz, 3 H) 1.37 (s, 3 H) 1.40 (s, 3 H) 1.46-1.90 (m, 7 H) 1.94-2.06 (m, 2 H) 2.10 (d, J = 14.65 Hz, 1 H) 2.28 (s, 6 H) 2.35 (s, 3 H) 2.38-2.65 (m, 10 H) 2.80-2.89 (m, 2 H) 2.92 (s, 3 H) 3.07 (q, J = 6.84 Hz, 1 H) 3.17 (dd, J = 10.25, 7.08 Hz, 1 H) 3.28 (s, 3 H) 3.40-3.51 (m, 2 H) 3.65 (d, J = 7.32 Hz, 1 H) 3.71 (d, J = 9.52 Hz, 1 H) 3.79 (s, 1 H) 4.09 (q, J = 6.35 Hz, 1 H) 4.26 (d, J = 14.16 Hz, 1 H) 4.30 (dd, J = 14.41, 4.64 Hz, 1 H) 4.62 (d, J = 17.09 Hz, 1 H) 4.67 (dd, J = 14.65, 6.84 Hz, 1 H) 4.96-5.02 (m, 2 H) 5.75-6.81 (m, 1 H) 7.18-7.32 (m, 5 H) |

TABLE 3-continued

Formula (D)

[Formula 33]

| Example | R$^{29b}$ | R$^{2a}$ | ESI MS (M + H) | $^1$H-NMR, CDCl$_3$, δ (ppm) |
|---|---|---|---|---|
| 173 | benzyl | (2-methylpyrrolidin-1-yl) | 1074.7 | (500 MHz): 0.69 (t, J = 7.40 Hz, 3 H) 0.95-1.28 (m, 25 H) 1.30-1.45 (m, 7 H) 1.46-2.20 (m, 12 H) 2.29 (s, 6 H) 2.32-2.70 (m, 9 H) 2.82-2.96 (m, 6 H) 3.02-3.20 (m, 4 H) 3.28 (s, 3 H) 3.42-3.50 (m, 1 H) 3.64-3.73 (m, 2 H) 3.78 (s, 1 H) 4.10 (q, J = 6.31 Hz, 1 H) 4.21-4.36 (m, 2 H) 4.41 (d, J = 7.40 Hz, 1 H) 4.55-4.69 (m, 2 H) 4.97-5.06 (m, 2 H) 6.79 (t, J = 5.76 Hz, 1 H) 7.16-7.34 (m, 5 H) |
| 174 | benzyl | N-ethyl-N-isopropyl | 1076.8 | (600 MHz): 0.68 (t, J = 7.34 Hz, 3 H) 0.94-1.13 (m, 16 H) 1.14-1.26 (m, 13 H) 1.37 (s, 3 H) 1.39-1.41 (m, 3 H) 1.47-1.60 (m, 1 H) 1.61-1.78 (m, 4 H) 1.81-1.89 (m, 2 H) 1.95-2.10 (m, 2 H) 2.28 (s, 6 H) 2.32-2.64 (m, 11 H) 2.80-2.99 (m, 6 H) 3.02-3.10 (m, 1 H) 3.14-3.20 (m, 1 H) 3.28 (s, 3 H) 3.43-3.50 (m, 1 H) 3.62-3.74 (m, 2 H) 3.78 (s, 1 H) 4.04-4.12 (m, 1 H) 4.23-4.33 (m, 2 H) 4.38-4.43 (m, 1 H) 4.58-4.71 (m, 2 H) 4.95-5.04 (m, 2 H) 6.74-6.80 (m, 1 H) 7.17-7.32 (m, 5 H) |
| 175 | benzyl | N-ethyl-N-(cyclopropylmethyl) | 1088.8 | (500 MHz): 0.08-0.13 (m, 2 H) 0.45-0.53 (m, 2 H) 0.69 (t, J = 7.26 Hz, 3 H) 0.84-0.93 (m, 1 H) 0.97-1.28 (m, 25 H) 1.34-1.39 (m, 3 H) 1.39-1.42 (m, 3 H) 1.46-2.14 (m, 10 H) 2.26-2.30 (m, 6 H) 2.30-2.70 (m, 12 H) 2.81-2.88 (m, 2 H) 2.91 (s, 3 H) 3.07 (q, J = 6.88 Hz, 1 H) 3.18 (dd, J = 10.32, 7.26 Hz, 1 H) 3.28 (s, 3 H) 3.42-3.51 (m, 1 H) 3.63-3.73 (m, 2 H) 3.78 (s, 1 H) 4.09 (q, J = 6.12 Hz, 1 H) 4.23-4.34 (m, 2 H) 4.41 (d, J = 7.26 Hz, 1 H) 4.57-4.69 (m, 2 H) 4.96-5.03 (m, 2 H) 6.76 (dd, J = 6.50, 4.97 Hz, 1 H) 7.18-7.23 (m, 1 H) 7.24-7.31 (m, 4 H) |
| 176 | benzyl | N-ethyl-N-butyl | 1090.8 | (500 MHz): 0.69 (t, J = 7.27 Hz, 3 H) 0.91 (t, J = 7.27 Hz, 3 H) 0.95-1.57 (m, 36 H) 1.61-2.12 (m, 8 H) 2.29 (s, 6 H) 2.35 (s, 3 H) 2.38-2.66 (m, 10 H) 2.78-2.94 (m, 5 H) 3.04-3.11 (m, 1 H) 3.18 (dd, J = 10.28, 7.27 Hz, 1 H) 3.28 (s, 3 H) 3.42-3.52 (m, 1 H) 3.61-3.73 (m, 2 H) 3.78 (s, 1 H) 4.06-4.14 (m, 1 H) 4.22-4.35 (m, 2 H) 4.41 (d, J = 7.13 Hz, 1 H) 4.56-4.70 (m, 2 H) 4.98-5.03 (m, 2 H) 6.82 (dd, J = 6.44, 5.07 Hz, 1 H) 7.14-7.33 (m, 5 H) |
| 177 | phenyl | N,N-diethyl | 1048.7 | (400 MHz): 0.85 (t, J = 7.3 Hz, 3 H) 0.98-1.05 (m, 9 H) 1.07-1.25 (m, 20 H) 1.37 (s, 3 H) 1.39 (s, 3 H) 1.45-1.56 (m, 1 H) 1.62-1.68 (m, 1 H) 1.70-1.78 (m, 2 H) 1.81-1.91 (m, 2 H) 1.97 (dd, J = 14.9, 4.9 Hz, 1 H) 2.03 (d, J = 13.9 Hz, 1 H) 2.09 (d, J = 14.9 Hz, 1 H) 2.28 (s, 6 H) 2.34 (s, 3 H) 2.40-2.61 (m, 10 H) 2.83 (d, J = 14.6 Hz, 1 H) 2.89 (dd, J = 9.5, 7.1 Hz, 1 H) 2.95 (s, 3 H) 3.09 (q, J = 6.8 Hz, 1 H) 3.18 (dd, J = 10.3, 7.3 Hz, 1 H) 3.28 (s, 3 H) 3.36 (dt, J = 15.8, 4.6 Hz, 1 H) 3.41-3.52 (m, 2 H) 3.56-3.66 (m, 1 H) 3.66-3.73 (m, 3 H) 4.03-4.12 (m, 2 H) 4.26 (dt J = 15.8, 4.6 Hz, 1 H) 4.41 (d, J = 7.3 Hz, 1 H) 6.00 (d, J = 3.7 Hz, 1 H) 5.43 (dd, J = 10.9, 1.8 Hz, 1 H) 7.12 (tt, J = 6.7, 2.0 Hz, 1 H) 7.30-7.37 (m, 4 H) 7.73 (s, 1 H) |

TABLE 3-continued

Formula (D)

[Chemical structure of Formula (D) showing macrolide with R29b-NH-C(O)-CH2-N group and R2a substituent]

[Formula 33]

| Example | R29b | R2a | ESI MS (M + H) | 1H-NMR, CDCl3, δ (ppm) |
|---------|------|-----|----------------|------------------------|
| 178 | [3-pyridylmethyl group] | [N(CH2CH3)2 with CH3] | 1063 | (400 MHz): 0.68 (t, J = 7.32 Hz, 3 H) 0.99 (d, J = 6.84 Hz, 3 H) 1.03 (t, J = 7.08 Hz, 6 H) 1.08 (d, J = 7.57 Hz, 3 H) 1.12 (d, J = 7.08 Hz, 3 H) 1.17 (s, 3 H) 1.17-1.26 (m, 1 H) 1.20 (d, J = 6.10 Hz, 6 H) 1.24 (d, J = 6.10 Hz, 3 H) 1.37 (s, 3 H) 1.40 (s, 3 H) 1.48-1.88 (m, 7 H) 1.97-2.07 (m, 2 H) 2.09 (d, J = 14.89 Hz, 1 H) 2.28 (s, 6 H) 2.35 (s, 3 H) 2.38-2.65 (m, 10 H) 2.84 (d, J = 14.65 Hz, 1 H) 2.84-2.91 (m, 1 H) 2.89 (s, 3 H) 3.07 (q, J = 7.08 Hz, 1 H) 3.18 (dd, J = 10.25, 7.32 Hz, 1 H) 3.28 (s, 3 H) 3.40-3.50 (m, 2 H) 3.84 (d, J = 7.57 Hz, 1 H) 3.69 (d, J = 9.03 Hz, 1 H) 3.77 (s, 1 H) 4.09 (q, J = 6.35 Hz, 1 H) 4.27 (d, J = 17.09 Hz, 1 H) 4.31 (dd, J = 14.89, 4.88 Hz, 1 H) 4.40 (d, J = 7.32 Hz, 1 H) 4.67 (d, J = 10.09 Hz, 1 H) 4.70 (dd, J = 14.41, 6.84 Hz, 1 H) 4.91 (dd, J = 10.74, 1.95 Hz, 1 H) 4.97-5.01 (m, 1 H) 6.99 (dd, J = 11.96, 5.13 Hz, 1 H) 7.23 (dd, J = 7.32, 4.88 Hz, 1 H) 7.69 (dt, J = 5.86, 1.95 Hz, 1 H) 8.48 (dd, J = 4.88, 1.71 Hz, 1 H) 8.52 (d, J = 1.71 Hz, 1 H) |
| 179 | H3C-N(CH3)-S(O)2- | [N(CH2CH3)2 with CH3] | 1079 | (400 MHz): 0.84 (t, J = 7.32 Hz, 3 H) 1.02 (d, J = 7.32 Hz, 3 H) 1.03 (t, J = 7.08 Hz, 6 H) 1.07 (d, J = 7.81 Hz, 3 H) 1.12 (d, J = 6.84 Hz, 3 H) 1.14 (s, 3 H) 1.17 (d, J = 6.35 Hz, 3 H) 1.20 (d, J = 8.30 Hz, 3 H) 1.22 (d, J = 6.10 Hz, 3 H) 1.35 (s, 3 H) 1.42 (s, 3 H) 1.46-1.58 (m, 1 H) 1.62-1.69 (m, 1 H) 1.69-1.75 (m, 2 H) 1.86-1.95 (m, 3 H) 2.00 (t, J = 15.4 Hz, 1 H) 2.08 (d, J = 14.9 Hz, 1 H) 2.28 (s, 6 H) 2.34 (s, 3 H) 2.38-2.65 (m, 10 H) 2.74 (s, 6 H) 2.79-2.89 (m, 2 H) 2.95 (s, 3 H) 3.01 (q, J = 7.08 Hz, 1 H) 3.18 (dd, J = 10.3, 7.32 Hz, 1 H) 3.27 (s, 3 H) 3.39-3.50 (m, 1 H) 3.59-3.72 (m, 3 H) 4.07-4.25 (m, 2 H) 4.36-4.47 (m, 2 H) 4.96 (d, J = 4.40 Hz, 1 H) |
| 180 | H3C-CH2- | [N(CH2CH3)2 with CH3] | 1000.7 | (400 MHz): 0.84-0.91 (m, 3 H) 0.95-1.30 (m, 29 H) 1.38 (s, 3 H) 1.43 (s, 3 H) 1.52-1.83 (m, 5 H) 1.83-2.15 (m, 5 H) 2.29 (s, 6 H) 2.34 (s, 3 H) 2.38-2.66 (m, 9 H) 2.79-3.00 (m, 5 H) 3.04-3.13 (m, 1 H) 3.13-3.23 (m, 1 H) 3.24-3.32 (m, 4 H) 3.34-3.51 (m, 3 H) 3.62-3.68 (m, 1 H) 3.70-3.76 (m, 1 H) 3.78 (s, 1 H) 4.04-4.14 (m, 1 H) 4.22 (d, J = 17.1 Hz, 1 H) 4.40 (d, J = 7.1 Hz, 1 H) 4.58 (d, J = 16.8 Hz, 1 H) 4.95-5.02 (m, 1 H) 5.10 (d, J = 10.0 Hz, 1 H) 6.38-6.47 (m, 1 H) |
| 181 | CH3-S(O)2- | [N(CH2CH3)2 with CH3] | 1050 | (400 MHz): 0.85 (t, J = 7.32 Hz, 3 H) 0.99-1.35 (m, 28 H) 1.38 (s, 3 H) 1.42 (s, 3 H) 1.44-1.80 (m, 5 H) 1.81-2.15 (m, 5 H) 2.36 (s, 6 H) 2.40 (s, 3 H) 2.50-2.73 (m, 10 H) 2.73-2.90 (m, 2 H) 2.93 (s, 3 H) 2.99 (s, 3 H) 3.15-3.25 (m, 1 H) 3.27 (s, 3 H) 3.35-3.73 (m, 5 H) 4.02-4.18 (m, 2 H) 4.41 (d, J = 7.32 Hz, 1 H) 4.43-4.50 (m, 1 H) 4.98 (br s, 1 H) 5.70 (br s, 1 H) |

TABLE 3-continued

Formula (D)

[Structure of Formula (D) showing macrolide compound with R²⁹ᵇ-NH and R²ᵃ substituents]

[Formula 33]

| Example | R²⁹ᵇ | R²ᵃ | ESI MS (M + H) | ¹H-NMR, CDCl₃, δ (ppm) |
|---|---|---|---|---|
| 182 | H₃C-NH-S(=O)(=O)- | -N(CH₂CH₃)(CH₂CH₃) branching | 1065 | (400 MHz): 0.87 (t, J = 7.32 Hz, 3 H) 1.02 (d, J = 6.84 Hz, 3 H) 1.06 (d, J = 7.57 Hz, 3 H) 1.16-1.26 (m, 19 H) 1.16 (s, 3 H) 1.22 (d, J = 6.10 Hz, 6 H) 1.33 (s, 3 H) 1.42 (s, 3 H) 1.43-1.53 (m, 1 H) 1.62-1.76 (m, 3 H) 1.88-2.12 (m, 5 H) 2.29 (s, 6 H) 2.34 (s, 3 H) 2.39-2.48 (m, 1 H) 2.50-2.87 (m, 10 H) 2.91 (s, 3 H) 2.99 (q, J = 6.84 Hz, 1 H) 3.17 (dd, J = 10.25, 7.32 Hz, 1 H) 3.27 (s, 3 H) 3.36-3.50 (m, 2 H) 3.59 (d, J = 7.32 Hz, 1 H) 3.66-3.73 (m, 2 H) 3.68 (s, 1 H) 4.12 (q, J = 5.86 Hz, 1 H) 4.13-4.23 (m, 1 H) 4.38 (d, J = 7.32 Hz, 1 H) 4.45 (d, J = 7.58 Hz, 1 H) 4.98 (s, 1 H) 5.20-5.33 (m, 1 H) 5.77-5.96 (m, 1 H) |

Example 172

By using the compound represented by the formula (A) obtained in Example 1, (5) (100 mg) and the compound obtained in Reference Example 88 (94 mg) as starting materials, the compound shown in Table 3 (54 mg) was obtained in the same manners as those of Example 2, (1), (2) and Example 11.

Example 173

(1) By using the compound represented by the formula (A) obtained in Example 1, (5) (5.0 g) and 2-amino-N-benzylacetamide hydrochloride (5.71 g) as starting materials, a deacetylated compound (1.95 g) was obtained in the same manners as those of Example 15, (1) and Example 2, (2).
(2) By using the compound obtained in (1) mentioned above (200 mg) and the compound obtained in Reference Example 1 (91.6 mg) as starting materials, the compound shown in Table 3 (130 mg) was obtained in the same manner as that of Example 4, (8).

Example 174

By using the compound obtained in Example 173, (1) (200 mg) and the compound obtained in Reference Example 4 (92.9 mg) as starting materials, the compound shown in Table 3 (102 mg) was obtained in the same manner as that of Example 4, (8).

Example 175

By using the compound obtained in Example 173, (1) (200 mg) and the compound obtained in Reference Example 5 (100.6 mg) as starting materials, the compound shown in Table 3 (126 mg) was obtained in the same manner as that of Example 4, (8).

Example 176

By using the compound obtained in Example 173, (1) (200 mg) and the compound obtained in Reference Example 3 (101.9 mg) as starting materials, the compound shown in Table 3 (141 mg) was obtained in the same manner as that of Example 4, (8).

Example 177

(1) By using the compound represented by the formula (A) obtained in Example 1, (5) (200 mg) and the compound obtained in Reference Example 89 (171 mg) as starting materials, a deacetylated compound (93.6 mg) was obtained in the same manners as those of Example 2, (1) and (2).
(2) By using the compound obtained in (1) mentioned above (50 mg) as a starting material, the compound shown in Table 3 (39.8 mg) was obtained in the same manner as that of Example 11.

Example 178

By using the compound represented by the formula (A) obtained in Example 1, (5) (100 mg) and the compound obtained in Reference Example 90 (94 mg) as starting materials, the compound shown in Table 3 (62 mg) was obtained in the same manners as those of Example 2, (1), (2) and Example 11.

Example 179

By using the compound represented by the formula (A) obtained in Example 1, (5) (100 mg) and the compound obtained in Reference Example 92 (83 mg) as starting materials, the compound shown in Table 3 (49 mg) was obtained in the same manners as those of Example 2, (1), (2) and Example 11.

Example 180

(1) By using the compound represented by the formula (A) obtained in Example 1, (5) (200 mg) and the compound obtained in Reference Example 94 (116 mg) as starting materials, a deacetylated compound (133 mg) was obtained in the same manners as those of Example 2, (1) and (2).
(2) By using the compound obtained in (1) mentioned above (50 mg) as a starting material, the compound shown in Table 3 (43.9 mg) was obtained in the same manner as that of Example 11.

Example 181

By using the compound represented by the formula (A) obtained in Example 1, (5) (100 mg) and the compound obtained in Reference Example 91 (87 mg) as starting materials, the compound shown in Table 3 (45 mg) was obtained in the same manners as those of Example 2, (1), (2) and Example 11.

Example 182

By using the compound represented by the formula (A) obtained in Example 1, (5) (131 mg) and the compound obtained in Reference Example 95 (125 mg) as starting materials, the compound shown in Table 3 (50 mg) was obtained in the same manners as those of Example 2, (1), (2) and Example 11.

Examples 183 to 188

Preparation methods of the compounds represented by the formula (E) having $R^{29}$ and $R^{1a}$ defined in Table 4 are shown below.

TABLE 4

Formula (E)

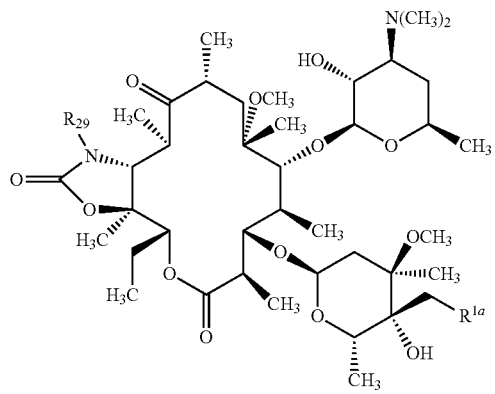

[Formula 34]

| Example | $R^{29}$ | $R^{1a}$ | ESI MS (M + H) | $^1$H-NMR, CDCl$_3$, δ (ppm) |
|---|---|---|---|---|
| 183 | H₃C (branched) | —N(CH₃)CH₂CH₂N(CH₃)₂ | 901.8 | (600 MHz): 0.84 (t, J = 7.57 Hz, 3 H) 1.03 (d, J = 6.88 Hz, 3 H) 1.09 (d, J = 7.34 Hz, 3 H) 1.12 (d, J = 6.88 Hz, 3 H) 1.18 (s, 3 H) 1.18-1.24 (m, 10 H) 1.38 (s, 3 H) 1.39 (s, 3 H) 1.46-1.76 (m, 4 H) 1.85-2.04 (m, 4 H) 2.12-2.17 (m, 1 H) 2.22-2.27 (m, 7 H) 2.30 (s, 6 H) 2.35 (s, 3 H) 2.36-2.66 (m, 6 H) 2.79-2.90 (m, 2 H) 3.02 (s, 3 H) 3.09 (s, 3 H) 3.17-3.22 (m, 1 H) 3.28 (s, 3 H) 3.38-3.42 (m, 1 H) 3.43-3.51 (m, 1 H) 3.56 (s, 1 H) 3.67-3.70 (m, 1 H) 3.70-3.75 (m, 1 H) 4.09-4.14 (m, 1 H) 4.42 (d, J = 6.88 Hz, 1 H) 4.92-5.01 (m, 2 H) |
| 184 | 2-pyrimidinyl-NH-(CH₂)₄- | —N(CH₂CH₃)₂ | 1007.6 | (500 MHz): 0.83 (t, J = 7.40 Hz, 3 H) 0.98-1.03 (m, 9 H) 1.08-1.16 (m, 12 H) 1.20-1.28 (m, 7 H) 1.39 (s, 6 H) 1.48-1.80 (m, 8 H) 1.87-2.00 (m, 3 H) 2.03-2.13 (m, 2 H) 2.31 (s, 6 H) 2.42-2.52 (m, 1 H) 2.55-2.76 (m, 5 H) 2.82 (d, J = 15.08 Hz, 1 H) 2.85-2.93 (m, 1 H) 3.01 (s, 3 H) 3.06-3.13 (m, 1 H) 3.16-3.23 (m, 1 H) 3.29 (s, 3 H) 3.42-3.61 (m, 3 H) 3.59-3.76 (m, 5 H) 4.07-4.15 (m, 1 H) 4.43 (d, J = 7.13 Hz, 1 H) 4.95-5.03 (m, 2 H) 5.41-5.49 (m, 1 H) 6.46 (t, J = 4.80 Hz, 1 H) 8.25 (d, J = 4.66 Hz, 2 H) |

TABLE 4-continued

Formula (E)

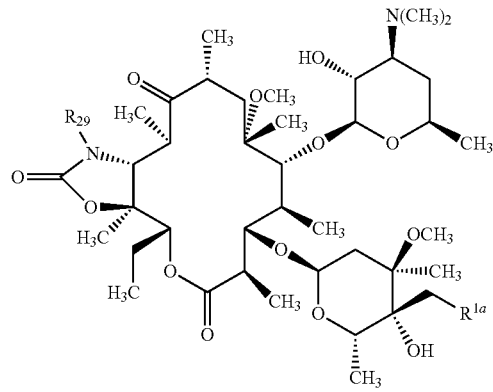

[Formula 34]

| Example | R²⁹ | R¹ᵃ | ESI MS (M + H) | ¹H-NMR, CDCl₃, δ (ppm) |
|---|---|---|---|---|
| 185 | 2-pyrimidinylamino-hexyl | cyclopropylmethyl-aminomethyl | 1005.7 | (600 MHz): 0.08-0.13 (m, 2 H) 0.45-0.51 (m, 2 H) 0.83 (t, J = 7.57 Hz, 3 H) 0.87-0.93 (m, 1 H) 1.01 (d, J = 6.88 Hz, 3 H) 1.10 (d, J = 7.79 Hz, 3 H) 1.13 (d, J = 6.88 Hz, 3 H) 1.15 (s, 3 H) 1.17 (d, J = 6.42 Hz, 3 H) 1.18-1.26 (m, 7 H) 1.39 (s, 3 H) 1.40 (s, 3 H) 1.47-1.79 (m, 8 H) 1.87-1.98 (m, 3 H) 2.02-2.08 (m, 1 H) 2.28 (s, 6 H) 2.39-2.50 (m, 4 H) 2.57-2.65 (m, 1 H) 2.86-2.93 (m, 2 H) 3.01 (s, 3 H) 3.06-3.12 (m, 1 H) 3.16-3.21 (m, 1 H) 3.29 (s, 3 H) 3.41-3.50 (m, 2 H) 3.55-3.77 (m, 6 H) 4.27-4.32 (m, 1 H) 4.39-4.44 (m, 1 H) 4.94-5.02 (m, 2 H) 5.40-5.45 (m, 1 H) 6.44-6.48 (m, 1 H) 8.24 (d, J = 4.59 Hz, 2 H) |
| 186 | methanesulfonamido-propyl | N-(2-diethylaminoethyl)amino | 1022.7 | (600 MHz): 0.83-0.91 (m, 6 H) 0.99-1.04 (m, 6 H) 1.09-1.33 (m, 19 H) 1.40 (s, 3 H) 1.40 (s, 3 H) 1.54-1.67 (m, 2 H) 1.74 (d, J = 6.42 Hz, 2 H) 1.84-2.06 (m, 4 H) 2.28 (s, 6 H) 2.33-2.38 (m, 1 H) 2.40-2.68 (m, 10 H) 2.88-2.95 (m, 2 H) 2.98 (s, 3 H) 3.05 (s, 3 H) 3.09-3.14 (m, 1 H) 3.16-3.20 (m, 1 H) 3.28 (s, 3 H) 3.30-3.36 (m, 1 H) 3.49-3.57 (m, 2 H) 3.59 (s, 1 H) 3.70 (d, J = 7.34 Hz, 2 H) 3.77-3.83 (m, 1 H) 3.84-3.91 (m, 1 H) 4.23 (q, J = 6.42 Hz, 1 H) 4.42 (d, J = 7.34 Hz, 1 H) 4.93-5.00 (m, 2 H) 5.48-5.58 (m, 1 H) |
| 187 | methanesulfonamido-propyl | N-(2-(N-methanesulfonyl-N-diethylaminoethyl))amino | 1100.6 | (600 MHz): 0.86 (t, J = 7.34 Hz, 3 H) 1.00-1.07 (m, 9 H) 1.07-1.22 (m, 13 H) 1.27 (s, 3 H) 1.33 (d, J = 6.42 Hz, 3 H) 1.41 (s, 3 H) 1.42 (s, 3 H) 1.56 (s, 8 H) 2.23-2.31 (m, 7 H) 2.50-2.70 (m, 8 H) 2.80 (s, 3 H) 2.86-2.95 (m, 1 H) 2.99 (s, 3 H) 3.02 (s, 3 H) 3.10-3.14 (m, 1 H) 3.15-3.22 (m, 1 H) 3.25 (s, 3 H) 3.27-3.42 (m, 4 H) 3.52-3.68 (m, 4 H) 3.77-3.83 (m, 2 H) 3.84-3.91 (m, 1 H) 4.29-4.34 (m, 1 H) 4.41 (d, J = 6.88 Hz, 1 H) 4.90-4.98 (m, 2 H) 5.54 (t, J = 5.73 Hz, 1 H) |
| 188 | methanesulfonamido-propyl | N-(2-(N-acetyl-N-diethylaminoethyl))amino | 1064.6 | (500 MHz): 0.86 (t, J = 7.26 Hz, 3 H) 0.99-1.30 (m, 28 H) 1.40 (s, 3 H) 1.41 (s, 3 H) 1.51-2.03 (m, 9H) 2.11-2.16 (m, 3 H) 2.25-2.31 (m, 6 H) 2.37-2.63 (m, 7 H) 2.87-2.93 (m,1 H) 2.99 (s, 3 H) 3.03 (s, 3 H) 3.09-3.15 (m, 2 H) 3.17-3.23 (m, 1 H) 3.28-3.61 (m, 9 H) 3.63-3.91 (m, 5 H) 4.19 (q, J = 6.50 Hz, 1 H) 4.39 (d, J = 7.26 Hz, 1 H) 4.86-4.98 (m, 2 H) 5.49-5.55 (m, 1 H) |

Example 183

(1) By using the compound represented by the formula (SM1) (5.0 g) obtained by the method described in the publication (International Patent Publication WO93/21199) and 40% aqueous methylamine (4.7 ml) as starting materials, an epoxy compound (1.92 g) was obtained in the same manners as those of Example 2, (1), (2), Example 1, (1), (3), Example 4, (6) and Example 1, (4).

(2) By using the compound obtained in (1) mentioned above (300 mg) as a starting material, the compound shown in Table 4 (245 mg) was obtained in the same manner as that of Example 4, (8).

Example 184

By using the compound obtained in Example 6, (4) (50 mg) and diethylamine (56 μl) as starting materials, the compound shown in Table 4 (62 mg) was obtained in the same manner as that of Example 4, (8).

Example 185

By using the compound obtained in Example 6, (4) (50 mg) and cyclopropylmethylamine (38 mg) as starting materials, the compound shown in Table 4 (55 mg) was obtained in the same manner as that of Example 4, (8).

Example 186

By using the compound obtained in Example 86, (1) (1 g) and N,N-diethylethylene-1,2-diamine (320.6 mg) as starting materials, the compound shown in Table 4 (881 mg) was obtained in the same manner as that of Example 2, (5).

Example 187

By using the compound obtained in Example 186 (50 mg) as a starting material, the compound shown in Table 4 (18 mg) was obtained in the same manner as that of Example 71, (2).

Example 188

The compound obtained in Example 186 (100 mg) was dissolved in chloroform (1.0 ml), acetic anhydride (9.2 μl) was added to the solution, and the resulting mixture was stirred at room temperature for 4 hours. The reaction mixture was concentrated under reduced pressure, saturated aqueous sodium hydrogencarbonate and ethyl acetate were added to the resulting residue, and the layers were separated. The organic layer was dried over anhydrous magnesium sulfate, and filtered. The filtrate was concentrated under reduced pressure, and the resulting residue was purified by silica gel column chromatography (chloroform:methanol:28% aqueous ammonia=30:1:0.1 to 10:1:0.1) to obtain the compound shown in Table 4 (54 mg).

Example 189

A preparation method of the compound represented by the formula (F) is shown below.

Formula (F)

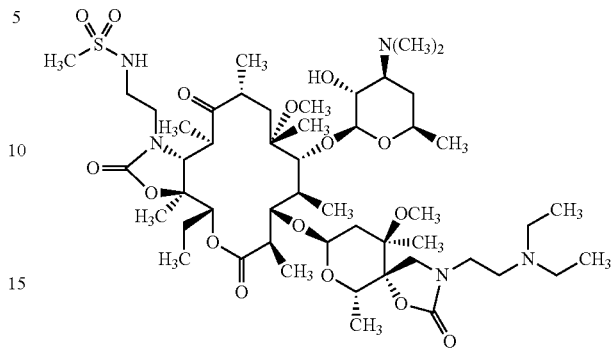

[Formula 35]

Example 189

The compound obtained in Example 186 (30 mg) was dissolved in chloroform (1 ml), and pyridine (47.5 μl) was added to the solution. A solution of triphosgene (8.7 mg) in chloroform (0.1 ml) was added to the reaction mixture over 1.5 hours under ice cooling, and the resulting mixture was stirred. Distilled water and chloroform were added to the reaction mixture, and the layers were separated. The organic layer was concentrated under reduced pressure to obtain a residue. The resulting residue was purified by silica gel column chromatography (chloroform:methanol:28% aqueous ammonia=30:1:0.1 to 10:1:0.1) to obtain the aforementioned objective compound (20 mg).

MS (ESI) m/z=1048.6 [M+H]$^+$ $^1$H-NMR (600 MHz, CDCl$_3$) δ (ppm): 0.86 (t, J=7.22 Hz, 3H), 0.97-1.04 (m, 9H), 1.09-1.28 (m, 19H), 1.40 (s, 6H), 1.52-1.68 (m, 3H), 1.74 (d, J=6.19 Hz, 2H), 1.85-1.97 (m, 3H), 2.17 (d, J=15.28 Hz, 1H), 2.29 (s, 6H), 2.36-2.43 (m, 1H), 2.50-2.65 (m, 6H), 2.91-3.08 (m, 8H), 3.09-3.14 (m, 1H), 3.16-3.21 (m, 1H), 3.27-3.48 (m, 7H), 3.52-3.66 (m, 3H), 3.72 (t, J=9.50 Hz, 2H), 3.77-3.91 (m, 2H), 4.25 (q, J=6.19 Hz, 1H), 4.36 (d, J=7.02 Hz, 1H), 4.94-4.99 (m, 2H), 5.48-5.53 (m, 1H)

Example 190

A preparation method of the compound represented by the formula (G) is shown below.

Formula (G)

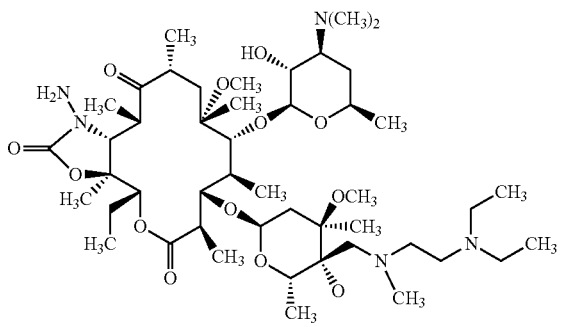

[Formula 36]

Example 190

(1) By using the compound represented by the formula (A) obtained in Example 1, (5) (400 mg) and hydrazine monohydrate (90 μl) as starting materials, a cyclized compound (414 mg) was obtained in the same manner as that of Example 2, (1).

(2) The compound obtained in (1) mentioned above (100 mg), 4-dimethylaminopyridine (6 mg) and triethylamine (83 μl) were dissolved in chloroform (4 ml) and dimethylformamide (1 ml), a solution of sulfamoyl chloride (41 mg) in chloroform (1 ml) was added to the solution, and the resulting mixture was stirred at room temperature for 11 hours. 4-Dimethylaminopyridine (12 mg), triethylamine (165 μl) and sulfamoyl chloride (80 mg) were added to the reaction mixture, and the resulting mixture was further stirred at room temperature for 2 hours, and then stirred at 40° C. for 3 hours. Saturated aqueous sodium hydrogencarbonate and ethyl acetate were added to the reaction mixture, the layers were separated, and the aqueous layer was extracted with ethyl acetate. The combined organic layer was washed with saturated aqueous sodium chloride, then dried over anhydrous magnesium sulfate, and filtered. The filtrate was concentrated under reduced pressure, and the resulting residue was purified by preparative thin layer chromatography (chloroform:methanol:28% aqueous ammonia=15:1:0.1) to obtain a sulfamoyl compound (48 mg).

(3) By using the compound obtained in (2) mentioned above (47 mg) as a starting material, a deacetylated compound (20 mg) and a deacetylated compound isomerized at the 10-position (9.2 mg) were obtained in the same manner as that of Example 2, (2).

(4) By using the deacetylated compound isomerized at the 10-position (9.2 mg) obtained in (3) mentioned above as a starting material, the aforementioned objective compound (3 mg) was obtained in the same manner as that of Example 11.

MS (ESI) m/z=930 [M+H]$^+$ $^1$H-NMR (400 MHz, CDCl$_3$) δ (ppm): 0.86 (t, J=7.6 Hz, 3H), 1.01 (t, J=6.8 Hz, 6H), 1.03 (d, J=7.1 Hz, 3H), 1.07 (d, J=7.1 Hz, 3H), 1.13-1.20 (m, 10H), 1.23-1.27 (m, 6H), 1.34 (s, 3H), 1.54-1.68 (m, 3H), 1.63 (s, 3H), 1.76-1.85 (m, 2H), 1.90-2.09 (m, 6H), 2.29 (s, 6H), 2.33 (s, 3H), 2.38-2.64 (m, 8H), 2.72-2.90 (m, 2H), 3.14-3.19 (m, 1H), 3.20 (s, 3H), 3.26-3.30 (m, 1H), 3.30 (s, 3H), 3.39 (d, J=2.4 Hz, 1 h) 3.41-3.47 (m, 1H), 3.55 (dd, J=7.8, 2.6 Hz, 1H), 3.60-3.62 (m, 2H), 3.79-3.81 (m, 1H), 3.83 (s, 1H), 4.14 (q, J=6.1 Hz, 1H), 4.34 (d, J=t.3 Hz, 1H), 4.91 (dd, J=10.5, 2.0 Hz, 1H), 5.09 (d, J=4.6 Hz, 1H)

Examples 191 to 232

Preparation methods of the compounds represented by the formula (H) having $R^{29c}$ and $R^{2b}$ defined in Table 5 are shown below.

TABLE 5

Formula (H)

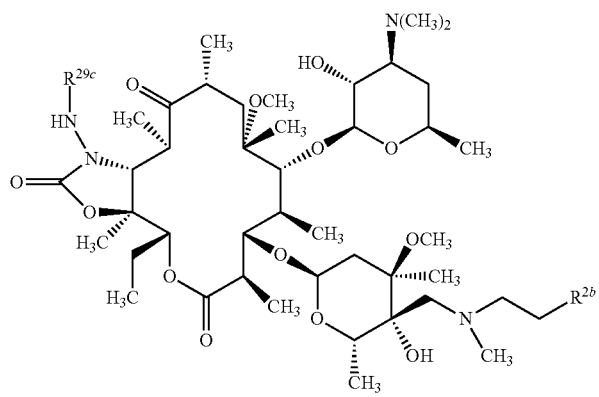

[Formula 37]

| Example | $R^{29c}$ | $R^{2b}$ | ESI MS (M+H) | $^1$H-NMR, CDCl$_3$, δ (ppm) |
|---|---|---|---|---|
| 191 | H | ![structure with N(CH3)(CH2CH3)] | 930 | (400 MHz): 0.83 (t, J = 7.3 Hz, 3 H) 1.02 (t, J = 7.1 Hz, 6 H) 1.07 (d, J = 6.6 Hz, 3 H) 1.08 (d, J = 7.3 Hz, 3 H) 1.15 (d, J = 6.1 Hz, 3 H) 1.16 (s, 3 H) 1.18 (d, J = 6.4 Hz, 3 H) 1.20 (d, J = 7.3 Hz, 3 H) 1.23 (d, J = 6.1 Hz, 3 H) 1.36 (s, 3 H) 1.39 (s, 3 H) 1.46-1.56 (m, 1 H) 1.58-1.68 (m, 1 H) 1.74-1.78 (m, 2 H) 1.82-2.04 (m, 5 H) 2.08 (d, J = 14.9 Hz, 1 H) 2.28 (s, 6 H) 2.33 (s, 3 H) 2.40-2.68 (m, 9 H) 2.83 (d, J = 14.7 Hz, 1 H) 2.88 (dd, J = 9.5, 2.0 Hz, 1 H) 3.02 (s, 3 H) 3.04-3.09 (m, 1 H) 3.17 (dd, J = 10.3, 7.3 Hz, 1 H) 3.27 (s, 3 H) 3.40-3.50 (m, 2 H) 3.60 (s, 1 H) 3.68 (d, J = 7.3 Hz, 1 H) 3.71 (d, J = 9.3 Hz, 1 H) 4.09 (q, J = 6.4 Hz, 1 H) 4.40 (d, J = 7.3 Hz, 1 H) 4.50 (s, 1 H) 4.98 (d, J = 3.9 Hz, 1 H) 5.02 (dd, J = 10.7. 2.2 Hz, 1 H) |

TABLE 5-continued

| | | | | |
|---|---|---|---|---|
| 192 | H₃C-S(=O)(=O)- group with gem-dimethyl | N(CH₂CH₃)₂ with gem-dimethyl | 1008 | (400 MHz): 0.89 (t, J = 7.3 Hz, 3 H) 1.01 (t, 7.1 Hz, 3 H) 1.02 (d, J = 7.1 Hz, 3 H) 1.06 (d, J = 6.6 Hz, 3 H) 1.08 (d, J = 6.6 Hz, 3 H) 1.16 (d, J = 7.1 Hz, 3 H) 1.20 (d, J = 7.3 Hz, 3 H) 1.22 (d, J = 6.1 Hz, 3 H) 1.37 (s, 3 H) 1.45 (s, 3 H) 1.51-1.58 (m, 1 H) 1.61-1.67 (m, 1 H) 1.71-2.02 (m, 8 H) 2.09 (d, J = 14.7 Hz 1 H) 2.28 (s, 6 H) 2.33 (s, 3 H) 2.40-2.60 (m, 12 H) 2.67-2.74 (m, 1 H) 2.79-2.91 (m, 5 H) 3.07 (s, 3 H) 3.16 (s, 3 H) 3.16-3.19 (m, 2 H) 3.23-3.27 (m, 1 H) 3.27 (s, 3 H) 3.39-3.52 (m, 2 H) 3.69-3.75 (m, 2 H) 3.92 (s, 1 H) 4.05 (q, J = 6.4 Hz, 1 H) 4.44 (d, J = 7.3 Hz, 1 H) 4.95-4.99 (m, 1 H) 5.40 (dd, J = 10.3, 3.2 Hz, 1 H) |
| 193 | H₃C-NH-S(=O)(=O)- group with gem-dimethyl | N(CH₂CH₃)₂ with gem-dimethyl | 1023 | (400 MHz): 0.83 (t, J = 7.6 Hz, 3 H) 1.02 (t, J = 7.1 Hz, 3 H) 1.08 (d, J = 6.8 Hz, 3 H) 1.09 (d, J = 7.3 Hz, 3 H) 1.15 (d, J = 7.3 Hz, 3 H) 1.16 (s, 3 H) 1.19 (d, J = 6.4 Hz, 3 H) 1.22 (d, J = 4.9 Hz, 3 H) 1.23 (d, J = 6.1 Hz, 3 H) 1.36 (s, 3 H) 1.40 (s, 3 H) 1.48-1.56 (m, 2 H) 1.62-1.68 (m, 2 H) 1.74-2.02 (m, 8 H) 2.09 (d, J = 14.9 Hz, 1 H) 2.28 (s, 6 H) 2.34 (s, 3 H) 2.39-2.68 (m, 11 H) 2.80-2.92 (m, 3 H) 3.02 (s, 3 H) 3.18 (dd, J = 10.3, 7.3 Hz, 1 H) 3.28 (s, 3 H) 3.38-3.50 (m, 2 H) 3.61 (s, 1 H) 3.68 (d, J = 7.3 Hz, 1 H) 3.74 (d, J = 4.2 Hz, 1 H) 4.09 (q, J = 6.4 Hz, 1 H) 4.41 (d, J = 7.3 Hz, 1 H) 4.50 (s, 2 H) 4.98-5.00 (m, 1 H) 5.02 (dd, J = 10.7, 2.0 Hz, 1 H) |
| 194 | phenyl-propyl with gem-dimethyl | N(CH₂CH₃)₂ with gem-dimethyl | 1048 | (400 MHz): 0.82 (t, J = 7.3 Hz, 3 H) 1.02 (t, J = 7.1 Hz, 6 H) 1.05 (d, J = 7.6 Hz, 3 H) 1.11 (d, J = 7.6 Hz, 3 H) 1.14 (d, J = 9.1 Hz, 3 H) 1.16 (s, 3 H) 1.19 (d, J = 6.1 Hz, 3 H) 1.22 (d, J = 7.1 Hz, 3 H) 1.23 (d, J = 6.10 Hz, 3 H) 1.37 (s, 3 H) 1.39 (s, 3 H) 1.47-1.56 (m, 1 H) 1.62-1.93 (m, 9 H) 1.99-2.06 (m, 2 H) 2.09 (d, J = 14.7 Hz, 1 H) 2.28 (s, 6 H) 2.35 (s, 3 H) 2.38-2.67 (m, 10 H) 2.73 (t, J = 7.8 Hz, 2 H) 2.83 (d, J = 14.9 Hz 1 H) 2.86-2.96 (m, 3 H) 3.02 (s, 3 H) 3.10-3.20 (m, 2 H) 3.28 (s, 3 H) 3.42-3.51 (m, 2 H) 3.70-3.75 (m, 2 H) 3.79 (s, 1 H) 4.10 (q, J = 6.4 Hz, 1 H) 4.42 (d, J = 7.1 Hz, 1 H) 4.99-5.06 (m, 2 H) 5.46 (t, J = 4.9 Hz, 1 H) 7.12-7.17 (m, 1 H) 7.19-7.27 (m, 4 H) |
| 195 | H₃C-alkyl chain with gem-dimethyl | N(CH₂CH₃)₂ with gem-dimethyl | 972 | (400 MHz): 0.83 (t, J = 7.3 Hz, 3 H) 0.97 (t, J = 7.5 Hz, 3 H) 1.01 (d, J = 7.1 Hz, 3 H) 1.04 (d, J = 6.4 Hz, 3 H) 1.11 (d, J = 7.6 Hz, 3 H) 1.14 (d, J = 7.6 Hz, 3 H) 1.16 (s, 3 H) 1.19 (d, J = 6.4 Hz, 3 H) 1.23 (d, J = 6.4 Hz, 3 H) 1.37 (s, 3 H) 1.41 (s, 3 H) 1.46-2.02 (m, 14 H) 2.09 (d, J = 14.9 Hz, 1 H) 2.29 (s, 6 H) 2.32 (s, 3 H) 2.40-2.70 (m, 9 H) 2.77-2.86 (m, 3 H) 2.88-2.96 (m, 1 H) 3.08 (s, 3 H) 3.01-3.20 (m, 2 H) 3.28 (s, 3 H) 3.42-3.52 (m, 1 H) 3.69-3.76 (m, 2 H) 3.79 (s, 1 H) 4.10 (q, J = 6.4 Hz, 1 H) 4.42 (d, J = 7.3 Hz, 1 H) 4.99-5.01 (m, 1 H) 5.04 (dd, J = 11.0, 2.0 Hz, 1 H) 5.37 (t, J = 5.4 Hz, 1 H) |
| 196 | cyclopropylmethyl-NH-C(=O)- group with gem-dimethyl | N(CH₂CH₃)₂ with gem-dimethyl | 1027.7 | (400 MHz): 0.84-0.91 (m, 3 H) 0.18-0.22 (m, 2 H) 0.40-0.48 (m, 2 H) 0.90 (t, J = 7.3 Hz, 1 H) 0.96-1.25 (m, 26 H) 1.36 (s, 3 H) 1.44 (s, 3 H) 1.50-1.88 (m, 8 H) 1.89-2.05 (m, 3 H) 2.09 (d, J = 14.9 Hz, 1 H) 2.29 (s, 6 H) 2.34 (s, 3 H) 2.38-2.71 (m, 10 H) 2.80-2.90 (m, 2 H) 2.91 (s, 3 H) 2.93-3.01 (m, 1 H) 3.08 (q, J = 6.8 Hz, 1 H) 3.14-3.26 (m, 2 H) 3.27 (s, 3 H) 3.36-3.52 (m, 2 H) 3.66 (d, J = 7.1 Hz, 1 H) 3.72 (d, J = 9.0 Hz, 1 H) 3.79 (s, 1 H) 4.07 (q, J = 6.3 Hz, 1 H) 4.42 (d, J = 7.3 Hz, 1 H) 4.97 (d, J = 4.4 Hz, 1 H) 5.24-5.30 (m, 2 H) 5.34 (d, J = 10.3 Hz, 1 H) 7.67 (s, 1 H) |
| 197 | quinolin-4-yl-propyl with gem-dimethyl | N(CH₂CH₃)₂ with gem-dimethyl | 1099 | (400 MHz): 0.76 (t, J = 7.3 Hz, 3 H) 1.02 (t, J = 7.1 Hz, 6 H) 1.06 (d, J = 6.8 Hz, 3 H) 1.11 (d, J = 7.3 Hz, 3 H) 1.15 (d, J = 7.3 Hz, 3 H) 1.16 (s, 3 H) 1.19 (d, J = 6.1 Hz, 3 H) 1.23 (d, J = 5.6 Hz, 3 H) 1.38 (s, 3 H) 1.39 (s, 3 H) 1.46-1.56 (m, 1 H) 1.62-1.68 (m, 1 H) 1.72-1.93 (m, 5 H) 1.99-2.12 (m, 6 H) 2.28 (s, 6 H) 2.34 (s, 3 H) 2.39-2.68 (m, 10 H) 2.83 (d, J = 14.7 Hz, 1 H) 2.88-3.10 (m, 3 H) 3.05 (s, 3 H) 3.16-3.31 (m, 4 H) 3.28 (s, 3 H) 3.46-3.52 (m, 2 H) 3.72 (dd, J = 9.8, 7.1 Hz, 1 H) 3.79 (s, 1 H) 4.10 (q, J = 6.4 Hz, 1 H) 4.42 (d, J = 7.3 Hz, 1 H) 4.98-5.03 (m, 2 H) 5.61-5.65 (m, 1 H) 7.29 (d, J = 4.4 Hz, 1 H) 7.50-7.55 (m, 1 H) 7.64-7.68 (m, 1 H) 8.08 (d, J = 8.6 Hz, 1 H) 8.13 (d, J = 8.3 Hz, 1 H) 8.78 (d, J = 4.39 Hz, 1 H) |

TABLE 5-continued

| | | | |
|---|---|---|---|
| 198 | benzyl-NH-C(O)-C(CH3)2- structure | -C(CH3)2-N(CH2CH3)2 | 1063 | (400 MHz): 0.78 (t, J = 7.3 Hz, 3 H) 1.02 (t, J = 7.1 Hz, 6 H) 1.05-1.09 (m, 6 H) 1.12 (d, J = 6.8 Hz, 3 H) 1.16 (s, 3 H) 1.19 (d, J = 6.4 Hz, 3 H) 1.20 (d, J = 7.3 Hz, 3 H) 1.23 (d, J = 6.1 Hz, 3 H) 1.34 (s, 3 H) 1.41 (s, 3 H) 1.48-1.57 (m, 1 H) 1.61-1.90 (m, 8 H) 1.97 (dd, J = 10.0, 4.9 Hz, 1 H) 2.01 (s, 1 H) 2.09 (d, J = 14.6 Hz, 1 H) 2.28 (s, 6 H) 2.34 (s, 3 H) 2.39-2.67 (m, 11 H) 2.80-2.86 (m, 3 H) 2.88 (s, 3 H) 3.06 (q, J = 6.8 Hz, 1 H) 3.16 (dd, J = 10.0, 7.1 Hz, 1 H) 3.27 (s, 1 H) 3.40-3.49 (m, 2 H) 3.66 (d, J = 7.1 Hz, 1 H) 3.72 (d, J = 8.8 Hz, 1 H) 3.78 (s, 1 H) 4.07 (q, J = 6.4 Hz, 1 H) 4.30 (dd, J = 14.4, 4.6 Hz, 1 H) 4.41 (d, J = 7.3 Hz, 1 H) 4.53 (dd, J = 14.4, 6.6 Hz, 1 H) 5.00 (d, J = 3.4 Hz, 1 H) 5.24 (d, J = 10.0 Hz, 1 H) 5.43-5.49 (m, 1 H) 7.18-7.34 (m, 5 H) 7.76 (s, 1 H) |
| 199 | phenyl-CH2CH2-C(O)- structure | -C(CH3)2-N(CH2CH3)2 | 1062 | (400 MHz): 0.93 (t, J = 7.3 Hz, 3 H) 1.01 (d, J = 7.1 Hz, 3 H) 1.03 (d, J = 7.3 Hz, 3 H) 1.05-1.09 (m, 5 H) 1.13 (d, J = 6.6 Hz, 3 H) 1.14 (d, J = 7.3 Hz, 3 H) 1.15 (s, 3 H) 1.16 (d, J = 6.5 Hz, 3 H) 1.20 (d, J = 7.3 Hz, 3 H) 1.21 (d, J = 5.9 Hz, 3 H) 1.33 (s, 3 H) 1.42 (s, 3 H) 1.48-1.56 (m, 1 H) 1.61-1.67 (m, 1 H) 1.74-1.85 (m, 3 H) 1.90-2.05 (m 3 H) 2.08 (d, J = 14.9 Hz, 1 H) 2.28 (s, 6 H) 2.35 (s, 3 H) 2.39-2.63 (m, 12 H) 2.77-2.82 (m, 2 H) 2.85 (s, 3 H 9 2.99-3.07 (m, 3 H) 3.16 (dd, J = 10.0, 7.3 Hz, 1 H) 3.26 (s, 3 H) 3.42-3.52 (m, 2 H) 3.63 (s, 1 H) 3.67-3.70 (m, 2 H) 4.04 (q, J = 6.4 Hz, 1 H) 4.41 (d, J = 7.3 Hz, 1 H) 4.94-4.99 (m, 1 H) 5.75-5.82 (m, 1 H) 7.17-7.31 (m, 5 H) 8.55 (s, 1 H) |
| 200 | benzyl-NH-C(O)-C(CH3)2- structure | isothiazolidine-1,1-dioxide-N-C(CH3)2- | 1111 | (400 MHz): 0.78 (t, J = 7.3 Hz, 3 H) 0.91 (t, J = 7.3 Hz, 6 H) 1.07 (d, J = 7.6 Hz, 3 H) 1.08 (d, J = 6.6 Hz, 3 H) 1.13 (d, J = 9.5 Hz, 3 H) 1.15 (s, 3 H) 1.18 (d, J = 6.6 Hz, 3 H) 1.20 (d, J = 8.8 Hz, 3 H) 1.23 (d, J = 6.4 Hz, 3 H) 1.34 (s, 3 H) 1.42 (8, 3 H) 1.48-1.90 (m, 8 H) 1.96 (dd, J = 15.1, 5.4 Hz, 1 H) 2.03-2.11 (m, 2 H) 2.28 (s, 6 H) 2.34-2.39 (m, 1 H) 2.40 (s, 3 H) 2.60-2.74 (m, 3 H) 2.82-2.92 (m, 2 H) 2.88 (s, 3 H) 3.04-3.20 (m, 4 H) 3.28 (s, 3 H) 3.28-3.32 (m, 2 H) 3.39-3.45 (m, 1 H) 3.46 (s, 1 H) 3.63 (d, J = 7.3 Hz, 1 H) 3.74 (d, J = 8.8 Hz, 1 H) 3.78 (s, 1 H) 4.10 (q, J = 6.6 Hz, 1 H) 4.31 (dd, J = 14.4, 4.9 Hz, 1 H) 4.39 (d, J = 7.1 Hz, 1 H) 4.51 (dd, J = 14.7, 6.6 Hz, 1 H) 4.58 (s, 1 H) 4.99 (d, J = 4.9 Hz, 1 H) 5.26 (d, J = 10.0 Hz, 1 H) 5.41-5.45 (m, 1 H) 7.19-7.34 (m, 5 H) 7.75 (s, 1 H) |
| 201 | benzyl-NH-C(O)-C(CH3)2- structure | -C(CH3)2-N(CH2CH3)(CH(CH3)2) | 1077 | (400 MHz): 0.78 (t, J = 7.3 Hz, 3 H) 0.92 (t, J = 7.3 Hz, 3 H) 0.95-0.98 (m, 6 H) 1.08 (d, J = 6.8 Hz, 3 H) 1.13 (d, J = 7.1 Hz, 3 H) 1.16 (s, 3 H) 1.20 (s, 3 H) 1.21 (d, J = 7.6 Hz, 3 H) 1.23 (d, J = 6.4 Hz, 3 H) 1.35 (s, 3 H) 1.42 (s, 3H) 1.48-1.90 (m, 11 H) 1.94-2.03 (m, 2 H)) 2.06 (d, J = 14.2 Hz, 1 H) 2.28 (s, 6 H) 2.35 (s, 3 H) 2.40-2.60 (m, 5 H) 2.82-2.87 (m, 2 H) 2.88 (s, 3 H) 3.07 (q, J = 7.3 Hz, 1 H) 3.17 (dd, J = 10.3, 7.3 Hz, 1 H) 3.28 (s, 3 H) 3.44 (s, 1 H) 3.44-3.49 (m, 1 H) 3.66 (d, J = 7.3 Hz, 1 H) 3.73 (d, J = 8.6 Hz, 1 H) 3.79 (s, 1 H) 4.07 (q, J = 6.6 Hz, 1 H) 4.31 (dd, J = 14.2, 4.6 Hz, 1 H) 4.42 (d, J = 7.3 Hz, 1 H) 4.53 (dd, J = 14.4, 6.4 Hz, 1 H) 5.01 (d, J = 4.1 Hz, 1 H) 5.21-5.29 (m, 2 H) 5.44-5.48 (m, 1 H) 7.15-7.35 (m, 5 H) 7.77 (s, 1 H) |
| 202 | benzyl-NH-C(O)-C(CH3)2- structure | -C(CH3)2-N(CH2CH3)(CH2CH2CH3) | 1091 | (400 MHz): 0.78 (t, J = 7.6 Hz, 3 H) 0.90 (t, J = 7.3 Hz, 3 H) 1.02 (t, J = 7.1 Hz, 6 H) 1.07 (d, J = 7.6 Hz, 3 H) 1.08 (d, J = 7.6 Hz, 3 H) 1.13 (d, J = 7.1 Hz, 3 H) 1.16 (s, 3 H) 1.19 (d, J = 5.9 Hz, 3 H) 1.21-1.32 (m, 4H) 1.35 (s, 3 H) 1.38-1.44 (m, 1 H) 1.42 (s, 3 H) 1.48-1.90 (m, 14 H) 1.97 (dd, J = 14.7, 4.9 Hz, 1 H) 2.01-2.06 (m, 1 H) 2.08 (d, J = 14.7 Hz, 1 H) 2.28 (s, 6 H) 2.34 (s, 3 H) 2.38-2.66 (m, 9 H) 2.80-2.87 (m, 2 H) 2.89 (s, 3 H) 3.07 (q, J = 6.4 Hz, 1 H) 3.17 (dd, J = 10.3, 7.3 Hz, 1 H) 3.28 (s, 3 H) 3.41-3.51 (m, 2 H) 3.66 (d, J = 7.1 Hz, 1 H) 3.73 (d, J = 9.0 Hz, 1 H) 3.79 (s, 1 H) 4.08 (q, J = 6.4 Hz, 1 H) 4.32 (dd, J = 14.4, 4.6 Hz, 1 H) 4.42 (d, J = 7.3 Hz, 1 H) 4.53 (dd, J = 14.4, 6.4 Hz, 1 H) 5.00 (d, J = 4.4 Hz, 1 H) 5.25 (d, J = 10.5 Hz, 1 H) 5.43-5.48 (m, 1 H) 7.19-7.35 (m, 5 H) 7.74 (s, 1 H) |

TABLE 5-continued

| 203 | 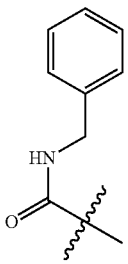 [SMILES: *C(=O)NCc1ccccc1] | 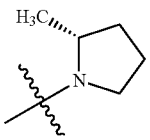 [SMILES: *N1CCC[C@H]1C] | 1075 | (400 MHz): 0.79 (t, J = 7.6 Hz, 3 H) 1.07 (d, J = 6.8 Hz, 3 H) 1.08 (d, J = 6.8 Hz, 3 H) 1.09 (d, J = 5.9 Hz, 3 H) 1.13 (d, J = 7.1 Hz, 3 H) 1.15 (s, 3 H) 1.19 (d, J = 6.1 Hz, 3 H) 1.21 (d, J = 7.1 Hz, 3 H) 1.23 (d, J = 6.1 Hz, 3 H) 1.34 (s, 3 H) 1.42 (s, 3 H) 1.48-2.18 (m, 16 H) 2.28 (s, 6 H) 2.31-2.36 (m, 1 H) 2.37 (s, 3 H) 2.38-2.47 (m, 1 H) 2.60-2.67 (m, 3 H) 2.81-2.96 (m, 3 H) 2.88 (s, 3 H) 3.07 (q, J = 7.1 Hz, 1 H) 3.13-3.19 (m, 2 H) 3.28 (s, 3 H) 3.42-3.50 (m, 2 H) 3.68 (d, J = 7.1 Hz, 1 H) 3.72 (d, J = 9.3 Hz, 1 H) 3.79 (s, 1 H) 4.08 (q, J = 6.4 Hz, 1 H) 4.33 (dd, J = 14.4, 4.9 Hz, 1 H) 4.42 (d, J = 7.3 Hz, 1 H) 4.52 (dd, J = 14.4, 6.4 Hz, 1 H) 4.98-5.02 (m, 1 H) 5.27 (d, J = 9.8 Hz, 1 H) 5.41-5.47 (m, 1 H) 7.19-7.35 (m, 5 H) 7.76 (s, 1 H) |
|---|---|---|---|---|
| 204 | 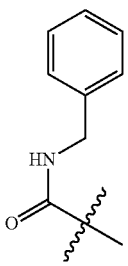 [SMILES: *C(=O)NCc1ccccc1] | 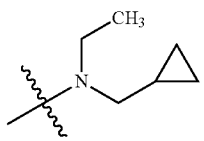 [SMILES: *N(CC)CC1CC1] | 1089 | (400 MHz): 0.085-0.11 (m, 2 H) 0.46-0.51 (m, 2 H) 0.78 (t, J = 7.3 Hz, 3 H) 0.84-0.93 (m, 1 H) 1.03 (t, J = 7.3 Hz, 3 H) 1.07 (d, J = 7.3 Hz, 3 H) 1.08 (d, J = 6.8 Hz, 3 H) 1.13 (d, J = 6.8 Hz, 3 H) 1.17 (s, 3 H) 1.19 (d, J = 6.4 Hz, 3 H) 1.20 (d, J = 5.1 Hz, 3 H) 1.23 (d, J = 6.1 Hz, 3 H) 1.35 (s, 3 H) 1.42 (s, 3 H) 1.48-1.90 (m, 8 H) 1.94-2.06 (m, 2 H) 2.10 (d, J = 14.7 Hz, 1 H) 2.28 (s, 6 H) 2.31-2.68 (m, 8 H) 2.36 (s, 3 H) 2.81-2.86 (m, 2H) 2.88 (s, 3 H) 3.06 (q, J = 6.8 Hz, 1 H) 3.17 (dd, J = 10.3, 7.3 Hz, 1 H) 3.28 (s, 3 H) 3.40-3.51 (m, 2 H) 3.67 (d, J = 7.1 Hz, 1 H) 3.73 (d, J = 8.8 Hz, 1 H) 3.79 (s, 1 H) 4.08 (q, J = 6.4 Hz, 1 H) 4.31 (dd, J = 14.4, 4.6 Hz, 1 H) 4.42 (d, J = 7.1 Hz, 1 H) 4.53 (dd, J = 14.7, 6.4 Hz, 1 H) 4.99-5.01 (m, 1 H) 5.00 (d, J = 3.7 Hz, 1 H) 5.25 (d, J = 9.8 Hz, 1 H) 5.43-5.48 (m, 1 H) 7.18-7.35 (m, 5 H) 7.76 (s, 1 H) |
| 205 | 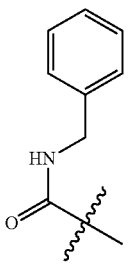 [SMILES: *C(=O)NCc1ccccc1] | 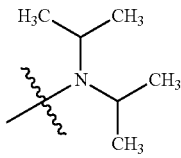 | 1091 | (400 MHz): 0.79 (t, J = 7.32 Hz, 3 H) 1.01 (d, J = 5.86 Hz, 6 H) 1.03 (d, J = 5.62 Hz, 6 H) 1.08 (d, J = 7.60 Hz, 3 H) 1.08 (d, J = 6.80 Hz, 3 H) 1.13 (d, J = 7.57 Hz, 3 H) 1.14 (s, 3 H) 1.18 (d, J = 6.35 Hz, 3 H) 1.20 (d, J = 7.32 Hz, 3 H) 1.23 (d, J = 6.10 Hz, 3 H) 1.26-1.24 (m, 1H) 1.35 (s, 3 H) 1.42 (s, 3 H) 1.50-1.92 (m, 6 H) 1.93-2.08 (m, 3 H) 2.29 (s, 6 H) 2.36 (s, 3 H) 2.38-2.69 (m, 6 H) 2.81-2.87 (m, 2H) 2.88 (s, 3 H) 2.99-3.09 (m, 3 H) 3.17 (dd, J = 10.3, 7.32 Hz, 1 H) 3.28 (s, 3 H) 3.39-3.50 (m, 1 H) 3.65 (d, J = 7.08 Hz, 1 H) 3.74 (d, J = 9.03 Hz, 1 H) 3.79 (s, 3 H) 4.08 (q, J = 6.35 Hz, 1 H) 4.31 (dd, J = 14.5, 4.76 Hz, 1 H) 4.41 (d, J = 7.32 Hz, 1 H) 4.53 (dd, J = 14.5, 6.59 Hz, 1 H) 5.00 (d, J = 4.64 Hz, 1 H) 5.26 (d, J = 10.7 Hz, 1 H) 5.51 (br s, 1 H) 7.18-7.35 (m, 5 H) 7.74 (s, 1 H) |
| 206 | 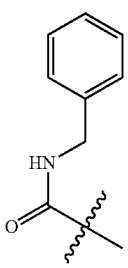 [SMILES: *C(=O)NCc1ccccc1] | 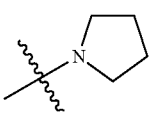 [SMILES: *N1CCCC1] | 1061 | (400 MHz): 0.79 (t, J = 7.32 Hz, 3 H) 1.08 (t, J = 7.32 Hz, 3 H) 1.08 (d, J = 6.59 Hz, 3 H) 1.13 (d, J = 6.84 Hz, 3 H) 1.17 (s, 3 H) 1.19 (d, J = 6.35 Hz, 3 H) 1.21 (d, J = 6.84 Hz, 3 H) 1.23 (d, J = 6.10 Hz, 3 H) 1.26-1.24 (m, 1 H) 1.34 (s, 3 H) 1.42 (s, 3 H) 1.49-1.91 (m, 10 H) 1.96 (dd, J = 14.77, 5.00 Hz, 1H) 2.03 (d, J = 14.77 Hz, 1H) 2.15 (d, J = 14.9 Hz, 1 H) 2.29 (s, 6 H) 2.36 (s, 3 H) 2.40-2.47 (m, 1 H) 2.49-2.71 (m, 9 H) 2.84-2.88 (m, 2 H) 2.88 (s, 3H) 3.07 (q, J = 7.00 Hz, 1 H) 3.17 (dd, J = 10.3, 7.10 Hz, 1 H) 3.28 (s, 3 H) 3.37-3.52 (m, 1 H) 3.67 (d, J = 7.20 Hz, 1 H) 3.72 (d, J = 10.8 Hz, 1 H) 3.79 (s, 3 H) 4.10 (q, J = 6.35 Hz, 1 H) 4.42 (d, J = 7.10 Hz, 1 H) 4.32 (dd, J = 14.4, 4.88 Hz, 1 H) 4.52 (dd, J = 14.4, 6.23 Hz, 1 H) 4.99 (d, J = 3.66 Hz, 1 H) 5.27 (d, J = 10.3 Hz, 1 H) 5.41-5.47 (m, 1 H) 7.18-7.36 (m, 5 H) 7.74 (s, 1 H) |

TABLE 5-continued

| | | | | |
|---|---|---|---|---|
| 207 | H3C-S(=O)(=O)-CH2-C(CH3)2-~ | | 1036 | (400 MHz): 0.87 (t, J = 7.32 Hz, 3 H) 1.02 (t, J = 7.08 Hz, 6 H) 1.03 (d, J = 7.08 Hz, 3 H) 1.11 (d, J = 7.57 Hz, 3H) 1.15 (d, J = 8.30 Hz, 3 H) 1.16 (s, 3 H) 1.17-1.26 (m, 1 H) 1.19 (d, J = 6.10 Hz, 3 H) 1.20 (d, J = 5.62 Hz, 3 H) 1.24 (d, J = 6.10 Hz, 3 H) 1.38 (s, 3 H) 1.41 (s, 3 H) 1.49-2.06 (m, 8 H) 2.09 (d, J = 14.65 Hz, 1 H) 2.29 (s, 6 H) 2.34 (s, 3 H) 2.35-2.70 (m, 10 H) 2.83 (d, J = 12.94 Hz, 1 H) 2.88-2.96 (m, 1 H) 3.00-3.12 (m, 1 H) 3.05 (s, 3 H) 3.14-3.21 (m, 2 H) 3.24 (s, 3 H) 3.26-3.52 (m, 5 H) 3.28 (s, 3 H) 3.68 (d, J = 10.25 Hz, 1 H) 3.72 (d, J = 7.08 Hz, 1 H) 3.74 (s, 1 H) 4.09 (q, J = 6.35 Hz, 1 H) 4.42 (d, J = 7.32 Hz, 1 H) 4.91 (dd, J = 10.99, 1.95 Hz, 1 H) 4.96-5.01 (m, 1 H) 5.90-5.94 (m, 1 H) |
| 208 | 2-fluorobenzyl amide | N,N-diethyl | 1081 | (400 MHz): 0.85 (t, J = 7.32 Hz, 3 H) 1.04 (t, J = 6.84 Hz, 6 H) 1.07 (d, J = 7.57 Hz, 3 H) 1.08 (d, J = 6.83 Hz, 3 H) 1.13 (d, J = 7.08 Hz, 3 H) 1.17 (s, 3 H) 1.19 (d, J = 6.35 Hz, 3 H) 1.20 (d, J = 5.37 Hz, 3 H) 1.23 (d, J = 6.10 Hz, 3 H) 1.34 (s, 3 H) 1.42 (s, 3 H) 1.48-1.96 (m, 7 H) 1.96-2.03 (m, 1 H) 2.10 (d, J = 14.9 Hz, 1 H) 2.29 (s, 6 H) 2.34 (s, 3 H) 2.38-2.64 (m, 10 H) 2.84 (d, J = 14.9 Hz, 1 H) 3.07 (q, J = 7.08 Hz, 1 H) 3.17 (dd, J = 10.3, 2.93 Hz, 1 H) 3.27 (s, 3 H) 3.37-3.51 (m, 2 H) 3.66 (d, J = 7.32 Hz, 1 H) 3.69 (d, J = 9.03 Hz, 1 H) 3.78 (s, 1 H) 4.07 (q, J = 6.35 Hz, 1 H) 4.41 (d, J = 7.08 Hz, 1 H) 4.43 (dd, J = 15.1, 7.08 Hz, 1 H) 4.54 (dd, J = 15.1, 6.35 Hz, 1 H) 4.97 (d, J = 3.66 Hz, 1 H) 5.31 (d, J = 9.03 Hz, 1 H) 5.49-5.57 (m, 1 H) 6.98 (dt, J = 8.30, 1.22 Hz, 1 H) 7.06 (dt, J = 7.57, 1.22 Hz, 1 H) 7.19-7.26 (m, 1 H) 7.41 (dt, J = 7.57, 1.71 Hz, 1 H) 7.57 (s, 1 H) |
| 209 | 4-methoxybenzyl amide | N,N-diethyl | 1093 | (400 MHz): 0.79 (t, J = 7.32 Hz, 3 H) 1.03 (t, J = 7.08 Hz, 6 H) 1.08 (d, J = 7.08 Hz, 6 H) 1.13 (d, J = 7.08 Hz, 3 H) 1.17 (s, 3 H) 1.17 (d, J = 6.18 Hz, 3 H) 1.21 (d, J = 7.32 Hz, 3 H) 1.23 (d, J = 6.10 Hz, 3 H) 1.24-1.26 (m, 1 H) 1.36 (s, 3 H) 1.42 (s, 3 H) 1.49-1.96 (m, 1 H) 1.64-1.90 (m, 5H) 1.95-2.06 (m, 2 H) 2.10 (d, J = 14.9 Hz, 1 H) 2.29 (s, 6 H) 2.34 (s, 3 H) 2.40-2.88 (m, 10 H) 2.81-2.90 (m, 2 H) 2.91 (s, 3 H) 3.07 (q, J = 7.08 Hz, 1 H) 3.17 (dd, J = 10.3, 7.32 Hz, 1 H) 3.28 (s, 3 H) 3.40-3.51 (m, 1 H) 3.67 (d, J = 7.08 Hz, 1 H) 3.73 (d, J = 8.79 Hz, 1 H) 3.78 (s, 3 H) 3.78 (s, 1 H) 4.07 (q, J = 6.18 Hz, 1 H) 4.27 (dd, J = 14.1, 4.88 Hz, 1 H) 4.42 (d, J = 7.32 Hz, 1 H) 4.44 (dd, J = 14.1, 5.98 Hz, 1 H) 5.00 (d, J = 3.66 Hz, 1 H) 5.25 (d, J = 9.52 Hz, 1 H) 5.39 (s, 1 H) 6.79-6.84 (m, 2 H) 7.22-7.27 (m, 2 H) 7.72 (s, 1 H) |
| 210 | N-ethyl amide | N,N-diethyl | 1001 | (400 MHz): 0.89 (t, J = 7.32 Hz, 3 H) 1.02 (t, J = 7.08 Hz, 6 H) 1.08 (d, J = 7.32 Hz, 6 H) 1.13 (d, J = 6.10 Hz, 3 H) 1.14 (t, J = 7.08 Hz, 3H) 1.16 (s, 3 H) 1.17 (d, J = 6.35 Hz, 3 H) 1.17-1.26 (m, 1 H) 1.21 (d, J = 7.08 Hz, 3 H) 1.23 (d, J = 5.62 Hz, 3 H) 1.36 (s, 3 H) 1.44 (s, 3 H) 1.60-2.06 (m, 8 H) 2.09 (d, J = 14.89 Hz, 1 H) 2.29 (s, 6 H) 2.34 (s, 3 H) 2.39-2.70 (m, 10 H) 2.79-2.91 (m, 2 H) 2.92 (s, 3 H) 3.07 (q, J = 6.59 Hz, 1 H) 3.17 (dd, J = 10.01, 7.08 Hz, 1 H) 3.21-3.32 (m, 2 H) 3.28 (s, 3 H) 3.38-3.52 (m, 1 H) 3.65 (d, J = 7.08 Hz, 1 H) 3.73 (d, J = 9.03 Hz, 1 H) 3.78 (s, 1 H) 4.08 (4, J = 5.86 Hz, 1 H) 4.42 (d, J = 7.32 Hz, 1 H) 4.98 (d, J = 4.40 Hz, 1 H) 5.10-5.17 (m, 1 H) 5.31 (d, J = 10.01 Hz, 1 H) 7.62 (s, 1 H) |
| 211 | N-isopropyl amide | N,N-diethyl | 1015 | (400 MHz): 0.90 (t, J = 7.32 Hz, 3 H) 1.02 (t, J = 7.08 Hz, 6 H) 1.08 (d, J = 7.08 Hz, 6 H) 1.11-1.22 (m, 13 H) 1.16 (s, 3 H) 1.21 (d, J = 7.32 Hz, 3H) 1.23 (d, J = 5.86 Hz, 3 H) 1.36 (s, 3 H) 1.43 (s, 3 H) 1.50-2.06 (m, 8 H) 2.09 (d, J = 14.65 Hz, 1 H) 2.28 (s, 6 H) 2.34 (s, 3 H) 2.39-2.68 (m, 10 H) 2.79-2.90 (m, 2 H) 2.93 (s, 3H) 3.06 (q, J = 7.32 Hz, 1 H) 3.17 (dd, J = 10.25, 7.32 Hz, 1 H) 3.27 (s, 3 H) 3.37-3.52 (m, 1 H) 3.67 (d, J = 7.08 Hz, 1 H) 3.72 (d, J = 9.03 Hz, 1 H) 3.75 (s, 1 H) 3.87-3.98 (m, 1 H) 4.07 (q, J = 6.35 Hz, 1 H) 4.42 (d, J = 7.32 Hz, 1 H) 4.88 (d, J = 7.32 Hz, 1 H) 4.98 (d, J = 3.91 Hz, 1 H) 5.37 (d, J = 10.25 Hz, 1 H) 7.61 (s, 1 H) |

TABLE 5-continued

| 212 | 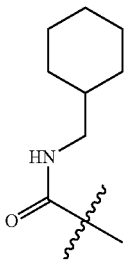 [SMILES: *C(=O)NCC1CCCCC1] | 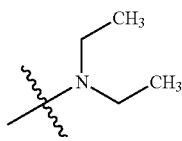 [SMILES: *N(CC)CC] | 1069 | (400 MHz): 0.88 (t, J = 7.32 Hz, 3 H) 1.02 (t, J = 7.08 Hz, 6 H) 1.08 (d, J = 7.08 Hz, 6 H) 1.13 (d, J = 7.08 Hz, 3 H) 1.16 (s, 3 H) 1.17-1.28 (m, 1 H) 1.17 (d, J = 6.59 Hz, 3 H) 1.21 (d, J = 6.35 Hz, 3 H) 1.23 (d, J = 5.86 Hz, 3 H) 1.36 (s, 3 H) 1.43 (s, 3 H) 1.50-2.05 (m, 19 H) 2.09 (d, J = 14.89 Hz, 1 H) 2.28 (s, 6 H) 2.34 (s, 3 H) 2.38-2.69 (m, 10 H) 2.79-2.89 (m, 2 H) 2.90 (s, 3 H) 2.90-3.02 (m, 1 H) 3.07 (q, J = 6.84 Hz, 1 H) 3.12-3.20 (m, 2 H) 3.27 (s, 3 H) 3.37-3.51 (m, 1 H) 3.67 (d, J = 7.08 Hz. 1 H) 3.72 (d, J = 9.03 Hz, 1 H) 3.78 (s, 1 H) 4.07 (q, J = 6.35 Hz, 1 H) 4.42 (d, J = 7.32 Hz, 1 H) 4.98 (d, J = 3.66 Hz, 1 H) 5.15-5.24 (m, 1 H) 5.32 (d, J = 10.50 Hz, 1 H) 7.61 (s, 1 H) |
|---|---|---|---|---|
| 213 | 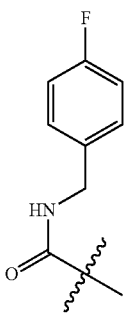 [SMILES: *C(=O)NCc1ccc(F)cc1] | 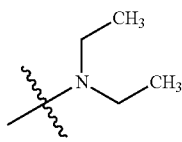 | 1081 | (400 MHz): 0.79 (t, J = 7.20 Hz, 3 H) 1.03 (t, J = 7.08 Hz, 6 H) 1.08 (d, J = 7.08 Hz, 6 H) 1.13 (d, J = 7.08 Hz, 3 H) 1.17 (s, 3 H) 1.19 (d, J = 6.10 Hz, 3 H) 1.21 (d, J = 7.32 Hz, 3 H) 1.23 (d, J = 9.03 Hz, 3 H) 1.24-1.25 (m, 1H) 1.35 (s, 3 H) 1.42 (s, 3 H) 1.50-1.90 (m, 6 H) 1.96-2.02 (m, 2 H) 2.10 (d, J = 14.9 Hz, 1 H) 2.29 (s, 6 H) 2.35 (s, 3 H) 2.40-2.67 (m, 10 H) 2.82-2.86 (m, 2 H) 2.87 (s, 3 H) 3.07 (q, J = 7.08 Hz, 1 H) 3.17 (dd, J = 10.3, 7.32 Hz, 1 H) 3.28 (s, 3 H) 3.41-3.51 (m, 1 H) 3.67 (d, J = 7.32 Hz, 1 H) 3.73 (d, J = 9.28 Hz, 1 H) 3.79 (s, 1 H) 4.08 (s, J = 6.10 Hz, 1 H) 4.27 (dd, J = 14.8, 4.76 Hz, 1 H) 4.42 (d, J = 7.32 Hz, 1 H) 4.49 (dd, J = 14.8, 6.47 Hz, 1 H) 5.00 (d, J = 3.17 Hz, 1 H) 5.21 (d, J = 9.28 Hz, 1 H) 5.50-5.54 (m, 1 H) 6.94-7.00 (m, 2 H) 7.28-7.33 (m, 2 H) 7.72 (s, 1 H) |
| 214 | 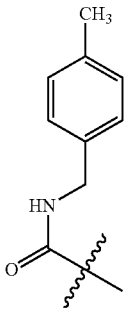 [SMILES: *C(=O)NCc1ccc(C)cc1] | 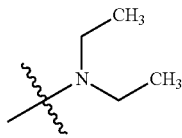 [SMILES: *N(CC)CC] | 1077 | (400 MHz): 0.80 (t, J = 7.32 Hz, 3 H) 1.03 (t, J = 7.08 Hz, 6 H) 1.08 (d, J = 6.84 Hz, 6 H) 1.13 (d, J = 6.84 Hz, 3 H) 1.17 (s, 3 H) 1.19 (d, J = 6.27 Hz, 3 H) 1.21 (d, J = 7.08 Hz, 3 H) 1.23 (d, J = 6.10 Hz, 3 H) 1.23-1.25 (m, 1H) 1.35 (s, 3H) 1.42 (s, 3 H) 1.47-1.90 (m, 6 H) 1.94-2.03 (m, 2 H) 2.10 (d, J = 14.9 Hz, 1 H) 2.29 (s, 6 H) 2.31 (s, 3 H) 2.35 (s, 3 H) 2.40-2.67 (m, 10 H) 2.81-2.88 (m, 2 H) 2.90 (s, 3 H) 3.08 (q, J = 6.84 Hz, 1 H) 3.17 (dd, J = 10.3, 7.32 Hz, 1 H) 3.28 (s, 3 H) 3.40-3.50 (m, 1 H) 3.67 (d, J = 7.32 Hz, 1 H) 3.73 (d, J = 9.03 Hz, 1 H) 3.78 (s, 1 H) 4.08 (q, J = 6.27 Hz, 1 H) 4.29 (dd, J = 14.3, 4.52 Hz, 1 H) 4.42 (d, J = 7.32 Hz, 1 H) 4.47 (dd, J = 14.3, 6.10 Hz, 1 H) 5.00 (d, J = 3.17 Hz, 1 H) 5.27 (d, J = 9.77 Hz, 1 H) 5.38 (s, 1 H) 7.09 (d, J = 7.81 Hz, 2 H) 7.21 (d, J = 7.81 Hz, 2 H) 7.71 (s, 1 H) |
| 215 | 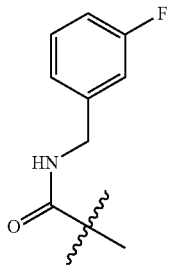 [SMILES: *C(=O)NCc1cccc(F)c1] | 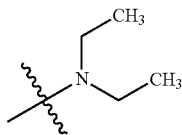 [SMILES: *N(CC)CC] | 1081 | (400 MHz): 0.80 (t, J = 7.20 Hz, 3 H) 1.03 (t, J = 7.20 Hz, 6 H) 1.08 (d, J = 7.57 Hz, 3 H) 1.08 (d, 7.08 Hz, 3H) 1.13 (d, J = 6.84 Hz, 3 H) 1.17 (s, 3 H) 1.19 (d, J = 6.35 Hz, 3H) 1.21 (d, J = 7.57 Hz, 3 H) 1.23 (d, J = 6.10 Hz, 3 H) 1.24-1.25 (m, 1H) 1.35 (s, 3 H) 1.42 (s, 3 H) 1.51-1.90 (m, 6 H) 1.95-2.02 (m, 2 H) 2.10 (d, J = 14.9 Hz, 1 H) 2.29 (s, 6 H) 2.35 (s, 3 H) 2.40-2.69 (m, 10 H) 2.82-2.86 (m, 2 H) 2.87 (s, 3 H) 3.07 (q, J = 7.08 Hz, 1 H) 3.17 (dd, J = 10.3, 7.32 Hz, 1 H) 3.28 (s, 3 H) 3.39-3.51 (m, 1 H) 3.67 (d, J = 7.32 Hz, 1 H) 3.71 (d, J = 8.79 Hz, 1 H) 3.80 (s, 1 H) 4.08 (q, J = 6.35 Hz, 1 H) 4.30 (dd, J = 14.9, 4.88 Hz, 1 H) 4.42 (d, J = 7.32 Hz, 1 H) 4.52 (dd, J = 14.9, 6.59 Hz, 1 H) 4.99 (d, J = 3.42 Hz, 1 H) 5.20 (d, J = 9.52 Hz, 1 H) 5.58 (s, 1 H) 6.92 (m, 1 H) 7.06 (m, 1 H) 7.13 (d, J = 7.57 Hz, 1 H) 7.22-7.28 (m, 1 H) 7.75 (s, 1 H) |

TABLE 5-continued

| 216 | 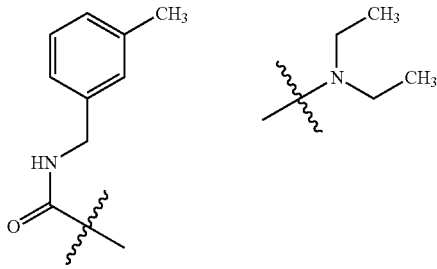 | | 1077 | (400 MHz): 0.80 (t, J = 7.32 Hz, 3 H) 1.03 (t, J = 7.08 Hz, 6 H) 1.08 (d, J = 7.57 Hz, 3 H) 1.08 (d, J = 6.92 Hz, 3 H) 1.13 (d, J = 6.84 Hz, 3 H) 1.17 (s, 3 H) 1.19 (d, J = 6.35 Hz, 3 H) 1.21 (d, J = 7.81 Hz, 3 H) 1.23 (d, J = 6.10 Hz, 3 H) 1.23-1.25 (m, 1H) 1.35 (s, 3 H) 1.42 (s, 3 H) 1.49-1.90 (m, 6 H) 1.95-2.02 (m, 2 H) 2.10 (d, J = 14.9 Hz, 1 H) 2.29 (s, 6 H) 2.31 (s, 3 H) 2.35 (s, 3 H) 2.41-2.66 (m, 10 H) 2.81-2.87 (m, 2 H) 2.91 (s, 3 H) 3.07 (q, J = 6.92 Hz, 1 H) 3.17 (dd, J = 10.3, 7.32 Hz, 1 H) 3.28 (s, 3 H) 3.38-3.51 (m, 1 H) 3.68 (d, J = 7.08 Hz, 1 H) 3.73 (d, J = 8.79 Hz, 1 H) 3.78 (s, 1 H) 4.08 (q, J = 6.35 Hz, 1 H) 4.28 (d, J = 14.4, 4.64 Hz, 1 H) 4.42 (d, J = 7.32 Hz, 1 H) 4.48 (dd, J = 14.4, 6.35 Hz, 1 H) 5.00 (d, J = 3.42 Hz, 1 H) 5.28 (d, J = 9.28 Hz, 1 H) 5.36-5.39 (m, 1 H) 7.04 (d, J = 7.57 Hz, 1 H) 7.11-7.20 (m, 3 H) 7.74 (s, 1 H) |
| 217 | 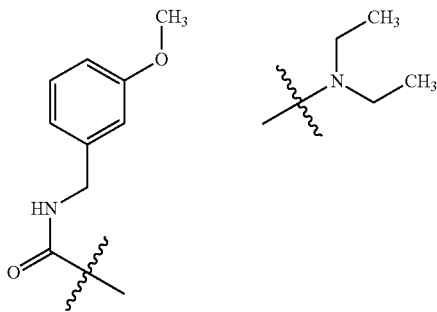 | | 1093 | (400 MHz): 0.80 (t, J = 7.32 Hz, 3 H) 1.03 (t, J = 7.08 Hz, 6 H) 1.08 (d, J = 7.32 Hz, 3 H) 1.08 (d, J = 6.84 Hz, 3 H) 1.13 (d, J = 6.84 Hz, 3 H) 1.17 (s, 3 H) 1.19 (d, J = 8.59 Hz, 3 H) 1.20 (d, J = 7.81 Hz, 3 H) 1.23 (d, J = 6.10 Hz, 3 H) 1.23-1.25 (m, 1H) 1.35 (s, 3 H) 1.42 (s, 3 H) 1.50-1.90 (m, 6 H) 1.95-2.01 (m, 2 H) 2.10 (d, J = 14.9 Hz, 1 H) 2.29 (s, 6 H) 2.35 (s, 3 H) 2.40-2.68 (m, 10 H) 2.81-2.88 (m, 2 H) 2.89 (s, 3 H) 3.07 (q, J = 6.84 Hz, 1 H) 3.17 (dd, J = 10.1. 7.32 Hz, 1 H) 3.28 (s, 3 H) 3.40-3.51 (m, 1 H) 3.67 (d, J = 7.08 Hz, 1 H) 3.73 (d, J = 9.28 Hz, 1 H) 3.79 (s, 3 H) 3.79 (s, 1 H) 4.08 (q, J = 6.59 Hz, 1 H) 4.30 (dd, J = 14.5, 4.76 Hz, 1 H) 4.42 (d, J = 7.32 Hz, 1 H) 4.51 (dd, J = 14.5, 6.47 Hz, 1 H) 4.99 (d, J = 3.42 Hz, 1 H) 5.26 (d, J = 9.28 Hz, 1 H) 5.45-5.48 (m, 1 H) 6.77 (dd, J = 8.18, 2.32 Hz, 1 H) 6.88-6.93 (m, 2 H) 7.20 (t, J = 8.18 Hz, 1 H) 7.73 (s, 1 H) |
| 218 | 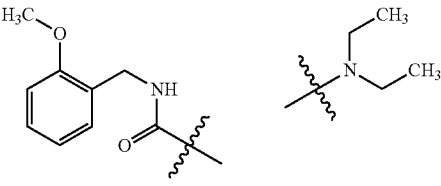 | | 1093 | (400 MHz): 0.86 (t, J = 7.32 Hz, 3 H) 1.03 (t, J = 7.08 Hz, 6 H) 1.06 (d, J = 7.81 Hz, 3 H) 1.09 (d, J = 6.84 Hz, 3 H) 1.14 (d, J = 7.06 Hz, 3 H) 1.16 (s, 3 H) 1.17-1.26 (m, 1 H) 1.18 (d, J = 6.35 Hz, 3 H) 1.20 (d, J = 6.84 Hz, 3 H) 1.23 (d, J = 6.10 Hz, 3 H) 1.32 (s, 3 H) 1.42 (s, 3 H) 1.48-2.02 (m, 8 H) 2.10 (d, J = 14.65 Hz, 1 H) 2.28 (s, 6 H) 2.34 (s, 3 H) 2.40-2.66 (m, 10 H) 2.78-2.86 (m, 2 H) 2.83 (s, 3 H) 3.06 (q, J = 6.84 Hz, 1 H) 3.17 (dd, J = 10.25, 7.32 Hz, 1 H) 3.28 (s, 3 H) 3.37-3.52 (m, 2 H) 3.66 (d, J = 7.08 Hz, 1 H) 3.70 (d, J = 8.55 Hz, 1 H) 3.74 (s, 1 H) 4.06 (q, J = 6.35 Hz, 1 H) 4.34-4.49 (m, 3 H) 4.98 (d, J = 3.66 Hz, 1 H) 5.38-5.51 (m, 2 H) 6.83 (d, J = 8.06 Hz, 1 H) 6.87 (t, J = 7.32 Hz, 1 H) 7.18-7.31 (m, 2 H) 7.73 (s, 1 H) |
| 219 | 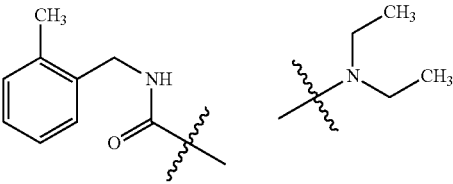 | | 1077 | (400 MHz): 0.76 (t, J = 7.32 Hz, 3 H) 1.03 (t, J = 7.08 Hz, 6 H) 1.08 (d, J = 6.35 Hz, 6 H) 1.13 (d, J = 6.84 Hz, 3 H) 1.16 (s, 3 H) 1.17-1.28 (m, 1 H) 1.19 (d, J = 6.35 Hz, 3 H) 1.20 (d, J = 6.35 Hz, 3 H) 1.24 (d, J = 5.86 Hz, 3 H) 1.36 (s, 3 H) 1.41 (s, 3 H) 1.47-1.90 (m, 5 H) 1.94-2.06 (m, 3 H) 2.10 (d, J = 14.65 Hz, 1 H) 2.28 (s, 6 H) 2.34 (s, 3 H) 2.35 (s, 3 H) 2.39-2.70 (m, 10 H) 2.79-2.87 (m, 2 H) 2.93 (s, 3 H) 3.07 (q, J = 6.35 Hz, 1 H) 3.17 (dd, J = 10.25, 7.32 Hz, 1 H) 3.28 (s, 3 H) 3.36-3.52 (m, 2 H) 3.68 (d, J = 7.08 Hz, 1 H) 3.73 (d, J = 9.28 Hz, 1 H) 3.79 (s, 1 H) 4.08 (q, J = 6.35 Hz, 1 H) 4.29 (dd, J = 14.41, 4.40 Hz, 1 H) 4.42 (d, J = 7.32 Hz, 1 H) 4.56 (dd, J = 14.40, 6.84 Hz, 1 H) 5.00 (d, J = 3.42 Hz, 1 H) 5.21 (d, J = 10.01 Hz, 1 H) 5.30-5.38 (m, 1 H) 7.08-7.15 (m, 3H) 7.25-7.29 (m, 1 H) 7.71 (s, 1 H) |

TABLE 5-continued

| 220 | 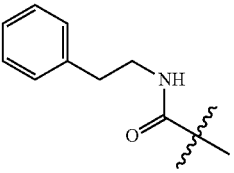 [SMILES: *C(=O)NCCc1ccccc1] | 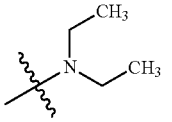 | 1077 | (400 MHz): 0.86 (t, J = 7.32 Hz, 3 H) 1.02 (t, J = 7.08 Hz, 6 H) 1.07 (d, J = 7.08 Hz, 6 H) 1.13 (d, J = 7.08 Hz, 3 H) 1.16 (s, 3 H) 1.17-1.26 (m, 1 H) 1.17 (d, J = 6.59 Hz, 3 H) 1.20 (d, J = 7.32 Hz, 3 H) 1.23 (d, J = 6.10 Hz, 3 H) 1.34 (s, 3 H) 1.42 (s, 3 H) 1.48-2.04 (m, 8 H) 2.09 (d, J = 14.89 Hz, 1 H) 2.28 (s, 6 H) 2.34 (s, 3 H) 2.38-2.67 (m, 10 H) 2.78-2.87 (m, 4 H) 2.88 (s, 3 H) 3.06 (q, J = 6.84 Hz, 1 H) 3.17 (dd, J = 10.25, 7.32 Hz, 1 H) 3.27 (s, 3 H) 3.36-3.50 (m, 3 H) 3.51-3.62 (m, 1 H) 3.66 (d, J = 7.08 Hz, 1 H) 3.71 (d, J = 9.28 Hz, 1 H) 3.74 (s, 1 H) 4.06 (q, J = 6.35 Hz, 1 H) 4.41 (d, J = 7.32 Hz, 1 H) 4.97 (d, J = 3.42 Hz, 1 H) 5.13-5.28 (m, 2 H) 7.16-7.32 (m, 5 H) 7.62 (s, 1 H) |
|---|---|---|---|---|
| 221 | 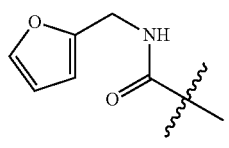 [SMILES: *C(=O)NCc1ccco1] | 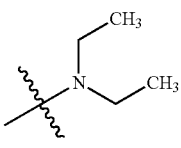 [SMILES: *N(CC)CC] | 1053 | (400 MHz): 0.88 (t, J = 7.57 Hz, 3 H) 1.03 (t, J = 7.32 Hz, 6 H) 1.07 (d, J = 7.57 Hz, 3 H) 1.08 (d, J = 6.84 Hz, 3 H) 1.13 (d, J = 7.08 Hz, 3 H) 1.16 (s, 3 H) 1.17-1.26 (m, 1 H) 1.18 (d, J = 6.35 Hz, 3 H) 1.21 (d, J = 7.57 Hz, 3 H) 1.23 (d, J = 6.10 Hz, 3 H) 1.34 (s, 3 H) 1.43 (s, 3 H) 1.49-2.06 (m, 8 H) 2.08 (d, J = 14.89 Hz, 1 H) 2.28 (s, 6 H) 2.34 (s, 3 H) 2.38-2.66 (m, 10 H) 2.79-2.86 (m, 2 H) 2.84 (s, 3 H) 3.06 (s, J = 7.08 Hz, 1 H) 3.17 (dd, J = 10.01, 7.08 Hz, 1 H) 3.27 (s, 3 H) 3.38-3.52 (m, 2 H) 3.66 (d, J = 7.08 Hz, 1 H) 3.71 (d, J = 8.55 Hz, 1 H) 3.76 (s, 1 H) 4.07 (q, J = 6.35 Hz, 1 H) 4.34 (dd, J = 15.63, 5.13 Hz, 1 H) 4.42 (d, J = 7.08 Hz, 1 H) 4.49 (dd, J = 15.63, 6.10 Hz, 1 H) 4.98 (d, J = 3.66 Hz, 1 H) 5.32-5.48 (m, 2 H) 6.21-6.28 (m, 2 H) 7.24-7.32 (m, 1 H) 7.74 (s, 1 H) |
| 222 | 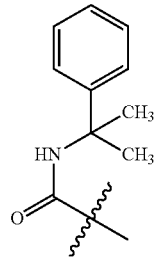 [SMILES: *C(=O)NC(C)(C)c1ccccc1] | 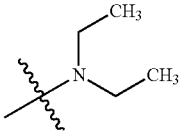 [SMILES: *N(CC)CC] | 1091 | (400 MHz): 0.79 (t, J = 7.32 Hz, 3 H) 1.04 (t, J = 7.20 Hz, 6 H) 1.07 (d, J = 6.59 Hz, 3 H) 1.08 (d, J = 6.84 Hz, 3 H) 1.13 (d, J = 7.08 Hz, 3 H) 1.17 (s, 3 H) 1.19 (d, J = 6.10 Hz, 3 H) 1.21 (d, J = 6.84 Hz, 3 H) 1.23 (d, J = 6.10 Hz, 3 H) 1.23-1.25 (m, 1H) 1.36 (s, 3 H) 1.43 (s, 3 H) 1.50-1.92 (m. 6 H) 1.96-2.02 (m, 2 H) 2.10 (d, J = 14.9 Hz, 1 H) 2.29 (s, 6 H) 2.35 (s, 3 H) 2.40-2.68 (m, 10 H) 2.82-2.89 (m, 2 H) 2.94 (s, 3 H) 3.06 (q, J = 6.84 Hz, 1 H) 3.17 (dd, J = 10.1, 7.32 Hz, 1 H) 3.28 (s, 3 H) 3.40-3.51 (m, 1 H) 3.66 (d, J = 7.32 Hz, 1 H) 3.77 (d, J = 9.03 Hz, 1 H) 3.80 (s, 1 H) 4.10 (q, J = 6.10 Hz, 1 H) 4.42 (d, J = 7.32 Hz, 1 H) 5.02 (d, J = 3.91 Hz, 1 H) 5.17 (d, J = 9.77 Hz, 1 H) 5.48 (s, 1 H) 7.16-7.20 (m, 1 H) 7.28-7.32 (m, 2 H) 7.47-7.50 (m, 2 H) 7.67 (s, 1 H) |
| 223 | 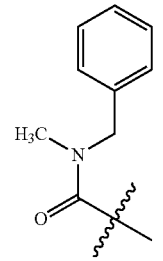 [SMILES: *C(=O)N(C)Cc1ccccc1] | 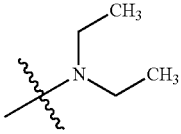 | 1077 | (400 MHz): 0.94 (t, J = 7.32 Hz, 3 H) 1.03 (t, J = 7.08 Hz, 6 H) 1.07 (d, J = 7.32 Hz, 3 H) 1.14-1.25 (m, 16 H) 1.16 (s, 3 H) 1.33 (s, 3 H) 1.44 (s, 3 H) 1.48-1.87 (m, 6 H) 1.92-2.01 (m, 2 H) 2.10 (d, J = 14.7 Hz, 1 H) 2.29 (s, 6 H) 2.35 (s, 3 H) 2.41-2.62 (m, 10 H) 2.76-2.86 (m, 2 H) 2.80 (s, 3 H) 2.92 (s, 3 H) 3.09 (q, J = 6.67 Hz, 1 H) 3.17 (dd, J = 10.3, 7.32 Hz, 1 H) 3.28 (s, 3 H) 3.44-3.52 (m, 1 H) 3.83 (s, 1 H) 3.68 (d, J = 6.80 Hz, 1 H) 3.72 (d, J = 8.40 Hz, 1 H) 4.07 (q, J = 6.35 Hz, 1 H) 4.43 (d, J = 7.32 Hz, 1 H) 4.49 (d, J = 15.1 Hz, 1 H) 4.58 (d, J = 15.1 Hz, 1 H) 5.01 (d, J = 3.66 Hz, 1 H) 5.85 (dd, J = 10.1, 3.05 Hz, 1 H) 7.23-7.31 (m, 5 H) 8.18 (s, 1 H) |
| 224 | 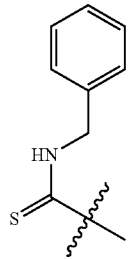 [SMILES: *C(=S)NCc1ccccc1] | 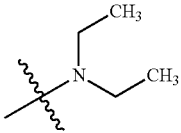 [SMILES: *N(CC)CC] | 1078 | (400 MHz): 0.64 (t, J = 7.32 Hz, 3 H) 1.03 (t, J = 7.08 Hz, 6 H) 1.07 (d, J = 7.57 Hz, 3 H) 1.10 (d, J = 7.08 Hz, 3 H) 1.13 (d, J = 7.08 Hz, 3 H) 1.17 (s, 3 H) 1.17-1.28 (m, 7 H) 1.24 (d, J = 6.10 Hz, 3 H) 1.38 (s, 3 H) 1.41 (s, 3 H) 1.47-1.83 (m, 5 H) 1.99-2.06 (m, 3 H) 2.10 (d, J = 14.65 Hz, 1 H) 2.28 (s, 6 H) 2.35 (s, 3 H) 2.38-2.63 (m, 9 H) 2.66-2.76 (m, 1 H) 2.80-2.91 (m, 2 H) 2.94 (s, 3 H) 3.07 (q, J = 7.08 Hz, 1 H) 3.17 (dd, J = 10.50, 7.32 Hz, 1 H) 3.28 (s, 3 H) 3.40-3.51 (m, 2 H) 3.66 (d, J = 7.08 Hz, 1 H) 3.73 (d, J = 9.28 Hz, 1 H) 3.87 (s, 1 H) 4.08 (q, J = 6.35 Hz, 1 H) 4.42 (d, J = 7.08 Hz, 1 H) 4.51 (dd, J = 14.65, 3.42 Hz, 1 H) 4.83-4.92 (m, 1 H) 4.98-5.02 (m, 1 H) 5.10 (dd, J = 14.65, 6.59 Hz, 1 H) 6.88-6.95 (m, 1 H) 7.20-7.30 (m, 3 H) 7.38 (d, J = 7.08 Hz, 2 H) 8.94 (s, 1 H) |

TABLE 5-continued

| 225 | naphthalen-1-ylmethyl-NH-C(O)-C(CH3) | -N(CH2CH3)2 C(CH3)2 | 1113 | (400 MHz): 0.71 (t, J = 7.20 Hz, 3 H) 1.05 (t, J = 7.08 Hz, 6 H) 1.06 (d, J = 5.62 Hz, 3 H) 1.07 (d, J = 6.67 Hz, 3 H) 1.12 (d, J = 7.08 Hz, 3 H) 1.17 (d, J = 6.84 Hz, 3 H) 1.18 (s, 3 H) 1.21-1.25 (m, 7H) 1.35 (s, 3 H) 1.40 (s, 3 H) 1.46-1.54 (m, 1 H) 1.65-2.13 (m, 8 H) 2.29 (s, 6 H) 2.36 (s, 3 H) 2.41-2.65 (m, 10 H) 2.79-2.87 (m, 2 H) 2.92 (s, 3 H) 3.06 (q, J = 6.67 Hz, 1 H) 3.17 (dd, J = 10.1, 7.20 Hz, 1 H) 3.28 (s, 3 H) 3.45-3.61 (m, 1 H) 3.67 (d, J = 7.08 Hz, 1 H) 3.71 (d, J = 8.79 Hz, 1 H) 3.78 (s, 1 H) 4.09 (q, J = 6.84 Hz, 1 H) 4.34 (s, 1 H) 4.42 (d, J = 7.20 Hz, 1 H) 4.77 (dd, J = 14.4, 4.15 Hz, 1 H) 4.99 (d, J = 3.17 Hz, 1 H) 5.03 (dd, J = 14.4, 6.59 Hz, 1 H) 5.22 (d, J = 9.77 Hz, 1 H) 5.51 (br s, 1 H) 7.37-7.57 (m, 4 H) 7.75-7.89 (m, 3 H) 8.07-8.11 (m, 1 H) |
| 226 | naphthalen-2-ylmethyl-NH-C(O)-C(CH3) | -N(CH2CH3)2 C(CH3)2 | 1113 | (400 MHz): 0.72 (t, J = 7.32 Hz, 3 H) 1.06 (t, J = 7.08 Hz, 6 H) 1.07 (d, J = 7.57 Hz, 3 H) 1.09 (d, J = 7.08 Hz, 3 H) 1.14 (d, J = 7.32 Hz, 3 H) 1.16 (d, J = 7.32 Hz, 3 H) 1.18 (s, 3 H) 1.19 (d, J = 6.35 Hz, 3 H) 1.23 (d, J = 6.10 Hz, 3 H) 1.27-1.25 (m, 1H) 1.35 (s, 3 H) 1.42 (s, 3 H) 1.47-1.55 (m, 1 H) 1.65-2.12 (m, 8 H) 2.30 (s, 6 H) 2.36 (s, 3 H) 2.43-2.67 (m, 10 H) 2.81-2.87 (m, 2 H) 2.93 (s, 3 H) 3.08 (q, J = 7.08 Hz, 1 H) 3.18 (dd, J = 10.5, 7.08 Hz, 1 H) 3.28 (s, 3 H) 3.43-3.50 (m, 1 H) 3.87 (d, J = 7.08 Hz, 1 H) 3.73 (d, J = 8.79 Hz, 1 H) 3.81 (s, 1 H) 4.09 (q, J = 7.32 Hz, 1 H) 4.42 (d, J = 7.08 Hz, 1 H) 4.51 (dd, J = 14.8, 5.25 Hz, 1 H) 4.68 (dd, J = 14.8, 6.35 Hz, 1 H) 4.96-4.98 (m, 1 H) 5.26 (d, J = 10.0 Hz, 1 H) 5.58-5.61 (m, 1 H) 7.40-7.48 (m, 3 H) 7.76-7.82 (m, 5 H) |
| 227 | pyridin-2-ylmethyl-NH-C(O)-C(CH3) | -N(CH2CH3)2 C(CH3)2 | 1064 | (400 MHz): 0.89 (t, J = 7.45 Hz, 3 H) 1.03 (t, J = 7.20 Hz, 6 H) 1.06 (d, J = 7.32 Hz, 3 H) 1.11 (d, J = 6.84 Hz, 3 H) 1.13-1.25 (m, 13 H) 1.15 (s, 3 H) 1.33 (s, 3 H) 1.44 (s, 3 H) 1.51-1.59 (m, 1 H) 1.61-2.12 (m, 8 H) 2.28 (s, 6 H) 2.34 (s, 3 H) 2.40-2.67 (m, 10 H) 2.77-2.85 (m, 2 H) 2.83 (s, 3 H) 3.08 (q, J = 6.84 Hz, 1 H) 3.17 (dd, J = 10.1, 7.32 Hz, 1 H) 3.27 (s, 3 H) 3.41-3.50 (m, 1 H) 3.65 (d, J = 7.32 Hz, 1 H) 3.69 (d, J = 8.79 Hz, 1 H) 3.76 (s, 1 H) 4.05 (q, J = 6.36 Hz, 1 H) 4.41 (d, J = 7.32 Hz, 1 H) 4.52 (dd, J = 16.0, 5.00 Hz, 1 H) 4.58 (dd, J = 16.0, 5.37 Hz, 1 H) 4.94 (d, J = 3.66 Hz, 1 H) 5.51 (d, J = 8.54 Hz, 1 H) 6.19 (t, J = 5.13 Hz, 1 H) 7.14 (dd, J = 7.51, 4.88 Hz, 1 H) 7.33 (d, J = 7.51 Hz, 1 H) 7.63 (td, J = 7.51, 1.79 Hz, 1 H) 7.88 (s, 1 H) 8.49 (d, J = 4.88 Hz, 1 H) |
| 228 | pyridin-3-ylmethyl-NH-C(O)-C(CH3) | -N(CH2CH3)2 C(CH3)2 | 1064 | (400 MHz): 0.80 (t, J = 7.20 Hz, 3 H) 1.04 (t, J = 7.45 Hz, 6 H) 1.07 (d, J = 8.05 Hz, 6 H) 1.13 (d, J = 7.08 Hz, 3 H) 1.17 (s, 3 H) 1.19 (d, J = 6.43 Hz, 3 H) 1.21 (d, J = 6.84 Hz, 1 H) 1.23 (d, J = 6.10 Hz, 1 H) 1.21-1.25 (m, 1 H) 1.34 (s, 3 H) 1.42 (s, 3 H) 1.50-2.12 (m, 9 H) 2.29 (s, 6 H) 2.35 (s, 3 H) 2.41-2.67 (m, 10 H) 2.79-2.88 (m, 2 H) 2.80 (s, 3 H) 3.06 (q, J = 8.06 Hz, 1 H) 3.17 (dd, J = 10.3, 7.32 Hz, 1 H) 3.28 (s, 3 H) 3.43-3.50 (m, 1 H) 3.64 (d, J = 7.60 Hz, 1 H) 3.68 (d, J = 8.80 Hz, 1 H) 3.77 (s, 1 H) 4.08 (q, J = 6.43 Hz, 1 H) 4.41 (d, J = 7.32 Hz, 1 H) 4.34 (dd, J = 14.9, 5.13 Hz, 1 H) 4.52 (dd, J = 14.9, 6.35 Hz, 1 H) 4.98-5.00 (m, 1 H) 5.18 (d, J = 10.3 Hz, 1 H) 5.70-6.74 (m, 1 H) 7.22-7.26 (m, 1 H) 7.75 (s, 1 H) 7.77 (dt, J = 7.81, 1.95 Hz, 1 H) 8.49 (dd, J = 4.88, 1.95 Hz, 1 H) 8.54 (d, J = 1.95 Hz, 1 H) |
| 229 | pyridin-4-ylmethyl-NH-C(O)-C(CH3) | -N(CH2CH3)2 C(CH3)2 | 1064 | (400 MHz): 0.80 (t, J = 7.32 Hz, 3 H) 1.04 (t, J = 7.20 Hz, 6 H) 1.08 (d, J = 7.57 Hz, 3 H) 1.09 (d, J = 6.84 Hz, 3 H) 1.14 (d, J = 7.08 Hz, 3 H) 1.17 (s, 3 H) 1.18-1.25 (m, 10 H) 1.36 (s, 3 H) 1.44 (s, 3 H) 1.53-2.11 (m, 9H) 2.29 (s, 6 H) 2.35 (s, 3 H) 2.41-2.70 (m, 10 H) 2.82-2.87 (m, 2 H) 2.88 (s, 3 H) 3.08 (q, J = 6.84 Hz, 1 H) 3.17 (dd, J = 10.4, 7.32 Hz, 1 H) 3.28 (s, 3 H) 3.42-3.50 (m, 1 H) 3.66 (d, J = 7.32 Hz, 1 H) 3.71 (d, J = 9.03 Hz, 1 H) 3.81 (s, 1 H) 4.09 (q, J = 6.27 Hz, 1 H) 4.31 (dd, J = 15.8, 5.49 Hz, 1 H) 4.41 (d, J = 7.32 Hz, 1 H) 4.57 (dd, J = 15.8, 6.47 Hz, 1 H) 4.98 (d, J = 2.93 Hz, 1 H) 5.17 (d, J = 9.77 Hz, 1 H) 5.77-5.81 (m, 1 H) 7.25-7.28 (m, 2 H) 7.80 (s, 1 H) 8.52 (dd, J = 4.52, 1.59 Hz, 1 H) |

TABLE 5-continued

| | | | |
|---|---|---|---|
| 230 | 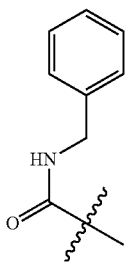 [SMILES: *C(=O)NCc1ccccc1] | 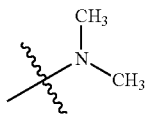 | 1035 | (400 MHz): 0.79 (t, J = 7.32 Hz, 3 H) 1.07 (d, J = 7.57 Hz, 6 H) 1.08 (d, J = 6.84 Hz, 3 H) 1.13 (d, J = 7.08 Hz, 3 H) 1.18 (s, 3 H) 1.20 (d, J = 6.35 Hz, 3 H) 1.20 (d, J = 5.37 Hz, 3 H) 1.23 (d, J = 6.10 Hz, 3 H) 1.35 (s, 3 H) 1.42 (s, 3 H) 1.47-1.60 (m, 1 H) 1.62-1.93 (m, 5 H) 1.96 (dd, J = 14.9, 5.13 Hz, 1 H) 2.03 (d, J = 14.9, 1 H) 2.15 (d, J = 14.6 Hz, 1 H) 2.26 (s, 6 H) 2.30 (s, 6 H) 2.35 (s, 3 H) 2.35-2.69 (m, 6 H) 2.82 (d, J = 14.6 Hz, 1 H) 2.88 (s, 3 H) 3.07 (q, J = 6.35 Hz, 1 H) 3.18 (dd, J = 10.3, 7.32 Hz, 1 H) 3.28 (s, 3 H) 3.35-3.53 (m, 2 H) 3.68 (d, J = 7.32 Hz, 1 H) 3.72 (d, J = 9.03 Hz, 1 H) 3.79 (s, 1 H) 4.10 (q, J = 6.35 Hz, 1 H) 4.32 (dd, J = 14.4, 4.64 Hz, 1 H) 4.43 (d, J = 7.32 Hz, 1 H) 4.52 (dd, J = 14.4, 6.35 Hz, 1 H) 5.00 (d, J = 3.42 Hz, 1 H) 5.27 (d, J = 10.3 Hz, 1 H) 5.40-5.49 (m, 1 H) 7.19-7.95 (m, 5 H) 7.73 (s, 1 H) |
| 231 | 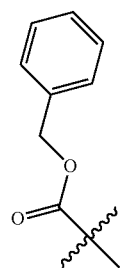 [SMILES: *C(=O)OCc1ccccc1] | 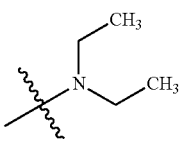 [SMILES: *N(CC)CC] | 1064 | (400 MHz): 0.35-0.40 (m, 0.8 H) 0.91-0.96 (m, 2.2 H) 1.03 (t, J = 7.08 Hz, 6 H) 1.06 (d, J = 7.57 Hz, 3 H) 1.11 (d, J = 8.84 Hz, 3 H) 1.13 (d, J = 8.06 Hz, 3 H) 1.16 (s, 3 H) 1.16-1.26 (m, 10 H) 1.31-1.43 (m, 6 H) 1.63-1.85 (m, 6 H) 1.93-2.05 (m, 3 H) 2.10 (d, J = 14.7 Hz, 1 H) 2.28 (s, 6 H) 2.34 (s, 3 H) 2.40-2.61 (m, 10 H) 2.75-2.90 (m, 5 H) 2.99-3.05 (m, 1 H) 3.17 (dd, J = 10.3, 7.32 Hz, 1 H) 3.28 (s, 3 H) 3.43-3.51 (m, 1 H) 3.64-3.77 (m, 2 H) 3.67 (s, 1 H) 4.07 (m, 1 H) 4.42 (d, J = 7.32 Hz, 1 H) 5.00 (m, 1 H) 5.12-5.24 (m, 2 H) 5.48-5.52 (m, 0.35 H) 5.66-5.69 (m, 0.65 H) 7.23-7.40 (m, 5 H) 7.93 (s, 0.35 H) 8.09 (s, 0.65 H) |
| 232 | 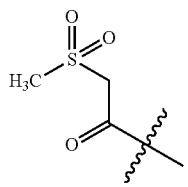 | 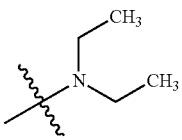 [SMILES: *N(CC)CC] | 1050.7 | (600 MHz): 0.91 (t, J = 7.34 Hz, 3 H) 1.00-1.04 (m, 6 H) 1.07 (d, J = 7.79 Hz, 3 H) 1.13-1.18 (m, 12 H) 1.19 (d, J = 7.34 Hz, 3 H) 1.20-1.25 (m, 1 H) 1.23 (d, J = 6.42 Hz, 3H) 1.38 (s, 3 H) 1.44 (s, 3 H) 1.50-1.56 (m, 1 H) 1.62-1.67 (m, 1 H) 1.74-1.83 (m, 3 H) 1.90-1.96 (m, 2 H) 1.98-2.02 (m, 1 H) 2.09 (d, J = 14.67 Hz, 1 H) 2.28 (s, 6 H) 2.34 (s, 3 H) 2.40-2.66 (m, 10 H) 2.77-2.85 (m, 2 H) 2.91 (s, 3 H) 3.05 (q, J = 6.88 Hz, 1 H) 3.15-3.20 (m, 1 H) 3.20 (s, 3 H) 3.27 (s, 3 H) 3.41 (br. s., 1 H) 3.44-3.50 (m, 1 H) 3.67-3.71 (m, 3 H) 3.88-3.97 (m, 2 H) 4.03-4.08 (m, 1 H) 4.42 (d, J = 7.34 Hz, 1 H) 4.95-4.96 (m, 1 H) 5.62-5.65 (m, 1 H) 9.29 (br. s., 1 H) |

Example 191

By using the deacetylated compound obtained in Example 190, (3) (20 mg) as a starting material, the compound shown in Table 5 (14 mg) was obtained in the same manner as that of Example 11.

Example 192

(1) The compound obtained in Example 190, (1) (245 mg) was dissolved in methylene chloride (2 ml), triethylamine (25 µl) was added to the solution, methanesulfonyl chloride (6.9 µl) was added to the mixture under ice cooling, and the resulting mixture was stirred at the same temperature for 1 hour. Ethyl acetate and saturated aqueous sodium hydrogencarbonate were added to the reaction mixture, the layers were separated, and the aqueous layer was extracted with ethyl acetate. The combined organic layer was washed with saturated aqueous sodium chloride, dried over anhydrous magnesium sulfate, and filtered. The filtrate was concentrated under reduced pressure, and the resulting residue was purified by preparative thin layer chromatography (isopropyl ether:methanol:triethylamine=9:1:1) to obtain a methanesulfonyl compound (22 mg).

(2) By using the compound obtained in (1) mentioned above (21 mg) as a starting material, the compound shown in Table 5 (10 mg) was obtained in the same manners as those of Example 4, (6) and Example 11.

Example 193

(1) The compound obtained in Example 190, (1) (30 mg) and 4-dimethylaminopyridine (1 mg) were dissolved in chloroform (1 ml), triethylamine (15 µl) and methylsulfamoyl chloride (12 mg) were added to the solution, and the resulting mixture was stirred at 70° C. for 2 hours. Saturated aqueous sodium hydrogencarbonate and ethyl acetate were added to the reaction mixture, the layers were separated, and the aqueous layer was extracted with ethyl acetate. The combined organic layer was washed with saturated aqueous sodium chloride, then dried over anhydrous magnesium sulfate, and filtered. The filtrate was concentrated under reduced pressure, and the resulting residue was purified by preparative thin layer chromatography (chloroform:methanol=10:1) to obtain a methylsulfamoyl compound (23 mg).

(2) By using the compound obtained in (1) mentioned above (23 mg) as a starting material, the compound shown in Table 5 (8 mg) was obtained in the same manners as those of Example 4, (6) and Example 11.

Example 194

(1) The compound obtained in Example 190, (1) (50 mg) and 3-phenylpropionaldehyde (10 µl) were dissolved in chloroform (1 ml), acetic acid (18 µl) and sodium cyanoborohydride (13 mg) were added to the solution, and the resulting mixture was stirred overnight at room temperature. Ethyl acetate and saturated aqueous sodium hydrogencarbonate were added to the reaction mixture, and the layers were separated. The organic layer was washed with saturated aqueous sodium chloride, dried over anhydrous magnesium sulfate, and filtered. The filtrate was concentrated under reduced pressure, and the resulting residue was purified by preparative thin layer chromatography (chloroform:methanol:28% aqueous ammonia=20:1:0.1) to obtain a phenylpropyl compound (20 mg).

(2) By using the compound obtained in (1) mentioned above (47 mg) as a starting material, a deprotected compound (17 mg) was obtained in the same manner as that of Example 2, (2).

(3) By using the compound obtained in (2) mentioned above (33 mg) as a starting material, the compound shown in Table 5 (24 mg) was obtained in the same manner as that of Example 11.

Example 195

By using the compound obtained in Example 190, (1) (70 mg) and propionaldehyde (24 µl) as starting materials, the compound shown in Table 5 (43 mg) was obtained in the same manners as those of Example 194, (1), Example 2, (2) and Example 11.

Example 196

(1) The compound obtained in Example 190, (1) (2.0 g) was dissolved in pyridine (23.4 ml), bis(4-nitrophenyl)carbonate (1.08 g) was added to the solution at room temperature, and the resulting mixture was stirred at room temperature for 3 hours. Ethyl acetate and saturated aqueous sodium hydrogencarbonate were added to the reaction mixture, and the layers were separated. Then, the organic layer was washed twice with saturated aqueous sodium hydrogencarbonate and once with 0.75% aqueous sodium hydroxide, dried over anhydrous sodium sulfate, and filtered. The filtrate was concentrated under reduced pressure, the resulting residue was dissolved in pyridine (20 ml), bis(4-nitrophenyl)carbonate (542 mg) was added to the solution at room temperature, and the resulting mixture was stirred at room temperature for 1 hour. Ethyl acetate and saturated aqueous sodium hydrogencarbonate were added to the reaction mixture, and the layers were separated. Then, the organic layer was washed once with saturated aqueous sodium hydrogencarbonate and twice with saturated aqueous sodium chloride, dried over anhydrous sodium sulfate, and filtered. The filtrate was concentrated under reduced pressure, and the resulting residue was purified by silica gel column chromatography (hexane:acetone=90:10 to 34:66) to obtain a carbamate compound (2.28 g).

(2) The compound obtained in (1) mentioned above (100 mg) was dissolved in tetrahydrofuran (0.5 ml), cyclopropylmethylamine (17.2 µl) was added to the solution at room temperature, and the resulting mixture was stirred at room temperature for 45 minutes. Ethyl acetate and saturated aqueous sodium hydrogencarbonate were added to the reaction mixture, the layers were separated, and the organic layer was washed twice with saturated aqueous sodium hydrogencarbonate. The organic layer was dried over anhydrous sodium sulfate, and filtered, and then the filtrate was concentrated under reduced pressure to obtain a urea compound (91.5 mg).

(3) By using the compound obtained in (2) mentioned above (91.5 mg) as a starting material, the compound shown in Table 5 (67.9 mg) was obtained in the same manners as those of Example 4, (6) and Example 11.

Example 197

By using the compound obtained in Example 190, (1) (70 mg) and 3-(quinolin-4-yl)propanal (20 mg) obtained by the method described in the literature (Journal of Medicinal Chemistry, 1998, vol. 41, No. 21, p. 4080) as starting materials, the compound shown in Table 5 (38 mg) was obtained in the same manners as those of Example 194, (1), Example 2, (2) and Example 11.

Example 198

(1) The compound obtained in Example 190, (1) (87 mg) was dissolved in toluene (2 ml), and benzyl isocyanate (14 µl) was added to the solution. 1,4-Diazabicyclo-[2,2,2]octane (4.7 µl) was added to the mixture under ice cooling, and the resulting mixture was warmed to room temperature and stirred for 2 hours. Ethyl acetate and saturated aqueous sodium hydrogencarbonate were added to the reaction mixture, the layers were separated, and the aqueous layer was extracted with ethyl acetate. The combined organic layer was washed with saturated aqueous sodium chloride, dried over anhydrous magnesium sulfate, and filtered. The filtrate was concentrated under reduced pressure, and the resulting residue was purified by preparative thin layer chromatography (chloroform:methanol:28% aqueous ammonia=20:1:0.1) to obtain a benzylurea compound (62 mg).

(2) By using the compound obtained in (1) mentioned above (62 mg) as a starting material, a deprotected compound (55 mg) was obtained in the same manner as that of Example 2, (2).

(3) By using the compound obtained in (2) mentioned above (55 mg) as a starting material, the compound shown in Table 5 (20 mg) was obtained in the same manner as that of Example 11.

Example 199

(1) 3-Phenylpropionic acid (12 mg) was dissolved in tetrahydrofuran (2 ml), and triethylamine (12 µl) and isobutyl chloroformate (11 µl) were added to the solution under ice cooling. The reaction mixture was stirred at the same temperature for 1 hour, and then a solution of the compound obtained in Example 190, (1) in tetrahydrofuran (1 ml) was slowly added dropwise to the reaction mixture at −78° C. The reaction mixture was gradually warmed to room temperature, and stirred overnight. Then, ethyl acetate and saturated aqueous sodium hydrogencarbonate were added to the reaction mixture, and the layers were separated. The aqueous layer was extracted with ethyl acetate, and the combined organic layer was washed with saturated aqueous sodium chloride, dried over anhydrous magnesium sulfate, and filtered. The filtrate was concentrated under reduced pressure, and the resulting residue was purified by preparative thin layer chromatography (chloroform:methanol:28% aqueous ammonia=20:1:0.1) to obtain a phenylpropionamide compound (22 mg).

(2) By using the compound obtained in (1) mentioned above (22 mg) as a starting material, the compound shown in Table 5 (15 mg) was obtained in the same manners as those of Example 4, (6) and Example 11.

Example 200

By using the compound obtained in Example 198, (2) (50 mg) and the compound obtained in Reference Example 2 (48 mg) as starting materials, the compound shown in Table 5 (35 mg) was obtained in the same manner as that of Example 4, (8).

Example 201

By using the compound obtained in Example 198, (2) (60 mg) and the compound obtained in Reference Example 4 (46 mg) as starting materials, the compound shown in Table 5 (35 mg) was obtained in the same manner as that of Example 4, (8).

Example 202

By using the compound obtained in Example 198, (2) (60 mg) and the compound obtained in Reference Example 3 (51 mg) as starting materials, the compound shown in Table 5 (60 mg) was obtained in the same manner as that of Example 4, (8).

Example 203

By using the compound obtained in Example 198, (2) (60 mg) and the compound obtained in Reference Example 1 (46 mg) as starting materials, the compound shown in Table 5 (45 mg) was obtained in the same manner as that of Example 4, (8).

Example 204

By using the compound obtained in Example 198, (2) (60 mg) and the compound obtained in Reference Example 5 (51 mg) as starting materials, the compound shown in Table 5 (49 mg) was obtained in the same manner as that of Example 4, (8).

Example 205

By using the compound obtained in Example 198, (2) (70 mg) and the compound obtained in Reference Example 98 (24 mg) as starting materials, the compound shown in Table 5 (58 mg) was obtained in the same manner as that of Example 4, (8).

Example 206

By using the compound obtained in Example 198, (2) (50 mg) and the compound obtained in Reference Example 99 (14 mg) as starting materials, the compound shown in Table 5 (36 mg) was obtained in the same manner as that of Example 4, (8).

Example 207

(1) The compound represented by the formula (A) obtained in Example 1, (5) (99 mg) was dissolved in 1-methyl-2-pyrrolidinone (1 ml), the compound obtained in Reference Example 96 (119 mg) and 1,8-diazabicyclo[5.4.0]-7-undecene (169 μl) were added to the solution, and the resulting mixture was stirred at room temperature for 3 hours. Distilled water and ethyl acetate were added to the reaction mixture, and the layers were separated. The organic layer was dried over anhydrous sodium sulfate, and filtered, and then the filtrate was concentrated under reduced pressure to obtain a cyclized compound (170 mg).

(2) By using the compound obtained in (1) mentioned above (170 mg) as a starting material, the compound shown in Table 5 (7.7 mg) was obtained in the same manners as those of Example 2, (2) and Example 11.

Example 208

By using the compound obtained in Example 190, (1) (300 mg) and 2-fluorobenzyl isocyanate (55 μl) as starting materials, the compound shown in Table 5 (46 mg) was obtained in the same manners as those of Example 198, (1), Example 2, (2) and Example 129, (3).

Example 209

By using the compound obtained in Example 190, (1) (300 mg) and 4-methoxybenzyl isocyanate (660) as starting materials, the compound shown in Table 5 (19 mg) was obtained in the same manners as those of Example 198, (1), Example 2, (2) and Example 11.

Example 210

By using the compound obtained in Example 190, (1) (300 mg) and ethyl isocyanate (99 μl) as starting materials, the compound shown in Table 5 (56 mg) was obtained in the same manners as those of Example 198, (1), Example 2, (2) and Example 11.

Example 211

By using the compound obtained in Example 190, (1) (300 mg) and isopropyl isocyanate (123 μl) as starting materials, the compound shown in Table 5 (74 mg) was obtained in the same manners as those of Example 198, (1), Example 2, (2) and Example 11.

Example 212

By using the compound obtained in Example 190, (1) (300 mg) and cyclohexanemethyl isocyanate (178.3 μl) as starting materials, the compound shown in Table 5 (70 mg) was obtained in the same manners as those of Example 198, (1), Example 2, (2) and Example 11.

Example 213

(1) By using the compound obtained in Example 190, (1) (300 mg) and 4-fluorobenzyl isocyanate (59 μl) as starting materials, a deprotected compound (122 mg) was obtained in the same manners as those of Example 198, (1) and Example 2, (2).

(2) By using the compound obtained in (1) mentioned above (51 mg) as a starting material, the compound shown in Table 5 (32 mg) was obtained in the same manner as that of Example 11.

Example 214

(1) By using the compound obtained in Example 190, (1) (301 mg) and 4-methylbenzyl isocyanate (65 μl) as starting materials, a deprotected compound (122 mg) was obtained in the same manners as those of Example 198, (1) and Example 2, (2).
(2) By using the compound obtained in (1) mentioned above (52 mg) as a starting material, the compound shown in Table 5 (33 mg) was obtained in the same manner as that of Example 11.

Example 215

(1) By using the compound obtained in Example 190, (1) (300 mg) and 3-fluorobenzyl isocyanate (59 μl) as starting materials, a deprotected compound (196 mg) was obtained in the same manners as those of Example 198, (1) and Example 2, (2).
(2) By using the compound obtained in (1) mentioned above (50 mg) as a starting material, the compound shown in Table 5 (29 mg) was obtained in the same manner as that of Example 11.

Example 216

(1) By using the compound obtained in Example 190, (1) (300 mg) and 3-methylbenzyl isocyanate (65 μl) as starting materials, a deprotected compound (167 mg) was obtained in the same manners as those of Example 198, (1) and Example 2, (2).
(2) By using the compound obtained in (1) mentioned above (50 mg) as a starting material, the compound shown in Table 5 (31 mg) was obtained in the same manner as that of Example 11.

Example 217

(1) By using the compound obtained in Example 190, (1) (300 mg) and 3-methoxybenzyl isocyanate (66 μl) as starting materials, a deprotected compound (167 mg) was obtained in the same manners as those of Example 198, (1) and Example 2, (2).
(2) By using the compound obtained in (1) mentioned above (50 mg) as a starting material, the compound shown in Table 5 (30 mg) was obtained in the same manner as that of Example 11.

Example 218

By using the compound obtained in Example 190, (1) (300 mg) and 2-methoxybenzyl isocyanate (192 μl) as starting materials, the compound shown in Table 5 (113 mg) was obtained in the same manners as those of Example 198, (1), Example 2, (2) and Example 11.

Example 219

By using the compound obtained in Example 190, (1) (300 mg) and 2-methylbenzyl isocyanate (173 μl) as starting materials, the compound shown in Table 5 (39 mg) was obtained in the same manners as those of Example 198, (1), Example 2, (2) and Example 11.

Example 220

By using the compound obtained in Example 190, (1) (300 mg) and phenethyl isocyanate (173 μl) as starting materials, the compound shown in Table 5 (57 mg) was obtained in the same manners as those of Example 198, (1), Example 2, (2) and Example 11.

Example 221

By using the compound obtained in Example 190, (1) (300 mg) and furfuryl isocyanate (134 μl) as starting materials, the compound shown in Table 5 (42 mg) was obtained in the same manners as those of Example 198, (1), Example 2, (2) and Example 11.

Example 222

By using the compound obtained in Example 196, (1) (100 mg) and 2-phenylpropan-2-amine (29 μl) as starting materials, the compound shown in Table 5 (35 mg) was obtained in the same manners as those of Example 196, (2), Example 2, (2) and Example 11.

Example 223

(1) The compound obtained in Example 196, (1) (100 mg) was dissolved in pyridine (1 ml), N-methyl-1-phenylmethanamine (26 μl) was added to the solution at room temperature, and the resulting mixture was stirred at room temperature for 4.5 hours. The reaction mixture was concentrated under reduced pressure, and the resulting residue was purified by silica gel column chromatography (ethyl acetate:methanol:28% aqueous ammonia=13:1:0.1) to obtain a urea compound (81.4 mg).
(2) By using the compound obtained in (1) mentioned above (81 mg) as a starting material, the compound shown in Table 5 (42 mg) was obtained in the same manners as those of Example 2, (2) and Example 11.

Example 224

(1) The compound obtained in Example 190, (1) (100 mg) was dissolved in toluene (2 ml), 1,4-diazabicyclo[2.2.2]octane (2.7 mg), benzyl isothiocyanate (31.4 μl) and pyridine (19.2 μl) were added to the solution, and the resulting mixture was stirred at 50° C. for 1 hour, and at 60° C. for 4 hours. Distilled water and ethyl acetate were added to the reaction mixture, the layers were separated, and the organic layer was concentrated under reduced pressure to obtain a thiourea compound (147 mg).
(2) By using the compound obtained in (1) mentioned above (147 mg) as a starting material, the compound shown in Table 5 (25 mg) was obtained in the same manners as those of Example 4, (6) and Example 11.

Example 225

By using the compound obtained in Example 196, (1) (150 mg) and naphthalen-1-ylmethanamine (44 μl) as starting materials, the compound shown in Table 5 (38 mg) was obtained in the same manners as those of Example 223, (1), Example 4, (6) and Example 11.

Example 226

By using the compound obtained in Example 196, (1) (150 mg) and naphthalen-2-ylmethanamine hydrochloride (58 mg) as starting materials, the compound shown in Table 5 (17 mg) was obtained in the same manners as those of Example 223, (1), Example 4, (6) and Example 11.

Example 227

By using the compound obtained in Example 196, (1) (150 mg) and pyridin-2-ylmethanamine (46 µl) as starting materials, the compound shown in Table 5 (54 mg) was obtained in the same manners as those of Example 223, (1), Example 4, (6) and Example 11.

Example 228

By using the compound obtained in Example 196, (1) (150 mg) and pyridin-3-ylmethanamine (45 µl) as starting materials, the compound shown in Table 5 (41 mg) was obtained in the same manners as those of Example 223, (1), Example 4, (6) and Example 11.

Example 229

By using the compound obtained in Example 196, (1) (100 mg) and pyridin-4-ylmethanamine (30 µl) as starting materials, the compound shown in Table 5 (36 mg) was obtained in the same manners as those of Example 223, (1), Example 4, (6) and Example 11.

Example 230

By using the compound obtained in Example 198, (2) (78 mg) and N,N,N'-trimethylethane-1,2-diamine (33 as starting materials, the compound shown in Table 5 (65 mg) was obtained in the same manner as that of Example 129, (3).

Example 231

(1) The compound obtained in Example 190, (1) (200 mg) was dissolved in tetrahydrofuran (2 ml), pyridine (58 µl) and benzyl chloroformate (68 µl) were added to the solution, and the resulting mixture was stirred at room temperature for 10 minutes. Distilled water and ethyl acetate were added to the reaction mixture, and the layers were separated. The organic layer was washed with saturated aqueous sodium chloride, then dried over anhydrous sodium sulfate, and filtered. The filtrate was concentrated under reduced pressure, and the resulting residue was purified by silica gel column chromatography (ethyl acetate:methanol:28% aqueous ammonia=8:1:0.1) to obtain a benzyl carbamate compound (191 mg).
(2) By using the compound obtained in (1) mentioned above (186 mg) as a starting material, a deprotected compound (156 mg) was obtained in the same manner as that of Example 4, (6).
(3) By using the compound obtained in (2) mentioned above (60 mg) as a starting material, the compound shown in Table 5 (65 mg) was obtained in the same manner as that of Example 11.

Example 232

(1) The compound obtained in Example 190, (1) (100 mg) was dissolved in dimethylformamide (2 ml), 4-dimethylaminopyridine (29 mg), triethylamine (66 µl), hydroxybenzotriazole (55 mg), methanesulfonylacetic acid (49 mg), and N-ethyl-N'-(3-dimethylaminopropyl)carbodiimide hydrochloride (68 mg) were added to the solution, and the resulting mixture was stirred at room temperature for 16 hours. Ethyl acetate and saturated aqueous ammonium chloride were added to the reaction mixture, and the layers were separated. The organic layer was washed with saturated aqueous sodium hydrogencarbonate and saturated aqueous sodium chloride, then dried over anhydrous magnesium sulfate, and filtered. The filtrate was concentrated under reduced pressure, and the resulting residue was purified by silica gel column chromatography (chloroform:methanol:28% aqueous ammonia=100:1:0.1 to 5:1:0.1) to obtain an amide compound (102 mg).
(2) By using the compound obtained in (1) mentioned above (102 mg) as a starting material, the compound shown in Table 5 (43.2 mg) was obtained in the same manners as those of Example 4, (6) and Example 11.

Example 233

Synthesis of Compound of the Formula (C) Wherein R is (dimethylamino)methyleneamino Group (1) The compound obtained in Example 190, (1) (80 mg) and 4-dimethylaminopyridine (58 mg) were dissolved in dimethylformamide (1 ml), dimethylsulfamoyl chloride (55 mg) was added to the solution, and the resulting mixture was stirred at 75° C. for 10 hours. Ethyl acetate and saturated aqueous sodium hydrogencarbonate were added to the reaction mixture, the layers were separated, and the aqueous layer was extracted with ethyl acetate. The combined organic layer was washed with saturated aqueous sodium chloride, dried over anhydrous magnesium sulfate, and filtered. The filtrate was concentrated under reduced pressure, and the resulting residue was purified by preparative thin layer chromatography (isopropyl ether:methanol:triethylamine=9:1:1) to obtain a dimethylamidine compound (55 mg).
(2) By using the compound obtained in (1) mentioned above (55 mg) as a starting material, the title compound (30 mg) was obtained in the same manners as those of Example 4, (6) and Example 11.

MS (ESI) m/z=985 [M+H]$^+$
$^1$H-NMR (400 MHz, CDCl$_3$) δ (ppm): 0.85 (t, J=7.3 Hz, 3H), 1.00 (d, J=7.1 Hz, 3H), 1.02 (d, J=7.1 Hz, 3H), 1.03 (d, J=6.1 Hz, 3H), 1.11 (d, J=6.8 Hz, 3H), 1.15 (s, 3H), 1.18 (d, J=6.4 Hz, 3H), 1.22 (d, J=6.1 Hz, 3H), 1.24 (d, J=7.1 Hz, 3H), 1.41 (s, 3H), 1.43 (s, 3H), 1.48-1.65 (m, 5H), 1.77 (dd, J=14.7, 1.9 Hz, 1H), 1.84-2.02 (m, 4H), 2.08 (d, J=14.9 Hz, 1H), 2.25 (s, 6H), 2.33 (s, 3H), 2.36-2.62 (m, 9H), 2.72-2.85 (m, 7H), 2.91-3.01 (m, 2H), 3.07-3.15 (m, 3H), 3.26 (s, 3H), 3.27 (s, 3H), 3.38-3.46 (m, 2H), 3.70 (d, J=7.6 Hz, 1H), 3.80 (d, J=10.0 Hz, 1H), 4.13 (q, J=6.4 Hz, 1H), 4.25 (s, 1H), 4.33 (d, J=7.3 Hz, 1H), 5.01 (d, J=4.2 Hz, 1H), 5.21 (dd, J=10.5, 2.2 Hz, 1H), 7.76 (s, 1H)

Examples 234 to 330

Preparation methods of the compounds represented by the formula (I) having R$^{1b}$ defined in Table 6 are shown below.

TABLE 6

Formula (I)

[Formula 38]

| Example | R$^{1b}$ | ESI MS (M + H) | $^1$H-NMR, CDCl$_3$, δ (ppm) |
|---|---|---|---|
| 234 | -N(CH$_3$)CH$_2$-(1-ethylpyrrolidin-2-yl) | 927.8 | (500 MHz): 0.86 (t, J = 7.40 Hz, 3 H) 1.04-1.28 (m, 25 H) 1.38 (s, 3 H) 1.40 (s, 3 H) 1.46-1.58 (m, 1 H) 1.62-2.09 (m, 12 H) 2.16-2.39 (m, 4 H) 2.29 (s, 6 H) 2.34 (s, 3 H) 2.39-2.48 (m, 1 H) 2.50-2.65 (m, 3 H) 2.77-2.92 (m, 4 H) 2.96 (s, 3 H) 3.11-3.21 (m, 2 H) 3.28 (s, 3 H) 3.41-3.51 (m, 1 H) 3.64 (d, J = 7.40 Hz, 1 H) 3.69 (s, 1 H) 3.79 (d, J = 8.50 Hz, 1 H) 4.10 (m, 1 H) 4.40 (d, J = 7.40 Hz, 1 H) 4.99 (d, J = 4.94 Hz, 1 H) 5.10 (dd, J = 10.70, 2.19 Hz, 1 H) 5.78 (s, 1 H) |
| 235 | -N(CH$_3$)CH$_2$CH$_2$CH$_2$OCH$_2$CH$_3$ | 902.6 | (600 MHz): 0.86 (t, J = 7.34 Hz, 3 H) 1.08 (d, J = 7.79 Hz, 3 H) 1.09-1.25 (m, 22 H) 1.38 (s, 3 H) 1.40 (s, 3 H) 1.48-1.54 (m, 1 H) 1.63-2.08 (m, 10 H) 2.29 (s, 6 H) 2.32 (s, 3 H) 2.39-2.70 (m, 4 H) 2.79-2.91 (m, 3 H) 2.96 (s, 3 H) 3.15-3.21 (m, 1 H) 3.28 (s, 3 H) 3.39-3.49 (m, 6 H) 3.64 (d, J = 7.34 Hz, 1 H) 3.69 (s, 1 H) 3.79 (d, J = 8.25 Hz, 1 H) 4.05-4.16 (m, 1 H) 4.40 (d, J = 7.34 Hz, 1 H) 4.99 (d, J = 5.04 Hz, 1 H) 5.08-5.14 (m, 1 H) 5.77 (s, 1 H) |
| 236 | -N(CH$_3$)CH$_2$CH$_2$OCH$_2$CH$_3$ | 888.6 | (600 MHz): 0.86 (t, J = 7.57 Hz, 3 H) 1.07 (d, J = 7.79 Hz, 3 H) 1.11 (d, J = 6.88 Hz, 3 H) 1.13-1.25 (m, 19 H) 1.38 (s, 3 H) 1.40 (s, 3 H) 1.48-1.56 (m, 1 H) 1.62-1.68 (m, 1 H) 1.70-1.91 (m, 4 H) 1.97 (d, J = 5.50 Hz, 1 H) 2.02-2.06 (m, 1 H) 2.10 (d, J = 14.67 Hz, 1 H) 2.29 (s, 6 H) 2.38 (s, 3 H) 2.41-2.46 (m, 1 H) 2.51-2.57 (m, 1 H) 2.64-2.71 (m, 1 H) 2.74-2.90 (m, 4 H) 2.96 (s, 3 H) 3.15-3.20 (m, 1 H) 3.28 (s, 3 H) 3.41-3.52 (m, 5 H) 3.65 (d, J = 7.34 Hz, 1 H) 3.69 (s, 1 H) 3.78 (d, J = 8.71 Hz, 1 H) 4.07-4.13 (m, 1 H) 4.40 (d, J = 6.88 Hz, 1 H) 4.99 (d, J = 4.58 Hz, 1 H) 5.11 (dd, J = 10.55, 2.29 Hz, 1 H) 5.76 (s, 1 H) |
| 237 | -N(CH$_3$)CH$_2$CH$_2$CH(CH$_3$)CH$_2$OH | 902.6 | (600 MHz): 0.86 (t, J = 7.34 Hz, 3 H) 0.91-0.94 (m, 3 H) 1.07 (d, J = 7.34 Hz, 3 H) 1.11 (d, J = 7.34 Hz, 3 H) 1.13-1.26 (m, 18 H) 1.28-1.35 (m, 1 H) 1.38 (s, 3 H) 1.40 (s, 3 H) 1.48-1.98 (m, 9 H) 2.01-2.08 (m, 2 H) 2.29 (s, 6 H) 2.33 (s, 3 H) 2.39-2.47 (m, 1 H) 2.49-2.64 (m, 3 H) 2.78-2.90 (m, 3 H) 2.96 (s, 3 H) 3.16-3.21 (m, 1 H) 3.29 (s, 3 H) 3.41-3.50 (m, 3 H) 3.62-3.65 (m, 1 H) 3.68 (s, 1 H) 3.79 (d, J = 8.71 Hz, 1 H) 4.08-4.13 (m, 1 H) 4.38-4.41 (m, 1 H) 4.96-5.00 (m, 1 H) 5.08-5.13 (m, 1 H) 5.76 (s, 1 H) |
| 238 | 4-hydroxypiperidin-1-yl | 886.6 | (600 MHz): 0.86 (t, J = 7.34 Hz, 3 H) 1.16 (d, J = 15.59 Hz, 3 H) 1.16 (d, J = 2.75 Hz, 3 H) 1.05-1.27 (m, 16 H) 1.37 (s, 3 H) 1.40 (s, 3 H) 1.55 (br. s., 10 H) 1.93-2.08 (m, 3 H) 2.29 (br., s., 6 H) 2.39-2.47 (m, 1 H) 2.50-2.57 (m, 1 H) 2.74-2.91 (m, 7 H) 2.96 (s, 3 H) 3.15-3.20 (m, 1 H) 3.28 (s, 3 H) 3.38-3.46 (m, 2 H) 3.63 (d, J = 7.34 Hz, 1 H) 3.68 (s, 1 H) 3.78-3.80 (m, 1 H) 4.08-4.12 (m, 1 H) 4.39 (d, J = 7.34 Hz, 1 H) 4.98 (d, J = 5.04 Hz, 1 H) 5.09-5.12 (m, 1 H) 5.77 (s, 1 H) |
| 239 | -N(CH$_3$)CH$_2$CH$_2$CH$_2$-(2-oxopyrrolidin-1-yl) | 941.6 | (600 MHz): 0.86 (t, J = 7.34 Hz, 3 H) 1.07 (d, J = 7.79 Hz, 3 H) 1.09-1.17 (m, 12 H) 1.18-1.25 (m, 7 H) 1.38 (s, 3 H) 1.40 (s, 3 H) 1.49-1.56 (m, 1 H) 1.64-2.07 (m, 12 H) 2.29 (s, 6 H) 2.33 (s, 3 H) 2.35-2.58 (m, 7 H) 2.79-2.91 (m, 3 H) 2.96 (s, 3 H) 3.14-3.20 (m, 1 H) 3.25-3.32 (m, 4 H) 3.35-3.46 (m, 3 H) 3.63 (d, J = 7.34 Hz, 1 H) 3.68 (s, 1 H) 3.78 (d, J = 7.79 Hz, 1 H) 4.10 (d, J = 6.42 Hz, 1 H) 4.39 (d, J = 6.88 Hz, 1 H) 4.98 (d, J = 5.04 Hz, 1 H) 5.08-5.13 (m, 1 H) 5.77 (s, 1 H) |

TABLE 6-continued

| 240 | 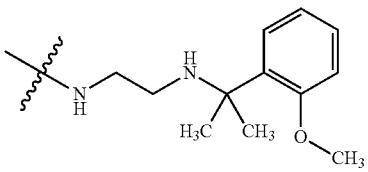 [SMILES: *NCCNC(C)(C)c1ccccc1OC] | 993.7 | (600 MHz): 0.86 (t, J = 7.34 Hz, 3 H) 1.07 (d, J = 7.79 Hz, 3 H) 1.09-1.23 (m, 19 H) 1.37 (s, 3 H) 1.40 (s, 3 H) 1.72 (s, 6 H) 1.46-1.97 (m, 7 H) 2.00-2.04 (m, 1 H) 2.24-2.32 (m, 9 H) 2.38-2.44 (m, 1 H) 2.50-2.58 (m, 1 H) 2.59-2.66 (m, 2 H) 2.79-2.91 (m, 3 H) 2.95 (s, 3 H) 3.14-3.19 (m, 1 H) 3.27 (s, 3 H) 3.39-3.42 (m, 1 H) 3.44-3.51 (m, 1 H) 3.63 (d, J = 7.34 Hz, 1 H) 3.69 (s, 1 H) 3.78 (d, J = 7.79 Hz, 1 H) 3.87 (s, 3 H) 4.18 (d, J = 6.42 Hz, 1 H) 4.39 (d, J = 7.34 Hz, 1 H) 4.97 (d, J = 4.13 Hz, 1 H) 5.09-5.13 (m, 1 H) 5.76 (s, 1 H) 6.89-6.94 (m, 2 H) 7.21-7.26 (m, 2 H) |
|---|---|---|---|
| 241 | 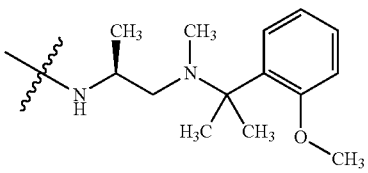 [SMILES: *N[C@@H](C)CN(C)C(C)(C)c1ccccc1OC] | 1021.7 | (500 MHz): 0.86 (t, J = 7.40 Hz, 3 H) 0.91 (d, J = 5.76 Hz, 3 H) 1.06-1.16 (m, 12 H) 1.16-1.28 (m, 10 H) 1.37 (s, 3 H) 1.40 (s, 3 H) 1.44 (s, 6 H) 1.48-2.04 (m, 10 H) 2.10-2.21 (m, 5 H) 2.29 (s, 6 H) 2.38-2.58 (m, 3 H) 2.61-2.71 (m, 1 H) 2.78-2.92 (m, 2 H) 2.96 (s, 3 H) 3.10 (d, J = 13.44 Hz, 1 H) 3.15-3.21 (m, 1 H) 3.31 (s, 3 H) 3.37-3.42 (m, 1 H) 3.45-3.54 (m, 1 H) 3.66-3.71 (m, 2 H) 3.74-3.84 (m, 4 H) 4.15-4.21 (m, 1 H) 4.44 (d, J = 7.40 Hz, 1 H) 4.98 (br. s., 1 H) 5.12 (dd, J = 10.56, 2.33 Hz, 1 H) 5.77 (s, 1 H) 6.85-6.92 (m, 2 H) 7.18-7.23 (m, 1 H) 7.42 (d, J = 7.40 Hz, 1 H) |
| 242 | 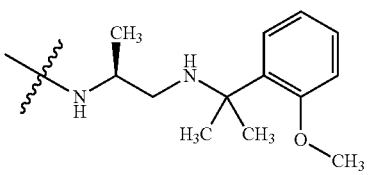 [SMILES: *N[C@@H](C)CNC(C)(C)c1ccccc1OC] | 1007.7 | (500 MHz): 0.86 (t, J = 7.40 Hz, 3 H) 0.95 (d, J = 6.31 Hz, 3 H) 1.05-1.27 (m, 22 H) 1.37 (s, 3 H) 1.39-1.43 (m, 3 H) 1.46-1.57 (m, 7 H) 1.59-1.65 (m, 1 H) 1.69-2.07 (m, 8 H) 2.14-2.23 (m, 1 H) 2.29 (s, 6 H) 2.30-2.66 (m, 5 H) 2.79-2.91 (m, 3 H) 2.95 (s, 3 H) 3.14-3.20 (m, 1 H) 3.29 (s, 3 H) 3.38-3.44 (m, 1 H) 3.45-3.52 (m, 1 H) 3.64 (d, J = 7.13 Hz, 1 H) 3.69 (s, 1 H) 3.78 (d, J = 8.23 Hz, 1 H) 3.88 (s, 3 H) 4.16-4.23 (m, 1 H) 4.41 (d, J = 7.40 Hz, 1 H) 4.98 (d, J = 3.84 Hz, 1 H) 5.08-5.14 (m, 1 H) 5.77 (s, 1 H) 6.89-6.98 (m, 2 H) 7.19-7.25 (m, 2 H) |
| 243 | 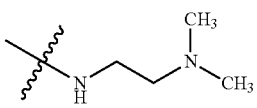 [SMILES: *NCCN(C)C] | 873.7 | (500 MHz): 0.86 (t, J = 7.27 Hz, 3 H) 1.05-1.28 (m, 22 H) 1.38 (s, 3 H) 1.40 (s, 3 H) 1.48-2.08 (m, 8 H) 2.22 (s, 6 H) 2.23 (s, 1 H) 2.29 (s, 6 H) 2.33-2.47 (m, 4 H) 2.49-2.59 (m, 1 H) 2.64-2.73 (m, 2 H) 2.79-2.92 (m, 3 H) 2.95 (s, 3 H) 3.18 (dd, J = 10.15, 7.40 Hz, 1 H) 3.29 (s, 3 H) 3.49-3.58 (m, 1 H) 3.64 (d, J = 7.68 Hz, 1 H) 3.69 (s, 1 H) 3.79 (d, J = 7.95 Hz, 1 H) 4.24 (d, J = 6.58 Hz, 1 H) 4.40 (d, J = 7.40 Hz, 1 H) 4.98 (d, J = 4.39 Hz, 1 H) 5.11 (dd, J = 10.70, 2.19 Hz, 1 H) 5.78 (s, 1 H) |
| 244 | 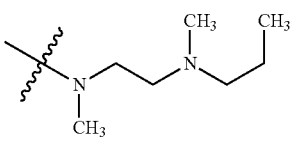 | 915.7 | (500 MHz): 0.83-0.90 (m, 6 H) 1.05-1.29 (m, 22 H) 1.38 (s, 3 H) 1.40 (s, 3 H) 1.43- 2.13 (m, 12 H) 2.23 (s, 3 H) 2.26-2.65 (m, 16 H) 2.77-2.92 (m, 3 H) 2.96 (s, 3 H) 3.18 (dd, J = 10.32, 7.26 Hz 1 H) 3.28 (s, 3 H) 3.43-3.51 (m, 1 H) 3.66 (d, J = 7.26 Hz, 1 H) 3.69 (s, 1 H) 3.77 (d, J = 8.41 Hz, 1 H) 4.09 (q, J = 6.24 Hz, 1 H) 4.41 (d, J = 7.26 Hz, 1 H) 4.99 (d, J = 4.59 Hz, 1 H) 5.11 (dd, J = 10.70, 2.29 Hz, 1 H) 5.77 (s, 1 H) |
| 245 | 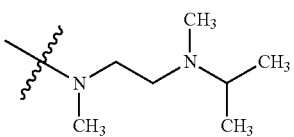 [SMILES: *N(C)CCN(C)C(C)C] | 915.7 | (500 MHz): 0.86 (t, J = 7.45 Hz, 3 H) 0.99 (m, 6 H) 1.05-1.26 (m, 22 H) 1.36-1.41 (m, 6 H) 1.52 (m, 1 H) 1.62-1.92 (m, 5 H) 1.93-2.06 (m, 2 H) 2.11 (d, J = 14.91 Hz, 1 H) 2.21 (s, 3 H) 2.29 (s, 6 H) 2.34 (s, 3 H) 2.35-2.63 (m, 6 H) 2.77-2.93 (m, 4 H) 2.96 (s, 3 H) 3.18 (dd, J = 10.32, 7.26 Hz, 1 H) 3.28 (s, 3 H) 3.43-3.51 (m, 1 H) 3.66 (d, J = 7.28 Hz, 1 H) 3.69 (s, 1 H) 3.77 (d, J = 8.41 Hz, 1 H) 4.09 (q, J = 6.50 Hz, 1 H) 4.41 (d, J = 7.26 Hz, 1 H) 4.99 (d, J = 4.20 Hz, 1 H) 5.11 (dd, J = 10.70, 2.29 Hz, 1 H) 5.77 (s, 1 H) |
| 246 | 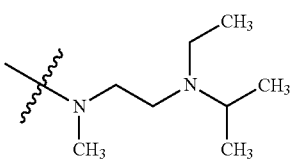 [SMILES: *N(C)CCN(CC)C(C)C] | 929.7 | (600 MHz): 0.86 (t, J = 7.34 Hz, 3 H) 0.94-1.26 (m, 31 H) 1.38 (s, 3 H) 1.40 (s, 3 H) 1.49-2.08 (m, 9 H) 2.29 (s, 6 H) 2.34 (s, 3 H) 2.39-2.59 (m, 7 H) 2.78-2.99 (m, 7 H) 3.15-3.20 (m, 1 H) 3.28 (s, 3 H) 3.43-3.50 (m, 1 H) 3.65 (d, J = 7.34 Hz, 1 H) 3.69 (s, 1 H) 3.78 (d, J = 8.71 Hz, 1 H) 4.08 (q, J = 6.11 Hz, 1 H) 4.41 (d, J = 7.34 Hz, 1 H) 4.99 (d, J = 4.58 Hz, 1 H) 5.11 (dd, J = 10.55, 2.29 Hz, 1 H) 5.76 (s, 1 H) |
| 247 | 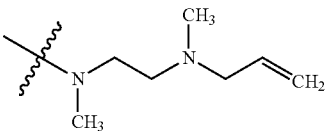 | 913.7 | (500 MHz): 0.86 (t, J = 7.45 Hz, 3 H) 1.06-1.27 (m, 22 H) 1.38 (s, 3 H) 1.40 (s, 3 H) 1.46-2.14 (m, 9 H) 2.24 (s, 3 H) 2.30 (s, 6 H) 2.33 (s, 3 H) 2.35-2.67 (m, 6 H) 2.77-2.92 (m, 3 H) 2.96 (s, 3 H) 2.97-3.08 (m, 2 H) 3.16-3.21 (m, 1 H) 3.28 (s, 3 H) 3.43-3.51 (m, 1 H) 3.66 (d, J = 7.26 Hz, 1 H) 3.69 (s, 1 H) 3.78 (d, J = 8.79 Hz, 1 H) 4.09 (q, J = 6.50 Hz, 1 H) 4.41 (d, J = 7.26 Hz, 1 H) 4.99 (d, J = 4.59 Hz, 1 H) 5.08-5.20 (m, 3 H) 5.77 (s, 1 H) 5.81-5.92 (m, 1 H) |

TABLE 6-continued

| # | Structure | Mass | NMR |
|---|---|---|---|
| 248 | 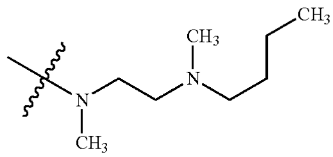 [SMILES: *N(C)CCN(C)CCCC] | 929.7 | (500 MHz): 0.86 (t, J = 7.26 Hz, 3 H) 0.90 (t, J = 7.26 Hz, 3 H) 1.03-1.48 (m, 32 H) 1.48-2.05 (m, 8 H) 2.11 (d, J = 14.52 Hz, 1 H) 2.23 (s, 3 H) 2.29 (s, 6 H) 2.31-2.67 (m, 7 H) 2.77-2.91 (m, 3 H) 2.96 (s, 3 H) 3.18 (dd, J = 10.32, 7.26 Hz, 1 H) 3.28 (s, 3 H) 3.43-3.51 (m, 1 H) 3.66 (d, J = 7.26 Hz, 1 H) 3.69 (s, 1 H) 3.77 (d, J = 8.79 Hz, 1 H) 4.09 (q, J = 6.50 Hz, 1 H) 4.41 (d, J = 7.26 Hz, 1 H) 4.99 (d, J = 4.20 Hz, 1 H) 5.11 (dd, J = 10.51, 2.48 Hz, 1 H) 5.76 (s, 1 H) |
| 249 | 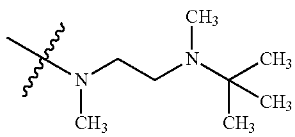 [SMILES: *N(C)CCN(C)C(C)(C)C] | 929.7 | (500 MHz): 0.86 (t, J = 7.40 Hz, 3 H) 1.03-1.26 (m, 31 H) 1.38 (s, 3 H) 1.40 (s, 3 H) 1.46-1.94 (m, 8 H) 1.97-2.02 (m, 2 H) 2.08 (d, J = 14.53 Hz, 1 H) 2.22 (s, 3 H) 2.29 (s, 6 H) 2.33 (s, 3 H) 2.37-2.57 (m, 4 H) 2.77-2.92 (m, 3 H) 2.96 (s, 3 H) 3.14-3.21 (m, 1 H) 3.28 (s, 3 H) 3.42-3.52 (m, 1 H) 3.65 (d, J = 7.40 Hz, 1 H) 3.87-3.72 (m, 1 H) 3.78 (d, J = 8.78 Hz, 1 H) 4.07 (q, J = 6.31 Hz, 1 H) 4.41 (d, J = 7.13 Hz, 1 H) 4.99 (dd, J = 4.25, 2.06 Hz, 1 H) 5.11 (dd, J = 10.56, 2.33 Hz, 1 H) 5.76 (s, 1 H) |
| 250 | 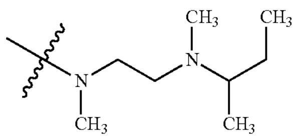 [SMILES: *N(C)CCN(C)C(C)CC] | 929.8 | (500 MHz): 0.83-0.97 (m, 9 H) 1.06-1.27 (m, 22 H) 1.38 (s, 3 H) 1.40 (s, 3 H) 1.48-2.13 (m, 11 H) 2.21 (s, 3 H) 2.29 (s, 6 H) 2.34 (s, 3 H) 2.39-2.63 (m, 7 H) 2.76-2.92 (m, 3 H) 2.96 (s, 3 H) 3.18 (dd, J = 10.15, 7.40 Hz, 1 H) 3.28 (s, 3 H) 3.42-3.51 (m, 1 H) 3.66 (d, J = 6.31 Hz, 1 H) 3.69 (s, 1 H) 3.78 (d, J = 8.78 Hz, 1 H) 4.08 (q, J = 6.31 Hz, 1 H) 4.41 (d, J = 7.40 Hz, 1 H) 4.99 (d, J = 4.39 Hz, 1 H) 5.11 (dd, J = 10.56, 2.33 Hz, 1 H) 5.76 (s, 1 H) |
| 251 | 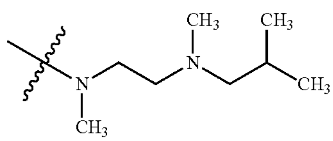 [SMILES: *N(C)CCN(C)CC(C)C] | 929.7 | (600 MHz): 0.83-0.91 (m, 9 H) 1.04-1.27 (m, 22 H) 1.38 (s, 3 H) 1.40 (s, 3 H) 1.44-2.12 (m, 12 H) 2.19 (s, 3 H) 2.30 (br. s., 6 H) 2.35 (s, 3 H) 2.37-2.65 (m, 6 H) 2.78-2.91 (m, 3 H) 2.96 (s, 3 H) 3.15-3.21 (m, 1 H) 3.28 (s, 3 H) 3.41-3.50 (m, 1 H) 3.61-3.66 (m, 1 H) 3.67-3.70 (m, 1 H) 3.75-3.81 (m, 1 H) 4.05-4.13 (m, 1 H) 4.38-4.43 (m, 1 H) 4.96-5.01 (m, 1 H) 5.07-5.15 (m, 1 H) 5.76 (s, 1 H) |
| 252 | 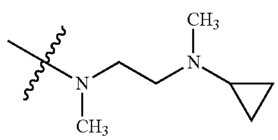 | 913.7 | (500 MHz): 0.38-0.47 (m, 4 H) 0.86 (t, J = 7.40 Hz, 3 H) 1.04-1.28 (m, 22 H) 1.38 (s, 3 H) 1.40 (s, 3 H) 1.47-2.11 (m, 12 H) 2.30 (br. s., 6 H) 2.33 (s, 3 H) 2.34 (s, 3 H) 2.40-2.67 (m, 6 H) 2.77-2.91 (m, 3 H) 2.96 (s, 3 H) 3.15-3.21 (m, 1 H) 3.28 (s, 3 H) 3.42-3.51 (m, 1 H) 3.65 (d, J = 7.13 Hz, 1 H) 3.67-3.70 (m, 1 H) 3.77 (d, J = 8.50 Hz, 1 H) 4.07 (q, J = 6.31 Hz, 1 H) 4.40 (d, J = 7.40 Hz, 1 H) 4.98 (d, J = 4.68 Hz, 1 H) 5.11 (dd, J = 10.70, 2.19 Hz, 1 H) 5.76 (s, 1 H) |
| 253 | 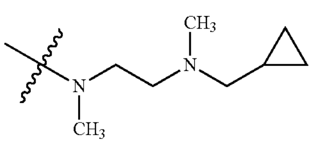 [SMILES: *N(C)CCN(C)CC1CC1] | 927.7 | (600 MHz): 0.09-0.12 (m, 2 H) 0.47-0.54 (m, 2 H) 0.83-0.88 (m, 4 H) 1.05-1.26 (m, 22 H) 1.38 (s, 3 H) 1.40 (s, 3 H) 1.47-2.05 (m, 9 H) 2.13 (d, J = 14.67 Hz, 1 H) 2.23-2.33 (m, 10 H) 2.35 (s, 3 H) 2.40-2.67 (m, 6 H) 2.77-2.91 (m, 3 H) 2.96 (s, H) 3.15-3.21 (m, 1 H) 3.28 (s, 3 H) 3.44-3.51 (m, 1 H) 3.66 (d, J = 7.34 Hz, 1 H) 3.69 (s, 1 H) 3.77 (d, J = 8.25 Hz, 1 H) 4.10 (q, J = 6.27 Hz, 1 H) 4.41 (d, J = 6.88 Hz, 1 H) 4.98 (d, J = 4.13 Hz, 1 H) 5.08-5.15 (m, 1 H) 5.76 (s, 1 H) |
| 254 | 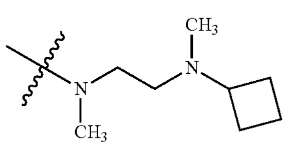 [SMILES: *N(C)CCN(C)C1CCC1] | 927.7 | (500 MHz): 0.86 (t, J = 7.40 Hz, 3 H) 1.06-1.26 (m, 22 H) 1.38 (s, 3 H) 1.39-1.42 (m, 3 H) 1.47-2.17 (m, 20 H) 2.29 (s, 6 H) 2.32-2.35 (m, 3 H) 2.40-2.64 (m, 4 H) 2.75-2.92 (m, 4 H) 2.98 (s, 3 H) 3.15-3.22 (m, 1 H) 3.28 (s, 3 H) 3.42-3.51 (m, 1 H) 3.66 (d, J = 7.40 Hz, 1 H) 3.69 (s, 1 H) 3.78 (d, J = 8.50 Hz, 1 H) 4.09 (q, J = 6.22 Hz, 1 H) 4.41 (d, J = 7.13 Hz, 1 H) 4.99 (d, J = 4.66 Hz, 1 H) 5.11 (dd, J = 10.70, 2.19 Hz, 1 H) 5.77 (s, 1 H) |
| 255 | 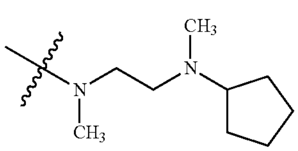 [SMILES: *N(C)CCN(C)C1CCCC1] | 941.7 | (500 MHz): 0.86 (t, J = 7.27 Hz, 3 H) 1.04-1.28 (m, 22 H) 1.33-2.15 (m, 23 H) 2.23 (s, 3 H) 2.29 (s, 6 H) 2.33 (s, 3 H) 2.38-2.92 (m, 10 H) 2.96 (s, 3 H) 3.15-3.21 (m, 1 H) 3.28 (s, 3 H) 3.43-3.50 (m, 1 H) 3.65 (d, J = 7.40 Hz, 1 H) 3.69 (s, 1 H) 3.77 (d, J = 7.95 Hz, 1 H) 4.08 (q, J = 6.31 Hz, 1 H) 4.41 (d, J = 7.40 Hz, 1 H) 4.99 (d, J = 4.11 Hz, 1 H) 5.11 (dd, J = 10.70, 2.19 Hz, 1 H) 5.76 (s, 1 H) |
| 256 | 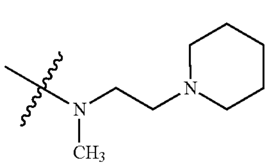 [SMILES: *N(C)CCN1CCCCC1] | 927.7 | (500 MHz): 0.86 (t, J = 7.40 Hz, 3 H) 1.04-1.26 (m, 22 H) 1.37 (s, 3 H) 1.39-2.05 (m, 20 H) 2.13 (d, J = 14.81 Hz, 1 H) 2.29 (s, 6 H) 2.31-2.67 (m, 10 H) 2.76-2.91 (m, 3 H) 2.96 (s, 3 H) 3.18 (dd, J = 10.15, 7.13 Hz, 1 H) 3.28 (s, 3 H) 3.44-3.53 (m, 1 H) 3.64-3.72 (m, 2 H) 3.76 (d, J = 8.50 Hz, 1 H) 4.09 (q, J = 6.31 Hz, 1 H) 4.42 (d, J = 7.13 Hz, 1 H) 4.98 (d, J = 3.29 Hz, 1 H) 5.11 (dd, J = 10.70, 2.19 Hz, 1 H) 5.77 (s, 1 H) |

| | | | |
|---|---|---|---|
| 257 | 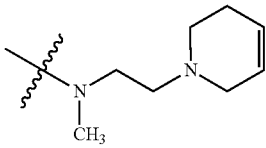 [SMILES: *N(C)CCN1CC=CCC1] | 925.7 | (500 MHz): 0.86 (t, J = 7.40 Hz, 3 H) 1.05-1.28 (m, 22 H) 1.37 (s, 3 H) 1.40 (s, 3 H) 1.48-2.05 (m, 8 H) 2.13 (d, J = 14.81 Hz, 3 H) 2.30 (s, 6 H) 2.36 (s, 3 H) 2.41-2.74 (m, 8 H) 2.79-3.05 (m, 8 H) 3.15-3.21 (m, 1 H) 3.28 (s, 3 H) 3.66 (d, J = 7.13 Hz, 1 H) 3.68-3.70 (m, 1 H) 3.76 (d, J = 8.23 Hz, 1 H) 4.09 (q, J = 6.67 Hz, 1 H) 4.41 (d, J = 7.40 Hz, 1 H) 4.97 (s, 1 H) 5.07-5.16 (m, 1 H) 5.60-5.79 (m, 3 H) |
| 258 | 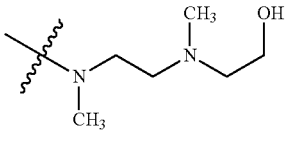 | 917.7 | (600 MHz): 0.86 (t, J = 7.34 Hz, 3 H) 1.05-1.27 (m, 22 H) 1.38 (s, 3 H) 1.40 (s, 3 H) 1.45-1.97 (m, 9 H) 2.01-2.05 (m, 1 H) 2.10-2.15 (m, 1 H) 2.30 (br. s, 6 H) 2.33 (s, 3 H) 2.36 (s, 3 H) 2.42-2.67 (m, 8 H) 2.79-2.90 (m, 3 H) 2.95 (s, 3 H) 3.16-3.22 (m, 1 H) 3.28 (s, 3 H) 3.44-3.50 (m, 1 H) 3.58-3.63 (m, 2 H) 3.65-3.67 (m, 1 H) 3.69 (s, 1 H) 3.77 (d, J = 8.71 Hz, 1 H) 4.10 (q, J = 6.57 Hz, 1 H) 4.41 (d, J = 7.34 Hz, 1 H) 4.98 (d, J = 4.58 Hz, 1 H) 5.11 (dd, J = 11.00, 2.29 Hz, 1 H) 5.76 (s, 1 H) |
| 259 | 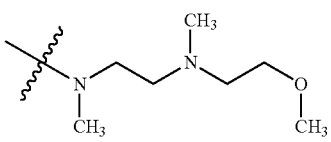 [SMILES: *N(C)CCN(C)CCOC] | 931.7 | (600 MHz): 0.86 (t, J = 7.34 Hz, 3 H) 1.06-1.26 (m, 22 H) 1.38 (s, 3 H) 140 (s, 3 H) 1.47-2.12 (m, 8 H) 2.17 (s, 3 H) 2.29 (br. s., 9 H) 2.34 (s, 3 H) 2.41-2.68 (m, 6 H) 2.78-2.91 (m, 3 H) 2.96 (s, 3 H) 3.16-3.21 (m, 1 H) 3.28 (s, 3 H) 3.34 (s, 3 H) 3.44-3.51 (m, 3 H) 3.65 (d, J = 7.34 Hz, 1 H) 3.69 (s, 1 H) 3.78 (d, J = 8.71 Hz, 1 H) 4.09 (q, J = 6.27 Hz, 1 H) 4.41 (d, J = 6.88 Hz, 1 H) 4.99 (d, J = 4.13 Hz, 1 H) 5.11 (dd, J = 11.00, 2.29 Hz, 1 H) 5.76 (s, 1 H) |
| 260 | 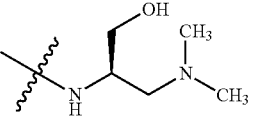 [SMILES: *N[C@@H](CO)CN(C)C] | 903.6 | (500 MHz): 0.86 (t, J = 7.45 Hz, 3 H) 1.05-1.29 (m, 22 H) 1.38 (s, 3 H) 1.41 (s, 3 H) 1.48-1.58 (m, 1 H) 1.64-1.95 (m, 7 H) 2.04 (d, J = 15.29 Hz, 1 H) 2.28 (s, 6 H) 2.29 (s, 6 H) 2.31-2.59 (m, 6 H) 2.72-2.97 (m, 7 H) 3.18 (dd, J = 9.94, 7.26 Hz, 1 H) 3.28 (s, 3 H) 3.49-3.57 (m, 2 H) 3.59-3.71 (m, 3 H) 3.79 (d, J = 8.41 Hz, 1 H) 4.29 (d, J = 6.50 Hz, 1 H) 4.38 (d, J = 6.88 Hz, 1 H) 4.96 (d, J = 4.97 Hz, 1 H) 5.10 (dd, J = 10.70, 2.29 Hz, 1 H) 5.78 (s, 1 H) |
| 261 | 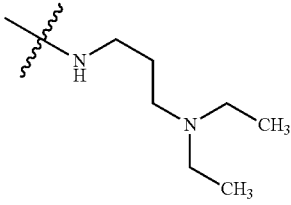 [SMILES: *NCCCN(CC)CC] | 915.7 | (500 MHz): 0.86 (t, J = 7.26 Hz, 3 H) 1.01 (t, J = 7.07 Hz, 6 H) 1.06-1.16 (m, 15 H) 1.17-1.26 (m, 7 H) 1.38 (s, 3 H) 1.40 (s, 3 H) 1.47-1.97 (m, 10 H) 2.01-2.07 (m, 1 H) 2.29 (s, 6 H) 2.37 (d, J = 13.76 Hz, 1 H) 2.40-2.57 (m, 8 H) 2.65 (t, J = 6.69 Hz, 2 H) 2.76-2.92 (m, 3 H) 2.95 (s, 3 H) 3.18 (dd, J = 10.32, 7.26 Hz, 1 H) 3.28 (s, 3 H) 3.51-3.58 (m, 1 H) 3.64 (d, J = 7.64 Hz, 1 H) 3.69 (s, 1 H) 3.79 (d, J = 8.41 Hz, 1 H) 4.24 (q, J = 6.50 Hz, 1 H) 4.41 (d, J = 7.26 Hz, 1 H) 4.97 (d, J = 4.59 Hz, 1 H) 5.11 (dd, J = 10.51, 2.10 Hz, 1 H) 5.77 (s, 1 H) |
| 262 | 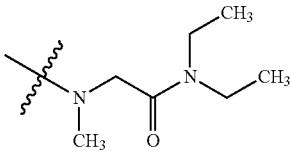 [SMILES: *N(C)CC(=O)N(CC)CC] | 929.7 | (500 MHz): 0.86 (t, J = 7.26 Hz, 3 H) 1.05-1.24 (m, 28 H) 1.37 (s, 3 H) 1.40 (s, 3 H) 1.48-2.09 (m, 10 H) 2.29 (s, 6 H) 2.34 (d, J = 15.67 Hz, 1 H) 2.39-2.58 (m, 5 H) 2.78-2.91 (m, 2 H) 2.96 (s, 3 H) 3.08-3.19 (m, 2 H) 3.21-3.29 (m, 4 H) 3.36 (q, J = 6.88 Hz, 3 H) 3.42-3.49 (m, 3 H) 3.64 (d, J = 7.64 Hz, 1 H) 3.68 (s, 1 H) 3.78 (d, J = 8.41 Hz, 1 H) 4.11 (q, J = 6.50 Hz, 1 H) 4.40 (d, J = 7.26 Hz, 1 H) 4.99 (d, J = 4.97 Hz, 1 H) 5.11 (dd, J = 10.70, 2.29 Hz, 1 H) 5.77 (s, 1 H) |
| 263 | 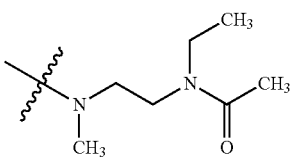 [SMILES: *N(C)CCN(CC)C(C)=O] | 929.7 | (600 MHz): 0.86 (t, J = 7.34 Hz, 3 H) 1.03-1.27 (m, 25 H) 1.37 (s, 3 H) 1.40 (s, 3 H) 1.48-1.97 (m, 8 H) 2.04-2.09 (m, 4 H) 2.30 (s, 6 H) 2.41 (s, 3 H) 2.50-2.93 (m, 6 H) 2.95 (s, 3 H) 3.15-3.21 (m, 1 H) 3.28 (s, 3 H) 3.31-3.46 (m, 5 H) 3.50-3.55 (m, 1 H) 3.62 (d, J = 7.34 Hz, 1 H) 3.68 (s, 1 H) 3.79 (d, J = 8.71 Hz, 1 H) 4.10 (d, J = 6.42 Hz, 1 H) 4.37-4.39 (m, 1 H) 4.98 (d, J = 5.50 Hz, 1 H) 5.10 (dd, J = 10.55, 2.29 Hz, 1 H) 5.77 (s, 1 H) |
| 264 | 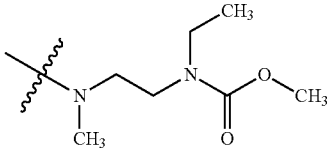 [SMILES: *N(C)CCN(CC)C(=O)OC] | 945.7 | (500 MHz): 0.86 (t, J = 7.40 Hz, 3 H) 1.05-1.27 (m, 25 H) 1.38 (s, 3 H) 1.40 (s, 3 H) 1.48-2.10 (m, 10 H) 2.29 (s, 6 H) 2.35-2.58 (m, 5 H) 2.79-2.91 (m, 3 H) 2.96 (s, 3 H) 3.14-3.46 (m, 10 H) 3.63 (d, J = 7.40 Hz, 1 H) 3.66-3.70 (m, 4 H) 3.79 (d, J = 8.50 Hz, 1 H) 4.10 (d, J = 6.58 Hz, 1 H) 4.39 (d, J = 7.13 Hz, 1 H) 4.98 (d, J = 4.94 Hz, 1 H) 5.11 (dd, J = 10.56, 2.33 Hz, 1 H) 5.78 (s, 1 H) |
| 265 | 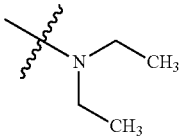 | 858.6 | (600 MHz): 0.86 (t, J = 7.34 Hz, 3 H) 0.97-1.28 (m, 28 H) 1.38 (s, 3 H) 1.40 (s, 3 H) 1.48-2.11 (m, 10 H) 2.30 (s, 6 H) 2.41-2.58 (m, 2 H) 2.63-2.75 (m, 3 H) 2.79-2.91 (m, 3 H) 2.96 (s, 3 H) 3.18 (dd, J = 10.09, 7.34 Hz, 1 H) 3.29 (s, 3 H) 3.43-3.50 (m, 1 H) 3.65 (d, J = 7.34 Hz, 1 H) 3.69 (s, 1 H) 3.79 (d, J = 8.25 Hz, 1 H) 4.11 (q, J = 6.42 Hz, 1 H) 4.42 (d, J = 7.34 Hz, 1 H) 4.98 (d, J = 5.04 Hz, 1 H) 5.11 (dd, J = 10.55, 2.29 Hz, 1 H) 5.77 (s, 1 H) |

TABLE 6-continued

| | | | |
|---|---|---|---|
| 266 | 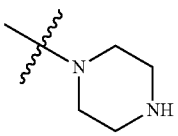 [SMILES: *N1CCNCC1] | 871.6 | (600 MHz): 0.86 (t, J = 7.34 Hz, 3 H) 1.06-1.25 (m, 22 H) 1.36-1.39 (m, 3 H) 1.39 (s, 3 H) 1.48-2.09 (m, 13 H) 2.29 (s, 6 H) 2.40-2.46 (m, 1 H) 2.51-2.58 (m, 1 H) 2.74-2.92 (m, 7 H) 2.96 (s, 3 H) 3.18 (dd, J = 10.09, 7.34 Hz, 1 H) 3.29 (s, 3 H) 3.39-3.47 (m, 1 H) 3.63 (d, J = 7.34 Hz, 1 H) 3.68 (s, 1 H) 3.79 (d, J = 8.71 Hz, 1 H) 4.11 (q, J = 6.42 Hz, 1 H) 4.39 (d, J = 7.34 Hz, 1 H) 4.98 (d, J = 5.04 Hz, 1 H) 5.11 (dd, J = 10.55, 2.29 Hz, 1 H) 5.79 (s, 1 H) |
| 267 | 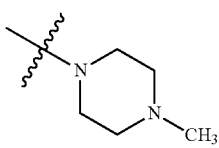 | 885.6 | (500 MHz): 0.86 (t, J = 7.45 Hz, 3 H) 1.04-1.27 (m, 22 H) 1.37 (s, 3 H) 1.40 (s, 3 H) 1.47-2.10 (m, 12 H) 2.27-2.32 (m, 9 H) 2.38-2.93 (m, 10 H) 2.96 (s, 3 H) 3.17 (dd, J = 10.32, 7.26 Hz, 1 H) 3.28 (s, 3 H) 3.38-3.47 (m, 1 H) 3.63 (d, J = 7.64 Hz, 1 H) 3.68 (s, 1 H) 3.79 (d, J = 8.41 Hz, 1 H) 4.10 (q, J = 6.37 Hz, 1 H) 4.39 (d, J = 7.26 Hz, 1 H) 4.98 (d, J = 4.97 Hz, 1 H) 5.11 (dd, J = 10.70, 2.29 Hz, 1 H) 5.77 (s, 1 H) |
| 268 | 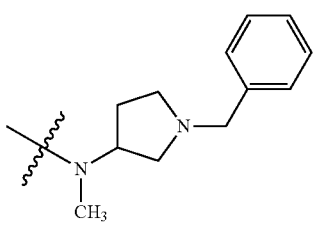 [SMILES: *N(C)C1CCN(Cc2ccccc2)C1] | 975.7 | (500 MHz): 0.85 (t, J = 7.40 Hz, 3 H) 1.03-1.25 (m, 22 H) 1.37 (s, 3 H) 1.40 (s, 3 H) 1.47-2.07 (m, 11 H) 2.28 (s, 6 H) 2.33 (s, 3 H) 2.37-2.64 (m, 5 H) 2.69-2.91 (m, 4 H) 2.95 (s, 3 H) 3.14-3.20 (m, 1 H) 3.25-3.29 (m, 2 H) 3.37-3.52 (m, 3 H) 3.60-3.71 (m, 3 H) 3.77 (d, J = 8.50 Hz, 1 H) 4.05-4.12 (m, 1 H) 4.38 (dd, J = 7.27, 3.70 Hz, 1 H) 4.97 (d, J = 4.94 Hz, 1 H) 5.10 (dd, J = 10.70, 2.19 Hz, 1 H) 5.77 (s, 1 H) 7.23-7.34 (m, 5 H) |
| 269 | 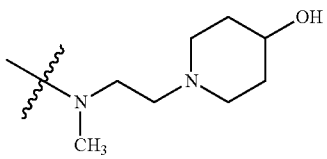 [SMILES: *N(C)CCN1CCC(O)CC1] | 943.7 | (500 MHz): 0.86 (t, J = 7.40 Hz, 3 H) 1.04-1.29 (m, 22 H) 1.38 (s, 3 H) 1.40 (s, 3 H) 1.48-2.23 (m, 18 H) 2.29 (s, 6 H) 2.32-2.67 (m, 9 H) 2.70-2.92 (m, 5 H) 2.93-2.97 (m, 3 H) 3.18 (dd, J = 10.28, 7.27 Hz, 1 H) 3.28 (s, 3 H) 3.43-3.52 (m, 1 H) 3.63-3.73 (m, 3 H) 3.76 (d, J = 8.50 Hz, 1 H) 4.09 (q, J = 6.22 Hz, 1 H) 4.42 (d, J = 7.13 Hz, 1 H) 4.98 (d, J = 3.29 Hz, 1 H) 5.11 (dd, J = 10.70, 2.19 Hz, 1 H) 5.78 (s, 1 H) |
| 270 | 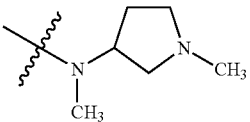 [SMILES: *N(C)C1CCN(C)C1] | 899.8 | (500 MHz): 0.86 (t, J = 7.45 Hz, 3 H) 1.05-1.27 (m, 22 H) 1.37 (s, 3 H) 1.40 (s, 3 H) 1.48-2.08 (m, 12 H) 2.28-2.34 (m, 12 H) 2.35-2.69 (m, 6 H) 2.78-2.92 (m, 3 H) 2.96 (s, 3 H) 3.18 (dd, J = 10.32, 7.26 Hz, 1 H) 3.29 (s, 3 H) 3.39-3.51 (m, 2 H) 3.64 (dd, J = 7.26, 3.06 Hz, 1 H) 3.69 (s, 1 H) 3.78 (d, J = 8.79 Hz, 1 H) 4.10 (q, J = 6.24 Hz, 1 H) 4.40 (d, J = 7.26 Hz, 1 H) 4.98 (d, J = 4.59 Hz, 1 H) 5.11 (dd, J = 10.70, 2.29 Hz, 1 H) 5.77 (s, 1 H) |
| 271 | 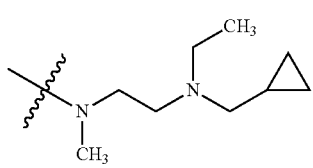 | 941.8 | (500 MHz): 0.05-0.12 (m, 2 H) 0.44-0.53 (m, 2 H) 0.81-0.91 (m, 4 H) 1.00-1.28 (m, 25 H) 1.38 (s, 3 H) 1.40 (s, 3 H) 1.47-2.13 (m, 9 H) 2.24-2.70 (m, 19 H) 2.78-2.92 (m, 3 H) 2.96 (s, 3 H) 3.18 (dd, J = 10.32, 7.26 Hz, 1 H) 3.28 (s, 3 H) 3.43-3.51 (m, 1 H) 3.66 (d, J = 7.26 Hz, 1 H) 3.69 (s, 1 H) 3.77 (d, J = 8.79 Hz, 1 H) 4.05-4.13 (m, 1 H) 4.41 (d, J = 7.26 Hz, 1 H) 4.99 (d, J = 4.20 Hz, 1 H) 5.11 (dd, J = 10.70, 2.29 Hz, 1 H) 5.77 (s, 1 H) |
| 272 | 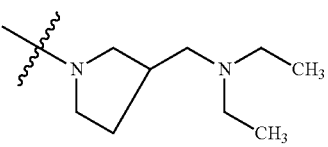 | 941.8 | (500 MHz): 0.86 (t, J = 7.40 Hz, 3 H) 0.96-1.02 (m, 6 H) 1.06-1.27 (m, 22 H) 1.38 (s, 3 H) 1.39-1.42 (m, 3 H) 1.43-1.58 (m, 2 H) 1.62-1.68 (m, 1 H) 1.70-2.00 (m, 7 H) 2.04-2.09 (m, 1 H) 2.13-2.19 (m, 1 H) 2.26-2.58 (m, 17 H) 2.74-2.91 (m, 3 H) 2.92-2.98 (m, 4 H) 3.17 (dd, J = 10.28, 7.27 Hz, 1 H) 3.28 (s, 3 H) 3.37-3.48 (m, 1 H) 3.64 (dd, J = 7.40, 1.65 Hz, 1 H) 3.69 (s, 1 H) 3.79 (d, J = 8.50 Hz, 1 H) 4.10 (q, J = 6.31 Hz, 1 H) 4.40 (d, J = 7.13 Hz, 1 H) 4.99 (d, J = 4.94 Hz, 1 H) 5.11 (dd, J = 10.42, 2.19 Hz, 1 H) 5.77 (s, 1 H) |
| 273 | 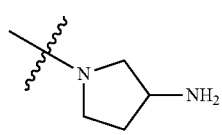 [SMILES: *N1CCC(N)C1] | 871.7 | (500 MHz): 0.86 (t, J = 7.40 Hz, 3 H) 1.05-1.28 (m, 22 H) 1.38 (s, 3 H) 1.40 (s, 3 H) 1.49-2.23 (m, 13 H) 2.29 (s, 5 H) 2.39-2.58 (m, 2 H) 2.67-3.01 (m, 8 H) 3.16-3.23 (m, 1 H) 3.29 (s, 3 H) 3.38-3.47 (m, 1 H) 3.52-3.59 (m, 1 H) 3.63 (d, J = 7.40 Hz, 1 H) 3.68 (s, 1 H) 3.79 (d, J = 8.23 Hz, 1 H) 4.11 (q, J = 6.12 Hz, 1 H) 4.40 (d, J = 7.13 Hz, 1 H) 4.99 (d, J = 5.21 Hz, 1 H) 5.10 (dd. J = 10.56, 2.33 Hz, 1 H) 5.80 (s, 1 H) |
| 274 | 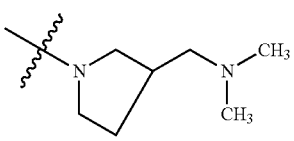 [SMILES: *N1CCC(CN(C)C)C1] | 913.8 | (500 MHz): 0.86 (t, J = 7.40 Hz, 3 H) 1.08 (d, J = 7.40 Hz, 3 H) 1.09-1.17 (m, 12 H) 1.17-1.28 (m, 7 H) 1.38 (s, 3 H) 1.40 (s, 3 H) 1.44-1.57 (m, 2 H) 1.62-2.09 (m, 10 H) 2.13-2.27 (m, 9 H) 2.29 (s, 6 H) 2.32-2.58 (m, 4 H) 2.79-3.00 (m, 7 H) 3.17 (dd, J = 10.28, 7.27 Hz, 1 H) 3.25-3.30 (m, 3 H) 3.37-3.48 (m, 1 H) 3.62-3.67 (m, H) 3.69 (s, 1 H) 3.79 (d, J = 8.78 Hz, 1 H) 4.10 (q, J = 6.30 Hz, 1 H) 4.40 (d, J = 7.13 Hz, 1 H) 4.99 (d, J = 4.94 Hz, 1 H) 5.11 (dd, J = 10.70, 2.19 Hz, 1 H) 5.77 (s, 1 H) |

TABLE 6-continued

| # | Structure | Mass | NMR |
|---|---|---|---|
| 275 | (pyrrolidine with N-CH2-CH3, CH2-N(CH3)- linker) | 927.8 | (500 MHz): 0.86 (t, J = 7.26 Hz, 3 H) 1.05-1.28 (m, 25 H) 1.35-1.44 (m, 7 H) 1.49- 1.58 (m, 1 H) 1.63-2.19 (m, 11 H) 2.29 (s, 6 H) 2.31-2.33 (m, 3 H) 2.38-2.58 (m, 7 H) 2.68-2.76 (m, 1 H) 2.77-2.93 (m, 3 H) 2.96 (s, 3 H) 3.18 (dd, J = 9.94, 7.26 Hz, 1 H) 3.27-3.30 (m, 3 H) 3.38-3.47 (m, 2 H) 3.63 (d, J = 7.64 Hz, 1 H) 3.69 (s, 1 H) 3.79 (d, J = 8.79 Hz, 1 H) 4.11 (q, J = 6.37 Hz, 1 H) 4.40 (d, J = 7.26 Hz, 1 H) 4.98 (d, J = 4.97 Hz, 1 H) 5.11 (dd, J = 10.70, 2.29 Hz, 1 H) 5.77 (s, 1 H) |
| 276 | (N-methyl pyrrolidine with CH2-N(CH3)- linker) | 913.8 | (500 MHz): 0.86 (t, J = 7.45 Hz, 3 H) 1.07 (d, J = 7.26 Hz, 3 H) 1.09-1.17 (m, 12 H) 1.18-1.27 (m, 7 H) 1.38 (s, 3 H) 1.40 (s, 3 H) 1.45-1.58 (m, 2 H) 1.63-2.09 (m, 9 H) 2.12-2.27 (m, 9 H) 2.29 (s, 6 H) 2.33-2.59 (m, 4 H) 2.79-2.91 (m, 3 H) 2.92-2.99 (m, 4 H) 3.18 (dd, J = 10.32, 7.26 Hz, 1 H) 3.28 (d, J = 0.76 Hz, 3 H) 3.39-3.47 (m, 1 H) 3.61-3.66 (m, 1 H) 3.69 (s, 1 H) 3.79 (d, J = 8.41 Hz, 1 H) 4.10 (q, J = 5.99 Hz, 1 H) 4.40 (d, J = 7.26 Hz, 1 H) 4.99 (d, J = 4.97 Hz, 1 H) 5.11 (dd, J = 10.70, 2.29 Hz, 1 H) 5.77 (s, 1 H) |
| 277 | (2-methyl pyrrolidine with ethyl-N(CH3)- linker) | 927.8 | (500 MHz): 0.86 (t, J = 7.40 Hz, 3 H) 1.05-1.28 (m, 25 H) 1.35-1.47 (m, 7 H) 1.47- 1.58 (m, 1 H) 1.63-2.22 (m, 13 H) 2.29 (s, 6 H) 2.34-2.38 (m, 4 H) 2.41-2.73 (m, 5 H) 2.76-2.94 (m, 4 H) 2.96 (s, 3 H) 3.18 (dd, J = 10.15, 7.13 Hz, 2 H) 3.26-3.30 (m, 3 H) 3.42-3.50 (m, 1 H) 3.62-3.70 (m, 2 H) 3.77 (t, J = 7.82 Hz, 1 H) 4.09 (q, J = 8.31 Hz, 1 H) 4.37-4.44 (m, 1 H) 4.98 (d, J = 4.66 Hz, 1 H) 5.08-5.14 (m, 1 H) 5.77 (s, 1 H) |
| 278 | (pyrrolidine-2-C(O)N(CH3)2 with ethyl-N(CH3)- linker) | 984.9 | (500 MHz): 0.86 (t, J = 7.40 Hz, 3 H) 1.07 (d, J = 7.40 Hz, 3 H) 1.09-1.18 (m, 12 H) 1.18-1.27 (m, 7 H) 1.38 (s, 3 H) 1.40 (s, 3 H) 1.48-1.59 (m, 1 H) 1.64-2.18 (m, 13 H) 2.30 (s, 6 H) 2.32-2.38 (m, 4 H) 2.39-2.74 (m, 5 H) 2.79-2.91 (m, 4 H) 2.93-2.98 (m, 6 H) 3.09 (s, 3 H) 3.18 (dd, J = 10.28, 7.27 Hz, 1 H) 3.21-3.29 (m, 4 H) 3.36-3.48 (m, 1 H) 3.63 (d, J = 7.68 Hz, 1 H) 3.68 (s, 1 H) 3.78 (d, J = 7.95 Hz, 1 H) 4.10 (q, J = 6.31 Hz, 1 H) 4.39 (d, J = 7.13 Hz, 1 H) 4.98 (d, J = 4.94 Hz, 1 H) 5.10 (dd, J = 10.56, 2.33 Hz, 1 H) 5.77 (s, 1 H) |
| 279 | (2-hydroxymethyl pyrrolidine with ethyl-N(CH3)- linker) | 943.9 | (500 MHz): 0.86 (t, J = 7.26 Hz, 3 H) 1.07 (d, J = 7.64 Hz, 3 H) 1.11 (d, J = 7.26 Hz, 3 H) 1.14 (d, J = 6.88 Hz, 3 H) 1.17-1.26 (m, 13 H) 1.38 (s, 3 H) 1.40 (s, 3 H) 1.48-2.06 (m, 13 H) 2.12 (d, J = 14.91 Hz, 1 H) 2.25-2.33 (m, 7 H) 2.35 (s, 3 H) 2.39-2.48 (m, 3 H) 2.49-2.58 (m, 2 H) 2.69-2.91 (m, 5 H) 2.93-3.00 (m, 4 H) 3.18 (dd, J = 10.32, 7.26 Hz, 1 H) 3.23-3.31 (m, 4 H) 3.36-3.49 (m, 3 H) 3.58-3.66 (m, 2 H) 3.68 (s, 1 H) 3.78 (d, J = 8.41 Hz, 1 H) 4.10 (q, J = 6.24 Hz, 1 H) 4.39 (d, J = 7.26 Hz, 1 H) 4.98 (d, J = 4.59 Hz, 1 H) 5.10 (dd, J = 10.70, 2.29 Hz, 1 H) 5.76 (s, 1 H) |
| 280 | (2-hydroxymethyl pyrrolidine, isomer, with ethyl-N(CH3)- linker) | 943.8 | (500 MHz): 0.86 (t, J = 7.26 Hz, 3 H) 1.07 (d, J = 7.64 Hz, 3 H) 1.11 (d, J = 6.88 Hz, 3 H) 1.14 (d, J = 6.50 Hz, 3 H) 1.17 (s, 3 H) 1.18-1.27 (m, 10 H) 1.37 (s, 3 H) 1.40 (s, 3 H) 1.47-1.58 (m, 1 H) 1.62-2.04 (m, 11 H) 2.14 (d, J = 14.91 Hz, 1 H) 2.27-2.34 (m, 7 H) 2.36 (s, 3 H) 2.41-2.72 (m, 6 H) 2.79-2.92 (m, 4 H) 2.96 (s, 3 H) 3.18 (dd, J = 9.94, 7.26 Hz, 1 H) 3.24-3.31 (m, 4 H) 3.36-3.43 (m, 1 H) 3.43-3.51 (m, 1 H) 3.60-3.64 (m, 1 H) 3.66-3.70 (m, 2 H) 3.75 (d, J = 8.79 Hz, 1 H) 4.09 (q, J = 6.50 Hz, 1 H) 4.41 (d, J = 7.26 Hz, 1 H) 4.98 (d, J = 4.59 Hz, 1 H) 5.11 (dd, J = 10.70, 2.29 Hz, 1 H) 5.77 (s, 1 H) |
| 281 | (2-methoxymethyl pyrrolidine with ethyl-N(CH3)- linker) | 957.9 | (500 MHz): 0.86 (t, J = 7.40 Hz, 3 H) 1.08 (d, J = 7.40 Hz, 3 H) 1.11 (d, J = 7.13 Hz, 3 H) 1.13-1.26 (m, 16 H) 1.38 (s, 3 H) 1.40 (s, 3 H) 1.49-2.21 (m, 14 H) 2.29 (s, 6 H) 2.31-2.37 (m, 4 H) 2.40-2.70 (m, 5 H) 2.78-2.91 (m, 3 H) 2.96 (s, 3 H) 3.01-3.09 (m, 1 H) 3.13-3.21 (m, 2 H) 3.26-3.32 (m, 4 H) 3.34 (s, 3 H) 3.37-3.50 (m, 3 H) 3.65 (d, J = 7.40 Hz, 1 H) 3.69 (s, 1 H) 3.79 (d, J = 8.23 Hz, 1 H) 4.09 (q, J = 6.12 Hz, 1 H) 4.41 (d, J = 7.13 Hz, 1 H) 4.99 (d, J = 4.66 Hz, 1 H) 5.11 (dd, J = 10.56, 2.33 Hz, 1 H) 5.76 (s, 1 H) |

TABLE 6-continued

| | | | |
|---|---|---|---|
| 282 | (structure) | 929.8 | (500 MHz): 0.85 (t, J = 7.27 Hz, 3 H) 1.04-1.26 (m, 22 H) 1.38 (s, 3 H) 1.40 (s, 3 H) 1.47-2.06 (m, 10 H) 2.11-2.33 (m, 9 H) 2.34-2.58 (m, 7 H) 2.60-2.70 (m, 2 H) 2.77-3.03 (m, 8 H) 3.18 (dd, J = 10.28, 7.27 Hz, 1 H) 3.27 (s, 3 H) 3.44-3.52 (m, 1 H) 3.65-3.71 (m, 2 H) 3.75 (d, J = 8.50 Hz, 1 H) 4.09 (q, J = 6.31 Hz, 1 H) 4.25-4.32 (m, 1 H) 4.41 (d, J = 7.13 Hz, 1 H) 4.96 (d, J = 4.11 Hz, 1 H) 5.11 (dd, J = 10.56, 2.33 Hz, 1 H) 5.78 (s, 1 H) |
| 283 | (structure) | 929.8 | (500 MHz): 0.85 (t, J = 7.40 Hz, 3 H) 1.03-1.28 (m, 22 H) 1.37 (s, 3 H) 1.40 (s, 3 H) 1.47-2.06 (m, 9 H) 2.11-2.34 (m, 9 H) 2.37 (s, 3 H) 2.41-2.65 (m, 7 H) 2.75-2.99 (m, 8 H) 3.18 (dd, J = 10.15, 7.40 Hz, 1 H) 3.28 (s, 3 H) 3.43-3.50 (m, 1 H) 3.66 (d, J = 7.13 Hz, 1 H) 3.69 (s, 1 H) 3.75 (d, J = 8.50 Hz, 1 H) 4.07 (q, J = 6.31 Hz, 1 H) 4.29-4.35 (m, 1 H) 4.41 (d, J = 7.40 Hz, 1 H) 4.95 (d, J = 4.11 Hz, 1 H) 5.11 (dd, J = 10.70, 2.19 Hz, 1 H) 5.79 (s, 1 H) |
| 284 | (structure) | 956.9 | (500 MHz): 0.86 (t, J = 7.26 Hz, 3 H) 1.04-1.27 (m, 22 H) 1.38 (s, 3 H) 1.40 (s, 3 H) 1.49-1.59 (m, 1 H) 1.62-2.15 (m, 11 H) 2.21 (s, 6 H) 2.29 (s, 6 H) 2.35 (s, 3 H) 2.41-2.87 (m, 7 H) 2.74-2.92 (m, 6 H) 2.96 (s, 3 H) 3.18 (dd, J = 10.13, 7.45 Hz, 1 H) 3.28 (s, 3 H) 3.43-3.51 (m, 1 H) 3.63-3.71 (m, 2 H) 3.77 (d, J = 8.41 Hz, 1 H) 4.06-4.13 (m, 1 H) 4.41 (d, J = 7.26 Hz, 1 H) 4.98 (d, J = 4.59 Hz, 1 H) 5.11 (dd, J = 10.70, 2.29 Hz, 1 H) 5.78 (s, 1 H) |
| 285 | (structure) | 956.8 | (500 MHz): 0.86 (t, J = 7.26 Hz, 3 H) 1.05-1.26 (m, 22 H) 1.38 (s, 3 H) 1.40 (s, 3 H) 1.48-2.15 (m, 12 H) 2.21 (s, 6 H) 2.29 (s, 6 H) 2.35 (s, 3 H) 2.40-2.67 (m, 7 H) 2.71-2.93 (m, 6 H) 2.94-2.98 (m, 3 H) 3.18 (dd, J = 10.32, 7.26 Hz, 1 H) 3.28 (s, 3 H) 3.44-3.49 (m, 1 H) 3.65 (d, J = 7.26 Hz, 1 H) 3.69 (s, 1 H) 3.77 (d, J = 8.41 Hz, 1 H) 4.09 (q, J = 6.50 Hz, 1 H) 4.41 (d, J = 7.26 Hz, 1 H) 4.98 (d, J = 4.59 Hz, 1 H) 5.11 (dd, J = 10.51, 2.10 Hz, 1 H) 5.78 (s, 1 H) |
| 286 | (structure) | 970.8 | (500 MHz): 0.86 (t, J = 7.40 Hz, 3 H) 1.08 (d, J = 7.40 Hz, 3 H) 1.11 (d, J = 7.13 Hz, 3 H) 1.14 (d, J = 6.58 Hz, 3 H) 1.16 (s, 3 H) 1.17 (d, J = 6.58 Hz, 3 H) 1.19-1.27 (m, 7 H) 1.38 (s, 3 H) 1.40 (s, 3 H) 1.46-2.17 (m, 18 H) 2.20-2.31 (m, 13 H) 2.36 (s, 3 H) 2.37-2.57 (m, 5 H) 2.63-2.72 (m, 1 H) 2.78-2.91 (m, 3 H) 2.96 (s, 3 H) 3.01-3.10 (m, 1 H) 3.18 (dd, J = 10.15, 7.13 Hz, 1 H) 3.28 (s, 3 H) 3.36-3.51 (m, 2 H) 3.64 (d, J = 7.40 Hz, 1 H) 3.69 (s, 1 H) 3.79 (d, J = 7.95 Hz, 1 H) 4.09 (q, J = 6.49 Hz, 1 H) 4.40 (d, J = 7.13 Hz, 1 H) 4.99 (d, J = 4.66 Hz, 1 H) 5.10 (dd, J = 10.56, 2.33 Hz, 1 H) 5.78 (s, 1 H) |
| 287 | (structure) | 943.7 | (500 MHz): 0.86 (t, J = 7.26 Hz, 3 H) 1.07 (d, J = 7.26 Hz, 3 H) 1.11 (d, J = 7.26 Hz, 3 H) 1.12-1.27 (m, 16 H) 1.40 (s, 3 H) 1.38 (s, 3 H) 1.47-1.58 (m, 1 H) 1.64-1.75 (m, 2 H) 1.77-1.91 (m, 4 H) 1.91-2.06 (m, 3 H) 2.11 (d, J = 14.52 Hz, 1 H) 2.30 (s, 6 H) 2.35 (s, 3 H) 2.40-2.89 (m, 9 H) 2.79-2.91 (m, 4 H) 2.96 (s, 3 H) 3.18 (dd, J = 10.32, 7.26 Hz, 1 H) 3.27 (s, 3 H) 3.28 (s, 3 H) 3.42-3.50 (m, 1 H) 3.65 (d, J = 7.26 Hz, 1 H) 3.69 (s, 1 H) 3.77 (d, J = 8.41 Hz, 1 H) 3.89-3.95 (m, 1 H) 4.10 (q, J = 6.24 Hz, 1 H) 4.41 (d, J = 7.26 Hz, 1 H) 4.98 (d, J = 4.59 Hz, 1 H) 5.11 (dd, J = 10.51, 2.10 Hz, 1 H) 5.77 (s, 1 H) |
| 288 | (structure) | 957.7 | (500 MHz): 0.86 (t, J = 7.40 Hz, 3 H) 1.07 (d, J = 7.40 Hz, 3 H) 1.11 (d, J = 6.86 Hz, 3 H) 1.13-1.26 (m, 16 H) 1.38 (s, 3 H) 1.40 (s, 3 H) 1.48-2.11 (m, 14 H) 2.17-2.24 (m, 1 H) 2.29 (s, 6 H) 2.36 (s, 3 H) 2.37-2.47 (m, 2 H) 2.49-2.66 (m, 4 H) 2.79-2.92 (m, 3 H) 2.96 (s, 3 H) 3.00-3.07 (m, 1 H) 3.14-3.20 (m, 2 H) 3.26-3.30 (m, 4 H) 3.33 (s, 3 H) 3.36-3.41 (m, 1 H) 3.42-3.49 (m, 1 H) 3.66 (d, J = 7.13 Hz, 1 H) 3.69 (s, 1 H) 3.77 (d, J = 8.23 Hz, 1 H) 4.09 (q, J = 6.30 Hz, 1 H) 4.41 (d, J = 7.40 Hz, 1 H) 4.99 (d, J = 4.11 Hz, 1 H) 5.11 (dd, J = 10.56, 2.33 Hz, 1 H) 5.77 (s, 1 H) |

TABLE 6-continued

| | | | |
|---|---|---|---|
| 289 | [structure: pyrrolidine with 2-methyl substituent, connected via N(CH3)CH2CH2 linker] | 927.8 | (500 MHz): 0.86 (t, J = 7.45 Hz, 3 H) 1.05-1.19 (m, 18 H) 1.19-1.26 (m, 7 H) 1.35- 1.46 (m, 7 H) 1.52 (dd, J = 10.51, 7.07 Hz, 1 H) 1.62-2.18 (m, 13 H) 2.29 (s, 6 H) 2.30-2.38 (m, 4 H) 2.39-2.47 (m, 1 H) 2.49-2.60 (m, 2 H) 2.63-2.73 (m, 1 H) 2.78-2.94 (m, 5 H) 2.94-2.98 (m, 3 H) 3.12-3.22 (m, 2 H) 3.28 (s, 3 H) 3.42-3.51 (m, 2 H) 3.62-3.66 (m, 1 H) 3.69 (s, 1 H) 3.78 (d, J = 8.79 Hz, 1 H) 4.09 (q, J = 6.50 Hz, 1 H) 4.40 (d, J = 7.26 Hz, 1 H) 4.99 (d, J = 4.97 Hz, 1 H) 5.11 (dd, J = 10.70, 2.29 Hz, 1 H) 5.76 (s, 1 H) |
| 290 | [structure: pyrrolidine with 2-methyl substituent (opposite stereochemistry), connected via N(CH3)CH2CH2 linker] | 927.8 | (500 MHz): 0.86 (t, J = 7.40 Hz, 3 H) 1.04-1.26 (m, 25 H) 1.38 (s, 3 H) 1.40 (s, 3 H) 1.48-1.58 (m, 1 H) 1.63-2.21 (m, 15 H) 2.29 (s, 6 H) 2.36 (s, 3 H) 2.41-2.48 (m, 1 H) 2.50-2.58 (m, 1 H) 2.65 (t, J = 6.72 Hz, 2 H) 2.77-2.94 (m, 4 H) 2.96 (s, 3 H) 3.13-3.21 (m, 2 H) 3.28 (s, 3 H) 3.42-3.51 (m, 1 H) 3.66 (d, J = 7.40 Hz, 1 H) 3.69 (s, 1 H) 3.77 (d, J = 8.50 Hz, 1 H) 4.09 (q, J = 6.31 Hz, 1 H) 4.41 (d, J = 7.40 Hz, 1 H) 4.98 (d, J = 4.11 Hz, 1 H) 5.11 (dd, J = 10.56, 2.33 Hz, 1 H) 5.78 (s, 1 H) |
| 291 | [structure: pyrrolidine with =N-OCH3 oxime substituent, connected via N(CH3)CH2CH2 linker] | 956.7 | (500 MHz): 0.83-0.89 (m, 3 H) 1.06-1.29 (m, 22 H) 1.36-1.42 (m, 6 H) 1.47- 1.58 (m, 1 H) 1.64-2.15 (m, 9 H) 2.28-2.32 (m, 6 H) 2.37 (s, 3 H) 2.41-2.90 (m, 12 H) 2.94-2.97 (m, 3 H) 3.16-3.37 (m, 6 H) 3.41-3.50 (m, 1 H) 3.63-3.72 (m, 2 H) 3.75-3.85 (m, 4 H) 4.10 (q, J = 6.12 Hz, 1 H) 4.37-4.44 (m, 1 H) 4.97 (d, J = 4.66 Hz, 1 H) 5.11 (dd, J = 10.56, 2.33 Hz, 1 H) 5.75-5.79 (m, 1 H) |
| 292 | [structure: pyrrolidine with 2-ethyl substituent, connected via N(CH3)CH2CH2 linker] | 941.7 | (500 MHz): 0.83-0.92 (m, 6 H) 1.07 (d, J = 7.64 Hz, 3 H) 1.11 (d, J = 6.88 Hz, 3 H) 1.13. 1.26 (m, 16 H) 1.34-1.47 (m, 7 H) 1.47-1.58 (m, 1 H) 1.61-2.21 (m, 16 H) 2.29 (s, 6 H) 2.34-2.37 (m, 3 H) 2.40-2.69 (m, 4 H) 2.79-2.97 (m, 7 H) 3.18 (dd, J = 10.32, 7.26 Hz, 2 H) 3.28 (s, 3 H) 3.36-3.50 (m, 2 H) 3.62-3.70 (m, 2 H) 3.75-3.81 (m, 1 H) 4.05-4.12 (m, 1 H) 4.38-4.43 (m, 1 H) 4.99 (d, J = 4.97 Hz, 1 H) 5.08-5.13 (m, 1 H) 5.76 (s, 1 H) |
| 293 | [structure: 2,5-dimethylpyrrolidine connected via N(CH3)CH2CH2 linker] | 941.7 | (500 MHz): 0.86 (t, J = 7.45 Hz, 3 H) 1.05-1.28 (m, 28 H) 1.33-1.42 (m, 7 H) 1.48- 1.58 (m, 1 H) 1.63-2.08 (m, 11 H) 2.29 (s, 6 H) 2.35 (s, 3 H) 2.40-2.47 (m, 1 H) 2.50-2.68 (m, 7 H) 2.79-2.91 (m, 3 H) 2.96 (s, 3 H) 3.18 (dd, J = 10.32, 7.26 Hz, 2 H) 3.28 (s, 3 H) 3.38-3.48 (m, 2 H) 3.64 (d, J = 7.26 Hz, 1 H) 3.69 (s, 1 H) 3.79 (d, J = 8.41 Hz, 1 H) 4.09 (q, J = 6.12 Hz, 1 H) 4.40 (d, J = 7.26 Hz, 1 H) 4.99 (d, J = 4.97 Hz, 1 H) 5.11 (dd, J = 10.32, 2.29 Hz, 1 H) 5.76 (s, 1 H) |
| 294 | [structure: 2,2-dimethylpyrrolidine connected via N(CH3)CH2CH2 linker] | 941.7 | (500 MHz): 0.88 (t, J = 7.40 Hz, 3 H) 0.95-1.00 (m, 6 H) 1.06-1.26 (m, 22 H) 1.38 (s, 3 H) 1.40 (s, 3 H) 1.48-2.10 (m, 13 H) 2.29 (s, 6 H) 2.35 (s, 3 H) 2.38-2.90 (m, 10 H) 2.96 (s, 3 H) 3.18 (dd, J = 10.28, 7.27 Hz, 1 H) 3.28 (s, 3 H) 3.42-3.50 (m. 1 H) 3.65 (d, J = 7.40 Hz, 1 H) 3.69 (s, 1 H) 3.78 (d, J = 8.78 Hz, 1 H) 4.08 (q, J = 6.31 Hz, 1 H) 4.41 (d, J = 7.40 Hz, 1 H) 4.99 (d, J = 4.39 Hz, 1 H) 5.11 (dd, J = 10.56, 2.33 Hz, 1 H) 5.77 (s, 1 H) |
| 295 | [structure: 2-methoxybenzenesulfonamide linked via NHCH2CH2N(CH3) group] | 1029.5 | (600 MHz): 0.86 (t, J = 7.34 Hz, 3 H) 1.01-1.27 (m, 22 H) 1.38 (s, 3 H) 1.40 (s, 3 H) 1.49-2.09 (m, 9 H) 2.18 (s, 3 H) 2.28 (s, 6 H) 2.38-3.03 (m, 11 H) 3.15-3.19 (m, 1 H) 3.28 (s, 3 H) 3.38-3.44 (m, 2 H) 3.61 (d, J = 7.79 Hz, 1 H) 3.68 (s, 1 H) 3.77-3.80 (m, 1 H) 4.00 (d, J = 6.42 Hz, 1 H) 4.12 (q, J = 6.42 Hz, 1 H) 4.37 (d, J = 7.34 Hz, 1 H) 4.96-5.00 (m, 1 H) 5.12 (s, 2 H) 5.77 (s, 1 H) 7.06 (d, J = 8.25 Hz, 1 H) 7.10 (m, 1 H) 7.53-7.58 (m, 1 H) 7.89-7.92 (m, 1 H) |
| 296 | [structure: methanesulfonamide linked via NHCH2CH2N(CH3) group] | 937.6 | (600 MHz): 0.86 (t, J = 7.57 Hz, 2 H) 1.06-1.27 (m, 22 H) 1.38 (s, 3 H) 1.40 (s, 3 H) 1.48-1.92 (m, 7 H) 2.06 (d, J = 15.13 Hz, 1 H) 2.14 (d, J = 14.67 Hz, 1 H) 2.29 (s, 6 H) 2.35 (s, 3 H) 2.39-2.91 (m, 6 H) 2.95 (s, 3 H) 2.98 (s, 3 H) 3.15-3.25 (m, 3 H) 3.30 (s, 3 H) 3.39-3.45 (m, 2 H) 3.59 (d, J = 7.79 Hz, 1 H) 3.68 (s, 1 H) 3.80 (s, 1 H) 4.18 (q, J = 6.27 Hz, 1 H) 4.37 (d, J = 7.34 Hz, 1 H) 4.76-4.80 (m, 1 H) 4.96 (d, J = 5.04 Hz, 1 H) 5.10 (dd, J = 10.55, 2.29 Hz, 1 H) 5.77 (s, 1 H) |
| 297 | [structure: isothiazolidine-1,1-dioxide (cyclic sulfonamide) linked via CH2CH2N(CH3) group] | 963.5 | (600 MHz): 0.86 (t, J = 7.57 Hz, 2 H) 1.05-1.26 (m, 22 H) 1.38 (s, 3 H) 1.39-1.41 (m, 3 H) 1.49-2.11 (m, 9 H) 2.29 (s, 6 H) 2.33-2.45 (m, 6 H) 2.50-2.92 (m, 5 H) 2.95 (s, 3 H) 3.12-3.21 (m, 4 H) 3.26-3.33 (m, 5 H) 3.39-3.47 (m, 2 H) 3.61-3.64 (m, 1 H) 3.68 (s, 1 H) 3.79 (d, J = 8.50 Hz, 1 H) 4.11 (q, J = 6.27 Hz, 1 H) 4.39 (d, J = 7.34 Hz, 1 H) 4.99 (d, J = 5.04 Hz, 1 H) 5.10 (dd, J = 10.77, 2.52 Hz, 1 H) 5.76 (s, 1 H) |

TABLE 6-continued

| | | | |
|---|---|---|---|
| 298 | [structure] | 943.8 | (600 MHz): 0.86 (t, J = 7.34 Hz, 3 H) 9.90 (t, J = 7.34 Hz, 3 H) 1.01 (t, J = 7.11 Hz, 3 H) 1.07 (d, J = 7.34 Hz, 3 H) 1.11 (d, J = 6.88 Hz, 3 H) 1.14 (d, J = 6.42 Hz, 3 H) 1.15 (s, 3 H) 1.24 (d, J = 7.79 Hz, 3 H) 1.24 (d, J = 11.46 Hz, 3 H) 1.24 (d, J = 6.88 Hz, 3 H) 1.16-1.32 (m, 4 H) 1.38 (s, 3 H) 1.40 (s, 3 H) 1.36-1.91 (m, 9 H) 2.04 (s, 3 H) 2.29 (s, 6 H) 2.34 (s, 3 H) 2.36-2.64 (m, 8 H) 2.82 (s, 3 H) 2.96 (s, 3 H) 3.15-3.20 (m, 1 H) 3.28 (s, 3 H) 3.40 (s, 1 H) 3.44-3.49 (m, 1 H) 3.65-3.67 (m, 1 H) 3.69 (s, 1 H) 3.77-3.79 (m, 1 H) 4.06-4.10 (m, 1 H) 4.41 (d, J = 7.34 Hz, 1 H) 4.98-5.01 (m, 1 H) 5.08-5.13 (m, 1 H) 5.76 (s, 1 H) |
| 299 | [structure] | 915.7 | (400 MHz): 0.86 (t, J = 7.3 Hz, 3 H) 1.01-1.26 (m, 25 H) 1.38 (s, 3 H) 1.40 (s, 3 H) 1.44-1.92 (m, 8 H) 1.96 (dd, J = 14.9, 4.9, 1 H) 2.03 (d, J = 15.1 Hz, 1 H) 2.09 (d, J = 14.6 Hz, 1 H) 2.29 (s, 6 H) 2.34 (s, 3 H) 2.39-2.65 (m, 10 H) 2.77-2.92 (m, 3 H) 2.96 (s, 3 H) 3.18 (dd, J = 10.3, 7.3 Hz 1 H) 3.28 (s, 3 H) 3.38-3.52 (m, 2 H) 3.66 (d, J = 7.3 Hz, 1 H) 3.69 (s, 1 H) 3.78 (d, J = 8.3 Hz, 1 H) 4.09 (q, J = 6.3 Hz, 1 H) 4.41 (d, J = 7.3 Hz, 1 H) 4.99 (d, J = 4.4 Hz, 1 H) 5.11 (dd, J = 10.7, 2.2 Hz, 1 H) 5.77 (s, 1 H) |
| 300 | [structure] | 913.7 | (400 MHz): 0.86 (t, J = 7.4 Hz, 3 H) 1.08 (d, J = 6.3 Hz, 3 H) 1.11 (d, J = 7.1 Hz, 3 H) 1.13-1.28 (m, 16 H) 1.38 (s, 3 H) 1.40 (s, 3H) 1.47-1.91 (m, 9 H) 1.95 (dd, J = 14.8, 4.8 Hz, 1 H) 2.02 (d, J = 14.6 Hz, 1 H) 2.14 (d, J = 14.9 Hz, 1 H) 2.29 (s, 6 H) 3.36 (s, 3 H) 2.39-2.72 (m, 9 H) 2.75-2.92 (m, 3 H) 2.96 (s, 3 H) 3.18 (dd, J = 10.4, 7.2 Hz, 1 H) 3.28 (s, 3 H) 3.37-3.52 (m, 2 H) 3.66 (d, J = 7.3 Hz, 1 H) 3.69 (s, 1 H) 3.77 (d, J = 8.5 Hz, 1 H) 4.10 (q, J = 6.3 Hz, 1 H) 4.41 (d, J = 7.3 Hz, 1 H) 4.98 (d, J = 4.2 Hz, 1 H) 5.11 (dd, J = 10.5, 2.2 Hz, 1 H) 5.77 (s, 1 H) |
| 301 | [structure] | 901.7 | (400 MHz): 0.86 (t, J = 7.4 Hz, 3 H) 1.00 (d, J = 7.1 Hz, 3 H) 1.01 (d, J = 7.3 Hz, 3 H) 1.08 (d, J = 7.6 Hz, 1 H) 1.10-1.27 (m, 19 H) 1.38 (s, 3 H) 1.40 (s, 3 H) 1.47-1.58 (m, 1 H) 1.61-1.99 (m, 8 H) 2.04 (d, J = 14.4 Hz, 1 H) 2.28 (s, 6 H) 2.37 (d, J = 13.4 Hz, 1 H) 2.40-2.58 (m, 8 H) 2.61-2.69 (m, 2 H) 2.76-2.93 (m, 3 H) 2.96 (s, 3 H) 3.18 (dd, J = 10.3, 7.3 Hz, 1 H) 3.29 (s, 3 H) 3.49-3.58 (m, 1 H ) 3.64 (d, J = 7.3 Hz, 1 H) 3.69 (s, 1 H) 3.79 (d, J = 8.1 Hz, 1 H) 4.23 (q, J = 6.3 Hz, 1H) 4.41 (d, J = 7.3 Hz, 1 H) 4.98 (d, J = 4.4 Hz, 1 H) 5.11 (dd, J = 10.7, 2.2 Hz, 1 H) 5.77 (s, 1 H) |
| 302 | [structure] | 899.6 | (400 MHz): 0.86 (t, J = 7.4 Hz, 3 H) 1.05-1.27 (m, 22 H) 1.38 (s, 3 H) 1.40 (s, 3 H) 1.46-1.98 (m, 12 H) 2.04 (d, J = 14.6 Hz, 1 H) 2.29 (s, 6 H) 2.39-2.62 (m, 8 H) 2.70-2.92 (m, 5 H) 2.95 (s, 3 H) 3.18 (dd, J = 10.0, 7.3 Hz, 1 H) 3.28 (s, 3 H) 3.51-3.60 (m, 1 H) 3.64 (d, J = 7.3 Hz, 1 H) 3.69 (s, 1H) 3.79 (d, J = 8.5 Hz, 1 H) 4.25 (q, J = 6.2 Hz, 1 H) 4.40 (d, J = 7.1 Hz, 1 H) 4.97 (d, J = 4.6 Hz, 1 H) 5.11 (dd, J = 10.6, 2.1 Hz, 1 H) 5.77 (s, 1 H) |
| 303 | [structure] | 892.6 | (400 MHz): 0.86 (t, J = 7.3 Hz, 3 H) 1.06-1.21 (m, 24 H) 1.37 (s, 3 H) 1.40 (s, 3 H) 1.47-1.68 (m, 5 H) 1.70-1.94 (m, 6 H) 2.03 (d, J = 15.4 Hz, 1 H) 2.22-2.47 (m, 2 H) 2.51-2.57 (m, 1 H) 2.79-2.89 (m, 3 H) 2.94 (s, 3 H) 3.15 (dd, J = 10.3, 7.1 Hz, 1 H) 3.27 (s, 3 H) 3.44-3.50 (m, 1 H) 3.60 (d, J = 7.6 Hz, 1 H) 3.68 (s, 1 H) 3.72-3.83 (m, 3 H) 4.08-4.12 (m, 1 H) 4.29 (q, J = 6.0 Hz, 1H) 4.37 (d, J = 7.1 Hz, 1 H) 4.95 (d, J = 4.6 Hz, 1 H) 5.10 (dd, J = 10.5, 2.2 Hz, 1 H) 5.77 (1 H, s) 7.23-7.35 (m, 5 H) |
| 304 | [structure] | 906.6 | (400 MHz): 0.86 (t, J = 7.3 Hz, 3 H) 1.09 (d, J = 7.6 Hz, 3 H) 1.11 (d, J = 7.1 Hz, 3 H) 1.12-1.29 (m, 15 H) 1.38 (s, 3 H) 1.41 (s, 3 H) 1.47-1.94 (m, 7 H) 1.99 (dd, J = 15.1, 5.4 Hz, 1 H) 2.09 (d, J = 14.6 Hz, 1 H) 2.17 (d, J = 14.9 Hz, 1 H) 2.23 (s, 3 H) 2.30 (s, 6 H) 2.40-2.50 (m, 1 H) 2.80-2.91 (m, 2 H) 2.97 (s, 3 H) 3.01 (s, 1 H) 3.19 (dd, J = 10.1, 7.4 Hz, 1 H) 3.31 (s, 3 H) 3.39-3.49 (m, 2 H) 3.62-3.71 (m, 4 H) 3.81 (d, J = 8.1 Hz, 1 H) 4.16 (q, J = 6.1 Hz, 1 H) 4.42 (d, J = 7.3 Hz, 1 H) 4.80 (s, 1 H) 5.01 (d, J = 4.9 Hz, 1 H) 5.10 (dd, J = 10.5, 2.0 Hz, 1 H) 5.78 (1 H, s) 7.24-7.38 (m, 5 H) |
| 305 | [structure] | 922.6 | (400 MHz): 0.85 (t, J = 7.4 Hz, 3 H) 0.91 (d, J = 6.1 Hz, 3 H) 1.00-1.11 (m, 13 H) 1.13 (d, J = 6.6 Hz, 3 H) 1.20 (d, J = 7.3 Hz, 3 H) 1.24 (s, 1 H) 1.33 (s, 3 H) 1.39 (s, 3 H) 1.44-1.92 (m, 13 H) 1.94-1.98 (m, 2 H) 2.17-2.27 (m, 7 H) 2.47-2.57 (m, 2 H) 2.78-2.88 (m, 2 H) 2.94 (s, 3 H) 3.04-3.11 (m, 2 H) 3.25 (s, 3 H) 3.35 (s, 1 H) 3.55 (d, J = 7.1 Hz, 1 H) 3.68 (s, 1 H) 3.75 (d, J = 8.8 Hz, 1 H) 3.86 (s, 3 H) 4.06 (q, J = 6.3 Hz, 1 H) 4.33 (d, J = 7.3 Hz, 1 H) 4.96 (t, J = 2.9 Hz, 1 H) 5.10 (dd, J = 10.7, 2.2 Hz, 1 H) 5.76 (s, 1 H) 6.86-6.94 (m, 2 H) 7.18-7.26 (m, 2 H) |

TABLE 6-continued

| 306 | 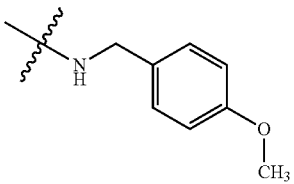 [SMILES: *NCc1ccc(OC)cc1] | 922.7 | (400 MHz): 0.86 (t, J = 7.3 Hz, 3 H) 1.04-1.17 (m, 20 H) 1.20 (d, J = 7.6 Hz, 3 H) 1.37 (s, 3 H) 1.40 (s, 3 H) 1.48-1.94 (m, 7 H) 2.02 (d, J = 14.6 Hz, 1 H) 2.27 (s, 6 H) 2.33-2.44 (m, 2 H) 2.49-2.58 (m, 1 H) 2.79-2.89 (m, 3 H) 2.94 (s, 3 H) 3.16 (dd, J = 10.1, 7.2 Hz, 1 H) 3.27 (s, 3 H) 3.45-3.54 (m, 1 H) 3.60 (d, J = 7.6 Hz, 1 H) 3.62-3.81 (m, 8 H) 4.18 (s, 1 H) 4.28 (q, J = 6.3 Hz, 1 H) 4.38 (d, J = 7.1 Hz, 1 H) 4.95 (d, J = 4.9 Hz, 1 H) 5.10 (dd, J = 10.6, 2.1 Hz, 1 H) 5.77 (s, 1H) 8.86 (d, J = 8.3 Hz, 2 H) 7.18 (d, J = 8.6 Hz, 2 H) |
| --- | --- | --- | --- |
| 307 | 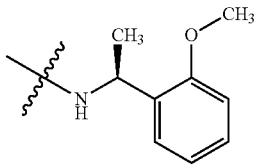 [SMILES: *N[C@@H](C)c1ccccc1OC] | 936.6 | (400 MHz): 0.85 (t, J = 7.4 Hz, 3 H) 0.99 (d, J = 6.1 Hz, 3 H) 1.02-1.17 (m, 18 H) 1.20 (d, J = 7.3 Hz, 3 H) 1.33-1.42 (m, 9 H) 1.46-1.93 (m, 7 H) 1.93-2.01 (m, 2 H) 2.05 (d, J = 13.7 Hz, 1 H) 2.24 (s, 6 H) 2.26-2.35 (m, 1 H) 2.53 (t, J = 7.7 Hz, 1 H) 2.76-2.90 (m, 3 H) 2.94 (s, 3 H) 3.12 (dd, J = 10.3, 7.3 Hz, 1 H) 3.25 (s, 3 H) 3.27-3.40 (m, 2 H) 3.58 (d, J = 7.3 Hz, 1 H) 3.68 (s, 1 H) 3.77 (d, J = 8.5 Hz, 1 H) 4.36 (d, J = 7.3 Hz, 1 H) 4.96 (d, J = 2.7 Hz, 1 H) 5.10 (dd, J = 10.5, 2.2 Hz, 1 H) 5.77 (s, 1 H) 6.84-6.95 (m, 2 H) 7.13-7.25 (m, 2 H) |
| 308 | 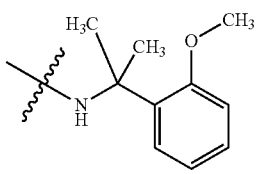 [SMILES: *NC(C)(C)c1ccccc1OC] | 950.6 | (400 MHz): 0.85 (t, J = 7.4 Hz, 3 H) 0.99 (d, J = 6.1 Hz, 3 H) 1.02-1.17 (m, 16 H) 1.20 (d, J = 7.3 Hz, 3 H) 1.33-1.42 (m, 9 H) 1.46-1.93 (m, 7 H) 1.93-2.01 (m, 2 H) 2.05 (d, J = 13.7 Hz, 1 H) 2.24 (s, 6 H) 2.26-2.35 (m, 1 H) 2.53 (t, J = 7.7 Hz, 1 H) 2.76-2.90 (m, 3 H) 2.94 (s, 3 H) 3.12 (dd, J = 10.3, 7.3 Hz, 1 H) 3.25 (s, 3 H) 3.27-3.40 (m, 2 H) 3.58 (d, J = 7.3 Hz, 1 H) 3.68 (s, 1 H) 3.77 (d, J = 8.5 Hz, 1 H) 4.35 (d, J = 7.3 Hz, 1 H) 4.96 (d, J = 2.7 Hz, 1 H) 5.10 (dd, J = 10.5, 2.2 Hz, 1 H) 5.77 (s, 1 H) 6.84-6.95 (m, 2 H) 7.13-7.25 (m, 2 H) |
| 309 | 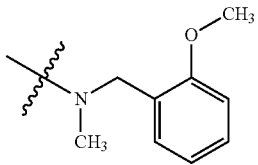 [SMILES: *N(C)Cc1ccccc1OC] | 936 | (400 MHz): 0.86 (t, J = 7.32 Hz, 3 H) 1.09 (d, J = 7.57 Hz, 3 H) 1.11 (d, J = 7.32 Hz, 3 H) 1.14 (d, J = 6.59 Hz, 3 H) 1.17-1.26 (m, 13 H) 1.38 (s, 3 H) 1.40 (s, 3 H) 1.46-1.93 (m, 7 H) 1.98-2.16 (m, 3 H) 2.18 (s, 3 H) 2.30 (s, 6 H) 2.40-2.59 (m, 2 H) 2.79-2.95 (m, 3 H) 2.97 (s, 3 H) 3.19 (dd, J = 9.77, 7.08 Hz, 1 H) 3.31 (s, 3 H) 3.38-3.61 (m, 2 H) 3.66 (d, J = 7.57 Hz, 1 H) 3.69 (s, 1 H) 3.80 (d, J = 8.30 Hz, 1 H) 3.86 (s, 3 H) 4.14 (q, J = 6.83 Hz, 1 H) 4.42 (d, J = 7.32 Hz, 1 H) 5.02 (d, J = 3.91 Hz, 1 H) 5.07-5.15 (m, 1 H) 5.78 (s, 1 H) 6.86-6.93 (m, 1 H) 7.16-7.20 (m, 1 H) 7.26-7.30 (m, 1 H) |
| 310 | 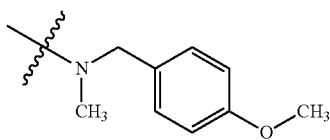 [SMILES: *N(C)Cc1ccc(OC)cc1] | 936 | (400 MHz): 0.86 (t, J = 7.32 Hz, 3 H) 1.08 (d, J = 7.57 Hz, 3 H) 1.11 (d, J = 7.08 Hz, 3 H) 1.14 (d, J = 6.59 Hz, 3 H) 1.17 (s, 3 H) 1.17-1.26 (m, 1 H) 1.22 (d, J = 6.10 Hz, 9 H) 1.38 (s, 3 H) 1.41 (s, 3 H) 1.98 (dd, J = 14.89, 5.13 Hz, 1 H) 2.09 (d, J = 14.65 Hz, 1 H) 2.10-2.22 (m, 1 H) 2.20 (s, 3 H) 2.30 (s, 6 H) 2.40-2.60 (m, 2 H) 2.79-2.93 (m, 3 H) 2.97 (s, 3 H) 3.19 (dd, J = 10.25, 7.32 Hz, 1 H) 3.31 (s, 3 H) 3.39-3.49 (m, 2 H) 3.50-3.65 (m, 1 H) 3.65 (d, J = 7.57 Hz, 1 H) 3.69 (s, 1 H) 3.79-3.82 (m, 1 H) 3.81 (s, 3 H) 4.14 (q, J = 6.10 Hz, 1 H) 4.41 (d, J = 7.32 Hz, 1 H) 5.00 (d, J = 4.88 Hz, 1 H) 5.11 (dd, J = 10.50, 2.20 Hz, 1 H) 5.78 (s, 1 H) 6.84-6.89 (m, 2 H) 7.17-7.22 (m, 2 H) |
| 311 | 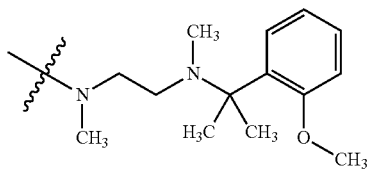 [SMILES: *N(C)CCN(C)C(C)(C)c1ccccc1OC] | 1021.7 | (500 MHz): 0.86 (t, J = 7.45 Hz, 3 H) 1.04-1.28 (m, 22 H) 1.37-1.46 (m, 12 H) 1.49- 1.58 (m, 1 H) 1.62-2.07 (m, 9 H) 2.18 (s, 3 H) 2.23-2.33 (m, 9 H) 2.40-2.57 (m, 5 H) 2.78-2.91 (m, 3 H) 2.96 (s, 3 H) 3.18 (dd, J = 10.32, 7.26 Hz, 1 H) 3.28 (s, 3 H) 3.40-3.48 (m, 1 H) 3.64 (d, J = 7.26 Hz, 1 H) 3.69 (s, 1 H) 3.76-3.81 (m, 4 H) 4.08 (q, J = 6.37 Hz, 1 H) 4.40 (d, J = 7.26 Hz, 1 H) 4.99 (d, J = 4.97 Hz, 1 H) 5.11 (dd, J = 10.70, 2.29 Hz, 1 H) 5.77 (s, 1 H) 6.84-6.91 (m, 2 H) 7.14-7.21 (m, 1 H) 7.61 (m, 1 H) |
| 312 | 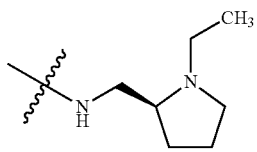 [SMILES: *NC[C@@H]1CCCN1CC] | 913.6 | (600 MHz): 0.86 (t, J = 7.34 Hz, 3 H) 1.06-1.23 (m, 25 H) 1.38 (s, 3 H) 1.39-1.41 (m, 3 H) 1.48-2.20 (m, 15 H) 2.29 (s, 6 H) 2.39-2.93 (m, 10 H) 2.95 (s, 3 H) 3.16-3.20 (m, 1 H) 3.29 (s, 3 H) 3.50-3.55 (m, 1 H) 3.64 (d, J = 7.79 Hz, 1 H) 3.69 (s, 1 H) 3.80 (d, J = 8.25 Hz, 1 H) 4.24 (q, J = 6.42 Hz, 1 H) 4.40 (d, J = 7.34 Hz, 1 H) 4.97 (d, J = 4.58 Hz, 1 H) 5.11 (dd, J = 10.55, 2.29 Hz, 1 H) 5.77 (s, 1 H) |

TABLE 6-continued

| | | | |
|---|---|---|---|
| 313 | (structure: -NH-CH2CH2CH2-N(morpholine)) | 929.7 | (600 MHz): 0.86 (t, J = 7.34 Hz, 3 H) 1.06-1.26 (m, 22 H) 1.38 (s, 3 H) 1.40 (s, 3 H) 1.48-2.08 (m, 10 H) 2.29 (s, 6 H) 2.34-2.70 (m, 10 H) 2.79-2.90 (m, 3 H) 2.95 (s, 3 H) 3.16-3.21 (m, 1 H) 3.29 (s, 3 H) 3.40 (s, 1 H) 3.51-3.59 (m, 1 H) 3.62-3.66 (m, 1 H) 3.66-3.73 (m, 5 H) 3.77-3.81 (m, 1 H) 4.25 (q, J = 6.11 Hz, 1 H) 4.40 (d, J = 7.34 Hz, 1 H) 4.52 (br, s, 1 H) 4.97 (d, J = 5.04 Hz, 1 H) 5.11 (dd, J = 10.32, 2.06 Hz, 1 H) 5.77 (s, 1 H) |
| 314 | (structure: -N(CH3)-CH2CH2CH2-N(morpholine)) | 943.8 | (600 MHz): 0.86 (t, J = 7.57 Hz, 3 H) 1.04-1.28 (m, 22 H) 1.38 (s, 3 H) 1.40 (s, 3 H) 1.49-2.06 (m, 11 H) 2.25-2.62 (m, 19 H) 2.78-2.91 (m, 3 H) 2.96 (s, 3 H) 3.15-3.21 (m, 1 H) 3.28 (s, 3 H) 3.38 (br. s, 1 H) 3.41-3.49 (m, 1 H) 3.65 (d, J = 7.34 Hz, 1 H) 3.68-3.74 (m, 5 H) 3.78 (d, J = 7.79 Hz, 1 H) 4.08 (q, J = 6.42 Hz, 1 H) 4.41 (d, J = 7.34 Hz, 1 H) 4.98 (d, J = 4.58 Hz, 1 H) 5.11 (dd, J = 10.77, 2.52 Hz, 1 H) 5.77 (s, 1 H) |
| 315 | (structure with CH3, CH3, N(CH3)2) | 887.7 | (500 MHz): 0.86 (t, J = 7.45 Hz, 3 H) 0.92-1.01 (m, 3 H) 1.05-1.27 (m, 22 H) 1.35-1.44 (m, 6 H) 1.48-2.10 (m, 9 H) 2.16-2.33 (m, 13 H) 2.40-3.04 (m, 10 H) 3.18 (dd, J = 10.32, 7.26 Hz, 1 H) 3.29 (s, 3 H) 3.48-3.59 (m, 1 H) 3.61-3.71 (m, 2 H) 3.74-3.83 (m, 1 H) 4.17-4.31 (m, 1 H) 4.37-4.45 (m, 1 H) 4.94-5.01 (m, 1 H) 5.07-5.15 (m, 1 H) 5.78 (s, 1 H) |
| 316 | (structure with CH3, CH3, N-CH3, N(CH3)2) | 901.8 | (500 MHz): 0.83-0.95 (m, 6 H) 1.05-1.27 (m, 22 H) 1.35-1.43 (m, 6 H) 1.53 (td, J = 7.06, 3.70 Hz, 1 H) 1.62-2.07 (m, 9 H) 2.19-2.37 (m, 16 H) 2.42-2.58 (m, 2 H) 2.77-2.91 (m, 4 H) 2.96 (s, 3 H) 3.16-3.22 (m, 1 H) 3.26-3.31 (m, 3 H) 3.46-3.57 (m, 1 H) 3.63-3.82 (m, 3 H) 4.08-4.14 (m, 1 H) 4.39-4.48 (m, 1 H) 4.95-5.02 (m, 1 H) 5.08-5.15 (m, 1 H) 5.74-5.81 (m, 1 H) |
| 317 | (structure with NH, N-Et, CH3, 2-methoxyphenyl) | 1007.7 | (500 MHz): 0.86 (t, J = 7.45 Hz, 3 H) 0.96 (t, J = 6.88 Hz, 3 H) 1.05-1.24 (m, 22 H) 1.28 (d, J = 5.50 Hz, 3 H) 1.38 (s, 3 H) 1.40 (s, 3 H) 1.48-1.65 (m, 2 H) 1.70-2.07 (m, 6 H) 2.25-2.32 (m, 7 H) 2.38-2.66 (m, 8 H) 2.78-2.91 (m, 3 H) 2.96 (s, 3 H) 3.17 (dd, J = 10.32, 7.26 Hz, 1 H) 3.28 (s, 3 H) 3.44-3.52 (m, 1 H) 3.65 (d, J = 7.26 Hz, 1 H) 3.69 (s, 1 H) 3.76-3.83 (m, 4 H) 4.15-4.23 (m, 1 H) 4.33-4.43 (m, 2 H) 4.98 (d, J = 4.59 Hz, 1 H) 5.11 (dd, J = 10.70, 2.29 Hz, 1 H) 5.77 (s, 1 H) 6.86 (d, J = 8.03 Hz, 1 H) 6.93 (t, J = 7.07 Hz, 1 H) 7.18-7.23 (m, 1 H) 7.31 (d, J = 7.26 Hz, 1 H) |
| 318 | (structure with N-CH3, N-CH3, C(CH3)2, 2-methoxypyridyl) | 1022.7 | (500 MHz): 0.86 (t, J = 7.40 Hz, 3 H) 1.05-1.27 (m, 22 H) 1.35-1.44 (m, 12 H) 1.48-1.58 (m, 1 H) 1.62-2.08 (m, 9 H) 2.19 (s, 3 H) 2.26 (s, 3 H) 2.29 (s, 6 H) 2.36-2.58 (m, 5 H) 2.77-2.91 (m, 3 H) 2.96 (s, 3 H) 3.18 (dd, J = 10.15, 7.13 Hz, 1 H) 3.29 (s, 3 H) 3.39-3.48 (m, 1 H) 3.64 (d, J = 7.40 Hz 1 H) 3.69 (s, 1 H) 3.79 (d, J = 8.50 Hz, 1 H) 3.92-3.93 (m, 3 H) 4.09 (q, J = 6.40 Hz, 1 H) 4.40 (d, J = 7.13 Hz, 1 H) 5.00 (d, J = 4.94 Hz, 1 H) 5.11 (dd, J = 10.56, 2.33 Hz, 1 H) 5.77 (s, 1 H) 6.82 (dd, J = 7.54, 4.80 Hz, 1 H) 7.93-8.02 (m, 2 H) |
| 319 | (structure with OH, NH, N-Et, CH3, 2-methoxyphenyl) | 1037.7 | (600 MHz): 0.86 (t, J = 7.57 Hz, 3 H) 0.94 (t, J = 7.34 Hz, 3 H) 1.03-1.24 (m, 22 H) 1.32-1.43 (m, 10 H) 1.49-2.06 (m, 9 H) 2.28 (s, 6 H) 2.36-2.57 (m, 5 H) 2.63-2.90 (m, 6 H) 2.94 (s, 3 H) 3.16 (dd, J = 10.09, 7.34 Hz, 1 H) 3.27 (s, 3 H) 3.40-3.69 (m, 5 H) 3.78 (d, J = 8.25 Hz, 1 H) 3.80-3.84 (m, 3 H) 4.23 (q, J = 6.27 Hz, 1 H) 4.36 (d, J = 7.34 Hz, 1 H) 4.44 (q, J = 6.88 Hz, 1 H) 4.95 (d, J = 5.04 Hz, 1 H) 5.10 (dd, J = 10.32, 2.52 Hz, 1 H) 5.76 (s, 1 H) 6.87-6.97 (m, 2 H) 7.22-7.30 (m, 2 H) |
| 320 | (structure with N, N-CH3, CH2CH2, N(CH3)2) | 887.6 | (600 MHz): 0.86 (t, J = 7.34 Hz, 3 H) 1.06-1.26 (m, 22 H) 1.38 (s, 3 H) 1.39-1.41 (m, 3 H) 1.49-2.05 (m, 7 H) 2.14 (d, J = 14.67 Hz, 1 H) 2.24 (s, 6 H) 2.29 (s, 6 H) 2.31-2.66 (m, 10 H) 2.79-2.91 (m, 3 H) 2.96 (s, 3 H) 3.18 (dd, J = 10.09, 7.34 Hz, 1 H) 3.28 (s, 3 H) 3.39 (s, 1 H) 3.44-3.51 (m, 1 H) 3.67 (d, J = 7.34 Hz, 1 H) 3.69 (s, 1 H) 3.77 (d, J = 8.71 Hz, 1 H) 4.10 (d, J = 6.42 Hz, 1 H) 4.41 (d, J = 7.34 Hz, 1 H) 4.98 (d, J = 4.13 Hz, 1 H) 5.11 (dd, J = 10.55, 2.29 Hz, 1 H) 5.76 (s, 1 H) |

TABLE 6-continued

| | | | |
|---|---|---|---|
| 321 | [structure] | 901.7 | (500 MHz): 0.86 (t, J = 7.45 Hz, 3 H) 1.03-1.27 (m, 25 H) 1.38 (s, 3 H) 1.40 (s, 3 H) 1.48-2.05 (m, 8 H) 2.12 (d, J = 14.52 Hz, 1 H) 2.23 (s, 3 H) 2.29 (s, 6 H) 2.34 (s, 3 H) 2.35-2.66 (m, 8 H) 2.79-2.93 (m, 3 H) 2.96 (s, 3 H) 3.18 (dd, J = 10.32, 7.26 Hz, 1 H) 3.28 (s, 3 H) 3.44-3.51 (m, 1 H) 3.66 (d, J = 7.26 Hz, 1 H) 3.69 (s, 1 H) 3.77 (d, J = 8.41 Hz, 1 H) 4.09 (q, J = 6.50 Hz, 1 H) 4.41 (d, J = 7.26 Hz, 1 H) 4.99 (d, J = 4.59 Hz, 1 H) 5.11 (dd, J = 10.51, 2.10 Hz, 1 H) 5.77 (s, 1 H) |
| 322 | [structure] | 917.7 | (600 MHz): 0.86 (t, J = 7.34 Hz, 3 H) 1.08 (d, J = 7.34 Hz, 3 H) 1.11 (d, J = 6.88 Hz, 3 H) 1.12-1.18 (m, 9 H) 1.18-1.27 (m, 7 H) 1.37 (s, 3 H) 1.40 (s, 3 H) 1.49-1.57 (m, 1 H) 1.65-1.75 (m, 2 H) 1.77-1.92 (m, 3 H) 1.93-1.99 (m, 1 H) 2.02-2.07 (m, 1 H) 2.12 (d, J = 14.67 Hz, 1 H) 2.27 (s, 3 H) 2.29 (s, 6 H) 2.32 (s, 6 H) 2.40-2.57 (m, 3 H) 2.73 (t, J = 11.46 Hz, 1 H) 2.79-2.90 (m, 3 H) 2.96 (s, 3 H) 3.09-3.14 (m, 1 H) 3.18 (dd, J = 10.09, 7.34 Hz, 1 H) 3.29 (s, 3 H) 3.40-3.47 (m, 1 H) 3.63 (d, J = 7.34 Hz, 1 H) 3.68 (s, 1 H) 3.77-3.83 (m, 2 H) 3.84-3.88 (m, 1 H) 4.12 (q, J = 6.27 Hz, 1 H) 4.40 (d, J = 7.34 Hz, 1 H) 4.98 (d, J = 5.04 Hz, 1 H) 5.11 (dd, J = 10.55, 2.29 Hz, 1 H) 5.77 (s, 1 H) |
| 323 | [structure] | 929.7 | (500 MHz): 0.86 (t, J = 7.45 Hz, 3 H) 1.02 (t, J = 7.07 Hz, 6 H) 1.05-1.18 (m, 15 H) 1.19-1.26 (m, 7 H) 1.38 (s, 3 H) 1.40 (s, 3 H) 1.48-1.57 (m, 1 H) 1.60-2.08 (m, 10 H) 2.29 (s, 6 H) 2.32 (s, 3 H) 2.38-2.60 (m, 10 H) 2.78-2.91 (m, 3 H) 2.96 (s, 3 H) 3.18 (dd, J = 10.32, 7.26 Hz, 1 H) 3.28 (s, 3 H) 3.41-3.48 (m, 1 H) 3.64 (d, J = 7.26 Hz, 1 H) 3.69 (s, 1 H) 3.79 (d, J = 8.41 Hz, 1 H) 4.10 (q, J = 6.12 Hz, 1 H) 4.40 (d, J = 7.26 Hz, 1 H) 4.98 (d, J = 4.97 Hz, 1 H) 5.11 (dd, J = 10.32, 2.29 Hz, 1 H) 5.77 (s, 1 H) |
| 324 | [structure] | 899.8 | (500 MHz): 0.86 (t, J = 7.27 Hz, 3 H) 1.05-1.25 (m, 22 H) 1.38 (s, 3 H) 1.40 (s, 3 H) 1.47-2.34 (m, 23 H) 2.38-3.01 (m, 13 H) 3.14-3.21 (m, 1 H) 3.26-3.31 (m, 3 H) 3.38-3.48 (m, 1 H) 3.62-3.65 (m, 1 H) 3.68 (s, 1 H) 3.79 (d, J = 8.50 Hz, 1 H) 4.07-4.15 (m, 1 H) 4.39 (dd, J = 7.13, 2.19 Hz, 1 H) 4.98 (d, J = 4.94 Hz, 1 H) 5.11 (dd, J = 10.70, 2.19 Hz, 1 H) 5.78 (s, 1 H) |
| 325 | [structure] | 885.8 | (500 MHz): 0.86 (t, J = 7.45 Hz, 3 H) 1.05-1.29 (m, 22 H) 1.38 (s, 3 H) 1.40 (s, 3 H) 1.48-1.57 (m, 1 H) 1.61-1.69 (m, 1 H) 1.70-2.17 (m, 10 H) 2.29 (s, 6 H) 2.31 (s, 3 H) 2.40-2.48 (m, 1 H) 2.49-2.58 (m, 1 H) 2.78-3.06 (m, 10 H) 3.18 (dd, J = 10.32, 7.26 Hz, 1 H) 3.29 (s, 3 H) 3.35-3.48 (m, 2 H) 3.61-3.65 (m, 1 H) 3.68 (s, 1 H) 3.78 (d, J = 8.41 Hz, 1 H) 4.12 (q, J = 6.50 Hz, 1 H) 4.40 (d, J = 7.26 Hz, 1 H) 4.98 (d, J = 4.97 Hz, 1 H) 5.11 (dd, J = 10.70, 2.29 Hz, 1 H) 5.80 (s, 1 H) |
| 326 | [structure] | 951.6 | (600 MHz): 0.86 (t, J = 7.34 Hz, 3 H) 1.07 (d, J = 7.79 Hz, 3 H) 1.11 (d, J = 6.88 Hz, 3 H) 1.13-1.15 (m, 6 H) 1.21 (d, J = 7.34 Hz, 3 H) 1.21 (d, J = 8.71 Hz, 3 H) 1.22 (d, J = 7.34 Hz, 3 H) 1.17-1.25 (m, 1 H) 1.38 (s, 3 H) 1.40 (s, 3 H) 1.48-1.92 (m, 6 H) 1.93-1.98 (m, 1 H) 2.03-2.08 (m, 1 H) 2.09-2.13 (m, 1 H) 2.29 (br. s, 6 H) 2.41 (s, 3 H) 2.41-2.47 (m, 1 H) 2.49-2.58 (m, 1 H) 2.83 (s, 3 H) 2.89 (s, 3 H) 2.69-2.94 (m, 5 H) 2.95 (s, 3 H) 3.15-3.28 (m, 3 H) 3.29 (s, 3 H) 3.39-3.47 (m, 2 H) 3.62 (d, J = 7.34 Hz, 1 H) 3.68 (s, 1 H) 3.79 (d, J = 8.25 Hz, 1 H) 4.09-4.15 (m, 1 H) 4.33-4.41 (m, 2 H) 4.98 (d, J = 5.04 Hz, 1 H) 5.08-5.12 (m, 1 H) 5.76 (s, 1 H) |
| 327 | [structure] | 1043.6 | (500 MHz): 0.86 (t, J = 7.40 Hz, 3 H) 1.05-1.27 (m, 22 H) 1.38 (s, 3 H) 1.40 (s, 3 H) 1.48-1.59 (m, 1 H) 1.69-2.14 (m, 8 H) 2.33 (s, 6 H) 2.40 (s, 3 H) 2.46-2.59 (m, 2 H) 2.72-2.91 (m, 7 H) 2.96 (s, 3 H) 3.16-3.38 (m, 6 H) 3.41-3.49 (m, 1 H) 3.63 (d, J = 7.68 Hz, 1 H) 3.69 (s, 1 H) 3.78 (d, J = 8.23 Hz, 1 H) 3.93 (s, 3 H) 4.11 (q, J = 6.31 Hz, 1 H) 4.40 (d, J = 7.40 Hz, 1 H) 4.98 (d, J = 4.94 Hz, 1 H) 5.11 (dd, J = 10.56, 2.33 Hz, 1 H) 5.77 (s, 1 H) 6.99-7.07 (m, 2 H) 7.49-7.56 (m, 1 H) 7.90 (dd, J = 7.82, 1.78 Hz, 1 H) |
| 328 | [structure] | 965.6 | (600 MHz): 0.86 (t, J = 7.34 Hz, 3 H) 1.07 (d, J = 7.34 Hz, 3 H) 1.10-1.25 (m, 22 H) 1.38 (s, 3 H) 1.40 (s, 3 H) 1.48-1.98 (m, 7 H) 2.03-2.13 (m, 2 H) 2.30 (br. s, 6 H) 2.40 (s, 3 H) 2.41-2.47 (m, 1 H) 2.50-2.58 (m, 1 H) 2.85 (s, 3 H) 2.70-2.93 (m, 6 H) 2.95 (s, 3 H) 3.14-3.21 (m, 1 H) 3.24-3.31 (m, 6 H) 3.39-3.46 (m, 2 H) 3.62 (d, J = 7.34 Hz, 1 H) 3.68 (s, 1 H) 3.79 (d, J = 8.25 Hz, 1 H) 4.09-4.14 (m, 1 H) 4.38 (d, J = 7.34 Hz, 1 H) 4.98 (d, J = 5.04 Hz, 1 H) 5.10 (dd, J = 10.55, 2.29 Hz, 1 H) 5.76 (s, 1 H) |

| | | | |
|---|---|---|---|
| 329 | 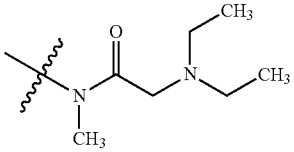 [SMILES: *N(C)C(=O)CN(CC)CC] | 929.8 | (500 MHz): 0.86 (t, J = 7.45 Hz, 3 H) 0.98-1.29 (m, 25 H) 1.34-1.42 (s, 6 H) 1.49-2.00 (m, 9 H) 2.29 (s, 6 H) 2.41-2.70 (m, 7 H) 2.76-2.84 (m, 1 H) 2.86-2.91 (m, 1 H) 2.94 (s, 3 H) 3.13-3.28 (m, 7 H) 3.31 (s, 3 H) 3.48-3.55 (m, 1 H) 3.68-3.75 (m, 4 H) 4.18-4.25 (m, 1 H) 4.41 (d, J = 7.26 Hz, 1 H) 4.48 (s, 3 H) 4.90-4.97 (m, 1 H) 5.11 (dd, J = 10.51, 2.48 Hz, 1 H) |
| 330 | 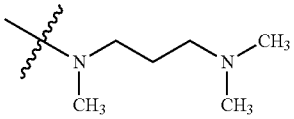 | 901.8 | (500 MHz): 0.86 (t, J = 7.40 Hz, 3 H) 1.08 (d, J = 7.68 Hz, 3 H) 1.09-1.15 (m, 9 H) 1.17 (d, J = 6.31 Hz, 3 H) 1.19-1.26 (m, 7 H) 1.38 (s, 3 H) 1.39-1.42 (m, 3 H) 1.49-1.56 (m, 1 H) 1.59-1.68 (m, 3 H) 1.70-1.93 (m, 4 H) 1.94-2.06 (m, 3 H) 2.20 (s, 6 H) 2.26-2.30 (m, 10 H) 2.39-2.60 (m, 5 H) 2.78-2.91 (m, 3 H) 2.96 (s, 3 H) 3.18 (dd, J = 10.28, 7.27 Hz, 1 H) 3.28 (s, 3 H) 3.38-3.48 (m, 2 H) 3.64 (d, J = 7.40 Hz, 1 H) 3.69 (s, 1 H) 3.78 (d, J = 8.23 Hz, 1 H) 4.09 (q, J = 6.31 Hz, 1 H) 4.40 (d, J = 7.13 Hz, 1 H) 4.98 (d, J = 4.39 Hz, 1 H) 5.11 (dd, J = 10.56, 2.33 Hz, 1 H) 5.77 (s, 1 H) |

Example 234

(1) Clarithromycin (200 g) was dissolved in chloroform (1 L), acetic anhydride (88.3 ml) was added dropwise to the solution, and the resulting mixture was stirred at room temperature for 1 hour. 4-Dimethylaminopyridine (16.3 g) was added to the reaction mixture, and the resulting mixture was stirred overnight. Saturated aqueous sodium hydrogencarbonate was added to the reaction mixture, the layers were separated, and the resulting organic layer was washed with saturated aqueous sodium hydrogencarbonate, dried over anhydrous magnesium sulfate, and filtered. The filtrate was concentrated under reduced pressure until solid deposited, then ethyl acetate was added to the filtrate, and the resulting mixture was concentrated again under reduced pressure. The resulting suspension was filtered, and the resulting solid was washed with a mixed solvent of hexane and ethyl acetate (3:1) to obtain a protected compound (138.4 g). The mother solution was concentrated under reduced pressure, and the resulting residue was subjected to the same operation to obtain the protected compound (66.2 g).

(2) The compound obtained in (1) mentioned above (212 g) was dissolved in a mixed solvent of tetrahydrofuran and dimethylformamide (2:1, 900 ml), 1,1'-carbonyldiimidazole (132 g) and 1,8-diazabicyclo[5,4,0]-7-undecene (7.6 ml) were added to the solution, and the resulting mixture was stirred at 40° C. for 5 hours and at room temperature for 4 days. The reaction mixture was cooled to −20° C., and then ammonia gas was bubbled into the reaction mixture. The reaction mixture was warmed to −10° C., ammonia gas was further bubbled into the reaction mixture for 1 hour, and then the reaction mixture was stirred overnight at room temperature. Potassium t-butoxide (47.2 g) was added to the reaction mixture, and the resulting mixture was stirred for 0.5 hour. Then, ethyl acetate and saturated aqueous sodium hydrogencarbonate were added to the reaction mixture, and the layers were separated. The resulting organic layer was washed with distilled water and saturated aqueous sodium chloride, then dried over anhydrous magnesium sulfate, and filtered. The resulting filtrate was concentrated under reduced pressure to obtain a carbamate compound (274 g).

(3) By using the compound obtained in (2) mentioned above (274 g) as a starting material, a deprotected compound (140.1 g) was obtained in the same manner as that of Example 2, (2).

(4) By using the compound obtained in (3) mentioned above (50 g) as a starting material, an acetyl compound (46.6 g) was obtained in the same manner as that of Example 1, (1).

(5) By using the compound obtained in (4) mentioned above (46.6 g) as a starting material, an epoxy compound (3.56 g) was obtained in the same manners as those of Example 1, (3), Example 4, (6) and Example 1, (4).

(6) By using the compound obtained in (5) mentioned above (100 mg) and (S)-1-(1-ethylpyrrolidin-2-yl)-N-methyl-methanamine (90.7 mg) as starting materials, the compound shown in Table 6 (75 mg) was obtained in the same manner as that of Example 4, (8).

In Examples 235 to 316, by using the compound obtained in Example 234, (5) and corresponding amine reagents, the compounds shown in Table 6 were synthesized in the same manner as that of Example 1, (8).

Example 317

The compound obtained in Example 234, (5) (66.4 mg) and the compound obtained in Reference Example 102 (47 mg) were dissolved in butanol (425 μl), and the solution was stirred at 120° C. for 6 hours. The reaction mixture was concentrated under reduced pressure, and the resulting residue was purified by preparative thin layer chromatography (chloroform:methanol:28% aqueous ammonia=10:1:0.1) to obtain the compound shown in Table 6 (49 mg).

In Examples 318 to 321, by using the compound obtained in Example 234, (5) and corresponding amine reagents, the compounds shown in Table 6 were synthesized in the same manner as that of Example 317.

Example 322

The compound obtained in Example 234, (5) (100 mg) and the compound obtained in Reference Example 110 (114 mg) were dissolved in ethanol (5 ml), diisopropylethylamine (170 μl) was added to the solution, and the resulting mixture was stirred at 90° C. for 18 hours. The reaction mixture was concentrated under reduced pressure, butanol (2 ml) was added to the resulting residue, and the resulting mixture was stirred at 130° C. for 3 hours. The reaction mixture was concentrated under reduced pressure, saturated aqueous ammonium chloride was added to the resulting residue, and the resulting mixture was extracted with chloroform. The organic layer was dried over anhydrous magnesium sulfate, and filtered. The filtrate was concentrated under reduced pressure, and the resulting residue was purified by silica gel column chromatography (chloroform:methanol:28% aqueous ammonia=30:1:0.1) to obtain the compound shown in Table 6 (28 mg).

Example 323

By using the compound obtained in Example 261 (0.15 g) as a starting material, the compound shown in Table 6 (56 mg) was obtained in the same manner as that of Example 73, (1).

Example 324

By using the compound obtained in Example 273 (50 mg) as a starting material, the compound shown in Table 6 (49 mg) was obtained in the same manner as that of Example 73, (1).

Example 325

The compound obtained in Example 268 (100 mg) was dissolved in methanol (0.5 ml), 20% palladium hydroxide/carbon (50 mg) was added to the solution, and the resulting mixture was stirred at room temperature for 4 hours under a hydrogen atmosphere of 1 atm. A mixed solvent of chloroform, methanol and 28% aqueous ammonia (10:1:0.1, 5 ml) was added to the reaction mixture, and the resulting mixture was stirred for 0.5 hour. The reaction mixture was filtered, the filtrate was concentrated under reduced pressure, and the resulting residue was purified by silica gel column chromatography (chloroform to chloroform:methanol:28% aqueous ammonia=10:1:0.1) to obtain the compound shown in Table 6 (47 mg).

Example 326

(1) By using the compound obtained in Example 234, (5) (500 mg) and N,N'-dimethylethylene-1,2-diamine (325 mg) as starting materials, an adduct compound (532 mg) was obtained in the same manner as that of Example 2, (5).
(2) By using the compound obtained in (1) mentioned above (200 mg) as a starting material, the compound shown in Table 6 (170 mg) was obtained in the same manner as that of Example 71, (2).

Example 327

By using the compound obtained in Example 326, (1) (50 mg) and 2-methoxybenzenesulfonyl chloride (11.8 mg) as starting materials, the compound shown in Table 6 (49 mg) was obtained in the same manner as that of Example 71, (2).

Example 328

(1) By using the compound obtained in Example 234, (5) (500 mg) and N-benzyl-N-ethyl-N'-methylethylene-1,2-diamine (600 mg) as starting materials, an adduct compound (445 mg) was obtained in the same manner as that of Example 2, (5).
(2) By using the compound obtained in (1) mentioned above (200 mg) as a starting material, the compound shown in Table 6 (153 mg) was obtained in the same manners as those of Example 325 and Example 71, (2).

Example 329

(1) By using the compound obtained in Example 234, (5) (200 mg) and a 40% solution of methylamine in methanol (260 μl) as starting materials, an adduct compound (0.21 g) was obtained in the same manner as that of Example 2, (5).
(2) The compound obtained in (1) mentioned above (100 mg) and chloroacetyl chloride (60 μl) were dissolved in chloroform (3 ml), saturated aqueous sodium hydrogencarbonate (3 ml) was added to the solution, and the resulting mixture was stirred at room temperature for 3 hours. The layers of the reaction mixture were separated, and the organic layer was dried over anhydrous magnesium sulfate, and filtered. The resulting filtrate was concentrated under reduced pressure to obtain an acyl compound.
(3) The compound obtained in (2) mentioned above was dissolved in acetonitrile (6 ml), diethylamine (130 μl) and pyridine (100 μl) were added to the solution, and the resulting mixture was stirred at 70° C. for 16 hours. The reaction mixture was concentrated under reduced pressure to obtain an amine compound.
(4) By using the compound obtained in (3) mentioned above as a starting material, the compound shown in Table 6 (40 mg) was obtained in the same manner as that of Example 4, (6).

Example 330

(1) The compound obtained in Example 234, (5) (200 mg) and N-carbobenzyloxy-1,3-diaminopropane hydrochloride (312 mg) were dissolved in ethanol (5 ml), diisopropylethylamine (225 μl) was added to the solution, and the resulting mixture was stirred at 90° C. for 18 hours. Saturated aqueous ammonium chloride was added to the reaction mixture, and the aqueous layer was extracted with chloroform. The organic layer was dried over anhydrous magnesium sulfate, and filtered, and then the filtrate was concentrated under reduced pressure. The resulting residue was purified by preparative thin layer chromatography (chloroform:methanol:28% aqueous ammonia=30:1:0.1) to obtain a carbamate compound (200 mg).
(2) By using the compound obtained in (1) mentioned above (50 mg) as a starting material, the compound shown in Table 6 (40 mg) was obtained in the same manners as those of Example 166, (2) and Example 73, (1).

Example 331

A preparation method of the compound represented by the formula (J) is shown below.

Formula (J)

[Formula 39]

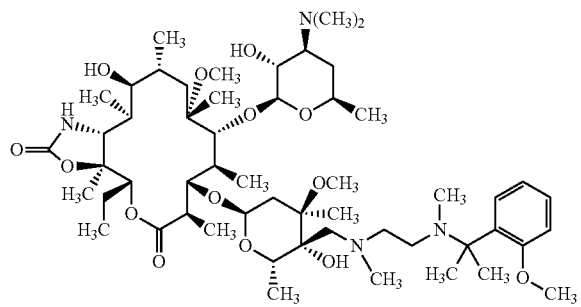

Example 331

The compound obtained in Example 311 (20 mg) was dissolved in methanol (0.5 ml), sodium borohydride (1.1 mg) was added to the solution under ice cooling, and the resulting mixture was stirred for 0.5 hour. Sodium borohydride (4 mg) was added to the reaction mixture, and the resulting mixture was stirred for 0.5 hour. Tetrahydrofuran (0.5 ml) and sodium borohydride (4 mg) were added to the reaction mixture, and the resulting mixture was stirred for 0.5 hour. Saturated aqueous sodium hydrogencarbonate and ethyl acetate were added to the reaction mixture, and the layers were separated. The organic layer was washed with saturated aqueous sodium hydrogencarbonate and saturated aqueous sodium chloride, then dried over anhydrous magnesium sulfate, and filtered. The filtrate was concentrated under reduced pressure, and the resulting residue was purified by silica gel column chromatography (chloroform:methanol:28% aqueous ammonia=30: 1:0.1 to 10:1:0.1) and preparative thin layer chromatography (chloroform:methanol:28% aqueous ammonia=10:1:0.1) to obtain the aforementioned objective compound (5 mg).

MS (ESI) m/z=1023.8 [M+H]$^+$ $^1$H-NMR (600 MHz, CDCl$_3$) δ (ppm): 0.86 (t, J=7.34 Hz, 3H), 0.96 (d, J=6.88 Hz, 3H), 1.04 (d, J=6.42 Hz, 3H), 1.09-1.15 (m, 6H), 1.17-1.34 (m, 13H), 1.39-1.58 (m, 14H), 1.61-1.67 (m, 1H), 1.78-2.08 (m, 7H), 2.18 (s, 3H), 2.26 (s, 3H), 2.28 (s, 6H), 2.39-2.66 (m, 4H), 2.82 (d, J=16.05 Hz, 1H), 2.91-2.97 (m, 1H), 3.14-3.20 (m, 1H), 3.28 (s, 3H), 3.40-3.45 (m, 1H), 3.57-3.61 (m, 1H), 3.71-3.75 (m, 1H), 3.76-3.82 (m, 4H), 4.10-4.18 (m, 1H), 4.39 (d, J=6.88 Hz, 1H), 5.01-5.05 (m, 2H), 5.06-5.11 (m, 1H), 6.85-6.90 (m, 2H), 7.15-7.19 (m, 1H), 7.60-7.64 (m, 1H)

Example 332

A preparation method of the compound represented by the formula (K) is shown below.

Formula (K)

[Formula 40]

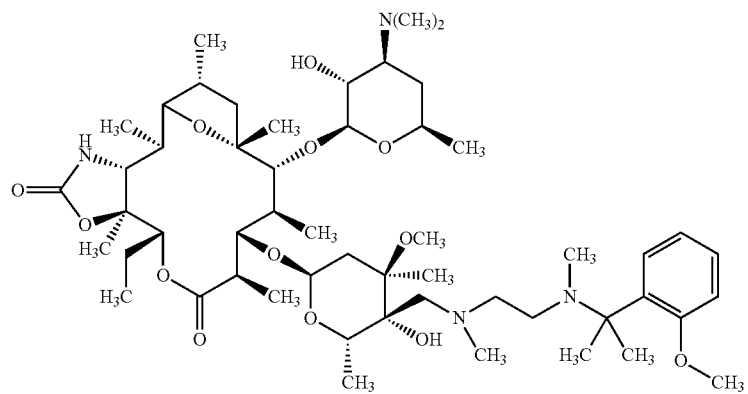

Example 332

(1) Erythromycin A (150 g) was dissolved in toluene (530 ml), potassium carbonate (75 g) and ethylene carbonate (75 g) were added to the solution, and the resulting mixture was stirred at room temperature for 5 days. Ethyl acetate was added to the reaction mixture, the resulting mixture was filtered thorough Celite, and then the filtrate was successively washed twice with distilled water, and twice with saturated aqueous sodium chloride. The organic layer was dried over anhydrous sodium sulfate, and filtered, then the filtrate was concentrated under reduced pressure, and diethyl ether was added to the resulting residue. The deposited crystals were collected by filtration to obtain a carbonate compound (79.9 g).

(2) The compound obtained in (1) mentioned above (45 g) was dissolved in dimethylformamide (225 ml), 1,1,3,3-tetramethylguanidine (15 ml) was added to the solution, and the resulting mixture was stirred at 100° C. for 3 hours. Ethyl acetate and distilled water were added to the reaction mixture, and the layers were separated. The organic layer was successively washed with distilled water and saturated aqueous sodium chloride, then dried over anhydrous sodium sulfate, and filtered. The filtrate was concentrated under reduced pressure, and the resulting residue was purified by silica gel column chromatography (ethyl acetate:methanol:28% aqueous ammonia=30:1:0.1 to 10:1:0.1) to obtain an enone compound (37.5 g).

(3) The compound obtained in (2) mentioned above (37 g) was dissolved in dimethylformamide (250 ml), ammonium chloride (1.4 g) and hexamethyldisilazane (22 ml) were added to the solution, and the resulting mixture was stirred at room temperature for 4 hours. Ethyl acetate and distilled water were added to the reaction mixture, the layers were separated, and the organic layer was successively washed twice with distilled water and with saturated aqueous sodium chloride. The organic layer was dried over anhydrous sodium sulfate, and filtered, and then the filtrate was concentrated under reduced pressure to obtain a protected compound (43.6 g).

(4) The compound obtained in (3) mentioned above (43.6 g) was dissolved in a mixed solvent of tetrahydrofuran and dimethylformamide (5:3, 222 ml), 1,1'-carbonyldiimidazole (12.4 g) and 55% sodium hydride (2.7 g) were added to the solution under ice cooling, and the resulting mixture was stirred for 1 hour under ice cooling. Ethyl acetate and distilled water were added to the reaction mixture under ice cooling, the layers were separated, and the organic layer was successively washed twice with distilled water and with saturated aqueous sodium chloride. The organic layer was dried over anhydrous sodium sulfate, and filtered, and then the filtrate was concentrated under reduced pressure to obtain an imidazolylcarbonyl compound (52.0 g).

(5) The compound obtained in (4) mentioned above (15.0 g) was dissolved in a mixed solvent of tetrahydrofuran and acetonitrile (3:2, 125 ml), 28% aqueous ammonia (60 ml) was added to the solution, and the resulting mixture was stirred at room temperature for 69 hours. Ethyl acetate and distilled water were added to the reaction mixture, and the layers were separated. The organic layer was successively washed with saturated aqueous sodium chloride, then dried over anhydrous sodium sulfate, and filtered. The filtrate was concentrated under reduced pressure, and the resulting residue was purified by silica gel column chromatography (hexane:acetone=5:1 to 3:1) to obtain a carbamate compound (5.64 g).
(6) The compound obtained in (5) mentioned above (1.35 g) was dissolved in ethanol (12 ml), sodium borohydride (565 mg) was added to the solution under ice cooling, and the resulting mixture was stirred overnight at room temperature. Ethyl acetate and distilled water were added to the reaction mixture, the layers were separated, and the organic layer was dried over anhydrous sodium sulfate, and filtered. The filtrate was concentrated under reduced pressure, the resulting residue was dissolved in tetrahydrofuran (13 ml), a 1 mol/L solution of tetrabutylammonium fluoride in tetrahydrofuran (2.98 ml) was added to the solution, and the resulting mixture was stirred at room temperature for 3.5 hours. Ethyl acetate and water were added to the reaction mixture, the layers were separated, and the organic layer was dried over anhydrous sodium sulfate, and filtered. The filtrate was concentrated under reduced pressure, and the resulting residue was purified by silica gel column chromatography (chloroform:methanol:28% aqueous ammonia=97:3:0.3) to obtain an alcohol compound (582 mg).
(7) By using the compound obtained in (6) mentioned above (510 mg) as a starting material, an acetyl compound (515 mg) was obtained in the same manner as that of Example 1, (1).
(8) The compound obtained in (7) mentioned above (100 mg) was dissolved in chloroform (1.0 ml), pyridine (670 μl) and a solution of triphosgene (222 mg) in chloroform (1.0 ml) was added to the solution under ice cooling, and the resulting mixture was stirred for 5 hours with warming to room temperature. Ethyl acetate and saturated aqueous sodium hydrogencarbonate were added to the reaction mixture, the layers were separated, and the organic layer was washed with saturated aqueous sodium hydrogencarbonate, then dried over anhydrous sodium sulfate, and filtered. The filtrate was concentrated under reduced pressure, and the resulting residue was purified by preparative thin layer chromatography (chloroform:methanol:28% aqueous ammonia=97:3:0.3), and then further purified by preparative thin layer chromatography (chloroform:methanol:28% aqueous ammonia=90:7:0.7) to obtain an ether compound (48.1 mg).
(9) By using the compound obtained in (8) mentioned above (69.6 mg) as a starting material, a deprotected compound (52.0 mg) was obtained in the same manners as those of Example 1, (3), Example 1, (4) and Example 4, (6).
(10) By using the compound obtained in (9) mentioned above (30.0 mg) and the compound obtained in Reference Example 104 (12.9 mg) as starting materials, the aforementioned objective compound (34.3 mg) was obtained in the same manner as that of Example 4, (8).

MS (FAB) m/z=991.6 [M+H]$^+$ $^1$H-NMR (400 MHz, CDCl$_3$) δ (ppm): 0.92 (t, J=7.4 Hz, 3H), 1.01-1.10 (m, 9H), 1.13 (s, 3H), 1.15-1.30 (m, 9H), 1.36-1.49 (m, 12H), 1.49-1.88 (m, 9H), 1.91-2.11 (m, 4H), 2.18 (s, 3H), 2.20-2.37 (m, 10H), 2.36-2.59 (m, 4H), 2.58-2.74 (m, 3H), 2.80 (d, J=14.4 Hz, 1H), 3.19 (dd, J=10.1, 7.4 Hz, 1H), 3.30 (s, 3H), 3.40-3.51 (m, 1H), 3.61 (d, J=10.3 Hz, 1H), 3.81 (s, 3H), 3.91 (d, J=9.8 Hz, 1H), 4.05-4.16 (m, 2H), 4.33 (d, J=7.3 Hz, 1H), 4.91 (dd, J=9.9, 3.1 Hz, 1H), 5.21 (s, 1H), 5.35 (d, J=4.9 Hz, 1H), 6.84-6.94 (m, 2H), 7.14-7.23 (m, 1H), 7.56-7.64 (m, 1H)

Examples 333 to 336

Preparation methods of the compounds represented by the formula (L) having $R^{24}$ and $R^{4a}$ defined in Table 7 are shown below.

TABLE 7

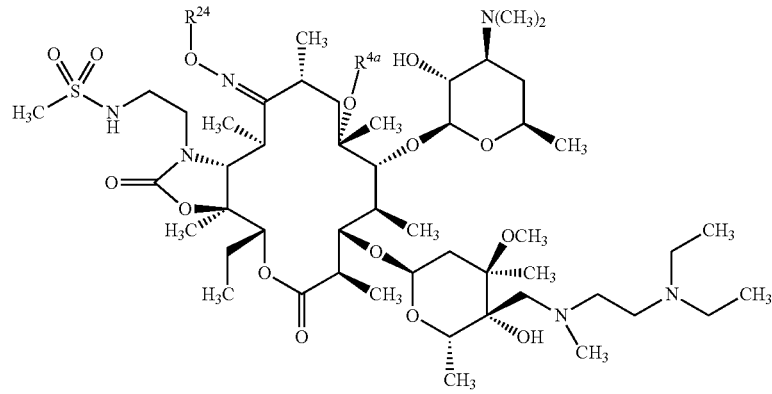

[Formula 41]

| Example | $R^{24}$ | $R^{4a}$ | ESI MS (M + H) | $^1$H-NMR, CDCl$_3$, δ (ppm) |
|---|---|---|---|---|
| 333 | CH$_3$ | CH$_3$ | 1065.7 | (500 MHz): 0.85 (t, J = 7.26 Hz, 3 H) 0.95 (d, J = 7.26 Hz, 3 H) 1.00-1.06 (m, 6 H) 1.06 (d, J = 6.88 Hz, 3 H) 1.08 (d, J = 7.26 Hz, 3 H) 1.16 (s, 3 H) 1.18-1.21 (m, 6 H) 1.24 (d, J = 6.12 Hz, 3 H) 1.24-1.27 (m, 1 H) 1.34-1.42 (m, 1 H) 1.40 (s, 3 H) 1.45 (s, 3 H) 1.53-1.61 (m, 2 H) 1.63-1.67 (m, 1 H) 1.85-1.98 (m, 2 H) 1.98-2.05 (m, 2 H) 2.09 (d, J = 14.91 Hz, 1 H) 2.29 (s, 6 H) 2.35 (s, 3 H) 2.40-2.63 (m, 8 H) 2.41-2.46 (m, 1 H) 2.61-2.66 (m, 1 H) 2.84 (d, J = 14.91 Hz, 1 H) 2.90-2.96 (m, 1 H) 2.99 (s, 3 H) 3.09 (s, 3 H) 3.17-3.22 (m, 1 H) 3.27 (s, 3 H) 3.35-3.53 (m, 3 H) 3.63-3.72 (m, 3 H) 3.69 (s, 1 H) 3.78 (s, 3 H) 3.88-4.01 (m, 2 H) 4.08-4.14 (m, 1 H) 4.40 (d, J = 7.26 Hz, 1 H) 4.94-5.00 (m, 2 H) 5.74-5.80 (m, 1 H) |

TABLE 7-continued

Formula (L)

[Formula 41]

| Example | R²⁴ | R⁴ᵃ | ESI MS (M + H) | ¹H-NMR, CDCl₃, δ (ppm) |
|---|---|---|---|---|
| 334 | H |  | 1051.7 | (600 MHz): 0.84 (t, J = 7.57 Hz, 3 H) 0.98 (d, J = 6.88 Hz, 3 H) 1.00-1.04 (m, 6 H) 1.07 (d, J = 7.34 Hz, 3 H) 1.10 (d, J = 6.88 Hz, 3 H) 1.16 (s, 3 H) 1.18-1.21 (m, 6 H) 1.22-1.27 (m, 1 H) 1.24 (d, J = 5.96 Hz, 3 H) 1.39 (s, 3 H) 1.40-1.44 (m, 1 H) 1.49 (s, 3 H) 1.51-1.58 (m, 1 H) 1.59-1.62 (m, 1 H) 1.63-1.67 (m, 1 H) 1.85-1.93 (m, 2 H) 1.95-2.05 (m, 2 H) 2.10 (d, J = 14.67 Hz, 1 H) 2.29 (s, 6 H) 2.34 (s, 3 H) 2.39-2.62 (m, 10 H) 2.82-2.86 (m, 1 H) 2.86-2.93 (m, 1 H) 2.98 (s, 3 H) 3.12 (s, 3 H) 3.17-3.22 (m, 1 H) 3.28 (s, 3 H) 3.37-3.42 (m, 1 H) 3.44-3.49 (m, 1 H) 3.54-3.61 (m, 2 H) 3.61-3.73 (m, 3 H) 3.70 (s, 1 H) 3.77-3.83 (m, 2 H) 4.11 (q, J = 6.42 Hz, 1 H) 4.41 (d, J = 7.34 Hz, 1 H) 4.85-4.89 (m, 1 H) 4.98 (d, J = 4.58 Hz, 1 H) 5.84-5.88 (m, 1 H) 7.85 (s, 1 H) |
| 335 | H | H | 1037.7 | (600 MHz): 0.83 (t, J = 7.34 Hz, 3 H) 1.00-1.10 (m, 15 H) 1.15 (s, 3 H) 1.17-1.27 (m, 10 H) 1.41 (s, 3 H) 1.44-1.68 (m, 4 H) 1.53 (s, 3 H) 1.88-2.14 (m, 5 H) 2.30 (s, 6 H) 2.34 (s, 3 H) 2.39-2.67 (m, 9 H) 2.69-2.92 (m, 3 H) 2.98 (s, 3 H) 3.22-4.16 (m, 11 H) 3.27 (s, 3 H) 4.35-4.38 (m, 1 H) 4.84-4.89 (m, 1 H) 4.91-4.93 (m, 1 H) |
| 336 |  | H | 1051.7 | (600 MHz): 0.85 (t, J = 7.34 Hz, 3 H) 0.98-1.04 (m, 9 H) 1.07-1.11 (m, 6 H) 1.15 (s, 3 H) 1.17-1.20 (m, 6 H) 1.23 (d, J = 5.96 Hz, 3 H) 1.24-1.28 (m, 1 H) 1.43 (s, 3 H) 1.47 (s, 3 H) 1.51-1.62 (m, 3 H) 1.62-1.67 (m, 1 H) 1.89-1.97 (m, 3 H) 1.99-2.04 (m, 1 H) 2.09 (d, J = 14.67 Hz, 1 H) 2.29 (s, 6 H) 2.34 (s, 3 H) 2.40-2.62 (m, 9 H) 2.65-2.71 (m, 1 H) 2.83 (d, J = 14.67 Hz, 2 H) 3.01 (s, 3 H) 3.20-3.25 (m, 1 H) 3.27 (s, 3 H) 3.28-3.35 (m, 2 H) 3.38 (br. s., 1 H) 3.44-3.49 (m, 1 H) 3.51 (d, J = 7.34 Hz, 1 H) 3.76-3.81 (m, 1 H) 3.83 (s, 3 H) 3.86-3.92 (m, 1 H) 3.98 (br. s., 1 H) 4.04 (d, J = 8.25 Hz, 1 H) 4.08-4.16 (m, 2 H) 4.40 (d, J = 7.34 Hz, 1 H) 4.90-4.95 (m, 2 H) 5.51 (t, J = 5.96 Hz, 1 H) |

Formula (SM2)

[Formula 42]

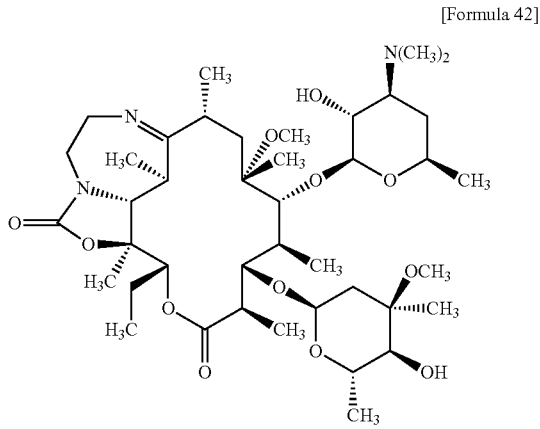

Example 333

(1) By using the compound represented by the formula (SM2) (13.9 g) obtained by the method described in the literature (The Journal of Antibiotics, 2001, vol. 54, No. 8, p. 664) as a starting material, an acetyl compound (9.74 g) was obtained in the same manner as that of Example 1, (1).
(2) By using the compound obtained in (1) mentioned above (2.0 g) as a starting material, an epoxy compound (1.58 g) was obtained in the same manners as those of Example 1, (3), Example 4, (6) and Example 1, (4).
(3) By using the compound obtained in (2) mentioned above (300 mg) as a starting material, an adduct compound (329 mg) was obtained in the same manner as that of Example 11.
(4) The compound obtained in (3) mentioned above (30 mg) was dissolved in ethanol (2 ml), imidazole (13.0 mg) and O-methylhydroxylamine hydrochloride (13.3 mg) were added to the solution, and the resulting mixture was stirred under reflux by heating for 10 hours. Chloroform and saturated aqueous ammonium chloride were added to the reaction mixture, the layers were separated, and the aqueous layer was extracted with chloroform. The organic layer was filtered with a phase separator to further separate the layers, the resulting organic layer was concentrated under reduced pressure, and the resulting residue was purified by preparative thin layer chromatography (chloroform:methanol:28% aqueous ammonia=10:1:0.1) to obtain an oxime compound (12.1 mg).
(5) By using the compound obtained in (4) mentioned above (12 mg) as a starting material, the compound shown in Table 7 (5.4 mg) was obtained in the same manner as that of Example 162.

Example 334

(1) The compound obtained in Example 333, (3) (158 mg) was dissolved in ethanol (4 ml), imidazole (68.6 mg) and hydroxylamine hydrochloride (58.4 mg) were added to the solution, and the resulting mixture was stirred under reflux by heating for 1 hour. Chloroform and saturated aqueous sodium hydrogencarbonate were added to the reaction mixture, the layers were separated, and the aqueous layer was extracted with chloroform. The organic layer was filtered with a phase separator to further separate the layers, the resulting organic layer was concentrated under reduced pressure, and the resulting residue was purified by silica gel column chromatography (chloroform:methanol:28% aqueous ammonia=100:1:0.1 to 10:1:0.1) to obtain an oxime compound (172 mg).
(2) By using the compound obtained in (1) mentioned above (120 mg) as a starting material, the compound shown in Table 7 (49.8 mg) was obtained in the same manner as that of Example 162.

Example 335

(1) 6-O-Allylerythromycin A (7.62 g) obtained by the method described in the publication (International Patent Publication WO97/42204) was dissolved in a mixed solvent of chloroform and pyridine (5:1, 120 ml), 4-dimethylaminopyridine (1.20 g) was added to the solution, a solution of acetic anhydride (2.33 ml) in chloroform (10 ml) was added dropwise to the mixture under ice cooling, and the resulting mixture was stirred at room temperature for 17 hours. Acetic anhydride (466 µl) was added to the reaction mixture, and the resulting mixture was stirred at room temperature for 1 hour. The reaction mixture was concentrated under reduced pressure, ethyl acetate and distilled water were added to the resulting residue, and the layers were separated. The organic layer was washed with saturated aqueous ammonium chloride and saturated aqueous sodium chloride, dried over anhydrous magnesium sulfate, and filtered. The filtrate was concentrated under reduced pressure, and the resulting residue was purified by silica gel column chromatography (chloroform:methanol: 28% aqueous ammonia=100:1:0.1 to 20:1:0.1) to obtain a silyl compound (4.74 g).
(2) By using the compound obtained in (1) mentioned above (4.74 g) as a starting material, an imidazolylcarbonyl compound (5.5 g) was obtained in the same manner as that of Example 1, (5).
(3) The compound obtained in (2) mentioned above (5.5 g) was dissolved in a mixed solvent of tetrahydrofuran and dimethylformamide (3:1, 80 ml), ethylenediamine (3.7 ml) was added to the solution, and the resulting mixture was stirred at room temperature for 18 hours. Distilled water (12 ml) was added to the reaction mixture, and the resulting mixture was stirred at room temperature for 20 hours. Ethyl acetate and distilled water were added to the reaction mixture, the layers were separated, and the organic layer was washed with aqueous sodium hydrogencarbonate and saturated aqueous sodium chloride, dried over anhydrous magnesium sulfate, and filtered. The resulting filtrate was concentrated under reduced pressure to obtain a carbamate compound (5.26 g).
(4) The compound obtained in (3) mentioned above (5.26 g) was dissolved in toluene (55 ml), acetic acid (813 µl) was added to the solution, and the resulting mixture was stirred at 120° C. for 2 hours. The reaction mixture was left to cool to room temperature, then saturated aqueous sodium hydrogencarbonate and distilled water were successively added to the reaction mixture, and the layers were separated. The organic layer was washed with saturated aqueous sodium hydrogencarbonate, dried over anhydrous magnesium sulfate, and filtered. The filtrate was concentrated under reduced pressure, and the resulting residue was purified by silica gel column chromatography (chloroform:methanol:28% aqueous ammonia=100:1:0.1 to 10:1:0.1) to obtain an imine compound (3.87 g).
(5) By using the compound obtained in (4) mentioned above (598 mg) as a starting material, an epoxy compound (247 mg) was obtained in the same manners as those of Example 2, (2), Example 1, (1), (3), (4) and Example 4, (6).
(6) By using the compound obtained in (5) mentioned above (153 mg) as a starting material, an adduct compound (163 mg) was obtained in the same manner as that of Example 11.
(7) By using the compound obtained in (6) mentioned above (40 mg) as a starting material, an oxime compound (43.2 mg) was obtained in the same manner as that of Example 334, (1).
(8) The compound obtained in (7) mentioned above (41.2 mg) was dissolved in tetrahydrofuran (1 ml), triethylamine (6.3 µl) and methanesulfonyl chloride (3.5 µl) were added to the solution under ice cooling, and the resulting mixture was stirred at the same temperature for 45 minutes. Chloroform and saturated aqueous sodium hydrogencarbonate were added to the reaction mixture, the layers were separated, and the aqueous layer was extracted with chloroform. The organic layer was filtered with a phase separator to further separate the layers, and the resulting organic layer was concentrated under reduced pressure, and the resulting residue was purified by preparative thin layer chromatography (chloroform:methanol:28% aqueous ammonia=10:1:0.1) to obtain a methanesulfonyl compound (22.1 mg).
(9) The compound obtained in (8) mentioned above (21.6 mg) was dissolved in a mixed solvent of dioxane and distilled water (6:1, 0.7 ml), formic acid (5.7 µl), triethylamine (8.4 µl), triphenylphosphine (16.8 mg), and palladium(II) acetate (3.6 mg) were added to the solution under a nitrogen atmosphere, and the resulting mixture was stirred under reflux by heating for 16 hours. The reaction mixture was left to cool to room temperature, and then ethyl acetate and saturated aqueous sodium hydrogencarbonate were added to the mixture. The layers were separated, and the organic layer was washed with saturated aqueous sodium chloride, dried over anhydrous magnesium sulfate, and filtered. The filtrate was concentrated under reduced pressure, and the resulting residue was successively purified by silica gel column chromatography (chloroform:methanol:28% aqueous ammonia=100:1:0.1 to 5:1:0.1) and preparative thin layer chromatography (chloroform:methanol:28% aqueous ammonia=10:1:0.1) to obtain the compound shown in Table 7 (1.3 mg).

Example 336

By using the compound obtained in Example 335, (6) (120 mg) as a starting material, the compound shown in Table 7 (27.7 mg) was obtained in the same manners as those of Example 333, (4), Example 335 (8) and (9).

Example 337

A preparation method of the compound represented by the formula (M) is shown below.

Formula (M)

[Formula 43]

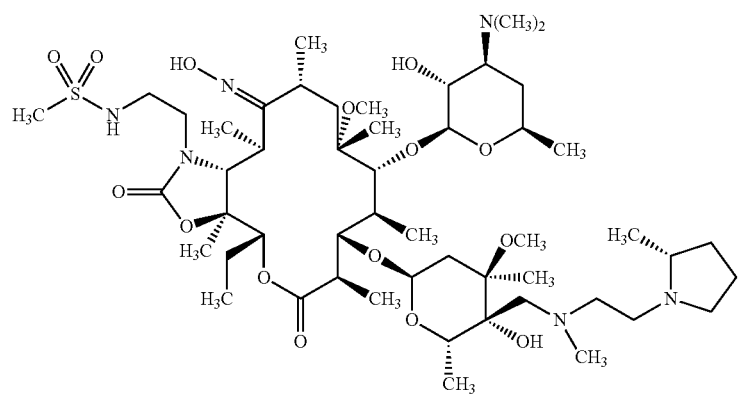

Example 337

(1) By using the compound obtained in Example 333, (2) (120 mg) and the compound obtained in Reference Example 1 (105 mg) as starting materials, the aforementioned objective compound (89.7 mg) was obtained in the same manners as those of Example 4, (8), Example 334, (1) and Example 162.

MS (ESI) m/z=1063.7 [M+H]$^+$ $^1$H-NMR (600 MHz, CDCl$_3$) δ (ppm): 0.84 (t, J=7.34 Hz, 3H), 0.98 (d, J=6.88 Hz, 3H), 1.06-1.11 (m, 9H), 1.15 (s, 3H), 1.18-1.22 (m, 6H), 1.23-1.25 (m, 1H), 1.24 (d, J=5.96 Hz, 3H), 1.39 (s, 3H), 1.40-1.44 (m, 2H), 1.49 (s, 3H), 1.52-1.70 (m, 4H), 1.73-1.80 (m, 1H), 1.85-1.94 (m, 3H), 1.95-2.05 (m, 2H), 2.08-2.19 (m, 3H), 2.29 (s, 6H), 2.31-2.35 (m, 1H), 2.37 (s, 3H), 2.40-2.46 (m, 1H), 2.57-2.67 (m, 3H), 2.84-2.94 (m, 3H), 2.98 (s, 3H), 3.12 (s, 3H), 3.13-3.17 (m, 1H), 3.20 (dd, J=10.32, 7.11 Hz, 1H), 3.28 (s, 3H), 3.36-3.42 (m, 1H), 3.42-3.49 (m, 1H), 3.54-3.61 (m, 2H), 3.62-3.66 (m, 1H), 3.67-3.73 (m, 3H), 3.77-3.85 (m, 2H), 4.08-4.15 (m, 1H), 4.41 (d, J=7.34 Hz, 1H), 4.88 (dd, J=11.00, 1.83 Hz, 1H), 4.99 (d, J=4.58 Hz, 1H), 5.87 (br. s., 1H), 7.88 (br. s., 1H)

Examples 338 and 339

Preparation methods of the compounds represented by the formula (N) having R$^{2c}$ defined in Table 8 are shown below.

TABLE 8

Formula (N)

[Structural diagram of macrolide compound with R²ᶜ substituent]

[Formula 44]

| Example | R²ᶜ | ESI MS (M + H) | ¹H-NMR, CDCl₃, δ (ppm) |
|---|---|---|---|
| 338 | [structure: -C(CH₃)₂-phenyl(2-OCH₃) with N(CH₃) linker] | 1046.7 | (600 MHz): 0.84 (t, J = 7.34 Hz, 3 H) 1.04 (d, J = 6.88 Hz, 3 H) 1.07 (d, J = 7.79 Hz, 3 H) 1.13 (s, 3 H) 1.17-1.26 (m, 13 H) 1.39-1.45 (m, 12 H) 1.49-1.66 (m, 4 H) 1.85-1.91 (m, 2 H) 1.95-2.00 (m, 1 H) 2.01-2.07 (m, 2 H) 2.18 (s, 3 H) 2.26 (s, 3 H) 2.29 (s, 6 H) 2.40-2.47 (m, 3 H) 2.51-2.58 (m, 1 H) 2.58-2.64 (m, 1 H) 2.66-2.72 (m, 1 H) 2.73-2.78 (m, 1 H) 2.79-2.89 (m, 2 H) 2.99-3.05 (m, 1 H) 3.10 (s, 3 H) 3.16-3.21 (m, 1 H) 3.28 (s, 3 H) 3.34-3.40 (m, 1 H) 3.41-3.47 (m, 1 H) 3.64-3.68 (m, 2 H) 3.73-3.83 (m, 3 H) 3.80 (s, 3 H) 3.96-4.00 (m, 1 H) 4.11 (q, J = 6.42 Hz, 1 H) 4.41 (d, J = 7.34 Hz, 1 H) 4.98-4.99 (m, 1 H) 5.00-5.01 (m, 1 H) 6.85-6.90 (m, 2 H) 7.15-7.19 (m, 1 H) 7.61 (d, J = 7.34 Hz, 1 H) |
| 339 | [structure: -N(CH₃)CH₂CH₃ type diethylmethylamine] | 940.7 | (600 MHz): 0.84 (t, J = 7.34 Hz, 3 H) 1.00-1.05 (m, 9 H) 1.08 (s, 3 H) 1.16 (s, 3 H) 1.18-1.22 (m, 9 H) 1.21-1.27 (m, 1 H) 1.24 (d, J = 6.42 Hz, 1 H) 1.40 (s, 3 H) 1.41 (s, 3 H) 1.48-1.55 (m, 1 H) 1.56-1.67 (m, 3 H) 1.84-1.91 (m, 2 H) 1.94-2.05 (m, 2 H) 2.10 (d, J = 15.13 Hz, 1 H) 2.29 (s, 6 H) 2.34 (s, 3 H) 2.40-2.62 (m, 9 H) 2.65-2.72 (m, 1 H) 2.73-2.77 (m, 1 H) 2.81-2.88 (m, 2 H) 2.99-3.04 (m, 1 H) 3.09 (s, 3 H) 3.19 (dd, J = 10.55, 7.34 Hz, 1 H) 3.28 (s, 3 H) 3.37 (br. s., 1 H) 3.44-3.50 (m, 1 H) 3.65-3.69 (m, 2 H) 3.73-3.84 (m, 3 H) 3.95-4.01 (m, 1 H) 4.09-4.13 (m, 1 H) 4.42 (d, J = 7.34 Hz, 1 H) 4.96-5.01 (m, 2 H) |

Example 338

By using the compound obtained in Example 333, (2) (60 mg) and the compound obtained in Reference Example 104 (53 mg) as starting materials, the compound shown in Table 8 (61.9 mg) was obtained in the same manner as that of Example 2, (5).

Example 339

By using the compound obtained in Example 333, (2) (50 mg) as a starting material, the compound shown in Table 8 (52.0 mg) was obtained in the same manner as that of Example 11.

Example 340

A preparation method of the compound represented by the formula (O) is shown below.

Formula (O)

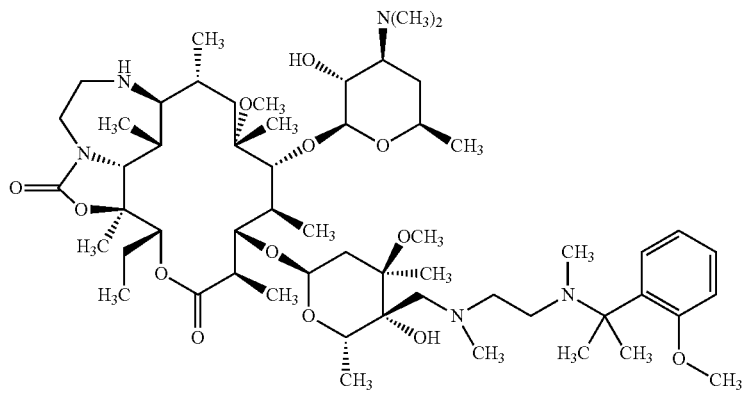

Example 340

(1) The compound obtained in Example 333, (2) (80 mg) was dissolved in ethanol (1.5 ml), acetic acid (50 μl) was added to the solution, sodium cyanoborohydride (31 mg) was added to the mixture under ice cooling, and the resulting mixture was stirred at room temperature for 2 days. Saturated aqueous sodium hydrogencarbonate and ethyl acetate were added to the reaction mixture, and the layers were separated. The organic layer was dried over anhydrous magnesium sulfate, and filtered. The filtrate was concentrated under reduced pressure, and the resulting residue was purified by preparative thin layer chromatography (chloroform:methanol:28% aqueous ammonia=10:1:0.1) to obtain a reduced compound (50.9 mg).

(2) By using the compound obtained in (1) mentioned above (47.2 mg) and the compound obtained in Reference Example 104 (41.2 mg) as starting materials, the aforementioned objective compound (43.9 mg) was obtained in the same manner as that of Example 2, (5).

MS (ESI) m/z=1048.8 [M+H]$^+$ $^1$H-NMR (600 MHz, CDCl$_3$) δ (ppm): 0.84 (t, J=7.57 Hz, 3H), 0.95 (d, J=7.34 Hz, 3H), 1.06-1.11 (m, 6H), 1.13 (s, 3H), 1.20 (d, J=6.42 Hz, 3H), 1.22 (d, J=7.34 Hz, 3H), 1.23-1.26 (m, 1H), 1.24 (d, J=6.42 Hz, 3H), 1.36 (br. s., 3H), 1.38-1.40 (m, 3H), 1.40-1.45 (m, 8H), 1.50-1.57 (m, 1H), 1.64 (d, J=11.92 Hz, 1H), 1.86-2.08 (m, 6H), 2.10-2.16 (m, 1H), 2.18 (s, 3H), 2.26 (s, 3H), 2.29 (s, 6H), 2.40-2.50 (m, 3H), 2.51-2.59 (m, 1H), 2.59-2.67 (m, 1H), 2.78 (d, J=12.84 Hz, 1H), 2.83 (d, J=14.67 Hz, 1H), 2.85-2.95 (m, 2H), 3.15-3.21 (m, 2H), 3.28 (s, 3H), 3.29-3.31 (m, 3H), 3.36-3.40 (m, 1H), 3.40-3.46 (m, 1H), 3.67 (s, 1H), 3.75 (d, J=7.79 Hz, 1H), 3.80 (s, 3H), 3.84 (d, J=9.63 Hz, 1H), 3.97-4.01 (m, 1H), 4.11-4.17 (m, 1H), 4.41 (d, J=6.88 Hz, 1H), 4.96 (d, J=9.63 Hz, 1H), 5.02 (d, J=5.04 Hz, 1H), 6.85-6.90 (m, 2H), 7.14-7.19 (m, 1H), 7.62 (d, J=6.88 Hz, 1H)

Example 341

A preparation method of the compound represented by the formula (P) is shown below.

Formula (P)

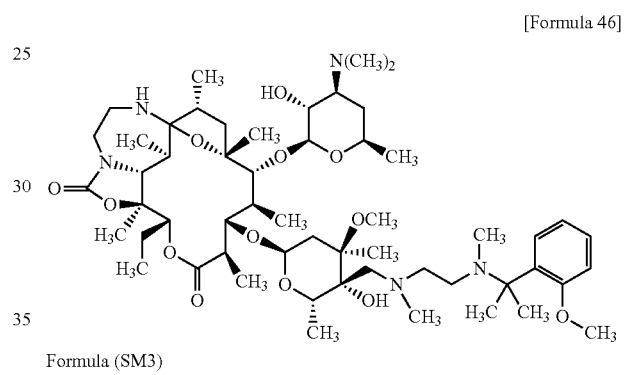

Formula (SM3)

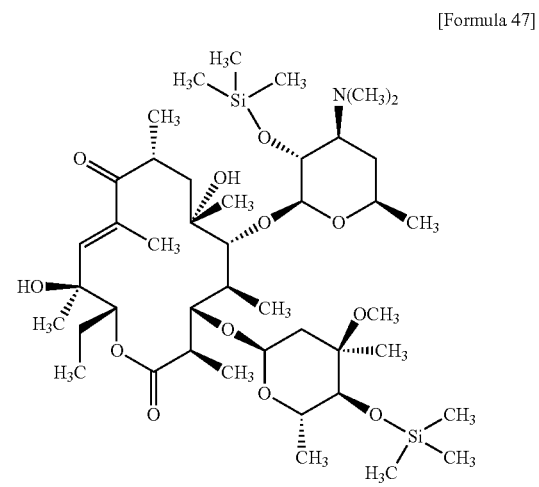

Example 341

(1) The compound represented by the formula (SM3) (22.6 g) obtained by the method described in the literature (The Journal of Antibiotics, 2003, vol. 56, p. 1062) as a starting material, an imidazolylcarbonyl compound (29.1 g) was obtained in the same manner as that of Example 1, (5).

(2) The compound obtained in (1) mentioned above (2.09 g) and ethylenediamine (1.5 ml) were dissolved in a mixed solvent of tetrahydrofuran and dimethylformamide (3:1, 20 ml), and the solution was stirred at room temperature for 16 hours. Distilled water was added to the reaction mixture, and the resulting mixture was stirred at room temperature for 9 hours. Ethyl acetate was added to the reaction mixture, the layers were separated, and the resulting organic layer was washed with saturated aqueous sodium chloride, dried over anhydrous magnesium sulfate, and filtered. The filtrate was concentrated under reduced pressure, the resulting residue and ethylenediamine (1.5 ml) were dissolved in a mixed solvent of tetrahydrofuran and dimethylformamide (3:1, 20 ml), potassium t-butoxide (0.25 g) was added to the solution, and the resulting mixture was stirred at room temperature for 0.5 hours. Saturated aqueous ammonium chloride was added to the reaction mixture, saturated aqueous sodium hydrogencarbonate was added to the mixture to adjust the mixture to pH 9, and the resulting mixture was extracted with chloroform. The organic layer was washed with saturated aqueous sodium chloride, dried over anhydrous magnesium sulfate, and filtered. The filtrate was concentrated under reduced pressure, the resulting residue was dissolved in tetrahydrofuran (40 ml), a 1 mol/L solution of tetrabutylammonium fluoride in tetrahydrofuran (4 ml) was added to the solution, and the resulting mixture was stirred at room temperature for 2 hours. Distilled water was added to the reaction mixture, and the resulting mixture was extracted with ethyl acetate. Saturated aqueous sodium hydrogencarbonate was added to the aqueous layer, and the resulting mixture was extracted with chloroform. The organic layer was dried over anhydrous magnesium sulfate, and filtered. The filtrate was concentrated under reduced pressure. the resulting residue was dissolved in ethanol (20 ml), acetic acid (0.44 ml) was added to the solution, and the resulting mixture was stirred at 60° C. for 16 hours. Saturated aqueous sodium hydrogencarbonate was added to the reaction mixture, and the resulting mixture was extracted with ethyl acetate. The organic layer was dried over anhydrous magnesium sulfate, and filtered. The filtrate was concentrated under reduced pressure, and the resulting residue was purified by silica gel column chromatography (hexane:acetone:triethylamine=20:10:0.2 to 5:10:0.2) to obtain a carbamate compound (262 mg).

(3) By using the compound obtained in (2) mentioned above (73 mg) as a starting material, an epoxy compound (50 mg) was obtained in the same manners as those of Example 1, (1), (3) and (4).

(4) By using the compound obtained in (3) mentioned above (50 mg) and the compound obtained in Reference Example 104 (38 mg) as starting materials, the aforementioned objective compound (40 mg) was obtained in the same manner as that of Example 2, (5).

MS (ESI) m/z=1032.8 [M+H]$^+$ $^1$H-NMR (500 MHz, CDCl$_3$) δ (ppm): 0.85-0.92 (m, 6H), 0.97 (d, J=6.86 Hz, 3H), 1.07-1.15 (m, 9H), 1.15-1.28 (m, 7H), 1.32 (s, 3H), 1.38-1.60 (m, 10H), 1.65-1.72 (m, 1H), 1.76-1.96 (m, 5H), 2.02-2.10 (m, 2H), 2.13-2.20 (m, 4H), 2.22-2.33 (m, 9H), 2.38-2.73 (m, 6H), 2.75-2.85 (m, 3H), 3.17-3.34 (m, 7H), 3.37-3.49 (m, 3H), 3.80 (br. s., 3H), 4.09-4.16 (m, 2H), 4.24 (d, J=7.13 Hz, 1H), 4.32 (s, 1H), 4.94 (dd, J=10.70, 1.92 Hz, 1H), 5.00 (d, J=4.39 Hz, 1H), 6.84-6.92 (m, 2H), 7.15-7.21 (m, 1H), 7.58-7.65 (m, 1H)

Examples 342 to 349

Preparation methods of the compounds represented by the formula (Q) having R$^{4b}$ and R$^{2d}$ defined in Table 9 are shown below.

TABLE 9

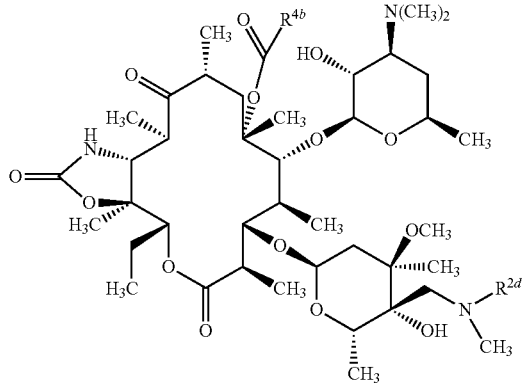

[Formula 48]

| Example | R$^{4b}$ | R$^{2d}$ | ESI MS (M + H) | $^1$H-NMR, CDCl$_3$, δ (ppm) |
|---|---|---|---|---|
| 342 | ⸺NH$_2$ | ⸺CH$_2$CH$_2$N(CH$_3$)C(CH$_3$)$_2$(2-OCH$_3$-C$_6$H$_4$) | 1050.7 | (600 MHz): 0.85 (t, J = 7.34 Hz, 3 H) 1.13 (s, 3 H) 1.15-1.19 (m, 9 H) 1.20-1.24 (m, 9 H) 1.23-1.26 (m, 1 H) 1.38-1.41 (m, 3 H) 1.43 (br. s., 6 H) 1.53-1.61 (m, 1 H) 1.61-1.66 (m, 1 H) 1.71-1.79 (m, 2 H) 1.74 (s, 3 H) 1.87-1.95 (m, 2 H) 1.96-2.01 (m, 1 H) 2.02-2.09 (m, 2 H) 2.18 (s, 3 H) 2.25 (s, 3 H) 2.29 (s, 6 H) 2.39-2.49 (m, 3 H) 2.52-2.62 (m, 2 H) 2.72-2.82 (m, 2 H) 2.93-2.99 (m, 1 H) 3.05-3.10 (m, 1 H) 3.15-3.21 (m, 1 H) 3.26 (s, 3 H) 3.42-3.54 (m, 2 H) 3.57 (s, 1 H) 3.79 (s, 3 H) 3.85-3.91 (m, 1 H) 3.96-4.03 (m, 1 H) 4.26 (d, J = 5.50 Hz, 1 H) 4.46-4.51 (m, 1 H) 4.56 (d, J = 7.34 Hz, 1 H) 5.00-5.05 (m, 1 H) 5.13 (dd, J = 11.00, 1.83 Hz, 1 H) 5.83 (s, 1 H) 6.84-6.91 (m, 2 H) 7.15-7.20 (m, 1 H) 7.59 (d, J = 7.79 Hz, 1 H) |

TABLE 9-continued

Formula (Q)

[Formula 48]

| Example | R$^{4b}$ | R$^{2d}$ | ESI MS (M + H) | $^1$H-NMR, CDCl$_3$, δ (ppm) |
|---|---|---|---|---|
| 343 | –NH$_2$ | –CH$_2$CH$_2$N(CH$_3$)$_2$ | 916.6 | (600 MHz): 0.85 (t, J = 7.34 Hz, 3 H) 1.14-1.19 (m, 12 H) 1.21 (d, J = 5.96 Hz, 3 H) 1.22-1.24 (m, 3 H) 1.22-1.26 (m, 1 H) 1.27 (d, J = 6.42 Hz, 3 H) 1.40 (s, 3 H) 1.49-1.58 (m, 1 H) 1.62-1.68 (m, 1 H) 1.72 (s, 3 H) 1.73-1.79 (m, 2 H) 1.85-1.92 (m, 2 H) 1.94-2.00 (m, 1 H) 2.02-2.10 (m, 1 H) 2.19-2.23 (m, 1 H) 2.23-2.24 (m, 6 H) 2.29 (s, 6 H) 2.33 (s, 3 H) 2.34-2.41 (m, 2 H) 2.43-2.50 (m, 1 H) 2.53-2.61 (m, 2 H) 2.71-2.76 (m, 1 H) 2.79 (d, J = 14.67 Hz, 1 H) 2.91-2.98 (m, 1 H) 3.04-3.10 (m, 1 H) 3.16-3.21 (m, 1 H) 3.26 (s, 3 H) 3.40-3.46 (m, 1 H) 3.52-3.57 (m, 1 H) 3.58 (s, 1 H) 3.85 (d, J = 10.55 Hz, 1 H) 4.00-4.07 (m, 1 H) 4.35 (d, J = 5.04 Hz, 1 H) 4.46 (br. s., 1 H) 4.58 (d, J = 7.34 Hz, 1 H) 5.02 (dd, J = 5.04, 2.75 Hz, 1 H) 5.14 (dd, J = 11.23, 2.06 Hz, 1 H) 5.83 (s, 1 H) |
| 344 | –N(CH$_3$)$_2$ | –CH$_2$CH$_2$N(CH$_3$)C(CH$_3$)$_2$-(2-OCH$_3$-C$_6$H$_4$) | 1078.9 | (600 MHz): 0.84 (t, J = 7.34 Hz, 3 H) 1.13 (s, 3 H) 1.15-1.18 (m, 6 H) 1.19-1.24 (m, 10 H) 1.31 (d, J = 6.42 Hz, 3 H) 1.40-1.45 (m, 9 H) 1.55-1.63 (m, 2 H) 1.66 (s, 3 H) 1.72-1.77 (m, 1 H) 1.78-1.82 (m, 1 H) 1.87-1.92 (m, 2 H) 1.94-1.99 (m, 1 H) 2.06-2.11 (m, 1 H) 2.14-2.17 (m, 1 H) 2.17-2.20 (m, 3 H) 2.25 (s, 3 H) 2.29 (s, 6 H) 2.40-2.51 (m, 3 H) 2.54-2.64 (m, 5 H) 2.66-2.73 (m, 1 H) 2.78-2.83 (m, 1 H) 2.83-2.89 (m, 3 H) 2.91-2.98 (m, 1 H) 3.16-3.21 (m, 2 H) 3.26 (s, 3 H) 3.38-3.43 (m, 1 H) 3.50-3.56 (m, 1 H) 3.53 (s, 1 H) 3.69-3.74 (m, 1 H) 3.79 (s, 3 H) 4.03 (q, J = 6.42 Hz, 1 H) 4.59-4.62 (m, 1 H) 4.86 (d, J = 4.58 Hz, 1 H) 5.04-5.07 (m, 1 H) 5.10-5.15 (m, 1 H) 5.59-5.62 (m, 1 H) 6.84-6.90 (m, 2 H) 7.14-7.19 (m, 1 H) 7.61 (d, J = 7.34 Hz, 1 H) |
| 345 | –N(CH$_3$)$_2$ | –CH$_2$CH$_2$N(CH$_3$)$_2$ | 944.7 | (600 MHz): 0.84 (t, J = 7.34 Hz, 3 H) 1.16 (t, J = 6.65 Hz, 6 H) 1.18-1.20 (m, 6 H) 1.20-1.23 (m, 6 H) 1.22-1.26 (m, 1 H) 1.33 (d, J = 6.42 Hz, 3 H) 1.42 (s, 3 H) 1.52-1.57 (m, 1 H) 1.65 (s, 3 H) 1.70-1.77 (m, 2 H) 1.78-1.81 (m, 1 H) 1.85-1.96 (m, 3 H) 2.13-2.20 (m, 1 H) 2.22-2.26 (m, 1 H) 2.24 (br. s., 6 H) 2.30 (br. s., 6 H) 2.34 (s, 3 H) 2.35-2.40 (m, 2 H) 2.47-2.63 (m, 9 H) 2.66-2.72 (m, 1 H) 2.70-2.83 (m, 1 H) 2.84-2.88 (m, 1 H) 2.90-2.96 (m, 1 H) 3.17-3.22 (m, 2 H) 3.26 (s, 3 H) 3.38-3.44 (m, 1 H) 3.53 (s, 1 H) 3.55-3.61 (m, 1 H) 3.69-3.72 (m, 1 H) 4.07 (q, J = 6.42 Hz, 1 H) 4.62 (d, J = 7.34 Hz, 1 H) 4.87-4.91 (m, 1 H) 5.03 (t, J = 4.13 Hz, 1 H) 5.11-5.15 (m, 1 H) 5.62 (s, 1 H) |

TABLE 9-continued

Formula (Q)

[Formula 48]

| Example | R^{4b} | R^{2d} | ESI MS (M + H) | ¹H-NMR, CDCl₃, δ (ppm) |
|---|---|---|---|---|
| 346 | H₃C-NH- | -CH₂C(CH₃)₂CH₂-N(CH₃)-C(CH₃)₂-(2-methoxyphenyl) | 1064.9 | (600 MHz): 0.85 (t, J = 7.34 Hz, 3 H) 1.12-1.18 (m, 12 H) 1.19-1.26 (m, 10 H) 1.39 (s, 3 H) 1.41-1.46 (m, 6 H) 1.52-1.60 (m, 1 H) 1.61-1.65 (m, 1 H) 1.71-1.77 (m, 2 H) 1.73 (s, 3 H) 1.85-2.08 (m, 5 H) 2.18 (s, 3 H) 2.25 (s, 3 H) 2.29 (s, 6 H) 2.39-2.48 (m, 3 H) 2.52-2.63 (m, 2 H) 2.72 (d, J = 5.04 Hz, 3 H) 2.75-2.82 (m, 2 H) 2.92-2.98 (m, 1 H) 3.06 (q, J = 6.57 Hz, 1 H) 3.18 (dd, J = 10.32, 7.11 Hz, 1 H) 3.26 (s, 3 H) 3.38-3.47 (m, 1 H) 3.48-3.52 (m, 1 H) 3.53-3.54 (m, 1 H) 3.80 (s, 3 H) 3.85 (d, J = 9.20 Hz, 1 H) 3.99-4.03 (m, 1 H) 4.20-4.24 (m, 1 H) 4.52-4.56 (m, 2 H) 5.01-5.04 (m, 1 H) 5.10-5.14 (m, 1 H) 5.83 (s, 1 H) 6.85-6.91 (m, 2 H) 7.17 (t, J = 7.34 Hz, 1 H) 7.60 (d, J = 7.79 Hz, 1 H) |
| 347 | H₃C-NH- | -CH₂C(CH₃)₂CH₂-N(CH₃)₂ | 930.7 | (600 MHz): 0.85 (t, J = 7.34 Hz, 3 H) 1.12-1.18 (m, 9 H) 1.18 (s, 3 H) 1.21-1.24 (m, 6 H) 1.23-1.25 (m, 1 H) 1.28 (d, J = 6.42 Hz, 3 H) 1.40 (s, 3 H) 1.53-1.66 (m, 2 H) 1.72 (s, 3 H) 1.73-1.77 (m, 2 H) 1.86-2.06 (m, 4 H) 2.21 (d, J = 14.67 Hz, 1 H) 2.23-2.25 (m, 6 H) 2.30 (s, 6 H) 2.34 (s, 3 H) 2.34-2.39 (m, 2 H) 2.43-2.51 (m, 1 H) 2.53-2.62 (m, 2 H) 2.72 (d, J = 5.04 Hz, 3 H) 2.73-2.78 (m, 1 H) 2.80 (d, J = 14.67 Hz, 1 H) 2.91-2.97 (m, 1 H) 3.06 (q, J = 6.42 Hz, 1 H) 3.19 (dd, J = 10.09, 7.34 Hz, 1 H) 3.26 (s, 3 H) 3.39-3.45 (m, 1 H) 3.52-3.58 (m, 1 H) 3.55 (s, 1 H) 3.84 (dd, J = 10.55, 1.38 Hz, 1 H) 4.06 (q, J = 6.42 Hz, 1 H) 4.30 (d, J = 5.04 Hz, 1 H) 4.47-4.51 (m, 1 H) 4.57 (d, J = 6.88 Hz, 1 H) 5.02 (dd, J = 5.04, 3.21 Hz, 1 H) 5.12 (dd, J = 11.00, 1.83 Hz, 1 H) 5.84 (s, 1 H) |
| 348 | quinolin-6-yl-CH=CH-CH₂-NH-C(CH₃)₂- | -CH₂C(CH₃)₂CH₂-N(CH₃)₂ | 1083.7 | (600 MHz): 0.82 (t, J = 7.34 Hz, 3 H) 1.13-1.19 (m, 15 H) 1.23 (d, J = 5.96 Hz, 3 H) 1.24-1.29 (m, 1 H) 1.31 (s, 3 H) 1.40 (s, 3 H) 1.51-1.59 (m, 1 H) 1.65 (d, J = 11.92 Hz, 1 H) 1.72-1.79 (m, 2 H) 1.77 (s, 3 H) 1.84-1.96 (m, 3 H) 2.03-2.09 (m, 1 H) 2.17-2.24 (m, 1 H) 2.22-2.24 (m, 6 H) 2.30 (s, 6 H) 2.34 (s, 3 H) 2.34-2.38 (m, 2 H) 2.44-2.50 (m, 1 H) 2.53-2.63 (m, 2 H) 2.75-2.83 (m, 2 H) 2.90-2.97 (m, 1 H) 3.06-3.11 (m, 1 H) 3.17-3.21 (m, 1 H) 3.26 (s, 3 H) 3.45 (br. s., 1 H) 3.53-3.58 (m, 1 H) 3.59 (s, 1 H) 3.84-3.91 (m, 2 H) 4.01-4.10 (m, 2 H) 4.29 (d, J = 4.58 Hz, 1 H) 4.57 (d, J = 7.34 Hz, 1 H) 4.88-4.92 (m, 1 H) 4.95-4.97 (m, 1 H) 5.13 (d, J = 11.00 Hz, 1 H) 5.83 (s, 1 H) 6.51 (dt, J = 15.82, 6.08 Hz, 1 H) 6.74 (d, J = 16.05 Hz, 1 H) 7.35 (dd, J = 8.02, 4.36 Hz, 1 H) 7.77 (s, 1 H) 7.88-7.92 (m, 1 H) 8.02 (d, J = 8.71 Hz, 1 H) 8.19 (d, J = 8.25 Hz, 1 H) 8.81-8.84 (m, 1 H) |

TABLE 9-continued

Formula (Q)

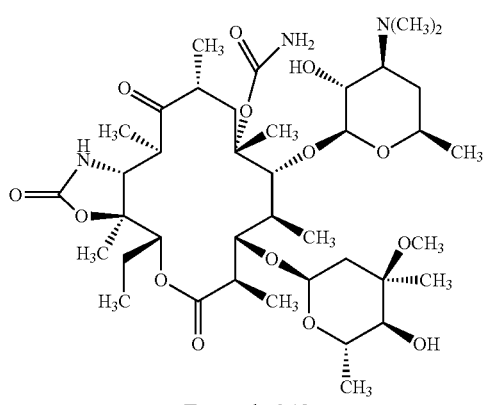

[Formula 48]

| Example | $R^{4b}$ | $R^{2d}$ | ESI MS (M + H) | $^1$H-NMR, CDCl$_3$, δ (ppm) |
|---|---|---|---|---|
| 349 | (quinolinyl-CH=CH-CH2-NH-) | (-CH(CH3)-) | 1026.7 | (600 MHz): 0.82 (t, J = 7.34 Hz, 3 H) 1.12-1.19 (m, 15 H) 1.22 (s, 3 H) 1.24-1.28 (m, 1 H) 1.27 (d, J = 6.42 Hz, 3 H) 1.39 (s, 3 H) 1.52-1.60 (m, 1 H) 1.63-1.68 (m, 1 H) 1.70-1.80 (m, 2 H) 1.78-1.79 (m, 3 H) 1.85-1.92 (m, 2 H) 1.95-2.03 (m, 2 H) 2.07 (dd, J = 15.13, 11.00 Hz, 1 H) 2.30 (br. s., 6 H) 2.36 (s, 6 H) 2.42-2.49 (m, 1 H) 2.73 (d, J = 14.21 Hz, 1 H) 2.77-2.83 (m, 1 H) 2.94-2.99 (m, 1 H) 3.06-3.11 (m, 1 H) 3.17-3.21 (m, 1 H) 3.26 (s, 3 H) 3.49-3.54 (m, 1 H) 3.59 (s, 1 H) 3.84-3.92 (m, 2 H) 4.02-4.09 (m, 2 H) 4.21 (d, J = 5.50 Hz, 1 H) 4.55 (d, J = 6.88 Hz, 1 H) 4.93-4.98 (m, 2 H) 5.13 (d, J = 9.17 Hz, 1 H) 5.82 (s, 1 H) 6.51 (dt, J = 15.93, 6.02 Hz, 1 H) 6.74 (d, J = 16.05 Hz, 1 H) 7.33-7.37 (m, 1 H) 7.75-7.79 (m, 1 H) 7.91 (dd, J = 8.94, 1.60 Hz, 1 H) 8.03 (d, J = 8.71 Hz, 1 H) 8.19 (d, J = 7.79 Hz, 1 H) 8.83 (dd, J = 4.13, 1.38 Hz, 1 H) |

Formula (SM4)

[Formula 49]

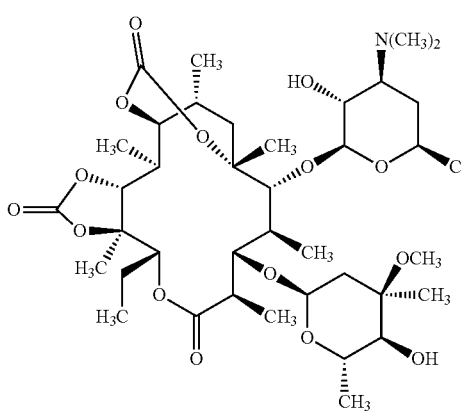

Example 342

(1) By using the compound represented by the formula (SM4) (335 mg) obtained by the method described in the publication (International Patent Publication WO08/014221) as a starting material, an epoxy compound (111 mg) was obtained in the same manners as those of Example 1, (1), (3), Example 4, (6) and Example 1, (4).
(2) By using the compound obtained in (1) mentioned above (105 mg) and the compound obtained in Reference Example 104 (91.5 mg) as starting materials, the compound shown in Table 9 (79.7 mg) was obtained in the same manner as that of Example 2, (5).

Example 343

By using the compound obtained in Example 342, (1) (100 mg) and N,N,N'-trimethylethylene-1,2-diamine (64 µl) as starting materials, the compound shown in Table 9 (28.3 mg) was obtained in the same manner as that of Example 2, (5).

Formula (SM5)

[Formula 50]

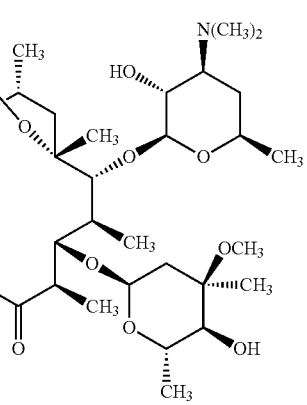

Example 344

(1) The compound represented by the formula (SM5) (600 mg) obtained by the method described in the literature (Journal of Medicinal Chemistry, 2003, vol. 46, p. 2706) was dissolved in tetrahydrofuran (10 ml), 50% aqueous dimethylamine (687 µl) was added to the solution, and the resulting mixture was stirred at room temperature for 2.5 days. The reaction mixture was concentrated under reduced pressure, and the resulting residue was purified by silica gel column chromatography (chloroform:methanol:28% aqueous ammonia=100:1:0.1 to 20:1:0.1) to obtain an amide compound (599 mg).

(2) By using the compound obtained in (1) mentioned above (590 mg) as a starting material, an epoxy compound (166 mg) was obtained in the same manners as those of Example 1, (1), (3) and (4).

(3) The compound obtained in (2) mentioned above (162 mg) was dissolved in a mixed solvent of tetrahydrofuran and dimethylformamide (2:1, 3 ml), 1,1'-carbonyldiimidazole (62.5 mg) and 60% sodium hydride (13.1 mg) were added to the solution under ice cooling, and the resulting mixture was stirred for 15 minutes. Aqueous sodium hydrogencarbonate and ethyl acetate were added to the reaction mixture, the layers were separated, and the organic layer was washed with saturated aqueous sodium hydrogencarbonate. The organic layer was dried over anhydrous magnesium sulfate, and filtered. The filtrate was concentrated under reduced pressure, the resulting residue was dissolved in a mixed solvent of tetrahydrofuran and acetonitrile (2:1, 3 ml), 28% aqueous ammonia (587 µl) was added to the solution, and the resulting mixture was stirred at room temperature for 40 hours. The reaction mixture was concentrated under reduced pressure, and the resulting residue was purified by silica gel column chromatography (chloroform:methanol:28% aqueous ammonia=100:1:0.1 to 30:1:0.1) to obtain a carbamate compound (84.5 mg).

(4) By using the compound obtained in (3) mentioned above (84.5 mg) as a starting material, a deprotected compound (79.2 mg) was obtained in the same manner as that of Example 4, (6).

(5) By using the compound obtained in (4) mentioned above (40 mg) and the compound obtained in Reference Example 104 (33.7 mg) as starting materials, the compound shown in Table 9 (16.8 mg) was obtained in the same manner as that of Example 4, (8).

Example 345

By using the compound obtained in Example 344, (4) (35 mg) as a starting material, the compound shown in Table 9 (16.5 mg) was obtained in the same manner as that of Example 4, (8).

Example 346

(1) By using the compound represented by the formula (SM5) (900 mg) obtained by the method described in the literature (Journal of Medicinal Chemistry, 2003, vol. 46, p. 2706), and 40% aqueous methylamine (887 µl) as starting materials, an epoxy compound (0.69 g) was obtained in the same manners as those of Example 344, (1), Example 1, (1), (3) and (4).

(2) By using the compound obtained in (1) mentioned above (0.47 g) as a starting material, a carbamate compound (269 mg) was obtained in the same manners as those of Example 344, (3) and Example 4, (6).

(3) By using the compound obtained in (2) mentioned above (90 mg) and the compound obtained in Reference Example 104 (77.1 mg) as starting materials, the compound shown in Table 9 (57.6 mg) was obtained in the same manner as that of Example 4, (8).

Example 347

By using the compound obtained in Example 346, (2) (40 mg) as a starting material, the compound shown in Table 9 (24.0 mg) was obtained in the same manner as that of Example 4, (8).

Example 348

(1) By using the compound represented by the formula (SM5) (900 mg) obtained by the method described in the literature (Journal of Medicinal Chemistry, 2003, vol. 46, p. 2706) and allylamine (257 µl) as starting materials, an amide compound (730 mg) was obtained in the same manner as that of Example 344, (1).

(2) The compound obtained in (1) mentioned above (350 mg) was dissolved in acetonitrile (8 ml), 6-bromoquinoline (190 µl), triethylamine (330 µl), tri-O-tolylphosphine (144 mg), and palladium(II) acetate (53.2 mg) were added to the solution under a nitrogen atmosphere, and the resulting mixture was stirred at 130° C. for 25 minutes under microwave irradiation. Ethyl acetate and saturated aqueous sodium hydrogencarbonate were added to the reaction mixture, and the layers were separated. The organic layer was dried over anhydrous magnesium sulfate, and filtered. The filtrate was concentrated under reduced pressure, and the resulting residue was purified by silica gel column chromatography (chloroform:methanol:28% aqueous ammonia=1:0:0 to 100:1:0.1 to 20:1:0.1) to obtain an adduct compound (326 mg).

(3) By using the compound obtained in (2) mentioned above (326 mg) as a starting material, an epoxy compound (31.9 mg) was obtained in the same manners as those of Example 1, (1), (3), (4), Example 344, (3), and Example 4, (6).

(4) By using the compound obtained in (3) mentioned above (14.0 mg) as a starting material, the compound shown in Table 9 (7.0 mg) was obtained in the same manner as that of Example 4, (8).

Example 349

By using the compound obtained in Example 348, (3) (14.0 mg) and 50% aqueous dimethylamine (6.4 µl) as starting materials, the compound shown in Table 9 (8.0 mg) was obtained in the same manner as that of Example 4, (8).

Examples 350 and 351

Preparation methods of the compounds represented by the formula (R) having $R^{24}$ and $R^{17}$ defined in Table 10 wherein $R^{4c}$ is methyl group are shown below.

TABLE 10

Formula (R)

[Formula 51]

| Example | R²⁴ | R¹⁷ | ESI MS (M + H) | ¹H-NMR, CDCl₃, δ (ppm) |
|---|---|---|---|---|
| 350 | piperidin-3-yl (H-N) | CH₃ | 960 | (400 MHz): 0.86 (t, J = 7.57 Hz, 3 H) 1.04 (d, J = 7.32 Hz, 3 H) 1.06 (d, J = 7.57 Hz, 3 H) 1.12 (s, 3 H) 1.16 (s, 3 H) 1.19 (d, J = 6.35 Hz, 6 H) 1.20-1.30 (m, 1 H) 1.24 (d, J = 6.10 Hz, 3 H) 1.27 (d, J = 7.08 Hz, 3 H) 1.38 (s, 3 H) 1.40-1.58 (m, 4 H) 1.62-2.07 (m, 12 H) 2.14 (d, J = 14.65 Hz, 1 H) 2.24 (s, 6 H) 2.30 (s, 3 H) 2.35 (s, 3 H) 2.36-2.66 (m, 8 H) 2.70-2.90 (m, 6 H) 2.95-3.12 (m, 1 H) 3.09 (s, 3 H) 3.21 (dd, J = 10.25, 7.32 Hz, 1 H) 3.29 (s, 3 H) 3.30-3.52 (m, 2 H) 3.65 (d, J = 7.32 Hz, 1 H) 3.76 (d, J = 8.52 Hz, 1 H) 3.95-4.02 (m, 2 H) 4.13 (q, J = 6.10 Hz, 1 H) 4.42 (d, J = 7.32 Hz, 1 H) 5.00 (d, J = 4.64 Hz, 1 H) 5.14 (dd, J = 11.23, 2.20 Hz, 1 H) |
| 351 | piperidin-3-yl (H-N) | 2-(2-methoxyphenyl)propan-2-yl (H₃C, CH₃, O-CH₃ on phenyl) | 1094 | (400 MHz): 0.83 (t, J = 7.57 Hz, 3 H) 1.04 (d, J = 7.08 Hz, 3 H) 1.06 (d, J = 7.32 Hz, 3 H) 1.12 (s, 6 H) 1.18 (d, J = 6.35 Hz, 3 H) 1.19 (d, J = 7.08 Hz, 3 H) 1.20-1.30 (m, 1 H) 1.23 (d, J = 6.10 Hz, 3 H) 1.27 (d, J = 7.08 Hz, 3 H) 1.39 (s, 3 H) 1.43 (s, 3 H) 1.44 (s, 3 H) 1.44-1.80 (m, 8 H) 1.86-2.08 (m, 7 H) 2.18 (s, 6 H) 2.26 (s, 3 H) 2.33 (s, 6 H) 2.39-2.90 (m, 1 H) 3.06-3.11 (m, 1 H) 3.10 (s, 3 H) 3.20 (dd, J = 10.25, 7.08 Hz, 1 H) 3.28 (s, 3 H) 3.30-3.48 (m, 2 H) 3.64 (d, J = 7.32 Hz, 1 H) 3.78 (d, J = 9.52 Hz, 1 H) 3.80 (s, 3 H) 3.95-4.02 (m, 2 H) 4.11 (q, J = 6.35 Hz, 1 H) 4.41 (d, J = 7.32 Hz, 1 H) 5.02 (d, J = 4.64 Hz, 1 H) 5.14 (dd, J = 11.23, 2.20 Hz, 1 H) 6.86-6.91 (m, 2 H) 7.15-7.20 (m, 1 H) 7.59-7.64 (m, 1 H) |

Example 350

(1) Clarithromycin (312 mg), the compound obtained in Reference Example 97 (693 mg), and imidazole (171 mg) were dissolved in ethanol (3.1 ml), and the solution was stirred at 70° C. for 3 days. Saturated aqueous sodium hydrogencarbonate and chloroform were added to the reaction mixture, the layers were separated, and the organic layer was dried over anhydrous sodium sulfate, and filtered. The filtrate was concentrated under reduced pressure, and the resulting residue was purified by silica gel column chromatography (ethyl acetate to ethyl acetate:ethanol:28% aqueous ammonia=5:1:0.1) to obtain an oxime compound. A 4 mol/L solution of hydrochloric acid in dioxane (523 μl) was added to the collected 4-nitrobenzyl(R)-3-(aminooxy)piperidine-1-carboxylate, and then the mixture was concentrated under reduced pressure. By using the resulting hydrochloride (410 mg), clarithromycin (185 mg), and imidazole (101 mg), reactions and purification were performed in the same manners as those described above to obtain an oxime compound (698 mg in total).

(2) By using the compound obtained in (1) mentioned above (348 mg) as a starting material, a 2'-acetyl compound (303 mg) was obtained in the same manner as that of Example 1, (1).

(3) By using the compound obtained in (2) mentioned above (272 mg) as a starting material, a ketone compound (339 mg) was obtained in the same manner as that of Example 6, (3).

(4) By using the compound obtained in (3) mentioned above (339 mg) as a starting material, a deprotected compound (214 mg) was obtained in the same manner as that of Example 4, (6).

(5) By using the compound obtained in (4) mentioned above (169 mg) as a starting material, an epoxy compound (54 mg) was obtained in the same manner as that of Example 1, (4).

(6) By using the compound obtained in (5) mentioned above (16 mg) and N,N,N'-trimethylethane-1,2-diamine (8.1 μl) as starting materials, an adduct compound (11 mg) was obtained in the same manner as that of Example 129, (3).

(7) The compound obtained in (6) mentioned above (11 mg) was dissolved in a mixed solvent of dioxane and distilled water (2:1, 228 µl), 5% palladium/carbon (11 mg) was added to the solution under an argon atmosphere, and the resulting mixture was stirred at room temperature for 4 hours under a hydrogen atmosphere of 1 atm. The reaction mixture was filtered thorough Celite, then the filtrate was concentrated under reduced pressure, and the resulting residue was purified by preparative thin layer chromatography (chloroform:methanol:28% aqueous ammonia=10:1:0.1) to obtain the compound shown in Table 10 (6.9 mg).

Example 351

By using the compound obtained in Example 350, (5) (38 mg) and the compound obtained in Reference Example 104 (35 mg) as starting materials, the compound shown in Table 10 (14 mg) was obtained in the same manners as those of Example 129, (3) and Example 350, (7).

Examples 352 and 353

Preparation methods of the compounds represented by the formula (R) having $R^{24}$ and $R^{17}$ defined in Table 11 wherein $R^{4c}$ is hydrogen atom are shown below.

Example 352

(1) (E)-Erythromycin A 9-oxime (22.0 g) obtained by the method described in the literature (The Journal of Antibiotics, 1991, vol. 44, No. 3, p. 313) was dissolved in tetrahydrofuran (250 ml), powder of 85% potassium hydroxide (2.3 g), tetrabutylammonium bromide (473 mg), and 2-chlorobenzyl chloride (4.5 ml) were added to the solution, and the resulting mixture was stirred at 45° C. for 2 hours. The reaction mixture was poured into distilled water under ice cooling, ethyl acetate was added to the mixture, and the layers were separated. The aqueous layer was extracted with ethyl acetate, the organic layers were combined, and successively washed twice with distilled water and saturated aqueous sodium chloride, and then the organic layer was dried over anhydrous sodium sulfate, and filtered. The filtrate was concentrated under reduced pressure, the resulting residue was dissolved in ethyl acetate, hexane was added to the solution, and the deposited solid was collected by filtration to obtain an alkyl compound (14.5 g). The filtrate was concentrated under reduced pressure, ethyl acetate and hexane were added to the resulting residue, and the mixture was similarly treated to obtain an alkyl compound (5.16 g).

(2) By using the compound obtained in (1) mentioned above (13.0 g) as a starting material, an acetyl compound (13.7 g) was obtained in the same manner as that of Example 1, (1).

(3) By using the compound obtained in (2) mentioned above (5.00 g) as a starting material, a ketone compound (4.97 g) was obtained in the same manner as that of Example 1, (3).

(4) By using the compound obtained in (3) mentioned above (4.97 g) as a starting material, a deprotected compound (4.74 g) was obtained in the same manner as that of Example 4, (6).

(5) By using the compound obtained in (4) mentioned above (4.74 g) as a starting material, an epoxy compound (4.67 g) was obtained in the same manner as that of Example 1, (4).

(6) 5% Palladium/carbon (1.77 g), ammonium formate (114 mg), methanol (17 ml), and formic acid (850 µl) were added to the compound obtained in (5) mentioned above (800 mg) under an argon atmosphere, and the resulting mixture was stirred at 45° C. for 2.5 hours under a hydrogen atmosphere of 1 atm. The reaction mixture was filtered, and then the filtrate was concentrated under reduced pressure. Ethyl acetate and saturated aqueous sodium hydrogencarbonate were added to

TABLE 11

| Example | $R^{24}$ | $R^{17}$ | ESI MS (M + H) | $^1$H-NMR, CDCl$_3$, δ (ppm) |
|---|---|---|---|---|
| 352 | H₃C–O–CH(CH₃)– | –C(CH₃)₂–(2-OCH₃-C₆H₄) | 1041.8 | (400 MHz): 0.84 (t, J = 7.3 Hz, 3 H) 1.05 (d, J = 7.1 Hz, 3 H) 1.07-1.30 (m, 22 H) 1.38-1.73 (m, 14 H) 2.18 (s, 3 H) 2.22-2.36 (m, 9 H) 2.38-2.74 (m, 6 H) 2.76-2.94 (m, 2 H) 3.10 (s, 1 H) 3.22 (dd, J = 9.9, 7.2 Hz, 1 H) 3.28 (s, 3 H) 3.37-3.50 (m, 5 H) 3.60 (d, J = 7.1 Hz, 1 H) 3.70-3.84 (m, 5 H) 4.04 (d, J = 9.3 Hz, 1 H) 4.09 (q, J = 6.2 Hz, 1 H) 4.26 (s, 1 H) 4.41 (d, J = 7.3 Hz, 1 H) 4.98 (d, J = 4.9 Hz, 1 H) 5.04 (d, J = 7.3 Hz, 1 H) 5.10 (dd, J = 11.2, 2.0 Hz, 1 H) 5.14 (d, J = 7.3 Hz, 1 H) 6.84-6.92 (m, 2 H) 7.18 (t, J = 7.3 Hz, 1 H) 7.61 (d, J = 7.3 Hz, 1 H) |
| 353 | (CH₃)₂N–CH₂CH₂CH₂– | –C(CH₃)₂–(2-OCH₃-C₆H₄) | 1068.8 | (400 MHz): 0.83 (t, J = 7.3 Hz, 3 H) 1.00 (d, J = 6.8 Hz, 3 H) 1.05-1.28 (m, 21 H) 1.39-1.69 (m, 15 H) 1.86-2.09 (m, 6 H) 2.18 (s, 3 H) 2.20 (s, 6 H) 2.26 (s, 3 H) 2.30 (s, 6 H) 2.38-2.68 (m, 6 H) 2.82 (d, J = 14.9 Hz, 1 H) 2.85-2.95 (m, 2 H) 3.17 (s, 1 H) 3.23 (dd, J = 9.9, 7.2 Hz, 1 H) 3.28 (s, 3 H) 3.33-3.39 (m, 1 H) 3.39-3.49 (m, 1 H) 3.52 (d, J = 8.3 Hz, 1 H) 3.62-3.72 (m, 1 H) 3.80 (s, 3 H) 3.93 (s, 1 H) 4.08-4.17 (m, 3 H) 4.23 (d, J = 10.0 Hz, 1 H) 4.37 (d, J = 7.3 Hz, 1H) 4.62-4.73 (m, 1 H) 4.95 (d, J = 4.9 Hz, 1 H) 5.12 (dd, J = 11.1, 2.1 Hz, 1 H) 5.88 (s, 1 H) 6.85-6.90 (m, 2 H) 7.14-7.20 (m, 1 H) 7.62-7.67 (m, 1H) | the resulting residue, the layers were separated, and the organic layer was dried over anhydrous sodium sulfate, and filtered. The filtrate was concentrated under reduced pressure, and the resulting residue was purified by column chromatography (chloroform:methanol:28% aqueous ammonia=95:5:0.5) to obtain an oxime compound (190 mg).

(7) The compound obtained in (6) mentioned above (50 mg) was dissolved in tetrahydrofuran (500 μl), potassium hydroxide (4.42 mg) and methoxymethyl chloride (6.0 μl) were added to the solution at room temperature, and the resulting mixture was stirred at room temperature for 55 minutes. Ethyl acetate and distilled water were added to the reaction mixture, the layers were separated, and the organic layer was dried over anhydrous sodium sulfate, and filtered. The filtrate was concentrated under reduced pressure, and the resulting residue was purified by silica gel column chromatography (chloroform:methanol:28% aqueous ammonia=94:6:0.6) to obtain a methoxymethyl compound (32.0 mg).

(8) By using the compound obtained in (7) mentioned above (22.0 mg) and the compound obtained in Reference Example 104 (12.9 mg) as starting materials, the compound shown in Table 11 (20.0 mg) was obtained in the same manner as that of Example 4, (8).

sium hydroxide (26.5 mg) were added to the compound obtained in Example 352, (6) (150 mg) at room temperature, and the resulting mixture was stirred overnight at 60° C. Further, 2-chloro-N,N-dimethylethanamine hydrochloride (34.1 mg) and powder of 85% potassium hydroxide (26.5 mg) were added to the mixture, and the resulting mixture was stirred at 50° C. for 5 hours. Ethyl acetate and saturated aqueous sodium hydrogencarbonate were added to the reaction mixture, and the layers were separated. The organic layer was dried over anhydrous sodium sulfate, and filtered. The filtrate was concentrated under reduced pressure, and the resulting residue was purified by preparative thin layer chromatography (chloroform:methanol:28% aqueous ammonia=9:0.8:0.08) to obtain a dimethylaminoethyl compound (63.1 mg).

(2) By using the compound obtained in (1) mentioned above (37.0 mg) and the compound obtained in Reference Example 104 (10.5 mg) as starting materials, the compound shown in Table 11 (31.0 mg) was obtained in the same manner as that of Example 4, (8).

Example 353

(1) Tetrahydrofuran (1.5 ml), 2-chloro-N,N-dimethylethanamine hydrochloride (34.1 mg), and powder of 85% potas- Examples 354 to 362

Preparation methods of the compounds represented by the formula (S) having $R^{1c}$ defined in Table 12 are shown below.

TABLE 12

Formula (S)

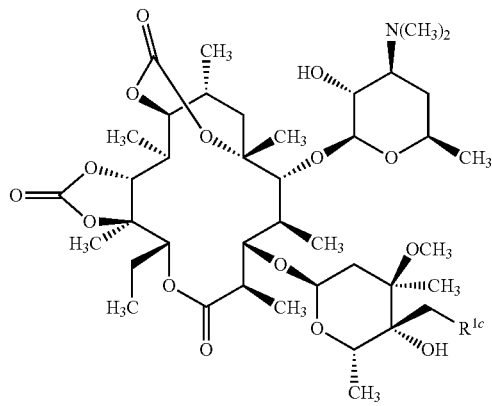

[Formula 52]

| Example | $R^{1c}$ | ESI MS (M + H) | $^1$H-NMR, CDCl$_3$, δ (ppm) |
|---|---|---|---|
| 354 | | 1036 | (400 MHz): 0.88 (t, J = 7.57 Hz, 3 H) 1.11 (d, J = 5.62 Hz, 9 H) 1.12 (s, 3 H) 1.17 (d, J = 6.35 Hz, 3 H) 1.20-1.30 (m, 1 H) 1.22 (d, J = 5.86 Hz, 3 H) 1.24 (d, J = 5.86 Hz, 3 H) 1.44 (s, 6 H) 1.48 (s, 3 H) 1.50-2.15 (m, 9 H) 1.69 (s, 3 H) 2.18 (s, 3 H) 2.26 (s, 3 H) 2.29 (s, 6 H) 2.37-2.71 (m, 7 H) 2.74-2.83 (m, 1 H) 2.82 (d, J = 14.88 Hz, 1 H) 3.21 (dd, J = 10.25, 7.32 Hz, 1 H) 3.24 (s, 3 H) 3.40-3.55 (m, 2 H) 3.81 (s, 3 H) 3.81-3.84 (m, 1 H) 3.93 (dd, J = 8.55, 2.20 Hz, 1 H) 4.09 (q, J = 6.35 Hz, 1 H) 4.14 (d, J = 9.52 Hz, 1 H) 4.33 (d, J = 7.08 Hz, 1 H) 4.68 (s, 1 H) 4.93 (d, J = 4.36 Hz, 1 H) 5.05 (dd, J = 10.74, 2.44 Hz, 1 H) 6.85-6.92 (m, 2 H) 7.15-7.22 (m, 1 H) 7.60 (d, J = 7.32 Hz, 1 H) |

TABLE 12-continued

Formula (S)

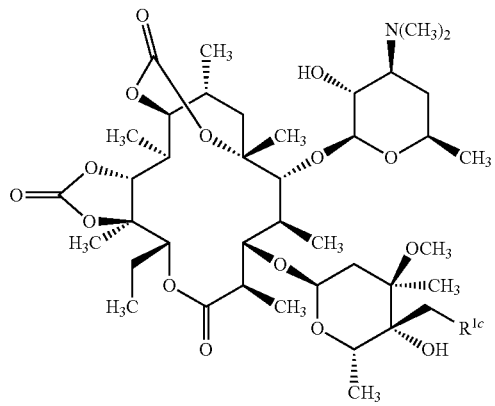

[Formula 52]

| Example | R[1c] | ESI MS (M + H) | $^1$H-NMR, CDCl[3], δ (ppm) |
|---|---|---|---|
| 355 | [structure: CH[2]-N(CH[3])-CH[2]CH[2]-N(CH[3])-C(CH[3])[2]-(3-pyridyl with 2-OCH[3])] | 1037 | (400 MHz): 0.88 (t, J = 7.57 Hz, 3 H) 1.11 (d, J = 7.57 Hz, 9 H) 1.13 (s, 3 H) 1.18 (d, J = 6.35 Hz, 3 H) 1.20-1.30 (m, 1 H) 1.23 (d, J = 7.08 Hz, 3 H) 1.24 (d, J = 6.10 Hz, 3 H) 1.42 (s, 6 H) 1.48 (s, 3 H) 1.50-2.14 (m, 9 H) 1.69 (s, 3 H) 2.19 (s, 3 H) 2.26 (s, 3 H) 2.30 (s, 6 H) 2.34-2.70 (m, 7 H) 2.74-2.85 (m, 1 H) 2.84 (d, J = 14.65 Hz, 1 H) 3.22 (dd, J = 10.01, 7.08 Hz, 1 H) 3.25 (s, 3 H) 3.40-3.56 (m, 2 H) 3.81 (d, J = 9.03 Hz, 1 H) 3.90-3.96 (m, 1 H) 3.93 (s, 3 H) 4.09 (q, J = 6.35 Hz, 1 H) 4.15 (d, J = 9.28 Hz, 1 H) 4.33 (d, J = 7.32 Hz, 1 H) 4.68 (s, 1 H) 4.94 (d, J = 4.64 Hz, 1 H) 5.05 (dd, J = 10.74, 2.44 Hz, 1 H) 6.82 (dd, J = 7.32, 4.88 Hz, 1 H) 7.96 (dd, J = 7.57, 1.71 Hz, 1 H) 8.02 (dd, J = 4.64, 1.71 Hz, 1 H) |
| 356 | [structure: CH[2]-NH-CH[2]CH[2]-N(Et)-CH(CH[3])-(2-methoxyphenyl)] | 1022.6 | (400 MHz): 0.88 (t, J = 7.3 Hz, 3 H) 0.82-1.02 (m, 3 H) 1.05-1.36 (m, 26 H) 1.48 (s, 3 H) 1.51-1.75 (m, 2 H) 1.75-2.19 (m, 7 H) 2.27 (s, 6 H) 2.38-2.87 (m, 14 H) 3.16-3.26 (m, 4 H) 3.44-3.58 (m, 1 H) 3.75-3.85 (m, 4 H) 3.93 (dd, J = 10.4, 2.3 Hz, 1 H) 4.16 (d, J = 9.3 Hz, 1 H) 4.20-4.29 (m, 1 H) 4.33 (d, J = 7.3 Hz, 1 H) 4.35-4.45 (m, 1 H) 4.69 (s, 1 H) 4.92 (d, J = 4.4 Hz, 1 H) 5.05 (dd, J = 10.4, 2.3 Hz, 1 H) 6.86 (d, J = 8.1 Hz, 1 H) 6.94 (t, J = 7.2 Hz, 1 H) 7.17-7.37 (m, 2 H) |
| 357 | [structure: CH[2]-NH-CH(CH[2]OH)-CH[2]-N(Et)-CH(CH[3])-(2-methoxyphenyl)] | 1052 FAB MASS | (400 MHz): 0.88 (t, J = 7.3 Hz, 3 H) 1.02-1.25 (m, 26 h) 1.35 (d, J = 6.8 Hz, 3 H) 1.48 (s, 3 H) 1.51-1.67 (m, 3 H) 1.68 (s, 3 H) 1.74-1.91 (m, 5 H) 2.02 (d, J = 14.6 Hz 1 H) 2.11 (t, J = 13.7 Hz, 1 H) 2.28 (s, 6 H) 2.33-2.61 (m, 6 H) 2.64-2.86 (m, 5 H) 3.15-3.22 (m, 1 H) 3.23 (s, 3 H), 3.41-3.62 (m, 3 H), 3.76 (d, J = 9.3 Hz, 1 H) 3.83 (s, 3 H) 3.94 (dd, J = 8.8, 2.0 Hz, 1 H) 4.16 (d, J = 9.0 Hz, 1 H) 4.25-4.31 (m, 2 H) 4.46 (q, J = 6.8 Hz, 1 H) 4.68 (s, 1 H), 4.90 (d, J = 4.4 Hz, 1 H) 5.05 (dd, J = 10.6, 2.3 Hz, 1 H) 6.89 (d, J = 8.1 Hz, 1 H) 6.95 (t, J = 7.1 Hz, 1 H) 7.22-7.30 (m, 2 H) |
| 358 | [structure: CH[2]-N(CH[3])-CH[2]CH[2]-N(CH[3])[2]] | 902 FAB MASS | (400 MHz): 0.88 (t, J = 7.3 Hz, 3H) 1.08-1.26 (m, 21 H) 1.48 (s, 3 H) 1.49-1.61 (m, 2 H) 1.66-1.71 (m, 5 H) 1.94 (dd J = 14.8, 4.8 Hz, 2 H), 2.01 (d, J = 13.9 Hz, 1 H) 2.09 (d, J = 12.7 Hz 1 H) 2.16 (d, J = 14.9 Hz, 1 H) 2.27 (s, 6 H) 2.30 (s, 6 H) 2.35 (s, 3 H) 2.39-2.58 (m 4 H) 2.58-2.69 (m, 1 H) 2.75-2.87 (m, 2 H) 3.21 (dd, J = 10.1, 7.4 Hz, 1 H) 3.25 (s, 3 H) 3.44-3.53 (m, 2 H) 3.83 (d, J = 9.0 Hz, 1 H) 3.93 (dd, J = 8.5, 2.2 Hz, 1 H) 4.08-4.14 (m, 2 H) 4.33 (d, J = 7.3 Hz, 1 H) 4.69 (s, 1 H) 4.91 (d, J = 3.9 Hz, 1 H) 5.05 (dd, J = 10.6, 2.6 Hz, 1 H) |

TABLE 12-continued

Formula (S)

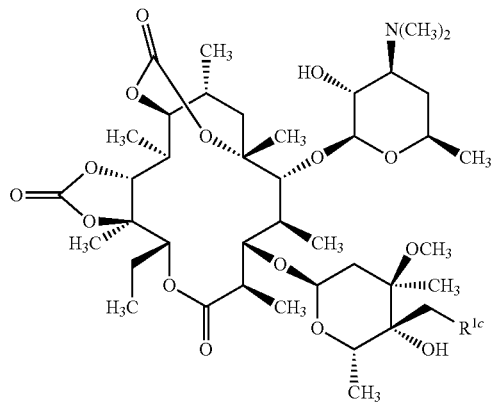

[Formula 52]

| Example | R[1c] | ESI MS (M + H) | $^1$H-NMR, CDCl[3], δ (ppm) |
|---|---|---|---|
| 359 | (structure: wavy-NH-CH(CH3)-CH2-N(CH3)-C(CH3)2-(2-methoxyphenyl)) | 1036 | (400 MHz): 0.88 (t, J = 7.57 Hz, 3 H) 0.92 (d, J = 6.10 Hz, 3 H) 1.11 (d, J = 6.84 Hz, 6 H) 1.12 (d, J = 7.08 Hz, 3 H) 1.14 (s, 3 H) 1.19 (d, J = 6.10 Hz, 3 H) 1.20 (d, J = 6.10 Hz, 3 H) 1.20-1.30 (m, 1 H) 1.23 (d, J = 7.08 Hz, 3 H) 1.44 (s, 6 H) 1.48 (s, 3 H) 1.50-2.28 (m, 9 H) 1.69 (s, 3 H) 2.13 (s, 3 H) 2.28 (s, 6 H) 2.39-2.52 (m, 4 H) 2.64-2.72 (m, 1 H) 2.76-2.85 (m, 1 H) 3.04 (d, J = 13.18 Hz, 1 H) 3.20 (dd, J = 10.01, 7.32 Hz, 1 H) 3.27 (s, 3 H) 3.44-3.56 (m, 2 H) 3.80 (s, 3 H) 3.80-3.87 (m, 1 H) 3.94 (dd, J = 8.30, 1.71 Hz, 1 H) 4.14 (d, J = 9.52 Hz, 1 H) 4.21 (q, J = 6.10 Hz, 1 H) 4.34 (d, J = 7.08 Hz, 1 H) 4.68 (s, 1 H) 4.91-4.95 (m, 1 H) 5.06 (dd, J = 10.74, 2.69 Hz, 1 H) 6.86-6.92 (m, 2 H) 7.18-7.23 (m, 1 H) 7.41-7.45 (m, 1 H) |
| 360 | (structure: wavy-NH-CH(CH3)-CH2-N(CH3)-C(CH3)2-(2-methoxypyridin-3-yl)) | 1037 | (400 MHz): 0.88 (t, J = 7.32 Hz, 3 H) 0.93 (d, J = 6.10 Hz, 3 H) 1.10 (s, 3 H) 1.11 (d, J = 6.59 Hz, 6 H) 1.12 (d, J = 7.08 Hz, 3 H) 1.14 (s, 3 H) 1.19 (d, J = 6.59 Hz, 3 H) 1.20-1.30 (m, 1 H) 1.21 (d, J = 6.35 Hz, 3 H) 1.23 (d, J = 9.28 Hz, 3 H) 1.40 (s, 3 H) 1.42 (s, 3 H) 1.48 (s, 6 H) 1.52-1.90 (m, 5 H) 1.69 (s, 3 H) 1.92-2.19 (m, 5 H) 2.12 (s, 3 H) 2.23-2.32 (m, 1 H) 2.28 (s, 6 H) 2.35-2.53 (m, 4 H) 2.60-2.71 (m, 1 H) 2.76-2.85 (m, 1 H) 3.02 (d, J = 13.18 Hz, 1 H) 3.20 (dd, J = 10.25, 7.32 Hz, 1 H) 3.27 (s, 3 H) 3.47-3.56 (m, 2 H) 3.83 (d, J = 8.79 Hz, 1 H) 3.92-3.96 (m, 1 H) 3.93 (s, 3 H) 4.14 (d, J = 9.52 Hz, 1 H) 4.23 (q, J = 6.35 Hz, 1 H) 4.34 (d, J = 7.08 Hz, 1 H) 4.68 (s, 1 H) 4.91-4.95 (m, 1 H) 5.06 (dd, J = 10.50, 2.44 Hz, 1 H) 6.83 (dd, J = 7.57, 4.88 Hz, 1 H) 7.73 (dd, J = 7.32, 1.71 Hz, 1 H) 8.04 (dd, J = 4.64, 1.71 Hz, 1 H) |
| 361 | (structure: wavy-N(CH3)-CH2-CH2-N(CH3)-C(CH3)2-phenyl) | 1006 | (400 MHz): 0.88 (t, J = 7.32 Hz, 3 H) 1.11 (d, J = 5.13 Hz, 9 H) 1.12 (s, 3 H) 1.19 (d, J = 6.35 Hz, 3 H) 1.20-1.30 (m, 1 H) 1.23 (d, J = 7.08 Hz, 3 H) 1.24 (d, J = 5.86 Hz, 3 H) 1.35 (s, 6 H) 1.48 (s, 3 H) 1.50-1.89 (m, 5 H) 1.70 (s, 3 H) 1.94-2.15 (m, 4 H) 1.98 (s, 3 H) 2.22-2.56 (m, 7 H) 2.26 (s, 3 H) 2.28 (s, 6 H) 2.75-2.84 (m, 2 H) 3.20 (dd, J = 10.01, 7.08 Hz, 1 H) 3.25 (s, 3 H) 3.41-3.54 (m, 2 H) 3.82 (d, J = 9.03 Hz, 1 H) 3.94 (dd, J = 8.79, 2.20 Hz, 1 H) 4.08 (q, J = 6.35 Hz, 1 H) 4.15 (d, J = 9.28 Hz, 1 H) 4.33 (d, J = 7.08 Hz, 1 H) 4.69 (s, 1 H) 4.96 (d, J = 4.15 Hz, 1 H) 5.06 (dd, J = 10.74, 2.44 Hz, 1 H) 7.15-7.20 (m, 1 H) 7.24-7.31 (m, 2 H) 7.52-7.56 (m, 2 H) |

TABLE 12-continued

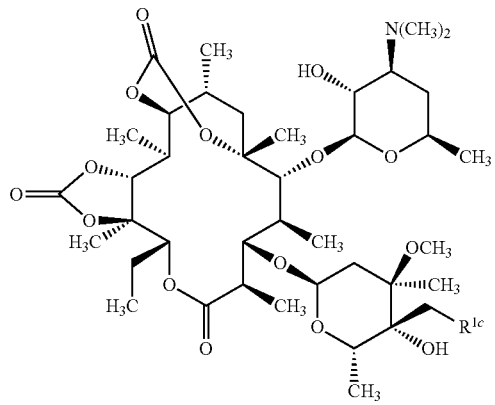

Formula (S)

[Formula 52]

| Example | $R^{1c}$ | ESI MS (M + H) | $^1$H-NMR, CDCl$_3$, δ (ppm) |
|---|---|---|---|
| 362 | 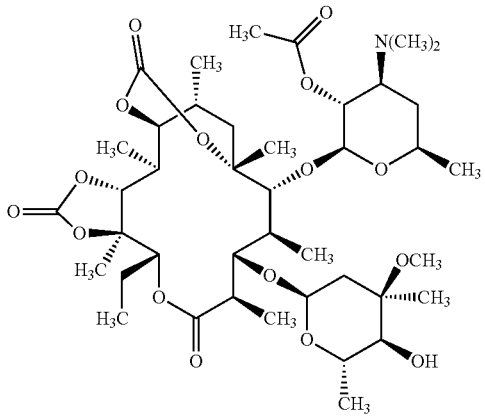 | 1022 | (400 MHz): 0.88 (t, J = 7.20 Hz, 3 H) 1.00-1.28 (m, 21 H) 1.27-1.45 (m, 2 H) 1.48 (s, 6 H) 1.52-1.74 (m, 4 H) 1.76-2.12 (m, 8 H) 2.16 (d, J = 14.9 Hz, 1 H) 2.27 and 2.30 (each s, 6 H) 2.39-2.47 (m, 5 H) 2.49 (s, 3 H) 2.73-2.84 (m, 1 H) 2.86 (s, 3 H) 2.91 (d, J = 14.9 Hz, 1 H) 3.17-3.21 (m, 1 H) 3.22 and 3.26 (each s, 3 H) 3.37-3.54 (m, 1 H) 3.76 and 3.80 (each d, J = 8.54 Hz, 1 H) 3.84 and 3.87 (each s, 3 H) 3.91-3.96 (m, 1 H) 4.02-4.23 (m, 2 H) 4.30 and 4.33 (each d, J = 7.07 Hz, 1 H) 4.67 and 4.68 (each s, 1 H) 4.91 and 4.93 (each d, J = 4.64 Hz, 1 H) 5.02-5.08 (m, 1 H) 6.92 (d, J = 8.3 Hz, 1 H) 6.99 (d, J = 7.45 Hz, 1 H) 7.17-7.24 (m, 1 H) 7.35 (t, J = 7.81 Hz, 1 H) |

Formula (SM6)

[Formula 53]

Example 354

(1) By using the compound represented by the formula (SM6) (10 g) obtained by the method described in the literature (Journal of Medicinal Chemistry, 2003, vol. 46, No. 13, p. 2706) as a starting material, a ketone compound (18.4 g) was obtained in the same manner as that of Example 1, (3).

(2) The compound obtained in (1) mentioned above (18.4 g) was dissolved in methanol (200 ml), and the solution was stirred at 50° C. for 5 hours. The reaction mixture was concentrated under reduced pressure, and the resulting residue was purified by silica gel column chromatography (chloroform to chloroform:methanol:28% aqueous ammonia=40:1:0.1). The resultant was further purified by silica gel column chromatography (ethyl acetate to chloroform:methanol:28% aqueous ammonia=10:1:0.1), and then dissolved in ethyl acetate (30 ml). Hexane (18 ml) was added to the solution with stirring, and the deposited solid was collected by filtration to obtain a deprotected compound (6.95 g).

(3) By using the compound obtained in (2) mentioned above (1.88 g) as a starting material, an epoxy compound (1.49 g) was obtained in the same manner as that of Example 1, (4).

(4) The compound obtained in (3) mentioned above (40 mg) was dissolved in ethanol (200 μl), the compound obtained in Reference Example 104 (36 mg) was added to the solution, and the resulting mixture was stirred at 40° C. for 15 hours. The reaction mixture was concentrated under reduced pressure, and the resulting residue was purified by preparative thin layer chromatography (chloroform to chloroform:methanol:28% aqueous ammonia=10:1:0.1), and then purified again by preparative thin layer chromatography (chloroform:methanol:28% aqueous ammonia=5:1:0.1) to obtain the compound shown in Table 12 (19.8 mg).

Example 355

By using the compound obtained in Example 354, (3) (80 mg) and the compound obtained in Reference Example 105 (48 mg) as starting materials, the compound shown in Table 12 (37 mg) was obtained in the same manner as that of Example 354, (4).

Example 356

Tetrahydrofuran (300 μl) and the compound obtained in Reference Example 102 (22.2 mg) were added to the compound obtained in Example 354, (3) (30.0 mg) and ytterbium tris(trifluoromethanesulfonate) (23.3 mg), and the resulting mixture was stirred at room temperature for 5 minutes, and then concentrated under reduced pressure until the mixture became a syrup-like substance. The resulting residue was stirred at 75° C. for 12 hours, and then the reaction mixture was purified by preparative thin layer chromatography (chloroform:methanol:28% aqueous ammonia=10:1:0.1) to obtain the compound shown in Table 12 (7.2 mg).

Example 357

By using the compound obtained in Example 354, (3) (30 mg) and the compound obtained in Reference Example 103 (25.0 mg) as starting materials, the compound shown in Table 12 (24.3 mg) was obtained in the same manner as that of Example 356.

Example 358

By using the compound obtained in Example 354, (3) (30 mg) and N,N,N'-trimethylethane-1,2-diamine (23.3 mg) as starting materials, the compound shown in Table 12 (10.1 mg) was obtained in the same manner as that of Example 356.

Example 359

The compound obtained in Example 354, (3) (10 mg) and the compound obtained in Reference Example 107 (5.9 mg) were dissolved in dimethylformamide (50 µl), potassium iodide (21 mg) was added to the solution, and the resulting mixture was stirred at 50° C. for 24 hours. Distilled water and ethyl acetate were added to the reaction mixture, the layers were separated, and the organic layer was dried over anhydrous sodium sulfate, and filtered. The filtrate was concentrated under reduced pressure, and the resulting residue was purified by preparative thin layer chromatography (methylene chloride:ethanol:28% aqueous ammonia=11:1:0.1) to obtain the compound shown in Table 12 (5.1 mg).

Example 360

By using the compound obtained in Example 354, (3) (64 mg) and the compound obtained in Reference Example 108 (38 mg) as starting materials, the compound shown in Table 12 (37 mg) was obtained in the same manner as that of Example 359.

Example 361

By using the compound obtained in Example 354, (3) (80 mg) and the compound obtained in Reference Example 109 (47 mg) as starting materials, the compound shown in Table 12 (94 mg) was obtained in the same manner as that of Example 359.

Example 362

By using the compound obtained in Example 354, (3) (60 mg) and the compound obtained in Reference Example 101 (34 mg) as starting materials, the compound shown in Table 12 (68 mg) was obtained in the same manner as that of Example 359.

Examples 363 to 366

Preparation methods of the compounds represented by the formula (T) having $R^{28}$ and $R^{17}$ defined in Table 13 are shown below.

TABLE 13

Formula (T)

[Formula 54]

| Example | $R^{28}$ | $R^{17}$ | ESI MS (M + H) | $^{1}$H-NMR, CDCl$_3$, δ (ppm) |
| --- | --- | --- | --- | --- |
| 363 | (structure) | (structure) | 1045.7 | (500 MHz): 0.90 (t, J = 7.26 Hz, 3 H) 1.04 (d, J = 6.50 Hz, 3 H) 1.07-1.28 (m, 19 H) 1.39 (s, 3 H) 1.41-1.50 (m, 9 H) 1.53-1.69 (m, 2 H) 1.73-2.07 (m, 7 H) 2.18 (s, 3 H) 2.22-2.34 (m, 9 H) 2.39-2.65 (m, 6 H) 2.78-2.91 (m, 2 H) 2.99-3.05 (m, 1 H) 3.06-3.13 (m, 4 H) 3.18 (dd, J = 9.94, 7.26 Hz, 1 H) 3.29 (s, 3 H) 3.42-3.50 (m, 1 H) 3.72 (d, J = 6.88 Hz, 1 H) 3.77-3.86 (m, 4 H) 4.05 (q, J = 6.12 Hz, 1 H) 4.44 (d, J = 7.26 Hz, 1 H) 4.72 (s, 1 H) 4.99 (d, J = 4.59 Hz, 1 H) 5.24 (dd, J = 10.13, 2.10 Hz, 1 H) 6.84-6.92 (m, 2 H) 7.14-7.22 (m, 1 H) 7.55-7.63 (m, 1 H) |

TABLE 13-continued

Formula (T)

[Formula 54]

| Example | R²⁸ | R¹⁷ | ESI MS (M + H) | ¹H-NMR, CDCl₃, δ (ppm) |
|---------|-----|-----|----------------|------------------------|
| 364 | (adenine-propyl-S- group) | —CH₃ | 1093.8 | (500 MHz): 0.88 (t, J = 7.40 Hz, 3 H) 1.06-1.14 (m, 9 H) 1.16-1.27 (m, 13 H) 1.38 (s, 3 H) 1.44 (s, 3 H) 1.49-2.05 (m, 8 H) 2.16 (d, J = 14.81 Hz, 1 H) 2.22-2.26 (m, 7 H) 2.30 (s, 6 H) 2.33-2.64 (m, 11 H) 2.70-2.90 (m, 3 H) 3.02-3.08 (m, 1 H) 3.10-3.17 (m, 4 H) 3.19 (dd, J = 10.28, 7.27 Hz, 1 H) 3.28 (s, 3 H) 3.46-3.54 (m, 1 H) 3.73-3.79 (m, 2 H) 4.09 (q, J = 6.22 Hz, 1 H) 4.35-4.54 (m, 4 H) 4.97-5.01 (m, 1 H) 5.42 (dd, J = 10.42, 2.47 Hz, 1 H) 5.65 (br. s., 2 H) 8.21 (s, 1 H) 8.36 (s. 1 H) |
| 365 | H₃C—S— | 2-methoxy-α,α-dimethylbenzyl | 1066.9 | (500 MHz): 0.87 (t, J = 7.40 Hz, 3 H) 1.06-1.14 (m, 12 H) 1.16 (d, J = 6.58 Hz, 3 H) 1.19-1.26 (m, 7 H) 1.38 (s, 3 H) 1.40-1.46 (m, 9 H) 1.49-2.07 (m, 9 H) 2.18 (s, 3 H) 2.25 (s, 3 H) 2.29 (s, 6 H) 2.42 (s, 3 H) 2.43-2.65 (m, 7 H) 2.78-2.89 (m, 2 H) 2.98-3.05 (m, 1 H) 3.10 (s, 3 H) 3.19 (dd, J = 10.28, 7.27 Hz, 1 H) 3.28 (s, 3 H) 3.41-3.47 (m, 1 H) 3.68-3.81 (m, 5 H) 4.04-4.11 (m, 1 H) 4.22-4.26 (m, 1 H) 4.43 (d, J = 7.40 Hz, 1 H) 4.99 (d, J = 4.39 Hz, 1 H) 5.55 (dd, J = 10.28, 2.61 Hz, 1 H) 6.84-6.91 (m, 2 H) 7.14-7.21 (m, 1 H) 7.60 (d, J = 7.13 Hz, 1 H) |
| 366 | H₃C—S— | —CH₃ (isopropyl) | 932.8 | (500 MHz): 0.86 (t, J = 7.40 Hz, 3 H) 1.06-1.13 (m, 9 H) 1.15-1.27 (m, 13 H) 1.37 (s, 3 H) 1.42 (s, 3 H) 1.49-1.58 (m, 1 H) 1.62-1.75 (m, 2 H) 1.79-2.04 (m, 5 H) 2.16 (d, J = 14.53 Hz, 1 H) 2.24 (s, 6 H) 2.29 (s, 6 H) 2.34 (s, 3 H) 2.35-2.38 (m, 2 H) 2.42 (s, 3 H) 2.43-2.49 (m, 1 H) 2.50-2.66 (m, 4 H) 2.78-2.88 (m, 2 H) 2.98-3.04 (m, 1 H) 3.09 (s, 3 H) 3.16-3.22 (m, 1 H) 3.27 (s, 3 H) 3.47-3.54 (m, 1 H) 3.71-3.78 (m, 2 H) 4.09 (q, J = 6.30 Hz, 1 H) 4.24 (d, J = 0.82 Hz, 1 H) 4.45 (d, J = 7.40 Hz, 1 H) 4.98 (dd, J = 5.07, 1.78 Hz, 1 H) 5.55 (dd, J = 10.42, 2.47 Hz, 1 H) |

Formula (SM7)

[Formula 55]

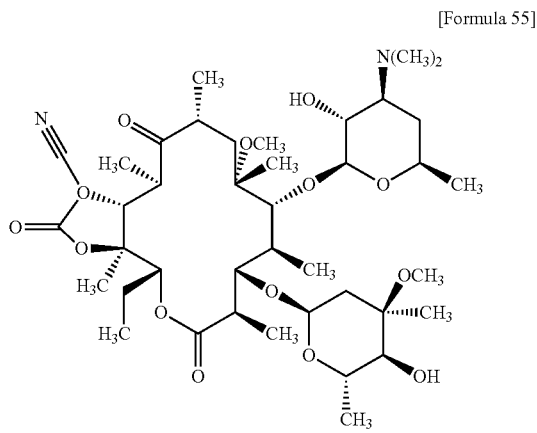

Example 363

(1) By using the compound represented by the formula (SM7) (1.5 g) obtained by the method described in the publication (International Patent Publication WO03/042228) as a starting material, an acetyl compound (1.17 g) was obtained in the same manner as that of Example 1, (1).
(2) By using the compound obtained in (1) mentioned above (100 mg) as a starting material, an epoxy compound (35 mg) was obtained in the same manners as those of Example 6, (3), Example 4, (6) and Example 1, (4).
(3) By using the compound obtained in (2) mentioned above (35 mg) and the compound obtained in Reference Example 104 (31 mg) as starting materials, the compound shown in Table 13 (31 mg) was obtained in the same manner as that of Example 2, (5).

Example 364

(1) By using 2'-O-Acetyl-6-O-methylerythromycin A 11,12-carbonate (1.11 g) obtained by the method described in the publication (Japanese Patent Unexamined Publication No. 1/96190) as a starting material, an epoxy compound (0.64 g) was obtained in the same manners as those of Example 6, (3) and Example 1, (4).
(2) The compound obtained in (1) mentioned above (0.64 g) was dissolved in chloroform (16 ml), chloroacetic anhydride (0.28 g), pyridine (0.14 ml) and 4-dimethylaminopyridine (50 mg) were added to the solution, and the resulting mixture was stirred at room temperature for 2 hours. Chloroacetic anhydride (0.28 g), pyridine (0.14 ml) and 4-dimethylaminopyridine (50 mg) were added to the reaction mixture, and the resulting mixture was stirred at room temperature for 2 hours. Saturated aqueous sodium hydrogencarbonate was added to the reaction mixture, and the resulting mixture was extracted with chloroform. The organic layer was dried over anhydrous magnesium sulfate, and filtered. The filtrate was concentrated under reduced pressure, and the resulting residue was successively purified by silica gel column chromatography (hexane:acetone:triethylamine=30:10:0.2 to 20:10:0.2), and silica gel column chromatography (hexane:acetone:triethylamine=20:10:0.2) to obtain an ester compound (0.65 g).
(3) The compound obtained in Reference Example 76 (0.22 g) was dissolved in dimethylformamide (50 ml), 70% sodium hydride (38 mg) was added to the solution, and the resulting mixture was stirred at room temperature for 1 hour. A solution of the compound obtained in (2) mentioned above (0.45 g) in dimethylformamide (10 ml) was added to the reaction mixture, and the resulting mixture was stirred at room temperature for 5 hours. 70% Sodium hydride (20 mg) was added to the reaction mixture, and the resulting mixture was stirred at room temperature for 1 hour. Saturated aqueous ammonium chloride was added to the reaction mixture, and the resulting mixture was extracted with ethyl acetate. The organic layer was washed with saturated aqueous sodium chloride, then dried over anhydrous magnesium sulfate, and filtered. The filtrate was concentrated under reduced pressure, and the resulting residue was purified by silica gel column chromatography (hexane:acetone:triethylamine=20:10:0.2) to obtain a lactone compound (176 mg).
(4) By using the compound obtained in (3) mentioned above (176 mg) as a starting material, a deprotected compound (78 mg) was obtained in the same manner as that of Example 4, (6).
(5) By using the compound obtained in (4) mentioned above (78 mg) and N,N,N'-trimethylethylene-1,2-diamine (40 mg) as starting materials, the compound shown in Table 13 (34 mg) was obtained in the same manner as that of Example 2, (5).

Example 365

(1) The compound obtained in Example 364, (2) (200 mg) was dissolved in dimethylformamide (10 ml), sodium methanethiolate (25 mg) was added to the solution, and the resulting mixture was stirred at room temperature for 5 hours. Saturated aqueous ammonium chloride was added to the reaction mixture, and the resulting mixture was extracted with ethyl acetate. The organic layer was washed with saturated aqueous sodium chloride, then dried over anhydrous magnesium sulfate, and filtered. The filtrate was concentrated under reduced pressure, the resulting residue was dissolved in tetrahydrofuran (6 ml) and dimethylformamide (2 ml), potassium t-butoxide (29 mg) was added to the solution, and the resulting mixture was stirred at room temperature for 1 hour. Saturated aqueous ammonium chloride was added to the reaction mixture, and the resulting mixture was extracted with ethyl acetate. The organic layer was washed with saturated aqueous sodium chloride, then dried over anhydrous magnesium sulfate, and filtered. The filtrate was concentrated under reduced pressure, and the resulting residue was purified by silica gel column chromatography (hexane:acetone:triethylamine=30:10:0.2 to 20:10:0.2) to obtain a lactone compound (137 mg).
(2) By using the compound obtained in (1) mentioned above (137 mg) as a starting material, a deprotected compound (45 mg) was obtained in the same manner as that of Example 4, (6).
(3) By using the compound obtained in (2) mentioned above (84 mg) and the compound obtained in Reference Example 104 (72 mg) as starting materials, the compound shown in Table 13 (49 mg) was obtained in the same manner as that of Example 2, (5).

Example 366

(1) By using the compound obtained in Example 365, (2) (72 mg) and N,N,N'-trimethylethylene-1,2-diamine (56 µl) as starting materials, the compound shown in Table 13 (54 mg) was obtained in the same manner as that of Example 2, (5).

Examples 367 and 368

Preparation methods of the compounds represented by the formula (U) having $R^{1d}$ defined in Table 14 wherein $X^1$ is NH, and $R^{4c}$ is hydrogen atom are shown below.

TABLE 14

Formula (U)

[Formula 56]

| Example | R$^{1d}$ | ESI MS (M + H) | $^1$H-NMR, CDCl$_3$, δ (ppm) |
|---------|----------|----------------|-------------------------------|
| 367 | (structure: -N(CH$_3$)-CH$_2$CH$_2$-N(CH$_3$)-C(CH$_3$)$_2$-(2-methoxyphenyl)) | 1009.9 | (600 MHz): 0.94 (t, J = 7.57 Hz, 3 H) 1.04-1.08 (m, 1 H) 1.09 (d, J = 7.34 Hz, 3 H) 1.11 (s, 3 H) 1.13-1.16 (m, 9 H) 1.19 (d, J = 7.34 Hz, 3 H) 1.22-1.25 (m, 9 H) 1.24-1.29 (m, 1 H) 1.43 (s, 6 H) 1.45-1.52 (m, 1 H) 1.64-1.68 (m, 1 H) 1.75-1.81 (m, 1 H) 1.88-1.97 (m, 3 H) 1.98-2.03 (m, 2 H) 2.15 (s, 3 H) 2.14-2.17 (m, 1 H) 2.24 (s, 3 H) 2.24-2.28 (m, 1 H) 2.31 (s, 6 H) 2.39-2.62 (m, 6 H) 2.78 (d, J = 14.21 Hz, 1 H) 2.91-2.95 (m, 1 H) 3.26-3.32 (m, 1 H) 3.27 (s, 3 H) 3.36-3.41 (m, 1 H) 3.52-3.57 (m, 1 H) 3.58-3.60 (m, 1 H) 3.80 (s, 3 H) 3.94-3.97 (m, 1 H) 4.04 (q, J = 6.11 Hz, 1 H) 4.08-4.12 (m, 1 H) 4.18-4.22 (m, 1 H) 4.53 (d, J = 7.34 Hz, 1 H) 4.84-4.88 (m, 1 H) 4.89-4.91 (m, 1 H) 4.93-4.97 (m, 1 H) 6.85-6.91 (m, 2 H) 7.15-7.20 (m, 1 H) 7.56 (d, J = 6.88 Hz, 1 H) |
| 368 | (structure: -N(CH$_3$)-CH$_2$CH$_2$-N(CH$_3$)$_2$) | 875.8 | (600 MHz): 0.94 (t, J = 7.34 Hz, 3 H) 1.04-1.08 (m, 1 H) 1.09 (d, J = 7.34 Hz, 3 H) 1.13-1.18 (m, 12 H) 1.19 (s, 3 H) 1.21-1.24 (m, 6 H) 1.25 (d, J = 5.96 Hz, 3 H) 1.26-1.31 (m, 1 H) 1.46-1.54 (m, 1 H) 1.66-1.70 (m, 1 H) 1.75-1.79 (m, 1 H) 1.89-1.99 (m, 4 H) 2.11-2.17 (m, 1 H) 2.16-2.20 (m, 1 H) 2.22-2.24 (m, 6 H) 2.25-2.27 (m, 1 H) 2.31 (s, 6 H) 2.33 (s, 3 H) 2.34-2.39 (m, 2 H) 2.49-2.56 (m, 2 H) 2.56-2.65 (m, 2 H) 2.79 (d, J = 14.67 Hz, 1 H) 2.89-2.93 (m, 1 H) 3.29 (s, 3 H) 3.29-3.33 (m, 1 H) 3.57-3.63 (m, 2 H) 3.98-4.02 (m, 1 H) 4.07 (q, J = 6.42 Hz, 1 H) 4.09-4.12 (m, 1 H) 4.18-4.21 (m, 1 H) 4.54 (d, J = 7.34 Hz, 1 H) 4.85-4.90 (m, 1 H) 4.92-4.96 (m, 1 H) 5.03-5.08 (m, 1 H) |

Example 367

(1) (9R)—[N-(Carbobenzyloxy)amino-9-deoxoerythromycin A] (877 mg) obtained by the method described in the literature (Journal of Medicinal Chemistry, 1991, vol. 34, p. 3390) was dissolved in isopropanol (18 ml), potassium carbonate (558 mg) was added to the solution, and the resulting mixture was stirred at 60° C. for 16 hours, and under reflux by heating for 10 hours. Chloroform and saturated aqueous sodium hydrogencarbonate were added to the reaction mixture, the layers were separated, and the aqueous layer was extracted with chloroform. The organic layers were combined, dried over anhydrous magnesium sulfate, and filtered. The filtrate was concentrated under reduced pressure, ethyl acetate was added to the resulting residue, and the deposited solid was collected by filtration to obtain a carbamate compound (237 mg).

(2) By using the compound obtained in (1) mentioned above (360 mg) as a starting material, an epoxy compound (220 mg) was obtained in the same manners as those of Example 1, (1), Example 6, (3), Example 4, (6) and Example 1, (4).

(3) By using the compound obtained in (2) mentioned above (90 mg) and the compound obtained in Reference Example 104 (83 mg) as starting materials, the compound shown in Table 14 (36.8 mg) was obtained in the same manner as that of Example 4, (8).

Example 368

By using the compound obtained in Example 367, (2) (80 mg) as a starting material, the compound shown in Table 14 (22.0 mg) was obtained in the same manner as that of Example 4, (8).

Example 369

A preparation method of the compound represented by the formula (U) wherein X$^1$ is oxygen atom, R$^{4c}$ is hydrogen atom, and R$^{1d}$ is

[Formula 57]

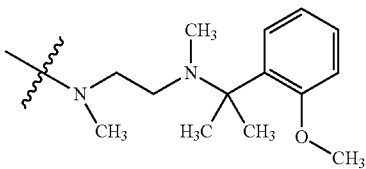

is shown below.

Example 369

(1) By using (9S)-9-dihydroerythromycin A (3.00 g) obtained by the method described in the literature (The Journal of Antibiotics, 1989, vol. 42, No. 2, p. 293) as a starting material, an acetyl compound (3.39 g) was obtained in the same manner as that of Example 1, (1).

(2) The compound obtained in (1) mentioned above (3.29 g) was dissolved in chloroform (30 ml), pyridine (5.47 ml) and triphosgene (1.88 g) were added to the solution under ice cooling, and the resulting mixture was stirred for 1.5 hours under ice cooling. Ice, saturated aqueous sodium hydrogencarbonate and chloroform were added to the reaction mixture, the layers were separated, and the organic layer was dried over anhydrous sodium sulfate, and filtered. The filtrate was concentrated under reduced pressure, and the resulting residue was purified by silica gel column chromatography (chloroform:methanol:28% aqueous ammonia=95:5:0.5) to obtain a carbonate compound (2.78 g).

(3) By using the compound obtained in (2) mentioned above (400 mg) as a starting material, a deprotected compound (91.2 mg) was obtained in the same manners as those of Example 1, (3), (4) and Example 4, (6).

(4) The compound obtained in (3) mentioned above (20.0 mg) was dissolved in tetrahydrofuran (60 μl), the compound obtained in Reference Example 104 (12.9 mg) was added to the solution, and the resulting mixture was stirred at 80° C. for 8.5 hours in a sealed tube. The reaction mixture was purified by preparative thin layer chromatography (chloroform:methanol:28% aqueous ammonia=95:5:0.5) to obtain the aforementioned objective compound (5.0 mg).

MS (FAB) m/z=1010 [M+H]$^+$ $^1$H-NMR (400 MHz, CDCl$_3$) δ (ppm): 0.93 (t, J=7.3 Hz, 3H), 1.08-1.32 (m, 32H), 1.35-1.59 (m, 8H), 1.59-1.97 (m, 9H), 1.99-2.10 (m, 2H), 2.14 (s, 2H), 2.27-2.38 (m, 12H), 2.42-2.74 (m, 4H), 2.81 (d, J=14.6 Hz, 1H), 3.27 (s, 3H), 3.48-3.56 (m, 1H), 3.66 (d, J=5.6 Hz, 1H), 3.79-3.92 (m, 4H), 4.05 (q, J=6.3 Hz, 1H), 4.37 (d, J=2.2 Hz, 1H), 4.51 (d, J=7.3 Hz, 1H), 4.91 (d, J=3.4 Hz, 1H), 4.99 (dd, J=9.6, 3.3 Hz, 1H), 6.86-6.95 (m, 2H), 7.49-7.60 (m, 1H)

Examples 370 to 376

Preparation methods of the compounds represented by the formula (U) having $R^{1d}$ defined in Table 15 wherein $X^1$ is oxygen atom, and $R^{4c}$ is methyl group are shown below.

TABLE 15

| Example | $R^{1d}$ | ESI MS (M + H) | $^1$H-NMR, CDCl$_3$, δ (ppm) |
|---|---|---|---|
| 370 | | 1024.8 | (400 MHz): 0.86 (t, J = 7.4 Hz, 3 H) 1.05 (d, J = 6.8 Hz, 3 H) 1.10-1.14 (m, 6 H) 1.17-1.34 (m, 18 H) 1.41-1.46 (m, 9 H) 1.47-1.69 (m, 4 H) 1.76-1.93 (m, 2 H) 1.97 (dd, J = 14.9, 4.9 Hz, 1 H) 2.03 (d, J = 9.8 Hz, 1 H) 2.06 (d, J = 9.8 Hz, 1 H) 2.18 (s, 3 H) 2.26 (s, 3 H) 2.27-2.31 (m, 8 H) 2.39-2.71 (m, 5 H) 2.79-2.89 (m, 2 H) 3.16 (dd, J = 10.0, 7.3 Hz, 1 H) 3.25 (s, 3 H) 3.27 (s, 3 H) 3.39-3.48 (m, 2 H) 3.72 (d, J = 7.8 Hz, 1 H) 3.79-3.83 (m, 4 H) 3.89 (d, J = 6.6 Hz, 1 H) 4.13 (q, J = 6.3 Hz, 1 H) 4.36 (d, J = 7.3 Hz, 1 H) 4.46 (d, J = 2.7 Hz, 1 H) 5.00 (d, J = 4.4 Hz, 1 H) 5.18 (dd, J = 10.7, 2.7 Hz, 1 H) 6.86-6.91 (m, 2 H) 7.15-7.21 (m, 1 H) 7.61-7.65 (m, 1 H) |
| 371 | | 1025.8 | (400 MHz): 0.86 (t, J = 7.3 Hz, 3 H) 1.05 (d, J = 6.8 Hz, 3 H) 1.09-1.16 (m, 22 H), 1.16-1.27 (m, 2 H) 1.30 (dd, J = 15.0, 6.7 Hz, 1 H) 1.36-1.45 (m, 3 H) 1.46-1.72 (m, 7 H) 1.75-2.10 (m, 5 H) 2.18 (s, 3 H) 2.26 (s, 4 H) 2.29 (s, 7 H) 2.35-2.67 (m, 5 H) 2.78-2.88 (m, 2 H) 3.16 (dd, J = 10.1, 7.4 Hz, 1 H) 3.25 (s, 3 H) 3.27 (s, 3 H) 3.38-3.48 (m, 2 H) 3.71 (d, J = 7.8 Hz, 1 H) 3.81 (d, J = 9.5 Hz, 1 H) 3.89 (d, J = 7.1 Hz, 1 H) 3.93 (s, 3 H) 4.14 (q, J = 6.0 Hz, 1 H) 4.36 (d, J = 7.1 Hz, 1 H) 4.46 (d, J = 2.7 Hz, 1 H) 5.00 (d, J = 4.6 Hz, 1 H) 5.17 (dd, J = 10.6, 2.6 Hz, 1 H) 6.82 (dd, J = 7.6, 4.9 Hz, 1 H) 7.96-8.00 (m, 1 H) 8.01 (dd, J = 4.9, 2.0 Hz, 1 H) |
| 372 | | 918.7 | (400 MHz): 0.85 (t, J = 7.4 Hz, 3 H) 0.99-1.07 (m, 9 H) 1.11 (d, J = 7.6 Hz, 3 H) 1.14-1.26 (m, 19 H) 1.30 (dd, J = 15.3, 7.2 Hz, 1 H) 1.41 (s, 3 H) 1.44-1.68 (m, 3 H) 1.74-1.92 (m, 2 H) 1.96 (dd, J = 14.8, 5.0 Hz, 1 H) 2.03 (d, J = 13.9 Hz, 1 H) 2.09 (d, J = 14.6 Hz, 1 H) 2.25 (m, 2 H) 2.28 (s, 6 H) 2.34 (s, 3 H) 2.38-2.64 (m, 9 H) 2.80-2.87 (m, 2 H) 3.16 (dd, J = 10.4, 7.2 Hz, 1 H) 3.24 (s, 3 H) 3.27 (s, 3 H) 3.40-3.49 (m, 2 H) 3.72 (d, J = 7.6 Hz, 1 H) 3.80 (d, J = 9.8 Hz, 1 H) 3.89 (d, J = 6.8 Hz, 1 H) 4.13 (q, J = 6.3 Hz, 1 H) 4.36 (d, J = 7.6 Hz, 1 H) 4.46 (d, J = 2.7 Hz, 1 H) 4.99 (d, J = 4.2 Hz, 1 H) 5.17 (dd, J = 11.0, 2.7 Hz, 1 H) |

TABLE 15-continued

| Example | R$^{1d}$ | ESI MS (M + H) | $^1$H-NMR, CDCl$_3$, δ (ppm) |
|---|---|---|---|
| 373 | (structure with OH, CH$_3$, NH, N, CH$_3$, OCH$_3$ phenyl group) | 1040.7 | (400 MHz): 0.85 (t, J = 7.3 Hz, 3 H) 1.04 (d, J = 6.8 Hz, 3 H) 1.07 (d, J = 7.1 Hz, 3 H) 1.08-1.14 (m, 10 H) 1.16-1.22 (m, 13 H) 1.34 (s, 3 H) 1.36 (s, 3 H) 1.40 (s, 3 H) 1.44-1.64 (m, 4 H) 1.78-1.93 (m, 2 H) 2.04 (d, J = 14.9 Hz, 1 H) 2.20-2.34 (m, 10 H) 2.35-2.54 (m, 4 H) 2.63-2.88 (m, 0 H) 3.14 (dd, J = 10.3, 7.3 Hz, 1 H) 3.22 (s, 3 H) 3.25 (s, 3 H) 3.41-3.54 (m, 3 H) 3.55-3.62 (m, 1 H) 3.67 (d, J = 8.1 Hz, 1 H) 3.80 (d, J = 9.5 Hz, 1 H) 3.82 (s, 3 H) 3.90 (d, J = 6.6 Hz, 1 H) 4.28 (q, J = 6.4 Hz, 1 H) 4.32 (d, J = 7.3 Hz, 1 H) 4.42-4.48 (m, 2 H) 4.95 (d, J = 4.6 Hz, 1 H) 5.17 (dd, J = 10.6, 2.6 Hz, 1 H) 6.89 (dd, J = 8.3, 1.0 Hz, 1 H) 6.95 (td, J = 7.5, 0.9 Hz, 1 H) 7.22-7.30 (m, 5 H) |
| 374 | (structure with NCH$_3$, ethyl, pyrrolidine with CH$_3$) | 930.6 | (400 MHz): 0.85 (t, J = 7.4 Hz, 3 H) 1.04 (d, J = 6.6 Hz, 3 H) 1.08 (d, J = 6.3 Hz, 3 H) 1.11 (d, J = 7.6 Hz, 3 H) 1.14 (s, 3 H) 1.16-1.26 (m, 14 H) 1.31 (dd, J = 14.9, 6.6 Hz, 1 H) 1.41 (s, 3 H) 1.45-1.71 (m, 7 H) 1.72-1.92 (m, 4 H) 1.96 (dd, J = 14.6, 4.9 Hz, 1 H) 2.03 (d, J = 14.2 Hz, 1 H) 2.07-2.19 (m, 3 H) 2.20-2.35 (m, 10 H) 2.36 (s, 3 H) 2.39-2.47 (m, 1 H) 2.60-2.67 (m, 2 H) 2.80-2.94 (m, 3 H) 3.11-3.19 (m, 2 H) 3.24 (s, 3 H) 3.27 (s, 3 H) 3.40-3.48 (m, 2 H) 3.72 (d, J = 7.8 Hz, 1 H) 3.79 (d, J = 9.8 Hz, 1 H) 3.89 (d, J = 6.8 Hz, 1 H) 4.13 (q, J = 6.3 Hz, 1 H) 4.36 (d, J = 7.1 Hz, 1 H) 4.47 (d, J = 2.7 Hz, 1 H) 4.99 (d, J = 4.4 Hz, 1 H) 5.17 (dd, J = 10.7, 2.7 Hz, 1 H) |
| 375 | (structure with CH$_3$, CH$_3$, NH, N-CH$_3$, gem-dimethyl, methoxyphenyl) | 1024.7 | (400 MHz): 0.86 (t, J = 7.3 Hz, 3 H) 0.91 (d, J = 6.1 Hz, 3 H) 1.04 (d, J = 6.6 Hz, 3 H) 1.11 (d, J = 7.6 Hz, 3 H) 1.13 (s, 3 H) 1.16-1.25 (m, 18 H) 1.32 (dd, J = 15.0, 6.5 Hz, 1 H) 1.41 (s, 3 H) 1.44 (s, 6 H) 1.47-1.58 (m, 2 H) 1.59-1.66 (m, 1 H) 1.78-1.94 (m, 2 H) 1.97-2.03 (m, 2 H) 2.13 (s, 3 H) 2.14-2.21 (m, 2 H) 2.22-2.33 (m, 9 H) 2.38-2.48 (m, 2 H) 2.63-2.72 (m, 1 H) 2.80-2.89 (m, 1 H) 3.10 (d, J = 13.4 Hz, 1 H) 3.16 (dd, J = 10.3, 7.3 Hz, 1 H) 3.24 (s, 3 H) 3.30 (s, 3 H) 3.41-3.52 (m, 2 H) 3.74 (d, J = 7.1 Hz, 1 H) 3.77-3.80 (m, 1 H) 3.80 (s, 4 H) 3.90 (d, J = 6.6 Hz, 1 H) 4.23 (q, J = 6.2 Hz, 1 H) 4.39 (d, J = 7.3 Hz, 1 H) 4.47 (d, J = 2.7 Hz, 1 H) 5.18 (dd, J = 10.6, 2.6 Hz, 1 H) 6.86-6.92 (m, 2 H) 7.18-7.23 (m, 1 H) 7.42 (dd, J = 7.8, 1.5 Hz, 1 H) |
| 376 | (structure with NH, N-ethyl, CH$_3$ with methoxyphenyl) | 1011 | (400 MHz): 0.86 (t, J = 7.4 Hz, 3 H) 0.95 (t, J = 7.0 Hz, 3 H) 1.05 (d, J = 6.6 Hz, 3 H) 1.08-1.25 (m, 22 H) 1.25-1.36 (m, 4 H) 1.41 (s, 3 H) 1.43 (s, 1 H) 1.45-1.65 (m, 3 H) 1.74-1.92 (m, 1 H) 1.95 (dd, J = 14.8, 5.0 Hz, 1 H) 2.05 (d, J = 14.9 Hz, 1 H) 2.26 (s, 8 H) 2.28-2.67 (m, 9 H) 2.75-2.89 (m, 2 H) 3.14 (dd, J = 10.1, 7.2 Hz, 1 H) 3.24 (s, 3 H) 3.27 (s, 3 H) 3.39-3.51 (m, 2 H) 3.71 (d, J = 7.8 Hz, 1 H) 3.79-3.84 (m, 4 H) 3.89 (d, J = 6.8 Hz, 1 H) 4.24 (q, J = 6.3 Hz, 1 H) 4.32-4.41 (m, 2 H) 4.46 (d, J = 2.7 Hz, 1 H) 4.98 (d, J = 4.4 Hz, 1 H) 5.17 (dd, J = 10.6, 2.6 Hz, 1 H) 6.86 (d, J = 8.3 Hz, 1 H) 6.93 (t, J = 7.6 Hz, 1 H) 7.18-7.23 (m, 1 H) 7.31 (d, J = 7.1 Hz, 1 H) |

Example 370

(1) (9S)-9-Dihydro-6-O-methylerythromycin A (2.00 g) obtained by the method described in the literature (The Journal of Antibiotics, 1990, vol. 43, No. 10, p. 1334) was dissolved in acetone (20 ml), acetic anhydride (334 μl) and tetrahydrofuran (15 ml) were added to the solution, and the resulting mixture was stirred overnight at room temperature. The reaction mixture was concentrated under reduced pressure, then ethyl acetate and saturated aqueous sodium hydrogencarbonate were added to the resulting residue, and the layers were separated. The organic layer was dried over anhydrous sodium sulfate, and filtered. The filtrate was concentrated under reduced pressure, and the resulting solid was collected by filtration to obtain an acetyl compound (1.53 g).
(2) By using the compound obtained in (1) mentioned above (1.15 g) as a starting material, a carbonate compound (1.07 g) was obtained in the same manner as that of Example 369, (2).
(3) By using the compound obtained in (2) mentioned above (948 mg) as a starting material, a ketone compound (921 mg) was obtained in the same manner as that of Example 1, (3).
(4) By using the compound obtained in (3) mentioned above (1.01 g) as a starting material, an epoxy compound (790 mg) was obtained in the same manners as those of Example 4, (6) and Example 1, (4).
(5) By using the compound obtained in (4) mentioned above (80.0 mg) and the compound obtained in Reference Example 104 (31.2 mg) as starting materials, the compound shown in Table 15 (65.4 mg) was obtained in the same manner as that of Example 359.

In Example 371 to 376, by using the compound obtained in Example 370, (4) and corresponding amine reagents, the compounds shown in Table 15 were synthesized in the same manner as that of Example 359.

Examples 377 to 381

Preparation methods of the compounds represented by the formula (V) having R$^{1e}$ defined in Table 16 wherein R$^{4c}$ is hydrogen atom are shown below.

TABLE 16

Formula (V)

[Formula 58]

| Example | R^1e | ESI MS (M + H) | ¹H-NMR, CDCl₃, δ (ppm) |
|---|---|---|---|
| 377 | (structure: -N(CH₃)-CH₂CH₂-N(CH₃)-C(CH₃)₂-(2-methoxyphenyl)) | 1023.7 | (600 MHz): 0.87 (t, J = 7.34 Hz, 3 H) 1.04 (d, J = 6.88 Hz, 3 H) 1.08 (d, J = 7.34 Hz, 3 H) 1.12 (s, 3 H) 1.15 (d, J = 6.42 Hz, 3 H) 1.17-1.27 (m, 10 H) 1.43 (s, 6 H) 1.46 (s, 3 H) 1.48-1.67 (m, 7 H) 1.81-1.96 (m, 3 H) 2.00-2.05 (m, 2 H) 2.18 (s, 3 H) 2.25 (s, 3 H) 2.29 (s, 6 H) 2.36-2.68 (m, 6 H) 2.77-2.88 (m, 2 H) 3.19-3.25 (m, 1 H) 3.26 (s, 3 H) 3.38-3.42 (m, 1 H) 3.42-3.48 (m, 1 H) 3.56 (d, J = 7.79 Hz, 1 H) 3.80 (s, 3 H) 3.83-3.91 (m, 1 H) 4.03-4.12 (m, 2 H) 4.39 (d, J = 6.88 Hz, 1 H) 4.84 (s, 1 H) 4.92-4.95 (m, 1 H) 4.98-5.03 (m, 1 H) 6.84-6.92 (m, 2 H) 7.14-7.20 (m, 1 H) 7.57-7.63 (m, 1 H) |
| 378 | (structure: -NH-CH₂CH₂-N(Et)-CH(CH₃)-(2-methoxyphenyl)) | 1009.7 | (500 MHz): 0.88 (t, J = 7.45 Hz, 3 H) 0.94-1.01 (m, 3 H) 1.01-1.06 (m, 3 H) 1.07-1.33 (m, 22 H) 1.46 (s, 3 H) 1.49-1.66 (m, 7 H) 1.81-2.04 (m, 5 H) 2.25-2.36 (m, 7 H) 2.41-2.68 (m, 7 H) 2.80-2.89 (m, 2 H) 3.19-3.27 (m, 4 H) 3.45-3.54 (m, 1 H) 3.56 (d, J = 7.64 Hz, 1 H) 3.81 (s, 3 H) 3.83-3.91 (m, 1 H) 4.07 (d, J = 8.41 Hz, 1 H) 4.17-4.24 (m, 1 H) 4.38 (d, J = 7.26 Hz, 2 H) 4.86 (s, 1 H) 4.92 (d, J = 4.97 Hz, 1 H) 5.00 (dd, J = 10.51, 2.48 Hz, 1 H) 6.86 (d, J = 8.03 Hz, 1 H) 6.91-6.97 (m, 1 H) 7.17-7.24 (m, 1 H) 7.31-7.38 (m, 1 H) |
| 379 | (structure: -N(CH₃)-CH₂CH₂-N(CH₃)-C(CH₃)₂-(2-methoxypyridin-3-yl)) | 1024.7 | (500 MHz): 0.88 (t, J = 7.40 Hz, 3 H) 1.05 (d, J = 7.13 Hz, 3 H) 1.08 (d, J = 7.40 Hz, 3 H) 1.10-1.31 (m, 16 H) 1.37-1.43 (m, 6 H) 1.47 (s, 3 H) 1.48-1.72 (m, 9 H) 1.81-2.06 (m, 7 H) 2.18 (s, 3 H) 2.22-2.54 (m, 12 H) 2.62-2.67 (m, 1 H) 2.78-2.88 (m, 2 H) 3.20-3.29 (m, 4 H) 3.42-3.50 (m, 1 H) 3.56 (d, J = 7.40 Hz, 1 H) 3.84-3.91 (m, 1 H) 3.92-3.95 (m, 3 H) 4.03-4.12 (m, 2 H) 4.39 (d, J = 7.13 Hz, 1 H) 4.83 (s, 1 H) 4.93 (d, J = 4.66 Hz, 1 H) 4.99 (dd, J = 10.28, 2.61 Hz, 1 H) 6.80-6.85 (m, 1 H) 7.93-7.96 (m, 1 H) 8.00-8.05 (m, 1 H) |
| 380 | (structure: -NH-CH(CH₂OH)-CH₂-N(Et)-CH(CH₃)-(2-methoxyphenyl)) | 1039.7 | (500 MHz): 0.88 (t, J = 7.45 Hz, 3 H) 1.02-1.28 (m, 25 H) 1.33-1.37 (m, 3 H) 1.44-1.65 (m, 12 H) 1.81-2.04 (m, 4 H) 2.29 (s, 6 H) 2.38-2.54 (m, 3 H) 2.60-2.88 (m, 6 H) 3.18-3.26 (m, 4 H) 3.42-3.61 (m, 4 H) 3.80-3.89 (m, 4 H) 4.05-4.10 (m, 1 H) 4.23-4.28 (m, 1 H) 4.35 (d, J = 7.26 Hz, 1 H) 4.42-4.47 (m, 1 H) 4.83 (s, 1 H) 4.87-4.90 (m, 1 H) 4.97-5.01 (m, 2 H) 6.86-6.96 (m, 2 H) 7.22-7.30 (m, 2 H) |
| 381 | (structure: -N(CH₃)-CH₂CH₂-N(CH₃)₂) | 889.6 | (600 MHz): 0.90 (t, J = 7.34 Hz, 3 H) 1.04 (d, J = 6.88 Hz, 3 H) 1.11 (d, J = 7.34 Hz, 3 H) 1.21 (s, 3 H) 1.23-1.34 (m, 13 H) 1.52 (s, 3 H) 1.61 (s, 3 H) 1.48-1.75 (m, 4 H) 1.84-1.97 (m, 3 H) 1.99-2.07 (m, 2 H) 2.21-2.28 (m, 1 H) 2.26-2.38 (m, 15 H) 2.48-2.56 (m, 2 H) 2.60-2.73 (m, 2 H) 2.78-2.90 (m, 2 H) 2.95-3.02 (m, 1 H) 3.25-3.34 (m, 4 H) 3.35-3.39 (m, 1 H) 3.45-3.53 (m, 1 H) 3.61 (d, J = 8.25 Hz, 1 H) 3.90-3.96 (m, 1 H) 4.10-4.19 (m, 2 H) 4.41 (d, J = 7.34 Hz, 1 H) 4.99 (d, J = 4.58 Hz, 1 H) 5.02 (s, 1 H) 5.04-5.10 (m, 1 H) |

Example 377

(1) By using (E)-erythromycin A 9-[O-(2-chlorobenzyl)] oxime (10 g) obtained by the method described in the literature (The Journal of Antibiotics, 1993, vol. 46, No. 7, p. 1163) as a starting material, an epoxy compound (3.51 g) was obtained in the same manners as those of Example 1, (1), (2), (3), Example 4, (6) and Example 1, (4).

(2) The compound obtained in (1) mentioned above (1.0 g) was dissolved in methanol (30 ml), 10% palladium/carbon (113 mg) was added to the solution, and the resulting mixture was stirred overnight at room temperature under a hydrogen atmosphere of 1 atm. The reaction mixture was filtered, and then the filtrate was concentrated under reduced pressure. The resulting residue was dissolved in methanol (3 ml), ammonium formate (303 mg) and formic acid (1.8 ml) were added to the solution, and the resulting mixture was stirred at 45° C. for 5 hours. The reaction mixture was filtered, then the filtrate was concentrated under reduced pressure, and distilled water (150 ml) was added to a solution of the resulting residue in methanol (50 ml). pH of the mixture was adjusted to about 10 with 10% aqueous sodium hydroxide, and the deposited solid was collected by filtration. The resulting solid was dissolved in ethyl acetate, and the solution was dried over anhydrous magnesium sulfate, and filtered. The filtrate was concentrated under reduced pressure, and the resulting residue was dissolved in a mixed solvent of chloroform and hexane, and the solution was concentrated under reduced pressure. The deposited solid was suspended in hexane, and collected by filtration to obtain a debenzylated compound (621 mg).

(3) By using the compound obtained in (2) mentioned above (71 mg) and the compound obtained in Reference Example 104 (53 mg) as starting materials, the compound shown in Table 16 (62.7 mg) was obtained in the same manner as that of Example 2, (5).

In Examples 378 to 380, by using the compound obtained in Example 377, (2) and corresponding amine reagents, the compounds shown in Table 16 were synthesized in the same manner as that of Example 317.

Example 381

By using the compound obtained in Example 377, (2) (50 mg) and N,N,N'-trimethylethylene-1,2-diamine (26 mg) as starting materials, the compound shown in Table 16 (33.6 mg) was obtained in the same manner as that of Example 2, (5).

Examples 382 to 385

Preparation methods of the compounds represented by the formula (V) having $R^{1e}$ defined in Table 17 wherein $R^{4c}$ is methyl group are shown below.

TABLE 17

| Example | $R^{1e}$ | ESI MS (M + H) | $^1$H-NMR, CDCl$_3$, δ (ppm) |
|---|---|---|---|
| 382 | | 1037.7 | (600 MHz): 0.87 (t, J = 7.34 Hz, 3 H) 0.98 (d, J = 7.34 Hz, 3 H) 1.06 (d, J = 7.79 Hz, 3 H) 1.13 (s, 3 H) 1.18 (d, J = 6.42 Hz, 3 H) 1.21 (d, J = 6.88 Hz, 3 H) 1.22-1.27 (m, 7 H) 1.37-1.44 (m, 7 H) 1.47 (s, 3 H) 1.49 (s, 3 H) 1.52-1.67 (m, 3 H) 1.81-2.06 (m, 5 H) 2.18 (s, 3 H) 2.26 (s, 3 H) 2.29 (s, 6 H) 2.40-2.64 (m, 6 H) 2.77-2.87 (m, 2 H) 3.07 (s, 3 H) 3.16-3.22 (m, 1 H) 3.28 (s, 3 H) 3.37 (br. s., 1 H) 3.41-3.48 (m, 1 H) 3.60-3.66 (m, 1 H) 3.75-3.84 (m, 2 H) 3.80 (s, 3 H) 4.10 (q, J = 6.11 Hz, 1 H) 4.40 (d, J = 6.88 Hz, 1 H) 4.79 (s, 1 H) 4.99 (d, J = 5.04 Hz, 1 H) 5.07 (dd, J = 10.77, 2.52 Hz, 1 H) 6.84-6.90 (m, 2 H) 7.01 (br. s., 1 H) 7.15-7.20 (m, 1 H) 7.61 (d, J = 6.88 Hz, 1 H) |
| 383 | | 1023.7 | (600 MHz): 0.85-0.89 (m, 3 H) 0.94-1.00 (m, 6 H) 1.04-1.30 (m, 22 H) 1.36-1.42 (m, 1 H) 1.46-1.51 (m, 6 H) 1.52-1.66 (m, 3 H) 1.81-2.11 (m, 4 H) 2.26-2.28 (m, 6 H) 2.28-2.31 (m, 1 H) 2.40-2.63 (m, 8 H) 2.81-2.87 (m, 2 H) 3.05-3.08 (m, 3 H) 3.16-3.22 (m, 1 H) 3.27-3.30 (m, 3 H) 3.45-3.52 (m, 1 H) 3.63 (d, J = 7.34 Hz, 1 H) 3.75-3.79 (m, 1 H) 3.79-3.82 (m, 3 H) 3.81-3.85 (m, 1 H) 4.21 (q, J = 6.11 Hz, 1 H) 4.34-4.48 (m, 2 H) 4.79 (s, 1 H) 4.94-4.98 (m, 1 H) 5.05-5.09 (m, 1 H) 6.86 (d, J = 7.79 Hz, 1 H) 6.90-6.94 (m, 1 H) 7.12-7.16 (m, 1 H) 7.18-7.22 (m, 1 H) 7.29-7.33 (m, 1 H) |
| 384 | | 1053.7 | (600 MHz): 0.87 (t, J = 7.34 Hz, 3 H) 0.98 (d, J = 6.88 Hz, 3 H) 1.05 (d, J = 7.34 Hz, 3 H) 1.07 (t, J = 7.11 Hz, 3 H) 1.10-1.14 (m, 6 H) 1.17 (d, J = 5.96 Hz, 3 H) 1.20 (d, J = 7.34 Hz, 3 H) 1.23 (d, J = 6.88 Hz, 3 H) 1.23-1.27 (m, 1 H) 1.35 (d, J = 6.88 Hz, 3 H) 1.36-1.44 (m, 1 H) 1.47 (s, 3 H) 1.49 (s, 3 H) 1.51-1.65 (m, 3 H) 1.82-1.93 (m, 3 H) 2.01-2.05 (m, 1 H) 2.28 (s, 6 H) 2.36-2.44 (m, 3 H) 2.45-2.50 (m, 1 H) 2.49-2.53 (m, 1 H) 2.63-2.70 (m, 2 H) 2.69-2.76 (m, 1 H) 2.77-2.85 (m, 2 H) 3.05 (s, 3 H) 3.15-3.21 (m, 1 H) 3.27 (s, 3 H) 3.38-3.51 (m, 2 H) 3.55-3.62 (m, 2 H) 3.75-3.78 (m, 1 H) 3.78-3.83 (m, 1 H) 3.82 (s, 3 H) 4.23-4.28 (m, 1 H) 4.36 (d, J = 7.34 Hz, 1 H) 4.42-4.47 (m, 1 H) 4.78 (s, 1 H) 4.93-4.95 (m, 1 H) 5.04-5.08 (m, 1 H) 6.90 (d, J = 0.92 Hz, 1 H) 6.92-6.97 (m, 1 H) 7.04-7.08 (m, 1 H) 7.22-7.30 (m, 2 H) |

TABLE 17-continued

| Example | R$^{1e}$ | ESI MS (M + H) | $^1$H-NMR, CDCl$_3$, δ (ppm) |
|---------|----------|----------------|------------------------------|
| 385 | [structure: N,N'-dimethyl ethylenediamine linker with a methyl-substituted carbon bearing a 2-methoxypyridin-3-yl group] | 1038.7 | (600 MHz): 0.87 (t, J = 7.34 Hz, 3 H) 0.98 (d, J = 7.34 Hz, 3 H) 1.06 (d, J = 7.34 Hz, 3 H) 1.14 (s, 3 H) 1.19 (d, J = 6.42 Hz, 3 H) 1.21 (d, J = 7.34 Hz, 3 H) 1.22-1.26 (m, 7 H) 1.39-1.42 (m, 1 H) 1.40 (s, 3 H) 1.41 (s, 3 H) 1.47 (s, 3 H) 1.50 (s, 3 H) 1.51-1.58 (m, 1 H) 1.60-1.67 (m, 2 H) 1.83-1.90 (m, 2 H) 1.95-2.00 (m, 1 H) 2.02-2.07 (m, 2 H) 2.19 (s, 3 H) 2.26 (s, 3 H) 2.27-2.33 (m, 2 H) 2.30 (s, 6 H) 2.42 (d, J = 18.34 Hz, 3 H) 2.49-2.53 (m, 1 H) 2.79-2.87 (m, 2 H) 3.07 (s, 3 H) 3.18-3.24 (m, 1 H) 3.28 (s, 3 H) 3.35-3.40 (m, 1 H) 3.41-3.47 (m, 1 H) 3.63 (d, J = 7.79 Hz, 1 H) 3.78 (d, J = 9.17 Hz, 1 H) 3.79-386 (m, 1 H) 3.92-3.93 (m, 3 H) 4.11 (q, J = 6.27 Hz, 1 H) 4.40 (d, J = 7.34 Hz, 1 H) 4.79 (s, 1 H) 4.99 (d, J = 5.04 Hz, 1 H) 5.04-5.08 (m, 1 H) 6.82 (dd, J = 7.34, 4.58 Hz, 1 H) 7.29-7.35 (m, 1 H) 7.94-7.98 (m, 1 H) 8.00-8.02 (m, 1 H) |

Example 382

(1) (E)-2',4"-O-Bis(trimethylsilyl)erythromycin A 9-[O-(2-chlorobenzyl)]oxime (14.0 g) obtained by the method described in the publication (International Patent Publication WO98/18808) was dissolved in a mixed solvent of tetrahydrofuran and dimethyl sulfoxide (1:1, 56 ml), iodomethane (1.19 ml) and potassium hydroxide (998 mg) were added to the solution under ice cooling, and the resulting mixture was stirred at the same temperature for 2.5 hours. Iodomethane (0.24 ml) and potassium hydroxide (178 mg) were added to the reaction mixture, and the resulting mixture was stirred at the same temperature for 1 hour. The reaction mixture was diluted with ethyl acetate, and washed with saturated aqueous ammonium chloride and saturated aqueous sodium chloride. The organic layer was dried over anhydrous magnesium sulfate, and filtered, and then the filtrate was concentrated under reduced pressure. The resulting residue was dissolved in toluene, and the solution was concentrated under reduced pressure to obtain a methyl compound (13.9 g).

(2) By using the compound obtained in (1) mentioned above (5.0 g) as a starting material, a carbonate compound (5.79 g) was obtained in the same manner as that of Example 1, (2).

(3) The compound obtained in (2) mentioned above (5.79 g) was dissolved in tetrahydrofuran (50 ml), a 1 mold, solution of tetrabutylammonium fluoride in tetrahydrofuran (11.2 ml) was added to the solution, and the resulting mixture was stirred overnight at room temperature. The reaction mixture was diluted with ethyl acetate, and washed with aqueous ammonium chloride and saturated aqueous sodium chloride. The organic layer was dried over anhydrous magnesium sulfate, and filtered, then the filtrate was concentrated under reduced pressure, and the resulting residue was purified by silica gel column chromatography (chloroform:methanol: 28% aqueous ammonia=100:1:0.1 to 20:1:0.1) to obtain a deprotected compound (2.89 g).

(4) By using the compound obtained in (3) mentioned above (2.89 g) as a starting material, an acetyl compound (2.64 g) was obtained in the same manner as that of Example 1, (1).

(5) By using the compound obtained in (4) mentioned above (1.2 g) as a starting material, an epoxy compound (0.97 g) was obtained in the same manners as those of Example 1, (3), Example 4, (6) and Example 1, (4).

(6) The compound obtained in (5) mentioned above (300 mg) was dissolved in methanol (3 ml), formic acid (150 μl), ammonium formate (40.9 mg), and 10% palladium/carbon (150 mg) were added to the solution, and the resulting mixture was stirred at 45° C. for 7 hours under a hydrogen atmosphere of 1 atm. The reaction mixture was filtered, and then the filtrate was concentrated under reduced pressure. The resulting residue was dissolved in methanol (3 ml), formic acid (150 μl), ammonium formate (40.9 mg) and 10% palladium/carbon (150 mg) were added to the solution, and the resulting mixture was stirred at 45° C. for 7 hours under a hydrogen atmosphere of 1 atm. The reaction mixture was filtered, and then the filtrate was concentrated under reduced pressure. The resulting residue was dissolved in methanol (3 ml), formic acid (150 μl), ammonium formate (40.9 mg) and 10% palladium/carbon (300 mg) were added to the solution, and the resulting mixture was stirred at 45° C. for 3 hours under a hydrogen atmosphere of 1 atm. The reaction mixture was filtered, and then the filtrate was concentrated under reduced pressure. The resulting residue was dissolved in ethyl acetate, 10% aqueous sodium hydroxide was added to the solution. Saturated aqueous sodium hydrogencarbonate was added to the reaction mixture, and the layers were separated. The organic layer was dried over anhydrous magnesium sulfate, and filtered, then the filtrate was concentrated under reduced pressure, and the resulting residue was purified by silica gel column chromatography (chloroform:methanol: 28% aqueous ammonia=40:1:0.1 to 10:1:0.1) to obtain a deprotected compound (114 mg).

(7) By using the compound obtained in (6) mentioned above (100 mg) and the compound obtained in Reference Example 104 (88.5 mg) as starting materials, the compound shown in Table 17 (74.5 mg) was obtained in the same manner as that of Example 2, (5).

In Examples 383 to 385, by using the compound obtained in Example 382, (6) and corresponding amine reagents, the compounds shown in Table 17 were synthesized in the same manner as that of Example 2, (5).

Examples 386 to 395

Preparation methods of the compounds represented by the formula (W) having $X^2$ defined in Table 18 are shown below.

TABLE 18-1

Formula (W)

[Formula 59]

| Example | X² | ESI MS (M + H) | ¹H-NMR, CDCl₃, δ (ppm) |
|---------|----|----|----|
| 386 | | 1009.7 | (500 MHz): 0.88 (t, J = 7.27 Hz, 3 H) 0.98 (d, J = 6.86 Hz, 3 H) 1.10 (s, 9 H) 1.14-1.23 (m, 9 H) 1.23-1.26 (m, 1 H) 1.28 (s, 3 H) 1.36-1.41 (m, 1 H) 1.42 (s, 6 H) 1.45 (s, 3 H) 1.47-1.60 (m, 2 H) 1.64 (d, J = 10.70 Hz, 1 H) 1.77-1.86 (m, 1 H) 1.87-2.08 (m, 6 H) 2.16 (s, 3 H) 2.24 (br. s., 3 H) 2.28 (s, 6 H) 2.35-2.67 (m, 5 H) 2.73-2.84 (m, 3 H) 3.20-3.28 (m, 1 H) 3.26 (s, 3 H) 3.41-3.51 (m, 1 H) 3.60 (d, J = 7.40 Hz, 1 H) 3.79 (s, 3 H) 4.06-4.13 (m, 1 H) 4.23 (d, J = 7.95 Hz, 1 H) 4.43 (d, J = 7.40 Hz, 1 H) 4.89 (s, 1 H) 4.93 (d, J = 4.66 Hz, 1 H) 4.98 (dd, J = 9.74, 2.88 Hz, 1 H) 6.82-6.90 (m, 2 H) 7.13-7.19 (m, 1 H) 7.54-7.63 (m, 1 H) |
| 387 | | 1037.7 | (600 MHz): 0.88 (t, J = 7.34 Hz, 3 H) 1.02 (d, J = 6.88 Hz, 3 H) 1.08 (d, J = 7.34 Hz, 3 H) 1.12 (s, 3 H) 1.14-1.26 (m, 13 H) 1.43 (s, 6 H) 1.46 (s, 6 H) 1.47-1.68 (m, 4 H) 1.81-1.97 (m, 3 H) 2.00-2.05 (m, 2 H) 2.18 (s, 3 H) 2.25 (s, 3 H) 2.29 (s, 6 H) 2.38-2.55 (m, 4 H) 2.57-2.64 (m, 2 H) 2.77-2.86 (m, 2 H) 3.22 (dd, J = 10.09, 7.34 Hz, 1 H) 3.27 (s, 3 H) 3.42-3.48 (m, 1 H) 3.54 (d, J = 7.34 Hz, 1 H) 3.72-3.77 (m, 1 H) 3.80 (s, 3 H) 3.85 (s, 3 H) 4.04-4.12 (m, 2 H) 4.39 (d, J = 7.34 Hz, 1 H) 4.79 (s, 1 H) 4.83 (d, J = 4.58 Hz, 1 H) 4.99 (dd, J = 10.09, 2.75 Hz, 1 H) 6.84-6.91 (m, 2 H) 7.17 (s, 1 H) 7.61 (d, J = 6.88 Hz, 1 H) |
| 388 | | 1094 | (400 MHz): 0.85 (t, J = 7.32 Hz, 3 H) 0.98 (d, J = 6.84 Hz, 3 H) 1.06 (d, J = 7.32 Hz, 6 H) 1.12 (s, 3 H) 1.18 (d, J = 6.10 Hz, 6 H) 1.22 (d, J = 7.08 Hz, 3 H) 1.24 (d, J = 6.35 Hz, 3 H) 1.44 (s, 6 H) 1.48 (s, 3 H) 1.50-1.74 (m, 6 H) 1.78-1.97 (m, 2 H) 1.98-2.08 (m, 1 H) 2.17 (s, 9 H) 2.26 (s, 3 H) 2.29 (s, 6 H) 2.37-2.50 (m, 2 H) 2.50-2.67 (m, 2 H) 2.69-2.78 (m, 2 H) 3.23 (dd, J = 10.3, 7.32 Hz, 1 H) 3.28 (s, 3 H) 3.32-3.45 (m, 1 H) 3.48 (d, J = 8.30 Hz, 1 H) 3.62-3.75 (m, 1 H) 3.78 (s, 3 H) 4.04-4.16 (m, 2 H) 4.25-4.37 (m, 3 H) 4.92 (d, J = 4.64 Hz, 1 H) 4.95 (s, 1 H) 5.07 (dd, J = 10.6, 1.57 Hz, 1 H) 6.07 (s, 6 H) 6.81-6.92 (m, 2 H) 7.17 (t, J = 7.20 Hz, 1 H) 7.64 (t, J = 7.32 Hz, 1 H) |
| 389 | | 1011.7 | (600 MHz): 0.84 (t, J = 7.34 Hz, 3 H) 1.02 (d, J = 7.34 Hz, 3 H) 1.08-1.25 (m, 22 H) 1.41-1.54 (m, 11 H) 1.60-1.67 (m, 2 H) 1.87-2.06 (m, 5 H) 2.18 (s, 3 H) 2.25 (s, 3 H) 2.29 (s, 6 H) 2.35-2.69 (m, 6 H) 2.81 (d, J = 14.67 Hz, 1 H) 2.85-2.91 (m, 1 H) 3.10 (s, 1 H) 3.22 (dd, J = 10.09, 7.34 Hz, 1 H) 3.28 (s, 3 H) 3.38 (br. s., 1 H) 3.43-3.49 (m, 1 H) 3.60 (d, J = 7.34 Hz, 1 H) 3.66-3.72 (m, 2 H) 3.80 (s, 3 H) 3.82 (s, 3 H) 4.02 (dd, J = 9.40, 1.15 Hz, 1 H) 4.08 (q, J = 6.42 Hz, 1 H) 4.37 (s, 1 H) 4.42 (d, J = 7.34 Hz, 1 H) 4.98 (d, J = 5.04 Hz, 1 H) 5.11 (dd, J = 10.77, 2.06 Hz, 1 H) 6.85-6.92 (m, 2 H) 7.17 (t, J = 7.11 Hz, 1 H) 7.61 (d, J = 7.34 Hz, 1 H) |

TABLE 18-1-continued

Formula (W)

[Formula 59]

| Example | X² | ESI MS (M + H) | ¹H-NMR, CDCl₃, δ (ppm) |
|---|---|---|---|
| 390 | | 1011.7 | (600 MHz): 0.88 (t, J = 7.57 Hz, 3 H) 1.05-1.30 (m, 28 H) 1.34-1.71 (m, 10 H) 1.88-2.09 (m, 5 H) 2.17 (s, 3 H) 2.23-2.33 (m, 9 H) 2.88 (s, 8 H) 3 25-3.44 (m, 6 H) 3.47-3.59 (m, 5 H) 3.79 (s, 3 H) 3.98-4.14 (m, 2 H) 4.46-4.51 (m, 1 H) 4.81-4.86 (m, 1 H) 4.94 (d, J = 5.04 Hz, 1 H) 6.87 (d, J = 7.79 Hz, 2 H) 7.14-7.20 (m, 1 H) 7.57-7.63 (m, 1 H) |
| 391 | | 1083 | (600 MHz): 0.87 (t, J = 7.57 Hz, 3 H) 1.06-1.12 (m, 9 H) 1.13-1.19 (m, 6 H) 1.22-1.30 (m, 13 H) 1.35 (s, 3 H) 1.43 (br. s., 6 H) 1.47-1.65 (m, 3 H) 1.69-1.75 (m, 1 H) 1.83-1.92 (m, 3 H) 2.00-2.08 (m, 3 H) 2.19 (br. s., 3 H) 2.25 (br. s., 3 H) 2.31 (br. s., 6 H) 2.45-2.97 (m, 8 H) 2.92 (br. s., 3 H) 3.26 (s, 3 H) 3.26-3.31 (m, 1 H) 3.47-3.53 (m, 1 H) 3.57-3.61 (m, 1 H) 3.70 (s, 3 H) 3.77-3,83 (m, 3 H) 4.07-4.12 (m, 1 H) 4.23-4.26 (m, 1 H) 4.45 (d, J = 7.34 Hz, 1 H) 4.74-4.78 (m, 1 H) 4.90-4.93 (m, 1 H) 5.06 (br. s., 1 H) 6.85-6.91 (m, 2 H) 7.15-7.20 (m, 1 H) 7.58-7.62 (m, 1 H) |
| 392 | | 967.7 | (600 MHz): 0.84-1.01 (m, 12 H) 1.09 (d, J = 7.34 Hz, 3 H) 1.12 (s, 3 H) 1.14-1.29 (m, 11 H) 1.31 (s, 3 H) 1.40-1.51 (m, 8 H) 1.62-1.69 (m, 2 H) 1.72-1.81 (m, 1 H) 1.90-1.97 (m, 2 H) 1.99-2.10 (m, 4 H) 2.18 (s, 3 H) 2.25 (s, 3 H) 2.30 (s, 6 H) 2.37-2.65 (m, 5 H) 2.78-2.90 (m, 3 H) 3.24-3.30 (m, 4 H) 3.45-3.51 (m, 1 H) 3.66 (d, J = 7.34 Hz, 1 H) 3.80 (s, 3 H) 3.89-3.94 (m, 1 H) 4.12 (m, 1 H) 4.20 (d, J = 7.79 Hz, 1 H) 4.46 (d, J = 7.34 Hz, 1 H) 5.02 (d, J = 5.04 Hz, 1 H) 5.07-5.12 (m, 1 H) 6.85-6.90 (m, 2 H) 7.15-7.20 (m, 1 H) 7.58-7.62 (m, 1 H) |
| 393 | | 993.7 | (600 MHz): 0.85-0.92 (m, 6 H) 0.98-1.05 (m, 4 H) 1.06 (d, J = 7.34 Hz, 3 H) 1.10-1.17 (m, 12 H) 1.24 (t, J = 2.98 Hz, 7 H) 1.43 (s, 7 H) 1.63-2.11 (m, 9 H) 2.16 (s, 3 H) 2.24 (s, 4 H) 2.31 (s, 6 H) 2.39-2.65 (m, 6 H) 2.78 (d, J = 14.21 Hz, 1 H) 3.00-3.03 (m, 1 H) 3.28 (s, 3 H) 3.53-3.62 (m, 2 H) 3.80 (s, 3 H) 3.93-4.04 (m, 3 H) 4.14 (d, J = 9.63 Hz, 1 H) 4.58 (d, J = 7.34 Hz, 1 H) 4.72-4.75 (m, 1 H) 4.89-4.93 (m, 1 H) 5.02-5.07 (m, 1 H) 6.88 (s, 2 H) 7.15-7.20 (m, 1 H) 7.54-7.59 (m, 1 H) |

TABLE 18-1-continued

Formula (W)

[Formula 59]

| Example | X² | ESI MS (M + H) | ¹H-NMR, CDCl₃, δ (ppm) |
|---|---|---|---|
| 394 | (structure with HO-N=, H₃C, HO, H₃C, position 9) | 981.8 | (600 MHz): 0.85-0.89 (m, 6 H) 1.01-1.06 (m, 6 H) 1.07-1.28 (m, 16 H) 1.41-1.50 (m, 10 H) 1.51-1.74 (m, 8 H) 1.92-1.98 (m, 1 H) 2.01-2.06 (m, 2 H) 2.09-2.14 (m, 1 H) 2.16-2.19 (m, 3 H) 2.23-2.33 (m, 9 H) 2.39-2.66 (m, 6 H) 2.78-2.83 (m, 1 H) 2.87-2.93 (m, 1 H) 3.21-3.25 (m, 1 H) 3.28 (s, 3 H) 3.38-3.42 (m, 1 H) 3.44-3.50 (m, 1 H) 3.57-3.60 (m, 1 H) 3.61-3.66 (m, 2 H) 3.80 (s, 4 H) 4.01-4.04 (m, 1 H) 4.07-4.11 (m, 1 H) 4.43 (d, J = 7.34 Hz, 1 H) 4.98 (d, J = 5.04 Hz, 1 H) 5.40-5.45 (m, 1 H) |
| 395 | (structure with O=, H₃C, HO, H₃C, position 9) | 967.1 | (500 MHz): 0.84-0.91 (m, 6 H) 0.99 (d, J = 6.86 Hz, 3 H) 1.08-1.28 (m, 19 H) 1.40-1.49 (m, 10 H) 1.58-1.77 (m, 6 H) 1.92-2.13 (m, 5 H) 2.17 (s, 3 H) 2.25 (s, 3 H) 2.27-2.32 (m, 6 H) 2.37-2.66 (m, 5 H) 2.71-2.92 (m, 3 H) 2.95-3.02 (m, 1 H) 3.18-3.24 (m, 1 H) 3.28 (s, 3 H) 3.42-3.49 (m, 1 H) 3.58 (d, J = 7.40 Hz, 3 H) 3.80 (s, 3 H) 4.02 (d, J = 9.05 Hz, 1 H) 4.08-4.13 (m, 1 H) 4.41 (d, J = 7.40 Hz, 1 H) 4.96 (d, J = 4.94 Hz, 1 H) 5.35 (dd, J = 9.60, 4.66 Hz, 1 H) 6.84-6.90 (m, 2 H) 7.15-7.21 (m, 1 H) 7.60 (d, J = 6.58 Hz, 1 H) |

Example 386

(1) (9R)-9-Amino-9-deoxoerythromycin A (5.0 g) obtained by the method described in the literature (Tetrahedron Letters, 1970, vol. 2, p. 157) was dissolved in chloroform (70 ml), distilled water (28 ml) and sodium hydrogencarbonate (2.57 g) were added to the solution, benzyl chloroformate (2.55 g) was added to the mixture under ice cooling, and the resulting mixture was stirred at room temperature for 1.5 hours. Benzyl chloroformate (0.2 ml) was added to the reaction mixture, and the resulting mixture was stirred at the same temperature for 15 minutes. Distilled water was added to the reaction mixture, and the resulting mixture was extracted with chloroform. The organic layer was dried over anhydrous sodium sulfate, and filtered. The filtrate was concentrated under reduced pressure to obtain a protected compound (7.29 g).

(2) By using the compound obtained in (1) mentioned above (7.29 g) as a starting material, an epoxy compound (197.5 mg) was obtained in the same manners as those of Example 1, (2), (3), Example 4, (6), Example 1, (4) and Example 170, (1).

(3) By using the compound obtained in (2) mentioned above (100 mg) and the compound obtained in Reference Example 104 (76.4 mg) as starting materials, the compound shown in Table 18 (66.1 mg) was obtained in the same manner as that of Example 2, (5).

Example 387

(1) Potassium hydroxide (14 mg) was suspended in tetrahydrofuran (2 ml), the compound obtained in Example 377, (2) (100 mg) and iodomethane (16 µl) were added to the suspension, and the resulting mixture was stirred at room temperature for 30 minutes. Iodomethane (80) and potassium hydroxide (7 mg) were added to the reaction mixture, and the resulting mixture was stirred for 30 minutes. Ethyl acetate and saturated aqueous ammonium chloride were added to the reaction mixture, the layers were separated, and the organic layer was dried over anhydrous magnesium sulfate, and filtered. The filtrate was concentrated under reduced pressure, and the resulting residue was purified by silica gel column chromatography (chloroform:methanol:28% aqueous ammonia=20:1:0.1) to obtain a methyl compound (72.5 mg).

(2) By using the compound obtained in (1) mentioned above (70 mg) and the compound obtained in Reference Example 104 (52 mg) as starting materials, the compound shown in Table 18 was obtained in the same manner as that of Example 2, (5).

Example 388

(1) The compound obtained in Example 352, (2) (6.0 g) was dissolved in chloroform (60 ml), pyridine (11 ml) and a solution of triphosgene (2.16 g) in chloroform (28 ml) were added to the solution under ice cooling, and the resulting mixture was stirred for 1 hour under ice cooling. Cold water was added to the reaction mixture under ice cooling, the resulting mixture was neutralized with 5 N aqueous sodium hydroxide, and then the organic layer and the aqueous layer were separated. The aqueous layer was extracted with chloroform, and the organic layers were combined, successively washed twice with distilled water, and with saturated aqueous sodium chloride, then dried over anhydrous sodium sulfate, and filtered. The organic layer was dried over anhydrous magnesium sulfate, and filtered. Ethyl acetate and distilled water were added to the filtrate, the layers were separated, and the organic layer was successively washed with distilled water and saturated aqueous sodium chloride, then dried over anhydrous sodium sulfate, and filtered. The filtrate was concentrated under reduced pressure, and the resulting residue was dissolved in ethyl acetate. Hexane was added to the solution, and deposited solid was collected by filtration to obtain a carbonate compound (3.03 g). The filtrate was concentrated under reduced pressure, and the resulting residue was purified by silica gel column chromatography (chloroform to chloroform:methanol=70:1 to 30:1). The resulting solid (2.0 g) was dissolved in ethyl acetate (10 ml), hexane (20 ml) was added to the solution, and the deposited solid was collected by filtration to obtain the carbonate compound (814 mg).
(2) By using the compound obtained in (1) mentioned above (3.84 g) as a starting material, a deacetylated compound (3.85 g) was obtained in the same manners as those of Example 1, (3) and Example 4, (6).
(3) By using the compound obtained in (2) mentioned above (2.05 g) as a starting material, an epoxy compound (1.25 g) was obtained in the same manner as that of Example 1, (4).
(4) The compound obtained in (3) mentioned above (43.6 g) was dissolved in methanol (15 ml), ammonium formate (232 mg) and 5% palladium/carbon (2.0 g) were added to the solution under an argon atmosphere, and then the resulting mixture was stirred at 45° C. for 3 hours under a hydrogen atmosphere of 1 atm. Saturated aqueous sodium hydrogencarbonate was added to the reaction mixture, the resulting mixture was filtered through Celite, and then filtrate was concentrated under reduced pressure. Ethyl acetate (100 ml) and methanol (14 ml) were added to the resulting residue, the residue was dissolved therein, and the organic layer was washed with saturated aqueous sodium hydrogencarbonate, distilled water and saturated aqueous sodium chloride, then dried over anhydrous sodium sulfate, and filtered. The filtrate was concentrated under reduced pressure, and the resulting residue was purified by silica gel column chromatography (chloroform to chloroform:methanol:28% aqueous ammonia=70:1:0.1 to 50:1:0.1) to obtain a debenzylated compound (1.07 g).
(5) The compound obtained in (4) mentioned above (70 mg) and 2-chloro-N,N-dimethylethanamine (100 mg) were dissolved in tetrahydrofuran (1 ml), powder of 85% potassium hydroxide (7 mg) and tetrabutylammonium bromide (1.5 mg) were added to the solution, and the resulting mixture was stirred at room temperature for 30 hours, and then stirred at 60° C. for 16 hours. Ethyl acetate and 20% aqueous ammonium chloride were added to the reaction mixture under ice cooling, the layers were separated, and the organic layer was washed twice with saturated aqueous sodium hydrogencarbonate and distilled water, and with saturated aqueous sodium chloride, then dried over anhydrous sodium sulfate, and filtered. The filtrate was concentrated under reduced pressure, and the resulting residue was purified by preparative thin layer chromatography (chloroform:methanol:28% aqueous ammonia=10:1:0.1) to obtain an alkyloxime compound (59 mg).
(6) By using the compound obtained in (5) mentioned above (98 mg) and the compound obtained in Reference Example 104 (54 mg) as starting materials, the compound shown in Table 18 (33 mg) was obtained in the same manner as that of Example 129, (3).

Example 389

By using the compound obtained in Example 387, (1) (70 mg) and the compound obtained in Reference Example 104 (52 mg) as starting materials, the compound shown in Table 18 was obtained in the same manner as that of Example 2, (5).

Example 390

(1) (E)-Erythromycin A 9-oxime (10 g) obtained by the method described in the publication (European Patent No. 0508726) was dissolved in tetrahydrofuran (60 ml), potassium hydroxide (825 mg), benzyl chloride (1.7 ml) and tetrabutylammonium bromide (215 mg) were added to the solution under ice cooling, and the resulting mixture was stirred at 45° C. for 2 hours. Ethyl acetate, distilled water and saturated aqueous sodium chloride were added to the reaction mixture, the resulting mixture was filtered, and then the layers were separated. The organic layer was washed with saturated aqueous sodium chloride, dried over anhydrous magnesium sulfate, and filtered. The filtrate was concentrated under reduced pressure to obtain a benzyl compound (10.49 g).
(2) The compound obtained in (1) mentioned above (10.49 g) was dissolved in dimethylformamide (125 ml), imidazole (6.41 g) and triethylsilyl chloride (4.71 g) were added to the solution under ice cooling, and the resulting mixture was stirred at room temperature for 3 days. Imidazole (1.28 g) and triethylsilyl chloride (942 mg) were added to the reaction mixture, and the resulting mixture was stirred for 7 hours. Imidazole (2.56 g) and triethylsilyl chloride (1.88 g) were added to the reaction mixture, and the resulting mixture was stirred overnight at room temperature. Ethyl acetate, distilled water and saturated aqueous ammonium chloride were added to the reaction mixture, and the layers were separated. The organic layer was washed with saturated aqueous ammonium chloride and saturated aqueous sodium chloride, then dried over anhydrous magnesium sulfate, and filtered. The filtrate was concentrated under reduced pressure, and the resulting residue was purified by silica gel column chromatography (hexane:acetone:triethylamine=40:1:0 to 8:1:0 to 3:1:0.2 to 2:1:0.2) to obtain a silyl compound (10.82 g).
(3) The compound obtained in (2) mentioned above (9.15 g) was dissolved in dimethylformamide (83 ml), boric acid (539 mg) was added to the solution, and the resulting mixture was stirred at room temperature for 0.5 hour. A 0.6 mol/L solution of trimethylsilyldiazomethane in hexane (69.2 ml) was added to the reaction mixture, and the resulting mixture was stirred overnight at room temperature. Saturated aqueous sodium hydrogencarbonate and ethyl acetate were added to the reaction mixture, and the layers were separated. The organic layer was washed twice with distilled water, dried over anhydrous magnesium sulfate, and filtered. The filtrate was concentrated under reduced pressure to obtain a methyl compound (10.3 g).
(4) The compound obtained in (3) mentioned above (10.3 g) was dissolved in tetrahydrofuran (30 ml), about 70% hydrogen fluoride/pyridine complex (11.8 ml) was added to the solution, and the resulting mixture was stirred at room temperature for 2 hours. Saturated aqueous sodium hydrogencarbonate was added to the reaction mixture to neutralize the mixture, then 1 N aqueous sodium hydroxide and ethyl acetate were added to the mixture, and the layers were separated. The organic layer was dried over anhydrous magnesium sulfate, and filtered. The filtrate was concentrated under reduced pressure, and the resulting residue was purified by silica gel column chromatography (chloroform to chloroform:methanol:28% aqueous ammonia=20:1:0.1 to 10:1:0.1) to obtain a deprotected compound (5.7 g).

(5) By using the compound obtained in (4) mentioned above (700 mg) as a starting material, an epoxy compound (507 mg) was obtained in the same manners as those of Example 1, (1), (3), Example 4, (6) and Example 1, (4).

(6) The compound obtained in (5) mentioned above (500 mg) was dissolved in methanol (15 ml), ammonium formate (739.2 mg), formic acid (0.45 ml) and 5% palladium/carbon (150 mg) were added to the solution, and the resulting mixture was stirred at room temperature for 4 hours. The reaction mixture was filtered, the filtrate was concentrated under reduced pressure, chloroform and saturated aqueous sodium hydrogencarbonate were added to the resulting residue, and the layers were separated. The organic layer was dried over anhydrous magnesium sulfate, and filtered. The filtrate was concentrated under reduced pressure, toluene was added to the resulting residue, and the resulting mixture was concentrated under reduced pressure. The resulting residue was purified by silica gel column chromatography (chloroform:methanol:28% aqueous ammonia=20:1:0.1) to obtain a deprotected compound (26 mg).

(7) By using the compound obtained in (6) mentioned above (26 mg) and the compound obtained in Reference Example 104 (39.6 mg) as starting materials, the compound shown in Table 18 (3 mg) was obtained in the same manner as that of Example 317.

Example 391

(1) By using (E)-erythromycin A 9-methyloxime (2.2 g) obtained by the method described in the literature (The Journal of Antibiotics, 1991, vol. 44, No. 3, p. 313) as a starting material, a carbonate compound (1.72 g) was obtained in the same manners as those of Example 1, (1) and (2).

(2) The compound obtained in (1) mentioned above (500 mg) was dissolved in methanol (5 ml), pyridine hydrochloride (13.9 mg) and 50% aqueous dimethylamine (5.0 ml) were added to the solution, and the resulting mixture was stirred at room temperature for 3 days. Chloroform and saturated aqueous sodium hydrogencarbonate were added to the reaction mixture, the layers were separated, and the aqueous layer was extracted with chloroform. The organic layers were combined, filtered with a phase separator to further separate the layers, the resulting organic layer was concentrated under reduced pressure, and the resulting residue was purified by silica gel column chromatography (chloroform:methanol:28% aqueous ammonia=100:1:0.1 to 10:1:0.1) to obtain an amide compound (327 mg).

(3) By using the compound obtained in (2) mentioned above (323 mg) as a starting material, an epoxy compound (48.2 mg) was obtained in the same manners as those of Example 1, (1), Example 6, (3), Example 4, (6) and Example 1, (4).

(4) By using the compound obtained in (3) mentioned above (28.0 mg) and the compound obtained in Reference Example 104 (23.5 mg) as starting materials, the compound shown in Table 18 (17.3 mg) was obtained in the same manner as that of Example 4, (8).

Example 392

(1) Erythromycin B (10 g) was dissolved in methanol (20 ml), 50% aqueous hydroxylamine (6.63 g) and 80% aqueous acetic acid (2.87 ml) were added to the solution, and the resulting mixture was stirred at room temperature for 15 minutes and at 50° C. for 18 hours. The reaction mixture was left to cool to room temperature, then ethyl acetate and distilled water were added to the reaction mixture, 25% aqueous sodium hydroxide was added so that pH became 9, and the layers were separated. The organic layer was washed with saturated aqueous sodium chloride, dried over anhydrous magnesium sulfate, and filtered. The filtrate was concentrated under reduced pressure to obtain an oxime compound (10.85 g).

(2) The compound obtained in (1) mentioned above (10.5 g) was dissolved in methanol (30 ml), ammonium formate (55.2 g), a solution of titanium(III) chloride in hydrochloric acid (21 ml) was added to the solution, and the resulting mixture was stirred at room temperature for 5 minutes. Sodium cyanoborohydride (4.5 g) was added to the reaction mixture, and the resulting mixture was stirred overnight at room temperature. Ethyl acetate and saturated aqueous sodium hydrogencarbonate were added to the reaction mixture, the layers were separated, and the organic layer was washed with saturated aqueous sodium hydrogencarbonate and saturated aqueous sodium chloride, dried over anhydrous magnesium sulfate, and filtered. The filtrate was concentrated under reduced pressure, and the resulting residue was purified by silica gel column chromatography (chloroform:methanol:28% aqueous ammonia=10:1:0.1) to obtain an amino compound (6.23 g).

(3) The compound obtained in (2) mentioned above (6.2 g) was dissolved in chloroform (15 ml), saturated aqueous sodium hydrogencarbonate (30 ml) was added to the solution, then a solution of benzyl chloroformate (2.46 ml) in chloroform (15 ml) was added dropwise to the mixture, and the resulting mixture was stirred overnight at room temperature. The layers of the reaction mixture were separated, and the organic layer was washed with saturated aqueous sodium hydrogencarbonate and saturated aqueous sodium chloride, dried over anhydrous magnesium sulfate, and filtered. The filtrate was concentrated under reduced pressure, and the resulting residue was purified by silica gel column chromatography (chloroform to chloroform:methanol:28% aqueous ammonia=100:1:0.1 to 20:1:0.1) to obtain a protected compound (390 mg).

(4) By using the compound obtained in (3) mentioned above (390 mg) as a starting material, an epoxy compound (115 mg)

329 was obtained in the same manners as those of Example 1, (3), Example 4, (6) and Example 1, (4).
(5) By using the compound obtained in (4) mentioned above (85 mg) and the compound obtained in Reference Example 104 (70 mg) as starting materials, an adduct compound (51 mg) was obtained in the same manner as that of Example 317.
(6) By using the compound obtained in (5) mentioned above (46 mg) as a starting material, the compound shown in Table 18 (10 mg) was obtained in the same manner as that of Example 166, (2).

Example 393

(1) By using the compound obtained in Example 392, (3) (390 mg) as a starting material, a cyclized compound (24 mg) was obtained in the same manners as those of Example 1, (3), Example 4, (6) and Example 1, (4).
(2) By using the compound obtained in (1) mentioned above (20 mg) and the compound obtained in Reference Example 104 (18.7 mg) as starting materials, the compound shown in Table 18 (15 mg) was obtained in the same manner as that of Example 317.

Example 394

(1) By using the compound obtained in Example 392, (1) (5 g) as a starting material, a diacetyl compound (5.16 g) was obtained in the same manner as that of Example 1, (1).

330

(2) By using the compound obtained in (1) mentioned above (1.45 g) as a starting material, an epoxy compound (485 mg) was obtained in the same manners as those of Example 6, (3), Example 1, (4) and Example 4, (6).
(3) By using the compound obtained in (2) mentioned above (50 mg) and the compound obtained in Reference Example 104 (47.5 mg) as starting materials, the compound shown in Table 18 (12 mg) was obtained in the same manner as that of Example 4, (8).

Example 395

(1) By using erythromycin B (2 g) as a starting material, an epoxy compound (295 mg) was obtained in the same manners as those of Example 1, (1), Example 6, (3), Example 4, (6) and Example 1, (4).
(2) By using the compound obtained in (1) mentioned above (150 mg) and the compound obtained in Reference Example 104 (121 mg) as starting materials, the compound shown in Table 18 (23 mg) was obtained in the same manner as that of Example 317.

Examples 396 to 398

Preparation methods of the compounds represented by the formula (X) having $X^3$ defined in Table 19 are shown below.

TABLE 19

Formula (X)

[Formula 60]

| Example | $X^3$ | ESI MS (M + H) | $^1$H-NMR, CDCl$_3$, δ (ppm) |
|---------|-------|----------------|------------------------------|
| 396 |  | 948.9 | (600 MHz) d ppm 0.87 (t, J = 7.34 Hz, 3 H) 1.06-1.11 (m, 6 H) 1.13-1.19 (m, 9 H) 1.21-1.30 (m, 10 H) 1.35 (s, 3 H) 1.47-1.54 (m, 1 H) 1.55-1.61 (m, 1 H) 1.64-1.68 (m, 1 H) 1.70-1.74 (m, 1 H) 1.84-1.92 (m, 3 H) 2.01 (d, J = 14.67 Hz, 1 H) 2.01-2.06 (m, 1 H) 2.15 (d, J = 15.13 Hz, 1 H) 2.24 (s, 6 H) 2.31 (s, 6 H) 2.33-2.37 (m, 1 H) 2.34 (s, 3 H) 2.37-2.43 (m, 1 H) 2.48-2.56 (m, 2 H) 2.60-2.66 (m, 1 H) 2.70-2.75 (m, 1 H) 2.82 (d, J = 14.67 Hz, 1 H) 2.84-2.88 (m, 1 H) 2.91-3.00 (m, 6 H) 3.27 (s, 3 H) 3.27-3.31 (m, 1 H) 3.49-3.55 (m, 1 H) 3.59 (d, J = 6.88 Hz, 1 H) 3.71 (s, 3 H) 4.09-4.13 (m, 1 H) 4.24 (d, J = 5.96 Hz, 1 H) 4.45 (d, J = 7.34 Hz, 1 H) 4.73-4.77 (m, 1 H) 4.92 (d, J = 4.58 Hz, 1 H) 5.07 (s, 1 H) |

TABLE 19-continued

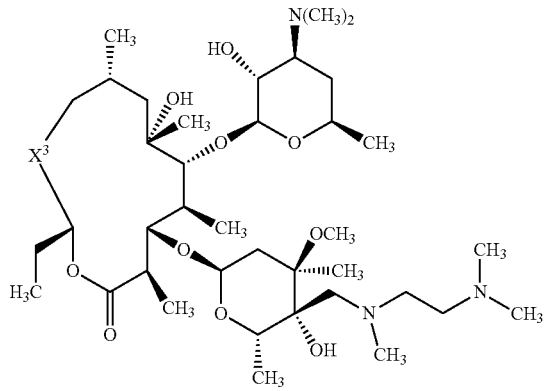

Formula (X)

[Formula 60]

| Example | X³ | ESI MS (M + H) | ¹H-NMR, CDCl₃, δ (ppm) |
|---|---|---|---|
| 397 | ![structure] | 832.7 | (500 MHz) d ppm 0.84-0.91 (m, 6 H) 0.99 (d, J = 6.86 Hz, 3 H) 1.10-1.28 (m, 19 H) 1.42-1.51 (m, 4 H) 1.57-1.76 (m, 4 H) 1.91-2.17 (m, 6 H) 2.21-2.26 (m, 6 H) 2.26-2.56 (m, 13 H) 2.58-2.66 (m, 1 H) 2.70-2.90 (m, 3 H) 2.95-3.02 (m, 1 H) 3.22 (dd, J = 10.28, 7.27 Hz, 1 H) 3.28 (s, 3 H) 3.48 (br. s., 1 H) 3.60 (d, J = 7.13 Hz, 1 H) 3.81 (d, J = 10.15 Hz, 1 H) 4.01-4.05 (m, 1 H) 4.12 (q, J = 6.40 Hz, 1 H) 4.42 (d, J = 7.40 Hz, 1 H) 4.95 (d, J = 4.39 Hz, 1 H) 5.34 (dd, J = 9.19, 4.53 Hz, 1 H) |
| 398 | ![structure] | 847.7 | (500 MHz) d ppm 0.83-0.89 (m, 6 H) 1.00 (d, J = 7.13 Hz, 6 H) 1.09 (d, J = 7.40 Hz, 3 H) 1.11-1.14 (m, 3 H) 1.17-1.30 (m, 10 H) 1.39-1.54 (m, 5 H) 1.57-1.71 (m, 4 H) 1.98-2.14 (m, 4 H) 2.22-2.37 (m, 15 H) 2.41-2.92 (m, 8 H) 3.21-3.29 (m, 4 H) 3.43-3.51 (m, 1 H) 3.61 (d, J = 7.40 Hz, 1 H) 3.72 (d, J = 9.32 Hz, 1 H) 3.79-3.85 (m, 1 H) 4.04 (d, J = 9.60 Hz, 1 H) 4.10 (q, J = 5.94 Hz, 1 H) 4.40 (d, J = 7.13 Hz, 1 H) 4.97 (br. s., 1 H) 5.45 (dd, J = 9.32, 4.11 Hz, 1 H) |

Example 396

By using the compound obtained in Example 391, (3) (18 mg) as a starting material, the compound shown in Table 19 (6.9 mg) was obtained in the same manner as that of Example 4, (8).

Example 397

By using the compound obtained in Example 395, (1) (50 mg) as a starting material, the compound shown in Table 19 (13 mg) was obtained in the same manner as that of Example 4, (8).

Example 398

By using the compound obtained in Example 394, (2) (50 mg) as a starting material, the compound shown in Table 19 (19 mg) was obtained in the same manner as that of Example 4, (8).

Examples 399 to 456

Preparation methods of the compounds represented by the formula (Y) having $R^{1f}$ and $R^{29d}$ defined in Table 20 are shown below.

TABLE 20-1

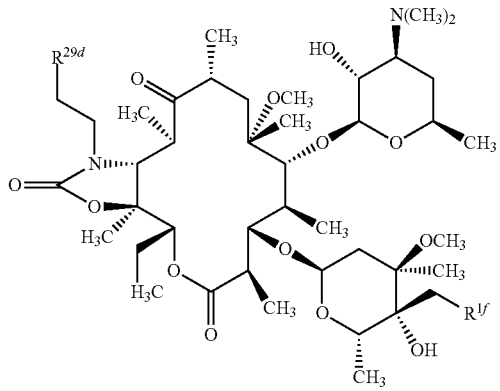

[Formula 61]

| Example | R²⁹ᵈ | Rⁱᶠ | ESI MS (M + H) | ¹H-NMR, CDCl₃, δ (ppm) |
|---|---|---|---|---|
| 399 | H₃C-S(O)₂-NH- | -N(CH₃)-CH₂CH₂-N(cyclopropyl)(CH₂CH₃) | 1048.6 | (500 MHz): 0.37-0.50 (m, 4 H) 0.86 (t, J = 7.45 Hz, 3 H) 0.99-1.29 (m, 25 H) 1.40 (s, 6 H) 1.50-1.81 (m, 5 H) 1.82-2.10 (m, 5 H) 2.30 (s, 6 H) 2.34 (s, 3 H) 2.40-2.74 (m, 8 H) 2.83 (d, J = 14.52 Hz, 1 H) 2.89-2.97 (m, 1 H) 2.99 (s, 3 H) 3.05 (s, 3 H) 3.12 (q, J = 7.01 Hz, 1 H) 3.19 (dd, J = 9.94, 7.26 Hz, 1 H) 3.24-3.36 (m, 1 H) 3.27 (s, 3 H) 3.40-3.57 (m, 2 H) 3.59 (s, 1 H) 3.66-3.73 (m, 2 H) 3.76-3.83 (m, 1 H) 3.84-3.92 (m, 1 H) 4.08 (q, J = 6.37 Hz, 1 H) 4.41 (d, J = 7.26 Hz, 1 H) 4.92-5.01 (m, 2 H) 5.55 (t, J = 5.73 Hz, 1 H) |
| 400 | H₃C-S(O)₂-NH- | -N(CH₃)-CH₂CH₂-N(cyclopropyl)(CH₃) | 1034.6 | (499 MHz): 0.37-0.48 (m, 4 H) 0.85 (t, J = 7.40 Hz, 3 H) 0.99-1.28 (m, 22 H) 1.40 (s, 6 H) 1.51-1.62 (m, 1 H) 1.63-1.71 (m, 2 H) 1.74 (d, J = 6.58 Hz, 2 H) 1.82-2.11 (m, 5 H) 2.29 (s, 6 H) 2.34 (s, 3 H) 2.40-2.48 (m, 1 H) 2.50-2.68 (m, 5 H) 2.83 (d, J = 14.53 Hz, 1 H) 2.93 (dd, J = 9.60, 7.13 Hz, 1 H) 2.98 (s, 3 H) 3.05 (s, 3 H) 3.12 (q, J = 6.86 Hz, 1 H) 3.18 (dd, J = 10.15, 7.40 Hz, 1 H) 3.27 (s, 3 H) 3.24-3.36 (m, 1 H) 3.40-3.50 (m, 1 H) 3.50-3.62 (m, 1 H) 3.58 (s, 1 H) 3.69 (t, J = 7.68 Hz, 2 H) 3.76-3.92 (m, 2 H) 4.08 (q, J = 6.12 Hz, 1 H) 4.41 (d, J = 7.13 Hz, 1 H) 4.92-5.01 (m, 2 H) 5.56 (t, J = 5.76 Hz, 1 H) |
| 401 | H₃C-S(O)₂-NH- | -N(CH₃)-CH₂CH₂-N(cyclopropyl)(CH(CH₃)₂) | 1062.7 | (500 MHz): 0.37-0.51 (m, 4 H) 0.86 (t, J = 7.26 Hz, 3 H) 0.99-1.27 (m, 28 H) 1.40 (s, 8 H) 1.51-1.62 (m, 1 H) 1.63-1.69 (m, 1 H) 1.74 (d, J = 6.50 Hz, 2 H) 1.82-2.08 (m, 6 H) 2.29 (s, 6 H) 2.34 (s, 3 H) 2.40-2.70 (m, 7 H) 2.82 (d, J = 14.52 Hz, 1 H) 2.89-3.03 (m, 1 H) 2.99 (s, 3 H) 3.06 (s, 3 H) 3.12 (q, J = 7.14 Hz, 1 H) 3.18 (dd, J = 10.32, 7.26 Hz, 1 H) 3.27 (s, 3 H) 3.28-3.36 (m, 1 H) 3.40-3.58 (m, 2 H) 3.58 (s, 1 H) 3.67-3.72 (m, 2 H) 3.76-3.83 (m, 1 H) 3.84-3.92 (m, 1 H) 4.08 (q, J = 6.12 Hz, 1 H) 4.41 (d, J = 7.26 Hz, 1 H) 4.96 (dd, J = 10.70, 1.91 Hz, 1 H) 4.98 (d, J = 4.59 Hz, 1 H) 5.55 (t, J = 5.73 Hz, 1 H) |
| 402 | H₃C-S(O)₂-NH- | -N(CH₃)-CH₂CH₂-N(cyclopropyl)(cyclopropyl) | 1060.6 | (500 MHz): 0.36-0.48 (m, 8 H) 0.86 (t, J = 7.28 Hz, 3 H) 1.02 (d, J = 6.88 Hz, 3 H) 1.07-1.28 (m, 19 H) 1.40 (s, 6 H) 1.51-1.69 (m, 2 H) 1.74 (d, J = 6.12 Hz, 2 H) 1.82-2.11 (m, 7 H) 2.29 (s, 6 H) 2.36 (s, 3 H) 2.39-2.47 (m, 1 H) 2.54-2.88 (m, 6 H) 2.94 (dd, J = 9.94, 7.28 Hz, 1 H) 2.99 (s, 3 H) 3.06 (s, 3 H) 3.12 (q, J = 6.88 Hz, 1 H) 3.18 (dd, J = 10.32, 7.26 Hz, 1 H) 3.25-3.36 (m, 1 H) 3.28 (s, 3 H) 3.39-3.61 (m, 2 H) 3.58 (s, 1 H) 3.66-3.73 (m, 2 H) 3.77-3.83 (m, 1 H) 3.84-3.92 (m, 1 H) 4.09 (q, J = 6.12 Hz, 1 H) 4.41 (d, J = 7.26 Hz, 1 H) 4.96 (dd, J = 10.70, 1.91 Hz, 1 H) 4.98 (d, J = 4.97 Hz, 1 H) 5.56 (t, J = 5.73 Hz, 1 H) |

TABLE 20-1-continued

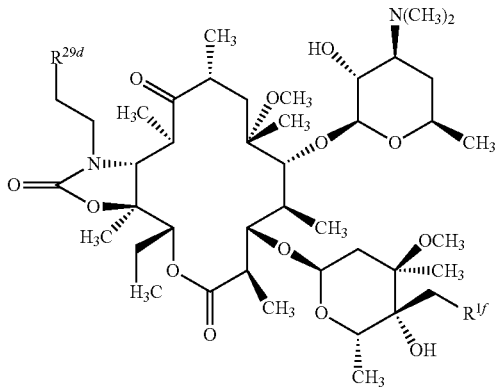

[Formula 61]

| Example | R[29d] | R[1f] | ESI MS (M + H) | $^1$H-NMR, CDCl$_3$, δ (ppm) |
|---|---|---|---|---|
| 403 | H$_3$C-S(=O)$_2$-NH- | -C(CH$_3$)-N(CH$_3$)-CH$_2$CH$_2$-N(propyl)(cyclopropyl) | 1062.7 | (500 MHz): 0.37-0.49 (m, 4 H) 0.85 (t, J = 7.45 Hz, 6 H) 1.02 (d, J = 6.88 Hz, 3 H) 1.07-1.29 (m, 19 H) 1.40 (s, 6 H) 1.48-1.81 (m, 7 H) 1.82-2.09 (m, 5 H) 2.29 (s, 6 H) 2.34 (s, 3 H) 2.40-2.76 (m, 6 H) 2.83 (d, J = 14.91 Hz, 1 H) 2.89-3.00 (m, 1 H) 2.99 (s, 3 H) 3.06 (s, 3 H) 3.12 (q, J = 6.88 Hz, 1 H) 3.18 (dd, J = 10.32, 7.26 Hz, 1 H) 3.25-3.36 (m, 1 H) 3.27 (s, 3 H) 3.40-3.61 (m, 2 H) 3.58 (s, 1 H) 3.66-3.73 (m, 2 H) 3.77-3.83 (m, 1 H) 3.84-3.92 (m, 1 H) 4.08 (q, J = 6.12 Hz, 1 H) 4.41 (d, J = 7.26 Hz, 1 H) 4.96 (dd, J = 11.08, 1.91 Hz, 1 H) 4.98 (d, J = 4.97 Hz, 1 H) 5.55 (t, J = 5.92 Hz, 1 H) |
| 404 | H$_3$C-S(=O)$_2$-NH- | -C(CH$_3$)-N(CH$_3$)-CH$_2$CH$_2$-N(iPr)$_2$ | 1064.7 | (500 MHz): 0.85 (t, J = 7.26 Hz, 3 H) 0.95-1.28 (m, 34 H) 1.40 (s, 6 H) 1.50-1.78 (m, 4 H) 1.82-2.09 (m, 5 H) 2.29 (s, 6 H) 2.33-2.38 (m, 3 H) 2.39-2.64 (m, 6 H) 2.83 (d, J = 14.91 Hz, 1 H) 2.90-3.03 (m, 6 H) 3.05 (s, 3 H) 3.09-3.21 (m, 2 H) 3.25-3.36 (m, 4 H) 3.40-3.55 (m, 2 H) 3.58 (s, 1 H) 3.66-3.73 (m, 2 H) 3.76-3.93 (m, 2 H) 4.05-4.13 (m, 1 H) 4.41 (d, J = 7.26 Hz, 1 H) 4.92-5.02 (m, 2 H) 5.52-5.59 (m, 1 H) |
| 405 | H$_3$C-S(=O)$_2$-NH- | -C(CH$_3$)-N(CH$_3$)-CH$_2$CH$_2$-N(CH$_3$)(iPr) | 1036.6 | (500 MHz): 0.85 (t, J = 7.26 Hz, 3 H) 0.96-1.04 (m, 9 H) 1.07-1.27 (m, 19 H) 1.40 (s, 6 H) 1.50-1.77 (m, 4 H) 1.82-2.14 (m, 5 H) 2.22 (s, 3 H) 2.29 (s, 6 H) 2.32-2.62 (m, 9 H) 2.78-2.96 (m, 3 H) 2.98 (s, 3 H) 3.05 (s, 3 H) 3.09-3.22 (m, 2 H) 3.24-3.36 (m, 4 H) 3.42-3.57 (m, 2 H) 3.59 (s, 1 H) 3.65-3.93 (m, 4 H) 4.05-4.13 (m, 1 H) 4.42 (d, J = 7.26 Hz, 1 H) 4.92-5.01 (m, 2 H) 5.50-5.61 (m, 1 H) |
| 406 | H$_3$C-S(=O)$_2$-NH- | -C(CH$_3$)-N(CH$_3$)-CH$_2$CH$_2$-N(Et)(propyl) | 1050.7 | (500 MHz): 0.81-0.90 (m, 6 H) 0.98-1.05 (m, 6 H) 1.08-1.29 (m, 19 H) 1.36-1.76 (m, 11 H) 1.82-2.11 (m, 5 H) 2.29 (s, 6 H) 2.31-2.64 (m, 13 H) 2.81-2.96 (m, 2 H) 2.99 (s, 3 H) 3.08 (s, 3 H) 3.08-3.21 (m, 2 H) 3.25-3.36 (m, 4 H) 3.41-3.57 (m, 3 H) 3.59 (s, 1 H) 3.65-3.74 (m, 2 H) 3.77-3.93 (m, 2 H) 4.04-4.14 (m, 1 H) 4.41 (d, J = 7.26 Hz, 1 H) 4.92-5.01 (m, 2 H) 5.51-5.60 (m, 1 H) |
| 407 | H$_3$C-S(=O)$_2$-NH- | -C(CH$_3$)-N(CH$_3$)-CH$_2$CH$_2$-N(iPr)(propyl) | 1064.7 | (500 MHz): 0.85 (t, J = 7.26 Hz, 6 H) 0.94-1.04 (m, 9 H) 1.07-1.27 (m, 19 H) 1.35-1.48 (m, 8 H) 1.51-1.77 (m, 4 H) 1.81-2.10 (m, 5 H) 2.26-2.63 (m, 16 H) 2.80-3.00 (m, 6 H) 3.06 (s, 3 H) 3.08-3.21 (m, 2 H) 3.24-3.36 (m, 4 H) 3.41-3.57 (m, 3 H) 3.58 (s, 1 H) 3.67-3.73 (m, 2 H) 3.76-3.93 (m, 2 H) 4.04-4.12 (m, 1 H) 4.41 (d, J = 7.26 Hz, 1 H) 4.93-5.01 (m, 2 H) 5.51-5.59 (m, 1 H) |

TABLE 20-1-continued

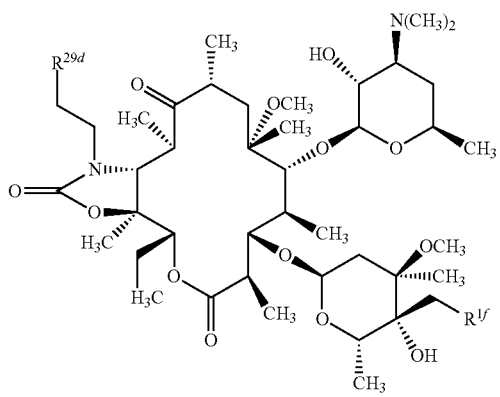

[Formula 61]

| Example | R²⁹ᵈ | R¹ᶠ | ESI MS (M + H) | ¹H-NMR, CDCl₃, δ (ppm) |
|---|---|---|---|---|
| 408 | H₃C-S(=O)₂-NH- | -N(CH₃)-CH₂CH₂-N(CH₃)-CH₂CH₂CH₃ | 1036.6 | (499 MHz): 0.82-0.91 (m, 6 H) 1.02 (d, J = 6.86 Hz, 3 H) 1.08-1.28 (m, 19 H) 1.40 (s, 6 H) 1.43-1.77 (m, 6 H) 1.82-2.14 (m, 5 H) 2.16-2.66 (m, 18 H) 2.81-2.96 (m, 2 H) 2.98 (s, 3 H) 3.05 (s, 3 H) 3.09-3.22 (m, 2 H) 3.25-3.35 (m, 4 H) 3.43-3.60 (m, 4 H) 3.66-3.74 (m, 2 H) 3.77-3.92 (m, 2 H) 4.07-4.13 (m, 1 H) 4.41 (d, J = 7.40 Hz, 1 H) 4.93-5.00 (m, 2 H) 5.53-5.59 (m, 1 H) |
| 409 | H₃C-S(=O)₂-NH- | -N(CH₃)-CH₂CH₂-N(CH₃)-cyclobutyl | 1048.6 | (499 MHz): 0.86 (t, J = 7.27 Hz, 3 H) 1.02 (d, J = 6.86 Hz, 3 H) 1.08-1.27 (m, 19 H) 1.40 (br. s., 6 H) 1.51-2.14 (m, 18 H) 2.24-2.36 (m, 10 H) 2.40-2.64 (m, 4 H) 2.77-3.00 (m, 6 H) 3.06 (s, 3 H) 3.09-3.21 (m, 2 H) 3.25-3.37 (m, 4 H) 3.42-3.60 (m, 4 H) 3.66-3.74 (m, 2 H) 3.76-3.93 (m, 2 H) 4.10 (q, J = 6.31 Hz, 1 H) 4.42 (d, J = 7.13 Hz, 1 H) 4.92-5.02 (m, 2 H) 5.52-5.59 (m, 1 H) |
| 410 | H₃C-S(=O)₂-NH- | -N(CH₃)-CH₂CH₂-N(CH₂CH₃)-cyclobutyl | 1062.7 | (499 MHz): 0.85 (t, J = 7.40 Hz, 3 H) 0.95-1.05 (m, 6 H) 1.08-1.28 (m, 19 H) 1.36-1.44 (m, 6 H) 1.51-1.77 (m, 6 H) 1.82-2.11 (m, 9 H) 2.29 (s, 6 H) 2.31-2.35 (m, 3 H) 2.38-2.63 (m, 8 H) 2.84 (d, J = 14.53 Hz, 1 H) 2.90-3.00 (m, 4 H) 3.03-3.21 (m, 6 H) 3.25-3.36 (m, 4 H) 3.43-3.60 (m, 4 H) 3.66-3.73 (m, 2 H) 3.77-3.92 (m, 2 H) 4.08 (q, J = 6.22 Hz, 1 H) 4.41 (d, J = 7.13 Hz, 1 H) 4.92-5.03 (m, 2 H) 5.53-5.60 (m, 1 H) |
| 411 | H₃C-S(=O)₂-NH- | -N(CH₃)-CH₂CH₂-N(CH₃)-CH₂-cyclopropyl | 1048.6 | (499 MHz): 0.06-0.14 (m, 2 H) 0.46-0.55 (m, 2 H) 0.81-0.93 (m, 4 H) 0.98-1.29 (m, 22 H) 1.40 (s, 6 H) 1.52-1.78 (m, 4 H) 1.83-2.16 (m, 5 H) 2.21-2.68 (m, 20 H) 2.83 (d, J = 14.81 Hz, 1 H) 2.88-3.01 (m, 4 H) 3.05 (s, 3 H) 3.09-3.22 (m, 2 H) 3.25-3.36 (m, 4 H) 3.43-3.57 (m, 2 H) 3.59 (s, 1 H) 3.66-3.82 (m, 4 H) 4.07-4.15 (m, 1 H) 4.42 (d, J = 7.40 Hz, 1 H) 4.92-5.01 (m, 2 H) 5.53-5.69 (m, 1 H) |
| 412 | H₃C-S(=O)₂-NH- | -N(CH₃)-CH₂CH₂-N(thiomorpholinyl with CH₃) | 1080.6 | (600 MHz): 0.86 (t, J = 7.43 Hz, 3 H) 1.02 (d, J = 7.02 Hz, 3 H) 1.11 (d, J = 7.43 Hz, 3 H) 1.13 (d, J = 7.02 Hz, 3 H) 1.15-1.20 (m, 9 H) 1.20-1.25 (m, 7 H) 1.40 (s, 6 H) 1.52-1.61 (m, 1 H) 1.63-1.68 (m, 1 H) 1.72-1.76 (m, 2 H) 1.84-1.89 (m, 1 H) 1.89-1.96 (m, 1 H) 2.01 (d, 2 H) 2.08 (d, J = 14.86 Hz, 1 H) 2.29 (s, 6 H) 2.33 (s, 3 H) 2.38-2.77 (m, 12 H) 2.80-2.85 (m, 1 H) 2.89-2.95 (m, 1 H) 2.96-3.02 (m, 1 H) 2.99 (s, 3 H) 3.05-3.07 (m, 3 H) 3.12 (q, J = 6.88 Hz, 1 H) 3.16-3.21 (m, 1 H) 3.28 (d, J = 3.72 Hz, 3 H) 3.30-3.36 (m, 1 H) 3.43-3.50 (m, 1 H) 3.51-3.57 (m, 1 H) 3.59 (s, 1 H) 3.69 (d, J = 11.15 Hz, 1 H) 3.72 (d, J = 4.54 Hz, 1 H) 3.77-3.83 (m, 1 H) 3.85-3.91 (m, 1 H) 4.05-4.10 (m, 1 H) 4.42 (d, J = 7.02 Hz, 1 H) 4.95-4.97 (m, 1 H) 4.98-5.01 (m, 1 H) 5.50-5.57 (m, 1 H) |

TABLE 20-1-continued

[Formula 61]

| Example | R²⁹ᵈ | R¹ᶠ | ESI MS (M + H) | ¹H-NMR, CDCl₃, δ (ppm) |
|---|---|---|---|---|
| 413 | H₃C-S(=O)₂-NH- (methylsulfonamide, attached via CH) | -N(CH₃)-CH₂CH₂-N(CH₂CH₃)₂ with additional CH₂CH₃ (diethylaminoethyl-methylamino) | 1050.7 | (600 MHz): 0.89 (t, J = 7.22 Hz, 3 H) 0.98-1.04 (m, 12 H) 1.11 (d, J = 7.43 Hz, 3 H) 1.13 (d, J = 7.02 Hz, 3 H) 1.16 (s, 3 H) 1.17-1.22 (m, 7 H) 1.23 (d, J = 6.19 Hz, 3 H) 1.40 (s, 6 H) 1.53-1.60 (m, 1 H) 1.62-1.66 (m, 1 H) 1.72-1.75 (m, 2 H) 1.83-1.89 (m, 1 H) 1.89-1.95 (m, 1 H) 1.98-2.01 (m, 2 H) 2.17 (d, J = 14.86 Hz, 1 H) 2.29 (s, 6 H) 2.40-2.63 (m, 10 H) 2.66-2.76 (m, 2 H) 2.87 (d, J = 14.86 Hz, 1 H) 2.92-2.96 (m, 1 H) 2.98 (s, 3 H) 3.05 (s, 3 H) 3.12 (q, J = 7.02 Hz, 1 H) 3.16-3.20 (m, 1 H) 3.28 (s, 3 H) 3.29-3.35 (m, 1 H) 3.45 (br. s., 1 H) 3.47-3.57 (m, 2 H) 3.59 (s, 1 H) 3.68 (d, J = 9.91 Hz, 1 H) 3.73 (d, J = 7.43 Hz, 1 H) 3.78-3.82 (m, 1 H) 3.85-3.91 (m, 1 H) 4.07-4.11 (m, 1 H) 4.43 (d, J = 7.02 Hz, 1 H) 4.96 (dd, J = 10.94, 1.86 Hz, 1 H) 4.97-4.99 (m, 1 H) 5.54 (t, J = 5.78 Hz, 1 H) |
| 414 | H₃C-S(=O)₂-CH₂- (methylsulfonylmethyl) | -N(CH₃)-CH₂CH₂-N(CH(CH₃)₂)₂ (diisopropylaminoethyl-methylamino) | 1063.6 | (500 MHz): 0.84 (t, J = 7.45 Hz, 3 H) 0.93-1.06 (m, 15 H) 1.07-1.30 (m, 19 H) 1.39 (s, 3 H) 1.40 (s, 3 H) 1.49-1.61 (m, 1 H) 1.62-1.69 (m, 1 H) 1.71-1.77 (m, 2 H) 1.84-2.08 (m, 5 H) 2.10-2.32 (m, 2 H) 2.29 (s, 6 H) 2.36 (s, 3 H) 2.38-2.65 (m, 6 H) 2.83 (d, J = 14.91 Hz, 1 H) 2.87-3.06 (m, 3 H) 2.93 (s, 3 H) 3.03 (s, 3 H) 3.06-3.21 (m, 4 H) 3.28 (s, 3 H) 3.40-3.49 (m, 1 H) 3.61-3.77 (m, 3 H) 3.63 (s, 1 H) 3.86-3.95 (m, 1 H) 4.09 (q, J = 6.12 Hz, 1 H) 4.40 (d, J = 7.26 Hz, 1 H) 4.89 (dd, J = 10.89, 2.10 Hz, 1 H) 4.98 (d, J = 4.59 Hz, 1 H) |
| 415 | H₃C-S(=O)₂-CH₂- | -N(CH₃)-CH₂CH₂-N(CH₃)(CH(CH₃)₂) | 1035.6 | (500 MHz): 0.84 (t, J = 7.26 Hz, 3 H) 0.95-1.03 (m, 9 H) 1.07-1.28 (m, 19 H) 1.39 (s, 3 H) 1.40 (s, 3 H) 1.50-1.60 (m, 1 H) 1.62-1.68 (m, 1 H) 1.71-1.78 (m, 2 H) 1.84-2.04 (m, 4 H) 2.11 (d, J = 14.52 Hz, 1 H) 2.13-2.31 (m, 2 H) 2.22 (s, 3 H) 2.29 (s, 6 H) 2.31-2.64 (m, 6 H) 2.34 (s, 3 H) 2.78-2.86 (m, 2 H) 2.87-2.95 (m, 1 H) 2.93 (s, 3 H) 3.03 (s, 3 H) 3.08-3.21 (m, 4 H) 3.28 (s, 3 H) 3.41-3.51 (m, 1 H) 3.63 (s, 1 H) 3.66-3.76 (m, 3 H) 3.86-3.93 (m, 1 H) 4.09 (q, J = 6.12 Hz, 1 H) 4.41 (d, J = 7.26 Hz, 1 H) 4.88 (dd, J = 10.89, 2.10 Hz, 1 H) 4.98 (d, J = 3.82 Hz, 1 H) |
| 416 | H₃C-S(=O)₂-CH₂- | -N(CH₃)-CH₂CH₂-N(CH₂CH₃)(CH₂CH₂CH₃) | 1049.6 | (500 MHz): 0.85 (dt, J = 10.13, 7.55 Hz, 6 H) 0.96-1.04 (m, 6 H) 1.07-1.29 (m, 19 H) 1.39 (s, 3 H) 1.40 (s, 3 H) 1.43-1.61 (m, 3 H) 1.63-1.69 (m, 1 H) 1.69-1.78 (m, 2 H) 1.84-2.05 (m, 4 H) 2.08 (d, J = 14.91 Hz, 1 H) 2.11-2.32 (m, 2 H) 2.29 (s, 6 H) 2.32-2.65 (m, 10 H) 2.34 (s, 3 H) 2.83 (d, J = 14.91 Hz, 1 H) 2.87-2.96 (m, 1 H) 2.93 (s, 3 H) 3.03 (s, 3 H) 3.06-3.21 (m, 4 H) 3.28 (s, 3 H) 3.41-3.50 (m, 1 H) 3.63 (s, 1 H) 3.66-3.76 (m, 3 H) 3.86-3.94 (m, 1 H) 4.09 (q, J = 6.12 Hz, 1 H) 4.41 (d, J = 7.26 Hz, 1 H) 4.89 (dd, J = 10.89, 2.10 Hz, 1 H) 4.98 (d, J = 4.59 Hz, 1 H) |

TABLE 20-1-continued

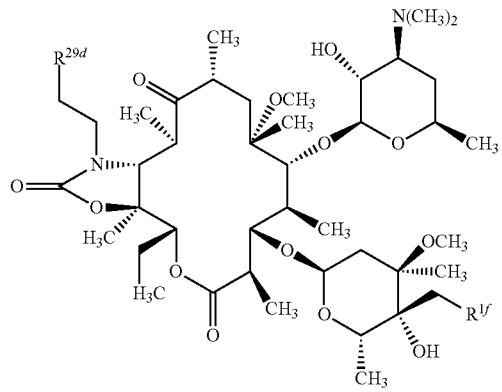

[Formula 61]

| Example | R[29d] | R[1f] | ESI MS (M + H) | $^1$H-NMR, CDCl$_3$, δ (ppm) |
|---|---|---|---|---|
| 417 | H$_3$C-SO$_2$-CH$_2$- (with CH$_3$) | -N(CH$_3$)-CH$_2$-CH$_2$-N(CH$_3$)(cyclobutyl) | 1047.6 | (600 MHz): 0.84 (t, J = 7.43 Hz, 3 H) 1.00 (d, J = 6.61 Hz, 3 H) 1.10 (d, J = 7.43 Hz, 3 H) 1.13 (d, J = 7.43 Hz, 3 H) 1.17 (s, 3 H) 1.18-1.22 (m, 7 H) 1.24 (d, J = 5.78 Hz, 3 H) 1.39 (s, 3 H) 1.40 (s, 3 H) 1.51-1.69 (m, 4 H) 1.72-1.76 (m, 2 H) 1.81-1.94 (m, 5 H) 1.97-2.04 (m, 3 H) 2.09 (s, 3 H) 2.09-2.12 (m, 1 H) 2.13-2.21 (m, 1 H) 2.22-2.31 (m, 3 H) 2.29 (s, 6 H) 2.33 (s, 3 H) 2.40-2.47 (m, 1 H) 2.47-2.55 (m, 1 H) 2.55-2.63 (m, 2 H) 2.77-2.84 (m, 1 H) 2.84 (d, J = 14.86 Hz, 1 H) 2.88-2.92 (m, 1 H) 2.93-2.94 (m, 3 H) 3.04 (s, 3 H) 3.08-3.20 (m, 4 H) 3.28 (s, 3 H) 3.43-3.49 (m, 2 H) 3.63 (s, 1 H) 3.67-3.75 (m, 3 H) 3.87-3.92 (m, 1 H) 4.10 (q, J = 6.19 Hz, 1 H) 4.41 (d, J = 7.43 Hz, 1 H) 4.87-4.90 (m, 1 H) 4.99 (d, J = 4.54 Hz, 1 H) |
| 418 | H$_3$C-SO$_2$-CH$_2$- (with CH$_3$) | -N(CH$_3$)-CH$_2$-CH$_2$-N(CH$_2$CH$_3$)(cyclobutyl) | 1061.6 | (600 MHz): 0.84 (t, J = 7.22 Hz, 3 H) 0.98 (t, J = 7.02 Hz, 3 H) 1.01 (s, 3 H) 1.10 (d, J = 7.43 Hz, 3 H) 1.13 (d, J = 7.02 Hz, 3 H) 1.16 (s, 3 H) 1.18-1.20 (m, 6 H) 1.21-1.26 (m, 1 H) 1.24 (d, J = 6.18 Hz, 3 H) 1.39 (s, 3 H) 1.40 (s, 3 H) 1.52-1.68 (m, 4 H) 1.72-1.76 (m, 2 H) 1.85-1.93 (m, 4 H) 1.96-2.05 (m, 4 H) 2.07 (d, J = 14.86 Hz, 1 H) 2.13-2.20 (m, 1 H) 2.23-2.28 (m, 1 H) 2.29 (s, 6 H) 2.33 (s, 3 H) 2.37-2.53 (m, 6 H) 2.54-2.62 (m, 2 H) 2.84 (d, J = 14.86 Hz, 1 H) 2.89-2.93 (m, 1 H) 2.93 (s, 3 H) 3.04 (s, 3 H) 3.08-3.20 (m, 5 H) 3.28 (s, 3 H) 3.43-3.49 (m, 2 H) 3.63 (s, 1 H) 3.68 (d, J = 7.43 Hz, 1 H) 3.69-3.76 (m, 2 H) 3.86-3.93 (m, 1 H) 4.09 (q, J = 6.19 Hz, 1 H) 4.41 (d, J = 7.02 Hz, 1 H) 4.66-4.92 (m, 1 H) 4.99 (d, J = 4.95 Hz, 1 H) |
| 419 | H$_3$C-SO$_2$-CH$_2$- (with CH$_3$) | -N(CH$_2$CH$_3$)-CH$_2$-CH$_2$-N(CH$_2$CH$_3$)$_2$ | 1049.6 | (600 MHz): 0.84 (t, J = 7.22 Hz, 3 H) 0.98-1.04 (m, 12 H) 1.10 (d, J = 7.43 Hz, 3 H) 1.13 (d, J = 7.02 Hz, 3 H) 1.16 (s, 3 H) 1.18-1.24 (m, 7 H) 1.23 (d, J = 6.19 Hz, 3 H) 1.39 (s, 3 H) 1.40 (s, 3 H) 1.52-1.59 (m, 1 H) 1.62-1.66 (m, 1 H) 1.71-1.75 (m, 2 H) 1.86-1.94 (m, 2 H) 1.97-2.02 (m, 2 H) 2.18-2.19 (m, 1 H) 2.22-2.28 (m, 1 H) 2.29 (s, 6 H) 2.39-2.44 (m, 1 H) 2.45-2.53 (m, 9 H) 2.66-2.75 (m, 2 H) 2.87 (d, J = 14.86 Hz, 1 H) 2.89-2.93 (m, 1 H) 2.93 (s, 3 H) 3.03 (s, 3 H) 3.07-3.21 (m, 4 H) 3.28 (s, 3 H) 3.44 (s, 1 H) 3.45-3.53 (m, 1 H) 3.64 (s, 1 H) 3.67-3.70 (m, 2 H) 3.71-3.75 (m, 1 H) 3.87-3.94 (m, 1 H) 4.06-4.12 (m, 1 H) 4.43 (d, J = 7.43 Hz, 1 H) 4.89 (dd, J = 10.94, 2.27 Hz, 1 H) 4.98 (d, J = 4.54 Hz, 1 H) |

TABLE 20-1-continued

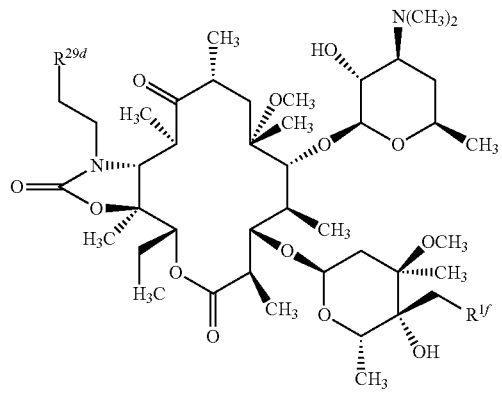

[Formula 61]

| Example | R²⁹ᵈ | R¹ᶠ | ESI MS (M + H) | ¹H-NMR, CDCl₃, δ (ppm) |
|---|---|---|---|---|
| 420 | H₃C-S(=O)₂-CH₂-C(CH₃)₂- | -N(CH₃)-CH₂CH₂-N(CH₃)-CH₂CH₂CH₃ | 1035.8 | (500 MHz): 0.84 (t, J = 7.45 Hz, 3 H) 0.88 (t, J = 7.26 Hz, 3 H) 1.00 (d, J = 6.88 Hz, 3 H) 1.10 (d, J = 7.64 Hz, 3 H) 1.13 (d, J = 6.88 Hz, 3 H) 1.15-1.27 (m, 1 H) 1.17 (s, 3 H) 1.18-1.20 (m, 6 H) 1.24 (d, J = 6.12 Hz, 3 H) 1.39 (s, 3 H) 1.40 (s, 3 H) 1.46-1.52 (m, 2 H) 1.51-1.59 (m, 1 H) 1.67 (d, J = 13.00 Hz, 1 H) 1.72-1.76 (m, 2 H) 1.84-1.96 (m, 2 H) 1.98-2.05 (m, 2 H) 2.11 (d, J = 14.91 Hz, 1 H) 2.13-2.20 (m, 1 H) 2.24 (s, 3 H) 2.24-2.30 (m, 1 H) 2.30 (s, 6 H) 2.30-2.35 (m, 2 H) 2.35 (s, 3 H) 2.37-2.48 (m, 3 H) 2.49-2.56 (m, 1 H) 2.58-2.66 (m, 2 H) 2.83 (d, J = 14.91 Hz, 1 H) 2.87-2.93 (m, 1 H) 2.93 (s, 3 H) 3.03 (s, 3 H) 3.07-3.21 (m, 4 H) 3.28 (s, 3 H) 3.43-3.50 (m, 1 H) 3.63 (s, 1 H) 3.67-3.76 (m, 3 H) 3.86-3.94 (m, 1 H) 4.10 (q, J = 6.12 Hz, 1 H) 4.41 (d, J = 7.26 Hz, 1 H) 4.89 (dd, J = 10.89, 2.10 Hz, 1 H) 4.98 (d, J = 4.59 Hz, 1 H) |
| 421 | H₃C-S(=O)₂-CH₂-C(CH₃)₂- | -N(CH₃)-CH₂CH₂-N(CH₃)-CH₂-cyclopropyl | 1047.8 | (500 MHz): 0.08-0.12 (m, 2 H) 0.48-0.53 (m, 2 H) 0.84 (t, J = 7.45 Hz, 3 H) 0.85-0.91 (m, 1 H) 1.00 (d, J = 6.88 Hz, 3 H) 1.10 (d, J = 7.64 Hz, 3 H) 1.13 (d, J = 6.88 Hz, 3 H) 1.16-1.26 (m, 1 H) 1.17 (s, 3 H) 1.18-1.21 (m, 6 H) 1.24 (d, J = 6.12 Hz, 3 H) 1.39 (s, 3 H) 1.40 (s, 3 H) 1.56 (d, J = 11.08 Hz, 1 H) 1.66 (d, J = 13.76 Hz, 1 H) 1.71-1.77 (m, 2 H) 1.85-1.96 (m, 2 H) 1.98-2.04 (m, 2 H) 2.13 (d, J = 14.91 Hz, 1 H) 2.13-2.20 (m, 1 H) 2.22-2.32 (m, 3 H) 2.29 (s, 6 H) 2.31 (s, 3 H) 2.35 (s, 3 H) 2.40-2.66 (m, 6 H) 2.83 (d, J = 14.52 Hz, 1 H) 2.88-2.94 (m, 1 H) 2.93 (s, 3 H) 3.03 (s, 3 H) 3.07-3.21 (m, 4 H) 3.28 (s, 3 H) 3.43-3.52 (m, 1 H) 3.63 (s, 1 H) 3.67-3.76 (m, 3 H) 3.86-3.93 (m, 1 H) 4.09-4.14 (m, 1 H) 4.41 (d, J = 7.26 Hz, 1 H) 4.89 (dd, J = 10.89, 2.10 Hz, 1 H) 4.98 (d, J = 4.59 Hz, 1 H) |
| 422 | (CH₃)₂CH-S(=O)₂- | -N(CH₃)-CH₂CH₂-N(CH₃)-CH₂CH₂CH₃ | 1021.7 | (500 MHz): 0.84 (t, J = 7.26 Hz, 3 H) 0.88 (t, J = 7.45 Hz, 3 H) 1.02 (d, J = 6.88 Hz, 3 H) 1.09 (d, J = 7.26 Hz, 3 H) 1.13 (d, J = 7.26 Hz, 3 H) 1.15-1.26 (m, 1 H) 1.17 (s, 3 H) 1.18-1.22 (m, 6 H) 1.23 (d, J = 6.12 Hz, 3 H) 1.38 (s, 3 H) 1.40 (s, 3 H) 1.44-1.57 (m, 3 H) 1.66 (d, J = 14.14 Hz, 1 H) 1.73-1.77 (m, 2 H) 1.82-1.91 (m, 2 H) 1.94-2.05 (m, 2 H) 2.11 (d, J = 14.52 Hz, 1 H) 2.23 (s, 3 H) 2.29 (s, 6 H) 2.29-2.33 (m, 2 H) 2.34 (s, 3 H) 2.37-2.48 (m, 3 H) 2.49-2.55 (m, 1 H) 2.56-2.65 (m, 2 H) 2.83 (d, J = 14.52 Hz, 1 H) 2.86-2.93 (m, 1 H) 3.02 (s, 3 H) 3.08 (s, 3 H) 3.06-3.12 (m, 1 H) 3.18 (dd, J = 10.32, 7.26 Hz, 1 H) 3.28 (s, 3 H) 3.41-3.50 (m, 2 H) 3.51-3.59 (m, 1 H) 3.63 (s, 1 H) 3.69-3.73 (m, 2 H) 4.00-4.18 (m, 3 H) 4.42 (d, J = 7.26 Hz, 1 H) 4.94-5.00 (m, 2 H) |

TABLE 20-1-continued

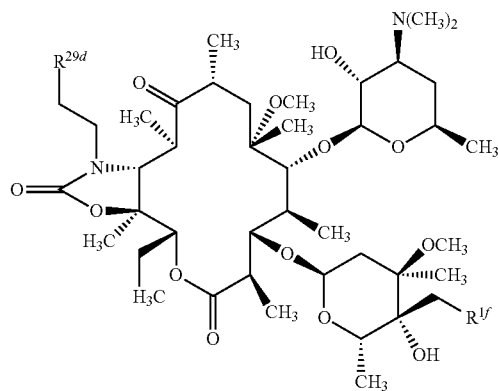

[Formula 61]

| Example | $R^{29d}$ | $R^{1f}$ | ESI MS (M + H) | $^1$H-NMR, CDCl$_3$, δ (ppm) |
|---|---|---|---|---|
| 423 | 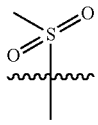 | 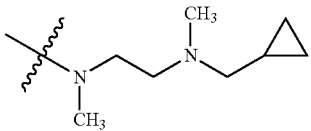 [SMILES: *N(C)CCN(C)CC1CC1] | 1033.7 | (500 MHz): 0.10 (q, J = 4.97 Hz, 2 H) 0.48-0.53 (m, 2 H) 0.84 (t, J = 7.45 Hz, 3 H) 0.83-0.93 (m, 1 H) 1.02 (d, J = 8.88 Hz, 3 H) 1.09 (d, J = 7.26 Hz, 3 H) 1.13 (d, J = 6.88 Hz, 3 H) 1.16-1.27 (m, 1 H) 1.17 (s, 3 H) 1.18-1.21 (m, 6 H) 1.23 (d, J = 5.73 Hz, 3 H) 1.39 (s, 3 H) 1.40 (s, 3 H) 1.49-1.58 (m, 1 H) 1.66 (d, J = 12.61 Hz, 1 H) 1.73-1.76 (m, 2 H) 1.81-1.91 (m, 2 H) 1.94-2.06 (m, 2 H) 2.13 (d, J = 14.52 Hz, 1 H) 2.25-2.30 (m, 2 H) 2.29 (s, 6 H) 2.31 (s, 3 H) 2.35 (s, 3 H) 2.40-2.67 (m, 6 H) 2.83 (d, J = 14.52 Hz, 1 H) 2.86-2.93 (m, 1 H) 3.02 (s, 3 H) 3.06-3.11 (m, 1 H) 3.07 (s, 3 H) 3.18 (dd, J = 10.32, 7.28 Hz, 1 H) 3.28 (s, 3 H) 3.40-3.50 (m, 2 H) 3.51-3.59 (m, 1 H) 3.63 (s, 1 H) 3.68-3.74 (m, 2 H) 4.00-4.18 (m, 3 H) 4.42 (d, J = 7.26 Hz, 1 H) 4.93-5.01 (m, 2 H) |
| 424 | 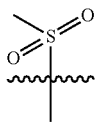 | 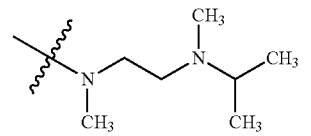 [SMILES: *N(C)CCN(C)C(C)C] | 1021.8 | (499 MHz): 0.84 (t, J = 7.27 Hz, 3 H) 0.96-1.27 (m, 28 H) 1.39 (s, 3 H) 1.40 (s, 3 H) 1.47-2.14 (m, 9 H) 2.22 (s, 3 H) 2.29 (s, 6 H) 2.34 (s, 3 H) 2.36-2.64 (m, 6 H) 2.79-2.94 (m, 3 H) 3.00-3.13 (m, 7 H) 3.15-3.21 (m, 1 H) 3.28 (s, 3 H) 3.40-3.59 (m, 3 H) 3.63 (s, 1 H) 3.68-3.74 (m, 2 H) 3.98-4.20 (m, 3 H) 4.42 (d, J = 7.40 Hz, 1 H) 4.92-5.02 (m, 2 H) |
| 425 | 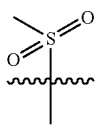 | 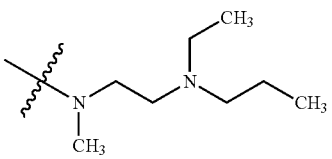 [SMILES: *N(C)CCN(CC)CCC] | 1035.8 | (499 MHz): 0.80-0.90 (m, 6 H) 0.98-1.28 (m, 25 H) 1.36-1.59 (m, 9 H) 1.62-1.78 (m, 3 H) 1.81-2.12 (m, 5 H) 2.29 (s, 6 H) 2.32-2.65 (m, 13 H) 2.80-2.94 (m, 2 H) 3.02 (s, 3 H) 3.05-3.12 (m, 4 H) 3.15-3.21 (m, 1 H) 3.28 (s, 3 H) 3.39-3.59 (m, 3 H) 3.63 (s, 1 H) 3.67-3.74 (m, 2 H) 4.00-4.19 (m, 3 H) 4.41 (d, J = 7.40 Hz, 1 H) 4.83-5.02 (m, 2 H) |
| 426 | 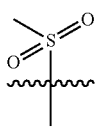 [SMILES: *S(C)(=O)=O] | 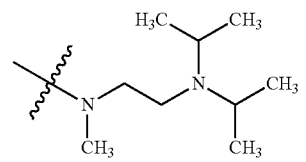 [SMILES: *N(C)CCN(C(C)C)C(C)C] | 1049.8 | (499 MHz): 0.84 (t, J = 7.27 Hz, 3 H) 0.98-1.27 (m, 34 H) 1.39 (s, 3 H) 1.41 (s, 3 H) 1.48-1.77 (m, 4 H) 1.80-2.07 (m, 5 H) 2.29 (s, 6 H) 2.35 (s, 3 H) 2.39-2.66 (m, 6 H) 2.81-2.95 (m, 2 H) 2.96-3.21 (m, 10 H) 3.28 (s, 3 H) 3.39-3.59 (m, 3 H) 3.63 (s, 1 H) 3.67-3.75 (m, 2 H) 4.00-4.18 (m, 3 H) 4.41 (d, J = 7.40 Hz, 1 H) 4.93-5.02 (m, 2 H) |

TABLE 20-1-continued

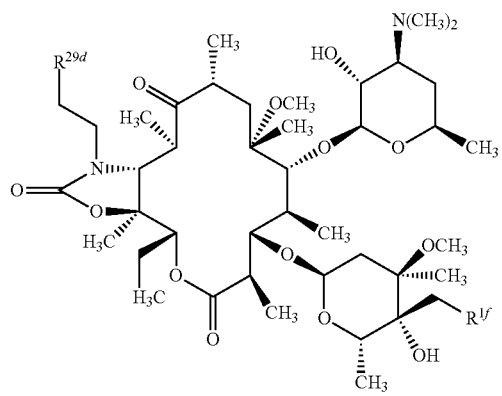

[Formula 61]

| Example | R²⁹ᵈ | R¹ᶠ | ESI MS (M + H) | ¹H-NMR, CDCl₃, δ (ppm) |
|---|---|---|---|---|
| 427 | methanesulfonyl | N,N-diethyl-N'-ethylethylenediamine | 1035.7 | (600 MHz): 0.84 (t, J = 7.43 Hz, 3 H) 0.99-1.04 (m, 12 H) 1.10 (d, J = 7.43 Hz, 3 H) 1.13 (d, J = 7.43 Hz, 3 H) 1.16 (s, 3 H) 1.18-1.27 (m, 7 H) 1.23 (d, J = 6.19 Hz, 3 H) 1.39 (s, 3 H) 1.40 (s, 3 H) 1.49-1.58 (m, 1 H) 1.61-1.67 (m, 1 H) 1.72-1.76 (m, 2 H) 1.62-1.92 (m, 2 H) 1.97-2.01 (m, 2 H) 2.17 (d, J = 14.86 Hz, 1 H) 2.29 (s, 6 H) 2.40-2.64 (m, 10 H) 2.65-2.76 (m, 2 H) 2.86 (d, J = 14.86 Hz, 1 H) 2.88-2.93 (m, 1 H) 3.02 (s, 3 H) 3.07 (s, 3 H) 3.07-3.11 (m, 1 H) 3.16-3.21 (m, 1 H) 3.28 (s, 3 H) 3.41-3.47 (m, 2 H) 3.48-3.52 (m, 1 H) 3.52-3.58 (m, 1 H) 3.63 (s, 1 H) 3.69-3.73 (m, 2 H) 4.00-4.17 (m, 3 H) 4.43 (d, J = 7.02 Hz, 1 H) 4.94-5.00 (m, 2 H) |
| 428 | methanesulfonyl | N-methyl-N-(2-(N-cyclobutyl-N-methylamino)ethyl)amine | 1033.7 | (600 MHz): 0.84 (t, J = 7.43 Hz, 3 H) 1.03 (d, J = 6.61 Hz, 3 H) 1.10 (d, J = 7.43 Hz, 3 H) 1.13 (d, J = 7.02 Hz, 3 H) 1.17 (s, 3 H) 1.19-1.22 (m, 6 H) 1.19-1.25 (m, 1 H) 1.24 (d, J = 5.78 Hz, 3 H) 1.38 (s, 3 H) 1.40 (s, 3 H) 1.48-1.56 (m, 1 H) 1.56-1.70 (m, 3 H) 1.73-1.77 (m, 2 H) 1.82-1.92 (m, 4 H) 1.96-2.05 (m, 4 H) 2.07-2.13 (m, 1 H) 2.09 (s, 3 H) 2.23-2.32 (m, 2 H) 2.29 (s, 6 H) 2.33 (s, 3 H) 2.41-2.46 (m, 1 H) 2.48-2.54 (m, 1 H) 2.54-2.63 (m, 2 H) 2.77-2.83 (m, 1 H) 2.84 (d, J = 14.45 Hz, 1 H) 2.87-2.92 (m, 1 H) 3.02 (s, 3 H) 3.06-3.11 (m, 1 H) 3.07 (s, 3 H) 3.18 (dd, J = 10.32, 7.43 Hz, 1 H) 3.28 (s, 3 H) 3.41-3.49 (m, 3 H) 3.51-3.59 (m, 1 H) 3.63 (s, 1 H) 3.69-3.74 (m, 2 H) 4.01-4.17 (m, 3 H) 4.42 (d, J = 7.43 Hz, 1 H) 4.96 (dd, J = 10.73, 2.06 Hz, 1 H) 4.88-5.01 (m, 1 H) |
| 429 | methanesulfonyl | N-methyl-N-(2-(N-cyclobutyl-N-ethylamino)ethyl)amine | 1047.7 | (600 MHz): 0.84 (t, J = 7.43 Hz, 3 H) 0.98 (t, J = 7.02 Hz, 3 H) 1.03 (d, J = 6.61 Hz, 3 H) 1.10 (d, J = 7.43 Hz, 3 H) 1.13 (d, J = 7.02 Hz, 3 H) 1.16 (s, 3 H) 1.18-1.21 (m, 6 H) 1.18-1.27 (m, 1 H) 1.24 (d, J = 5.78 Hz, 3 H) 1.38 (s, 3 H) 1.40 (s, 3 H) 1.48-1.68 (m, 4 H) 1.73-1.77 (m, 2 H) 1.83-1.93 (m, 4 H) 1.95-2.04 (m, 4 H) 2.07 (d, J = 14.86 Hz, 1 H) 2.29 (s, 6 H) 2.33 (s, 3 H) 2.38-2.63 (m, 8 H) 2.84 (d, J = 14.86 Hz, 1 H) 2.88-2.92 (m, 1 H) 3.02 (s, 3 H) 3.05-3.14 (m, 2 H) 3.07 (s, 3 H) 3.18 (dd, J = 10.11, 7.22 Hz, 1 H) 3.28 (s, 3 H) 3.41-3.49 (m, 3 H) 3.51-3.58 (m, 1 H) 3.63 (s, 1 H) 3.70 (d, J = 7.02 Hz, 1 H) 3.72 (d, J = 9.91 Hz, 1 H) 4.02-4.17 (m, 3 H) 4.41 (d, J = 7.02 Hz, 1 H) 4.96 (dd, J = 10.94, 1.86 Hz, 1 H) 5.00 (d, J = 4.13 Hz, 1 H) |

TABLE 20-1-continued

[Formula 61]

| Example | R[29d] | R[1f] | ESI MS (M + H) | $^1$H-NMR, CDCl₃, δ (ppm) |
|---|---|---|---|---|
| 430 | H₃C-S(=O)₂-NH- (methanesulfonamide) | -N(CH₃)CH₂CH₂N(CH₃)(CH₂CH₃) | 1022.6 | (500 MHz): 0.86 (t, J = 7.26 Hz, 3 H) 1.00-1.07 (m, 6 H) 1.11 (d, J = 7.26 Hz, 3 H) 1.13 (d, J = 7.26 Hz, 3 H) 1.17 (s 3 H) 1.19-1.22 (m, 6 H) 1.20-1.26 (m, 1 H) 1.23 (d, J = 6.12 Hz, 3 H) 1.40 (s, 6 H) 1.52-1.61 (m, 1 H) 1.65 (d, J = 11.80 Hz, 1 H) 1.71-1.77 (m, 2 H) 1.84-1.98 (m, 2 H) 1.97-2.02 (m, 2 H) 2.13 (d, J = 14.91 Hz, 1 H) 2.23 (s, 3 H) 2.29 (s, 6 H) 2.34 (s, 3 H) 2.36-2.48 (m, 5 H) 2.49-2.56 (m, 1 H) 2.56-2.66 (m, 2 H) 2.83 (d, J = 14.52 Hz, 1 H) 2.89-2.96 (m, 1 H) 2.98 (s, 3 H) 3.05 (s, 3 H) 3.09-3.14 (m, 1 H) 3.18 (dd, J = 10.32, 7.26 Hz, 1 H) 3.28 (s, 3 H) 3.29-3.37 (m, 1 H) 3.42-3.50 (m, 2 H) 3.51-3.56 (m, 1 H) 3.59 (s, 1 H) 3.69 (d, J = 9.94 Hz, 1 H) 3.72 (d, J = 7.26 Hz, 1 H) 3.76-3.84 (m, 1 H) 3.84-3.92 (m, 1 H) 4.10 (q, J = 6.50 Hz, 1 H) 4.42 (d, J = 6.88 Hz, 1 H) 4.93-5.00 (m, 2 H) 5.54 (t, J = 5.73 Hz, 1 H) |
| 431 | H₃C-S(=O)₂-NH- | -N(iPr)CH₂CH₂N(CH₂CH₃)₂ | 1064.7 | (600 MHz): 0.86 (t, J = 7.43 Hz, 3 H) 0.99-1.04 (m, 15 H) 1.10 (d, J = 7.43 Hz, 3 H) 1.13 (d, J = 7.43 Hz, 3 H) 1.19-1.26 (m, 13 H) 1.39 (s, 3 H) 1.40 (s, 3 H) 1.53-1.60 (m, 1 H) 1.61-1.65 (m, 1 H) 1.73 (d, J = 6.61 Hz, 2 H) 1.83-1.89 (m, 1 H) 1.90-1.95 (m, 1 H) 1.96-1.99 (m, 2 H) 2.25-2.29 (m, 1 H) 2.29 (s, 6 H) 2.41-2.63 (m, 10 H) 2.88-2.96 (m, 3 H) 2.98 (s, 3 H) 3.04 (s, 3 H) 3.11 (q, J = 6.74 Hz, 1 H) 3.16-3.21 (m, 1 H) 3.27 (s, 3 H) 3.30-3.35 (m, 1 H) 3.41-3.48 (m, 1 H) 3.51-3.57 (m, 2 H) 3.60 (s, 1 H) 3.63-3.66 (m, 1 H) 3.75 (d, J = 6.61 Hz, 1 H) 3.77-3.82 (m, 1 H) 3.84-3.91 (m, 1 H) 4.10 (q, J = 6.19 Hz, 1 H) 4.46 (d, J = 7.43 Hz, 1 H) 4.94-4.98 (m, 2 H) 5.55 (t, J = 5.78 Hz, 1 H) |
| 432 | H₃C-S(=O)₂-NH- | -N(CH₂CH₃)CH₂CH₂N(CH₂CH₃)₂ | 1064.7 | (600 MHz): 0.83-0.87 (m, 3 H) 0.92 (t, J = 7.43 Hz, 3 H) 0.99-1.04 (m, 9 H) 1.10 (d, J = 7.43 Hz, 3 H) 1.13 (d, J = 7.43 Hz, 3 H) 1.16 (s, 3 H) 1.17-1.25 (m, 1 H) 1.18-1.22 (m, 6 H) 1.23 (d, J = 6.19 Hz, 3 H) 1.40 (s, 6 H) 1.48-1.65 (m, 4 H) 1.73 (d, J = 6.61 Hz, 2 H) 1.83-1.90 (m, 1 H) 1.90-1.97 (m, 1 H) 1.97-2.03 (m, 2 H) 2.19 (d, J = 14.86 Hz, 1 H) 2.28 (s, 6 H) 2.40-2.46 (m, 1 H) 2.46-2.61 (m, 9 H) 2.62-2.64 (m, 1 H) 2.65-2.69 (m, 1 H) 2.68-2.95 (m, 2 H) 2.98 (s, 3 H) 3.05 (s, 3 H) 3.09-3.14 (m, 1 H) 3.15-3.21 (m, 1 H) 3.27 (s, 3 H) 3.28-3.34 (m, 1 H) 3.45 (s, 1 H) 3.47-3.57 (m, 2 H) 3.59 (s, 1 H) 3.67 (d, J = 9.91 Hz, 1 H) 3.72 (d, J = 7.02 Hz, 1 H) 3.77-3.83 (m, 1 H) 3.85-3.91 (m, 1 H) 4.06-4.11 (m, 1 H) 4.43 (d, J = 7.43 Hz, 1 H) 4.93-4.99 (m, 2 H) |

TABLE 20-1-continued

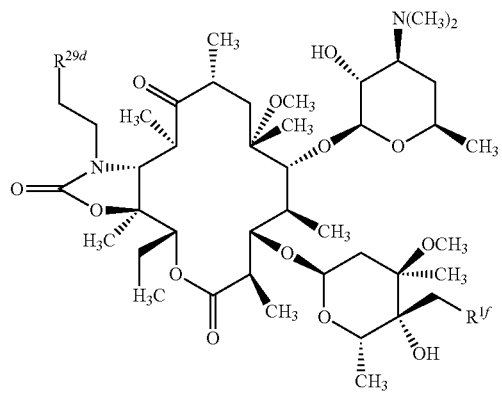

[Formula 61]

| Example | R[29d] | R[1f] | ESI MS (M + H) | $^1$H-NMR, CDCl$_3$, δ (ppm) |
|---|---|---|---|---|
| 433 | H$_3$C-S(=O)$_2$-NH- (on quaternary C with CH$_3$) | -N(CH$_2$CH$_3$)CH$_2$CH$_2$N(CH$_3$)(CH$_2$CH$_3$) with gem-dimethyl | 1036.7 | (600 MHz): 0.86 (t, J = 7.22 Hz, 3 H) 0.98-1.07 (m, 9 H) 1.11 (d, J = 7.43 Hz, 3 H) 1.13 (d, J = 7.02 Hz, 3 H) 1.15-1.25 (m, 1 H) 1.18 (s, 3 H) 1.19-1.22 (m, 6 H) 1.23 (d, J = 6.19 Hz, 3 H) 1.40 (s, 6 H) 1.53-1.60 (m, 1 H) 1.63-1.66 (m, 1 H) 1.74 (d, J = 6.61 Hz, 2 H) 1.84-1.90 (m, 1 H) 1.90-1.96 (m, 1 H) 1.98-2.00 (m, 2 H) 2.19-2.22 (m, 1 H) 2.22 (s, 3 H) 2.29 (s, 6 H) 2.34-2.47 (m, 5 H) 2.57-2.65 (m, 3 H) 2.66-2.73 (m, 2 H) 2.86 (d, J = 14.86 Hz, 1 H) 2.91-2.95 (m, 1 H) 2.98 (s, 3 H) 3.05 (s, 3 H) 3.12 (q, J = 6.88 Hz, 1 H) 3.16-3.21 (m, 1 H) 3.28 (s, 3 H) 3.29-3.34 (m, 1 H) 3.45 (br. s., 1 H) 3.47-3.57 (m, 2 H) 3.59 (s, 1 H) 3.67 (d, J = 9.91 Hz, 1 H) 3.73 (d, J = 7.02 Hz, 1 H) 3.78-3.82 (m, 1 H) 3.85-3.91 (m, 1 H) 4.10 (q, J = 6.19 Hz, 1 H) 4.44 (d, J = 7.43 Hz, 1 H) 4.94-4.99 (m, 2 H) 5.53-5.56 (m, 1 H) |
| 434 | H$_3$C-S(=O)$_2$-NH- (on quaternary C with CH$_3$) | -N(CH$_2$CH$_3$)CH$_2$CH$_2$N(CH$_3$)$_2$ with gem-dimethyl | 1022.6 | (600 MHz): 0.86 (t, J = 7.43 Hz, 3 H) 0.98-1.03 (m, 6 H) 1.11 (d, J = 7.43 Hz, 3 H) 1.13 (d, J = 7.02 Hz, 3 H) 1.15-1.25 (m, 1 H) 1.18 (s, 3 H) 1.19-1.22 (m, 6 H) 1.23 (d, J = 6.19 Hz, 3 H) 1.40 (s, 3 H) 1.40-1.40 (m, 3 H) 1.54-1.59 (m, 1 H) 1.64 (d, J = 12.39 Hz, 1 H) 1.73 (d, J = 6.61 Hz, 2 H) 1.84-1.88 (m, 1 H) 1.90-1.97 (m, 1 H) 1.97-2.00 (m, 2 H) 2.20-2.26 (m, 1 H) 2.22 (s, 6 H) 2.29 (s, 6 H) 2.32-2.41 (m, 2 H) 2.42-2.48 (m, 1 H) 2.55-2.64 (m, 3 H) 2.65-2.72 (m, 2 H) 2.85 (d, J = 14.86 Hz, 1 H) 2.90-2.96 (m, 1 H) 2.98 (s, 3 H) 3.05 (s, 3 H) 3.12 (q, J = 7.02 Hz, 1 H) 3.17-3.21 (m, 1 H) 3.28 (s, 3 H) 3.29-3.35 (m, 1 H) 3.42-3.46 (m, 1 H) 3.48-3.57 (m, 2 H) 3.59 (s, 1 H) 3.67 (d, J = 9.91 Hz, 1 H) 3.74 (d, J = 7.02 Hz, 1 H) 3.77-3.83 (m, 1 H) 3.84-3.91 (m, 1 H) 4.11 (q, J = 6.19 Hz, 1 H) 4.44 (d, J = 7.43 Hz, 1 H) 4.93-4.98 (m, 2 H) 5.54 (t, J = 5.78 Hz, 1 H) |
| 435 | H$_3$C-S(=O)$_2$-NH- (on quaternary C with CH$_3$) | -N(CH$_2$CH$_3$)CH$_2$CH$_2$N(CH$_3$)(CH(CH$_3$)$_2$) with gem-dimethyl | 1050.7 | (600 MHz): 0.86 (t, J = 7.43 Hz, 3 H) 0.87-1.01 (m, 9 H) 1.02 (d, J = 6.61 Hz, 3 H) 1.11 (d, J = 7.43 Hz, 3 H) 1.13 (d, J = 7.02 Hz, 3 H) 1.15-1.25 (m, 1 H) 1.18 (s, 3 H) 1.19-1.22 (m, 6 H) 1.23 (d, J = 5.78 Hz, 3 H) 1.40 (s, 6 H) 1.54-1.60 (m, 1 H) 1.61-1.66 (m, 1 H) 1.73 (d, J = 6.61 Hz, 2 H) 1.83-1.88 (m, 1 H) 1.89-1.96 (m, 1 H) 1.97-2.01 (m, 2 H) 2.17-2.19 (m, 1 H) 2.18-2.20 (m, 3 H) 2.29 (s, 6 H) 2.34-2.47 (m, 3 H) 2.56-2.62 (m, 3 H) 2.65-2.74 (m, 2 H) 2.80-2.86 (m, 1 H) 2.87 (d, J = 14.45 Hz, 1 H) 2.91-2.95 (m, 1 H) 2.98 (s, 3 H) 3.05 (s, 3 H) 3.12 (q, J = 6.74 Hz, 1 H) 3.16-3.21 (m, 1 H) 3.26-3.29 (m, 3 H) 3.28-3.36 (m, 1 H) 3.44 (s, 1 H) 3.48-3.57 (m, 2 H) 3.59 (s, 1 H) 3.67 (d, J = 9.50 Hz, 1 H) 3.73 (d, J = 7.43 Hz, 1 H) 3.77-3.82 (m, 1 H) 3.84-3.90 (m, 1 H) 4.09 (q, J = 6.19 Hz, 1 H) 4.44 (d, J = 7.02 Hz, 1 H) 4.96 (dd, J = 10.94, 1.86 Hz, 1 H) 4.97-5.00 (m, 1 H) 5.54 (t, J = 5.78 Hz, 1 H) |

TABLE 20-1-continued

[Formula 61]

| Example | R²⁹ᵈ | R¹ᶠ | ESI MS (M + H) | ¹H-NMR, CDCl₃, δ (ppm) |
|---|---|---|---|---|
| 436 | H₃C-S(=O)(=O)-NH- | -N(CH₃)-CH₂-N(CH₂-cyclopropyl)(CH₂CH₃) (with CH₃ and ethyl branches) | 1062.7 | (600 MHz): 0.10 (d, J = 4.13 Hz, 2 H) 0.50 (d, J = 7.84 Hz, 2 H) 0.86 (t, J = 7.22 Hz, 3 H) 0.86-0.91 (m, 1 H) 0.99-1.03 (m, 6 H) 1.11 (d, J = 7.84 Hz, 3 H) 1.13 (d, J = 7.02 Hz, 3 H) 1.15-1.24 (m, 1 H) 1.18 (s, 3 H) 1.19-1.22 (m, 6 H) 1.23 (d, J = 6.19 Hz, 3 H) 1.40 (s, 3 H) 1.40 (s, 3 H) 1.52-1.60 (m, 1 H) 1.62-1.66 (m, 1 H) 1.73 (d, J = 6.61 Hz, 2 H) 1.82-1.90 (m, 1 H) 1.90-1.97 (m, 1 H) 1.97-2.00 (m, 2 H) 2.21 (d, J = 14.86 Hz, 1 H) 2.26-2.30 (m, 2 H) 2.29 (s, 6 H) 2.30 (br. s., 3 H) 2.41-2.52 (m, 3 H) 2.58-2.61 (m, 1 H) 2.63-2.75 (m, 4 H) 2.87 (d, J = 14.86 Hz, 1 H) 2.91-2.95 (m, 1 H) 2.98 (s, 3 H) 3.05 (s, 3 H) 3.12 (q, J = 6.88 Hz, 1 H) 3.16-3.22 (m, 1 H) 3.28 (s, 3 H) 3.29-3.36 (m, 1 H) 3.42-3.47 (m, 1 H) 3.48-3.57 (m, 2 H) 3.59 (s, 1 H) 3.67 (d, J = 9.91 Hz, 1 H) 3.74 (d, J = 7.02 Hz, 1 H) 3.77-3.82 (m, 1 H) 3.84-3.91 (m, 1 H) 4.10 (q, J = 6.19 Hz, 1 H) 4.44 (d, J = 7.43 Hz, 1 H) 4.94-4.99 (m, 2 H) 5.54 (t, J = 5.78 Hz, 1 H) |
| 437 | H₃C-S(=O)(=O)-NH- | -N(CH₃)-CH₂CH₂-N(CH₃)(CH₂CH₂CH₃) with ethyl branch | 1050.7 | (600 MHz): 0.84-0.89 (m, 6 H) 1.00 (t, J = 7.02 Hz, 3 H) 1.11 (d, J = 7.43 Hz, 3 H) 1.13 (d, J = 7.43 Hz, 3 H) 1.15-1.26 (m, 1 H) 1.17 (s, 3 H) 1.18-1.22 (m, 6 H) 1.23 (d, J = 6.19 Hz, 3 H) 1.40 (s, 6 H) 1.46-1.51 (m, 2 H) 1.53-1.60 (m, 1 H) 1.62-1.67 (m, 1 H) 1.73 (d, J = 8.61 Hz, 2 H) 1.84-1.90 (m, 1 H) 1.90-1.97 (m, 1 H) 1.98-2.00 (m, 2 H) 2.19 (d, J = 15.28 Hz, 1 H) 2.22 (s, 3 H) 2.29 (s, 6 H) 2.29-2.33 (m, 2 H) 2.34-2.48 (m, 3 H) 2.56-2.65 (m, 3 H) 2.66-2.73 (m, 2 H) 2.86 (d, J = 14.86 Hz, 1 H) 2.89-2.96 (m, 1 H) 2.98 (s, 3 H) 3.05 (s, 3 H) 3.12 (q, J = 6.88 Hz, 1 H) 3.16-3.22 (m, 1 H) 3.25-3.29 (m, 3 H) 3.29-3.37 (m, 1 H) 3.44 (s, 1 H) 3.48-3.56 (m, 2 H) 3.59 (s, 3 H) 3.67 (d, J = 9.91 Hz, 1 H) 3.73 (s, 1 H) 3.77-3.83 (m, 1 H) 3.85-3.81 (m, 1 H) 4.10 (q, J = 6.19 Hz, 1 H) 4.43 (d, J = 7.02 Hz, 1 H) 4.93-5.00 (m, 2 H) 5.54 (t, J = 5.78 Hz, 1 H) |
| 438 | H₃C-S(=O)(=O)-NH- | -N(CH₂CH₃)-CH₂CH₂-N(CH₂CH₃)(CH₂CH₂CH₃) | 1064.7 | (499 MHz): 0.83-0.89 (m, 6 H) 0.99-1.03 (m, 9 H) 1.08-1.25 (m, 1 H) 1.1 J (d, J = 7.40 Hz, 3 H) 1.13 (d, J = 7.13 Hz, 3 H) 1.16 (s, 3 H) 1.19 (d, J = 6.31 Hz, 3 H) 1.21 (d, J = 7.13 Hz, 3 H) 1.23 (d, J = 6.03 Hz, 3 H) 1.40 (s, 6 H) 1.42-1.51 (m, 2 H) 1.53-1.60 (m, 1 H) 1.64 (d, J = 12.34 Hz, 1 H) 1.74 (d, J = 6.58 Hz, 2 H) 1.84-1.98 (m, 2 H) 1.98-2.05 (m, 2 H) 2.16 (d, J = 14.81 Hz, 1 H) 2.29 (s, 6 H) 2.35-2.55 (m, 7 H) 2.56-2.64 (m, 3 H) 2.66-2.76 (m, 2 H) 2.87 (d, J = 14.81 Hz, 1 H) 2.91-2.98 (m, 1 H) 2.98 (s, 3 H) 3.05 (s, 3 H) 3.12 (q, J = 6.86 Hz, 1 H) 3.18 (dd, J = 10.28, 7.27 Hz, 1 H) 3.28 (s, 3 H) 3.27-3.37 (m, 1 H) 3.42-3.56 (m, 3 H) 3.59 (s, 1 H) 3.68 (d, J = 9.87 Hz, 1 H) 3.72 (d, J = 7.13 Hz, 1 H) 3.76-3.83 (m, 1 H) 3.84-3.94 (m, 1 H) 4.10 (q, J = 6.22 Hz, 1 H) 4.43 (d, J = 7.40 Hz, 1 H) 4.92-5.01 (m, 2 H) 5.55 (t, J = 5.48 Hz, 1 H) |

TABLE 20-1-continued

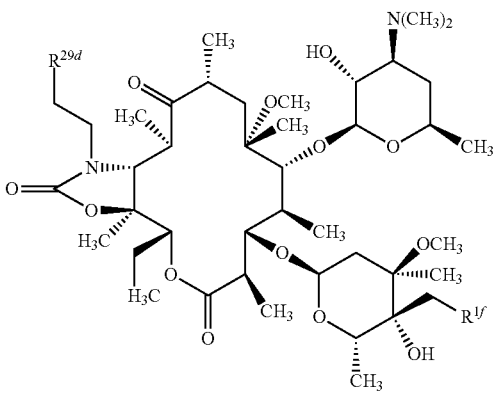

[Formula 61]

| Example | R[29d] | R[1f] | ESI MS (M + H) | $^1$H-NMR, CDCl$_3$, δ (ppm) |
|---|---|---|---|---|
| 439 | H$_3$C-S(=O)$_2$-NH-C(CH$_3$)- | -N(CH$_2$CH$_3$)CH$_2$CH$_2$N(CH(CH$_3$)$_2$)$_2$ | 1078.7 | (600 MHz): 0.86 (t, J = 7.22 Hz, 3 H) 0.98-1.03 (m, 18 H) 1.09-1.14 (m, 9 H) 1.17 (d, J = 6.19 Hz, 3 H) 1.17-1.24 (m, 1 H) 1.21 (d, J = 7.02 Hz, 3 H) 1.23 (d, J = 6.19 Hz, 3 H) 1.40 (s, 6 H) 1.53-1.61 (m, 1 H) 1.62-1.66 (m, 1 H) 1.74 (d, J = 5.78 Hz, 2 H) 1.84-1.89 (m, 1 H) 1.90-1.95 (m, 1 H) 1.96-2.06 (m, 2 H) 2.10 (d, J = 14.86 Hz, 1 H) 2.29 (s, 6 H) 2.41-2.50 (m, 3 H) 2.57 (t, J = 7.02 Hz, 3 H) 2.69-2.79 (m, 2 H) 2.87 (d, J = 14.86 Hz, 1 H) 2.91-3.02 (m, 3 H) 2.98 (s, 3 H) 3.05 (s, 3 H) 3.12 (q, J = 6.74 Hz, 1 H) 3.16-3.20 (m, 1 H) 3.27-3.29 (m, 3 H) 3.28-3.36 (m, 1 H) 3.44-3.49 (m, 2 H) 3.50-3.57 (m, 1 H) 3.59 (s, 1 H) 3.68-3.72 (m, 2 H) 3.78-3.82 (m, 1 H) 3.84-3.91 (m, 1 H) 4.09 (q, J = 6.19 Hz, 1 H) 4.42 (d, J = 7.43 Hz, 1 H) 4.96 (dd, J = 11.15, 2.06 Hz, 1 H) 4.99 (d, J = 4.95 Hz, 1 H) 5.54 (t, J = 5.78 Hz, 1 H) |
| 440 | cyclic sulfamide-C(CH$_3$)- | -N(CH$_3$)CH$_2$CH$_2$N(CH$_2$CH$_3$)$_2$ | 1063.7 | (600 MHz): 0.84 (t, J = 7.43 Hz, 3 H) 0.99-1.04 (m, 9 H) 1.10 (d, J = 7.43 Hz, 3 H) 1.14 (d, J = 7.02 Hz, 3 H) 1.16 (s, 3 H) 1.17-1.26 (m, 1 H) 1.18-1.21 (m, 6 H) 1.23 (d, J = 5.78 Hz, 3 H) 1.39 (s, 3 H) 1.40 (s, 3 H) 1.47-1.55 (m, 1 H) 1.63-1.68 (m, 1 H) 1.70-1.81 (m, 2 H) 1.86-1.94 (m, 2 H) 1.96-2.05 (m, 2 H) 2.09 (d, J = 14.88 Hz, 1 H) 2.29 (s, 6 H) 2.34 (s, 3 H) 2.40-2.61 (m, 10 H) 2.84 (d, J = 14.86 Hz, 1 H) 2.88-2.95 (m, 1 H) 3.04 (s, 3 H) 3.07-3.12 (m, 1 H) 3.13-3.22 (m, 2 H) 3.28 (s, 3 H) 3.37-3.41 (m, 1 H) 3.42-3.51 (m, 4 H) 3.52-3.58 (m, 1 H) 3.62 (s, 1 H) 3.64-3.71 (m, 4 H) 3.88-3.96 (m, 1 H) 4.06-4.13 (m, 1 H) 4.41 (d, J = 7.43 Hz, 1 H) 4.64-4.74 (m, 1 H) 4.98 (d, J = 4.54 Hz, 1 H) 5.29 (dd, J = 10.94, 2.27 Hz, 1 H) |
| 441 | H$_3$C-S(=O)$_2$-NH-C(CH$_3$)- | -N(CH$_2$CH$_2$NHC(=O)CH$_3$)CH$_2$CH$_2$N(CH$_2$CH$_3$)$_2$ | 1107.7 | (499 MHz): 0.86 (t, J = 7.27 Hz, 3 H) 1.00-1.05 (m, 9 H) 1.10 (d, J = 7.40 Hz, 3 H) 1.13 (d, J = 7.13 Hz, 3 H) 1.16-1.26 (m, 13 H) 1.40 (s, 6 H) 1.53-1.81 (m, 1 H) 1.66-1.70 (m, 1 H) 1.72-1.76 (m, 2 H) 1.84-1.88 (m, 1 H) 1.89-1.95 (m, 1 H) 1.95-2.03 (m, 2 H) 1.96 (s, 3 H) 2.25-2.31 (m, 1 H) 2.29 (s, 6 H) 2.39-2.61 (m, 8 H) 2.67-2.73 (m, 2 H) 2.73-2.79 (m, 2 H) 2.90-2.95 (m, 1 H) 2.97-3.02 (m, 1 H) 2.97-3.00 (m, 3 H) 3.04 (s, 3 H) 3.12 (q, J = 6.86 Hz, 1 H) 3.19 (dd, J = 10.28, 7.27 Hz, 1 H) 3.27 (s, 3 H) 3.29-3.49 (m, 5 H) 3.50-3.57 (m, 1 H) 3.59 (s, 1 H) 3.67 (d, J = 9.87 Hz, 1 H) 3.71 (d, J = 7.13 Hz, 1 H) 3.75-3.83 (m, 1 H) 3.83-3.92 (m, 1 H) 4.08-4.14 (m, 1 H) 4.39 (d, J = 7.13 Hz, 1 H) 4.83-4.98 (m, 2 H) 5.52-5.57 (m, 1 H) 6.18-6.24 (m, 1 H) |

TABLE 20-1-continued

[Formula 61]

| Example | R$^{29d}$ | R$^{1f}$ | ESI MS (M + H) | $^1$H-NMR, CDCl$_3$, δ (ppm) |
|---------|-----------|----------|----------------|------------------------------|
| 442 | H$_3$C-S(O)$_2$-NH- (methanesulfonamide) | N(CH$_2$CH$_2$N(Et)$_2$)(CH$_2$CH$_2$OH) | 1066.7 | (499 MHz): 0.66 (t, J = 7.40 Hz, 3 H) 1.01-1.06 (m, 9 H) 1.11 (d, J = 7.68 Hz, 3 H) 1.13 (d, J = 7.13 Hz, 3 H) 1.17-1.26 (m, 1 H) 1.18-1.22 (m, 9 H) 1.23 (d, J = 6.03 Hz, 3 H) 1.40 (s, 6 H) 1.53-1.61 (m, 1 H) 1.66 (d, J = 11.79 Hz, 1 H) 1.74 (d, J = 6.31 Hz, 2 H) 1.83-1.90 (m, 1 H) 1.90-1.97 (m, 1 H) 1.99-2.06 (m, 2 H) 2.29 (s, 6 H) 2.29-2.35 (m, 1 H) 2.40-2.47 (m, 1 H) 2.48-2.64 (m, 7 H) 2.74-2.86 (m, 4 H) 2.91-2.96 (m, 1 H) 2.98 (s, 3 H) 3.05 (s, 3 H) 3.05-3.09 (m, 1 H) 3.12 (q, J = 6.86 Hz, 1 H) 3.18 (dd, J = 10.28, 7.27 Hz, 1 H) 3.28 (s, 3 H) 3.28-3.36 (m, 1 H) 3.40-3.49 (m, 2 H) 3.50-3.58 (m, 1 H) 3.59 (s, 1 H) 3.65-3.72 (m, 4 H) 3.75-3.83 (m, 1 H) 3.83-3.91 (m, 1 H) 4.12 (q, J = 6.31 Hz, 1 H) 4.41 (d, J = 7.40 Hz, 1 H) 4.83-4.99 (m, 2 H) 5.50-5.57 (m, 1 H) |
| 443 | H$_3$C-S(O)$_2$-NH- | N(CH$_2$CH$_2$N(Et)$_2$)(CH$_2$CH$_2$OCH$_3$) | 1080.7 | (499 MHz): 0.86 (t, J = 7.27 Hz, 3 H) 0.99-1.05 (m, 9 H) 1.10 (d, J = 7.40 Hz, 3 H) 1.13 (d, J = 7.13 Hz, 3 H) 1.18 (s, 3 H) 1.18-1.27 (m, 1 H) 1.19-1.22 (m, 6 H) 1.23 (d, J = 6.31 Hz, 3 H) 1.40 (s, 8 H) 1.63-1.61 (m, 1 H) 1.61-1.67 (m, 1 H) 1.74 (d, J = 8.58 Hz, 2 H) 1.83-1.88 (m, 1 H) 1.89-1.96 (m, 1 H) 1.98-2.01 (m, 2 H) 2.27-2.32 (m, 1 H) 2.29 (s, 6 H) 2.40-2.61 (m, 8 H) 2.70 (t, J = 6.03 Hz, 2 H) 2.84 (q, J = 5.48 Hz, 2 H) 2.91-2.95 (m, 1 H) 2.97-3.02 (m, 1 H) 2.98 (s, 3 H) 3.05 (s, 3 H) 3.09-3.14 (m, 1 H) 3.16-3.20 (m, 1 H) 3.27 (s, 3 H) 3.30-3.36 (m, 1 H) 3.33 (s, 3 H) 3.42-3.57 (m, 5 H) 3.59 (s, 1 H) 3.67 (d, J = 9.87 Hz, 1 H) 3.73 (d, J = 7.13 Hz, 1 H) 3.76-3.83 (m, 1 H) 3.84-3.91 (m, 1 H) 4.08 (q, J = 6.12 Hz, 1 H) 4.43 (d, J = 7.40 Hz, 1 H) 4.93-5.00 (m, 2 H) 5.55 (t, J = 5.76 Hz, 1 H) |
| 444 | H$_3$C-S(O)$_2$-NH- | N(CH$_2$CH$_2$N(Et)$_2$)(CH$_2$CH$_2$NHS(O)$_2$CH$_3$) | 1143.7 | (500 MHz); 0.86 (t, J = 7.26 Hz, 3 H) 1.00-1.06 (m, 9 H) 1.10 (d, J = 7.64 Hz, 3 H) 1.13 (d, J = 7.26 Hz, 3 H) 1.16-1.28 (m, 1 H) 1.19-1.22 (m, 9 H) 1.24 (d, J = 6.12 Hz, 3 H) 1.40 (s, 6 H) 1.52-1.61 (m, 1 H) 1.67-1.71 (m, 1 H) 1.72-1.79 (m, 2 H) 1.84-1.89 (m, 1 H) 1.89-1.95 (m, 1 H) 1.96-2.05 (m, 2 H) 2.27-2.30 (m, 6 H) 2.33 (d, J = 14.91 Hz, 1 H) 2.39-2.63 (m, 8 H) 2.71-2.77 (m, 2 H) 2.81-2.87 (m, 2 H) 2.90-2.95 (m, 1 H) 2.93 (s, 3 H) 2.96-3.02 (m, 1 H) 2.99 (s, 3 H) 3.04 (s, 3 H) 3.11 (q, J = 6.88 Hz, 1 H) 3.16-3.25 (m, 1 H) 3.28 (s, 3 H) 3.28-3.30 (m, 3 H) 3.29-3.38 (m, 1 H) 3.40-3.48 (m, 2 H) 3.50-3.57 (m, 1 H) 3.58 (s, 1 H) 3.65-3.72 (m, 2 H) 3.75-3.90 (m, 2 H) 4.13 (q, J = 6.37 Hz, 1 H) 4.39 (d, J = 7.26 Hz, 1 H) 4.94-4.97 (m, 2 H) 5.51-5.56 (m, 1 H) |

TABLE 20-1-continued

[Chemical structure of macrolide compound with R²⁹ᵈ and R¹ᶠ substituents]

[Formula 61]

| Example | R²⁹ᵈ | R¹ᶠ | ESI MS (M + H) | $^1$H-NMR, CDCl$_3$, δ (ppm) |
|---------|------|-----|----------------|-------------------------------|
| 445 | H₃C-S(=O)₂-NH- (with gem-dimethyl linker) | -N(CH₂CH₂N(Et)(CH₂CH₂OEt))CH₃ type group with diethyl | 1121.7 | (500 MHz): 0.85 (t, J = 7.45 Hz, 3 H) 0.99-1.04 (m, 15 H) 1.10 (d, J = 7.64 Hz, 3 H) 1.13 (d, J = 6.88 Hz, 3 H) 1.16-1.28 (m, 1 H) 1.18-1.22 (m, 9 H) 1.23 (d, J = 6.12 Hz, 3 H) 1.40 (s, 3 H) 1.40 (s, 3 H) 1.52-1.61 (m, 1 H) 1.64 (d, J = 11.47 Hz, 1 H) 1.73 (d, J = 6.12 Hz, 2 H) 1.83-1.88 (m, 1 H) 1.89-1.96 (m, 1 H) 1.97-2.02 (m, 2 H) 2.23 (d, J = 14.91 Hz, 1 H) 2.28 (s, 6 H) 2.40-2.46 (m, 1 H) 2.46-2.57 (m, 12 H) 2.57-2.62 (m, 1 H) 2.63-2.74 (m, 4 H) 2.88-3.02 (m, 2 H) 2.98 (s, 3 H) 3.05 (s, 3 H) 3.09-3.14 (m, 1 H) 3.18 (dd, J = 10.32, 7.26 Hz, 1 H) 3.28 (s, 3 H) 3.30-3.36 (m, 1 H) 3.44 (s, 1 H) 3.46-3.56 (m, 2 H) 3.59 (s, 1 H) 3.67 (d, J = 9.94 Hz, 1 H) 3.73 (d, J = 6.88 Hz, 1 H) 3.76-3.84 (m, 1 H) 3.84-3.92 (m, 1 H) 4.07 (q, J = 5.73 Hz, 1 H) 4.43 (d, J = 7.26 Hz, 1 H) 4.94-4.99 (m, 2 H) 5.52-5.58 (m, 1 H) |
| 446 | H₃C-S(=O)₂-NH- (with gem-dimethyl linker) | -N(CH₃)CH₂CH₂-(azabicyclic ring) | 1060.6 | (500 MHz): 0.85 (t, J = 7.45 Hz, 3 H) 1.02 (d, J = 6.88 Hz, 3 H) 1.(0 (d, J = 7.28 Hz, 3 H) 1.13 (d, J = 7.26 Hz, 3 H) 1.16-1.26 (m, 1 H) 1.18 (s, 3 H) 1.19-1.22 (m, 6 H) 1.23 (d, J = 6.12 Hz, 3 H) 1.28 (d, J = 7.26 Hz, 4 H) 1.40 (s, 6 H) 1.53-1.61 (m, 1 H) 1.66 (d, J = 12.23 Hz, 1 H) 1.69-1.75 (m, 6 H) 1.84-1.89 (m, 1 H) 1.89-1.96 (m, 1 H) 1.98-2.01 (m, 2 H) 2.13 (d, J = 14.52 Hz, 1 H) 2.29 (s, 6 H) 2.33 (s, 3 H) 2.40-2.49 (m, 3 H) 2.53-2.67 (m, 3 H) 2.84 (d, J = 14.52 Hz, 1 H) 2.90-2.95 (m, 1 H) 2.98 (s, 3 H) 3.05 (s, 3 H) 3.09-3.14 (m, 1 H) 3.16-3.21 (m, 1 H) 3.23 (br. s., 2 H) 3.27 (s, 3 H) 3.29-3.37 (m, 1 H) 3.42-3.50 (m, 2 H) 3.51-3.57 (m, 1 H) 3.59 (s, 1 H) 3.68 (d, J = 9.56 Hz, 1 H) 3.73 (d, J = 6.88 Hz, 1 H) 3.77-3.83 (m, 1 H) 3 84-3.92 (m, 1 H) 4.10 (q, J = 6.12 Hz, 1 H) 4.42 (d, J = 7.26 Hz, 1 H) 4.93-5.00 (m, 2 H) 5.55 (t, J = 5.73 Hz, 1 H) |
| 447 | H₃C-S(=O)₂-CH₂- (with gem-dimethyl linker) | -N(CH₃)CH₂CH₂N(CH₃)(Et) | 1021.6 | (499 MHz): 0.84 (t, J = 7.40 Hz, 3 H) 1.00 (d, J = 6.86 Hz, 3 H) 1.05 (t, J = 7.13 Hz, 3 H) 1.10 (d, J = 7.68 Hz, 3 H) 1.13 (d, J = 7.13 Hz, 3 H) 1.16-1.26 (m, 1 H) 1.17 (s, 3 H) 1.18-1.20 (m, 6 H) 1.24 (d, J = 6.31 Hz, 3 H) 1.39 (s, 3 H) 1.40-1.41 (m, 3 H) 1.51-1.59 (m, 1 H) 1.63-1.68 (m, 1 H) 1.72-1.77 (m, 2 H) 1.85-1.95 (m, 2 H) 1.98-2.03 (m, 2 H) 2.12 (d, J = 14.81 Hz, 1 H) 2.15-2.19 (m, 1 H) 2.21-2.29 (m, 1 H) 2.23 (s, 3 H) 2.29 (s, 6 H) 2.34 (s, 3 H) 2.36-2.40 (m, 1 H) 2.41-2.47 (m, 4 H) 2.48-2.55 (m, 1 H) 2.55-2.66 (m, 2 H) 2.83 (d, J = 14.81 Hz, 1 H) 2.87-2.93 (m, 1 H) 2.92-2.95 (m, 3 H) 3.03 (s, 3 H) 3.07-3.21 (m, 4 H) 3.28 (s, 3 H) 3.44 (s, 1 H) 3.44-3.51 (m, 1 H) 3.63 (s, 1 H) 3.67-3.71 (m, 2 H) 3.71-3.76 (m, 1 H) 3.86-3.93 (m, 1 H) 4.10 (q, J = 6.22 Hz, 1 H) 4.41 (d, J = 7.13 Hz, 1 H) 4.89 (dd, J = 11.11, 2.06 Hz, 1 H) 4.97 (d, J = 4.11 Hz, 1 H) |

TABLE 20-1-continued

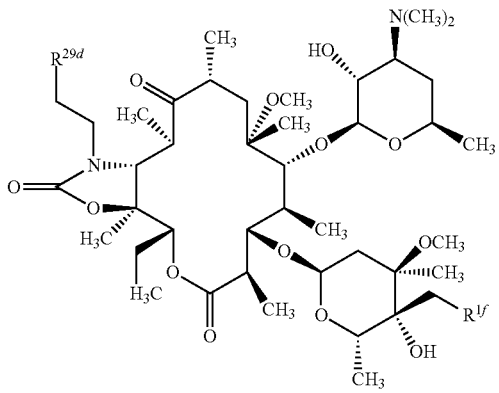

[Formula 61]

| Example | R^29d | R^1f | ESI MS (M + H) | 1H-NMR, CDCl3, δ (ppm) |
|---|---|---|---|---|
| 448 | H3C-S(=O)2-CH2-CH(CH3)- | -N(CH3)-CH2CH2-N(CH3)(CH2CH3) (approx.) | 1021.8 | (499 MHz): 0.84 (t, J = 7.40 Hz, 3 H) 0.98-0.03 (m, 6 H) 1.10 (d, J = 7.40 Hz, 3 H) 1.13 (d, J = 6.86 Hz, 3 H) 1.16-1.26 (m, 1 H) 1.17-1.20 (m, 9 H) 1.23 (d, J = 6.03 Hz, 3 H) 1.40 (s, 6 H) 1.51-1.58 (m, 1 H) 1.64 (d, J = 12.62 Hz, 1 H) 1.69-1.77 (m, 2 H) 1.85-1.95 (m, 2 H) 1.96-2.03 (m, 2 H) 2.11-2.26 (m, 3 H) 2.24 (s, 6 H) 2.29 (s, 6 H) 2.31-2.40 (m, 2 H) 2.41-2.48 (m, 1 H) 2.56-2.65 (m, 3 H) 2.66-2.72 (m, 2 H) 2.86 (d, J = 14.81 Hz, 1 H) 2.88-2.95 (m, 1 H) 2.91 (s, 3 H) 3.03 (s, 3 H) 3.07-3.22 (m, 4 H) 3.28 (s, 3 H) 3.43 (s, 1 H) 3.47-3.55 (m, 1 H) 3.64 (s, 1 H) 3.66-3.75 (m, 3 H) 3.85-3.93 (m, 1 H) 4.11 (q, J = 6.31 Hz, 1 H) 4.43 (d, J = 7.13 Hz, 1 H) 4.89 (dd, J = 10.97, 1.92 Hz, 1 H) 4.96 (d, J = 3.02 Hz, 1 H) |
| 449 | cyclic sulfamide (HN-S(O)2-N-CH2CH2) | -N(CH3)-CH2CH2-N(iPr)2 | 1091.7 | (600 MHz): 0.82-0.86 (m, 3 H) 0.98-1.03 (m, 15 H) 1.09-1.11 (m, 3 H) 1.13-1.15 (m, 6 H) 1.14-1.26 (m, 1 H) 1.17 (d, J = 6.61 Hz, 3 H) 1.20 (d, J = 7.02 Hz, 3 H) 1.23 (d, J = 6.19 Hz, 3 H) 1.39 (s, 3 H) 1.40 (s, 3 H) 1.48-1.55 (m, 1 H) 1.64-1.68 (m, 1 H) 1.70-1.81 (m, 2 H) 1.87-1.94 (m, 2 H) 1.96-2.09 (m, 3 H) 2.29 (s, 6 H) 2.35 (s, 3 H) 2.39-2.64 (m, 6 H) 2.81-2.85 (m, 1 H) 2.88-2.95 (m, 1 H) 2.95-3.01 (m, 2 H) 3.04 (s, 3 H) 3.06-3.11 (m, 1 H) 3.14-3.22 (m, 2 H) 3.28 (s, 3 H) 3.37-3.40 (m, 1 H) 3.41-3.49 (m, 4 H) 3.53-3.58 (m, 1 H) 3.62 (s, 1 H) 3.63-3.71 (m, 4 H) 3.91 (d, J = 5.37 Hz, 1 H) 4.10 (q, J = 6.19 Hz, 1 H) 4.40 (d, J = 7.02 Hz, 1 H) 4.66-4.72 (m, 1 H) 4.98 (d, J = 4.95 Hz, 1 H) 5.29 (dd, J = 11.15, 2.48 Hz, 1 H) |
| 450 | H3C-S(=O)2-CH2-CH(CH3)- | -N(CH3)-CH2CH2-N(azetidine/pyrrolidine) | 1059.7 | (499 MHz): 0.84 (t, J = 7.40 Hz, 3 H) 1.00 (d, J = 6.86 Hz, 3 H) 1.10 (d, J = 7.40 Hz, 3 H) 1.13 (d, J = 7.13 Hz, 3 H) 1.16-1.25 (m, 1 H) 1.17 (s, 3 H) 1.18-1.21 (m, 6 H) 1.23 (d, J = 6.03 Hz, 3 H) 1.28 (d, J = 7.40 Hz, 4 H) 1.39 (s, 3 H) 1.40 (s, 3 H) 1.50-1.59 (m, 1 H) 1.65 (d, J = 12.34 Hz, 1 H) 1.69-1.77 (m, 6 H) 1.86-1.95 (m, 2 H) 1.98-2.02 (m, 2 H) 2.12 (d, J = 14.53 Hz, 1 H) 2.13-2.20 (m, 1 H) 2.21-2.29 (m, 1 H) 2.29 (s, 6 H) 2.34 (s, 3 H) 2.40-2.49 (m, 3 H) 2.54-2.67 (m, 3 H) 2.84 (d, J = 14.81 Hz, 1 H) 2.88-2.93 (m, 1 H) 2.92-2.95 (m, 3 H) 3.03 (s, 3 H) 3.07-3.13 (m, 2 H) 3.14-3.21 (m, 2 H) 3.23 (br. s., 2 H) 3.28 (s, 3 H) 3.40-3.49 (m, 2 H) 3.64 (s, 1 H) 3.67-3.75 (m, 3 H) 3.85-3.93 (m, 1 H) 4.10 (q, J = 6.03 Hz, 1 H) 4.42 (d, J = 7.40 Hz, 1 H) 4.87-4.91 (m, 3 H) 4.97 (d, J = 3.29 Hz, 1 H) |
| 451 | CH3-NH-S(=O)2-CH2-CH(CH3)- | -N(CH3)-CH2CH2-N(iPr)2 | 1064.7 | (499 MHz): 0.85 (t, J = 7.38 Hz, 3 H) 0.95-1.05 (m, 15 H) 1.09 (d, J = 7.55 Hz, 3 H) 1.11-1.28 (m, 16 H) 1.38 (s, 3 H) 1.40 (s, 3 H) 1.46-1.57 (m, 1 H) 1.63-1.69 (m, 1 H) 1.71-1.79 (m, 2 H) 1.62-1.93 (m, 2 H) 1.95-2.08 (m, 3 H) 2.29 (s, 6 H) 2.35 (s, 3 H) 2.39-2.64 (m, 6 H) 2.80-2.96 (m, 4 H) 2.86-2.93 (m,. 1 H) 2.99 (dt, J = 12.78, 6.48 Hz, 2 H) 3.05 (s, 3 H) 3.09 (q, J = 6.86 Hz, 1 H) 3.18 (dd, J = 10.29, 7.20 Hz, 1 H) 3.28 (s, 3 H) 3.35-3.55 (m, 3 H) 3.66 (s, 1 H) 3.68 (d, J = 7.55 Hz, 1 H) 3.73 (d, J = 9.61 Hz, 1 H) 3.97-4.23 (m, 3 H) 4.41 (d, J = 7.20 Hz, 1 H) 4.98-5.06 (m, 2 H) 5.20 (dd, J = 10.98, 2.06 Hz, 1 H) |

TABLE 20-1-continued

[Formula 61]

| Example | R²⁹ᵈ | R¹ᶠ | ESI MS (M + H) | ¹H-NMR, CDCl₃, δ (ppm) |
|---------|------|-----|----------------|------------------------|
| 452 | H₃C-S(O)₂-CH₂- (methanesulfonylethyl) | -NH₂ | 922.5 | (499 MHz): 0.85 (t, J = 7.38 Hz, 3 H) 1.00 (d, J = 6.86 Hz, 3 H) 1.07-1.27 (m, 19 H) 1.40 (s, 3 H) 1.41 (s, 3 H) 1.50-1.78 (m, 4 H) 1.84-1.98 (m, 2 H) 1.98 (d, J = 5.15 Hz, 2 H) 2.10-2.33 (m, 2 H) 2.28 (s, 6 H) 2.39-2.46 (m, 1 H) 2.50 (d, J = 13.72 Hz, 1 H) 2.55-2.64 (m, 1 H) 2.87-2.97 (m, 1 H) 2.93 (s, 3 H) 3.01 (d, J = 13.72 Hz, 1 H) 3.03 (s, 3 H) 3.06-3.21 (m, 4 H) 3.29 (s, 3 H) 3.47-3.54 (m, 1 H) 3.63 (s, 1 H) 3.65-3.76 (m, 3 H) 3.86-3.83 (m, 1 H) 4.28 (q, J = 6.17 Hz, 1 H) 4.42 (d, J = 7.20 Hz, 1 H) 4.89 (d, J = 10.98 Hz, 1 H) 4.97 (d, J = 4.80 Hz, 1 H) |
| 453 | H₃C-S(O)₂-CH₂- | -NH-CH₃ | 936.5 | (499 MHz): 0.85 (t, J = 7.38 Hz, 3 H) 1.00 (d, J = 6.86 Hz, 3 H) 1.07-1.27 (m, 19 H) 1.40 (s, 3 H) 1.42 (s, 3 H) 1.50-1.61 (m, 1 H) 1.62-1.68 (m, 1 H) 1.68-1.80 (m, 2 H) 1.84-1.96 (m, 3 H) 2.05 (d, J = 15.09 Hz, 1 H) 2.11-2.33 (m, 2 H) 2.28 (s, 6 H) 2.40 (s, 3 H) 2.39-2.46 (m, 1 H) 2.49 (d, J = 13.38 Hz, 1 H) 2.56-2.64 (m, 1 H) 2.75 (d, J = 13 04 Hz, 1 H) 2.86-2.93 (m, 1 H) 2.93 (s, 3 H) 3.03 (s, 3 H) 3.06-3.20 (m, 4 H) 3.28 (s, 3 H) 3.61-3.76 (m, 5 H) 3.85-3.83 (m, 1 H) 4.37 (q, J = 6.40 Hz, 1 H) 4.41 (d, J = 7.20 Hz, 1 H) 4.88 (dd, J = 10.81, 1.89 Hz, 1 H) 4.94 (d, J = 4.80 Hz, 1 H) |
| 454 | H₃C-S(O)₂-CH₂- | -NH-CH₂CH₂-N(CH₂CH₃)₂ | 1021.6 | (499 MHz): 0.84 (t, J = 7.38 Hz, 3 H) 0.96-1.04 (m, 9 H) 1.08-1.28 (m, 19 H) 1.40 (s, 3 H) 1.40 (s, 3 H) 1.50-1.61 (m, 1 H) 1.62-1.68 (m, 1 H) 1.69-1.78 (m, 2 H) 1.85-2.07 (m, 4 H) 2.11-2.32 (m, 2 H) 2.29 (s, 6 H) 2.35 (d, J = 13.72 Hz, 1 H) 2.40-2.70 (m, 10 H) 2.87-2.97 (m, 2 H) 2.93 (s, 3 H) 3.03 (s, 3 H) 3.06-3.21 (m, 4 H) 3.29 (s, 3 H) 3.48-3.55 (m, 1 H) 3.63 (s, 1 H) 3.66-3.76 (m, 3 H) 3.86-3.93 (m, 1 H) 4.23 (q, J = 6.52 Hz, 1 H) 4.42 (d, J = 7.20 Hz, 1 H) 4.89 (dd, J = 10.98, 2.06 Hz, 1 H) 4.97 (d, J = 4.80 Hz, 1 H) |
| 455 | CH₃CH₂-S(O)₂-CH₂- | -N(CH₃)-CH₂CH₂-N(CH₂CH₃)₂ | 1049 | (400 MHz): 0.84 (t, J = 7.32 Hz, 3 H) 1.01 (t, J = 7.57 Hz, 6 H) 1.04 (d, J = 7.08 Hz, 3 H) 1.09 (d, J = 7.57 Hz, 3 H) 1.13 (d, J = 7.08 Hz, 3 H) 1.16 (s, 3 H) 1.18-1.20 (m, 6 H) 1.24 (d, J = 6.10 Hz, 3 H) 1.25-1.27 (m, 1 H) 1.37-1.42 (m, 9 H) 1.51-1.59 (m, 1 H) 1.64-1.68 (m, 2 H) 1.72-1.75 (m, 2 H) 1.84-1.93 (m, 2 H) 1.99-2.03 (m, 2 H) 2.09 (d, J = 14.7 Hz, 1 H) 2.13-2.18 (m, 1 H) 2.20-2.26 (m, 2 H) 2.29 (s, 6 H) 2.34 (s, 3 H) 2.40-2.84 (m, 10 H) 2.83 (d, J = 14.7 Hz, 1 H) 2.88-2.92 (m, 1 H) 3.00-3.04 (m, 5 H) 3.06-3.12 (m, 3 H) 3.19 (dd, J = 9.77, 7.08 Hz, 1 H) 3.28 (s, 3 H) 3.42-3.50 (m, 1 H) 3.63 (s, 1 H) 3.67-3.75 (m, 3 H) 3.86 (ddd, 14.0, 7.45, 5.62 Hz, 1 H) 4.09 (q, J = 6.18 Hz, 1 H) 4.41 (d, J = 7.08 Hz, 1 H) 4.89 (dd, J = 11.0, 2.20 Hz, 1H) 4.98 (d, J = 3.66 Hz, 1 H) |

TABLE 20-1-continued

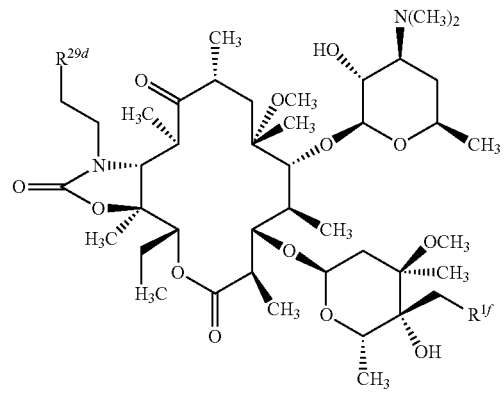

[Formula 61]

| Example | R²⁹ᵈ | R¹ᶠ | ESI MS (M + H) | ¹H-NMR, CDCl₃, δ (ppm) |
|---|---|---|---|---|
| 456 | $\text{O=S(=O)(NH_2)-O-}$ (sulfamate group) | H₃C-CH(CH₃)-N(CH₃)-CH₂CH₂-N(CH(CH₃)₂)- | 1066.7 | (600 MHz): 0.86 (t, J = 7.22 Hz, 3 H) 0.84-1.06 (m, 12 H) 1.09 (d, J = 7.43 Hz, 3 H) 1.11-1.28 (m, 19 H) 1.39 (s, 3 H) 1.42 (s, 3 H) 1.46-1.55 (m, 1 H) 1.63-1.78 (m, 3 H) 1.85-2.07 (m, 5 H) 2.29 (s., 6 H) 2.36 (s, 3 H) 2.38-2.64 (m, 6 H) 2.80-2.93 (m, 2 H) 2.95-3.05 (m, 2 H) 3.02 (s, 3 H) 3.09-3.13 (m, 1 H) 3.18 (dd, J = 10.11, 7.64 Hz, 1 H) 3.28 (s, 3 H) 3.43 (br. s., 1 H) 3.62-3.68 (m, 2 H) 3.66 (s, 1 H) 3.89-3.95(m, 1 H) 4.03-4.13 (m, 2 H) 4.20-4.25 (m, 1 H) 4.40 (d, J = 7.02 Hz, 1 H) 4.62 (ddd, J = 10.53, 7.64, 3.30 Hz, 1 H) 4.95 (d, J = 4.95 Hz, 1 H) 5.20 (dd, J = 10.32, 2.06 Hz, 1 H) 5.46 (br. a., 2 H) |

Example 399

By using the compound obtained in Example 86, (1) (300.0 mg) and N-cyclopropyl-N-ethyl-N'-methylethane-1,2-diamine (142.2 mg) as starting materials, the compound shown in Table 20 (129.0 mg) was obtained in the same manner as that of Example 4, (8).

Example 400

By using the compound obtained in Example 86, (1) (300.0 mg) and N,N'-dimethyl-N-cyclopropylethane-1,2-diamine (128.2 mg) as starting materials, the compound shown in Table 20 (206.0 mg) was obtained in the same manner as that of Example 4, (8).

Example 401

By using the compound obtained in Example 86, (1) (300.0 mg) and N-cyclopropyl-N-isopropyl-N'-methylethane-1,2-diamine (156.3 mg) as starting materials, the compound shown in Table 20 (256.0 mg) was obtained in the same manner as that of Example 4, (8).

Example 402

By using the compound obtained in Example 86, (1) (300.0 mg) and N,N-dicyclopropyl-N'-methylethane-1,2-diamine (154.3 mg) as starting materials, the compound shown in Table 20 (184.0 mg) was obtained in the same manner as that of Example 4, (8).

Example 403

By using the compound obtained in Example 86, (1) (300.0 mg) and N-cyclopropyl-N'-methyl-N-propylethane-1,2-diamine (156.3 mg) as starting materials, the compound shown in Table 20 (183.0 mg) was obtained in the same manner as that of Example 4, (8).

Example 404

By using the compound obtained in Example 86, (1) (200.0 mg) and N,N-diisopropyl-N'-methylethane-1,2-diamine (104.8 mg) as starting materials, the compound shown in Table 20 (145.0 mg) was obtained in the same manner as that of Example 2, (5).

Methanol (3.2 mL) was added to the compound obtained by the method of Example 404 (1.07 g), and the compound was completely dissolved with heating the mixture on a water bath at 65° C. Water (2.0 mL) was added dropwise to the solution at the same temperature, and then the mixture was returned to room temperature, and stirred overnight. The resulting crystals were collected by filtration, and washed with methanol/water=1/2 to obtain a compound identified with the following physicochemical data (725 mg).

Melting point: 118 to 126° C.
DSC (peak): 124.9° C.
XRD peak 2θ(°): 7.0, 10.1, 14.1, 15.9, 17.7, 20.2

Example 405

By using the compound obtained in Example 86, (1) (200.0 mg) and N,N'-dimethyl-N-isopropylethane-1,2-diamine (86.2 mg) as starting materials, the compound shown in Table 20 (155.0 mg) was obtained in the same manner as that of Example 2, (5).

Example 406

By using the compound obtained in Example 86, (1) (200.0 mg) and N-ethyl-N'-methyl-N-propylethane-1,2-diamine (95.5 mg) as starting materials, the compound shown in Table 20 (191.0 mg) was obtained in the same manner as that of Example 2, (5).

Example 407

By using the compound obtained in Example 86, (1) (200.0 mg) and N-isopropyl-N'-methyl-N-propylethane-1,2-diamine (104.8 mg) as starting materials, the compound shown in Table 20 (145.0 mg) was obtained in the same manner as that of Example 2, (5).

Example 408

By using the compound obtained in Example 86, (1) (200.0 mg) and N,N'-dimethyl-N-propylethane-1,2-diamine (86.2 mg) as starting materials, the compound shown in Table 20 (69.0 mg) was obtained in the same manner as that of Example 2, (5).

Example 409

By using the compound obtained in Example 86, (1) (200.0 mg) and N-cyclopropyl-N,N'-dimethylethane-1,2-diamine (94.2 mg) as starting materials, the compound shown in Table 20 (118.0 mg) was obtained in the same manner as that of Example 2, (5).

Example 410

By using the compound obtained in Example 86, (1) (200.0 mg) and the compound obtained in Reference Example 112 (103.5 mg) as starting materials, the compound shown in Table 20 (193.0 mg) was obtained in the same manner as that of Example 2, (5).

Example 411

By using the compound obtained in Example 86, (1) (200.0 mg) and N-(cyclopropylmethyl)-N,N'-dimethylethane-1,2-diamine (94.1 mg) as starting materials, the compound shown in Table 20 (149.0 mg) was obtained in the same manner as that of Example 2, (5).

Example 412

By using the compound obtained in Example 86, (1) (86.0 mg) and the compound obtained in Reference Example 113 (49.6 mg) as starting materials, the compound shown in Table 20 (73.2 mg) was obtained in the same manner as that of Example 4, (8).

Example 413

By using the compound obtained in Example 86, (1) (100 mg) and N,N,N'-triethylethane-1,2-diamine (59.7 µl) as starting materials, the compound shown in Table 20 (64.8 mg) was obtained in the same manner as that of Example 2, (5).

Example 414

By using the compound obtained in Example 35, (1) (300.0 mg) and N,N-diisopropyl-N'-methylethane-1,2-diamine (158.3 mg) as starting materials, the compound shown in Table 20 (277.0 mg) was obtained in the same manner as that of Example 4, (8).

Example 415

By using the compound obtained in Example 35, (1) (300.0 mg) and N-isopropyl-N,N'-dimethylethane-1,2-diamine (130.2 mg) as starting materials, the compound shown in Table 20 (284.0 mg) was obtained in the same manner as that of Example 4, (8).

Example 416

By using the compound obtained in Example 35, (1) (300.0 mg) and N-ethyl-N'-methyl-N-propylethane-1,2-diamine (144.3 mg) as starting materials, the compound shown in Table 20 (331.0 mg) was obtained in the same manner as that of Example 4, (8).

Example 417

By using the compound obtained in Example 35, (1) (300 mg) and N-cyclobutyl-N,N'-dimethylethane-1,2-diamine (141 mg) as starting materials, the compound shown in Table 20 (312 mg) was obtained in the same manner as that of Example 4, (8).

Example 418

By using the compound obtained in Example 35, (1) (300 mg) and the compound obtained in Reference Example 112 (155 mg) as starting materials, the compound shown in Table 20 (290 mg) was obtained in the same manner as that of Example 4, (8).

Example 419

By using the compound obtained in Example 35, (1) (300 mg) and N,N,N'-triethylethane-1,2-diamine (239 µl) as starting materials, the compound shown in Table 20 (262.5 mg) was obtained in the same manner as that of Example 4, (8).

Example 420

By using the compound obtained in Example 35, (1) (300 mg) and N,N'-dimethyl-N-propylethane-1,2-diamine (129 mg) as starting materials, the compound shown in Table 20 (256 mg) was obtained in the same manner as that of Example 4, (8).

Example 421

By using the compound obtained in Example 35, (1) (300 mg) and N-(cyclopropylmethyl)-N,N'-dimethylethane-1,2-diamine (141 mg) as starting materials, the compound shown in Table 20 (274 mg) was obtained in the same manner as that of Example 4, (8).

Example 422

By using the compound obtained in Example 31, (1) (300 mg) and N,N'-dimethyl-N-propylethane-1,2-diamine (263 mg) as starting materials, the compound shown in Table 20 (295 mg) was obtained in the same manner as that of Example 2, (5).

Example 423

By using the compound obtained in Example 31, (1) (300 mg) and N-(cyclopropylmethyl)-N,N'-dimethylethane-1,2-diamine (287 mg) as starting materials, the compound shown in Table 20 (296 mg) was obtained in the same manner as that of Example 2, (5).

Example 424

By using the compound obtained in Example 31, (1) (300 mg) and N-isopropyl-N,N'-dimethylethane-1,2-diamine (131.5 mg) as starting materials, the compound shown in Table 20 (260 mg) was obtained in the same manner as that of Example 2, (5).

Example 425

By using the compound obtained in Example 31, (1) (300 mg) and N-ethyl-N'-methyl-N-propylethane-1,2-diamine (145.7 mg) as starting materials, the compound shown in Table 20 (286 mg) was obtained in the same manner as that of Example 2, (5).

Example 426

By using the compound obtained in Example 31, (1) (300 mg) and N,N-diisopropyl-N'-methylethane-1,2-diamine (159.9 mg) as starting materials, the compound shown in Table 20 (217 mg) was obtained in the same manner as that of Example 2, (5).

Example 427

By using the compound obtained in Example 31, (1) (300 mg) and N,N,N'-triethylethane-1,2-diamine (182 µl) as starting materials, the compound shown in Table 20 (258 mg) was obtained in the same manner as that of Example 2, (5).

Example 428

By using the compound obtained in Example 31, (1) (300 mg) and N-cyclobutyl-N,N'-dimethylethane-1,2-diamine (144 mg) as starting materials, the compound shown in Table 20 (303 mg) was obtained in the same manner as that of Example 2, (5).

Example 429

By using the compound obtained in Example 31, (1) (300 mg) and the compound obtained in Reference Example 112 (158 mg) as starting materials, the compound shown in Table 20 (302 mg) was obtained in the same manner as that of Example 2, (5).

Example 430

By using the compound obtained in Example 86, (1) (50 mg) and N-ethyl-N,N'-dimethylethane-1,2-diamine (19 mg) as starting materials, the compound shown in Table 20 (46.6 mg) was obtained in the same manner as that of Example 2, (5).

Example 431

By using the compound obtained in Example 86, (1) (25 mg) and N,N-diethyl-N' isopropylethane-1,2-diamine (13 mg) as starting materials, the compound shown in Table 20 (6.5 mg) was obtained in the same manner as that of Example 2, (5).

Example 432

By using the compound obtained in Example 86, (1) (100 mg) and N,N-diethyl-N'-propylethane-1,2-diamine (52 mg) as starting materials, the compound shown in Table 20 (91.7 mg) was obtained in the same manner as that of Example 4, (8).

Example 433

By using the compound obtained in Example 86, (1) (100 mg) and N,N'-diethyl-N-methylethane-1,2-diamine (57 mg) as starting materials, the compound shown in Table 20 (99.2 mg) was obtained in the same manner as that of Example 4, (8).

Example 434

By using the compound obtained in Example 86, (1) (100 mg) and N-ethyl-N',N'-dimethylethane-1,2-diamine (70 µl) as starting materials, the compound shown in Table 20 (91.7 mg) was obtained in the same manner as that of Example 2, (5).

Example 435

By using the compound obtained in Example 86, (1) (100 mg) and N-ethyl-N'-isopropyl-N'-methylethane-1,2-diamine (48 mg) as starting materials, the compound shown in Table 20 (100.6 mg) was obtained in the same manner as that of Example 2, (5).

Example 436

By using the compound obtained in Example 86, (1) (100 mg) and N-(cyclopropylmethyl)-N'-ethyl-N-methylethane-1,2-diamine (52 mg) as starting materials, the compound shown in Table 20 (56.7 mg) was obtained in the same manner as that of Example 2, (5).

Example 437

By using the compound obtained in Example 86, (1) (100 mg) and N-ethyl-N'-methyl-N'-propylethane-1,2-diamine (48 mg) as starting materials, the compound shown in Table 20 (72.3 mg) was obtained in the same manner as that of Example 2, (5).

Example 438

By using the compound obtained in Example 86, (1) (100 mg) and N,N'-ethyl-N-propylethane-1,2-diamine (52 mg) as starting materials, the compound shown in Table 20 (86.4 mg) was obtained in the same manner as that of Example 2, (5).

Example 439

By using the compound obtained in Example 86, (1) (100 mg) and N-ethyl-N',N'-diisopropylethane-1,2-diamine (57 mg) as starting materials, the compound shown in Table 20 (83.9 mg) was obtained in the same manner as that of Example 2, (5).

Example 440

(1) By using the compound represented by the formula (A) obtained in Example 1, (5) (2.4 g) and the compound obtained in Reference Example 114 (1.4 g) as starting materials, a deacetylated compound (121 mg) was obtained in the same manners as those of Example 15, (1) and Example 2, (2).
(2) By using the compound obtained in (1) mentioned above (40.0 mg) as a starting material, the compound shown in Table 20 (7.8 mg) was obtained in the same manner as that of Example 15, (2).

Example 441

By using the compound obtained in Example 86, (1) (100 mg) and N-(2-{[2-(diethylamino)ethyl]amino}ethyl)acetamide (67 mg) as starting materials, the compound shown in Table 20 (54.4 mg) was obtained in the same manner as that of Example 2, (5).

Example 442

By using the compound obtained in Example 86, (1) (100 mg) and 2-(2-diethylaminoethylamino)ethanol (53 mg) as starting materials, the compound shown in Table 20 (73.0 mg) was obtained in the same manner as that of Example 2, (5).

Example 443

By using the compound obtained in Example 86, (1) (100 mg) and N,N-diethyl-N'-(2-methoxyethyl)ethane-1,2-diamine (58 mg) as starting materials, the compound shown in Table 20 (47.8 mg) was obtained in the same manner as that of Example 4, (8).

Example 444

By using the compound obtained in Example 86, (1) (60 mg) and N-(2-{([2-(diethylamino)ethyl]amino}ethyl)methanesulfonamide (47 mg) as starting materials, the compound shown in Table 20 (32.4 mg) was obtained in the same manner as that of Example 4, (8).

Example 445

By using the compound obtained in Example 86, (1) (100 mg) and N,N,N',N'-tetraethyldiethylenetriamine (88 µl) as starting materials, the compound shown in Table 20 (94.8 mg) was obtained in the same manner as that of Example 4, (8).

Example 446

By using the compound obtained in Example 86, (1) (50 mg) and the compound obtained in Reference Example 115 (26 mg) as starting materials, the compound shown in Table 20 (45.7 mg) was obtained in the same manner as that of Example 4, (8).

Example 447

By using the compound obtained in Example 35, (1) (100 mg) and N-ethyl-N,N'-dimethylethane-1,2-diamine (51 mg) as starting materials, the compound shown in Table 20 (106 mg) was obtained in the same manner as that of Example 2, (5).

Example 448

By using the compound obtained in Example 35, (1) (100 mg) and N-ethyl-N',N'-dimethylethane-1,2-diamine (70 µl) as starting materials, the compound shown in Table 20 (90.1 mg) was obtained in the same manner as that of Example 2, (5).

Example 449

By using the compound obtained in Example 440, (1) (40.0 mg) and N,N-diisopropyl-N'-methylethane-1,2-diamine (20.4 mg) as starting materials, the compound shown in Table 20 (8.4 mg) was obtained in the same manner as that of Example 2, (5).

Example 450

By using the compound obtained in Example 35, (1) (100 mg) and the compound obtained in Reference Example 115 (20 mg) as starting materials, the compound shown in Table 20 (44.8 mg) was obtained in the same manner as that of Example 2, (5).

Example 451

By using the compound obtained in Example 48, (1) (227.0 mg) and N,N-diisopropyl-N'-methylethane-1,2-diamine (119 mg) as starting materials, the compound shown in Table 20 (158 mg) was obtained in the same manner as that of Example 4, (8).

Example 452

By using the compound obtained in Example 35, (1) (50.0 mg) and 28% aqueous ammonia (135 µl) as starting materials, the compound shown in Table 20 (37.4 mg) was obtained in the same manner as that of Example 4, (8).

Example 453

By using the compound obtained in Example 35, (1) (50.0 mg) and 40% aqueous methylamine (43 µl) as starting materials, the compound shown in Table 20 (43.9 mg) was obtained in the same manner as that of Example 4, (8).

Example 454

By using the compound obtained in Example 35, (1) (50.0 mg) and N,N-diisopropylethylenediamine (64 mg) as starting materials, the compound shown in Table 20 (38.1 mg) was obtained in the same manner as that of Example 4, (8).

Example 455

(1) By using the compound represented by the formula (A) obtained in Example 1, (5) (300 mg) and the compound obtained in Reference Example 116 (192 mg) as starting materials, a deacetylated compound (292 mg) was obtained in the same manners as those of Example 15, (1) and Example 2, (2).
(2) By using the compound obtained in (1) mentioned above (80 mg) as a starting material, the compound shown in Table 20 (46 mg) was obtained in the same manner as that of Example 129, (3).

Example 456

By using the compound obtained in Example 1, (7) (450 mg) and N,N-diisopropyl-N'-methylethane-1,2-diamine (256 mg) as starting materials, the compound shown in Table 20

(112 mg) was obtained in the same manners as those of Example 4, (8), Example 1, (1), Example 81, (3) and Example 4, (6).

Example 457

Synthesis of Compound of the Formula (H) Wherein $R^{2b}$ is Diethylamino Group, and $R^{29c}$ is 3-methylbut-2-enylaminocarbonyl Group By using the compound obtained in Example 196, (1) (300 mg) and the compound obtained in Reference Example 117 (72 mg) as starting materials, the title compound (32 mg) was obtained in the same manners as those of Example 196, (2), Example 2, (2) and Example 11.

MS (ESI) m/z=1041 [M+H]$^+$ $^1$H-NMR (400 MHz, CDCl$_3$) δ (ppm): 0.88 (t, J=7.32 Hz, 3H), 1.03 (t, J=7.08 Hz, 6H), 1.08 (d, J=6.35 Hz, 3H), 1.08 (d, J=6.84 Hz, 3H), 1.14 (d, J=6.84 Hz, 3H), 1.16 (s, 3H), 1.17 (d, J=6.18 Hz, 3H), 1.21 (d, J=7.57 Hz, 1H), 1.23 (d, J=6.10 Hz, 1H), 1.24-1.26 (m, 1H), 1.36 (s, 3H), 1.43 (s, 3H), 1.52-2.11 (m, 9H), 1.65 (s, 3H), 1.68 (s, 3H), 2.29 (s, 6H), 2.34 (s, 3H), 2.41-2.67 (m, 10H), 2.81-2.89 (m, 2H), 2.92 (s, 3H), 3.07 (q, J=6.84 Hz, 1H), 3.17 (dd, J=10.1, 7.20 Hz, 1H), 3.27 (s, 3H), 3.40-3.51 (m, 1H), 3.67 (d, J=7.08 Hz, 1H), 3.73 (d, J=9.28 Hz, 1H), 3.76 (s, 1H), 3.76-3.88 (m, 2H), 4.07 (q, J=6.18 Hz, 1H), 4.42 (d, J=7.20 Hz, 1H), 4.98 (d, J=4.15 Hz, 1H), 5.24 (t, J=7.08 Hz, 1H), 5.33 (d, J=9.77 Hz, 1H), 7.67 (s, 1H)

Example 458

A preparation method of the compound represented by the formula (Z) is shown below.

Formula (Z)

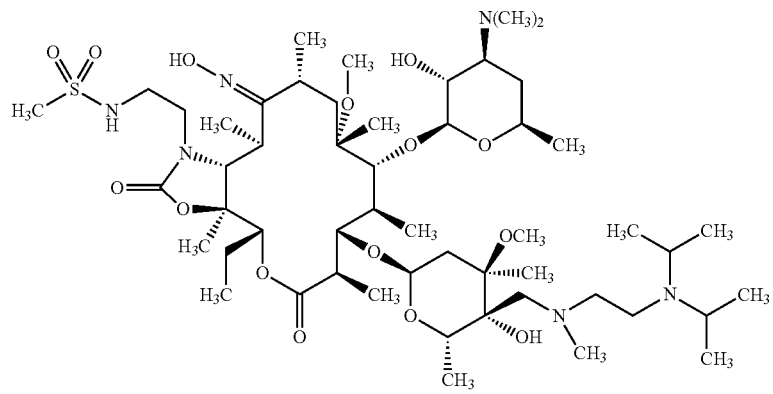

[Formula 62]

Example 458

By using the compound obtained in Example 333, (2) (80 mg) and N,N-diisopropyl-N'-methylethane-1,2-diamine (46.9 mg) as starting materials, the aforementioned objective compound (37.2 mg) was obtained in the same manners as those of Example 4, (8), Example 334, (1) and Example 162.

MS (ESI) m/z=1079.7 [M+H]$^+$ $^1$H-NMR (500 MHz, CDCl$_3$) δ (ppm): 0.84 (t, J=7.45 Hz, 3H), 0.96-1.04 (m, 15H), 1.07 (d, J=7.64 Hz, 3H), 1.09 (d, J=6.88 Hz, 3H), 1.13 (s, 3H), 1.16-1.27 (m, 1H), 1.18 (d, J=6.50 Hz, 3H), 1.20 (d, J=7.26 Hz, 3H), 1.24 (d, J=6.12 Hz, 3H), 1.38-1.44 (m, 1H), 1.39 (s, 3H), 1.49 (s, 3H), 1.51-1.57 (m, 1H), 1.60 (d, J=13.76 Hz, 1H), 1.65 (d, J=12.61 Hz, 1H), 1.84-1.92 (m, 2H), 1.94-2.07 (m, 3H), 2.29 (s, 6H), 2.36 (s, 3H), 2.39-2.63 (m, 6H), 2.84 (d, J=14.52 Hz, 1H), 2.88-2.93 (m, 1H), 2.94-3.01 (m, 2H), 2.98 (s, 3H), 3.12 (s, 3H), 3.20 (dd, J=9.94, 7.26 Hz, 1H), 3.27 (s, 3H), 3.39-3.48 (m, 2H), 3.51-3.67 (m, 3H), 3.68-3.74 (m, 2H), 3.77-3.88 (m, 3H), 4.11 (q, J=6.12 Hz, 1H), 4.40 (d, J=7.26 Hz, 1H), 4.88 (d, J=9.17 Hz, 1H), 4.99 (d, J=4.97 Hz, 1H), 5.90 (br. s., 1H), 8.02 (br. s., 1H)

Test Example 1

In Vitro Antibacterial Activity

In vitro antibacterial activities of the compounds of the present invention against various test bacteria were measured according to the microbroth dilution method (CLSI method). The used test bacteria are shown in Table 21. Among them, the bacteria C, D and E are erythromycin resistant bacteria. The MIC values (minimum inhibitory concentration, μg/ml) for the test bacteria A and B are exemplified in Table 22. The ranges of the MIC values shown by the compounds exemplified in Table 22 for the test bacteria C and D are shown below.

The MIC values (minimum inhibitory concentration, μg/ml) shown by the compounds of Examples 62, 94, 183, 263, 329, 332, 367, 390, 391 and 393 for the test bacterium C were not smaller than 0.5 and not larger than 2, the MIC values (minimum inhibitory concentration, μg/ml) shown by the compounds of Examples 1, 4, 15, 16, 24, 28, 30, 38, 48, 50, 53, 63, 70, 72, 76, 83, 87, 92, 103, 131, 141, 154, 170, 172, 191, 192, 193, 198, 208, 210, 233, 264, 299, 334, 338, 340, 341, 342, 348, 363, 366, 377, 395, 404, 413, 418, 440, 443, 445, 446, 451, 456, 457 and 458 for the test bacterium C were not smaller than 0.12 and not larger than 0.25, and the MIC values (minimum inhibitory concentration, μg/ml) shown by the compounds of Examples 3, 26, 73, 113, 114, 142, 231, 353, 354, 364 and 370 for the test bacterium C were not larger than 0.06.

The MIC values (minimum inhibitory concentration, μg/ml) shown by the compounds of Examples 1, 4, 30, 72, 94, 183, 192, 193, 233, 263, 264, 299, 329, 332, 366, 367, 390, 391, 393 and 395 for the test bacterium D were not smaller than 16, the MIC values (minimum inhibitory concentration, μg/ml) shown by the compounds of Examples 15, 16, 28, 38, 48, 50, 53, 62, 63, 70, 73, 76, 83, 87, 92, 103, 131, 141, 154, 170, 191, 208, 210, 334, 348, 413, 440, 443, 445, 446, 451, 457 and 458 for the test bacterium D were not smaller than 4 and not larger than 8, and the MIC values (minimum inhibitory concentration, μg/ml) shown by the compounds of Examples 3, 24, 26, 113, 114, 142, 172, 198, 231, 338, 340, 341, 342, 353, 354, 363, 364, 370, 377, 404, 418 and 456 for the test bacterium D were not larger than 2.

The ranges of the MIC values shown by the compounds of Examples 3, 15, 16, 26, 38, 62, 63, 70, 87, 92, 131, 142, 172, 198, 299, 334, 338, 340, 341, 342, 353, 354, 363, 364, 370, 377, 390, 395 and 404 for the test bacterium E are shown below. The MIC values (minimum inhibitory concentration, μg/ml) shown by the compounds of Examples 3, 62, 63, 299 and 395 for the test bacterium E were not smaller than 0.5 and not larger than 1, and the MIC values (minimum inhibitory concentration, μg/ml) shown by the compounds of Examples 15, 16, 26, 38, 70, 87, 92, 131, 142, 172, 198, 334, 338, 340, 341 342, 353, 354, 363, 364, 370, 377, 390 and 404 for the test bacterium E were not larger than 0.25.

TABLE 21

| Test bacteria | Symbols of bacteria |
| --- | --- |
| *Haemophilus infuenzae* ATCC43095 | A |
| *Streptococcus pneumoniae* ATCC49619 | B |
| *Streptococcus pneumoniae* ATCC700904 | C |
| *Streptococcus pyogenes* M808 | D |
| *Mycoplasma pneumoniae* MSC04933 | E |

TABLE 22

| Compound | A | B |
| --- | --- | --- |
| Comparative agent 1 | 4 | 0.03 |
| Example1 | 4 | 0.03 |
| Example3 | 8 | 0.03 |
| Example4 | 8 | 0.06 |
| Example15 | 4 | 0.03 |
| Example16 | 4 | 0.03 |
| Example24 | 8 | 0.06 |
| Example50 | 8 | 0.12 |
| Example26 | 4 | 0.06 |
| Example28 | 8 | 0.06 |
| Example30 | 8 | 0.06 |
| Example38 | 4 | 0.06 |
| Example48 | 4 | 0.03 |
| Example53 | 8 | 0.03 |
| Example62 | 4 | 0.016 |
| Example63 | 4 | 0.03 |
| Example70 | 4 | 0.06 |
| Example72 | 8 | 0.06 |
| Example73 | 4 | 0.03 |
| Example76 | 8 | 0.06 |
| Example83 | 4 | 0.06 |
| Example87 | 4 | 0.06 |
| Example92 | 4 | 0.06 |
| Example94 | 8 | 0.06 |
| Example103 | 4 | 0.03 |
| Example113 | 4 | 0.03 |
| Example114 | 4 | 0.03 |
| Example131 | 4 | 0.06 |
| Example141 | 16 | 0.06 |
| Example142 | 4 | 0.03 |
| Example154 | 4 | 0.06 |
| Example172 | 2 | 0.03 |
| Example183 | 8 | 0.016 |
| Example170 | 4 | 0.03 |
| Example191 | 4 | 0.016 |
| Example192 | 4 | 0.016 |

TABLE 22-continued

| Compound | A | B |
| --- | --- | --- |
| Example193 | 4 | 0.03 |
| Example198 | 2 | 0.03 |
| Example208 | 2 | 0.03 |
| Example210 | 8 | 0.12 |
| Example231 | 4 | 0.03 |
| Example233 | 8 | 0.03 |
| Example299 | 4 | 0.03 |
| Example263 | 8 | 0.06 |
| Example264 | 8 | 0.06 |
| Example329 | 8 | 0.03 |
| Example332 | 4 | 0.06 |
| Rxample334 | 4 | 0.06 |
| Example338 | 8 | 0.06 |
| Example340 | 4 | 0.06 |
| Example341 | 4 | 0.06 |
| Example342 | 4 | 0.06 |
| Example348 | 16 | 0.03 |
| Example353 | 4 | 0.06 |
| Example354 | 2 | 0.03 |
| Example363 | 8 | 0.06 |
| Example364 | 8 | 0.03 |
| Example366 | 8 | 0.03 |
| Example367 | 8 | 0.25 |
| Example370 | 4 | 0.03 |
| Example377 | 2 | 0.03 |
| Example390 | 4 | 0.03 |
| Example391 | 16 | 0.12 |
| Example393 | 4 | 0.06 |
| Example395 | 4 | 0.03 |
| Example404 | 4 | 0.03 |
| Example413 | 4 | 0.03 |
| Example418 | 4 | 0.03 |
| Example440 | 4 | 0.03 |
| Example443 | 4 | 0.03 |
| Example445 | 8 | 0.12 |
| Example446 | 4 | 0.03 |
| Example451 | 4 | 0.03 |
| Example456 | 2 | 0.03 |
| Example457 | 2 | 0.06 |
| Example458 | 4 | 0.06 |

INDUSTRIAL APPLICABILITY

The compounds of the present invention have potent antibacterial activity against various microorganisms, and even against erythromycin resistant bacteria (for example, resistant pneumococci, streptococci and mycoplasmas), and the like, against which sufficient antibacterial activity cannot be obtained with conventional macrolide antibiotics, and therefore, they can be used as medicaments for prophylactic and/or therapeutic treatment of various microbial infectious diseases.

The invention claimed is:

1. A compound represented by the following formula or a salt thereof, or a hydrate or a solvate thereof,

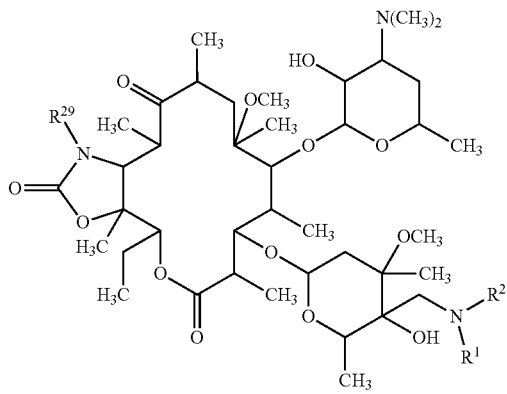

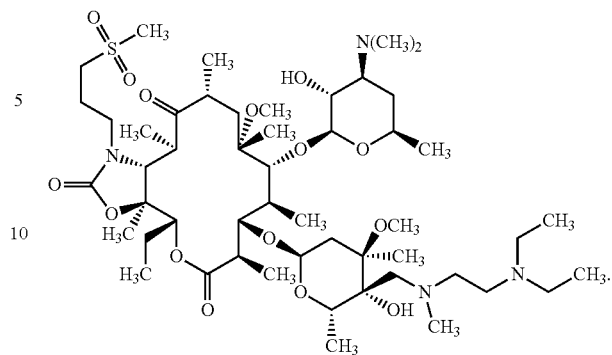

wherein $R^1$ represents a $C_{1-6}$ alkyl group, $R^2$ represents a $C_{1-6}$ alkyl group substituted with a hydroxyl group or with a group represented by the formula —$NR^{17}R^{18}$ wherein $R^{17}$ and $R^{18}$ may be the same or different and represent a hydrogen atom or a $C_{1-6}$ alkyl group that may be substituted with a $C_{3-6}$ cycloalkyl group, $R^{29}$ represents a $C_{1-6}$ alkyl group substituted with a group represented by the formula —$CONR^{59}R^{60}$ wherein $R^{59}$ and $R^{60}$ may be the same or different and represent a hydrogen atom or a $C_{1-6}$ alkyl group.

2. A compound represented by the following formula or a salt thereof, or a hydrate or a solvate thereof:

3. A medicament containing the compound according to claim 1, a salt thereof, a hydrate thereof, and a solvate thereof as an active ingredient, and further containing at least one pharmaceutical additive.

4. A medicament containing the compound according to claim 2, a salt thereof, a hydrate thereof, and a solvate thereof as an active ingredient, and further containing at least one pharmaceutical additive.

5. A method for therapeutic treatment of an bacterial infections comprising administering the compound according to claim 1 to a patient in need of such treatment.

6. A method for therapeutic treatment of an bacterial infections comprising administering the compound according to claim 2 to a patient in need of such treatment.

\* \* \* \* \*